United States Patent
Yin et al.

(10) Patent No.: US 10,604,543 B2
(45) Date of Patent: Mar. 31, 2020

(54) SELF-ASSEMBLY OF NUCLEIC ACID NANOSTRUCTURES

(71) Applicants: President and Fellows of Harvard College, Cambridge, MA (US); Dana-Farber Cancer Institute, Inc., Boston, MA (US)

(72) Inventors: Peng Yin, Brookline, MA (US); William M. Shih, Cambridge, MA (US); Yonggang Ke, Brighton, MA (US); Luvena L. Ong, Cambridge, MA (US)

(73) Assignees: President and Fellows of Harvard College, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 355 days.

(21) Appl. No.: 14/417,390

(22) PCT Filed: Jul. 24, 2013

(86) PCT No.: PCT/US2013/051891
§ 371 (c)(1),
(2) Date: Jan. 26, 2015

(87) PCT Pub. No.: WO2014/018675
PCT Pub. Date: Jan. 30, 2014

(65) Prior Publication Data
US 2015/0218204 A1    Aug. 6, 2015

Related U.S. Application Data

(60) Provisional application No. 61/773,715, filed on Mar. 6, 2013, provisional application No. 61/675,309, filed on Jul. 24, 2012.

(51) Int. Cl.
| | | |
|---|---|---|
| *G01N 33/00* | (2006.01) | |
| *C07H 21/04* | (2006.01) | |
| *G16B 15/00* | (2019.01) | |
| *C12Q 1/68* | (2018.01) | |
| *B82Y 5/00* | (2011.01) | |
| *B82Y 30/00* | (2011.01) | |
| *B82Y 40/00* | (2011.01) | |

(52) U.S. Cl.
CPC ............... *C07H 21/04* (2013.01); *B82Y 5/00* (2013.01); *C12Q 1/68* (2013.01); *G16B 15/00* (2019.02); *B82Y 30/00* (2013.01); *B82Y 40/00* (2013.01)

(58) Field of Classification Search
None
See application file for complete search history.

(56) References Cited

U.S. PATENT DOCUMENTS

| | | | |
|---|---|---|---|
| 6,255,469 B1 | 7/2001 | Seeman et al. | |
| 6,444,650 B1 * | 9/2002 | Cech | C12Y 207/07049 514/44 A |
| 6,444,661 B1 * | 9/2002 | Barton | C07F 15/008 514/185 |
| 7,745,594 B2 | 6/2010 | Seelig et al. | |
| 7,842,793 B2 | 11/2010 | Rothemund | |
| 8,877,438 B2 | 11/2014 | Yin | |
| 9,975,916 B2 * | 5/2018 | Yin | C12N 15/10 |
| 2003/0219790 A1 | 11/2003 | Seeman et al. | |
| 2006/0078910 A1 | 4/2006 | Seeman et al. | |
| 2007/0117109 A1 | 5/2007 | Rothemund | |
| 2007/0238096 A1 | 10/2007 | Reich et al. | |
| 2008/0221315 A1 | 9/2008 | Garibotti et al. | |
| 2009/0011943 A1 * | 1/2009 | Drmanac | C12N 15/64 506/4 |
| 2009/0227774 A1 | 9/2009 | Turberfield et al. | |
| 2010/0216978 A1 | 8/2010 | Shih | |
| 2010/0291485 A1 | 11/2010 | Lapsys et al. | |
| 2012/0022244 A1 | 1/2012 | Yin et al. | |
| 2012/0251583 A1 | 10/2012 | Rothemund | |
| 2013/0065777 A1 | 3/2013 | Altug et al. | |
| 2013/0316358 A1 | 11/2013 | Navon et al. | |
| 2014/0213778 A1 | 7/2014 | Yin et al. | |
| 2015/0329584 A1 | 11/2015 | Peng et al. | |
| 2019/0002971 A1 * | 1/2019 | Koslover | G01N 33/48 |

FOREIGN PATENT DOCUMENTS

| | | |
|---|---|---|
| CN | 1390253 A | 1/2003 |
| JP | 2004-510780 A | 4/2004 |
| JP | 2008-504846 A | 2/2008 |
| WO | WO 01/36624 A1 | 5/2001 |
| WO | WO 2005/024018 A1 | 3/2005 |
| WO | WO 2006/017432 A2 | 2/2006 |
| WO | WO 2007/012807 A2 | 2/2007 |
| WO | WO 2009/093558 A1 | 7/2009 |
| WO | WO 2012/058638 A2 | 5/2012 |
| WO | WO 2013/022694 A1 | 2/2013 |
| WO | WO 2013/088098 A2 | 6/2013 |
| WO | WO 2014/018675 A1 | 1/2014 |
| WO | WO 2014/074597 A1 | 5/2014 |

OTHER PUBLICATIONS

"Oligonucleotide definition," Merriam-Webster.com; accessed Aug. 23, 2017. (Year: 2017).*
"Oligonucleotide", Wikipedia.com, accessed Feb. 17, 2019. (Year: 2019).*
Acuna et al., Fluorescence enhancement at docking sites of DNA-directed self-assembled nanoantennas. Science. Oct. 26, 2012;338(6106):506-10. doi:10.1126/science.1228638.
Aldaye et al., Assembling materials with DNA as the guide. Science. Sep. 26, 2008;321(5897):1795-9. doi: 10.1126/science.1154533.
Aldaye et al., Modular access to structurally switchable 3D discrete DNA assemblies. J Am Chem Soc. Nov. 7, 2007;129(44):13376-7. Epub Oct. 16, 2007.

(Continued)

*Primary Examiner* — Bradley L. Sisson
(74) *Attorney, Agent, or Firm* — Wolf, Greenfield & Sacks, P.C.

(57) ABSTRACT

The invention involves the synthesis of nucleic acid structures of controlled size and shape and comprised of a plurality of oligonucleotides. The structures are formed, at least in part, by the self-assembly of single-stranded oligonucleotides. The location of each oligonucleotide in the resultant structure is known. Accordingly, the structures may be modified with specificity.

19 Claims, 78 Drawing Sheets

Specification includes a Sequence Listing.

(56) References Cited

OTHER PUBLICATIONS

Aldaye et al., Sequential self-assembly of a DNA hexagon as a template for the organization of gold nanoparticles. Angew Chem Int Ed Engl. Mar. 27, 2006;45(14):2204-9.

Andersen et al., Self-assembly of a nanoscale DNA box with a controllable lid. Nature. May 7, 2009;459(7243):73-6. doi:10.1038/nature07971.

Barish et al., An information-bearing seed for nucleating algorithmic self-assembly. Proc Natl Acad Sci U S A. Apr. 14, 2009;106(15):6054-9. doi: 10.1073/pnas.0808736106. Epub Mar. 24, 2009.

Bath et al., DNA nanomachines. Nat Nanotechnol. May 2007;2(5):275-84. doi:10.1038/nnano.2007.104.

Berardi et al., Mitochondrial uncoupling protein 2 structure determined by NMR molecular fragment searching. Nature. Jul. 24, 2011;476(7358):109-13. doi: 10.1038/nature10257.

Bhatia et al., Icosahedral DNA nanocapsules by modular assembly. Angew Chem Int Ed Engl. 2009;48(23):4134-7.doi:10.1002/anie.200806000.

Chen et al., DNA-directed assembly of single-wall carbon nanotubes. J Am Chem Soc. Jul. 18, 2007;129(28):8696-7. Epub Jun. 23, 2007.

Chen et al., Invadable self-assembly: combining robustness with efficiency. Proceeding SODA '04 Proceedings of the fifteenth annual ACM-SIAM symposium on Discrete algorithms. 2004:890-9.

Chen et al., Synthesis from DNA of a molecule with the connectivity of a cube. Nature. Apr. 18, 1991;350(6319):631-3.

Choi et al., Programmable in situ amplification for multiplexed imaging of mRNA expression. Nat Biotechnol. Nov. 2010;28(11):1208-12.doi: 10.1038/nbt.1692. Epub Oct. 31, 2010.

Chworos et al., Building programmable jigsaw puzzles with RNA. Science. Dec. 17, 2004;306(5704):2068-72.

Delebecque et al., Organization of intracellular reactions with rationally designed RNA assemblies. Science. Jul. 22, 2011;333(6041):470-4. doi: 10.1126/science.1206938. Epub Jun. 23, 2011.

Dietz et al., Folding DNA into twisted and curved nanoscale shapes. Science. Aug. 7, 2009;325(5941):725-30. doi: 10.1126/science.1174251.

Douglas et al., A logic-gated nanorobot for targeted transport of molecular payloads. Science. Feb. 17, 2012;335(6070):831-4. doi:10.1126/science.1214081.

Douglas et al., DNA-nanotube-induced alignment of membrane proteins for NMR structure determination. Proc Natl Acad Sci U S A. Apr. 17, 2007;104(16):6644-8. Epub Apr. 2, 2007.

Douglas et al., Rapid prototyping of 3D DNA-origami shapes with caDNAno. Nucleic Acids Res. Aug. 2009;37(15):5001-6. doi: 10.1093/nar/gkp436. Epub Jun. 16, 2009.

Douglas et al., Self-assembly of DNA into nanoscale three-dimensional shapes. Nature. May 21, 2009;459(7245):414-8.doi: 10.1038/nature08016.

Erben et al., A self-assembled DNA bipyramid. J Am Chem Soc. Jun. 6, 2007;129(22):6992-3. Epub May 15, 2007.

Feldkamp et al., Rational design of DNA nanoarchitectures. Angew Chem Int Ed Engl. Mar. 13, 2006;45(12):1856-76.

Fu et al., DNA double-crossover molecules. Biochemistry. Apr. 6, 1993;32(13):3211-20.

Fu et al., Interenzyme substrate diffusion for an enzyme cascade organized on spatially addressable DNA nanostructures. J Am Chem Soc. Mar. 28, 2012;134(12):5516-9. doi:10.1021/ja300897h. Epub Mar. 16, 2012.

Geary et al., A single-stranded architecture for cotranscriptional folding of RNA nanostructures. Science. Aug. 15, 2014;345(6198):799-804. doi: 10.1126/science.1253920.

Goodman et al., Rapid chiral assembly of rigid DNA building blocks for molecular nanofabrication. Science. Dec. 9, 2005;310(5754):1661-5.

Goodman et al., Reconfigurable, braced, three-dimensional DNA nanostructures. Nat Nanotechnol. Feb. 2008;3(2):93-6. doi: 10.1038/nnano 2008.3. Epub Feb. 3, 2008.

Han et al., DNA gridiron nanostructures based on four-arm junctions. Science. Mar. 22, 2013;339(6126):1412-5. doi: 10.1126/science.1232252.

Han et al., DNA origami with complex curvatures in three-dimensional space. Science. Apr. 15, 2011;332(6027):342-6. doi:10.1126/science.1202998.

Han et al., Folding and cutting DNA into reconfigurable topological nanostructures. Nat Nanotechnol. Oct. 2010;5(10):712-7. doi:10.1038/nnano 2010.193. Epub Oct. 3, 2010.

Hansma et al., DNA binding to mica correlates with cationic radius:assay by atomic force microscopy. Biophys J. Apr. 1996;70(4):1933-9.

He et al., Hierarchical self-assembly of DNA into symmetric supramolecular polyhedra. Nature. Mar. 13, 2008;452(7184):198-201. doi: 10.1038/nature06597.

Hell, Far-field optical nanoscopy. Science. May 25, 2007;316(5828):1153-8.

Huang et al., Three-dimensional super-resolution imaging by stochastic optical reconstruction microscopy. Science. Feb. 8, 2008;319(5864):810-3. doi: 10.1126/science.1153529. Epub Jan. 3, 2008.

Iinuma et al., Polyhedra self-assembled from DNA tripods and characterized with 3D DNA-Paint. Science. Apr. 4, 2014;344(6179):65-9. doi: 10.1126/science.1250944. Epub Mar. 13, 2014.

Jungmann et al., Multiplexed 3D cellular super-resolution imaging with DNA-Paint and Exchange-Paint. Nat Methods. Mar. 2014;11(3):313-8. doi: 10.1038/nmeth.2835. Epub Feb. 2, 2014.

Jungmann et al., Single-molecule kinetics and super-resolution microscopy by fluorescence imaging of transient binding on DNA origami. Nano Lett. Nov. 10, 2010;10(11):4756-61. doi:10.1021/nl103427w.

Kao et al., Tracking of single fluorescent particles in three dimensions: use of cylindrical optics to encode particle position. Biophys J. Sep. 1994;67(3):1291-300.

Ke et al., Multilayer DNA origami packed on a square lattice. J Am Chem Soc. Nov. 4, 2009;131(43):15903-8. doi:10.1021/ja906381y.

Ke et al., Multilayer DNA origami packed on hexagonal and hybrid lattices. J Am Chem Soc. Jan. 25, 2012;134(3):1770-4. doi:10.1021/ja209719k. Epub Jan. 13, 2012.

Ke et al., Scaffolded DNA origami of a DNA tetrahedron molecular container. Nano Lett. Jun. 2009;9(6):2445-7. doi:10.1021/nl901165f.

Ke et al., Three-dimensional structures self-assembled from DNA bricks. Science. Nov. 30, 2012;338(6111):1177-83. doi: 10.1126/science.1227268.

Ke, Designer three-dimensional DNA architectures. Curr Opin Struct Biol. Aug. 2014;27:122-8. doi: 10.1016/j.sbi.2014.07.010. Epub Aug. 11, 2014.

Killops et al., Robust, efficient, and orthogonal synthesis of dendrimers via thiol-ene "click" chemistry. J Am Chem Soc. Apr. 16, 2008;130(15):5062-4. doi: 10.1021/ja8006325. Epub Mar. 20, 2008.

Kuzuya et al., DNA origami: fold, stick, and beyond. Nanoscale. Mar. 2010;2(3):310-22. doi: 10.1039/b9nr00246d. Epub Nov. 24, 2009.

Kuzuya et al., Six-helix and eight-helix DNA nanotubes assembled from half-tubes. Nano Lett. Jun. 2007;7(6):1757-63. Epub May 15, 2007.

Kuzyk et al., DNA-based self-assembly of chiral plasmonic nanostructures with tailored optical response. Nature. Mar. 14, 2012;483(7389):311-4. doi:10.1038/nature10889.

Langecker et al., Synthetic lipid membrane channels formed by designed DNA nanostructures. Science. Nov. 16, 2012;338(6109):932-6. doi: 10.1126/science.1225624.

Le et al., DNA-Templated Self-Assembly of Metallic Nanocomponent Arrays on a Surface. Nano Lett. 2004;4(12):2343-7.

Leontis et al., Self-assembled RNA nanostructures. Science. Aug. 15, 2014;345(6198):732-3. doi:10.1126/science.1257989.

Li et al., Nucleic acid-based nanoengineering: novel structures for biomedical applications. Interface Focus. Oct. 6, 2011;1(5):702-24. doi: 10.1098/rsfs.2011.0040. Epub Jun. 28, 2011.

(56) References Cited

OTHER PUBLICATIONS

Li et al., Single-chain antibodies against DNA aptamers for use as adapter molecules on DNA tile arrays in nanoscale materials organization. Org Biomol Chem. Sep. 21, 2006;4(18):3420-6. Epub Jul. 28, 2006.

Liedl et al., Self-assembly of three-dimensional prestressed tensegrity structures from DNA. Nat Nanotechnol. Jul. 2010;5(7):520-4. doi: 10.1038/nnano 2010.107. Epub Jun. 20, 2010.

Lin et al., DNA tile based self-assembly: building complex nanoarchitectures. Chemphyschem. Aug. 11, 2006;7(8):1641-7.

Lin et al., Mirror image DNA nanostructures for chiral supramolecular assemblies. Nano Lett. Jan. 2009;9(1):433-6. doi:10.1021/nl803328v.

Lin et al., Submicrometre geometrically encoded fluorescent barcodes self-assembled from DNA. Nat Chem. 2012;4:832-9.

Linko et al., The enabled state of DNA nanotechnology. Curr Opin Biotechnol. Aug. 2013;24(4):555-61. doi: 10.1016/j.copbio.2013.02.001. Epub Apr. 6, 2013.

Liu et al., Approaching the limit: can one DNA oligonucleotide assemble into large nanostructures? Angew Chem Int Ed Engl. Mar. 13, 2006;45(12):1942-5.

Liu et al., Crystalline two-dimensional DNA-origami arrays. Angew Chem Int Ed Engl. Jan. 3, 2011;50(1):278-81. doi:10.1002/anie.201005911.

Liu et al., DNA nanotubes self-assembled from triple-crossover tiles as templates for conductive nanowires. Proc Natl Acad Sci U S A. Jan. 20, 2004;101(3):717-22. Epub Jan. 6, 2004.

Liu et al., Tensegrity: construction of rigid DNA triangles with flexible four-arm DNA junctions. J Am Chem Soc. Mar. 3, 2004;126(8):2324-5.

Liu et al., Three-dimensional plasmon rulers. Science. Jun. 17, 2011;332(6036):1407-10. doi:10.1126/science.1199958.

Mathieu et al., Six-helix bundles designed from DNA. Nano Lett. Apr. 2005;5(4):661-5.

Melosh et al., Ultrahigh-density nanowire lattices and circuits. Science. Apr. 4, 2003;300(5616):112-5. Epub Mar. 13, 2003.

Mitchell et al., Self-assembly of chiral DNA nanotubes. J Am Chem Soc. Dec. 22, 2004;126(50):16342-3.

Nie et al., Self-assembly of DNA nanoprisms with only two component strands. Chem Commun (Camb). Apr. 7, 2013;49(27):2807-9. doi:10.1039/c3cc39177a.

O'Neill et al., Sturdier DNA nanotubes via ligation. Nano Lett. Jul. 2006;6(7):1379-83.

Park et al., Finite-size, fully addressable DNA tile lattices formed by hierarchical assembly procedures. Angew Chem Int Ed Engl. Jan. 23, 2006;45(5):735-9. Erratum in: Angew Chem Int Ed Engl. Oct. 13, 2006;45(40):6607.

Park et al., Programmable DNA self-assemblies for nanoscale organization of ligands and proteins. Nano Lett. Apr. 2005;5(4):729-33.

Park et al., Three-helix bundle DNA tiles self-assemble into 2D lattice or 1D templates for silver nanowires. Nano Lett. Apr. 2005;5(4):693-6.

PIELES et al., Psoralen covalently linked to oligodeoxyribonucleotides: synthesis, sequence specific recognition of DNA and photo-cross-linking to pyrimidine residues of DNA. Nucleic Acids Res. Jan. 11, 1989;17(1):285-99.

Qi et al., A three-dimensional optical photonic crystal with designed point defects. Nature. Jun. 3, 2004;429(6991):538-42.

Qian et al., Scaling up digital circuit computation with DNA strand displacement cascades. Science. Jun. 3, 2011;332(6034):1196-201. doi:10.1126/science.1200520.

Rajendran et al., Photo-cross-linking-assisted thermal stability of DNA origami structures and its application for higher-temperature self-assembly. J Am Chem Soc. Sep. 21, 2011;133(37):14488-91. doi:10.1021/ja204546h. Epub Aug. 29, 2011.

Reif et al., Compact error-resilient computational DNA tiling assemblies. Proceeding DNA'04 Proceedings of the 10th international conference on DNA computing. 2004:293-307.

Reif et al., Complexity of graph self-assembly in accretive systems and self-destructible systems. Journal Theoretical Computer Science. 2011;412(17):1592-605.

Rothemund et al., Algorithmic Self-Assembly of DNA Sierpinski Triangles. PLoS Biology. 2004. 2004;2(12):e424. doi:10.1371/journal.pbio.0020424.

Rothemund et al., Design and characterization of programmable DNA nanotubes. J Am Chem Soc. Dec. 22, 2004;126(50):16344-52. Erratum in: J Am Chem Soc. Feb. 20, 2013;135(7):2864.

Rothemund et al., The program-size complexity of self-assembled squares. Extended Abstract. Proceeding STOC '00 Proceedings of the thirty-second annual ACM symposium on Theory of computing. ACM 2000:459-68.

Rothemund, Folding DNA to create nanoscale shapes and patterns. Nature. Mar. 16, 2006;440(7082):297-302.

Sahu et al., A self-assembly model of time-dependent glue strength. DNA'05 Proceedings of the 11th international conference on DNA Computing. 2005:290-304.

Schmied et al., DNA origami nanopillars as standards for three-dimensional superresolution microscopy. Nano Lett. Feb. 13, 2013;13(2):781-5. doi: 10.1021/nl304492y. Epub Feb. 5, 2013.

Schulman et al., Synthesis of crystals with a programmable kinetic barrier to nucleation. Proc Natl Acad Sci U S A. Sep. 25, 2007;104(39):15236-41. Epub Sep. 19, 2007.

Schweller et al., Multiplexed in situ immunofluorescence using dynamic DNA complexes. Angew Chem Int Ed Engl. Sep. 10, 2012;51(37):9292-6. doi: 10.1002/anie.201204304. Epub Aug. 15, 2012.

Seelig et al., Enzyme-free nucleic acid logic circuits. Science. Dec. 8, 2006;314(5805):1585-8.

Seeman et al., Nucleic acid nanostructures: Bottom-up control of geometry on the nanoscale. Rep. Prog. Phys, 2005, 68: 237-70.

Seeman, De novo design of sequences for nucleic acid structural engineering. J Biomol Struct Dyn. Dec. 1990;8(3):573-81.

Seeman, DNA in a material world. Nature. Jan. 23, 2003;421(6921):427-31.

Seeman, Nanomaterials based on DNA. Annu Rev Biochem. 2010;79:65-87. doi:10.1146/annurev-biochem-060308-102244.

Seeman, Nucleic acid junctions and lattices. J Theor Biol. Nov. 21, 1982;99(2):237-47.

Sekulić et al., A direct linkage between the phosphoinositide 3-kinase-AKT signaling pathway and the mammalian target of rapamycin in mitogen-stimulated and transformed cells. Cancer Res. Jul. 1, 2000;60(13):3504-13.

Sharma et al., Control of self-assembly of DNA tubules through integration of gold nanoparticles. Science. Jan. 2, 2009;323(5910):112-6. doi: 10.1126/science.1165831.

Sharma et al., DNA-tile-directed self-assembly of quantum dots into two-dimensional nanopatterns. Angew Chem Int Ed Engl. 2008;47(28):5157-9. doi:10.1002/anie.200801485.

Sharma et al., Toward reliable gold nanoparticle patterning on self-assembled DNA nanoscaffold. J Am Chem Soc. Jun. 25, 2008;130(25):7820-1. doi: 10.1021/ja802853r. Epub May 30, 2008.

Sharonov et al., Wide-field subdiffraction imaging by accumulated binding of diffusing probes. Proc Natl Acad Sci U S A. Dec. 12, 2006;103(50):18911-6. Epub Dec. 1, 2006.

Sherman et al., A Precisely Controlled DNA Biped Walking Device. Nano Letters. 2004;4(7):1203-7.

Shih et al., A 1.7-kilobase single-stranded DNA that folds into a nanoscale octahedron. Nature. Feb. 12, 2004;427(6975):618-21.

Shih et al., Knitting complex weaves with DNA origami. Curr Opin Struct Biol. Jun. 2010;20(3):276-82. doi: 10.1016/j.sbi.2010.03.009. Epub Apr. 22, 2010.

Shtengel et al., Interferometric fluorescent super-resolution microscopy resolves 3D cellular ultrastructure. Proc Natl Acad Sci U S A. Mar. 3, 2009;106(9):3125-30. doi:10.1073/pnas.0813131106. Epub Feb. 6, 2009.

Smith et al., A structurally variable hinged tetrahedron framework from DNA origami. J Nucleic Acids. 2011;2011:360954. doi: 10.4061/2011/360954. Epub Sep. 18, 2011.

Tang et al., Evolution of block copolymer lithography to highly ordered square arrays. Science. Oct. 17, 2008;322(5900):429-32. doi: 10.1126/science.1162950. Epub Sep. 25, 2008.

(56) References Cited

OTHER PUBLICATIONS

Tavakkoli et al., Templating three-dimensional self-assembled structures in bilayer block copolymer films. Science. Jun. 8, 2012;336(6086):1294-8. doi: 10.1126/science.1218437.
Tørring et al., DNA rigami: A quantum leap fr self-assembly f cmplex structures. Chem Sc Rev. Dec. 2011;40(12):5636-46. di: 10.1039/c1cs15057j. Epub May 19, 2011.
Venkataraman et al., Selective cell death mediated by small conditional RNAs. Proc Natl Acad Sci U S A. Sep. 28, 2010;107(39):16777-82. doi: 10.1073/pnas.1006377107. Epub Sep. 7, 2010. Retraction in: Dirks RM, Ueda CT, Pierce NA. Proc Natl Acad Sci U S A. Jan. 2, 2013;110(1):384.
Wei et al., Complex shapes self-assembled from single-stranded DNA tiles. Nature. May 30, 2012;485(7400):623-6. doi: 10.1038/nature11075.
Wei et al., Uniquimer: Software of De Novo DNA Sequence Generation for Dna Self-Assembly—An Introduction and the Related Applications in DNA Self-Assembly. J Comput Theor Nanosci. 2007;4(1):133-41.
Winfree et al., Design and self-assembly of two-dimensional DNA crystals. Nature. Aug. 6, 1998;394(6693):539-44.
Winfree, Algorithmic Self-Assembly of DNA. Doctoral Thesis. California Institute of Technology. Mar. 1998.
Woo et al., Programmable molecular recognition based on the geometry of DNA nanostructures. Nat Chem. Jul. 10, 2011;3(8):620-7. doi: 10.1038/nchem.1070. Erratum in: Nat Chem. Oct. 2011;3(10):829. Nat Chem. 2011;3(8):following 627.
Yan et al., A robust DNA mechanical device controlled by hybridization topology. Nature. Jan. 3, 2002;415(6867):62-5.
Yan et al., Directed nucleation assembly of DNA tile complexes for barcode-patterned lattices. Proc Natl Acad Sci U S A. Jul. 8, 2003;100(14):8103-8. Epub Jun. 23, 2003.
Yan et al., DNA-templated self-assembly of protein arrays and highly conductive nanowires. Science. Sep. 26, 2003;301(5641):1882-4.
Yang et al., Artificially expanded genetic information system: a new base pair with an alternative hydrogen bonding pattern. Nucleic Acids Res. 2006;34(21):6095-101. Epub Oct. 29, 2006.
Yang et al., Metal-nucleic acid cages. Nat Chem. Aug. 2009;1(5):390-6. doi: 10.1038/nchem.290.
Yevdokimov et al., Nanoconstructions based on double-stranded nucleic acids. Int J Biol Macromol. Jul. 2005;36(1-2):103-15.
Yin et al., A unidirectional DNA walker that moves autonomously along a track. Angew Chem Int Ed Engl. Sep. 20, 2004;43(37):4906-11.
Yin et al., Designs of autonomous unidirectional walking DNA devices. Proceeding DNA'04 Proceedings of the 10th international conference on DNA computing. 2004:410-25.
Yin et al., Programming biomolecular self-assembly pathways. Nature. Jan. 17, 2008;451(7176):318-22. doi: 10.1038/nature06451.
Yin et al., Programming DNA tube circumferences. Science. Aug. 8, 2008;321(5890):824-6.
Yin et al., Theoretical and practical advances in genome halving. Bioinformatics. Apr. 1, 2005;21(7):869-79. Epub Oct. 28, 2004.
Yurke et al., A DNA-fueled molecular machine made of DNA. Nature. Aug. 10, 2000;406(6796):605-8.
Zhang et al., Conformational flexibility facilitates self-assembly of complex DNA nanostructures. Proc Natl Acad Sci U S A. Aug. 5, 2008;105(31):10665-9. doi:10.1073/pnas.0803841105. Epub Jul. 30, 2008.
Zhang et al., Construction of a DNA-Truncated Octahedron. J Am Chem Soc 1994;116(5):1661-9.
Zhang et al., Symmetry controls the face geometry of DNA polyhedra. J Am Chem Soc. Feb. 4, 2009;131(4):1413-5. doi:10.1021/ja809666h.
Zhao et al., Organizing DNA origami tiles into larger structures using preformed scaffold frames. Nano Lett. Jul. 13, 2011;11(7):2997-3002. doi:10.1021/nl201603a. Epub Jun. 23, 2011.
Zheng et al., From molecular to macroscopic via the rational design of a self-assembled 3D DNA crystal. Nature. Sep. 3, 2009;461(7260):74-7. doi:10.1038/nature08274.
Zimmermann et al., Self-assembly of a DNA dodecahedron from 20 trisoligonucleotides with C(3h) linkers. Angew Chem Int Ed Engl. 2008;47(19):3626-30. doi: 10.1002/anie.200702682.
Alexander et al., On Types of Knotted Curves. Annals of Mathematics 1926-1927, 28(¼): 562-586.
Alexander, Topical Invariants of Knots and Links. Transations of the American Mathematical Society 1928, 30(2): 275-306.
Anthony, MIT and Harvard engineers create graphene electronics with DNA based lithography. Extremetech.com. Apr. 10, 2013. http://www.extremetech.com/computing/153046-mit-and-harvard-engineers-create-graphene-electronics-with-dna-based-lithography.
Bertrand et al., Flexibility of the B-DNA backbone: effects of local and neighbouring sequences on pyrimidine-purine steps. Nucleic Acids Res. Mar. 1, 1998;26(5):1261-7.
Cataldo et al., DNA degradation with ozone. Int J Biol Macromol. May 30, 2006;38(3-5):248-54. Epub Apr. 17, 2006.
Dimitrakakis et al., Top-down patterning of zeolitic imidazolate framework composite thin films by deep X-ray lithography. Chem Commun (Camb). Aug. 4, 2012;48(60):7483-5. doi: 10.1039/c2cc33292b. Epub Jun. 22, 2012.
Fratini et al., Reversible bending and helix geometry in a B-DNA dodecamer: CGCGAATTBrCGCG. J Biol Chem. Dec. 25, 1982;257(24):14686-707.
Han et al., Unidirectional scaffold-strand arrangement in DNA origami. Angew Chem Int Ed Engl. Aug. 19, 2013;52(34):9031-4. doi: 10.1002/anie.201302177. Epub Jul. 14, 2013.
Horiya et al., RNA LEGO: magnesium-dependent formation of specific RNA assemblies through kissing interactions. Chem Biol. Jul. 2003;10(7):645-54.
Jin et al., Metallized DNA nanolithography for encoding and transferring spatial information for graphene patterning. Nat Commun. 2013;4:1663. doi: 10.1038/ncomms2690.
Jones et al., Nanomaterials. Programmable materials and the nature of the DNA bond. Science. Feb. 20, 2015;347(6224):1260901. doi:10.1126/science.1260901.
Jungmann et al., DNA origami-based nanoribbons: assembly, length distribution, and twist. Nanotechnology. Jul. 8, 2011;22(27):275301. doi: 10.1088/0957-4484/22/27/275301. Epub May 20, 2011.
Ke et al., A study of DNA tube formation mechanisms using 4-, 8-, and 12-helix DNA nanostructures. J Am Chem Soc. Apr. 5, 2006;128(13):4414-21.
Ke et al., DNA brick crystals with prescribed depths. Nat Chem. Nov. 2014;6(11):994-1002. doi: 10.1038/nchem.2083. Epub Oct. 19, 2014.
Lee et al., Rate and molecular spectrum of spontaneous mutations in the bacterium *Escherichia coli* as determined by whole-genome sequencing. Proc Natl Acad Sci U S A. Oct. 9, 2012;109(41):E2774-83. doi: 10.1073/pnas.1210309109. Epub Sep. 18, 2012.
Li et al., A replicable tetrahedral nanostructure self-assembled from a single DNA strand. J Am Chem Soc. Sep. 16, 2009;131(36):13093-8. doi: 10.1021/ja903768f.
Lin et al., In vivo cloning of artificial DNA nanostructures. Proc Natl Acad Sci U S A. Nov. 18, 2008;105(46):17626-31. doi: 10.1073/pnas.0805416105. Epub Oct. 16, 2008.
Ma et al., Biotemplated nanostructures: directed assembly of electronic and optical materials using nanoscale complementarity. Journal of Materials Chemistry. 2008;18(9):954-64.
Mansfield, Are there knots in proteins? Nat Struct Biol. Apr. 1994;1(4):213-4.
Mao et al, Designed Two-Dimensional DNA Holliday Junction Arrays Visualized by Atomic Force Microscopy. J. Am. Chem. Soc., 1999, 121 (23), pp. 5437-5443.
Marchi et al, Toward larger DNA origami. Nano Lett. Oct. 8, 2014;14(10):5740-7. doi: 10.1021/nl502626s. Epub Sep. 8, 2014.
Matsui et al., Focused ion beam applications to solid state devices. Nanotechnology 1996, 7(3):247.
Monson et al., DNA-Templated Constructed of Copper Nanowires. Nano Letters. 2003;3(2):359-63. Epub Feb. 14, 2003.
Petty et al., DNA-templated Ag nanocluster formation. J Am Chem Soc. Apr. 28, 2004;126(16):5207-12.

(56) References Cited

OTHER PUBLICATIONS

Piner et al,. "Dip-Pen" nanolithography. Science. Jan. 29, 1999;283(5402):661-3.

Pinheiro et al., Challenges and opportunities for structural DNA nanotechnology. Nat Nanotechnol. Nov. 6, 2011;6(12):763-72. doi:10.1038/nnano.2011.187.

Rajesh et al,. Carbon Nanotubes Generated from Template Carbonization of Polyphenyl Acetylene as the Support for Electrooxidation of Methanol. J. Phys. Chem. B, 2003, 107 (12), pp. 2701-2708.

Randolph et al., Focused, Nanoscale Electron-Beam-Induced Deposition and Etching. Critical Reviews in Solid State and Material Sciences, 2006, 31(3):55-89.

Ravanat et al., Direct and indirect effects of UV radiation on DNA and its components. J Photochem Photobiol B. Oct. 2001;63(1-3):88-102.

Scheible et al., A Compact DNA Cube with Side Length 10 nm. Small. Oct. 21, 2015;11(39):5200-5. doi: 10.1002/smll.201501370. Epub Aug. 21, 2015.

Seeman et al., The design and engineering of nucleic acid nanoscale assemblies. Curr Opin Struct Biol. Aug. 1996;6(4):519-26.

Surwade et al., Molecular lithography through DNA-mediated etching and masking of SiO2. J Am Chem Soc. Aug. 10, 2011;133(31):11868-71. doi: 10.1021/ja2038886. Epub Jul. 19, 2011.

Surwade et al., Nanoscale growth and patterning of inorganic oxides using DNA nanostructure templates. J Am Chem Soc. May 8, 2013;135(18):6778-81. doi: 10.1021/ja401785h. Epub Apr. 25, 2013.

Takusagawa et al., A Real Knot in Protein. J. Am. Chem. Soc., 1996, 118 (37), pp. 8945-8946.

Taylor, A deeply knotted protein structure and how it might fold. Nature. Aug. 24, 2000;406(6798):916-9.

Wagner et al., A light-sensing knot revealed by the structure of the chromophore-binding domain of phytochrome. Nature. Nov. 17, 2005;438(7066):325-31.

Williams et al,. Tiamat: A Three-Dimensional Editing Tool for Complex DNA Structures. DNA Computing 2009, 90-101.

Winters et al., Surface science aspects of etching reactions. Surface Science Reports. 1992, 14(4-6): 162-269.

Wu et al., High aspect ratio silicon etch: A review. Journal of Applied Physics, 2010, 108(5): 051101-051101-20.

Xiao et al., Selfassembly of Metallic Nanoparticle Arrays by DNA Scaffolding. Journal of Nanoparticle Research. Aug. 1, 2002;4:313-7.

Yang et al., DNA Origami with Double-Stranded DNA as a Unified Scaffold. ACS Nano, 2012, 6(9): 8209-8215.

Zhang et al., Structural DNA nanotechnology: state of the art and future perspective. J Am Chem Soc. Aug. 13, 2014;136(32):11198-211. doi:10.1021/ja505101a. Epub Jul. 28, 2014.

U.S. Appl. No. 14/440,907, filed May 6, 2015, Published, 2015-0329584[1].

U.S. Appl. No. 15/312,854, filed Nov. 21, 2016, Pending.

U.S. Appl. No. 15/124,066, filed Sep. 7, 2016, Pending.

PCT/US2015/032198, Dec. 11, 2015, International Search Report and Written Opinion.

PCT/US2015/032198, Dec. 1, 2016, International Preliminary Report on Patentability.

PCT/US2015/019135, Sep. 22, 2016, International Preliminary Report on Patentability.

PCT/US2016/020893, May 31, 2016, International Search Report and Written Opinion.

\* cited by examiner

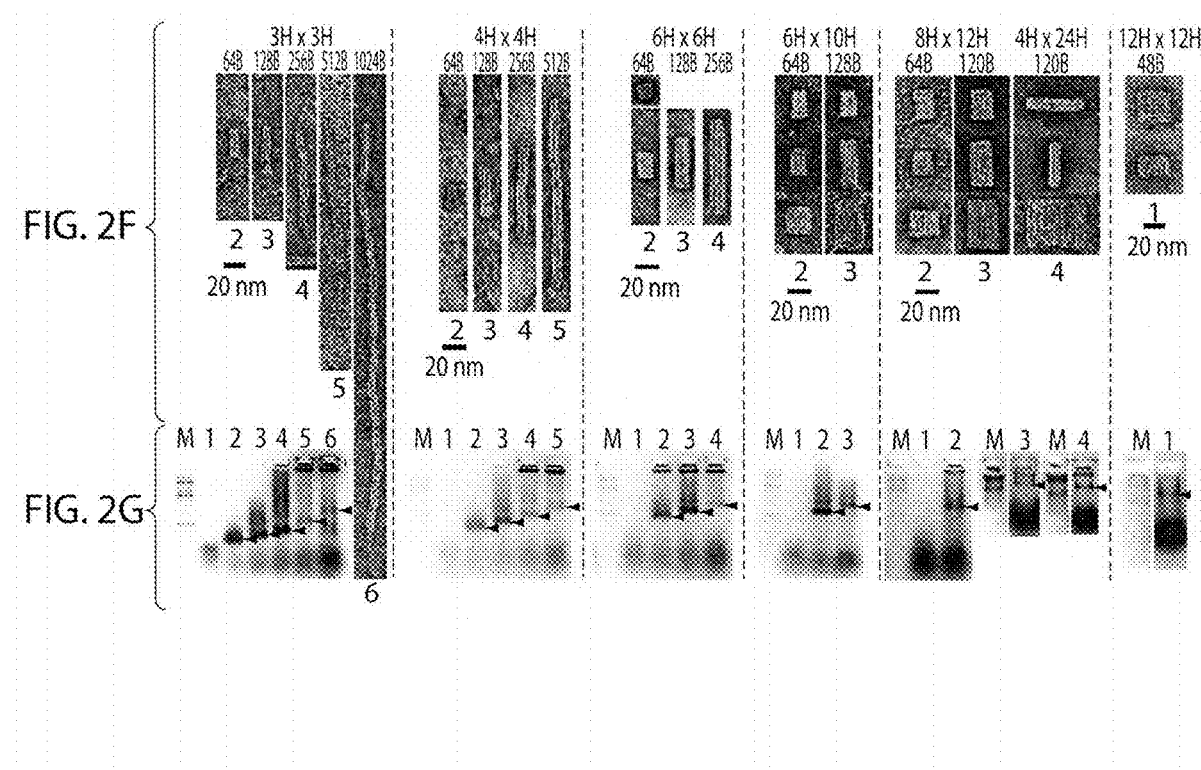

Single-stranded DNA building brick

To: FIG. 6B

From: FIG. 6A

To: FIG. 6C

From: FIG. 6B

Diamond-lattice

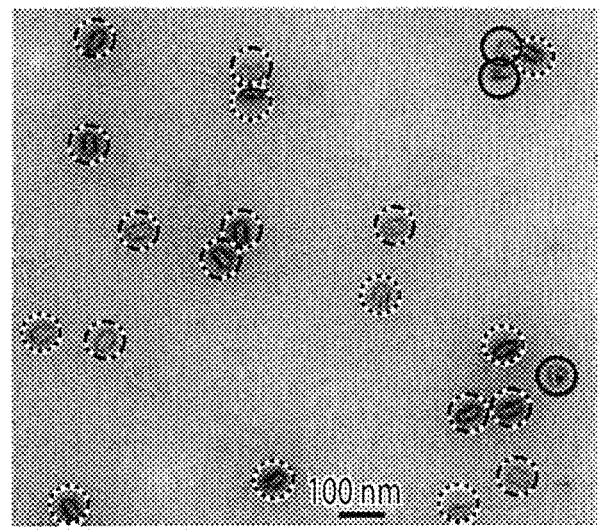
FIG. 12A
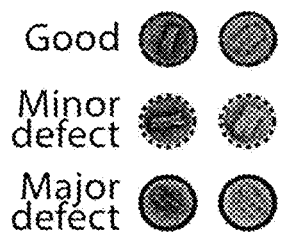
FIG. 12B
| Sample | Good | Ok | Bad | Yield (%) |
|---|---|---|---|---|
| 6Hx10Hx128B | 109 | 44 | 47 | 54.5 |
FIG. 12C Modified design = 8bp voxel = 8 bases Random Sequences

= TTTTTTTT

Four voxels

Three voxels

SELF-ASSEMBLY OF NUCLEIC ACID NANOSTRUCTURES

RELATED APPLICATIONS

This application is a national stage filing under 35 U.S.C. § 371 of international application number PCT/US2013/051891, filed Jul. 24, 2013, which claims the benefit under 35 U.S.C. § 119(e) of U.S. provisional application No. 61/675,309, filed Jul. 24, 2012, and U.S. provisional application No. 61/773,715, filed Mar. 6, 2013, each of which is incorporated by reference herein in its entirety.

GOVERNMENT SUPPORT

This invention was made with government support under OD004641 and OD007292 awarded by National Institutes of Health, under N000014-09-1-1118, N00014-10-1-0827, W911NF-12-1-0420, W911NF-12-1-0238, and N00014-11-1-0914 awarded by U.S. Department of Defense, and under 1054898 awarded by the National Science Foundation. The government has certain rights in the invention.

FIELD OF THE INVENTION

Aspects and embodiments of the invention relate to the field of nucleic acid nanotechnology.

BACKGROUND OF INVENTION

Self-assembly of informational polymers such as nucleic acids (e.g., DNA and RNA) provides an effective approach for constructing sophisticated synthetic molecular nanostructures and devices (N. C. Seeman, Nature 421, 427 (2003)). The fundamental principle for designing self-assembled nucleic acid nanostructures is that sequence complementarity in nucleic acid strands is encoded such that, by pairing up complementary segments, the nucleic acid strands self-organize into a predefined nanostructure under appropriate physical conditions. From this basic principle (N. C. Seeman, J. Theor. Biol. 99, 237 (1982)), researchers have created diverse synthetic nucleic acid nanostructures (N. C. Seeman (2003); W. M. Shih, C. Lin, Curr. Opin. Struct. Biol. 20, 276 (2010)) such as lattices (E. Winfree, et al. Nature 394, 539 (1998); H. Yan, et al. Science 301, 1882 (2003); H. Yan, et al. Proc. Natl. Acad. of Sci. USA 100, 8103 (2003); D. Liu, et al. J. Am. Chem. Soc. 126, 2324 (2004); P. W. K. Rothemund, et al. PLoS Biology 2, 2041 (2004)), ribbons (S. H. Park, et al. Nano Lett. 5, 729 (2005); P. Yin, et al. Science 321, 824 (2008)), tubes (H. Yan Science (2003); P. Yin (2008)), finite two-dimensional (2D) and three dimensional (3D) objects with defined shapes (J. Chen, N. C. Seeman, Nature 350, 631 (1991); P. W. K. Rothemund, Nature 440, 297 (2006); Y. He, et al. Nature 452, 198 (2008); Y. Ke, et al. Nano. Lett. 9, 2445 (2009); S. M. Douglas, et al. Nature 459, 414 (2009); H. Dietz, et al. Science 325, 725 (2009); E. S. Andersen, et al. Nature 459, 73 (2009); T. Liedl, et al. Nature Nanotech. 5, 520 (2010); D. Han, et al. Science 332, 342 (2011)), and macroscopic crystals (J. P. Meng, et al. Nature 461, 74 (2009)). Many dynamic devices have been constructed in parallel (J. Bath, A. J. Turberfield Nature Nanotech. 2, 275 (2007)), including tweezers (B. Yurke, et al. Nature 406, 605 (2000)), switches (H. Yan, et al. Nature 415, 62 (2002)), walkers, (W. B. Sherman, N. C. Seeman, Nano Letters 4, 1203 (2004); P. Yin, et al. Nature 451, 318 (2008); T. Omabegho, et al. Science 324, 67 (2009)) and circuits (P. Yin (2008); G. Seelig, et al. Science 314, 1585 (2006); L. Qian, E. Winfree, Science 332, 1196 (2011)). Additionally, as DNA and RNA can be interfaced with other functional molecules in a technologically relevant way, synthetic nucleic acid nanostructures promise diverse applications. Researchers are using synthetic DNA/RNA nanostructures and devices to direct functional material arrangements (E A. Aldaye, et al. Science 321, 1795 (2008)), to develop bioimaging probes (H. M. T. Choi, et al. Nature Biotechnol. 28, 1208 (2010)), to organize and regulate molecular pathways in living cells (S. Venkataraman, et al. Proc. Natl Acad. Sci. USA 107, 16777 (2010); C. J. Delebecque, et al. Science 333, 470 (2011)), and to facilitate nuclear magnetic resonance (NMR) protein nanostructure determination (M. J. Berardi, et al. Nature 476, 109 (2011)).

An effective method for assembling megadalton nanoscale 2D (P. W. K. Rothemund (2006)) and 3D shapes (S. M. Douglas (2009); E. S. Andersen (2009); D. Han (2011)) is DNA origami, in which a long "scaffold" strand is folded to a predesigned shape via interactions with short "staple" strands. The requirement of a long scaffold-strand component (often viral genomic DNA) has limited the sequence and material choices of DNA origami nanostructures. Furthermore, each shape typically requires a new scaffold routing and therefore a completely different set of staple strands.

SUMMARY OF INVENTION

The present invention generally provides methods for self-assembly of nucleic acid structures of known, predetermined and thus controlled size, shape and complexity, as well as the nucleic acid structures themselves. More specifically, in various aspects, the invention provides modular methods for producing complex nucleic acid structures using a subset of defined and predetermined oligonucleotides without the need for a longer scaffold strand that is essential in a DNA origami approach. The nucleic acid structures of the invention self-assemble in a sequence-specific manner through local interactions, typically in a one-step annealing reaction. The nucleic acid structures, and the single-stranded oligonucleotides that are used to produce such structures, are designed so that the oligonucleotide and therefore the nucleotide sequence at each location in the structure is known. The knowledge facilitates modification of the structure in a defined and controlled manner.

The invention provides, in part, methods for making three-dimensional (3D) nucleic acid structures of arbitrary, predefined shape and size using as a theoretical starting point a 3D canvas of desired height, depth and width made up of known oligonucleotides at known positions. By selecting only a subset of the oligonucleotides that make up the entire canvas, an end user can generate a nucleic acid structure of virtually any size, shape and complexity.

The oligonucleotides that form a nucleic acid structure are typically comprised of domains. Typically, domains in one oligonucleotide hybridize to domains in other oligonucleotides. Some oligonucleotides are 4-domain oligonucleotides and each domain hybridizes to a domain in separate oligonucleotides. A duplex is formed by hybridization of complementary domains, each domain located on one neighboring oligonucleotide (one domain on one oligonucleotide binds to another domain in another nearby oligonucleotide). Typically, an approximately 90° dihedral angle is formed by hybridization of complementary domains, each domain located on physically separate oligonucleotides. Nucleic acid structures of the invention are comprised of nucleic acid duplexes (i.e., a pair of hybridized or partially hybridized oligonucleotides), with adjacent duplexes connected by a single phosphate bond (i.e., crossover). Typically, a plurality of single-stranded oligonucleotides anneals to form adjacent duplexes. In some instances, during self-assembly, a 4-domain oligonucleotide adopts a helical conformation such that two (of the four) domains reside in one duplex and the remaining two domains reside in an adjacent duplex.

The invention also provides the single-stranded oligonucleotides used to generate the nucleic acid structures. Different pluralities of single-stranded oligonucleotides are provided, with the nature and composition of those pluralities depending on the design, including shape, size and complexity, of the desired structure. As explained in greater detail herein, these pluralities typically comprise 2-domain or 4-domain oligonucleotides (though, they may contain 3 domains or more than 4 domains). In some instances, the domains are of equal nucleotide length (e.g., 8 nt length). Each domain of an oligonucleotide may unique (i.e., it may have a nucleotide sequence that is present only once per oligonucleotide, or present only once per nucleic acid structure), or only one, two or three or more domains in an oligonucleotide may be unique. Each single-stranded oligonucleotide in a nucleic acid structure may be unique (i.e., it may be present only once per structure), or it may be present once, twice, three times, or even more frequently. It is to be understood that an oligonucleotide may be unique within the structure even if one or more of its domains is not.

The single-stranded oligonucleotides and the nucleic acid structures of the invention are modular in nature. The methods of the invention allow for variously shaped nucleic acid structures to be made by inclusion, exclusion and/or modification (including replacement) of a subset of known oligonucleotides. The methods described herein contemplate modular assembly of nucleic acid structures to each other, for example by annealing such structures to each other based on sequence specificity. In some of these embodiments, the nucleic acid structures that are annealed to each other may share a common shape (e.g., both may be cubes or abstract shapes). The methods also contemplate composite nucleic acid structures made by linking two or more nucleic acid structures to each other using linkers that may or may not be integral to the nucleic acid structure. In these embodiments, nucleic acid structures that are linked to each other may be of the same or of different shape.

Methods of synthesis of nucleic acid structures are also contemplated herein. Synthesis methods may comprise combining a plurality of known single-stranded oligonucleotides in a single vessel and allowing the oligonucleotides to self-assemble, in a predetermined manner, under suitable conditions. Similarly, two or more nucleic acid structures may be combined in a single vessel and allowed to self-assemble based on nucleotide sequence complementarity in a predetermined manner, under suitable conditions, thereby forming a larger nucleic acid structure.

Thus, in one aspect, the invention provides a nucleic acid structure comprising two single-stranded oligonucleotides, each comprising at least four domains arranged to form an approximately 90° dihedral angle by hybridization of two complementary domains, one in each of the oligonucleotides.

In some embodiments, the structure comprises five single-stranded oligonucleotides, each comprising at least four domains, wherein four of the single-stranded oligonucleotides are hybridized to separate domains of the fifth single stranded oligonucleotide, thereby forming an approximately 90° dihedral angle between each pair of hybridized oligonucleotides.

In some embodiments, the at least four domains are of equal nucleotide length. In some embodiments, each oligonucleotide comprises two or more unique domains. In some embodiments, at least one domain comprises a poly-thymine (T) oligonucleotide. In some embodiments, at least two domains comprise a poly-thymine(T) oligonucleotide. In some embodiments, each domain is 8 nucleotides in length. In some embodiments, the nucleic acid structure further comprises single-stranded 2-domain oligonucleotides.

In some embodiments, the oligonucleotides are DNA oligonucleotides. In some embodiments, the oligonucleotides are L-DNA oligonucleotides. In some embodiments, the oligonucleotides are crosslinked.

In some embodiments, the structure comprises 100, 500, or 1000 single stranded oligonucleotides. In some embodiments, all of the single stranded oligonucleotides are unique in sequence. In some embodiments, all of the domains are unique in sequence. In some embodiments, all of the domains except for poly-T domains are unique in sequence. In another aspect, the invention provides a plurality of any of the foregoing nucleic acid structures. In some embodiments, the nucleic acid structures are hybridized to form a 3D structure. In some embodiments, the 3D structure is defined by a "x" helices in the x direction, "y" helices in the y direction, and "z" bases (or base pairs) in the z direction. In some embodiments, the 3D structure is a cuboid structure, a cylindrical structure, a sheet, a honeycomb structure, or a hexagonal lattice structure. In some embodiments, the 3D structure is a Z-crystal, a ZX-crystal, a Y-crystal, an X-crystal or an XY-crystal.

In some embodiments, each single-stranded oligonucleotide in the plurality of structure is unique.

In another aspect, the invention provides a composition comprising the plurality of any of the foregoing nucleic acid structures.

In another aspect, the invention provides a method comprising annealing in a vessel a plurality of unique single-stranded oligonucleotides, each comprising at least four domains arranged to form an approximately 90° dihedral angle by hybridization of two complementary domains, each in a physically separate oligonucleotide. In some embodiments, the plurality of single-stranded oligonucleotides comprises 4-domain and 2-domain oligonucleotides.

In some embodiments, the single-stranded oligonucleotides are present at approximately equal molar concentrations. In some embodiments, the annealing occurs through a temperature transition over a period of time. In some embodiments, the temperature transition is a change in temperature from an elevated temperature to about room temperature. In some embodiments, the temperature transition is a change in temperature from about 90° C. to about room temperature.

In some embodiments, the annealing occurs over a period of about 12-24 hours. In some embodiments, the oligonucleotides are at least 32 nucleotides in length. In some embodiments, each domain is 8 nucleotides in length.

In some embodiments, the single-stranded oligonucleotides are DNA oligonucleotides. In some embodiments, the single-stranded DNA oligonucleotides are L-DNA oligonucleotides.

In another aspect, the invention provides a method comprising providing a three-dimensional (3D) computer-generated canvas of single-stranded oligonucleotides arranged as $N_x \times N_y \times N_z$ voxels, wherein N is a single 8 bp region comprised of two complementary hybridized domains from separate single stranded oligonucleotides that form an approximately 90° dihedral angle upon said hybridization, X is any number along the x-axis of the 3D canvas, Y is any number along the y-axis of the 3D canvas, and Z is any number along the z-axis of the 3D canvas; removing from the 3D computer-generated canvas one or more voxels to produce a 3D nucleic acid structure of a desired shape and/or size; and identifying a subset of single-stranded oligonucleotides required for assembly of the 3D nucleic acid structure.

In another aspect, the invention provides a composition comprising a first oligonucleotide comprising at least four domains hybridized to a second oligonucleotide, wherein the second oligonucleotide is hybridized at one of the four domains of the first oligonucleotide, thereby forming a 90° dihedral angle between the first and second oligonucleotides.

In some embodiments, a third oligonucleotide is hybridized to the first oligonucleotide at one of the remaining domains of the first oligonucleotide, thereby forming a 90° dihedral angle between the first and third oligonucleotides. In some embodiments, a fourth oligonucleotide is hybridized to the first oligonucleotide at the remaining domain of the first oligonucleotide, thereby forming a 90° dihedral angle between the first and fourth oligonucleotides. In some embodiments, hybridization of two complementary domains, each from physically separate oligonucleotides, results in a double helix. In some embodiments, the second, third and fourth oligonucleotides consist of 2 domains, 3 domains, 4 domains, or more than 4 domains. In some embodiments, the second, third and fourth oligonucleotides are each hybridized to one, two, three or more oligonucleotides, thereby forming 90° dihedral angles between hybridized oligonucleotides.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE FIGURES

It is to be understood that the Figures are not necessarily to scale, emphasis instead being placed upon generally illustrating the various concepts discussed herein.

FIG. 2F shows TEM images of 3D DNA-block nanostructures in FIG. 2E. FIG. 2G shows images of agarose gel electrophoresis for 3D DNA-block nanostructures. For each group of nanostructures, lane M shows a 1 kb ladder; other lanes are labeled with numbers matching their designs in FIG. 2E. Product bands (indicated by gray arrows) were extracted for purification and TEM imaging.

FIG. 5A shows that DNA bricks can be designated as north-bricks, west-bricks, south-bricks, or east-bricks, based on their orientations. Arrows indicate the 3' ends. FIG. 5B shows two bricks that interact via hybridization of two complementary 8 nucleotide domains.

FIG. 6A shows a cylinder model of a 4H×4H×64B cuboid 3D nanostructure (or 4 voxels×4 voxels×8 voxels). Each voxel represents an 8 base pair duplex that is formed by base-pairing of a pair of a X-brick and a Y-brick. FIGS. 6B and 6C show a 3D strand diagram. Each strand has its unique sequence. FIGS. 6D and 6E show helix and strand diagrams in caDNAno format, which is used by our custom programs. FIG. 6D shows an X-Y cross-section looking down the Z- direction. FIG. 6E shows a detailed strand diagram of all strands. The numbers in columns represent the helices. The numbers at the top and bottom indicate the position of the base-pairs along Z-axis. X-bricks are represented by the dark gray lines, and Y-bricks are represented by the light gray lines. Arrows indicate the 3' end of strands. FIG. 6F shows a 3D strand diagram showing all X-bricks and Y-bricks.

FIG. 7A shows a 32 nucleotide DNA brick. FIG. 7B shows another drawing representing the same 32 nt strand. Each 8 nucleotide segment is labeled A, B, C or D. FIG. 7C shows interactions between an X-brick and its four neighboring Y-bricks. Complementarity is indicated by similar colors and associating symbols. For instance, segment A is complementary to segment A*; the two segments are also shown by the matching color. FIG. 7D shows the X-bricks, and its four neighboring Y-bricks are shown in close proximity. FIG. 7E shows a ball-and-stick model showing the connection between an X-brick and its four neighboring Y-bricks. They form a tetrahedron structure, with the X-brick at the center and each of four Y-brick occupying a vertex. FIG. 7F shows the connection pattern of a large group of DNA strands resembles a diamond-lattice.

FIG. 8A shows the 6H×6H×64B structure that was used for this experiment. All samples were self-assembled using 72-hour annealing protocol. FIG. 8B shows an agarose gel assaying self-assembly of a 6H×6H×64B structure with a random sequence design. Lane M shows 1 kb ladder. Lane 1 to lane 6 show 6H×6H×64B self-assembled at 200 nM concentration with 10, 20, 30, 40, 50, 60 mM $MgCl_2$. 20 μL sample is loaded into each lane from 1 to 6. FIG. 8C shows an agarose gel assaying self-assembly of 6H×6H×64B with designed sequence. Lane M shows 1 kb ladder. Lane 1 to lane 6 show 6H×6H×64B self-assembled at 200 nM concentration with 10, 20, 30, 40, 50, 60 mM $MgCl^2$. A 20 μL sample is loaded into each lane from 1 to 6.

FIG. 9A shows a 5H×5H×48B cylinder model of 3D structures. FIG. 9B shows the Y1-layer contains five helices—X1, X2, X3, X4, X5. Only X-bricks in the Y1-layer are shown. Some strands (i, ii, iii, iv) on the boundary form short 16 nucleotide boundary strands. FIG. 9C shows most of these short 16 nucleotide boundary strand can be connected with the 32 nucleotide strand on their left to form 48 nucleotide boundary strands.

FIG. 10A shows a 6H×6H×64B structure that was used to test the 16 nucleotide short boundary strands and 48 nucleotide long boundary strands. The design using 16 nucleotide boundary strands is designated 6H×6H×64B-S. The oligonucleotide sequences used to produce a 6H×6H×64B-S nucleic acid structure of the invention are designated SEQ ID NOs. 1-78, 157-225 and 295-336. (See also Appendix, Table 1 of U.S. provisional application No. 61/675,309, filed Jul. 24, 2012, incorporated by reference herein.) The design using 48 nucleotide boundary strands is designated 6H×6H×64B. The oligonucleotide sequences used to produce a 6H×6H×64B nucleic acid structure of the invention are designated SEQ ID NOs. 79-156 and 226-294. (See also Appendix, Table 1 of U.S. provisional application No. 61/675,309, filed Jul. 24, 2012, incorporated by reference herein.) All samples were self-assembled using a 3-day annealing protocol. FIG. 10B shows an agarose gel assaying the self-assembly of a 6H×6H×64B-S structure. Lane M shows 1 kb ladder. Lane 1 to lane 8 show a 6H×6H×64B-S structure self-assembled at 100 nM concentration with 10, 20, 30, 40, 50, 60, 70, 80 mM $MgCl_2$. Lanes 9 to 16 show a 6H×6H×64B-S structure self-assembled at 200 nM concentration with 10, 20, 30, 40, 50, 60, 70, 80 mM $MgCl_2$. A 20 μL sample was loaded into each lane from 1 to 16. FIG. 10C shows an agarose gel assaying self-assembly of a 6H×6H×64B structure. Lane M shows a 1 kb ladder. Lane 1 to lane 8 show a 6H×6H×64B structure self-assembled at 100 nM concentration with 10, 20, 30, 40, 50, 60, 70, 80 mM MgCl$_2$. Lanes 9 to 16 show a 6H×6H×64B structure self-assembled at 200 nM concentration with 10, 20, 30, 40, 50, 60, 70, 80 mM MgCl$_2$. A 20 μL sample was loaded into each lane from 1 to 16.

FIGS. 12A-12C show yield analysis of agarose gel electrophoresis purified 6H×10H×128B structures based on TEM images. FIG. 12A is a representative TEM image of purified 6H×10H×128B. Particles circled in medium gray are categorized as "good" particles with no visible defect. Particles/structures circled in light gray/white are categorized as "minor defect" particles with minor defects. Particles circles in dark gray are categorized as "major defect" particles that have major defects or are even broken. FIG. 12B shows examples of "good", "minor defect," and "major defect" particles of purified 6H×10H×128B. FIG. 12C Data showing yield with numbers under "good," "minor defect," and "major defect," indicating the number of particles counted.

FIG. 13A shows a cylinder model of a 5H×5H×48B 3D structure. Each voxel is 8 base pairs. FIG. 13B shows the X1-layer of a 5H×5H×48B structure that is designed using the original strategy. Only the Y-bricks in the X1-layer are shown. Notice that the 48 nucleotide boundary strands (FIG. 10) are implemented. Arrows and asterisks (*) point to the positions where the crossover are removed for generating modified version. FIG. 13C shows the X1-layer of a 5H×5H×48B structure using the modified design. Compared to the original design, four crossovers were removed, and the new strands (i, ii, iii, iv, v) were incorporated by merging together the pair of strands located in the same duplex.

FIG. 14A shows an agarose gel assay of 6H×10H×128B-M structures. Lane 1 shows 6H×10H×128B structures as a control sample. Lane 2 shows 6H×10H×128B-M structures. Both samples are annealed at the same condition (200 nm per strand, 0.5×Tris buffer with 40 mM MgCl$_2$, 72-hour annealing ramp). The 6H×10H×128B-M design generates 2.9 times higher yield than 6H×10H×128B. FIG. 14B shows a representative TEM image and TEM yield of purified 6H×10H×128B-M structures. The oligonucleotide sequences used to produce 6H×10H×128B-M nucleic acid structures of the invention are designated SEQ ID NOs. 337-590. (See also Appendix, Table 6 of U.S. provisional application No. 61/675,309, filed Jul. 24, 2012, incorporated by reference herein.)

FIG. 16A depicts symbols used in this Figure. FIG. 16B shows a typical strand with four 8 nucleotide random-sequence domains. Each 8 nucleotide domain is located within a 8 base pair voxel—V1, V2, V3, or V4. V1 and V2 are on the same helix. V3 and V4 are on another adjacent helix. FIGS. 16C to 16F show other types of strand derived from the strand with four 8 nucleotide random-sequence domains. FIG. 16C shows that when one of the four 8 base pair voxel is removed, the 8 nucleotide domain corresponding to that 8 base pair voxel is changed to eight consecutive Ts. FIG. 16D shows that when two of the four 8 base pair voxels are removed, the two 8 nucleotide domains corresponding to those 8 base pair voxels are either changed to eight consecutive Ts, or deleted. The latter case happens if the two removed 8 base pair voxels are from the same helix. FIG. 16E shows that when three of the four 8 base pair voxels are removed, the two 8 nucleotide domains corresponding to the two removed voxels from the same helix are deleted. Another 8 nucleotide domain corresponding to the third removed voxel is changed to eight consecutive Ts. FIG. 16F shows that for each strand shown in B, two types of 48 nucleotide boundary strands are created. FIG. 16G shows that each strand is labeled by the positions of the voxels it covers. Each pair of numbers represents one voxel. The first number indicates the helix and the second number indicate the voxel position on the helix. Numbers (0, 0) means a domain with eight consecutive thymidines (Ts) or an empty domain.

FIG. 18A shows s 10×10×10 voxel 3D canvas. Each sphere represents one voxel. FIG. 18B shows how shape editing is performed by removal of unwanted voxels. FIGS. 18C and 18B show caDNAno files corresponding to the 10×10×10 voxel 3D canvas in FIG. 18A and the shape in FIG. 18B, respectively. The conversion from the 3D depiction to the caDNAno format was done by a custom program.

FIG. 19A shows a cylinder model of 4H×4H×64B-A (alternating design) structures. Each voxel represents 8 base pairs. FIG. 19B shows the details of strands in 4H×4H×64B-A structures. Strands point in alternating directions in along the layers. For instance, Y-bricks in X1-layer and Y-bricks in X2-layer are pointing to opposite directions, −Z and +Z direction, respectively. Accordingly, the directions of each strand is depicted as "Left" (L) or "Right" (R). FIG. 19C shows a 6H×10H×64B-A structure that was used to test the alternating design strategy. FIG. 19D shows results of an agarose gel electrophoresis assay. Lane M shows a 1 kb ladder. Lane 1 shows 6H×10H×64B-A structures. The structures were self-assembled in 0.5×Tris buffer with 40 mM MgCl$_2$, using 72-hour annealing ramp. The concentration of each strand is 200 nM. A distinctive bright band correspond to the product was extracted from the gel. FIG. 19E shows TEM images of the 6H×10H×64B-A structures after agarose gel purification. Scale bar is 100 nM for the zoom-out image and 20 nm for the zoom-in images.

FIG. 20D shows a 1D crystal growing along the Z-axis. FIG. 20E shows a 2D crystal growing along the Z-axis and the X-axis. FIG. 20F shows a 2D crystal growing along the X-axis and the Y-axis. FIG. 20H shows a 1D Z-crystal with a tunnel and periodic cavities. FIG. 20I shows a 2D ZX-crystal with two groups of parallel tunnels. FIG. 20J shows a 2D XY-crystal with periodic cavities. FIG. 20K shows a 3D ZXY-crystal with periodic cavities. Unit cells of crystals are denoted using blue-colored boxes. Arrows indicate the directions of crystal growth.

(FIG. 24A) Top, a 6H×6H×24B cuboid discrete DNA-brick structure. Bottom, the intersection of the 6H×6H×24B cuboid. (FIG. 24B) the detailed strand diagram of the 6H×6H×24B cuboid. The numbers on the left and the right indicate the helices. The numbers on the top and the bottom indicate the position of the base-pairs along the Z-axis. X-bricks are represented with dark gray lines, and Y-bricks are represented with light gray lines. (FIGS. 24C-24D) Connection patterns of one-dimensional-growth: Z-growth (FIG. 24C), X-growth (FIG. 24C), and Y-growth (FIG. 24D). (FIG. 24E) Connection patterns of two-dimensional-growth: ZX-growth and XY-growth. FIG. 24F shows a TEM image of the Z-6H×6H×32B-cuboid crystal.

FIGS. 26A-25H show TEM images of ZX-crystals. (A) ZX-4H×4H×32B-cuboid crystal; (B) ZX-4H×6H×32B-cuboid crystal; (C) ZX-4H×10H×32B-cuboid crystal; (D) ZX-4H×20H×32B-cuboid crystal; (E) ZX-32H×64B-channel crystal; (F) ZX-32H×64B-cross-channel crystal; (G) ZX-6H×6H×64B-pore crystal; and (H) ZX-96H×64B-cross-tunnel crystal.

FIGS. 27A-25I show TEM images of XY-crystals. (A) XY-48H×64B-pore crystal; (B) XY-64H×64B-pore crystal; (C) XY-4H×4H×64B-cuboid crystal; (D) XY-4H×4H×128B-cuboid crystal; (E) XY-4H×4H×192B-cuboid crystal; (F) XY-4H×4H×256B-cuboid crystal; (G) XY-32H×64B-pore crystal; (H) XY-32H×128B-pore crystal; and (I) XY-8H×4H×96B-channel crystal.

Figure 1A:
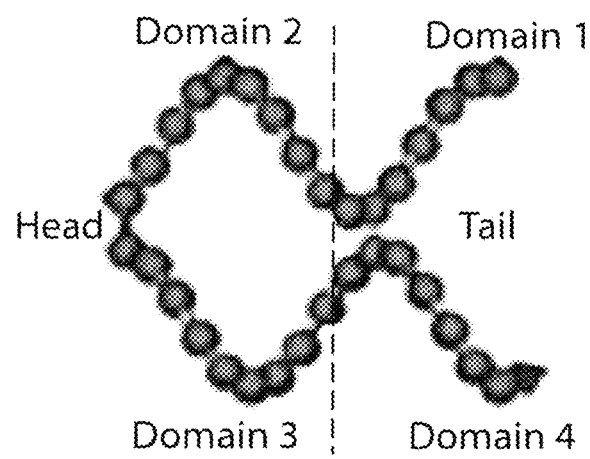
FIG. 1A is a schematic of a 32 nucleotide 4-domain single-stranded DNA oligonucleotide (also referred to herein interchangeably as a DNA "block" or a DNA "brick"). Each domain is 8 nucleotides in length. The connected domain 2 and domain 3 are "head domains"; domain 1 and domain 4 are "tail domains".

The specification further incorporates by reference in its entirety the Sequence Listing submitted herewith as a separate ASCII text file, named "H0498.70443WO00—Sequence Listing," created on Jul. 23, 2013, and having a size of 2.34 MB.

DETAILED DESCRIPTION OF INVENTION

The invention relates, in its broadest sense, to methods of making nucleic acid structures of predetermined, and thus controlled, shape, size and complexity, to the structures so made, and to the oligonucleotide pluralities used in the process. The invention is premised, in part, on the unexpected finding that select pluralities of single-stranded oligonucleotides can be self-assembled to form 3D nucleic acid structures of controlled shape, size, complexity and modification. It was considered surprising, inter alia, that stable 3D nucleic acid structures of various predetermined shapes and controlled sizes could be formed using only a plurality of relatively short single-stranded oligonucleotides (e.g., compared to the scaffold strands required for DNA origami techniques).

More particularly, various aspects of the invention relate to a method, using single-stranded 2- or 4-domain oligonucleotides (also referred to herein as "nucleic acid bricks" or "DNA bricks"), that extends modular self-assembly of nucleic acid nanostructures to three dimensions. The generality of this method was demonstrated by successfully designing and characterizing 123 nanostructures, including two 8 MDa cuboids, 102 intricate three-dimensional (3D) shapes constructed from a common cuboid "3D canvas," and 19 three-dimensional nanostructures assembled from modular nucleic acid motifs that obey alternate packing geometries. Also provided herein in various aspects is a computer program that translates a simple three-dimensional model into the set of nucleic acid strands required to generate the desired corresponding nucleic acid structure.

The nucleic acid structures of the invention comprise a plurality of oligonucleotides arranged (via sequence-specific annealing) into three-dimensional shapes in a predetermined or known manner. As a result, the position of each oligonucleotide in the structure is known. In this way, the structure may be modified, for example, by adding, removing or replacing oligonucleotides at particular positions. The structure may also be modified, for example, by attachment of moieties, at particular positions. This may be accomplished by using a modified oligonucleotide as a starting material or by modifying a particular oligonucleotide after the structure is formed. Therefore, knowing the position of each of the starting oligonucleotides in the resultant structure provides addressability to the structure.

The nucleic acid structures of the invention may be made, in some instances, through a process of self-assembly of single-stranded oligonucleotides. In these self-assembly methods, the single-stranded oligonucleotides are combined in a single vessel and allowed to anneal to each other, based on sequence complementarity. In some instances, this annealing process involves placing the oligonucleotides at an elevated temperature and then reducing the temperature gradually in order to favor sequence-specific binding. As used herein, the term "self-assembly" refers to the ability of oligonucleotides (and in some instances nucleic acid structures) to anneal to each other, in a sequence-specific manner, in a predicted manner and without external control (e.g., by sequential addition of oligonucleotides or nucleic acid structures).

The invention therefore provides, inter alia, compositions comprising the single-stranded oligonucleotides of the invention, methods of making nucleic acid structures of various predetermined or known size, shape, complexity and modification, nucleic acid structures of various predetermined or known size, shape, complexity and modification, pluralities of nucleic acids wherein such pluralities may self-assemble to form three-dimensional nucleic acid structures, composite structures comprising two or more nucleic acid structures, and methods of making such composite structures. The invention also provides methods of using the nucleic acid structures and the composite structures of the invention. These aspects and embodiments of the invention will be described in greater detail herein.

Nucleic Acid Structures

Figure 5A:
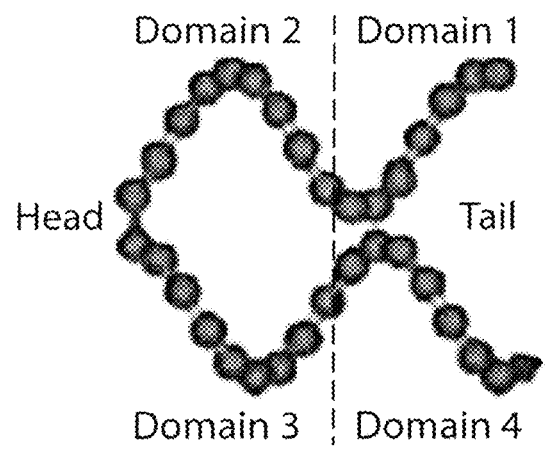
FIGS. 5A and 5B show a LEGO®-like model that differentiates each domain within a DNA brick.

The nucleic acid structures of the invention are comprised of a plurality of oligonucleotides that are bound to each other in a sequence-specific manner to form 3D shapes. The oligonucleotides of the invention may have four domains, though in some embodiments, an oligonucleotide can have 2, 3, 4, 5, 6, 7, 8, 9, 10, 11, 12, 13, 14, 15, 16, 17, 18, 19, 20, or more domains. The number of domains depends, at least is part, on the length of the oligonucleotide. Thus, longer oligonucleotides greater than 200 nucleotides, for example, can have more than 20 domains. FIGS. 1A and 5A provide a schematic of a 4-domain oligonucleotide, each domain having eight nucleotides. Prior to the annealing process that forms the nucleic acid structure, the oligonucleotides are in a single-stranded form. The nucleotide sequence of the domains and/or oligonucleotides may be random (provided that the requisite hybridization between domains occurs). As described in greater detail herein, some domains have a poly-T sequence. Thus, some structures are comprised of random sequence domains and poly-T domains.

An oligonucleotide can be conceptualized as a "brick" (similar to a LEGO® brick, see below) having, for example, four contiguous 8-nucleotide domains, totaling 32 nucleotides in length. The domains can be designated 1, 2, 3, 4, respectively (FIG. 1A). (For clarity, in some instances the Figures may refer to X1, X2, X3 and X4 domains to indicate the four domains of an "X" brick, and Y1, Y2, Y3 and Y4 domains to indicate the four domains of a "Y" brick.) Each DNA brick bears a distinct nucleotide sequence, in some instances. All DNA bricks adopt an identical global shape when incorporated into the target structure: two 16 base pair (16-mer) antiparallel helices joined by a single phosphate linkage. The two domains adjacent to the linkage are designated as "head" domains and the other two are designated as "tail" domains. A DNA brick with a tail domain bearing sequence "a" can interact productively with a neighboring brick with a complementary "a*" head domain in a stereo-specific fashion. Each pairing between bricks defines three parallel helices packed to produce a 90° dihedral angle (FIG. 1B, top); this angle derives from the ¾ right-handed helical twist of 8 base pairs of DNA.

Figure 1B:
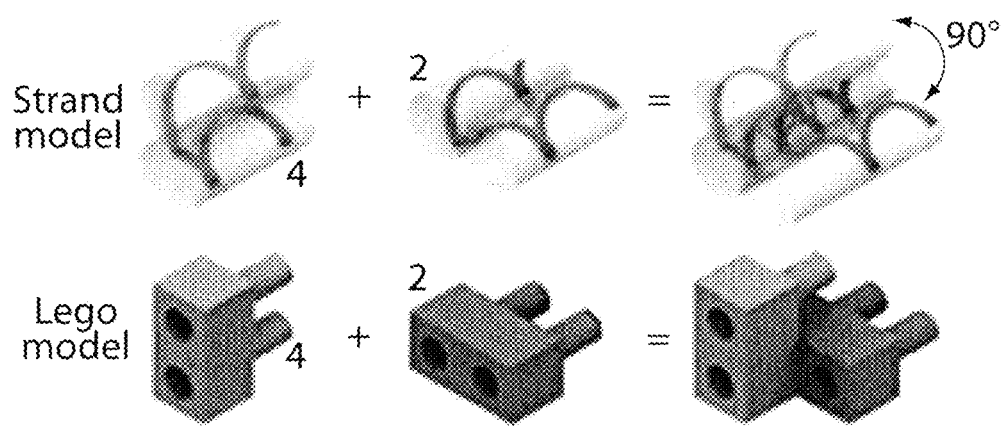
FIG. 1B is a schematic of two models that depict a DNA block and its binding interaction.
Figure 5B:
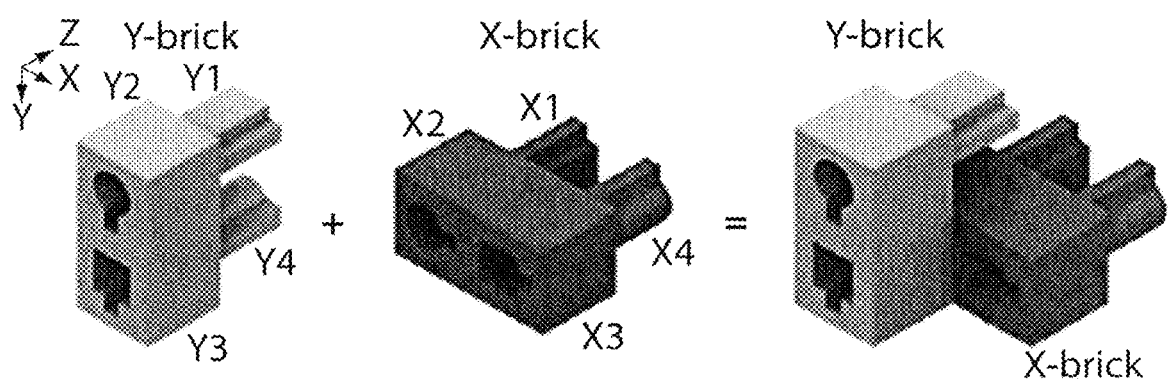
Figure 5C:
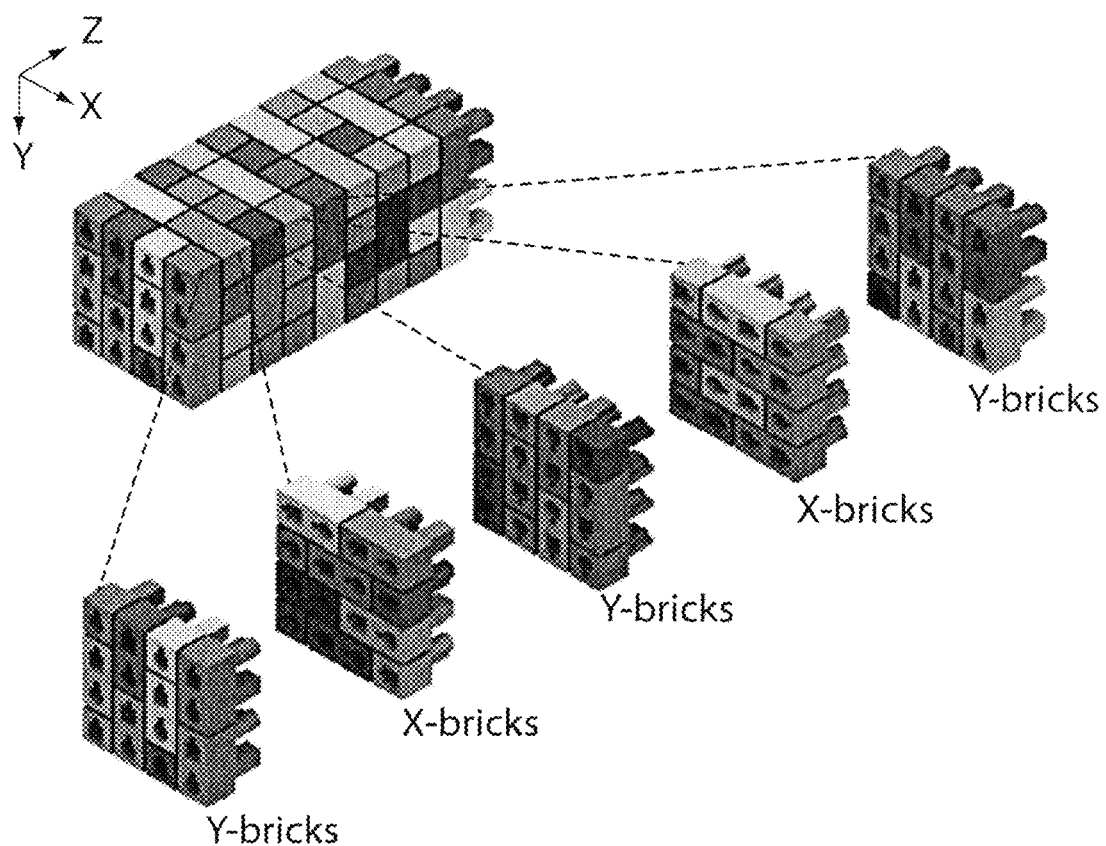
FIG. 5C is a LEGO®-like model of a 4H×4H×64B cuboid in FIG. 6. Each brick has a unique sequence, as indicated by distinct colors. In the Z+ direction, DNA bricks have same orientation within each layer; DNA bricks rotate 90° counter-clockwise with each successive layer along the Z+ direction.
Figure 6A:
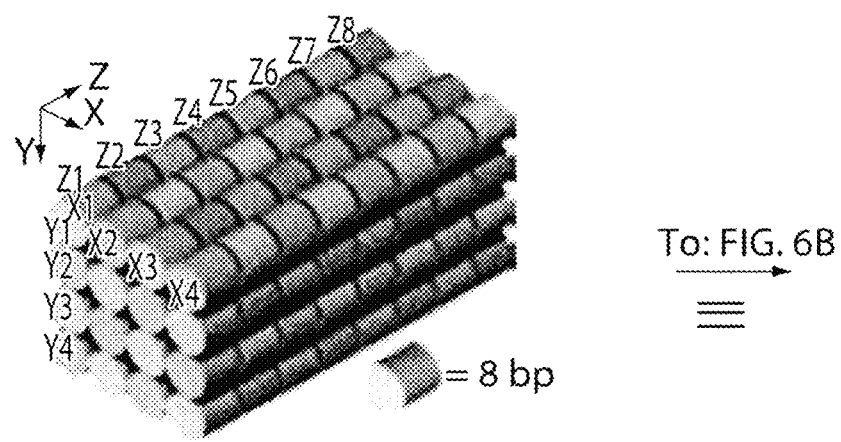
FIGS. 6A-6F show a strand diagram of DNA three-dimensional nanostructures.
Figure 6B:
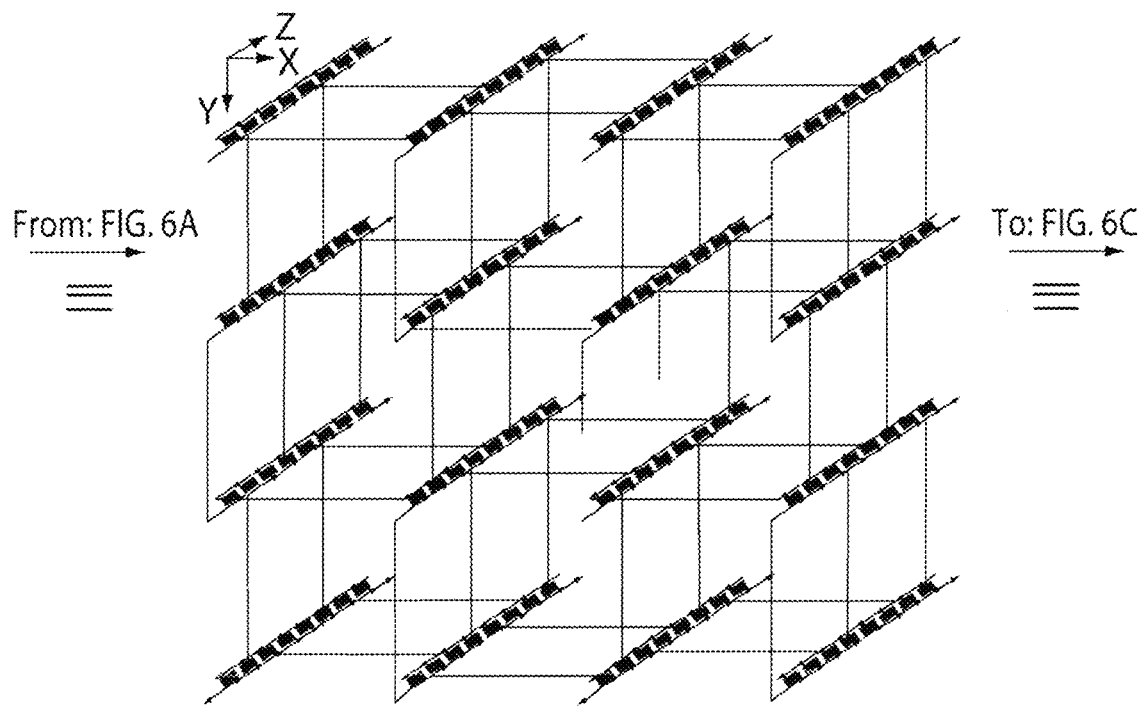
Figure 6C:
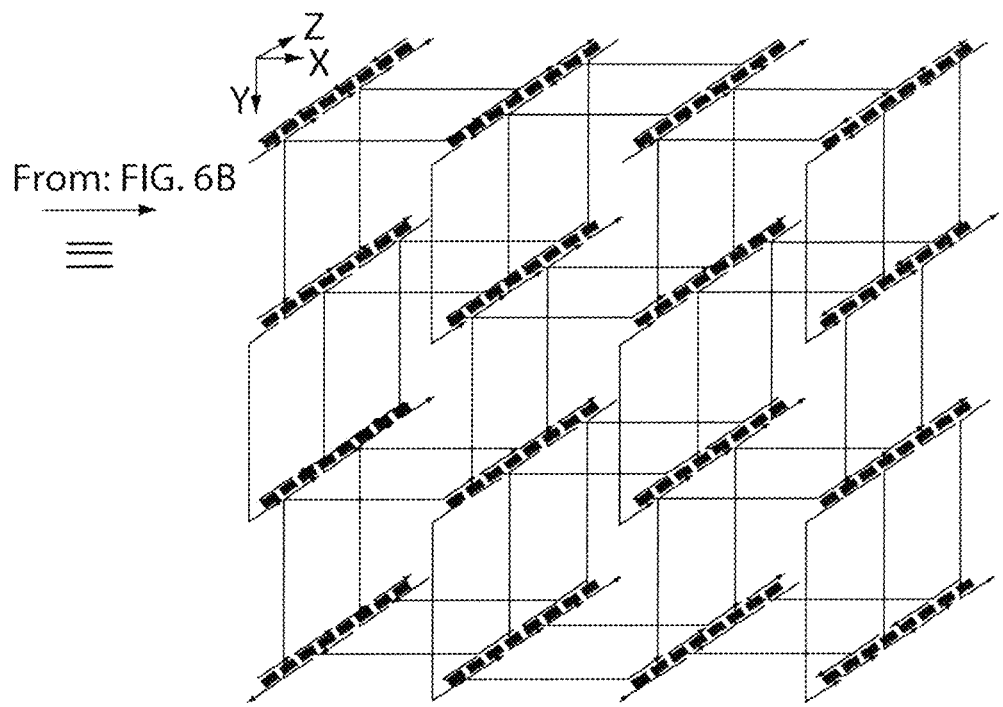
Figure 6D:
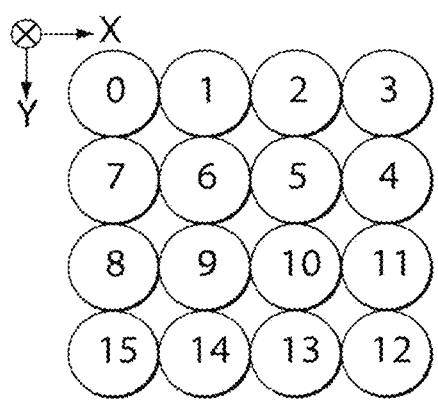
Figure 6E:
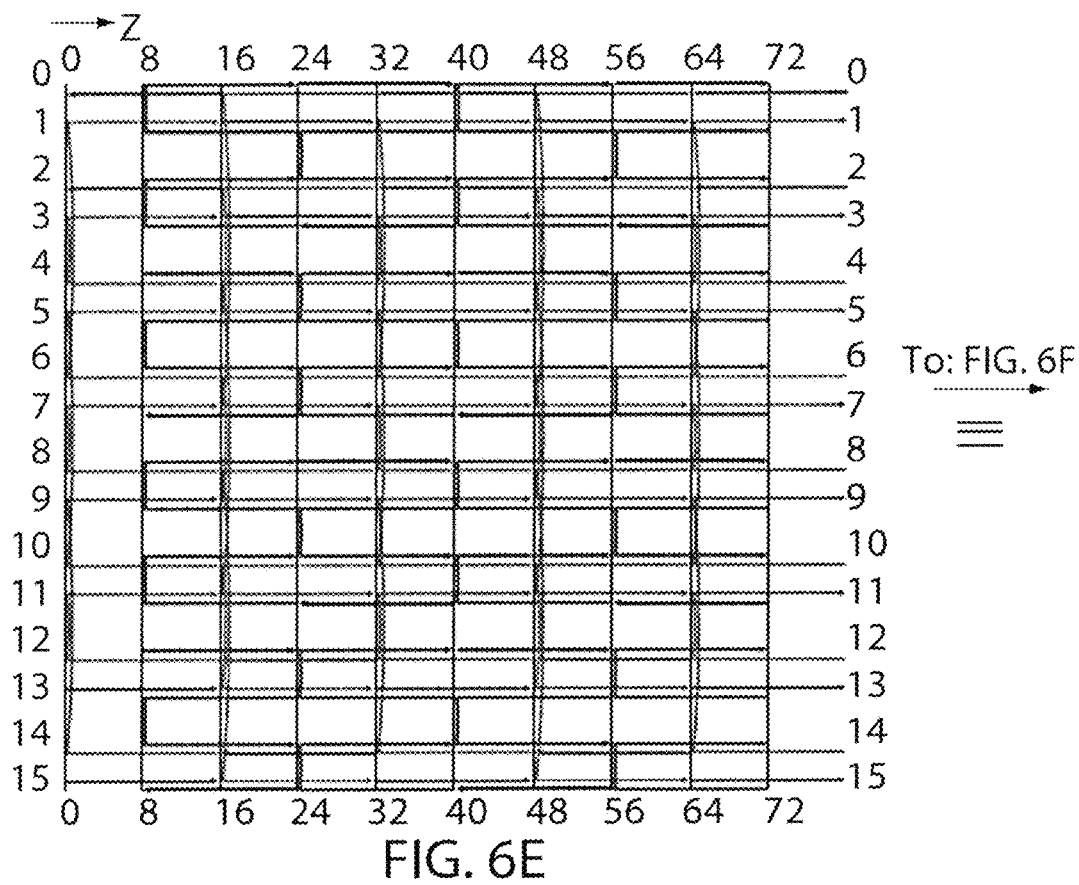
Figure 6F:
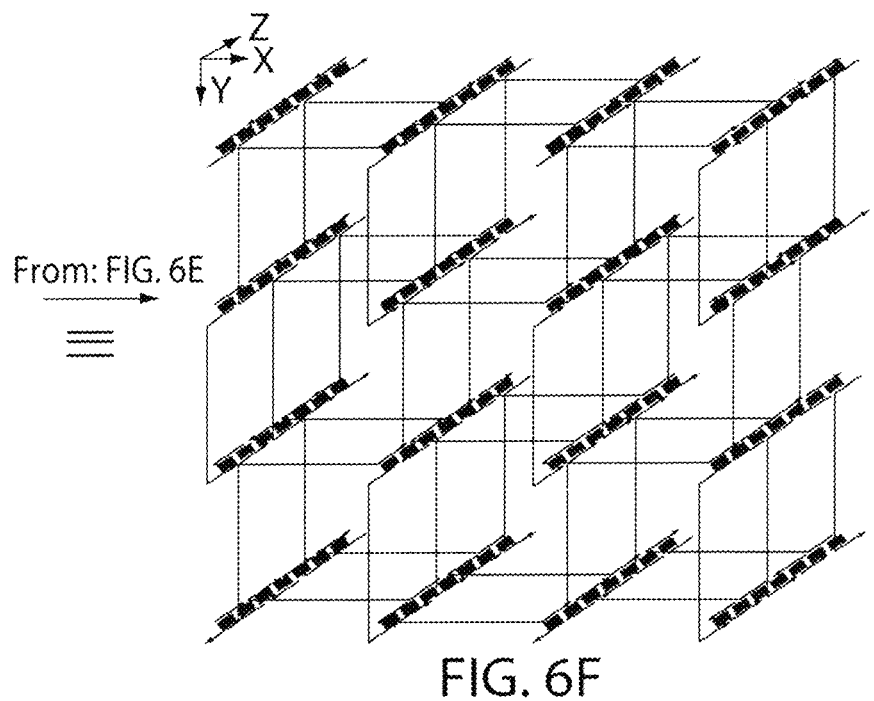
Figure 7A:
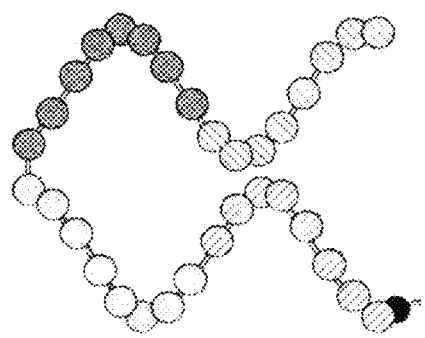
FIGS. 7A-7F show the connection between X-bricks and Y-bricks.
Figure 7B:
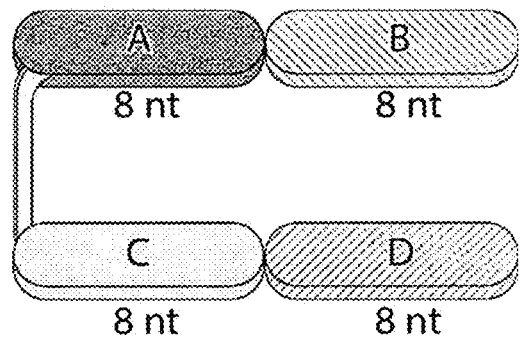
Figure 7C:
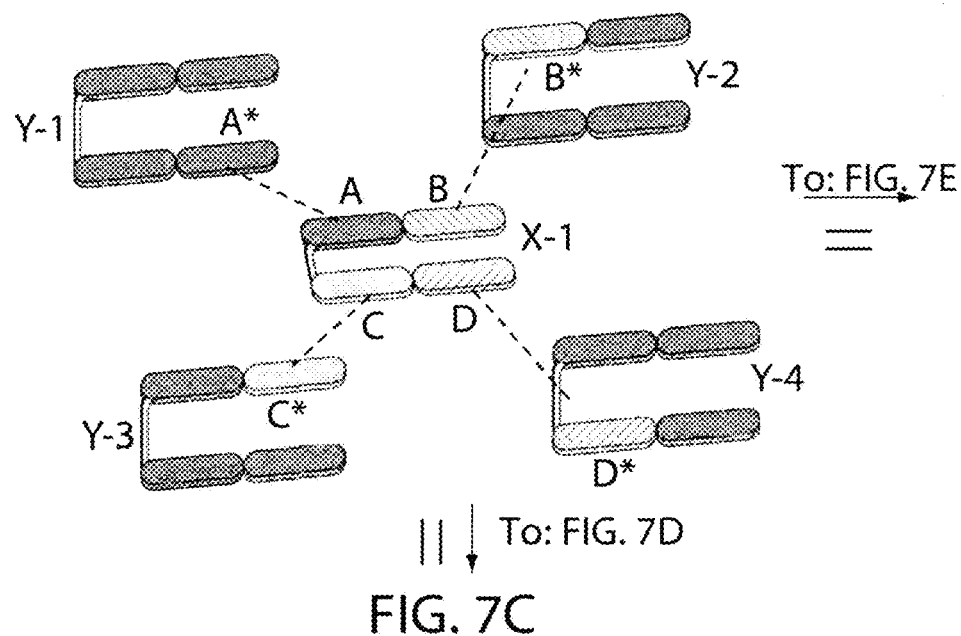
Figure 7D:
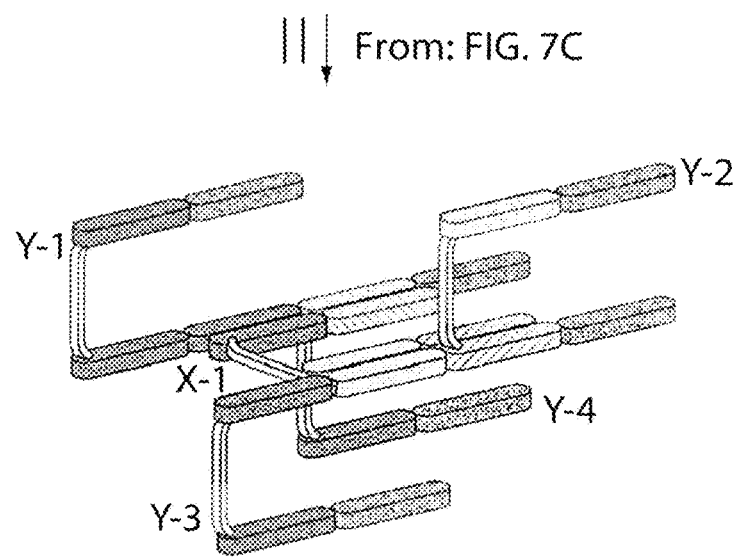
Figure 7E:
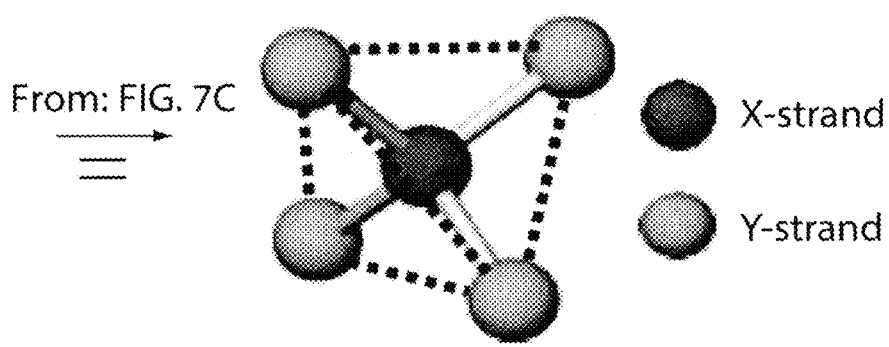
Figure 7F:
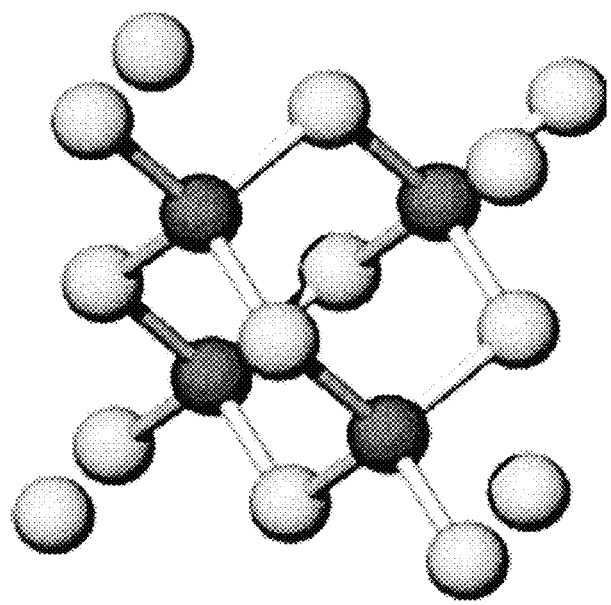

A LEGO®-like model can be used herein to depict the design in a simple manner (FIG. 1B, bottom and FIG. 5). The model overlooks the detailed helical structure and strand polarity but preserves information on aspect ratios and some of the orientational constraints on interactions between DNA bricks: the two protruding round plugs, pointing in the same direction as the helical axes, represent the two tail domains; the two connected cubes with recessed round holes represent the two head domains. A brick must adopt one of two types of orientations, horizontal or vertical (FIG. 1B). The two bricks connect to form a 90° angle via hybridization, represented as the insertion of a plug into a hole. An insertion is only allowed between a plug and a hole that carry complementary sequences with matching polarity (which is not graphically depicted in the current model for expositional simplicity). A more detailed LEGO®-like model that specifies strand polarities and stereospecific constraints on the interaction between bricks is shown in FIG. 5.

FIG. 5 shows nucleic acid bricks along successive 8 base pair layers that have orientations designated herein as north, west, south, and east. Bricks with north and south orientations may be restricted to a subset containing one helix from each double helix. Similarly, bricks with west and east orientations may be restricted to the complementary subset of helices (also see FIG. 6). Thus, it can be convenient to group the bricks oriented north and south together as Y-bricks, and to group the bricks oriented west and east together as X-bricks. In terms of domain-domain hybridization, there may be connections between a tail domain on one oligonucleotide with a head domain of another oligonucleotide in FIG. 5. Here a LEGO® model is shown that uses different protruding shapes (for tail domains 1 and 4) and matching cavities (for head domains 2 and 3). A tail domain Y4 and head domain X2 connection is demonstrated (FIG. 5B). In addition, the shapes and cavities are designed to force a pair of bricks to form a 90° dihedral angle.

Figure 1C:
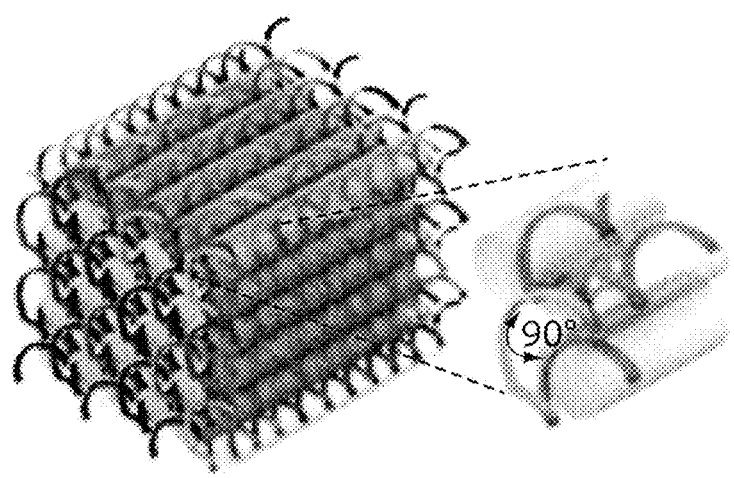
FIG. 1C is a schematic of a molecular model that shows the helical structure of a 6H (helix)×6H×48B (bp) cuboid three-dimensional DNA nanostructure. Each strand has a unique sequence. The inset shows a pair of X-strand and Y-strand.
Figure 1D:
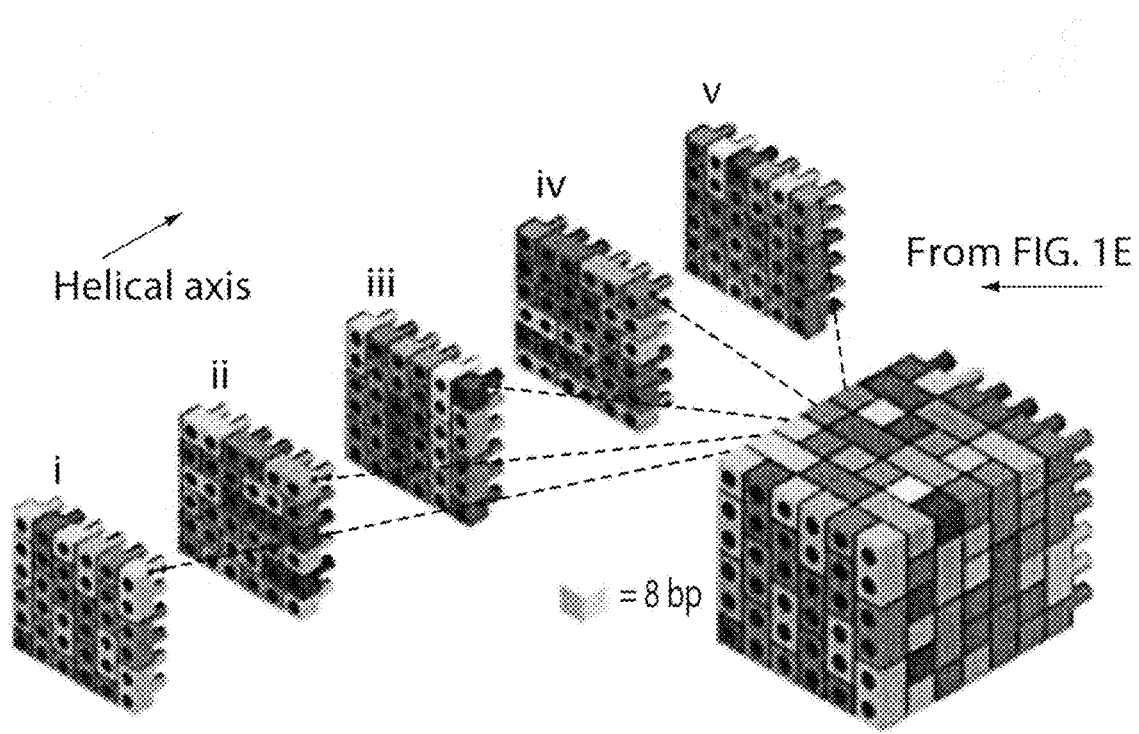
FIG. 1D is a schematic of a LEGO® model of the 6H×6H×48B cuboid. Each block has a unique sequence. There are half-blocks (i.e., 2-domain oligonucleotides) on the boundary of each layer.
Figure 1E:
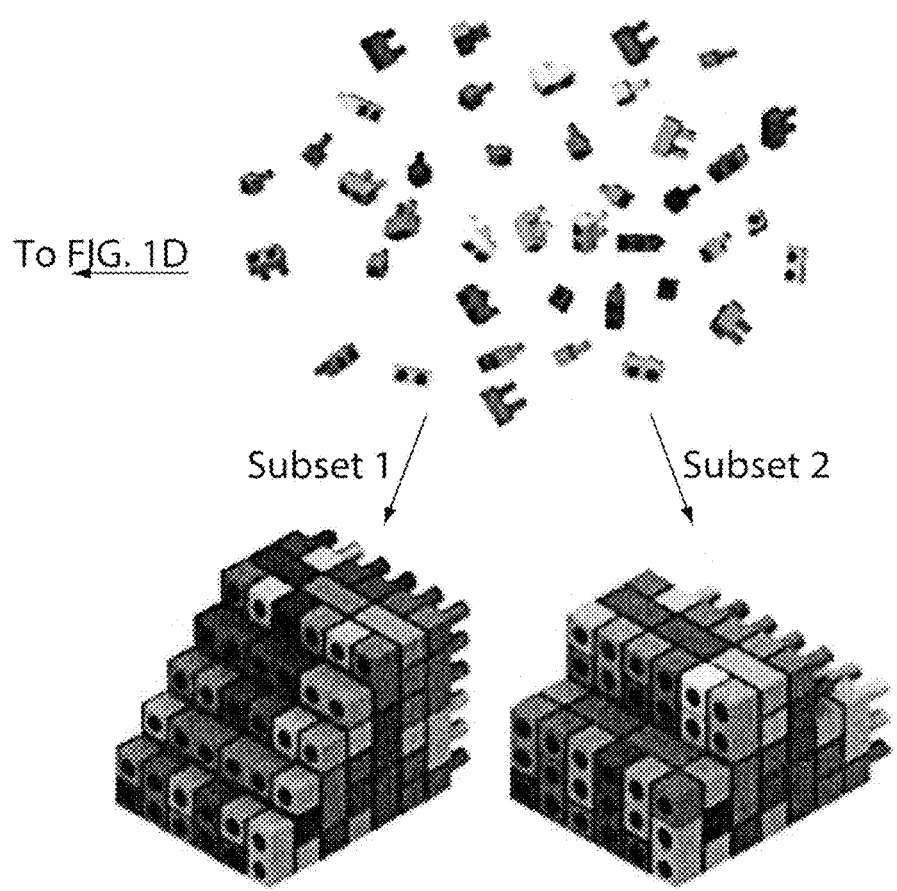
FIG. 1E is a schematic of a 6H×6H×48B cuboid self-assembled by DNA blocks. The blocks are not interchangeable during self-assembly because of the sequence uniqueness of each block. Using the 6H×6H×48B as a 3D "molecular canvas," a smaller shape can be constructed using a subset of the blocks.
Figure 1F:
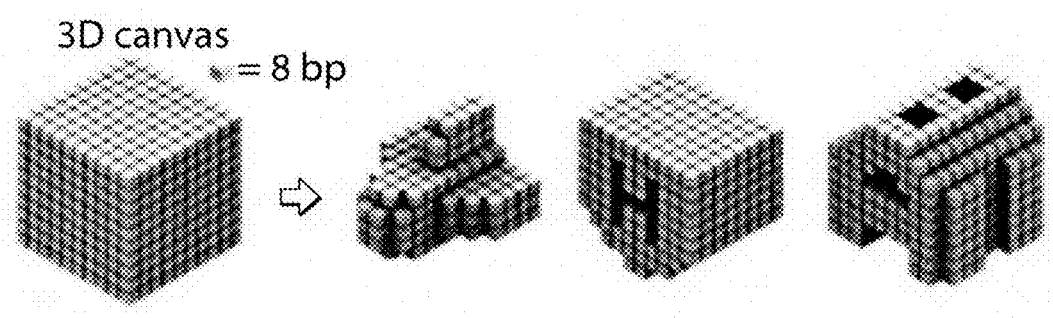
FIG. 1F is a schematic of complex arbitrary 3D shapes designed and assembled from a large 10×10×10 voxel "3D canvas." Each voxel represents a duplex of a single domain (e.g., 8 nucleotide domain) of, for example, a 4-domain oligonucleotide, formed by base-pairing of two single-stranded oligonucleotides.

Structural periodicities of the design can be illustrated in a 6H (helix)×6H (helix)×48B (base pair) cuboid nanostructure (FIGS. 1C, 1D). Bricks can be grouped in 8 base pair layers that contain their head domains. Bricks follow a 90° clockwise rotation along successive 8 base pair layers, therefore every four layers is a repeating unit in terms of orientation and arrangement of the bricks. For example, the first and fifth 8 base pair layers in FIG. 1D can share the same arrangement of bricks. Within an 8 base pair layer, all bricks can share the same orientation, and form chains with their pairs of holes defining a line. These chains pack laterally with a staggered arrangement to tile the plane defined by the layer. On the boundary of each layer, some nucleic acid bricks need to be bisected to half-bricks (i.e., 2 domain oligonucleotides), representing a single helix with two domains. The cuboid can be self-assembled from nucleic acid bricks in a one-step reaction. In some instances, each brick can carry a unique sequence that directs it to fit only to its predesigned position. Due to its modularity, a predesigned nucleic acid brick nanostructure can be used for construction of smaller custom and arbitrary shapes assembled from subsets of bricks (FIG. 1E).

The Lego-like model can be further abstracted to a 3D model that contains only positional information of each 8 bp duplex. A 10H×10H×80B cuboid is conceptualized as a 3D canvas that contains 10×10×10 voxels, each voxel corresponding to an 8 bp duplex (FIG. 1E). Based on the 3D canvas, a computer program first generates a full set of DNA bricks, including full-bricks and half-bricks, which can be used to build any custom shape. Using a 3D modeling software, designers then only need to define the target shapes by removing unwanted voxels from the 3D canvas—a process resembles 3D sculpting. Subsequently the computer program can analyze the shape and automatically chooses the correct subset of oligonucleotides (bricks) for self-assembly of the shape.

A nucleic acid structure may be designed prior to synthesis and its size, shape, complexity and modification may be prescribed and controlled by using certain select oligonucleotides in the synthesis process. The location of each domain and each oligonucleotide in the structure is known and provided for before synthesizing a nanostructure of a particular shape.

Typically, each domain of an oligonucleotide has a unique sequence. A pair of neighboring oligonucleotides form a duplex via hybridization of two complementary domains (e.g., head domain 1 and a tail domain 3), each located in one of the oligonucleotides (FIG. 1B, top). In some instances, however, certain domains of an oligonucleotide may not bind to another domain in a nucleic acid structure. In such instances, oligonucleotides having a poly-T domain are present in the structure, preferably at borders and in configurations that result in the poly-T domains being single-stranded. Thus, in some embodiments, at least one or at least two domains of a four (or more) domain oligonucleotide may be a poly-T domain (e.g., consist of T nucleotides).

In some instances, at least one domain in a nucleic acid structure will be unique, intending that the domain appears only once in that structure. A structure may be comprised of one or more unique domains, including 1, 2, 3, 4, 5, 6, 7, 8, 9, 10, 20, 30, 40, 50, 60, 70, 80, 90, 100, 200, 300, 400, 500, 600, 700, 800, 900, 1000 or more unique domains. In some embodiments, at least 10%, 20%, 30%, 40%, 50%, 60%, 70%, 80%, 80%, or 90% of the domains in the structure are unique. As an example, a structure may comprise a first plurality of domains each of which appears only once in the structure and these unique domains may present 75% of the total domains in the structure, and a second plurality of domains each of which appears more than once in the structure and these repeating domains may represent 25% of the total domains in the structure. It will be apparent that other percentages are also possible. In some embodiments, every domain in a structure is unique. In some embodiments, every domain in a structure is unique except for the poly-T domains. Every domain in a composite structure (i.e., a structure comprising two or more nucleic acid structures linked to each other with a spacer-linker) may or may not be unique.

In some instances, at least one domain in a double helix in a structure will be unique, intending that the domain appears only once in that double helix. The domain may be present in other helices within the same structure, and so in some instances, it may not be unique in the context of the entire nucleic acid structure. There may be 1, 2, 3, 4, 5, 6, 7, 8, 9, 10 or more domains in a helix that are unique in the context of that helix. The unique domains in a helix may represent at least 10%, 20%, 30%, 40%, 50%, 60%, 70%, 80%, 80%, 90%, or 100% of the domains in that helix. The unique domains in a helix may be located at or near the ends of the structure. The unique domains in a helix may be contiguous to each other or they may be spread apart from each other. They may be separated from each other by repeating domains (i.e., domains that appear more than once in a helix).

The structures may comprise one or more helices having unique domains. This type of helix may represent at least 10%, 20%, 30%, 40%, 50%, 60%, 70%, 80% or 90% or 100% of the helices present in the structure. If more than one of this helix type is present in the structure, they may be adjacent to each other or they may be separated by other helices including helices that do not contain unique domains. As an example, helices having unique domains may alternate in the structure with helices lacking unique domains.

Thus, in some instances, the nucleic acid structure may comprise two or more helices each having one or more unique domains, wherein the domain is unique in the context of an individual helix itself, and possibly unique within the context of the structure as a whole. The unique domain(s) in an individual helix may be present in other helices in the structure. The unique domain(s) in an individual helix may be the unique domain(s) in other helices in the structure.

In some instances, one or more helices in the structure each may be comprised entirely of unique domains, intending that each of those domains is present only once per helix or is present only once per structure.

Thus, in some instances, the nucleic acid structures of the invention comprise at least one unique double helix. A unique double helix is a helix having a domain composition that is different from any other helix in the structure. The unique double helix would therefore also have a nucleotide sequence that is different from any other helix in the structure.

In still other instances, the nucleic acid structures of the invention may be designed such that they comprise one region that is comprised of unique domains and another region that is comprised of non-unique or repeating domains.

The structures described may be defined, at least in part, based on a number of helices formed in an X direction, a number of helices formed in a Y direction, and a depth of such helices (indicated by the number of base pairs of such helices). It is to be understood that the helices so formed (and referred to) may be discontinuous helices (i.e., there may be double-stranded nicks in the helices along their length) since they are comprised of a plurality of hybridizing domains from separate oligonucleotides. The methods of the invention have been used to generate 3D canvases (from which a variety of arbitrarily shaped nucleic acid structures may be formed) of varying sizes including cuboids such as 3H×3H (×32b, ×64b, ×128b, ×256b, ×512b, ×1024b), 4H×4H (×32b, ×64b, ×128b, ×256b, ×512b), 6H×6H (×32b, ×64b, ×128b, ×256b), 12H×12H×48b, cylinders such as 6H×10H (×32b, ×64b, ×128b), strands such as 30H×1H× 126b, honey-comb lattices such as 6H×6H×84b-HC, and hexagonal lattices such as 6H×7H×108b-HL.

Figure 2A:
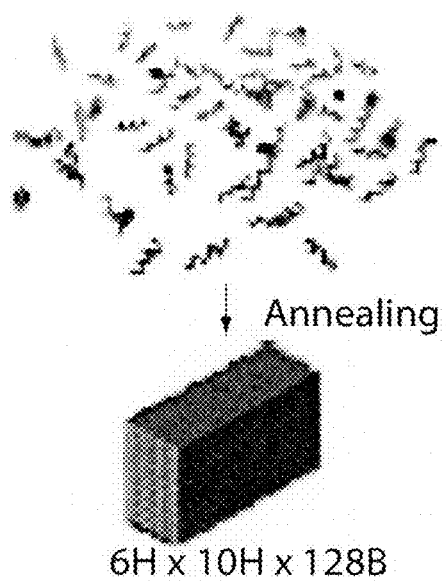
FIG. 2A is a schematic of one-step thermal annealing for self-assembly of DNA-block nanostructures.
Figure 2B:
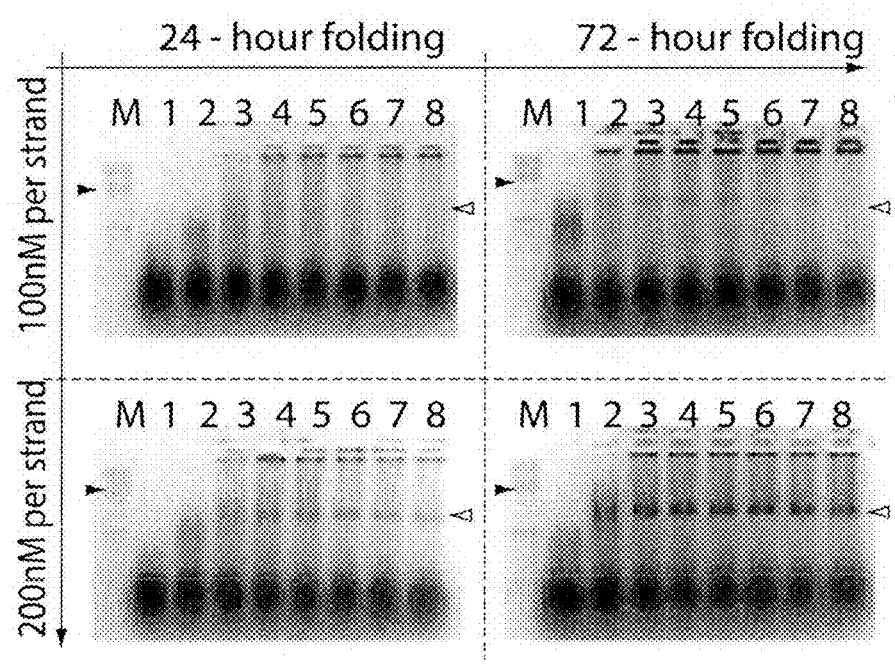
FIG. 2B shows images of agarose gel electrophoresis for a 6H×10H×128B nanostructure. The nanostructure was self-assembled at the following conditions: 24 hours or 72 hours annealing ramp, 100 nM or 200 nM for each DNA strand, 0.5×TE buffer at pH 7.9, $MgCl_2$ concentration at 10, 20, 30, 40, 50, 60, 70, or 80 mM. For each agarose gel, lane M shows a 1 kb ladder, lanes 1 to 8 show the 6H×10H×128B structure annealed with ascending $MgCl_2$ concentrations. The product bands (pointed by gray arrows) are compared to the 3 kb marker band (indicated by black arrows) to estimate the self-assembly yields of each condition. Maximum yield was achieved when 200 nM (per strand) strands were annealed for 72 hours at 40 mM $MgCl_2$.
Figure 2C:
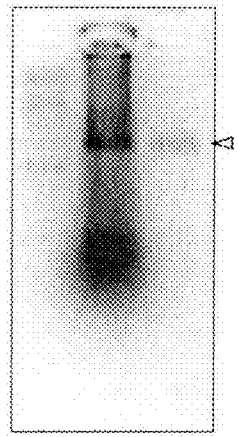
FIG. 2C shows images of agarose gel electrophoresis comparing unpurified 6H×10H×128B structures and purified 6H×10H×128B structures. Lane M shows a 1 kb ladder. Lane 1 shows unpurified 6H×10H×128B structures annealed at the optimal conditions shown in FIG. 2B and FIG. 2C. Lane 2 shows purified 6H×10H×128B structures. The gray arrow points to the 6H×10H×128B product band.
Figure 2D:
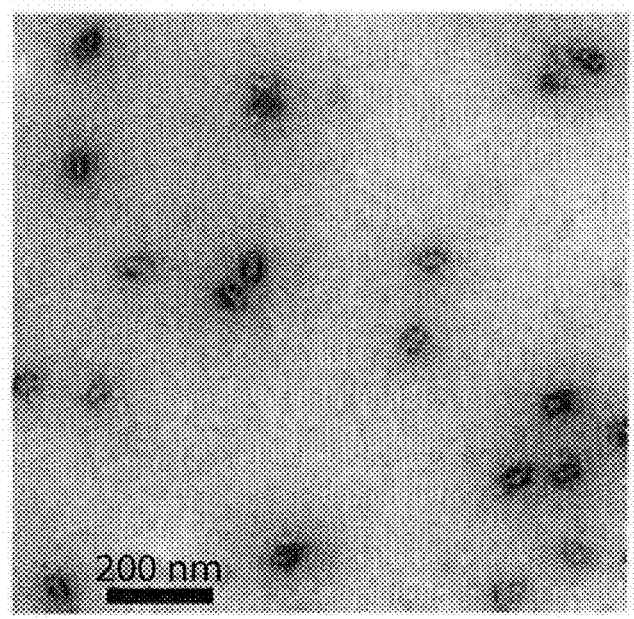
FIG. 2D shows transmission electron microscopy (TEM) images of purified 6H×10H×128B structures. Higher magnification images show three views of complete structures (also referred to herein as "particles"), corresponding to X-Y plane, X-Z plane and Y-Z plane projection of 6H×10H×128B, respectively. Computer-generated projection views are shown to the right of the high magnification TEM images.
Figure 2D:
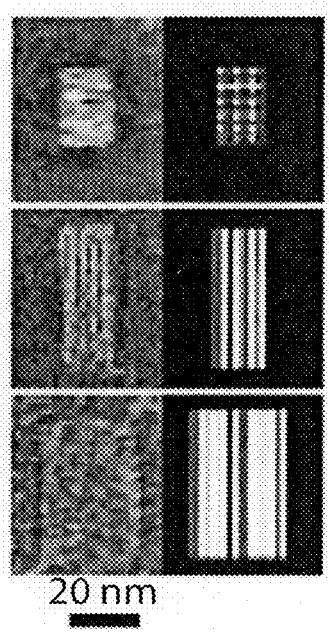
Figure 2E:
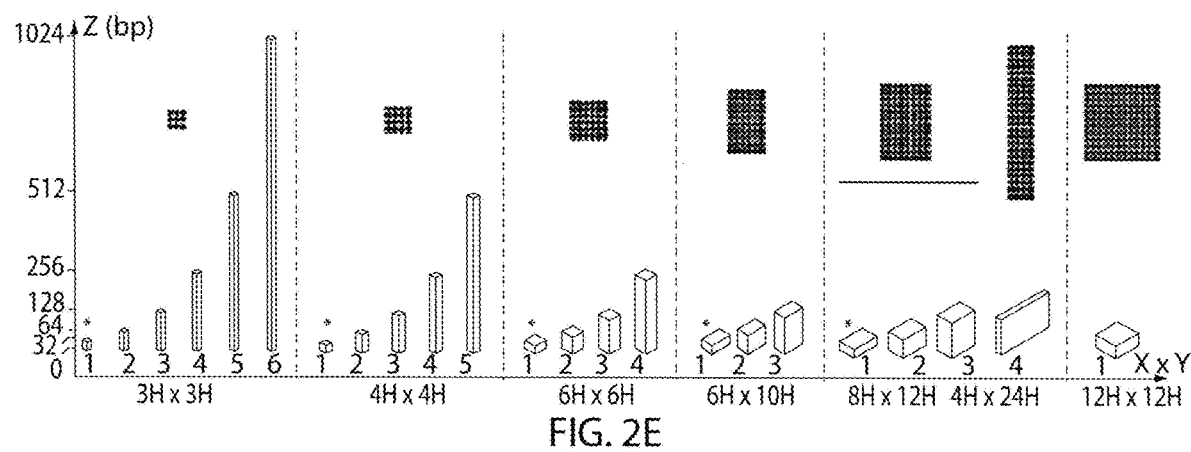
FIG. 2E shows schematic designs of 3D DNA-block nanostructures of a variety of dimensions.

The structures are formed, at least in part, by annealing a plurality of known oligonucleotides in a single vessel. FIG. 2A shows a schematic of one-step thermal annealing for self-assembly of oligonucleotide-block nanostructures. The Figure shows the schematic of the expected cuboid structure. FIG. 2D shows transmission electron microscopy (TEM) images of a purified 6H×10H×128B structure, post-annealing process. Higher magnification images show three views of complete nanostructures, corresponding to X-Y plane, X-Z plane and Y-Z plane projection of 6H×10H× 128B, respectively. Computer-generated projection views are shown to the right of the magnified TEM images. The gel electrophoresis analysis of the post-annealing process shows unpurified 6H×10H×128B structure annealed at the optimal conditions (lane 1) and purified 6H×10H×128B structure (lane 2). The gray arrow points to the 6H×10H×128B product band. Starting with a known pool of oligonucleotides that can be used to generate a three-dimensional shape of a certain size, select oligonucleotides may be excluded from the pool in order to form different shaped and/or sized structures.

Figure 3A:
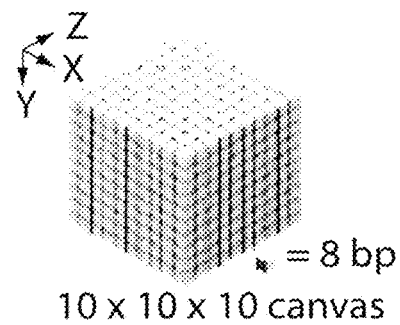
FIG. 3A is a schematic of a 10 voxel×10 voxel×10 voxel three-dimensional canvas.
Figure 3B:
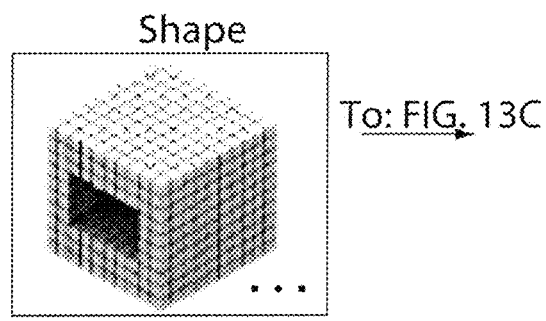
FIG. 3B is a schematic of a target nucleic acid structure designed by removing unnecessary voxels from the 3D canvas (in this case, from the interior).
Figure 3C:
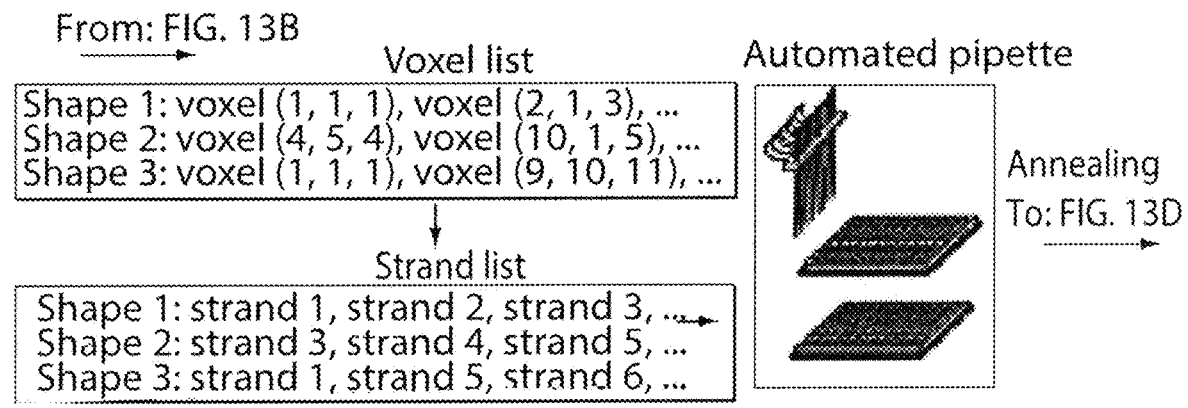
FIG. 3C is a schematic showing a computer-generated list of oligonucleotides strands needed to form the desired structure/shape. Structures were analyzed by a computer program, which recognizes the remaining voxels and generates a list of necessary oligonucleotides. A liquid handling robot then mixes strands for each shape.
Figure 3D:
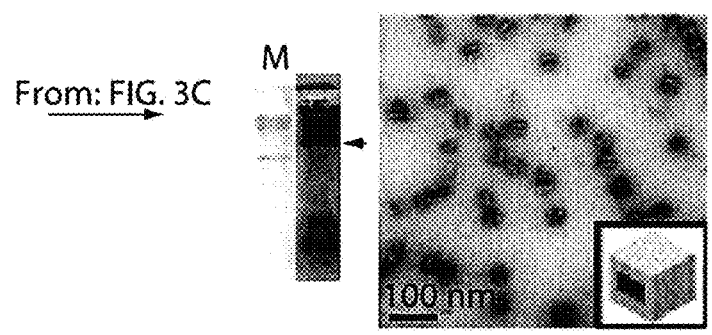
FIG. 3D shows images of nanostructures after annealing, characterized by agarose gel electrophoresis (left) and TEM imaging (right). Lane M shows a 1 kb ladder. The major product band is denoted by the arrow.
Figure 3E:
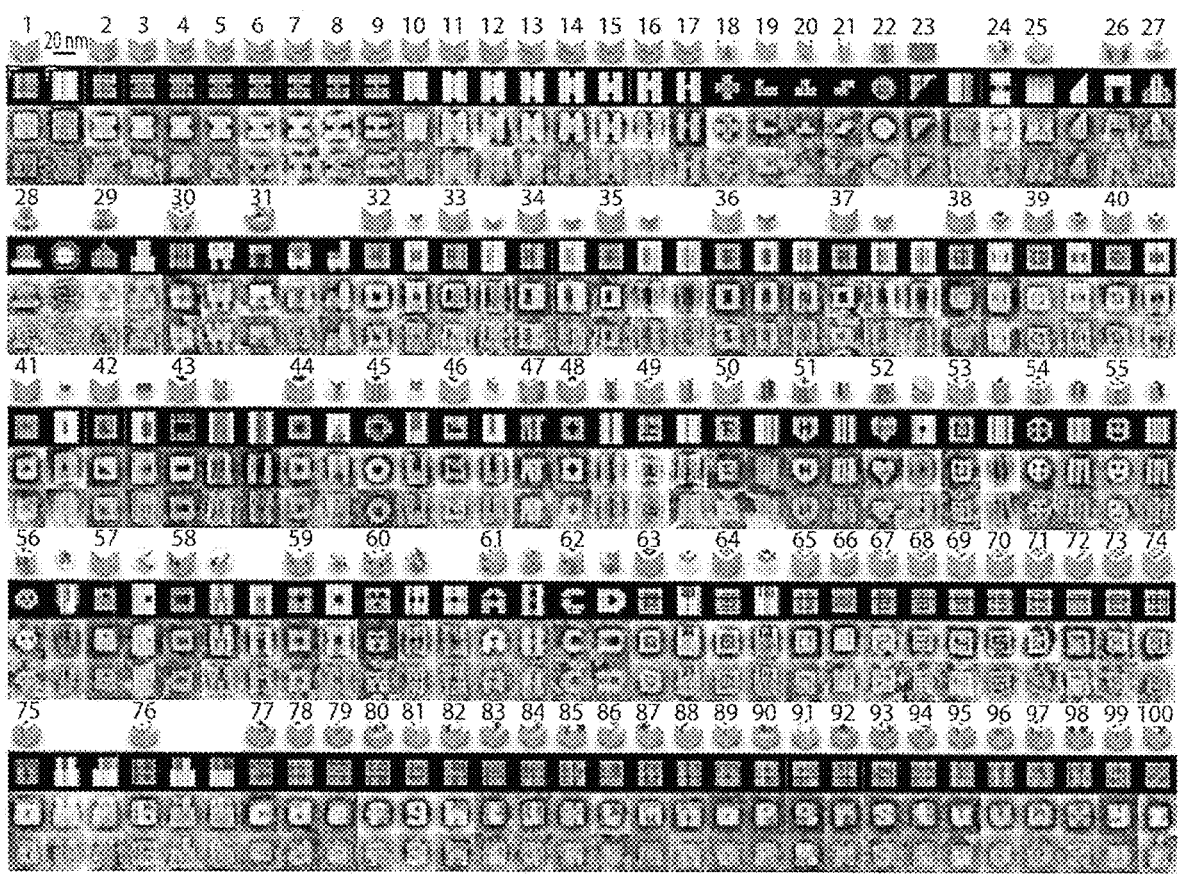
FIG. 3E shows images of various examples nanostructure (of particular shapes). The top image for each structure depicts a 3D model, followed below by computer-generated projection views. An image was averaged from 6 different structures/particles visualized using TEM and raw TEM images. Some structures are depicted with additional transparent 3D views that highlight the deleted voxels (i.e., deleted oligonucleotide domains). The individual oligonucleotide sequences used to produce the 100 different nucleic acid structures of FIG. 3E are designated SEQ ID NOs. 6842-11296 (i.e., strands 0-4454, respectively). (See also Table 14 of U.S. provisional application No. 61/675,309, filed Jul. 24, 2012, incorporated by reference herein.) Table 2 shows, for each shape, the total number of strands used and a list of each strand (bracketed). (See also Table 15 of U.S. provisional application No. 61/675,309, filed Jul. 24, 2012.)

A variety of structures that may be made using these methods are shown in FIG. 3E. Also shown are the post-annealing products resulting from such methods. The invention contemplates exclusion of oligonucleotides internal to a structure. As an example, FIG. 3B illustrates a structure having an internal void pattern (i.e., a predetermined region lacking any oligonucleotides).

Thus, in some instances, an end user designs a nucleic acid structure, such as for example a cuboid having a particular length, width and depth dimension, with knowledge of the particular oligonucleotide present at each position in the structure. In effect, the end user has a physical map that denotes the precise location of each oligonucleotide within the structure. Knowledge of the identity of each oligonucleotide at each location in the map (and thus in the nucleic acid structure) allows the end user to engineer particular patterns or shapes using a particular structure as a starting point. Such engineering can occur by excluding one or more known oligonucleotides from the mixture of oligonucleotides combined to form the nucleic acid structure and/or including additional known oligonucleotides.

Thus, as an example and as demonstrated herein, an end user may design a three dimensional cube having a particular length (Y-axis), width (X-axis) and depth (Z-axis), and comprised of a plurality of unique oligonucleotides. The end user knows the identity of the oligonucleotide at each position in the lattice. In addition to being able to synthesize the cube itself, the end user is also able to design and synthesize one or more other nucleic acid structures using the cube as a starting point. As demonstrated herein, variously shaped nucleic acid structures may be synthesized by excluding one and usually more oligonucleotides from the pool that would be used to make the entire cube. These shapes include without limitation any of the shapes depicted in FIG. 3E.

The invention therefore provides a methodology for synthesizing a number of different nucleic acid structures without having to design each structure de novo. Rather, starting with an initial nucleic acid structure, such as a cube, a variety of other nucleic acid structures may be formed simply by excluding preselected oligonucleotides and/or including preselected oligonucleotides. In this way, the end user uses the single-stranded oligonucleotides in a modular manner, including or excluding members of the plurality depending upon the ultimate shape and size of nucleic acid structure desired. The interactions between oligonucleotide members of the plurality are not expected to change appreciably and therefore it is not necessary for an end user to design, essentially from scratch, every new nucleic acid structure. Instead, the end user prepares stocks of each oligonucleotide and combines various stocks together, at relative concentrations corresponding to their relative frequency in the structure and in a single vessel, in order to form a nucleic acid structure of desired shape, size and complexity.

The selection and arrangement of single-stranded oligonucleotides in a nucleic acid structure of desired shape and size can be done manually or by computer algorithm. An example of such a computer algorithm is Uniquimer, which is openly available to the public.

As illustrated in some of the Figures herein, the size of the nucleic acid structures of the invention may be controlled during the annealing process. This size control is achieved by designing structures having one or more unique domains, or one or more unique helices and thus using select populations of oligonucleotides in the annealing process. The size of the nucleic acid structure thus is typically also predetermined.

The size of a nucleic acid structure may be represented by distance of one, two or three of its dimensions. Such dimensions may each independently be nanometers or micrometers in length, or longer. As an example, the structure may comprise one, two or three dimensions each having a length, width and/or depth in the range of 5-100 nanometers, 5-500 nanometers, 5-1000 nanometers, including 10-100 nanometers, 10-500 nanometers, or 10-1000 nanometers. In some embodiments, they may have one or more dimensions of about 5, 10, 20, 30, 40, 50, 60, 70, 80, 90, 100, 110, 120, 130, 140, 150, 160, 170, 180, 190, 200, 300, 400, 500, 600, 700, 800, 900 nm or more.

The size of the nucleic acid structure may also be presented by the number of double helices as well as the length of those double helices. The length of a double helix may be expressed as the number of helical turns in the helix. It is to be understood that the invention contemplates making structures that are in the nanometer and micrometer scale, and larger.

In some embodiments, a nucleic acid structure may comprise 2, 4, 8, 12, 16, 20, 24, 28, 32, 36, 40, 44, 48, 52, 56, 60, 64, 68, 72, 76, 80, 120, 160, 200, 240, 280, 320, or 360 helices. For example, a nucleic acid structure may be presented as a 6 helix (H)×6H×64 base pair (bp) structure (i.e., 6H×6H×64B). Other examples of structures include without limitation a 3H×3H×64B structure, a 3H×3H×128B structure, a 3H×3H×256B structure, a 3H×3H×512B structure, a 3H×3H×1024B structure, 4H×4H×64B structure, a 4H×4H×128B structure, a 4H×4H×256B structure, a 4H×4H×512B structure, a 4H×4H×1024B structure, a 6H×6H×64B structure, a 6H×6H×128B structure, a 6H×6H×256B structure, a 6H×6H×512B structure, a 6H×6H×1024B structure, 8H×8H×64B structure, a 8H×8H×128B structure, a 8H×8H×256B structure, a 8H×8H×512B structure, a 8H×8H×1024B structure, 12H×12H×64B structure, a 12H×12H×128B structure, a 12H×12H×256B structure, a 12H×12H×512B structure, or a 12H×12H×1024B structure. Additional examples include without limitation structures of 6H×10H×64B, 6H×10H×128B, 4H×12H×120B, 8H×12H×32B, 8H×12H×64B, 8H×12H×120B, 4H×24H×120B, 30H×1H×126B, 6H×7H×108B.

The nucleic acid structures of the invention may take any shape or form. Examples of various shapes and forms that may be created using the methods of the invention are illustrated in FIGS. 3A-3E, FIGS. 21A-21C, FIGS. 22A-22E and FIGS. 23A-23D. Importantly, using the methodology of the invention, it is possible to predetermine and thus predesign the shape, form and size of the nucleic acid structure with precise control based on knowledge of the identity (and thus sequence) of oligonucleotides at every location in the structure.

As discussed herein, nucleic acid structures may be synthesized by combining and annealing a plurality of single-stranded oligonucleotides in a single annealing reaction to yield a nucleic acid structure of desired shape, size, complexity and modification. The invention also contemplates synthesis of nucleic acid structures by annealing separate smaller nucleic acid structures to each other, in a modular manner.

In some embodiments, the nucleic acids and/or structures are annealed by subjecting them to an elevated temperature and then a slow cooling process. The elevated temperature may be about 50° C., about 45° C., or about 40° C., and the cooling process is intended to cool the solution to about room temperature (e.g., about 25° C.). The cooling period may be several minutes, several hours including 2, 3, 4, 5, 6, 7, 8, 9, or 10 hours, or more, including 24, 36, 48, 60, 72, 84, 96, 108, 120, 132, 144, 156 or 168 hours.

In some embodiments, the nucleic acid structures are crystal-like structures (referred to herein as "crystals"). Crystals may be assembled by using "connecting" bricks between discrete three-dimensional DNA-brick structures. In some embodiments, the assembly (also referred to as "growth") of a crystal may be non-hierarchical, while in other embodiments, the assembly of a crystal may be hierarchical. Non-hierarchical growth of a DNA brick crystal herein refers to the assembly of a crystal from individual DNA bricks, without first forming a repeating functional unit. Thus, individual DNA bricks are incorporated individually into the crystal as it grows. In such embodiments, a DNA-brick crystal may be designed based on a repeating unit where the connecting bricks are the same as the other bricks in size and function. By contrast, hierarchical growth of a DNA brick crystal herein refers to the assembly of a crystal from "pre-formed" repeating functional units (e.g., larger structures pre-formed from DNA bricks). In some embodiments, the DNA bricks on the surfaces of a discrete DNA-brick design may be modified to connect individual structures and extend the growth of crystals along the X-axis, Y-axis and Z-axis individually to generate one-dimensional-growth crystals. In some embodiments, the DNA bricks on the surfaces of a discrete DNA-brick design may be modified to connect individual structures and extend the growth of crystals along the X-axis, Y-axis and Z-axis combinatorially to generate two-dimensional-growth crystals or three-dimensional-growth crystals.

In order to achieve multimerization along the Z-axis, the sequences of the first layer of domains may be modified, in some embodiments, to be complementary to those in the last layer of domains. The multimerization along the X-axis or Y-axis may be achieved by substituting the bricks on the boundary along X-axis or Y-axis with new 32-nt bricks. Each of these new 32-nt bricks may contain two domains complementary to one side of the cuboid and another two domains complementary to the opposite side of the cuboid. Thus, these 32-nt bricks may connect the cuboid monomers to achieve continuous growth.

Figure 20A:
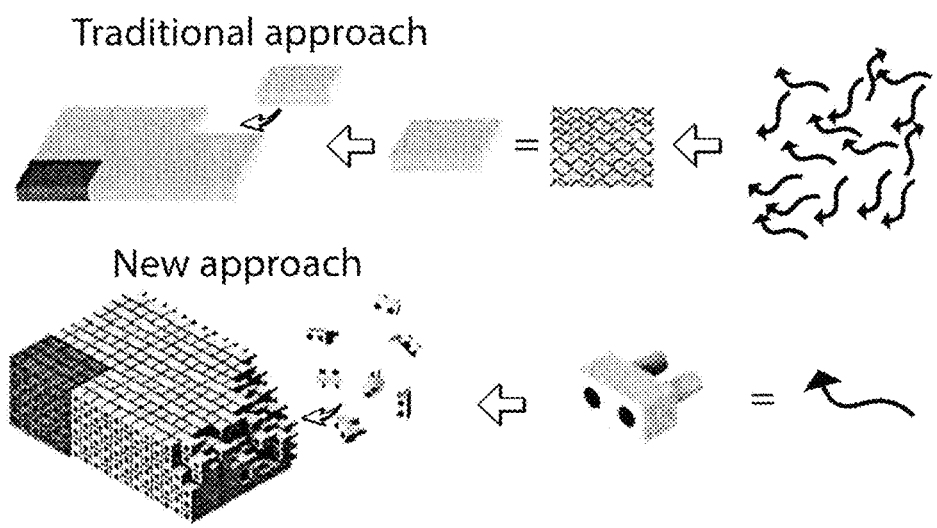
FIG. 20A shows a proposed assembly mechanism of a traditional DNA assembly approach (top) compared to a proposed assembly mechanism of a DNA crystal of the invention (bottom). Individual DNA strands, rather than pre-assembled multi-stranded blocks, are directly incorporated into a growing DNA crystal, enabling a general and robust framework for building complex crystals with prescribed depths and three-dimensional features.

As used herein, a "Z-crystal" refers to a one-dimensional crystal extended along the Z-axis. Similarly, an "X-crystal" or a "Y-crystal" refers to a one-dimensional crystal extended along the X-axis or the Y-axis, respectively. A "ZX-crystal" refers to a two-dimensional crystal extended along the Z-axis and the X-axis. An "XY-crystal" refers to a two-dimensional crystal extended along the X-axis and the Y-axis. FIG. 20F shows complex DNA crystals in three-dimensional space. Using different designs of repeating units, DNA-brick crystals with prescribed dimension(s) and pattern(s) can be made. Accordingly, a crystal design is named as "[the growth direction(s)]-[the size of the repeating unit]-[basic feature of its shape]." For example, an XY-4H×4H×64B-cuboid crystal is a two-dimensional crystal (XY-crystal) that is designed based on a repeating unit of a 4H×4H×64B cuboid. Like the discrete DNA-brick structures, sequences of DNA-brick crystals may be randomly generated, according to the teachings provided herein.

A crystal may be assembled by combining DNA bricks (purified or unpurified) at approximately equal ratios (e.g., 100 nm for each strand) in buffer (e.g., TE/MgCl$_2$), and then performing a single-step thermal annealing for 72, 84, 96, 108, 120, 132, 144, 156, 168 hours, or more.

In other embodiments, the invention contemplates staggered or sequential addition (and annealing) of structures, as compared to simultaneous mixture and annealing of all structures. Sequential addition may be particularly useful in the synthesis of more complex structures. In some instances, these and other annealing methods can be carried out either in a static environment or under flow. A flow environment allows non-annealed oligonucleotides or nucleic structures to be removed prior to the addition of subsequent components.

The invention also provides pluralities of nucleic acid structures. As used herein, the term plurality intends more than one, and may be used interchangeably with the term population. Such pluralities may comprise 10, 50, 100, 500, 1000 or more structures. Such pluralities may have varying degrees of homogeneity intending that a percentage of the nucleic acid structures in the plurality are identical to each other with respect to size, shape, complexity and/or modification. The plurality of structures therefore may be at least 20%, 30%, 40%, 50%, 60%, 70%, 80%, 90%, or 100% homogeneous in structures having a certain characteristic. As an example, a plurality of cuboid shaped structures may be at least 50% homogeneous intending that at least 50% of the structures in that plurality are cuboid shaped.

Such pluralities may be monodisperse intending that their members may be identical in terms of one or more characteristics including size, shape, complexity and/or modification. The pluralities may be monodisperse for all of these characteristics.

The degree of homogeneity (and conversely heterogeneity) in a plurality may be determined using a number of techniques, including but not limited to atomic force microscopy (AFM) or transmission electron microscopy (TEM), and gel electrophoresis. These techniques have been used to determine the degree of homogeneity in prepared populations of structures, as discussed in the Examples. Importantly, it has been found that the annealing methods provided herein reproducibly yield populations having a predominant nucleic acid structure species. Moreover, that predominant species appears identical to the species that was intended using the design and mapping approach of the invention.

As illustrated in a number of the Figures, in some instances, once a nucleic acid structure is formed, there may still be domains that are single-stranded. These may exist, for example, at the borders. Such borders are represented by the left and right borders of the structures provided in the Figures. It has been found in accordance with the invention that the nature of such domains can impact the efficiency and yield of the annealing process. More specifically, if these single-stranded regions are of a mixed nucleotide sequence, then the structures are more likely to agglomerate and yield is reduced. Such agglomeration can be reduced by manipulating the nucleotide sequence of these single-stranded regions. Specifically, single-stranded regions that are poly-T in sequence are less likely to cause agglomeration, resulting in better yields of structures. Poly-A and poly-C sequences may also be used. In some embodiments, therefore, certain single-stranded domains may be present in a structure and such domains may be identical to each other in sequence.

In certain embodiments, border regions may be comprised of a mixture of poly-T domains and other domains of mixed sequence, provided that the structures do not agglomerate substantially. In these instances, the mixed sequence domains can be used to anneal two or more structures to each other. The number of such domains may be 6, 8, 10 or more.

The structures of the invention may be modified during synthesis or post-synthesis. They may be modified during synthesis by using oligonucleotides that are modified. For example, one or more oligonucleotides used to generate a structure may be conjugated to a moiety of interest. Modified oligonucleotides may be used to generate the structures of the invention provided such modifications do not interfere with the ability of the oligonucleotide to bind to other oligonucleotides as required in order to form the desired structure. Additionally or alternatively, the structure may be modified post-synthesis.

Any modification is contemplated provided it does not interfere with the annealing of oligonucleotides to each other and it does not render the structure less stable, unless that is otherwise intended by the modification. Modification may be but is not limited to chemical or enzymatic in nature. Modification may involve the use of nucleic acid conjugated moieties. The moieties may be, without limitation, metallic, organic and inorganic in nature. The moieties may be conjugated to nucleic acids that are able to recognize and bind to oligonucleotides in the structure. Such nucleic acids may be triplex forming oligonucleotides, as an example. In other instances, one or more non-nucleic acid moieties may be attached, permanently or transiently, covalently or non-covalently, to the structures. The invention contemplates that unique and/or non-unique oligonucleotides may be modified. The oligonucleotides in a structure may themselves be conjugated to one or more domains that do not contribute to the structure but rather are used to bind moieties to the structure. It is to be understood that, since the location of each oligonucleotide and each domain in the structure can be predetermined, the location of each modification to the ultimate resulting structure can also be predetermined. In other words, knowledge of the location of each oligonucleotide in the structure facilitates the addressability of the structure.

In addition, the specification further incorporates in its entirety the appendix submitted with U.S. provisional application No. 61/675,309, filed Jul. 24, 2012, which provides various oligonucleotide sequences used to produce some of the nanostructures of the invention. The oligonucleotide sequences used to produce 6H×6H×64B-S nucleic acid structures of the invention are designated SEQ ID NOs. 1-78, 157-225 and 295-336, and the corresponding 5' end coordinates are shown respectively in Table 3A. (See also Appendix, Table 1 of U.S. provisional application No. 61/675,309, filed Jul. 24, 2012, incorporated by reference herein.)

TABLE 3A

[0, 32], [0, 64], [1, 31], [1, 47], [1, 63], [1, 79], [3, 31], [3, 47], [3, 63], [3, 79], [5, 31], [5, 47], [5, 63], [5, 79], [6, 16], [6, 48], [7, 31], [7, 47], [7, 63], [7, 79], [9, 31], [9, 47], [9, 63], [9, 79], [11, 31], [11, 47], [11, 63], [11, 79], [12, 32], [12, 64], [13, 31], [13, 47], [13, 63], [13, 79], [15, 31], [15, 47], [15, 63], [15, 79], [17, 31], [17, 47], [17, 63], [17, 79], [18, 16], [18, 48], [19, 31], [19, 47], [19, 63], [19, 79], [21, 31], [21, 47], [21, 63], [21, 79], [23, 31], [23, 47], [23, 63], [23, 79], [24, 32], [24, 64], [25, 31], [25, 47], [25, 63], [25, 79], [27, 31], [27, 47], [27, 63], [27, 79], [29, 31], [29, 47], [29, 63], [29, 79], [30, 16], [30, 48], [31, 31], [31, 47], [31, 63], [31, 79], [33, 31], [33, 47], [33, 63], [33, 79], [35, 31], [35, 47], [35, 63], [35, 79], [0, 23], [0, 39], [0, 55], [0, 71], [0, 87], [1, 24], [1, 56], [2, 23], [2, 39], [2, 55], [2, 71], [2, 87], [3, 24], [3, 56], [4, 23], [4, 39], [4, 55], [4, 71], [4, 87], [5, 24], [5, 56], [6, 23], [6, 39], [6, 55], [6, 71], [6, 87], [8, 23], [8, 39], [8, 55], [8, 71], [8, 87], [10, 23], [10, 39], [10, 55], [10, 71], [10, 87], [12, 23], [12, 39], [12, 55], [12, 71], [12, 87], [14, 23], [14, 39], [14, 55], [14, 71], [14, 87], [16, 23], [16, 39], [16, 55], [16, 71], [16, 87], [18, 23], [18, 39], [18, 55], [18, 71], [18, 87], [20, 23], [20, 39], [20, 55], [20, 71], [20, 87], [22, 23], [22, 39], [22, 55], [22, 71], [22, 87], [24, 23], [24, 39], [24, 55], [24, 71], [24, 87], [26, 23], [26, 39], [26, 55], [26, 71], [26, 87], [28, 23], [28, 39], [28, 55], [28, 71], [28, 87], [30, 23], [30, 39], [30, 55], [30, 71], [30, 87], [31, 8], [31,40], [31, 72], [32, 23], [32, 39], [32, 55], [32, 71], [32, 87], [33, 8], [33, 40], [33, 72], [34, 23], [34, 39], [34, 55], [34, 71], [34, 87], [35, 8], [35, 40], [35, 72]

The oligonucleotide sequences used to produce 6H×6H×64B nucleic acid structures of the invention are designated SEQ ID NOs. 79-156 and 226-294, and the corresponding 5' end coordinates are shown respectively in Table 3B. (See also Appendix, Table 1 of U.S. provisional application No. 61/675,309, filed Jul. 24, 2012, incorporated by reference herein.)

Random oligonucleotide sequences used to produce 6H×6H×64B nucleic acid structures of the invention are designated SEQ ID NOs. 591-737, and the corresponding 5' end coordinates are shown respectively in Table 5A. (See also Appendix, Table 3 of U.S. provisional application No. 61/675,309, filed Jul. 24, 2012, incorporated by reference herein.)

TABLE 3B

[0, 23], [0, 55], [0, 87], [1, 31], [1, 47], [1, 63], [1, 79], [2, 23], [2, 55], [2, 87], [3, 31], [3, 47], [3, 63], [3, 79], [4, 23], [4, 55], [4, 87], [5, 47], [5, 79], [6, 16], [6, 23], [6, 39], [6, 55], [6, 71], [6, 87], [7, 31], [7, 47], [7, 63], [7, 79], [8, 23], [8, 39], [8, 55], [8, 71], [8, 87], [9, 31], [9, 47], [9, 63], [9, 79], [10, 23], [10, 39], [10, 55], [10, 71], [10, 87], [11, 31], [11, 63], [11, 79], [12, 23], [12, 39], [12, 55], [12, 71], [12, 87], [13, 31], [13,47], [13, 63], [13, 79], [14, 23], [14, 39], [14, 55], [14, 71], [14, 87], [15, 31], [15, 47], [15, 63], [15, 79], [16, 23], [16, 39], [16, 55], [16, 71], [16, 87], [17, 47], [17, 79], [18, 16], [18, 23], [18, 39], [18, 55], [18, 71], [18, 87], [19, 31], [19, 47], [19, 63], [19, 79], [20, 23], [20, 39], [20, 55], [20, 71], [20, 87], [21, 31], [21, 47], [21, 63], [21, 79], [22, 23], [22, 39], [22, 55], [22, 71], [22, 87], [23, 31], [23, 63], [23, 79], [24, 23], [24, 39], [24, 55], [24, 71], [24, 87], [25, 31], [25, 47], [25, 63], [25, 79], [26, 23], [26, 39], [26, 55], [26, 71], [26, 87], [27, 31], [27, 47], [27, 63], [27, 79], [28, 23], [28, 39], [28, 55], [28, 71], [28, 87], [29, 47], [29, 79], [30, 16], [30, 39], [30, 71], [30, 87], [31, 8], [31, 31], [31, 47], [31, 63], [31, 79], [32, 39], [32, 71], [32, 87], [33, 8], [33, 31], [33, 47], [33, 63], [33, 79], [34, 39], [34, 71], [34, 87], [35, 8], [35, 31], [35, 63], [35, 79]

The oligonucleotide sequences used to produce 6H×10H×64B-M nucleic acid structures of the invention are designated SEQ ID NOs. 337-590, and the corresponding 5' end coordinates are shown respectively in Table 4. (See also Appendix, Table 2 of U.S. provisional application No. 61/675,309, filed Jul. 24, 2012, incorporated by reference herein.)

TABLE 5A

[1, 31], [1, 47], [1, 63], [1, 79], [3, 31], [3, 47], [3, 63], [3, 79], [5, 47], [5, 79], [6, 16], [7, 31], [7, 47], [7, 63], [7, 79], [9, 31], [9, 47], [9, 63], [9, 79], [11, 31], [11, 63], [11, 79], [13, 31], [13, 47], [13, 63], [13, 79], [15, 31], [15, 47], [15, 63], [15, 79], [17, 47], [17, 79], [18, 16], [19, 31], [19, 47], [19, 63], [19, 79],

TABLE 4

[1, 23], [1, 55], [1, 39], [1, 71], [3, 23], [3, 55], [3, 39], [3, 71], [5, 39], [5, 71], [6, 56], [6, 8], [6, 24], [8, 24], [8, 56], [8, 8], [8, 40], [10, 24], [10, 56], [10, 8], [10, 40], [11, 71], [13, 23], [13, 55], [13, 39], [13, 71], [15, 23], [15, 55], [15, 39], [15, 71], [17, 39], [17, 71], [18, 56], [18, 8], [18, 24], [20, 24], [20, 56], [20, 8], [20, 40], [22, 24], [22, 56], [22, 8], [22, 40], [23, 71], [25, 23], [25, 55], [25, ,39], [25, 71], [27, 23], [27, 55], [27, 39], [27, 71], [29, 39], [29, 71], [30, 56], [30, 8], [30, 24], [32, 24], [32, 56], [32, 8], [32, 40], [34, 24], [34, 56],

[34, 8], [34, 40], [35, 71], [37, 23], [37, 55], [37, 39], [37, 71], [39, 23], [39, 55], [39, 39], [39, 71], [41, 39], [41, 71], [42, 56], [42, 8], [42, 24], [44, 24], [44, 56], [44, 8], [44, 40], [46, 24], [46, 56], [46, 8], [46, 40], [47, 71], [49, 23], [49, 55], [49, 39], [49, 71], [51, 23], [51, 55], [51, 39], [51, 71], [53, 39], [53, 71], [54, 56], [54, 8], [54, 24], [56, 24], [56, 56], [56, 8], [56, 40], [58, 24], [58, 56], [58, 8],

[58, 40], [59, 71], [0, 15], [1, 64], [2, 15], [3, 64], [4, 15], [5, 64], [0, 47], [0, 79], [1, 0], [1, 32], [2, 47], [2, 79], [3, 0], [3, 32], [4, 47], [4, 79], [5, 0], [5, 32], [12, 15], [12, 47], [12, 79], [13, 0], [13, 32], [13, 64], [14, 15], [14,47], [14, 79], [15, 0], [15, 32], [15, 64], [16, 15], [16, 47], [16, 79], [17, 0], [17, 32], [17, 64], [12, 31], [12, 63], [13, 16], [13, 48], [14, 31], [14, 63], [15, 16], [15, 48], [16, 31], [16, 63], [17, 16], [17, 48], [24, 15], [24, 47], [24, 79], [25, 0], [25, 32], [25, 64], [26, 15], [26,47], [26, 79], [27, 0], [27, 32], [27, 64], [28, 15], [28, 47], [28, 79], [29, 0], [29, 32], [29, 64], [24, 31], [24, 63], [25, 16], [25, 48], [26, 31], [26, 63], [27, 16], [27, 48], [28, 31], [28, 63], [29, 16], [29, 48], [36, 15], [36, 47], [36, 79], [37, 0], [37, 32], [37, 64], [38, 15], [38, 47], [38, 79], [39, 0], [39, 32], [39, 64], [40, 15], [40, 47], [40, 79], [41, 0], [41, 32], [41, 64], [36, 31], [36, 63], [37, 16], [37, 48], [38, 31], [38, 63], [39, 16], [39, 48], [40, 31], [40, 63], [41, 16], [41, 48], [48, 15], [48, 47], [48, 79], [49, 0], [49, 32], [49, 64], [50, 15], [50, 47], [50, 79], [51, 0], [51, 32], [51, 64], [52, 15], [52, 47], [52, 79], [53, 0], [53, 32], [53, 64], [48, 31], [48, 63], [49, 16], [49, 48], [50, 31], [50, 63], [51, 16], [51, 48], [52, 31], [52, 63], [53, 16], [53, 48], [54, 79], [55, 0], [56, 79], [57, 0], [58, 79], [59, 0]

TABLE 5A-continued

[21, 31], [21, 47], [21, 63], [21, 79], [23, 31], [23, 63], [23, 79], [25, 31], [25, 47], [25, 63], [25, 79], [27, 31], [27, 47], [27, 63], [27, 79], [29, 47], [29, 79], [30, 16], [31, 31], [31, 47], [31, 63], [31, 79], [33, 31], [33, 47], [33, 63], [33, 79], [35, 31], [35, 63], [35, 79], [0, 23], [0, 55], [0, 87], [2, 23], [2, 55], [2, 87], [4, 23], [4, 55], [4, 87], [6, 23], [6, 39], [6, 55], [6, 71], [6, 87], [8, 23], [8, 39], [8, 55], [8, 71], [8, 87], [10, 23], [10, 39], [10, 55], [10, 71], [10, 87], [12, 23], [12, 39], [12, 55], [12, 71], [12, 87], [14, 23], [14, 39], [14, 55], [14, 71], [14, 87], [16, 23], [16, 39], [16, 55], [16, 71], [16, 87], [18, 23], [18, 39], [18, 55], [18, 71], [18, 87], [20, 23], [20, 39], [20, 55], [20, 71], [20, 87], [22, 23], [22, 39], [22, 55], [22, 71], [22, 87], [24, 23], [24, 39], [24, 55], [24, 71], [24, 87], [26, 23], [26, 39], [26, 55], [26, 71], [26, 87], [28, 23], [28, 39], [28, 55], [28, 71], [28, 87], [30, 39], [30, 71], [30, 87], [31, 8], [32, 39], [32, 71], [32, 87], [33, 8], [34, 39], [34, 71], [34, 87], [35, 8]

Designed oligonucleotide sequences used to produce 6H×6H×64B nucleic acid structures of the invention are designated SEQ ID NOs. 738-884, and the corresponding 5' end coordinates are shown respectively in Table 5B. (See also Appendix, Table 3 of U.S. provisional application No. 61/675,309, filed Jul. 24, 2012, incorporated by reference herein.)

TABLE 5B

[1, 31], [1, 47], [1, 63], [1, 79], [3, 31], [3, 47], [3, 63], [3, 79], [5, 47], [5, 79], [6, 16], [7, 31], [7, 47], [7, 63], [7, 79], [9, 31], [9, 47], [9, 63], [9, 79], [11, 31], [11, 63], [11, 79], [13, 31], [13, 47], [13, 63], [13, 79], [15, 31], [15,47], [15, 63], [15, 79], [17,47], [17, 79], [18, 16], [19, 31], [19, 47], [19, 63], [19, 79], [21, 31], [21, 47], [21, 63], [21, 79], [23, 31], [23, 63], [23, 79], [25, 31], [25, 47], [25, 63], [25, 79], [27, 31], [27, 47], [27, 63], [27, 79], [29, 47], [29, 79], [30, 16], [31, 31], [31, 47], [31, 63], [31, 79], [33, 31], [33, 47], [33, 63], [33, 79], [35, 31], [35, 63], [35, 79], [0, 23], [0, 55], [0, 87], [2, 23], [2, 55], [2, 87], [4, 23], [4, 55], [4, 87], [6, 23], [6, 39], [6, 55], [6, 71], [6, 87], [8, 23], [8, 39], [8, 55], [8, 71], [8, 87], [10, 23], [10, 39], [10, 55], [10, 71], [10, 87], [12, 23], [12, 39], [12, 55], [12, 71], [12, 87], [14, 23], [14, 39], [14, 55], [14, 71], [14, 87], [16, 23], [16, 39], [16, 55], [16, 71], [16, 87], [18, 23], [18, 39], [18, 55], [18, 71], [18, 87], [20, 23], [20, 39], [20, 55], [20, 71], [20, 87], [22, 23], [22, 39], [22, 55], [22, 71], [22, 87], [24, 23], [24, 39], [24, 55], [24, 71], [24, 87], [26, 23], [26, 39], [26, 55], [26, 71], [26, 87], [28, 23], [28, 39], [28, 55], [28, 71], [28, 87], [30, 39], [30, 71], [30, 87], [31, 8], [32, 39], [32, 71], [32, 87], [33, 8], [34, 39], [34, 71], [34, 87], [35, 8]

One set of oligonucleotide sequences used to produce 4H×12H×120B nucleic acid structures of the invention are designated SEQ ID NOs. 885-1220, and the corresponding 5' end coordinates are shown respectively in Table 6A. (See also Appendix, Table 4 of U.S. provisional application No. 61/675,309, filed Jul. 24, 2012, incorporated by reference herein.)

TABLE 6A

[1, 23], [1, 39], [1, 55], [1, 71], [1, 87], [1, 103], [1, 119], [1, 135], [3, 39], [3, 71], [3, 103], [3, 135], [4, 8], [5, 23], [5, 39], [5, 55], [5, 71], [5, 87], [5, 103], [5, 119], [5, 135], [7, 23], [7, 55], [7, 87], [7, 119], [7, 135], [9, 23], [9, 39], [9, 55], [9, 71], [9, 87], [9, 103], [9, 119], [9, 135], [11, 39], [11, 71], [11, 103], [11, 135], [12, 8], [13, 23], [13, 39], [13, 55], [13, 71], [13, 87], [13, 103], [13, 119], [13, 135], [15, 23], [15, 55], [15, 87], [15, 119], [15, 135], [17, 23], [17, 39], [17, 55], [17, 71], [17, 87], [17, 103], [17, 119], [17, 135], [19, 39], [19, 71], [19, 103], [19, 135], [20, 8], [21, 23], [21, 39], [21, 55], [21, 71], [21, 87], [21, 103], [21, 119], [21, 135], [23, 23], [23, 55], [23, 87], [23, 119], [23, 135], [25, 23], [25, 39], [25, 55], [25, 71], [25, 87], [25, 103], [25, 119], [25, 135], [27, 39], [27, 71], [27, 103], [27, 135], [28, 8], [29, 23], [29, 39], [29, 55], [29, 71], [29, 87], [29, 103], [29, 119], [29, 135], [31, 23], [31, 55], [31, 87], [31, 119], [31, 135], [33, 23], [33, 39], [33, 55], [33, 71], [33, 87], [33, 103], [33, 119], [33, 135], [35, 39], [35, 71], [35, 103], [35, 135], [36, 8], [37, 23], [37, 39], [37, 55], [37, 71], [37, 87], [37, 103], [37, 119], [37, 135], [39, 23], [39, 55], [39, 87], [39, 119], [39, 135], [41, 23], [41, 39], [41, 55], [41, 71], [41, 87], [41, 103], [41, 119], [41, 135], [43, 39], [43, 71], [43, 103], [43, 135], [44, 8], [45, 23], [45, 39], [45, 55], [45, 71], [45, 87], [45, 103], [45, 119], [45, 135], [47, 23], [47, 55], [47, 87], [47, 119], [47, 135], [0, 47], [0, 79], [0, 111], [0, 143], [1, 16], [2, 47], [2, 79], [2, 111], [2, 143], [3, 16], [4, 31], [4, 47], [4, 63], [4, 79], [4, 95], [4, 111], [4, 127], [4, 143], [6, 31], [6, 47], [6, 63], [6, 79], [6, 95], [6, 111], [6, 127], [6, 143], [8, 31], [8, 47], [8, 63], [8, 79], [8, 95], [8, 111], [8, 127], [8, 143], [10, 31], [10, 47], [10, 63], [10, 79], [10, 95], [10, 111], [10, 127], [10, 143], [12, 31], [12, 47], [12, 63], [12, 79], [12, 95], [12, 111], [12, 127], [12, 143], [14, 31], [14, 47], [14, 63], [14, 79], [14, 95], [14, 111], [14, 127], [14, 143], [16, 31], [16, 47], [16, 63], [16, 79], [16, 95], [16, 111], [16, 127], [16, 143], [18, 31], [18, 47], [18, 63], [18, 79], [18, 95], [18, 111], [18, 127], [18, 143], [20, 31], [20, 47], [20, 63], [20, 79], [20, 95], [20, 111], [20, 127], [20, 143], [22, 31], [22, 47], [22, 63], [22, 79], [22, 95], [22, 111], [22, 127], [22, 143], [24, 31], [24, 47], [24, 63], [24, 79], [24, 95], [24, 111], [24, 127], [24, 143], [26, 31], [26, 47], [26, 63], [26, 79], [26, 95], [26, 111], [26, 127], [26, 143], [28, 31], [28, 47], [28, 63], [28, 79], [28, 95], [28, 111], [28, 127], [28, 143], [30, 31], [30, 47], [30, 63], [30, 79], [30, 95], [30, 111], [30, 127], [30, 143], [32, 31], [32, 47], [32, 63], [32, 79], [32, 95], [32, 111], [32, 127], [32, 143], [34, 31], [34, 47], [34, 63], [34, 79], [34, 95], [34, 111], [34, 127], [34, 143], [36, 31], [36, 47], [36, 63], [36, 79], [36, 95], [36, 111], [36, 127], [36, 143], [38, 31], [38, 47], [38, 63], [38, 79], [38, 95], [38, 111], [38, 127], [38, 143], [40, 31], [40, 47], [40, 63], [40, 79], [40, 95], [40, 111], [40, 127], [40, 143], [42, 31], [42, 47], [42, 63], [42, 79], [42, 95], [42, 111], [42, 127], [42, 143], [44, 31], [44, 63], [44, 95], [44, 127], [44, 143], [46, 31], [46, 63], [46, 95], [46, 127], [46, 143]

Another set of oligonucleotide sequences used to produce 4H×12H×120B nucleic acid structures of the invention are designated SEQ ID NOs. 1221-1556, and the corresponding 5' end coordinates are shown respectively in Table 6B. (See also Appendix, Table 4 of U.S. provisional application No. 61/675,309, filed Jul. 24, 2012, incorporated by reference herein.)

TABLE 6B

[1, 23], [1, 39], [1, 55], [1, 71], [1, 87], [1, 103], [1, 119], [1, 135], [3, 39], [3, 71], [3, 103], [3, 135], [4, 8], [5, 23], [5, 39], [5, 55], [5, 71], [5, 87], [5, 103], [5, 119], [5, 135], [7, 23], [7, 55], [7, 87], [7, 119], [7, 135], [9, 23], [9, 39], [9, 55], [9, 71], [9, 87], [9, 103], [9, 119], [9, 135], [11, 39], [11, 71], [11, 103], [11, 135], [12, 8], [13, 23], [13, 39], [13, 55], [13, 71], [13, 87], [13, 103], [13, 119], [13, 135], [15, 23], [15, 55], [15, 87], [15, 119], [15, 135], [17, 23], [17, 39], [17, 55], [17, 71], [17, 87], [17, 103], [17, 119], [17, 135], [19, 39], [19, 71], [19, 103], [19, 135], [20, 8], [21, 23], [21, 39], [21, 55], [21, 71], [21, 87], [21, 103], [21, 119], [21, 135], [23, 23], [23, 55], [23, 87], [23, 119], [23, 135], [25, 23], [25, 39], [25, 55], [25, 71], [25, 87], [25, 103], [25, 119], [25, 135], [27, 39], [27, 71], [27, 103], [27, 135], [28, 8], [29, 23], [29, 39], [29, 55], [29, 71], [29, 87], [29, 103], [29, 119], [29, 135], [31, 23], [31, 55], [31, 87], [31, 119], [31, 135], [33, 23], [33, 39], [33, 55], [33, 71], [33, 87], [33, 103], [33, 119], [33, 135], [35, 39], [35, 71], [35, 103], [35, 135], [36, 8], [37, 23], [37, 39], [37, 55], [37, 71], [37, 87], [37, 103], [37, 119], [37, 135], [39, 23], [39, 55], [39, 87], [39, 119], [39, 135], [41, 23], [41, 39], [41, 55], [41, 71], [41, 87], [41, 103], [41, 119], [41, 135], [43, 39], [43, 71], [43, 103], [43, 135], [44, 8], [45, 23], [45, 39], [45, 55], [45, 71], [45, 87], [45, 103], [45, 119], [45, 135], [47, 23], [47, 55], [47, 87], [47, 119], [47, 135], [0, 47], [0, 79], [0, 111], [0, 143], [1, 16], [2, 47], [2, 79], [2, 111], [2, 143], [3, 16], [4, 31], [4, 47], [4, 63], [4, 79], [4, 95], [4, 111], [4, 127], [4, 143], [6, 31], [6, 47], [6, 63], [6, 79], [6, 95], [6, 111], [6, 127], [6, 143], [8, 31], [8, 47], [8, 63], [8, 79], [8, 95], [8, 111], [8, 127], [8, 143], [10, 31], [10, 47], [10, 63], [10, 79], [10, 95], [10, 111], [10, 127], [10, 143], [12, 31], [12, 47], [12, 63], [12, 79], [12, 95], [12, 111], [12, 127], [12, 143], [14, 31], [14, 47], [14, 63], [14, 79], [14, 95], [14, 111], [14, 127], [14, 143], [16, 31], [16, 47], [16, 63], [16, 79], [16, 95], [16, 111], [16, 127], [16, 143], [18, 31], [18, 47], [18, 63], [18, 79], [18, 95], [18, 111], [18, 127], [18, 143], [20, 31], [20, 47], [20, 63], [20, 79], [20, 95], [20, 111], [20, 127], [20, 143], [22, 31], [22, 47], [22, 63], [22, 79], [22, 95], [22, 111], [22, 127], [22, 143], [24, 31], [24, 47], [24, 63], [24, 79], [24, 95], [24, 111], [24, 127], [24, 143], [26, 31], [26, 47], [26, 63], [26, 79], [26, 95], [26, 111], [26, 127], [26, 143], [28, 31], [28, 47], [28, 63], [28, 79], [28, 95], [28, 111], [28, 127], [28, 143], [30, 31], [30, 47], [30, 63], [30, 79], [30, 95], [30, 111], [30, 127], [30, 143], [32, 31], [32, 47], [32, 63], [32, 79], [32, 95], [32, 111], [32, 127], [32, 143], [34, 31], [34, 47], [34, 63], [34, 79], [34, 95], [34, 111], [34, 143], [36, 31], [36, 47], [36, 63], [36, 79], [36, 95], [36, 111], [36, 127], [36, 143], [38, 31], [38, 47], [38, 63], [38, 79], [38, 95], [38, 111], [38, 127], [38, 143], [40, 31], [40, 47], [40, 63], [40, 79], [40, 95], [40, 111], [40, 127], [40, 143], [42, 31], [42, 47], [42, 63], [42, 79], [42, 95], [42, 111], [42, 127], [42, 143], [44, 31], [44, 63], [44, 95], [44, 127], [44, 143], [46, 31], [46, 63], [46, 95], [46, 127], [46, 143]

Yet another set of oligonucleotide sequences used to produce 4H×12H×120B nucleic acid structures of the invention are designated SEQ ID NOs.1557-1892, and the corresponding 5' end coordinates are shown respectively in Table 6C. (See also Appendix, Table 4 of U.S. provisional application No. 61/675,309, filed Jul. 24, 2012, incorporated by reference herein.)

TABLE 6C

[1, 23], [1, 39], [1, 55], [1, 71], [1, 87], [1, 103], [1, 119], [1, 135], [3, 39], [3, 71], [3, 103], [3, 135], [4, 8], [5, 23], [5, 39], [5, 55], [5, 71], [5, 87], [5, 103], [5, 119], [5, 135], [7, 23], [7, 55], [7, 87], [7, 119], [7, 135], [9, 23], [9, 39], [9, 55], [9, 71], [9, 87], [9, 103], [9, 119], [9, 135], [11, 39], [11, 71], [11, 103], [11, 135], [12, 8], [13, 23], [13, 39], [13, 55], [13, 71], [13, 87], [13, 103], [13, 119], [13, 135], [15, 23], [15, 55], [15, 87], [15, 119], [15, 135], [17, 23], [17, 39], [17, 55], [17, 71], [17, 87], [17, 103], [17, 119], [17, 135], [19, 39], [19, 71], [19, 103], [19, 135], [20, 8], [21, 23], [21, 39], [21, 55], [21, 71], [21, 87], [21, 103], [21, 119], [21, 135], [23, 23], [23, 55], [23, 87], [23, 119], [23, 135], [25, 23], [25, 39], [25, 55], [25, 71], [25, 87], [25, 103], [25, 119], [25, 135], [27, 39], [27, 71], [27, 103], [27, 135], [28, 8], [29, 23], [29, 39], [29, 55], [29, 71], [29, 87], [29, 103], [29, 119], [29, 135], [31, 23], [31, 55], [31, 87], [31, 119], [31, 135], [33, 23], [33, 39], [33, 55], [33, 71], [33, 87], [33, 103], [33, 119], [33, 135], [35, 39], [35, 71], [35, 103], [35, 135], [36, 8], [37, 23], [37, 39], [37, 55], [37, 71], [37, 87], [37, 103], [37, 119], [37, 135], [39, 23], [39, 55], [39, 87], [39, 119], [39, 135], [41, 23], [41, 39], [41, 55], [41, 71], [41, 87], [41, 103], [41, 119], [41, 135], [43, 39], [43, 71], [43, 103], [43, 135], [44, 8], [45, 23], [45, 39], [45, 55], [45, 71], [45, 87], [45, 103], [45, 119], [45, 135], [47, 23], [47, 55], [47, 87], [47, 119], [47, 135], [0, 47], [0, 79], [0, 111], [0, 143], [1, 16], [2, 47], [2, 79], [2, 111], [2, 143], [3, 16], [4, 31], [4, 47], [4, 63], [4, 79], [4, 95], [4, 111], [4, 127], [4, 143], [6, 31], [6, 47], [6, 63], [6, 79], [6, 95], [6, 111], [6, 127], [6, 143], [8, 31], [8, 47], [8, 63], [8, 79], [8, 95], [8, 111], [8, 127], [8, 143], [10, 31], [10, 47], [10, 63], [10, 79], [10, 95], [10, 111], [10, 127], [10, 143], [12, 31], [12, 47], [12, 63], [12, 79], [12, 95], [12, 111], [12, 127], [12, 143], [14, 31], [14, 47], [14, 63], [14, 79], [14, 95], [14, 111], [14, 127], [14, 143], [16, 31], [16, 47], [16, 63], [16, 79], [16, 95], [16, 111], [16, 127], [16, 143], [18, 31], [18, 47], [18, 63], [18, 79], [18, 95], [18, 111], [18, 127], [18, 143], [20, 31], [20, 47], [20, 63], [20, 79], [20, 95], [20, 111], [20, 127], [20, 143], [22, 31], [22, 47], [22, 63], [22, 79], [22, 95], [22, 111], [22, 127], [22, 143], [24, 31], [24, 47], [24, 63], [24, 79], [24, 95], [24, 111], [24, 127], [24, 143], [26, 31], [26, 47], [26, 63], [26, 79], [26, 95], [26, 111], [26, 127], [26, 143], [28, 31], [28, 47], [28, 63], [28, 79], [28, 95], [28, 111], [28, 127], [28, 143], [30, 31], [30, 47], [30, 63], [30, 79], [30, 95], [30, 111], [30, 127], [30, 143], [32, 31], [32, 47], [32, 63], [32, 79], [32, 95], [32, 111], [32, 127], [32, 143], [34, 31], [34, 47], [34, 63], [34, 79], [34, 95], [34, 111], [34, 143], [36, 31], [36, 47], [36, 63], [36, 79], [36, 95], [36, 111], [36, 127], [36, 143], [38, 31], [38, 47], [38, 63], [38, 79], [38, 95], [38, 111], [38, 127], [38, 143], [40, 31], [40, 47], [40, 63], [40, 79], [40, 95], [40, 111], [40, 127], [40, 143], [42, 31], [42, 47], [42, 63], [42, 79], [42, 95], [42, 111], [42, 127], [42, 143], [44, 31], [44, 63], [44, 95], [44, 127], [44, 143], [46, 31], [46, 63], [46, 95], [46, 127], [46, 143]

The oligonucleotide sequences used to produce 6H×10H×128B nucleic acid structures of the invention are designated SEQ ID NOs. 1893-2351, and the corresponding 5' end coordinates are shown respectively in Table 7. (See also Appendix, Table 5 of U.S. provisional application No. 61/675,309, filed Jul. 24, 2012, incorporated by reference herein.)

TABLE 7

[1, 23], [1, 39], [1, 55], [1, 71], [1, 87], [1, 103], [1, 119], [1, 135], [3, 23], [3, 39], [3, 55], [3, 71], [3, 87], [3, 103], [3, 119], [3, 135], [5, 39], [5, 71], [5, 103], [5, 135], [6, 8], [7, 23], [7, 39], [7, 55], [7, 71], [7, 87], [7, 103], [7, 119], [7, 135], [9, 23], [9, 39], [9, 55], [9, 71], [9, 87], [9, 103], [9, 119], [9, 135], [11, 23], [11, 55], [11, 87], [11, 119], [11, 135], [13, 23], [13, 39], [13, 55], [13, 71], [13, 87], [13, 103], [13, 119], [13, 135], [15, 23], [15, 39], [15, 55], [15, 71], [15, 87], [15, 103], [15, 119], [15, 135], [17, 39], [17, 71], [17, 103], [17, 135], [18, 8], [19, 23], [19, 39], [19, 55], [19, 71], [19, 87], [19, 103], [19, 119], [19, 135], [21, 23], [21, 39], [21, 55], [21, 71], [21, 87], [21, 103], [21, 119], [21, 135], [23, 23], [23, 55], [23, 87], [23, 119], [23, 135], [25, 23], [25, 39], [25, 55], [25, 71], [25, 87], [25, 103], [25, 119], [25, 135], [27, 23], [27, 39], [27, 55], [27, 71], [27, 87], [27, 103], [27, 119], [27, 135], [29, 39], [29, 71],

TABLE 7-continued

[29, 103], [29, 135], [30, 8], [31, 23], [31, 39], [31, 55], [31, 71], [31, 87], [31, 103], [31, 119], [31, 135], [33, 23], [33, 39], [33, 55], [33, 71], [33, 87], [33, 103], [33, 119], [33, 135], [35, 23], [35, 55], [35, 87], [35, 119], [35, 135], [37, 23], [37, 39], [37, 55], [37, 71], [37, 87], [37, 103], [37, 119], [37, 135], [39, 23], [39, 39], [39, 55], [39, 71], [39, 87], [39, 103], [39, 119], [39, 135], [41, 39], [41, 71], [41, 103], [41, 135], [42, 8], [43, 23], [43, 39], [43, 55], [43, 71], [43, 87], [43, 103], [43, 119], [43, 135], [45, 23], [45, 39], [45, 55], [45, 71], [45, 87], [45, 103], [45, 119], [45, 135], [47, 23], [47, 55], [47, 87], [47, 119], [47, 135], [49, 23], [49, 39], [49, 55], [49, 71], [49, 87], [49, 103], [49, 119], [49, 135], [51, 23], [51, 39], [51, 55], [51, 71], [51, 87], [51, 103], [51, 119], [51, 135], [53, 39], [53, 71], [53, 103], [53, 135], [54, 8], [55, 23], [55, 39], [55, 55], [55, 71], [55, 87], [55, 103], [55, 119], [55, 135], [57, 23], [57, 39], [57, 55], [57, 71], [57, 87], [57, 103], [57, 119], [57, 135], [59, 23], [59, 55], [59, 87], [59, 119], [59, 135], [0, 15], [0, 47], [0, 79], [0, 111], [0, 143], [2, 15], [2, 47], [2, 79], [2, 111], [2, 143], [4, 15], [4, 47], [4, 79], [4, 111], [4, 143], [6, 15], [6, 31], [6, 47], [6, 63], [6, 79], [6, 95], [6, 111], [6, 127], [6, 143], [8, 15], [8, 31], [8, 47], [8, 63], [8, 79], [8, 95], [8, 111], [8, 127], [8, 143], [10, 15], [10, 31], [10, 47], [10, 63], [10, 79], [10, 95], [10, 111], [10, 127], [10, 143], [12, 15], [12, 31], [12, 47], [12, 63], [12, 79], [12, 95], [12, 111], [12, 127], [12, 143], [14, 15], [14, 31], [14, 47], [14, 63], [14, 79], [14, 95], [14, 111], [14, 127], [14, 143], [16, 15], [16, 31], [16, 47], [16, 63], [16, 79], [16, 95], [16, 111], [16, 127], [16, 143], [18, 15], [18, 31], [18, 47], [18, 63], [18, 79], [18, 95], [18, 111], [18, 127], [18, 143], [20, 15], [20, 31], [20, 47], [20, 63], [20, 79], [20, 95], [20, 111], [20, 127], [20, 143], [22, 15], [22, 31], [22, 47], [22, 63], [22, 79], [22, 95], [22, 111], [22, 127], [22, 143], [24, 15], [24, 31], [24, 47], [24, 63], [24, 79], [24, 95], [24, 111], [24, 127], [24, 143], [26, 15], [26, 31], [26, 47], [26, 63], [26, 79], [26, 95], [26, 111], [26, 127], [26, 143], [28, 15], [28, 31], [28, 47], [28, 63], [28, 79], [28, 95], [28, 111], [28, 127], [28, 143], [30, 15], [30, 31], [30, 47], [30, 63], [30, 79], [30, 95], [30, 111], [30, 127], [30, 143], [32, 15], [32, 31], [32, 47], [32, 63], [32, 79], [32, 95], [32, 111], [32, 127], [32, 143], [34, 15], [34, 31], [34, 47], [34, 63], [34, 79], [34, 95], [34, 111], [34, 127], [34, 143], [36, 15], [36, 31], [36, 47], [36, 63], [36, 79], [36, 95], [36, 111], [36, 127], [36, 143], [38, 15], [38, 31], [38, 47], [38, 63], [38, 79], [38, 95], [38, 111], [38, 127], [38, 143], [40, 15], [40, 31], [40, 47], [40, 63], [40, 79], [40, 95], [40, 111], [40, 127], [40, 143], [42, 15], [42, 31], [42, 47], [42, 63], [42, 79], [42, 95], [42, 111], [42, 127], [42, 143], [44, 15], [44, 31], [44, 47], [44, 63], [44, 79], [44, 95], [44, 111], [44, 127], [44, 143], [46, 15], [46, 31], [46, 47], [46, 63], [46, 79], [46, 95], [46, 111], [46, 127], [46, 143], [48, 15], [48, 31], [48, 47], [48, 63], [48, 79], [48, 95], [48, 111], [48, 127], [48, 143], [50, 15], [50, 31], [50, 47], [50, 63], [50, 79], [50, 95], [50, 111], [50, 127], [50, 143], [52, 15], [52, 31], [52, 47], [52, 63], [52, 79], [52, 95], [52, 111], [52, 127], [52, 143], [54, 31], [54, 63], [54, 95], [54, 127], [54, 143], [55, 0], [56, 31], [56, 63], [56, 95], [56, 127], [56, 143], [57, 0], [58, 31], [58, 63], [58, 95], [58, 127], [58, 143], [59, 0]

The oligonucleotide sequences used to produce 6H×10H×128B-M nucleic acid structures of the invention are designated SEQ ID NOs. 2352-2810, and the corresponding 5' end coordinates are shown respectively in Table 8. (See also Appendix, Table 6 of U.S. provisional application No. 61/675,309, filed Jul. 24, 2012, incorporated by reference herein.)

TABLE 8

[1, 23], [1, 39], [1, 55], [1, 71], [1, 87], [1, 103], [1, 119], [1, 135], [3, 23], [3, 39], [3, 55], [3, 71], [3, 87], [3, 103], [3, 119], [3, 135], [5, 39], [5, 71], [5, 103], [5, 135], [6, 8], [7, 23], [7, 39], [7, 55], [7, 71], [7, 87], [7, 103], [7, 119], [7, 135], [9, 23], [9, 39], [9, 55], [9, 71], [9, 87], [9, 103], [9, 119], [9, 135], [11, 23], [11, 55], [11, 87], [11, 119], [11, 135], [13, 23], [13, 39], [13, 55], [13, 71], [13, 87], [13, 103], [13, 119], [13, 135], [15, 23], [15, 39], [15, 55], [15, 71], [15, 87], [15, 103], [15, 119], [15, 135], [17, 39], [17, 71], [17, 103], [17, 135], [18, 8], [19, 23], [19, 39], [19, 55], [19, 71], [19, 87], [19, 103], [19, 119], [19, 135], [21, 23], [21, 39], [21, 55], [21, 71], [21, 87], [21, 103], [21, 119], [21, 135], [23, 23], [23, 55], [23, 87], [23, 119], [23, 135], [25, 23], [25, 39], [25, 55], [25, 71], [25, 87], [25, 103], [25, 119], [25, 135], [27, 23], [27, 39], [27, 55], [27, 71], [27, 87], [27, 103], [27, 119], [27, 135], [29, 39], [29, 71], [29, 103], [29, 135], [30, 8], [31, 23], [31, 39], [31, 55], [31, 71], [31, 87], [31, 103], [31, 119], [31, 135], [33, 23], [33, 39], [33, 55], [33, 71], [33, 87], [33, 103], [33, 119], [33, 135], [35, 23], [35, 55], [35, 87], [35, 119], [35, 135], [37, 23], [37, 39], [37, 55], [37, 71], [37, 87], [37, 103], [37, 119], [37, 135], [39, 23], [39, 39], [39, 55], [39, 71], [39, 87], [39, 103], [39, 119], [39, 135], [41, 39], [41, 71], [41, 103], [41, 135], [42, 8], [43, 23], [43, 39], [43, 55], [43, 71], [43, 87], [43, 103], [43, 119], [43, 135], [45, 23], [45, 39], [45, 55], [45, 71], [45, 87], [45, 103], [45, 119], [45, 135], [47, 23], [47, 55], [47, 87], [47, 119], [47, 135], [49, 23], [49, 39], [49, 55], [49, 71], [49, 87], [49, 103], [49, 119], [49, 135], [51, 23], [51, 39], [51, 55], [51, 71], [51, 87], [51, 103], [51, 119], [51, 135], [53, 39], [53, 71], [53, 103], [53, 135], [54, 8], [55, 23], [55, 39], [55, 55], [55, 71], [55, 87], [55, 103], [55, 119], [55, 135], [57, 23], [57, 39], [57, 55], [57, 71], [57, 87], [57, 103], [57, 119], [57, 135], [59, 23], [59, 55], [59, 87], [59, 119], [59, 135], [0, 47], [0, 79], [0, 111], [0, 143], [1, 0], [2, 47], [2, 79], [2, 111], [2, 143], [3, 0], [4, 47], [4, 79], [4, 111], [4, 143], [5, 0], [6, 31], [6, 47], [6, 63], [6, 79], [6, 95], [6, 111], [6, 127], [6, 143], [7, 0], [8, 31], [8, 47], [8, 63], [8, 79], [8, 95], [8, 111], [8, 127], [8, 143], [9, 0], [10, 31], [10, 47], [10, 63], [10, 79], [10, 95], [10, 111], [10, 127], [10, 143], [11, 0], [12, 31], [12, 47], [12, 63], [12, 79], [12, 95], [12, 111], [12, 127], [12, 143], [13, 0], [14, 31], [14, 47], [14, 63], [14, 79], [14, 95], [14, 111], [14, 127], [14, 143], [15, 0], [16, 31], [16, 47], [16, 63], [16, 79], [16, 95], [16, 111], [16, 127], [16, 143], [17, 0], [18, 31], [18, 47], [18, 63], [18, 79], [18, 95], [18, 111], [18, 127], [18, 143], [19, 0], [20, 31], [20, 47], [20, 63], [20, 79], [20, 95], [20, 111], [20, 127], [20, 143], [21, 0], [22, 31], [22, 47], [22, 63], [22, 79], [22, 95], [22, 111], [22, 127], [22, 143], [23, 0], [24, 31], [24, 47], [24, 63], [24, 79], [24, 95], [24, 111], [24, 127], [24, 143], [25, 0], [26, 31], [26, 47], [26, 63], [26, 79], [26, 95], [26, 111], [26, 127], [26, 143], [27, 0], [28, 31], [28, 47], [28, 63], [28, 79], [28, 95], [28, 111], [28, 127], [28, 143], [29, 0], [30, 31], [30, 47], [30, 63], [30, 79], [30, 95], [30, 111], [30, 127], [30, 143], [31, 0], [32, 31], [32, 47], [32, 63], [32, 79], [32, 95], [32, 111], [32, 127], [32, 143], [33, 0], [34, 31], [34, 47], [34, 63], [34, 79], [34, 95], [34, 111], [34, 127], [34, 143], [35, 0], [36, 31], [36, 47], [36, 63], [36, 79], [36, 95], [36, 111], [36, 127], [36, 143], [37, 0], [38, 31], [38, 47], [38, 63], [38, 79], [38, 95], [38, 111], [38, 127], [38, 143], [39, 0], [40, 31], [40, 47], [40, 63], [40, 79], [40, 95], [40, 111], [40, 127], [40, 143], [41, 0], [42, 31], [42, 47], [42, 63], [42, 79], [42, 95], [42, 111], [42, 127], [42, 143], [43, 0], [44, 31], [44, 47], [44, 63], [44, 79], [44, 95], [44, 111], [44, 127], [44, 143], [45, 0], [46, 31], [46, 47], [46, 63], [46, 79], [46, 95], [46, 111], [46, 127], [46, 143], [47, 0], [48, 31], [48, 47], [48, 63], [48, 79], [48, 95], [48, 111], [48, 127], [48, 143], [49, 0], [50, 31], [50, 47], [50, 63], [50, 79], [50, 95], [50, 111], [50, 127], [50, 143], [51, 0], [52, 31], [52, 47], [52, 63], [52, 79], [52, 95], [52, 111], [52, 127], [52, 143], [53, 0], [54, 31], [54, 63], [54, 95], [54, 127], [54, 143], [55, 0], [56, 31], [56, 63], [56, 95], [56, 127], [56, 143], [57, 0], [58, 31], [58, 63], [58, 95], [58, 127], [58, 143], [59, 0]

The core oligonucleotide sequences used to produce 3H×3H×32B nucleic acid structures of the invention are designated SEQ ID NOs. 2811-2822, and the corresponding voxel coordinates are shown respectively in Table 9A. The end oligonucleotide sequences used to produce 3H×3H×32B nucleic acid structures of the invention are designated SEQ ID NOs. 3195-3203, and the corresponding voxel coordinates are shown respectively in Table 9B. (See also Appendix, Table 7 of U.S. provisional application No. 61/675,309, filed Jul. 24, 2012, incorporated by reference herein.)

TABLE 9A

[0, 0, 0, 1, 0, 0, 0, 0], [0, 0, 2, 1, 0, 0, 0, 0], [0, 0, 7, 1, 0, 0, 0, 0], [0, 0, 4, 1, 0, 0, 1, 1, 1, 2, 1, 3], [2, 1, 2, 2, 0, 0, 0, 0], [5, 1, 5, 2, 0, 0, 0, 0], [8, 1, 8, 2, 0, 0, 0, 0], [1, 1, 1, 2, 0, 1, 0, 2, 0, 3, 0, 4], [7, 1, 7, 2, 6, 1, 6, 2, 6, 3, 6, 4], [6, 2, 6, 3, 0, 0, 6, 1, 0, 0, 5, 1], [8, 2, 8, 3, 0, 0, 8, 1, 0, 0, 3, 1], [3, 3, 3, 4, 3, 1, 3, 2, 4, 1, 4, 2].

TABLE 9B

[4, 2, 4, 3, 7, 2, 7, 3, 7, 4, 0, 0], [1, 3, 1, 4, 2, 3, 2, 4], [5, 3, 5, 4, 4, 3, 4, 4], [7, 3, 7, 4, 8, 3, 8, 4], [4, 4, 0, 0, 1, 4, 0, 0], [6, 4, 0, 0, 5, 4, 0, 0], [8, 4, 0, 0, 3, 4, 0, 0], [0, 4, 0, 0, 0, 2, 0, 3, 5, 2, 5, 3], [2, 4, 0, 0, 2, 2, 2, 3, 3, 2, 3, 3]

The core oligonucleotide sequences used to produce 3H×3H×64B nucleic acid structures of the invention are designated SEQ ID NOs. 2811-2834, and the corresponding voxel coordinates are shown respectively in Table 10A. The end oligonucleotide sequences used to produce 3H×3H×64B nucleic acid structures of the invention are designated SEQ ID NOs. 3203-3212, and the corresponding voxel coordinates are shown respectively in Table 10B. (See also Appendix, Table 7 of U.S. provisional application No. 61/675,309, filed Jul. 24, 2012, incorporated by reference herein.)

TABLE 10A

[0, 0, 0, 1, 0, 0, 0, 0], [0, 0, 2, 1, 0, 0, 0, 0], [0, 0, 7, 1, 0, 0, 0, 0], [0, 0, 4, 1, 0, 0, 1, 1, 1, 2, 1, 3], [2, 1, 2, 2, 0, 0, 0, 0], [5, 1, 5, 2, 0, 0, 0, 0], [8, 1, 8, 2, 0, 0, 0, 0], [1, 1, 1, 2, 0, 1, 0, 2, 0, 3, 0, 4], [7, 1, 7, 2, 6, 1, 6, 2, 6, 3, 6, 4], [6, 2, 6, 3, 0, 0, 6, 1, 0, 0, 5, 1], [8, 2, 8, 3, 0, 0, 8, 1, 0, 0, 3, 1], [3, 3, 3, 4, 3, 1, 3, 2, 4, 1, 4, 2], [4, 2, 4, 3, 7, 2, 7, 3, 7, 4, 7, 5], [1, 3, 1, 4, 2, 3, 2, 4, 2, 5, 2, 6], [7, 3, 7, 4, 8, 3, 8, 4, 8, 5, 8, 6], [0, 4, 0, 5, 0, 2, 0, 3, 5, 2, 5, 3], [4, 4, 4, 5, 1, 4, 1, 5, 1, 6, 1, 7], [2, 4, 2, 5, 2, 2, 2, 3, 3, 2, 3, 3], [1, 5, 1, 6, 0, 5, 0, 6, 0, 7, 0, 8], [5, 5, 5, 6, 5, 3, 5, 4, 4, 3, 4, 4], [7, 5, 7, 6, 6, 5, 6, 6, 6, 7, 6, 8], [6, 6, 6, 7, 6, 4, 6, 5, 5, 4, 5, 5], [8, 6, 8, 7, 8, 4, 8, 5, 3, 4, 3, 5][3, 7, 3, 8, 3, 5, 3, 6, 4, 5, 4, 6]

TABLE 10B

[2, 4, 0, 0, 2, 2, 2, 3, 3, 2, 3, 3], [4, 6, 4, 7, 7, 6, 7, 7, 7, 8, 0, 0], [1, 7, 1, 8, 2, 7, 2, 8], [5, 7, 5, 8, 4, 7, 4, 8], [7, 7, 7, 8, 8, 7, 8, 8], [4, 8, 0, 0, 1, 8, 0, 0], [6, 8, 0, 0, 5, 8, 0, 0], [8, 8, 0, 0, 3, 8, 0, 0], [0, 8, 0, 0, 6, 0, 7, 5, 6, 5, 7], [2, 8, 0, 0, 2, 6, 2, 7, 3, 6, 3, 7]

The core oligonucleotide sequences used to produce 3H×3H×128B nucleic acid structures of the invention are designated SEQ ID NOs. 2811-2858, and the corresponding voxel coordinates are shown respectively in Table 11A. The end oligonucleotide sequences used to produce 3H×3H×128B nucleic acid structures of the invention are designated SEQ ID NOs. 3213-3221, and the corresponding voxel coordinates are shown respectively in Table 11B. (See also Appendix, Table 7 of U.S. provisional application No. 61/675,309, filed Jul. 24, 2012, incorporated by reference herein.)

TABLE 11A

[0, 0, 0, 1, 0, 0, 0, 0], [0, 0, 2, 1, 0, 0, 0, 0], [0, 0, 7, 1, 0, 0, 0, 0], [0, 0, 4, 1, 0, 0, 1, 1, 1, 2, 1, 3], [2, 1, 2, 2, 0, 0, 0, 0], [5, 1, 5, 2, 0, 0, 0, 0], [8, 1, 8, 2, 0, 0, 0, 0], [1, 1, 1, 2, 0, 1, 0, 2, 0, 3, 0, 4], [7, 1, 7, 2, 6, 1, 6, 2, 6, 3, 6, 4], [6, 2, 6, 3, 0, 0, 6, 1, 0, 0, 5, 1], [8, 2, 8, 3, 0, 0, 8, 1, 0, 0, 3, 1], [3, 3, 3, 4, 3, 1, 3, 2, 4, 1, 4, 2], [4, 2, 4, 3, 7, 2, 7, 3, 7, 4, 7, 5], [1, 3, 1, 4, 2, 3, 2, 4, 2, 5, 2, 6], [7, 3, 7, 4, 8, 3, 8, 4, 8, 5, 8, 6], [0, 4, 0, 5, 0, 2, 0, 3, 5, 2, 5, 3], [4, 4, 4, 5, 1, 4, 1, 5, 1, 6, 1, 7], [2, 4, 2, 5, 2, 2, 2, 3, 3, 2, 3, 3], [1, 5, 1, 6, 0, 5, 0, 6, 0, 7, 0, 8], [5, 5, 5, 6, 5, 3, 5, 4, 4, 3, 4, 4], [7, 5, 7, 6, 6, 5, 6, 6, 6, 7, 6, 8], [6, 6, 6, 7, 6, 4, 6, 5, 5, 4, 5, 5], [8, 6, 8, 7, 8, 4, 8, 5, 3, 4, 3, 5], [3, 7, 3, 8, 3, 5, 3, 6, 4, 5, 4, 6], [4, 6, 4, 7, 7, 6, 7, 7, 7, 8, 7, 9], [1, 7, 1, 8, 2, 7, 2, 8, 2, 9, 2, 10], [7, 7, 7, 8, 8, 7, 8, 8, 8, 9, 8, 10], [0, 8, 0, 9, 0, 6, 0, 7, 5, 6, 5, 7], [4, 8, 4, 9, 1, 8, 1, 9, 1, 10, 1, 11], [2, 8, 2, 9, 2, 6, 2, 7, 3, 6, 3, 7], [1, 9, 1, 10, 0, 9, 0, 10, 0, 11, 0, 12], [5, 9, 5, 10, 5, 7, 5, 8, 4, 7, 4, 8], [7, 9, 7, 10, 6, 9, 6, 10, 6, 11, 6, 12], [6, 10, 6, 11, 6, 8, 6, 9, 5, 8, 5, 9], [4, 10, 4, 11, 7, 10, 7, 11, 7, 12, 7, 13], [8, 10, 8, 11, 8, 8, 8, 9, 3, 8, 3, 9], [1, 11, 1, 12, 2, 11, 2, 12, 2, 13, 2, 14], [3, 11, 3, 12, 3, 9, 3, 10, 4, 9, 4, 10], [7, 11, 7, 12, 8, 11, 8, 12, 8, 13, 8, 14], [0, 12, 0, 13, 0, 10, 0, 11, 5, 10, 5, 11], [4, 12, 4, 13, 1, 12, 1, 13, 1, 14, 1, 15], [2, 12, 2, 13, 2, 10, 2, 11, 3, 10, 3, 11], [1, 13, 1, 14, 0, 13, 0, 14, 0, 15, 0, 16], [5, 13, 5, 14, 5, 11, 5, 12, 4, 11, 4, 12], [7, 13, 7, 14, 6, 13, 6, 14, 6, 15, 6, 16], [6, 14, 6, 15, 6, 12, 6, 13, 5, 12, 5, 13], [8, 14, 8, 15, 8, 12, 8, 13, 3, 12, 3, 13], [3, 15, 3, 16, 3, 13, 3, 14, 4, 13, 4, 14]

TABLE 11B

[4, 14, 4, 15, 7, 14, 7, 15, 7, 16, 0, 0], [1, 15, 1, 16, 2, 15, 2, 16], [5, 15, 5, 16, 4, 15, 4, 16], [7, 15, 7, 16, 8, 15, 8, 16], [4, 16, 0, 0, 1, 16, 0, 0], [6, 16, 0, 0, 5, 16, 0, 0], [8, 16, 0, 0, 3, 16, 0, 0], [0, 16, 0, 0, 0, 14, 0, 15, 5, 14, 5, 15] and [2, 16, 0, 0, 2, 14, 2, 15, 3, 14, 3, 15]

The core oligonucleotide sequences used to produce 3H×3H×256B nucleic acid structures of the invention are designated SEQ ID NOs. 2811-2906 and the corresponding voxel coordinates are shown respectively in Table 12A. The end oligonucleotide sequences used to produce 3H×3H×256B nucleic acid structures of the invention are designated SEQ ID NOs. 3222-3230, and the corresponding voxel coordinates are shown respectively in Table 12B. (See also Appendix, Table 7 of U.S. provisional application No. 61/675,309, filed Jul. 24, 2012, incorporated by reference herein.)

TABLE 12A

[0, 0, 0, 1, 0, 0, 0, 0], [0, 0, 2, 1, 0, 0, 0, 0], [0, 0, 7, 1, 0, 0, 0, 0], [0, 0, 4, 1, 0, 0, 1, 1, 1, 2, 1, 3], [2, 1, 2, 2, 0, 0, 0, 0], [5, 1, 5, 2, 0, 0, 0, 0], [8, 1, 8, 2, 0, 0, 0, 0], [1, 1, 1, 2, 0, 1, 0, 2, 0, 3, 0, 4], [7, 1, 7, 2, 6, 1, 6, 2, 6, 3, 6, 4], [6, 2, 6, 3, 0, 0, 6, 1, 0, 0, 5, 1], [8, 2, 8, 3, 0, 0, 8, 1, 0, 0, 3, 1], [3, 3, 3, 4, 3, 1, 3, 2, 4, 1, 4, 2], [4, 2, 4, 3, 7, 2, 7, 3, 7, 4, 7, 5], [1, 3, 1, 4, 2, 3, 2, 4, 2, 5, 2, 6], [7, 3, 7, 4, 8, 3, 8,

TABLE 12A-continued 4, 8, 5, 8, 6], [0, 4, 0, 5, 0, 2, 0, 3, 5, 2, 5, 3], [4, 4, 4, 5, 1, 4, 1, 5, 1, 6, 1, 7], [2, 4, 2, 5, 2, 2, 2, 3, 3, 2, 3, 3], [1, 5, 1, 6, 0, 5, 0, 6, 0, 7, 0, 8], [5, 5, 5, 6, 5, 3, 5, 4, 4, 3, 4, 4], [7, 5, 7, 6, 6, 5, 6, 6, 6, 7, 6, 8], [6, 6, 6, 7, 6, 4, 6, 5, 5, 4, 5, 5], [8, 6, 8, 7, 8, 4, 8, 5, 3, 4, 3, 5], [3, 7, 3, 8, 3, 5, 3, 6, 4, 5, 4, 6], [4, 6, 4, 7, 7, 6, 7, 7, 7, 8, 7, 9], [1, 7, 1, 8, 2, 7, 2, 8, 2, 9, 2, 10], [7, 7, 7, 8, 8, 7, 8, 8, 8, 9, 8, 10], [0, 8, 0, 9, 0, 6, 0, 7, 5, 6, 5, 7], [4, 8, 4, 9, 1, 8, 1, 9, 1, 10, 1, 11], [2, 8, 2, 9, 2, 6, 2, 7, 3, 6, 3, 7], [1, 9, 1, 10, 0, 9, 0, 10, 0, 11, 0, 12], [5, 9, 5, 10, 5, 7, 5, 8, 4, 7, 4, 8], [7, 9, 7, 10, 6, 9, 6, 10, 6, 11, 6, 12], [6, 10, 6, 11, 6, 8, 6, 9, 5, 8, 5, 9], [4, 10, 4, 11, 7, 10, 7, 11, 7, 12, 7, 13], [8, 10, 8, 11, 8, 8, 8, 9, 3, 8, 3, 9], [1, 11, 1, 12, 2, 11, 2, 12, 2, 13, 2, 14], [3, 11, 3, 12, 3, 9, 3, 10, 4, 9, 4, 10], [7, 11, 7, 12, 8, 11, 8, 12, 8, 13, 8, 14], [0, 12, 0, 13, 0, 10, 0, 11, 5, 10, 5, 11], [4, 12, 4, 13, 1, 12, 1, 13, 1, 14, 1, 15], [2, 12, 2, 13, 2, 10, 2, 11, 3, 10, 3, 11], [1, 13, 1, 14, 0, 13, 0, 14, 0, 15, 0, 16], [5, 13, 5, 14, 5, 11, 5, 12, 4, 11, 4, 12], [7, 13, 7, 14, 6, 13, 6, 14, 6, 15, 6, 16], [6, 14, 6, 15, 6, 12, 6, 13, 5, 12, 5, 13], [8, 14, 8, 15, 8, 12, 8, 13, 3, 12, 3, 13], [3, 15, 3, 16, 3, 13, 3, 14, 4, 13, 4, 14], [4, 14, 4, 15, 7, 14, 7, 15, 7, 16, 7, 17], [1, 15, 1, 16, 2, 15, 2, 16, 2, 17, 2, 18], [7, 15, 7, 16, 8, 15, 8, 16, 8, 17, 8, 18], [0, 16, 0, 17, 0, 14, 0, 15, 5, 14, 5, 15], [4, 16, 4, 17, 1, 16, 1, 17, 1, 18, 1, 19], [2, 16, 2, 17, 2, 14, 2, 15, 3, 14, 3, 15], [1, 17, 1, 18, 0, 17, 0, 18, 0, 19, 0, 20], [5, 17, 5, 18, 5, 15, 5, 16, 4, 15, 4, 16], [7, 17, 7, 18, 6, 17, 6, 18, 6, 19, 6, 20], [6, 18, 6, 19, 6, 16, 6, 17, 5, 16, 5, 17], [4, 18, 4, 19, 7, 18, 7, 19, 7, 20, 7, 21], [8, 18, 8, 19, 8, 16, 8, 17, 3, 16, 3, 17], [1, 19, 1, 20, 2, 19, 2, 20, 2, 21, 2, 22], [3, 19, 3, 20, 3, 17, 3, 18, 4, 17, 4, 18], [7, 19, 7, 20, 8, 19, 8, 20, 8, 21, 8, 22], [0, 20, 0, 21, 0, 18, 0, 19, 5, 18, 5, 19], [4, 20, 4, 21, 1, 20, 1, 21, 1, 22, 1, 23], [2, 20, 2, 21, 2, 18, 2, 19, 3, 18, 3, 19], [1, 21, 1, 22, 0, 21, 0, 22, 0, 23, 0, 24], [5, 21, 5, 22, 5, 19, 5, 20, 4, 19, 4, 20], [7, 21, 7, 22, 6, 21, 6, 22, 6, 23, 6, 24], [6, 22, 6, 23, 6, 20, 6, 21, 5, 20, 5, 21], [4, 22, 4, 23, 7, 22, 7, 23, 7, 24, 7, 25], [8, 22, 8, 23, 8, 20, 8, 21, 3, 20, 3, 21], [1, 23, 1, 24, 2, 23, 2, 24, 2, 25, 2, 26], [3, 23, 3, 24, 3, 21, 3, 22, 4, 21, 4, 22], [7, 23, 7, 24, 8, 23, 8, 24, 8, 25, 8, 26], [0, 24, 0, 25, 0, 22, 0, 23, 5, 22, 5, 23], [4, 24, 4, 25, 1, 24, 1, 25, 1, 26, 1, 27], [2, 24, 2, 25, 2, 22, 2, 23, 3, 22, 3, 23], [1, 25, 1, 26, 0, 25, 0, 26, 0, 27, 0, 28], [5, 25, 5, 26, 5, 23, 5, 24, 4, 23, 4, 24], [7, 25, 7, 26, 6, 25, 6, 26, 6, 27, 6, 28], [6, 26, 6, 27, 6, 24, 6, 25, 5, 24, 5, 25], [4, 26, 4, 27, 7, 26, 7, 27, 7, 28, 7, 29], [8, 26, 8, 27, 8, 24, 8, 25, 3, 24, 3, 25], [1, 27, 1, 28, 2, 27, 2, 28, 2, 29, 2, 30], [3, 27, 3, 28, 3, 25, 3, 26, 4, 25, 4, 26], [7, 27, 7, 28, 8, 27, 8, 28, 8, 29, 8, 30], [0, 28, 0, 29, 0, 26, 0, 27, 5, 26, 5, 27], [4, 28, 4, 29, 1, 28, 1, 29, 1, 30, 1, 31], [2, 28, 2, 29, 2, 26, 2, 27, 3, 26, 3, 27], [1, 29, 1, 30, 0, 29, 0, 30, 0, 31, 0, 32], [5, 29, 5, 30, 5, 27, 5, 28, 4, 27, 4, 28], [7, 29, 7, 30, 6, 29, 6, 30, 6, 31, 6, 32], [6, 30, 6, 31, 6, 28, 6, 29, 5, 28, 5, 29], [8, 30, 8, 31, 8, 28, 8, 29, 3, 28, 3, 29], [3, 31, 3, 32, 3, 29, 3, 30, 4, 29, 4, 30]

TABLE 12B

[4, 30, 4, 31, 7, 30, 7, 31, 7, 32, 0, 0], [1, 31, 1, 32, 2, 31, 2, 32], [5, 31, 5, 32, 4, 31, 4, 32], [7, 31, 7, 32, 8, 31, 8, 32], [4, 32, 0, 0, 1, 32, 0, 0], [6, 32, 0, 0, 5, 32, 0, 0], [8, 32, 0, 0, 3, 32, 0, 0], [0, 32, 0, 0, 0, 30, 0, 31, 5, 30, 5, 31], [2, 32, 0, 0, 2, 30, 2, 31, 3, 30, 3, 31],

The core oligonucleotide sequences used to produce 3H×3H×512B nucleic acid structures of the invention are designated SEQ ID NOs. 2811-3002, and the corresponding voxel coordinates are shown respectively in Table 13A. The end oligonucleotide sequences used to produce 3H×3H×512B nucleic acid structures of the invention are designated SEQ ID NOs. 3231-3239, and the corresponding voxel coordinates are shown respectively in Table 13B. (See also Appendix, Table 7 of U.S. provisional application No. 61/675,309, filed Jul. 24, 2012, incorporated by reference herein.)

TABLE 13A

[0, 0, 0, 1, 0, 0, 0, 0], [0, 0, 2, 1, 0, 0, 0, 0], [0, 0, 7, 1, 0, 0, 0, 0], [0, 0, 4, 1, 0, 0, 1, 1, 1, 2, 1, 3], [2, 1, 2, 2, 0, 0, 0, 0], [5, 1, 5, 2, 0, 0, 0, 0], [8, 1, 8, 2, 0, 0, 0, 0], [1, 1, 1, 2, 0, 1, 0, 2, 0, 3, 0, 4], [7, 1, 7, 2, 6, 1, 6, 2, 6, 3, 6, 4], [6, 2, 6, 3, 0, 0, 6, 1, 0, 0, 5, 1], [8, 2, 8, 3, 0, 0, 8, 1, 0, 0, 3, 1], [3, 3, 3, 4, 3, 1, 3, 2, 4, 1, 4, 2], [4, 2, 4, 3, 7, 2, 7, 3, 7, 4, 7, 5], [1, 3, 1, 4, 2, 3, 2, 4, 2, 5, 2, 6], [7, 3, 7, 4, 8, 3, 8, 4, 8, 5, 8, 6], [0, 4, 0, 5, 0, 2, 0, 3, 5, 2, 5, 3], [4, 4, 4, 5, 1, 4, 1, 5, 1, 6, 1, 7], [2, 4, 2, 5, 2, 2, 2, 3, 3, 2, 3, 3], [1, 5, 1, 6, 0, 5, 0, 6, 0, 7, 0, 8], [5, 5, 5, 6, 5, 3, 5, 4, 4, 3, 4, 4], [7, 5, 7, 6, 6, 5, 6, 6, 6, 7, 6, 8], [6, 6, 6, 7, 6, 4, 6, 5, 5, 4, 5, 5], [8, 6, 8, 7, 8, 4, 8, 5, 3, 4, 3, 5], [3, 7, 3, 8, 3, 5, 3, 6, 4, 5, 4, 6], [4, 6, 4, 7, 7, 6, 7, 7, 7, 8, 7, 9], [1, 7, 1, 8, 2, 7, 2, 8, 2, 9, 2, 10], [7, 7, 7, 8, 8, 7, 8, 8, 8, 9, 8, 10], [0, 8, 0, 9, 0, 6, 0, 7, 5, 6, 5, 7], [4, 8, 4, 9, 1, 8, 1, 9, 1, 10, 1, 11], [2, 8, 2, 9, 2, 6, 2, 7, 3, 6, 3, 7], [1, 9, 1, 10, 0, 9, 0, 10, 0, 11, 0, 12], [5, 9, 5, 10, 5, 7, 5, 8, 4, 7, 4, 8], [7, 9, 7, 10, 6, 9, 6, 10, 6, 11, 6, 12], [6, 10, 6, 11, 6, 8, 6, 9, 5, 8, 5, 9], [4, 10, 4, 11, 7, 10, 7, 11, 7, 12, 7, 13], [8, 10, 8, 11, 8, 8, 8, 9, 3, 8, 3, 9], [1, 11, 1, 12, 2, 11, 2, 12, 2, 13, 2, 14], [3, 11, 3, 12, 3, 9, 3, 10, 4, 9, 4, 10], [7, 11, 7, 12, 8, 11, 8, 12, 8, 13, 8, 14], [0, 12, 0, 13, 0, 10, 0, 11, 5, 10, 5, 11], [4, 12, 4, 13, 1, 12, 1, 13, 1, 14, 1, 15], [2, 12, 2, 13, 2, 10, 2, 11, 3, 10, 3, 11], [1, 13, 1, 14, 0, 13, 0, 14, 0, 15, 0, 16], [5, 13, 5, 14, 5, 11, 5, 12, 4, 11, 4, 12], [7, 13, 7, 14, 6, 13, 6, 14, 6, 15, 6, 16], [6, 14, 6, 15, 6, 12, 6, 13, 5, 12, 5, 13], [8, 14, 8, 15, 8, 12, 8, 13, 3, 12, 3, 13], [3, 15, 3, 16, 3, 13, 3, 14, 4, 13, 4, 14], [4, 14, 4, 15, 7, 14, 7, 15, 7, 16, 7, 17], [1, 15, 1, 16, 2, 15, 2, 16, 2, 17, 2, 18], [7, 15, 7, 16, 8, 15, 8, 16, 8, 17, 8, 18], [0, 16, 0, 17, 0, 14, 0, 15, 5, 14, 5, 15], [4, 16, 4, 17, 1, 16, 1, 17, 1, 18, 1, 19], [2, 16, 2, 17, 2, 14, 2, 15, 3, 14, 3, 15], [1, 17, 1, 18, 0, 17, 0, 18, 0, 19, 0, 20], [5, 17, 5, 18, 5, 15, 5, 16, 4, 15, 4, 16], [7, 17, 7, 18, 6, 17, 6, 18, 6, 19, 6, 20], [6, 18, 6, 19, 6, 16, 6, 17, 5, 16, 5, 17], [4, 18, 4, 19, 7, 18, 7, 19, 7, 20, 7, 21], [8, 18, 8, 19, 8, 16, 8, 17, 3, 16, 3, 17], [1, 19, 1, 20, 2, 19, 2, 20, 2, 21, 2, 22], [3, 19, 3, 20, 3, 17, 3, 18, 4, 17, 4, 18], [7, 19, 7, 20, 8, 19, 8, 20, 8, 21, 8, 22], [0, 20, 0, 21, 0, 18, 0, 19, 5, 18, 5, 19], [4, 20, 4, 21, 1, 20, 1, 21, 1, 22, 1, 23], [2, 20, 2, 21, 2, 18, 2, 19, 3, 18, 3, 19], [1, 21, 1, 22, 0, 21, 0, 22, 0, 23, 0, 24], [5, 21, 5, 22, 5, 19, 5, 20, 4, 19, 4, 20], [7, 21, 7, 22, 6, 21, 6, 22, 6, 23, 6, 24], [6, 22, 6, 23, 6, 20, 6, 21, 5, 20, 5, 21], [4, 22, 4, 23, 7, 22, 7, 23, 7, 24, 7, 25], [8, 22, 8, 23, 8, 20, 8, 21, 3, 20, 3, 21], [1, 23, 1, 24, 2, 23, 2, 24, 2, 25, 2, 26], [3, 23, 3, 24, 3, 21, 3, 22, 4, 21, 4, 22], [7, 23, 7, 24, 8, 23, 8, 24, 8, 25, 8, 26], [0, 24, 0, 25, 0, 22, 0, 23, 5, 22, 5, 23], [4, 24, 4, 25, 1, 24, 1, 25, 1, 26, 1, 27], [2, 24, 2, 25, 2, 22, 2, 23, 3, 22, 3, 23], [1, 25, 1, 26, 0, 25, 0, 26, 0, 27, 0, 28], [5, 25, 5, 26, 5, 23, 5, 24, 4, 23, 4, 24], [7, 25, 7, 26, 6, 25, 6, 26, 6, 27, 6, 28], [6, 26, 6, 27, 6, 24, 6, 25, 5, 24, 5, 25], [4, 26, 4, 27, 7, 26, 7, 27, 7, 28, 7, 29], [8, 26, 8, 27, 8, 24, 8, 25, 3, 24, 3, 25], [1, 27, 1, 28, 2, 27, 2, 28, 2, 29, 2, 30], [3, 27, 3, 28, 3, 25, 3, 26, 4, 25, 4, 26], [7, 27, 7, 28, 8, 27, 8, 28, 8, 29, 8, 30], [0, 28, 0, 29, 0, 26, 0, 27, 5, 26, 5, 27], [4, 28, 4, 29, 1, 28, 1, 29, 1, 30, 1, 31], [2, 28, 2, 29, 2, 26, 2, 27, 3, 26, 3, 27], [1, 29, 1, 30, 0, 29, 0, 30, 0, 31, 0, 32], [5, 29, 5, 30, 5, 27, 5, 28, 4, 27, 4, 28], [7, 29, 7, 30, 6, 29, 6, 30, 6, 31, 6, 32], [6, 30, 6, 31, 6, 28, 6, 29, 5, 28, 5, 29], [8, 30, 8, 31, 8, 28, 8, 29, 3, 28, 3, 29], [3, 31, 3, 32, 3, 29, 3, 30, 4, 29, 4, 30], [4, 30, 4, 31, 7, 30, 7, 31, 7, 32, 7, 33], [1, 31, 1, 32, 2, 31, 2, 32, 2, 33, 2, 34], [7, 31, 7, 32, 8, 31, 8, 32, 8, 33, 8, 34], [0, 32, 0, 33, 0, 30, 0, 31, 5, 30, 5, 31], [4, 32, 4, 33, 1, 32, 1, 33, 1, 34, 1, 35], [2, 32, 2, 33, 2, 30, 2, 31, 3, 30, 3, 31], [1, 33, 1, 34, 0, 33, 0, 34, 0, 35, 0, 36], [5, 33, 5, 34, 5, 31, 5, 32, 4, 31, 4, 32], [7, 33, 7, 34, 6, 33, 6, 34, 6, 35, 6, 36], [6, 34, 6, 35, 6, 32, 6, 33, 5, 32, 5, 33], [4, 34, 4, 35, 7, 34, 7, 35, 7, 36, 7, 37], [8, 34, 8, 35, 8, 32, 8, 33, 3, 32, 3, 33], [1, 35, 1, 36, 2, 35, 2, 36, 2, 37, 2, 38], [3, 35, 3, 36, 3, 33, 3, 34, 4, 33, 4, 34], [7, 35, 7, 36, 8, 35, 8, 36, 8, 37, 8, 38], [0, 36, 0, 37, 0, 34, 0, 35, 5, 34, 5, 35], [4, 36, 4, 37, 1, 36, 1, 37, 1, 38, 1, 39], [2, 36, 2, 37, 2, 34, 2, 35, 3, 34, 3, 35], [1, 37, 1, 38, 0, 37, 0, 38, 0, 39, 0, 40], [5, 37, 5, 38, 5, 35, 5, 36, 4, 35, 4, 36], [7, 37, 7, 38, 6, 37, 6, 38, 6, 39, 6, 40], [6, 38, 6, 39, 6, 36, 6, 37, 5, 36, 5, 37], [4, 38, 4, 39, 7, 38, 7, 39, 7, 40, 7, 41], [8, 38, 8, 39, 8, 36, 8, 37, 3, 36, 3, 37], [1, 39, 1, 40, 2, 39, 2, 40, 2, 41, 2, 42], [3, 39, 3, 40, 3, 37, 3, 38, 4, 37, 4, 38], [7, 39, 7, 40, 8, 39, 8, 40, 8, 41, 8, 42], [0, 40, 0, 41, 0, 38, 0, 39, 5, 38, 5, 39], [4, 40, 4, 41, 1, 40, 1, 41, 1, 42, 1, 43], [2, 40, 2, 41, 2, 38, 2, 39, 3, 38, 3, 39], [1, 41, 1, 42, 0, 41, 0, 42, 0, 43, 0, 44], [5, 41, 5, 42, 5, 39, 5, 40, 4, 39, 4, 40], [7, 41, 7, 42, 6, 41, 6, 42, 6, 43, 6, 44], [6, 42, 6, 43, 6, 40, 6, 41, 5, 40, 5, 41], [4, 42, 4, 43, 7, 42, 7, 43, 7, 44, 7, 45], [8, 42, 8, 43, 8, 40, 8, 41, 3, 40, 3, 41], [1, 43, 1, 44, 2, 43, 2, 44, 2, 45, 2, 46], [3, 43, 3, 44, 3, 41, 3, 42, 4, 41, 4, 42], [7, 43, 7, 44, 8, 43, 8, 44, 8, 45, 8, 46], [0, 44, 0, 45, 0, 42, 0, 43, 5, 42, 5, 43], [4, 44, 4, 45, 1, 44, 1, 45, 1, 46, 1, 47], [2, 44, 2, 45, 2, 42, 2, 43, 3, 42, 3, 43], [1, 45, 1, 46, 0, 45, 0, 46, 0, 47, 0, 48], [5, 45, 5, 46, 5, 43, 5, 44, 4, 43, 4, 44], [7, 45, 7, 46, 6, 45, 6, 46, 6, 47, 6, 48], [6, 46, 6, 47, 6, 44, 6, 45, 5, 44, 5, 45], [4, 46, 4, 47, 7, 46, 7, 47, 7, 48, 7, 49], [8, 46, 8, 47, 8, 44, 8, 45, 3, 44, 3, 45], [1, 47, 1, 48, 2,

TABLE 13A-continued 47, 2, 48, 2, 49, 2, 50], [3, 47, 3, 48, 3, 45, 3, 46, 4, 45, 4, 46], [7, 47, 7, 48, 8, 47, 8, 48, 8, 49, 8, 50], [0, 48, 0, 49, 0, 46, 0, 47, 5, 46, 5, 47], [4, 48, 4, 49, 1, 48, 1, 49, 1, 50, 1, 51], [2, 48, 2, 49, 2, 46, 2, 47, 3, 46, 3, 47], [1, 49, 1, 50, 0, 49, 0, 50, 0, 51, 0, 52], [5, 49, 5, 50, 5, 47, 5, 48, 4, 47, 4, 48], [7, 49, 7, 50, 6, 49, 6, 50, 6, 51, 6, 52], [6, 50, 6, 51, 6, 48, 6, 49, 5, 48, 5, 49], [4, 50, 4, 51, 7, 50, 7, 51, 7, 52, 7, 53], [8, 50, 8, 51, 8, 48, 8, 49, 3, 48, 3, 49], [1, 51, 1, 52, 2, 51, 2, 52, 2, 53, 2, 54], [3, 51, 3, 52, 3, 49, 3, 50, 4, 49, 4, 50], [7, 51, 7, 52, 8, 51, 8, 52, 8, 53, 8, 54], [0, 52, 0, 53, 0, 50, 0, 51, 5, 50, 5, 51], [4, 52, 4, 53, 1, 52, 1, 53, 1, 54, 1, 55], [2, 52, 2, 53, 2, 50, 2, 51, 3, 50, 3, 51], [1, 53, 1, 54, 0, 53, 0, 54, 0, 55, 0, 56], [5, 53, 5, 54, 5, 51, 5, 52, 4, 51, 4, 52], [7, 53, 7, 54, 6, 53, 6, 54, 6, 55, 6, 56], [6, 54, 6, 55, 6, 52, 6, 53, 5, 52, 5, 53], [4, 54, 4, 55, 7, 54, 7, 55, 7, 56, 7, 57], [8, 54, 8, 55, 8, 52, 8, 53, 3, 52, 3, 53], [1, 55, 1, 56, 2, 55, 2, 56, 2, 57, 2, 58], [3, 55, 3, 56, 3, 53, 3, 54, 4, 53, 4, 54], [7, 55, 7, 56, 8, 55, 8, 56, 8, 57, 8, 58], [0, 56, 0, 57, 0, 54, 0, 55, 5, 54, 5, 55], [4, 56, 4, 57, 1, 56, 1, 57, 1, 58, 1, 59], [2, 56, 2, 57, 2, 54, 2, 55, 3, 54, 3, 55], [1, 57, 1, 58, 0, 57, 0, 58, 0, 59, 0, 60], [5, 57, 5, 58, 5, 55, 5, 56, 4, 55, 4, 56], [7, 57, 7, 58, 6, 57, 6, 58, 6, 59, 6, 60], [6, 58, 6, 59, 6, 56, 6, 57, 5, 56, 5, 57], [4, 58, 4, 59, 7, 58, 7, 59, 7, 60, 7, 61], [8, 58, 8, 59, 8, 56, 8, 57, 3, 56, 3, 57], [1, 59, 1, 60, 2, 59, 2, 60, 2, 61, 2, 62], [3, 59, 3, 60, 3, 57, 3, 58, 4, 57, 4, 58], [7, 59, 7, 60, 8, 59, 8, 60, 8, 61, 8, 62], [0, 60, 0, 61, 0, 58, 0, 59, 5, 58, 5, 59], [4, 60, 4, 61, 1, 60, 1, 61, 1, 62, 1, 63], [2, 60, 2, 61, 2, 58, 2, 59, 3, 58, 3, 59], [1, 61, 1, 62, 0, 61, 0, 62, 0, 63, 0, 64], [5, 61, 5, 62, 5, 59, 5, 60, 4, 59, 4, 60], [7, 61, 7, 62, 6, 61, 6, 62, 6, 63, 6, 64], [6, 62, 6, 63, 6, 60, 6, 61, 5, 60, 5, 61], [8, 62, 8, 63, 8, 60, 8, 61, 3, 60, 3, 61], [3, 63, 3, 64, 3, 61, 3, 62, 4, 61, 4, 62]

TABLE 13B

[4, 62, 4, 63, 7, 62, 7, 63, 7, 64, 0, 0], [1, 63, 1, 64, 4, 63, 4, 64], [7, 64, 2, 63, 2, 64], [5, 63, 5, 63, 7, 64, 8, 63, 8, 64], [4, 64, 0, 0, 1, 64, 0, 0], [6, 64, 0, 0, 5, 64, 0, 0], [8, 64, 0, 0, 3, 64, 0, 0], [0, 64, 0, 0, 0, 62, 0, 63, 5, 62, 5, 63], [2, 64, 0, 0, 2, 62, 2, 63, 3, 62, 3, 63]

The core oligonucleotide sequences used to produce 3H×3H×1024B nucleic acid structures of the invention are designated SEQ ID NOs. 2811-3194, and the corresponding voxel coordinates are shown respectively in Table 14A. The end oligonucleotide sequences used to produce 3H×3H×1024B nucleic acid structures of the invention are designated SEQ ID NOs. 3240-3248, and the corresponding voxel coordinates are shown respectively in Table 14B. (See also Appendix, Table 7 of U.S. provisional application No. 61/675,309, filed Jul. 24, 2012, incorporated by reference herein.)

TABLE 14A

[0, 0, 0, 1, 0, 0, 0, 0], [0, 0, 2, 1, 0, 0, 0, 0], [0, 0, 7, 1, 0, 0, 0, 0], [0, 0, 4, 1, 0, 0, 1, 1, 1, 2, 1, 3], [2, 1, 2, 2, 0, 0, 0, 0], [5, 1, 5, 2, 0, 0, 0, 0], [8, 1, 8, 2, 0, 0, 0, 0], [1, 1, 1, 2, 0, 1, 0, 2, 0, 3, 0, 4], [7, 1, 7, 2, 6, 1, 6, 2, 6, 3, 6, 4], [6, 2, 6, 3, 0, 0, 6, 1, 0, 0, 5, 1], [8, 2, 8, 3, 0, 0, 8, 1, 0, 0, 0, 3, 1], [3, 3, 3, 4, 3, 1, 3, 2, 4, 1, 4, 2], [4, 2, 4, 3, 7, 2, 7, 3, 7, 4, 7, 5], [1, 3, 1, 4, 2, 3, 2, 4, 2, 5, 2, 6], [7, 3, 7, 4, 8, 3, 8, 4, 8, 5, 8, 6], [0, 4, 0, 5, 0, 2, 0, 3, 5, 2, 5, 3], [4, 4, 4, 5, 1, 4, 1, 5, 1, 6, 1, 7], [2, 4, 2, 5, 2, 2, 2, 3, 3, 2, 3, 3], [1, 5, 1, 6, 0, 5, 0, 6, 0, 7, 0, 8], [5, 5, 5, 6, 5, 3, 5, 4, 4, 3, 4, 4], [7, 5, 7, 6, 6, 5, 6, 6, 6, 7, 6, 8], [6, 6, 6, 7, 6, 4, 6, 5, 5, 4, 5, 5], [8, 6, 8, 7, 8, 4, 8, 5, 3, 4, 3, 5], [3, 7, 3, 8, 3, 5, 3, 6, 4, 5, 4, 6], [4, 6, 4, 7, 7, 6, 7, 7, 7, 8, 7, 9], [1, 7, 1, 8, 2, 7, 2, 8, 2, 9, 2, 10], [7, 7, 7, 8, 8, 7, 8, 8, 8, 9, 8, 10], [0, 8, 0, 9, 0, 6, 0, 7, 5, 6, 5, 7], [4, 8, 4, 9, 1, 8, 1, 9, 1, 10, 1, 11], [2, 8, 2, 9, 2, 6, 2, 7, 3, 6, 3, 7], [1, 9, 1, 10, 0, 9, 0, 10, 0, 11, 0, 12], [5, 9, 5, 10, 5, 7, 5, 8, 4, 7, 4, 8], [7, 9, 7, 10, 6, 9, 6, 10, 6, 11, 6, 12], [6, 10, 6, 11, 6, 8, 6, 9, 5, 8, 5, 9], [4, 10, 4, 11, 7, 10, 7, 11, 7, 12, 7, 13], [8, 10, 8, 11, 8, 8, 8, 9, 3, 8, 3, 9], [1, 11, 1, 12, 2, 11, 2, 12, 2, 13, 2, 14], [3, 11, 3, 12, 3, 9, 3, 10, 4, 9, 4, 10], [7, 11, 7, 12, 8, 11, 8, 12, 8, 13, 8, 14], [0, 12, 0, 13, 0, 10, 0, 11, 5, 10, 5, 11], [4, 12, 4, 13, 1, 12, 1, 13, 1, 14, 1, 15], [2, 12, 2, 13, 2, 10, 2, 11, 3, 10, 3, 11], [1, 13, 1, 14, 0, 13, 0, 14, 0, 15, 0, 16], [5, 13, 5, 14, 5, 11, 5, 12, 4, 11, 4, 12], [7, 13, 7, 14, 6, 13, 6, 14, 6, 15, 6, 16], [6, 14, 6, 15, 6, 12, 6, 13, 5, 12, 5, 13], [8, 14, 8, 15, 8, 12, 8, 13, 3, 12, 3, 13], [3, 15, 3, 16, 3, 13, 3, 14, 4, 13, 4, 14], [4, 14, 4, 15, 7, 14, 7, 15, 7, 16, 7, 17], [1, 15, 1, 16, 2, 15, 2, 16, 2, 17, 2, 18], [7, 15, 7, 16, 8, 15, 8, 16, 8, 17, 8, 18], [0, 16, 0, 17, 0, 14, 0, 15, 5, 14, 5, 15], [4, 16, 4, 17, 1, 16, 1, 17, 1, 18, 1, 19], [2, 16, 2, 17, 2, 14, 2, 15, 3, 14, 3, 15], [1, 17, 1, 18, 0, 17, 0, 18, 0, 19, 0, 20], [5, 17, 5, 18, 5, 15, 5, 16, 4, 15, 4, 16], [7, 17, 7, 18, 6, 17, 6, 18, 6, 19, 6, 20], [6, 18, 6, 19, 6, 16, 6, 17, 5, 16, 5, 17], [4, 18, 4, 19, 7, 18, 7, 19, 7, 20, 7, 21], [8, 18, 8, 19, 8, 16, 8, 17, 3, 16, 3, 17], [1, 19, 1, 20, 2, 19, 2, 20, 2, 21, 2, 22], [3, 19, 3, 20, 3, 17, 3, 18, 4, 17, 4, 18], [7, 19, 7, 20, 8, 19, 8, 20, 8, 21, 8, 22], [0, 20, 0, 21, 0, 18, 0, 19, 5, 18, 5, 19], [4, 20, 4, 21, 1, 20, 1, 21, 1, 22, 1, 23], [2, 20, 2, 21, 2, 18, 2, 19, 3, 18, 3, 19], [1, 21, 1, 22, 0, 21, 0, 22, 0, 23, 0, 24], [5, 21, 5, 22, 5, 19, 5, 20, 4, 19, 4, 20], [7, 21, 7, 22, 6, 21, 6, 22, 6, 23, 6, 24], [6, 22, 6, 23, 6, 20, 6, 21, 5, 20, 5, 21], [4, 22, 4, 23, 7, 22, 7, 23, 7, 24, 7, 25], [8, 22, 8, 23, 8, 20, 8, 21, 3, 20, 3, 21], [1, 23, 1, 24, 2, 23, 2, 24, 2, 25, 2, 26], [3, 23, 3, 24, 3, 21, 3, 22, 4, 21, 4, 22], [7, 23, 7, 24, 8, 23, 8, 24, 8, 25, 8, 26], [0, 24, 0, 25, 0, 22, 0, 23, 5, 22, 5, 23], [4, 24, 4, 25, 1, 24, 1, 25, 1, 26, 1, 27], [2, 24, 2, 25, 2, 22, 2, 23, 3, 22, 3, 23], [1, 25, 1, 26, 0, 25, 0, 26, 0, 27, 0, 28], [5, 25, 5, 26, 5, 23, 5, 24, 4, 23, 4, 24], [7, 25, 7, 26, 6, 25, 6, 26, 6, 27, 6, 28], [6, 26, 6, 27, 6, 24, 6, 25, 5, 24, 5, 25], [4, 26, 4, 27, 7, 26, 7, 27, 7, 28, 7, 29], [8, 26, 8, 27, 8, 24, 8, 25, 3, 24, 3, 25], [1, 27, 1, 28, 2, 27, 2, 28, 2, 29, 2, 30], [3, 27, 3, 28, 3, 25, 3, 26, 4, 25, 4, 26], [7, 27, 7, 28, 8, 27, 8, 28, 8, 29, 8, 30], [0, 28, 0, 29, 0, 26, 0, 27, 5, 26, 5, 27], [4, 28, 4, 29, 1, 28, 1, 29, 1, 30, 1, 31], [2, 28, 2, 29, 2, 26, 2, 27, 3, 26, 3, 27], [1, 29, 1, 30, 0, 29, 0, 30, 0, 31, 0, 32], [5, 29, 5, 30, 5, 27, 5, 28, 4, 27, 4, 28], [7, 29, 7, 30, 6, 29, 6, 30, 6, 31, 6, 32], [6, 30, 6, 31, 6, 28, 6, 29, 5, 28, 5, 29], [8, 30, 8, 31, 8, 28, 8, 29, 3, 28, 3, 29], [3, 31, 3, 32, 3, 29, 3, 30, 4, 29, 4, 30], [4, 30, 4, 31, 7, 30, 7, 31, 7, 32, 7, 33], [1, 31, 1, 32, 2, 31, 2, 32, 2, 33, 2, 34], [7, 31, 7, 32, 8, 31, 8, 32, 8, 33, 8, 34], [0, 32, 0, 33, 0, 30, 0, 31, 5, 30, 5, 31], [4, 32, 4, 33, 1, 32, 1, 33, 1, 34, 1, 35], [2, 32, 2, 33, 2, 30, 2, 31, 3, 30, 3, 31], [1, 33, 1, 34, 0, 33, 0, 34, 0, 35, 0, 36], [5, 33, 5, 34, 5, 31, 5, 32, 4, 31, 4, 32], [7, 33, 7, 34, 6, 33, 6, 34, 6, 35, 6, 36], [6, 34, 6, 35, 6, 32, 6, 33, 5, 32, 5, 33], [4, 34, 4, 35, 7, 34, 7, 35, 7, 36, 7, 37], [8, 34, 8, 35, 8, 32, 8, 33, 3, 32, 3, 33], [1, 35, 1, 36, 2, 35, 2, 36, 2, 37, 2, 38], [3, 35, 3, 36, 3, 33, 3, 34, 4, 33, 4, 34], [7, 35, 7, 36, 8, 35, 8, 36, 8, 37, 8, 38], [0, 36, 0, 37, 0, 34, 0, 35, 5, 34, 5, 35], [4, 36, 4, 37, 1, 36, 1, 37, 1, 38, 1, 39], [2, 36, 2, 37, 2, 34, 2, 35, 3, 34, 3, 35], [1, 37, 1, 38, 0, 37, 0, 38, 0, 39, 0, 40], [5, 37, 5, 38, 5, 35, 5, 36, 4, 35, 4, 36], [7, 37, 7, 38, 6, 37, 6, 38, 6, 39, 6, 40], [6, 38, 6, 39, 6, 36, 6, 37, 5, 36, 5, 37], [4, 38, 4, 39, 7, 38, 7, 39, 7, 40, 7, 41], [8, 38, 8, 39, 8, 36, 8, 37, 3, 36, 3, 37], [1, 39, 1, 40, 2, 39, 2, 40, 2, 41, 2, 42], [3, 39, 3, 40, 3, 37, 3, 38, 4, 37, 4, 38], [7, 39, 7, 40, 8, 39, 8, 40, 8, 41, 8, 42], [0, 40, 0, 41, 0, 38, 0, 39, 5, 38, 5, 39], [4, 40, 4, 41, 1, 40, 1, 41, 1, 42, 1, 43], [2, 40, 2, 41, 2, 38, 2, 39, 3, 38, 3, 39], [1, 41, 1, 42, 0, 41, 0, 42, 0, 43, 0, 44], [5, 41, 5, 42, 5, 39, 5, 40, 4, 39, 4, 40], [7, 41, 7, 42, 6, 41, 6, 42, 6, 43, 6, 44], [6, 42, 6, 43, 6, 40, 6, 41, 5, 40, 5, 41], [4, 42, 4, 43, 7, 42, 7, 43, 7, 44, 7, 45], [8, 42, 8, 43, 8, 40, 8, 41, 3, 40, 3, 41], [1, 43, 1, 44, 2, 43, 2, 44, 2, 45, 2, 46], [3, 43, 3, 44, 3, 41, 3, 42, 4, 41, 4, 42], [7, 43, 7, 44, 8, 43, 8, 44, 8, 45, 8, 46], [0, 44, 0, 45, 0, 42, 0, 43, 5, 42, 5, 43], [4, 44, 4, 45, 1, 44, 1, 45, 1, 46, 1, 47], [2, 44, 2, 45, 2, 42, 2, 43, 3, 42, 3, 43], [1, 45, 1, 46, 0, 45, 0, 46, 0, 47, 0, 48], [5, 45, 5, 46, 5, 43, 5, 44, 4, 43, 4, 44], [7, 45, 7, 46, 6, 45, 6, 46, 6, 47, 6, 48], [6, 46, 6, 47, 6, 44, 6, 45, 5, 44, 5, 45], [4, 46, 4, 47, 7, 46, 7, 47, 7, 48, 7, 49], [8, 46, 8, 47, 8, 44, 8, 45, 3, 44, 3, 45], [1, 47, 1, 48, 2, 47, 2, 48, 2, 49, 2, 50], [3, 47, 3, 48, 3, 45, 3, 46, 4, 45, 4, 46], [7, 47, 7, 48, 8, 47, 8, 48, 8, 49, 8, 50], [0, 48, 0, 49, 0, 46, 0, 47, 5, 46, 5, 47], [4, 48, 4, 49, 1, 48, 1, 49, 1, 50, 1, 51], [2, 48, 2, 49, 2, 46, 2, 47, 3, 46, 3, 47], [1, 49, 1, 50, 0, 49, 0, 50, 0, 51, 0, 52], [5, 49, 5, 50, 5, 47, 5, 48, 4, 47, 4, 48], [7, 49, 7, 50, 6, 49, 6, 50, 6, 51, 6, 52], [6, 50, 6, 51, 6, 48, 6, 49, 5, 48, 5, 49], [4, 50, 4, 51, 7, 50, 7, 51, 7, 52, 7, 53], [8, 50, 8, 51, 8, 48, 8, 49, 3, 48, 3, 49], [1, 51, 1, 52, 2, 51, 2, 52, 2, 53, 2, 54], [3, 51, 3, 52, 3, 49, 3, 50, 4, 49, 4, 50], [7, 51, 7, 52, 8, 51, 8, 52, 8, 53, 8, 54], [0, 52, 0, 53, 0, 50, 0, 51, 5, 50, 5, 51], [4, 52, 4, 53, 1, 52, 1, 53, 1, 54, 1, 55], [2, 52, 2, 53, 2, 50, 2, 51, 3, 50, 3, 51], [1, 53, 1, 54, 0, 53, 0, 54, 0, 55, 0, 56], [5, 53, 5, 54, 5, 51, 5, 52, 4, 51, 4, 52], [7, 53, 7, 54, 6, 53, 6, 54, 6, 55, 6, 56], [6, 54, 6, 55, 6, 52, 6, 53, 5, 52, 5, 53], [4, 54, 4, 55, 7, 54, 7, 55, 7, 56, 7, 57], [8, 54, 8, 55, 8, 52, 8, 53, 3, 52, 3, 53], [1, 55, 1, 56, 2, 55, 2, 56, 2, 57, 2, 58], [3, 55, 3, 56, 3, 53, 3, 54, 4, 53, 4, 54], [7, 55, 7, 56, 8, 55, 8, 56, 8, 57, 8, 58], [0, 56, 0, 57, 0, 54, 0, 55, 5, 54, 5, 55], [4, 56, 4, 57, 1, 56, 1, 57, 1, 58, 1, 59], [2, 56, 2, 57, 2, 54, 2, 55, 3, 54, 3, 55], [1, 57, 1, 58, 0, 57, 0, 58, 0, 59, 0, 60], [5, 57,

TABLE 14A-continued 5, 58, 5, 55, 5, 56, 4, 55, 4, 56], [7, 57, 7, 58, 6, 57, 6, 58, 6, 59, 6, 60], [6, 58, 6, 59, 6, 56, 6, 57, 5, 56, 5, 57], [4, 58, 4, 59, 7, 58, 7, 59, 7, 60, 7, 61], [8, 58, 8, 59, 8, 56, 8, 57, 3, 56, 3, 57], [1, 59, 1, 60, 2, 59, 2, 60, 2, 61, 2, 62], [3, 59, 3, 60, 3, 57, 3, 58, 4, 57, 4, 58], [7, 59, 7, 60, 8, 59, 8, 60, 8, 61, 8, 62], [0, 60, 0, 61, 0, 58, 0, 59, 5, 58, 5, 59], [4, 60, 4, 61, 1, 60, 1, 61, 1, 62, 1, 63], [2, 60, 2, 61, 2, 58, 2, 59, 3, 58, 3, 59], [1, 61, 1, 62, 0, 61, 0, 62, 0, 63, 0, 64], [5, 61, 5, 62, 5, 59, 5, 60, 4, 59, 4, 60], [7, 61, 7, 62, 6, 61, 6, 62, 6, 63, 6, 64], [6, 62, 6, 63, 6, 60, 6, 61, 5, 60, 5, 61], [8, 62, 8, 63, 8, 60, 8, 61, 3, 60, 3, 61], [3, 63, 3, 64, 3, 61, 3, 62, 4, 61, 4, 62], [4, 62, 4, 63, 7, 62, 7, 63, 7, 64, 7, 65], [1, 63, 1, 64, 2, 63, 2, 64, 2, 65, 2, 66], [7, 63, 7, 64, 8, 63, 8, 64, 8, 65, 8, 66], [0, 64, 0, 65, 0, 62, 0, 63, 5, 62, 5, 63], [4, 64, 4, 65, 1, 64, 1, 65, 1, 66, 1, 67], [2, 64, 2, 65, 2, 62, 2, 63, 3, 62, 3, 63], [1, 65, 1, 66, 0, 65, 0, 66, 0, 67, 0, 68], [5, 65, 5, 66, 5, 63, 5, 64, 4, 63, 4, 64], [7, 65, 7, 66, 6, 65, 6, 66, 6, 67, 6, 68], [6, 66, 6, 67, 6, 64, 6, 65, 5, 64, 5, 65], [4, 66, 4, 67, 7, 66, 7, 67, 7, 68, 7, 69], [8, 66, 8, 67, 8, 64, 8, 65, 3, 64, 3, 65], [1, 67, 1, 68, 2, 67, 2, 68, 2, 69, 2, 70], [3, 67, 3, 68, 3, 65, 3, 66, 4, 65, 4, 66], [7, 67, 7, 68, 8, 67, 8, 68, 8, 69, 8, 70], [0, 68, 0, 69, 0, 66, 0, 67, 5, 66, 5, 67], [4, 68, 4, 69, 1, 68, 1, 69, 1, 70, 1, 71], [2, 68, 2, 69, 2, 66, 2, 67, 3, 66, 3, 67], [1, 69, 1, 70, 0, 69, 0, 70, 0, 71, 0, 72], [5, 69, 5, 70, 5, 67, 5, 68, 4, 67, 4, 68], [7, 69, 7, 70, 6, 69, 6, 70, 6, 71, 6, 72], [6, 70, 6, 71, 6, 68, 6, 69, 5, 68, 5, 69], [4, 70, 4, 71, 7, 70, 7, 71, 7, 72, 7, 73], [8, 70, 8, 71, 8, 68, 8, 69, 3, 68, 3, 69], [1, 71, 1, 72, 2, 71, 2, 72, 2, 73, 2, 74], [3, 71, 3, 72, 3, 69, 3, 70, 4, 69, 4, 70], [7, 71, 7, 72, 8, 71, 8, 72, 8, 73, 8, 74], [0, 72, 0, 73, 0, 70, 0, 71, 5, 70, 5, 71], [4, 72, 4, 73, 1, 72, 1, 73, 1, 74, 1, 75], [2, 72, 2, 73, 2, 70, 2, 71, 3, 70, 3, 71], [1, 73, 1, 74, 0, 73, 0, 74, 0, 75, 0, 76], [5, 73, 5, 74, 5, 71, 5, 72, 4, 71, 4, 72], [7, 73, 7, 74, 6, 73, 6, 74, 6, 75, 6, 76], [6, 74, 6, 75, 6, 72, 6, 73, 5, 72, 5, 73], [4, 74, 4, 75, 7, 74, 7, 75, 7, 76, 7, 77], [8, 74, 8, 75, 8, 72, 8, 73, 3, 72, 3, 73], [1, 75, 1, 76, 2, 75, 2, 76, 2, 77, 2, 78], [3, 75, 3, 76, 3, 73, 3, 74, 4, 73, 4, 74], [7, 75, 7, 76, 8, 75, 8, 76, 8, 77, 8, 78], [0, 76, 0, 77, 0, 74, 0, 75, 5, 74, 5, 75], [4, 76, 4, 77, 1, 76, 1, 77, 1, 78, 1, 79], [2, 76, 2, 77, 2, 74, 2, 75, 3, 74, 3, 75], [1, 77, 1, 78, 0, 77, 0, 78, 0, 79, 0, 80], [5, 77, 5, 78, 5, 75, 5, 76, 4, 75, 4, 76], [7, 77, 7, 78, 6, 77, 6, 78, 6, 79, 6, 80], [6, 78, 6, 79, 6, 76, 6, 77, 5, 76, 5, 77], [4, 78, 4, 79, 7, 78, 7, 79, 7, 80, 7, 81], [8, 78, 8, 79, 8, 76, 8, 77, 3, 76, 3, 77], [1, 79, 1, 80, 2, 79, 2, 80, 2, 81, 2, 82], [3, 79, 3, 80, 3, 77, 3, 78, 4, 77, 4, 78], [7, 79, 7, 80, 8, 79, 8, 80, 8, 81, 8, 82], [0, 80, 0, 81, 0, 78, 0, 79, 5, 78, 5, 79], [4, 80, 4, 81, 1, 80, 1, 81, 1, 82, 1, 83], [2, 80, 2, 81, 2, 78, 2, 79, 3, 78, 3, 79], [1, 81, 1, 82, 0, 81, 0, 82, 0, 83, 0, 84], [5, 81, 5, 82, 5, 79, 5, 80, 4, 79, 4, 80], [7, 81, 7, 82, 6, 81, 6, 82, 6, 83, 6, 84], [6, 82, 6, 83, 6, 80, 6, 81, 5, 80, 5, 81], [4, 82, 4, 83, 7, 82, 7, 83, 7, 84, 7, 85], [8, 82, 8, 83, 8, 80, 8, 81, 3, 80, 3, 81], [1, 83, 1, 84, 2, 83, 2, 84, 2, 85, 2, 86], [3, 83, 3, 84, 3, 81, 3, 82, 4, 81, 4, 82], [7, 83, 7, 84, 8, 83, 8, 84, 8, 85, 8, 86], [0, 84, 0, 85, 0, 82, 0, 83, 5, 82, 5, 83], [4, 84, 4, 85, 1, 84, 1, 85, 1, 86, 1, 87], [2, 84, 2, 85, 2, 82, 2, 83, 3, 82, 3, 83], [1, 85, 1, 86, 0, 85, 0, 86, 0, 87, 0, 88], [5, 85, 5, 86, 5, 83, 5, 84, 4, 83, 4, 84], [7, 85, 7, 86, 6, 85, 6, 86, 6, 87, 6, 88], [6, 86, 6, 87, 6, 84, 6, 85, 5, 84, 5, 85], [4, 86, 4, 87, 7, 86, 7, 87, 7, 88, 7, 89], [8, 86, 8, 87, 8, 84, 8, 85, 3, 84, 3, 85], [1, 87, 1, 88, 2, 87, 2, 88, 2, 89, 2, 90], [3, 87, 3, 88, 3, 85, 3, 86, 4, 85, 4, 86], [7, 87, 7, 88, 8, 87, 8, 88, 8, 89, 8, 90], [0, 88, 0, 89, 0, 86, 0, 87, 5, 86, 5, 87], [4, 88, 4, 89, 1, 88, 1, 89, 1, 90, 1, 91], [2, 88, 2, 89, 2, 86, 2, 87, 3, 86, 3, 87], [1, 89, 1, 90, 0, 89, 0, 90, 0, 91, 0, 92], [5, 89, 5, 90, 5, 87, 5, 88, 4, 87, 4, 88], [7, 89, 7, 90, 6, 89, 6, 90, 6, 91, 6, 92], [6, 90, 6, 91, 6, 88, 6, 89, 5, 88, 5, 89], [4, 90, 4, 91, 7, 90, 7, 91, 7, 92, 7, 93], [8, 90, 8, 91, 8, 88, 8, 89, 3, 88, 3, 89], [1, 91, 1, 92, 2, 91, 2, 92, 2, 93, 2, 94], [3, 91, 3, 92, 3, 89, 3, 90, 4, 89, 4, 90], [7, 91, 7, 92, 8, 91, 8, 92, 8, 93, 8, 94], [0, 92, 0, 93, 0, 90, 0, 91, 5, 90, 5, 91], [4, 92, 4, 93, 1, 92, 1, 93, 1, 94, 1, 95], [2, 92, 2, 93, 2, 90, 2, 91, 3, 90, 3, 91], [1, 93, 1, 94, 0, 93, 0, 94, 0, 95, 0, 96], [5, 93, 5, 94, 5, 91, 5, 92, 4, 91, 4, 92], [7, 93, 7, 94, 6, 93, 6, 94, 6, 95, 6, 96], [6, 94, 6, 95, 6, 92, 6, 93, 5, 92, 5, 93], [4, 94, 4, 95, 7, 94, 7, 95, 7, 96, 7, 97], [8, 94, 8, 95, 8, 92, 8, 93, 3, 92, 3, 93], [1, 95, 1, 96, 2, 95, 2, 96, 2, 97, 2, 98], [3, 95, 3, 96, 3, 93, 3, 94, 4, 93, 4, 94], [7, 95, 7, 96, 8, 95, 8, 96, 8, 97, 8, 98], [0, 96, 0, 97, 0, 94, 0, 95, 5, 94, 5, 95], [4, 96, 4, 97, 1, 96, 1, 97, 1, 98, 1, 99], [2, 96, 2, 97, 2, 94, 2, 95, 3, 94, 3, 95], [1, 97, 1, 98, 0, 97, 0, 98, 0, 99, 0, 100], [5, 97, 5, 98, 5, 95, 5, 96, 4, 95, 4, 96], [7, 97, 7, 98, 6, 97, 6, 98, 6, 99, 6, 100], [6, 98, 6, 99, 6, 96, 6, 97, 5, 96, 5, 97], [4, 98, 4, 99, 7, 98, 7, 99, 7, 100, 7, 101], [8, 98, 8, 99, 8, 96, 8, 97, 3, 96, 3, 97], [1, 99, 1, 100, 2, 99, 2, 100, 2, 101, 2, 102], [3, 99, 3, 100, 3, 97, 3, 98, 4, 97, 4, 98], [7, 99, 7, 100, 8, 99, 8, 100, 8, 101, 8, 102], [0, 100, 0, 101, 0, 98, 0, 99, 5, 98, 5, 99], [4, 100, 4, 101, 1, 100, 1, 101, 1, 102, 1, 103], [2, 100, 2, 101, 2, 98, 2, 99, 3, 98, 3, 99], [1, 101, 1, 102, 0, 101, 0, 102, 0, 103, 0, 104], [5, 101, 5, 102, 5, 99, 5, 100, 4, 99, 4, 100], [7, 101, 7, 102, 6, 101, 6, 102, 6, 103, 6, 104], [6, 102, 6, 103, 6, 100, 6, 101, 5, 100, 5, 101], [4, 102, 4, 103, 7, 102, 7, 103, 7, 104, 7, 105], [8, 102, 8, 103, 8, 100, 8, 101, 3, 100, 3, 101], [1, 103, 1, 104, 2, 103, 2, 104, 2, 105, 2, 106], [3, 103, 3, 104, 3, 101, 3, 102, 4, 101, 4, 102], [7, 103, 7, 104, 8, 103, 8, 104, 8, 105, 8, 106], [0, 104, 0, 105, 0, 102, 0, 103, 5, 102, 5, 103], [4, 104, 4, 105, 1, 104, 1, 105, 1, 106, 1, 107], [2, 104, 2, 105, 2, 102, 2, 103, 3, 102, 3, 103], [1, 105, 1, 106, 0, 105, 0, 106, 0, 107, 0, 108], [5, 105, 5, 106, 5, 103, 5, 104, 4, 103, 4, 104], [7, 105, 7, 106, 6, 105, 6, 106, 6, 107, 6, 108], [6, 106, 6, 107, 6, 104, 6, 105, 5, 104, 5, 105], [4, 106, 4, 107, 7, 106, 7, 107, 7, 108, 7, 109], [8, 106, 8, 107, 8, 104, 8, 105, 3, 104, 3, 105], [1, 107, 1, 108, 2, 107, 2, 108, 2, 109, 2, 110], [3, 107, 3, 108, 3, 105, 3, 106, 4, 105, 4, 106], [7, 107, 7, 108, 8, 107, 8, 108, 8, 109, 8, 110], [0, 108, 0, 109, 0, 106, 0, 107, 5, 106, 5, 107], [4, 108, 4, 109, 1, 108, 1, 109, 1, 110, 1, 111], [2, 108, 2, 109, 2, 106, 2, 107, 3, 106, 3, 107], [1, 109, 1, 110, 0, 109, 0, 110, 0, 111, 0, 112], [5, 109, 5, 110, 5, 107, 5, 108, 4, 107, 4, 108], [7, 109, 7, 110, 6, 109, 6, 110, 6, 111, 6, 112], [6, 110, 6, 111, 6, 108, 6, 109, 5, 108, 5, 109], [4, 110, 4, 111, 7, 110, 7, 111, 7, 112, 7, 113], [8, 110, 8, 111, 8, 108, 8, 109, 3, 108, 3, 109], [1, 111, 1, 112, 2, 111, 2, 112, 2, 113, 2, 114], [3, 111, 3, 112, 3, 109, 3, 110, 4, 109, 4, 110], [7, 111, 7, 112, 8, 111, 8, 112, 8, 113, 8, 114], [0, 112, 0, 113, 0, 110, 0, 111, 5, 110, 5, 11 1], [4, 112, 4, 113, 1, 112, 1, 113, 1, 114, 1, 115], [2, 112, 2, 113, 2, 110, 2, 111, 3, 110, 3, 11 1], [1, 113, 1, 114, 0, 113, 0, 114, 0, 115, 0, 116], [5, 113, 5, 114, 5, 111, 5, 112, 4, 111, 4, 112], [7, 113, 7, 114, 6, 113, 6, 114, 6, 115, 6, 116], [6, 114, 6, 115, 6, 112, 6, 113, 5, 112, 5, 113], [4, 114, 4, 115, 7, 114, 7, 115, 7, 116, 7, 117], [8, 114, 8, 115, 8, 112, 8, 113, 3, 112, 3, 113], [1, 115, 1, 116, 2, 115, 2, 116, 2, 117, 2, 118], [3, 115, 3, 116, 3, 113, 3, 114, 4, 113, 4, 114], [7, 115, 7, 116, 8, 115, 8, 116, 8, 117, 8, 118], [0, 116, 0, 117, 0, 114, 0, 115, 5, 114, 5, 115], [4, 116, 4, 117, 1, 116, 1, 117, 1, 118, 1, 119], [2, 116, 2, 117, 2, 114, 2, 115, 3, 114, 3, 115], [1, 117, 1, 118, 0, 117, 0, 118, 0, 119, 0, 120], [5, 117, 5, 118, 5, 115, 5, 116, 4, 115, 4, 116], [7, 117, 7, 118, 6, 117, 6, 118, 6, 119, 6, 120], [6, 118, 6, 119, 6, 116, 6, 117, 5, 116, 5, 117], [4, 118, 4, 119, 7, 118, 7, 119, 7, 120, 7, 121], [8, 118, 8, 119, 8, 116, 8, 117, 3, 116, 3, 117], [1, 119, 1, 120, 2, 119, 2, 120, 2, 121, 2, 122], [3, 119, 3, 120, 3, 117, 3, 118, 4, 117, 4, 118], [7, 119, 7, 120, 8, 119, 8, 120, 8, 121, 8, 122], [0, 120, 0, 121, 0, 118, 0, 119, 5, 118, 5, 119], [4, 120, 4, 121, 1, 120, 1, 121, 1, 122, 1, 123], [2, 120, 2, 121, 2, 118, 2, 119, 3, 118, 3, 119], [1, 121, 1, 122, 0, 121, 0, 122, 0, 123, 0, 124], [5, 121, 5, 122, 5, 119, 5, 120, 4, 119, 4, 120], [7, 121, 7, 122, 6, 121, 6, 122, 6, 123, 6, 124], [6, 122, 6, 123, 6, 120, 6, 121, 5, 120, 5, 121], [4, 122, 4, 123, 7, 122, 7, 123, 7, 124, 7, 125], [8, 122, 8, 123, 8, 120, 8, 121, 3, 120, 3, 121], [1, 123, 1, 124, 2, 123, 2, 124, 2, 125, 2, 126], [3, 123, 3, 124, 3, 121, 3, 122, 4, 121, 4, 122], [7, 123, 7, 124, 8, 123, 8, 124, 8, 125, 8, 126], [0, 124, 0, 125, 0, 122, 0, 123, 5, 122, 5, 123], [4, 124, 4, 125, 1, 124, 1, 125, 1, 126, 1, 127], [2, 124, 2, 125, 2, 122, 2, 123, 3, 122, 3, 123], [1, 125, 1, 126, 0, 125, 0, 126, 0, 127, 0, 128], [5, 125, 5, 126, 5, 123, 5, 124, 4, 123, 4, 124], [7, 125, 7, 126, 6, 125, 6, 126, 6, 127, 6, 128], [6, 126, 6, 127, 6, 124, 6, 125, 5, 124, 5, 125], [8, 126, 8, 127, 8, 124, 8, 125, 3, 124, 3, 125], [3, 127, 3, 128, 3, 125, 3, 126, 4, 125, 4, 126]

TABLE 14B

[4, 126, 4, 127, 7, 126, 7, 127, 7, 128, 0, 0], [1, 127, 1, 128, 2, 127, 2, 128], [5, 127, 5, 128, 4, 127, 4, 128], [7, 127, 7, 128, 8, 127, 8, 128], [4, 128, 0, 0, 1, 128, 0, 0], [6, 128, 0, 0, 5, 128, 0, 0], [8, 128, 0, 0, 3, 128, 0, 0], [0, 128, 0, 0, 0, 126, 0, 127, 5, 126, 5, 127], [2, 128, 0, 0, 2, 126, 2, 127, 3, 126, 3, 127]

The core oligonucleotide sequences used to produce 4H×4H×32B nucleic acid structures of the invention are designated SEQ ID NOs. 3249-3272, and the corresponding voxel coordinates are shown respectively in Table 15A. The end oligonucleotide sequences used to produce 4H×4H×32B nucleic acid structures of the invention are designated SEQ ID NOs. 3633-3646, and the corresponding voxel coordinates are shown respectively in Table 15B. (See also Appendix, Table 8 of U.S. provisional application No. 61/675,309, filed Jul. 24, 2012, incorporated by reference herein.)

TABLE 15A

[0, 0, 0, 1, 0, 0, 0, 0], [0, 0, 2, 1, 0, 0, 0, 0], [0, 0, 13, 1, 0, 0, 0, 0], [0, 0, 15, 1, 0, 0, 0, 0], [0, 0, 8, 1, 0, 0, 7, 1], [0, 0, 10, 1, 0, 0, 5, 1], [0, 0, 6, 1, 0, 0, 1, 1, 1, 2, 1, 3], [0, 0, 4, 1, 0, 0, 3, 1, 3, 2, 3, 3], [4, 1, 4, 2, 0, 0, 0, 0], [7, 1, 7, 2, 0, 0, 0, 0], [12, 1, 12, 2, 0, 0, 0, 0], [15, 1, 15, 2, 0, 0, 0, 0], [5, 1, 5, 2, 6, 1, 6, 2], [13, 1, 13, 2, 14, 1, 14, 2], [1, 1, 1, 2, 0, 1, 0, 2, 0, 3, 0, 4], [9, 1, 9, 2, 8, 1, 8, 2, 8, 3, 8, 4], [4, 2, 4, 3, 11, 2, 11, 3], [6, 2, 6, 3, 9, 2, 9, 3], [12, 2, 12, 3, 0, 0, 12, 1, 0, 0, 11, 1], [14, 2, 14, 3, 0, 0, 14, 1, 0, 0, 9, 1], [1, 3, 1, 4, 2, 3, 2, 4], [9, 3, 9, 4, 10, 3, 10, 4], [3, 3, 3, 4, 3, 1, 3, 2, 2, 1, 2, 2], [1 1, 3, 11, 4, 11, 1, 11, 2, 10, 1, 10, 2]

TABLE 15B

[10, 2, 10, 3, 13, 2, 13, 3, 13, 4, 0, 0], [8, 2, 8, 3, 15, 2, 15, 3, 15, 4, 0, 0], [5, 3, 5, 4, 4, 3, 4, 4], [7, 3, 7, 4, 6, 3, 6, 4], [13, 3, 13, 4, 12, 3, 12, 4], [15, 3, 15, 4, 14, 3, 14, 4], [4, 4, 0, 0, 3, 4, 0, 0], [6, 4, 0, 0, 1, 4, 0, 0], [8, 4, 0, 0, 7, 4, 0, 0], [10, 4, 0, 0, 5, 4, 0, 0], [12, 4, 0, 0, 11, 4, 0, 0], [14, 4, 0, 0, 9, 4, 0, 0], [0, 4, 0, 0, 0, 2, 0, 3, 7, 2, 7, 3], [2, 4, 0, 0, 2, 2, 2, 3, 5, 2, 5, 3]

The core oligonucleotide sequences used to produce 4H×4H×64B nucleic acid structures of the invention are designated SEQ ID NOs. 3249-3296, and the corresponding voxel coordinates are shown respectively in Table 16A. The end oligonucleotide sequences used to produce 4H×4H×64B nucleic acid structures of the invention are designated SEQ ID NOs. 3647-3660, and the corresponding voxel coordinates are shown respectively in Table 16B. (See also Appendix, Table 8 of U.S. provisional application No. 61/675,309, filed Jul. 24, 2012, incorporated by reference herein.)

TABLE 16A

[0, 0, 0, 1, 0, 0, 0, 0], [0, 0, 2, 1, 0, 0, 0, 0], [0, 0, 13, 1, 0, 0, 0, 0], [0, 0, 15, 1, 0, 0, 0, 0], [0, 0, 8, 1, 0, 0, 7, 1], [0, 0, 10, 1, 0, 0, 5, 1], [0, 0, 6, 1, 0, 0, 1, 1, 1, 2, 1, 3], [0, 0, 4, 1, 0, 0, 3, 1, 3, 2, 3, 3], [4, 1, 4, 2, 0, 0, 0, 0], [7, 1, 7, 2, 0, 0, 0, 0], [12, 1, 12, 2, 0, 0, 0, 0], [15, 1, 15, 2, 0, 0, 0, 0], [5, 1, 5, 2, 6, 1, 6, 2], [13, 1, 13, 2, 14, 1, 14, 2], [1, 1, 1, 2, 0, 1, 0, 2, 0, 3, 0, 4], [9, 1, 9, 2, 8, 1, 8, 2, 8, 3, 8, 4], [4, 2, 4, 3, 11, 2, 11, 3], [6, 2, 6, 3, 9, 2, 9, 3], [12, 2, 12, 3, 0, 0, 12, 1, 0, 0, 11, 1], [14, 2, 14, 3, 0, 0, 14, 1, 0, 0, 9, 1], [1, 3, 1, 4, 2, 3, 2, 4], [9, 3, 9, 4, 10, 3, 10, 4], [3, 3, 3, 4, 3, 1, 3, 2, 2, 1, 2, 2], [11, 3, 11, 4, 11, 1, 11, 2, 10, 1, 10, 2], [10, 2, 10, 3, 13, 2, 13, 3, 13, 4, 13, 5], [8, 2, 8, 3, 15, 2, 15, 3, 15, 4, 15, 5], [5, 3, 5, 4, 4, 3, 4, 4, 4, 5, 4, 6], [13, 3, 13, 4, 12, 3, 12, 4, 12, 5, 12, 6], [8, 4, 8, 5, 7, 4, 7, 5], [10, 4, 10, 5, 5, 4, 5, 5], [0, 4, 0, 5, 0, 2, 0, 3, 7, 2, 7, 3], [6, 4, 6, 5, 1, 4, 1, 5, 1, 6, 1, 7], [2, 4, 2, 5, 2, 2, 2, 3, 5, 2, 5, 3], [4, 4, 4, 5, 3, 4, 3, 5, 3, 6, 3, 7], [5, 5, 5, 6, 6, 5, 6, 6], [13, 5, 13, 6, 14, 5, 14, 6], [1, 5, 1, 6, 0, 5, 0, 6, 0, 7, 0, 8], [7, 5, 7, 6, 7, 3, 7, 4, 6, 3, 6, 4], [9, 5, 9, 6, 8, 5, 8, 6, 8, 7, 8, 8], [15, 5, 15, 6, 15, 3, 15, 4, 14, 3, 14, 4], [4, 6, 4, 7, 11, 6, 11, 7], [6, 6, 6, 7, 9, 6, 9, 7], [12, 6, 12, 7, 12, 4, 12, 5, 11, 4, 11, 5], [14, 6, 14, 7, 14, 4, 14, 5, 9, 4, 9, 5], [1, 7, 1, 8, 2, 7, 2, 8], [9, 7, 9, 8, 10, 7, 10, 8], [3, 7, 3, 8, 3, 5, 3, 6, 2, 5, 2, 6], [11, 7, 11, 8, 11, 5, 11, 6, 10, 5, 10, 6]

TABLE 16B

[10, 6, 10, 7, 13, 6, 13, 7, 13, 8, 0, 0], [8, 6, 8, 7, 15, 6, 15, 7, 15, 8, 0, 0], [5, 7, 5, 8, 4, 7, 4, 8], [7, 7, 7, 8, 6, 7, 6, 8], [13, 7, 13, 8, 12,7, 12, 8], [15, 7, 15, 8, 14, 7, 14, 8], [4, 8, 0, 0, 3, 8, 0, 0], [6, 8, 0, 0, 1, 8, 0, 0], [8, 8, 0, 0, 7, 8, 0, 0], [10, 8, 0, 0, 5, 8, 0, 0], [12, 8, 0, 0, 11, 8, 0, 0], [14, 8, 0, 0, 9, 8, 0, 0], [0, 8, 0, 0, 0, 6, 0, 7, 7, 6, 7, 7], [2, 8, 0, 0, 2, 6, 2, 7, 5, 6, 5, 7]

The core oligonucleotide sequences used to produce 4H×4H×128B nucleic acid structures of the invention are designated SEQ ID NOs. 3249-3344, and the corresponding voxel coordinates are shown respectively in Table 17A. The end oligonucleotide sequences used to produce 4H×4H×128B nucleic acid structures of the invention are designated SEQ ID NOs. 3661-3674, and the corresponding voxel coordinates are shown respectively in Table 17B. (See also Appendix, Table 8 of U.S. provisional application No. 61/675,309, filed Jul. 24, 2012, incorporated by reference herein.)

TABLE 17A

[0, 0, 0, 1, 0, 0, 0, 0], [0, 0, 2, 1, 0, 0, 0, 0], [0, 0, 13, 1, 0, 0, 0, 0], [0, 0, 15, 1, 0, 0, 0, 0], [0, 0, 8, 1, 0, 0, 7, 1], [0, 0, 10, 1, 0, 0, 5, 1], [0, 0, 6, 1, 0, 0, 1, 1, 1, 2, 1, 3], [0, 0, 4, 1, 0, 0, 3, 1, 3, 2, 3, 3], [4, 1, 4, 2, 0, 0, 0, 0], [7, 1, 7, 2, 0, 0, 0, 0], [12, 1, 12, 2, 0, 0, 0, 0], [15, 1, 15, 2, 0, 0, 0, 0], [5, 1, 5, 2, 6, 1, 6, 2], [13, 1, 13, 2, 14, 1, 14, 2], [1, 1, 1, 2, 0, 1, 0, 2, 0, 3, 0, 4], [9, 1, 9, 2, 8, 1, 8, 2, 8, 3, 8, 4], [4, 2, 4, 3, 11, 2, 11, 3], [6, 2, 6, 3, 9, 2, 9, 3], [12, 2, 12, 3, 0, 0, 12, 1, 0, 0, 11, 1], [14, 2, 14, 3, 0, 0, 14, 1, 0, 0, 9, 1], [1, 3, 1, 4, 2, 3, 2, 4], [9, 3, 9, 4, 10, 3, 10, 4], [3, 3, 3, 4, 3, 1, 3, 2, 2, 1, 2, 2], [11, 3, 11, 4, 11, 1, 11, 2, 10, 1, 10, 2], [10, 2, 10, 3, 13, 2, 13, 3, 13, 4, 13, 5], [8, 2, 8, 3, 15, 2, 15, 3, 15, 4, 15, 5], [5, 3, 5, 4, 4, 3, 4, 4, 4, 5, 4, 6], [13, 3, 13, 4, 12, 3, 12, 4, 12, 5, 12, 6], [8, 4, 8, 5, 7, 4, 7, 5], [10, 4, 10, 5, 5, 4, 5, 5], [0, 4, 0, 5, 0, 2, 0, 3, 7, 2, 7, 3], [6, 4, 6, 5, 1, 4, 1, 5, 1, 6, 1, 7], [2, 4, 2, 5, 2, 2, 2, 3, 5, 2, 5, 3], [4, 4, 4, 5, 3, 4, 3, 5, 3, 6, 3, 7], [5, 5, 5, 6, 6, 5, 6, 6], [13, 5, 13, 6, 14, 5, 14, 6], [1, 5, 1, 6, 0, 5, 0, 6, 0, 7, 0, 8], [7, 5, 7, 6, 7, 3, 7, 4, 6, 3, 6, 4], [9, 5, 9, 6, 8, 5, 8, 6, 8, 7, 8, 8], [15, 5, 15, 6, 15, 3, 15, 4, 14, 3, 14, 4], [4, 6, 4, 7, 11, 6, 11, 7], [6, 6, 6, 7, 9, 6, 9, 7], [12, 6, 12, 7, 12, 4, 12, 5, 11, 4, 11, 5], [14, 6, 14, 7, 14, 4, 14, 5, 9, 4, 9, 5], [1, 7, 1, 8, 2, 7, 2, 8], [9, 7, 9, 8, 10, 7, 10, 8], [3, 7, 3, 8, 3, 5, 3, 6, 2, 5, 2, 6], [11, 7, 11, 8, 11, 5, 11, 6, 10, 5, 10, 6], [10, 6, 10, 7, 13, 6, 13, 7, 13, 8, 13, 9], [8, 6, 8, 7, 15, 6, 15, 7, 15, 8, 15, 9], [5, 7, 5, 8, 4, 7, 4, 8, 4, 9, 4, 10], [13, 7, 13, 8, 12, 7, 12, 8, 12, 9, 12, 10], [8, 8, 8, 9, 7, 8, 7, 9], [10, 8, 0, 0, 9, 0, 0, 6, 0, 7, 7, 6, 7, 7], [6, 8, 6, 9, 1, 8, 1, 9, 1, 10, 1, 11], [2, 8, 2, 9, 2, 6, 2, 7, 5, 6, 5, 7], [4, 8, 4, 9, 3, 8, 3, 9, 3, 10, 3, 11], [5, 9, 5, 10, 6, 9, 6, 10], [13, 9, 13, 10, 14, 9, 14, 10], [1, 9, 1, 10, 0, 9, 0, 10, 0, 11, 0, 12], [7, 9, 7, 10, 7, 7, 7, 8, 6, 7, 6, 8], [9, 9, 9, 10, 8, 9, 8, 10, 8, 11, 8, 12], [15, 9, 15, 10, 15, 7, 15, 8, 14, 7, 14, 8], [4, 10, 4, 11, 11, 10, 11, 11], [6, 10, 6, 11, 9, 10, 9, 11], [12, 10, 12, 11, 12, 8, 12, 9, 11, 8, 11, 9], [10, 10, 10, 11, 13, 10, 13, 11, 13, 12, 13, 13], [14, 10, 14, 11, 14, 8, 14, 9, 9, 8, 9, 9], [8, 10, 8, 11, 15, 10, 15, 11, 15, 12, 15, 13], [1, 11, 1, 12, 2, 11, 2, 12], [9, 11, 9, 12, 10, 11, 10, 12], [3, 11, 3, 12, 3, 9, 3, 10, 2, 9, 2, 10], [5, 11, 5, 12, 4, 11, 4, 12, 4, 13, 4, 14], [1 1, 11, 11, 12, 11,

TABLE 17A-continued 9, 11, 10, 10, 9, 10, 10], [13, 11, 13, 12, 12, 11, 12, 12, 12, 13, 12, 14], [8, 12, 8, 13, 7, 12, 7, 13], [10, 12, 10, 13, 5, 12, 5, 13], [0, 12, 0, 13, 0, 10, 0, 11, 7, 10, 7, 11], [6, 12, 6, 13, 1, 12, 1, 13, 1, 14, 1, 15], [2, 12, 2, 13, 2, 10, 2, 11, 5, 10, 5, 11], [4, 12, 4, 13, 3, 12, 3, 13, 3, 14, 3, 15], [5, 13, 5, 14, 6, 13, 6, 14], [13, 13, 13, 14, 14, 13, 14, 14], [1, 13, 1, 14, 0, 13, 0, 14, 0, 15, 0, 16], [7, 13, 7, 14, 7, 11, 7, 12, 6, 11, 6, 12], [9, 13, 9, 14, 8, 13, 8, 14, 8, 15, 8, 16], [15, 13, 15, 14, 15, 11, 15, 12, 14, 11, 14, 12], [4, 14, 4, 15, 11, 14, 11, 15], [6, 14, 6, 15, 9, 14, 9, 15], [12, 14, 12, 15, 12, 12, 12, 13, 11, 12, 11, 13], [14, 14, 14, 15, 14, 12, 14, 13, 9, 12, 9, 13], [1, 15, 1, 16, 2, 15, 2, 16], [9, 15, 9, 16, 10, 15, 10, 16], [3, 15, 3, 16, 3, 13, 3, 14, 2, 13, 2, 14], [11, 15, 11, 16, 11, 13, 11, 14, 10, 13, 10, 14]

TABLE 17B

[10, 14, 10, 15, 13, 14, 13, 15, 13, 16, 0, 0], [8, 14, 8, 15, 15, 14, 15, 15, 15, 16, 0, 0], [5, 15, 5, 16, 4, 15, 4, 16], [7, 15, 7, 16, 6, 15, 6, 16], [13, 15, 13, 16, 12, 15, 12, 16], [15, 15, 15, 16, 14, 15, 14, 16], [4, 16, 0, 0, 3, 16, 0, 0], [6, 16, 0, 0, 1, 16, 0, 0], [8, 16, 0, 0, 7, 16, 0, 0], [10, 16, 0, 0, 5, 16, 0, 0], [12, 16, 0, 0, 11, 16, 0, 0], [14, 16, 0, 0, 9, 16, 0, 0], [0, 16, 0, 0, 0, 14, 0, 15, 7, 14, 7, 15], [2, 16, 0, 0, 2, 14, 2, 15, 5, 14, 5, 15]

The core oligonucleotide sequences used to produce 4H×4H×256B nucleic acid structures of the invention are designated SEQ ID NOs. 3249-3440, and the corresponding voxel coordinates are shown respectively in Table 18A. The end oligonucleotide sequences used to produce 4H×4H×256B nucleic acid structures of the invention are designated SEQ ID NOs. 3675-3688, and the corresponding voxel coordinates are shown respectively in Table 18B. (See also Appendix, Table 8 of U.S. provisional application No. 61/675,309, filed Jul. 24, 2012, incorporated by reference herein.)

TABLE 18A

[0, 0, 0, 1, 0, 0, 0, 0], [0, 0, 2, 1, 0, 0, 0, 0], [0, 0, 13, 1, 0, 0, 0, 0], [0, 0, 15, 1, 0, 0, 0, 0], [0, 0, 8, 1, 0, 0, 7, 1], [0, 0, 10, 1, 0, 0, 5, 1], [0, 0, 6, 1, 0, 0, 1, 1, 1, 2, 1, 3], [0, 0, 4, 1, 0, 0, 3, 1, 3, 2, 3, 3], [4, 1, 4, 2, 0, 0, 0, 0], [7, 1, 7, 2, 0, 0, 0, 0], [12, 1, 12, 2, 0, 0, 0, 0], [15, 1, 15, 2, 0, 0, 0, 0], [5, 1, 5, 2, 6, 1, 6, 2], [13, 1, 13, 2, 14, 1, 14, 2], [1, 1, 1, 2, 0, 1, 0, 2, 0, 3, 0, 4], [9, 1, 9, 2, 8, 1, 8, 2, 8, 3, 8, 4], [4, 2, 4, 3, 11, 2, 11, 3], [6, 2, 6, 3, 9, 2, 9, 3], [12, 2, 12, 3, 0, 0, 12, 1, 0, 0, 11, 1], [14, 2, 14, 3, 0, 0, 14, 1, 0, 0, 9, 1], [1, 3, 1, 4, 2, 3, 2, 4], [9, 3, 9, 4, 10, 3, 10, 4], [3, 3, 3, 4, 3, 1, 3, 2, 2, 1, 2, 2], [11, 3, 11, 4, 11, 1, 11, 2, 10, 1, 10, 2], [10, 2, 10, 3, 13, 2, 13, 3, 13, 4, 13, 5], [8, 2, 8, 3, 15, 2, 15, 3, 15, 4, 15, 5], [5, 3, 5, 4, 4, 3, 4, 4, 4, 5, 4, 6], [13, 3, 13, 4, 12, 3, 12, 4, 12, 5, 12, 6], [8, 4, 8, 5, 7, 4, 7, 5], [10, 4, 10, 5, 5, 4, 5, 5], [0, 4, 0, 5, 0, 2, 0, 3, 7, 2, 7, 3], [6, 4, 6, 5, 1, 4, 1, 5, 1, 6, 1, 7], [2, 4, 2, 5, 2, 2, 2, 3, 5, 2, 5, 3], [4, 4, 4, 5, 3, 4, 3, 5, 3, 6, 3, 7], [5, 5, 5, 6, 6, 5, 6, 6], [13, 5, 13, 6, 14, 5, 14, 6], [1, 5, 1, 6, 0, 5, 0, 6, 0, 7, 0, 8], [7, 5, 7, 6, 7, 3, 7, 4, 6, 3, 6, 4], [9, 5, 9, 6, 8, 5, 8, 6, 8, 7, 8, 8], [15, 5, 15, 6, 15, 3, 15, 4, 14, 3, 14, 4], [4, 6, 4, 7, 11, 6, 11, 7], [6, 6, 6, 7, 9, 6, 9, 7], [12, 6, 12, 7, 12, 4, 12, 5, 11, 4, 11, 5], [14, 6, 14, 7, 14, 4, 14, 5, 9, 4, 9, 5], [1, 7, 1, 8, 2, 7, 2, 8], [9, 7, 9, 8, 10, 7, 10, 8], [3, 7, 3, 8, 3, 5, 3, 6, 2, 5, 2, 6], [11, 7, 11, 8, 11, 5, 11, 6, 10, 5, 10, 6], [10, 6, 10, 7, 13, 6, 13, 7, 13, 8, 13, 9], [8, 6, 8, 7, 15, 6, 15, 7, 15, 8, 15, 9], [5, 7, 5, 8, 4, 7, 4, 8, 4, 9, 4, 10], [13, 7, 13, 8, 12, 7, 12, 8, 12, 9, 12, 10], [8, 8, 8, 9, 7, 8, 7, 9], [10, 8, 10, 9, 5, 8, 5, 9], [0, 8, 0, 9, 0, 6, 0, 7, 7, 6, 7, 7], [6, 8, 6, 9, 1, 8, 1, 9, 1, 10, 1, 11], [2, 8, 2, 9, 2, 6, 2, 7, 5, 6, 5, 7], [4, 8, 4, 9, 3, 8, 3, 9, 3, 10, 3, 11], [5, 9, 5, 10, 6, 9, 6, 10], [13, 9, 13, 10, 14, 9, 14, 10], [1, 9, 1, 10, 0, 9, 0, 10, 0, 11, 0, 12], [7, 9, 7, 10, 7, 7, 7, 8, 6, 7, 6, 8], [9, 9, 9, 10, 8, 9, 8, 10, 8, 11, 8, 12], [15, 9, 15, 10, 15, 7, 15, 8, 14, 7, 14, 8], [4, 10, 4, 11, 11, 10, 11, 11], [6, 10, 6, 11, 9, 10, 9, 11], [12, 10, 12, 11, 12, 8, 12, 9, 11, 8, 11, 9], [10, 10, 10, 11, 13, 10, 13, 11, 13, 12, 13, 13], [14, 10, 14, 11, 14, 8, 14, 9, 9, 8, 9, 9], [8, 10, 8, 11, 15, 10, 15, 11, 15, 12, 15, 13], [1, 11, 1, 12, 2, 11, 2, 12], [9, 11, 9, 12, 10, 11, 10, 12], [3, 11, 3, 12, 3, 9, 3, 10, 2, 9, 2, 10], [5, 11, 5, 12, 4, 11, 4, 12, 4, 13, 4, 14], [1, 1, 11, 11, 12, 11, 9, 11, 10, 10, 9, 10, 10], [13, 11, 13, 12, 12, 11, 12, 12, 12, 13, 12, 14], [8, 12, 8, 13, 7, 12, 7, 13], [10, 12, 10, 13, 5, 12, 5, 13], [0, 12, 0, 13, 0, 10, 0, 11, 7, 10, 7, 11], [6, 12, 6, 13, 1, 12, 1, 13, 1, 14, 1, 15], [2, 12, 2, 13, 2, 10, 2, 11, 5, 10, 5, 11], [4, 12, 4, 13, 3, 12, 3, 13, 3, 14, 3, 15], [5, 13, 5, 14, 6, 13, 6, 14], [13, 13, 13, 14, 14, 13, 14, 14], [1, 13, 1, 14, 0, 13, 0, 14, 0, 15, 0, 16], [7, 13, 7, 14, 7, 11, 7, 12, 6, 11, 6, 12], [9, 13, 9, 14, 8, 13, 8, 14, 8, 15, 8, 16], [15, 13, 15, 14, 15, 11, 15, 12, 14, 11, 14, 12], [4, 14, 4, 15, 11, 14, 11, 15], [6, 14, 6, 15, 9, 14, 9, 15], [12, 14, 12, 15, 12, 12, 12, 13, 11, 12, 11, 13], [14, 14, 14, 15, 14, 12, 14, 13, 9, 12, 9, 13], [1, 15, 1, 16, 2, 15, 2, 16], [9, 15, 9, 16, 10, 15, 10, 16], [3, 15, 3, 16, 3, 13, 3, 14, 2, 13, 2, 14], [11, 15, 11, 16, 11, 13, 11, 14, 10, 13, 10, 14], [10, 14, 10, 15, 13, 14, 13, 15, 13, 16, 13, 17], [8, 14, 8, 15, 15, 14, 15, 15, 15, 16, 15, 17], [5, 15, 5, 16, 4, 15, 4, 16, 4, 17, 4, 18], [13, 15, 13, 16, 12, 15, 12, 16, 12, 17, 12, 18], [8, 16, 8, 17, 7, 16, 7, 17], [10, 16, 10, 17, 5, 16, 5, 17], [0, 16, 0, 17, 0, 14, 0, 15, 7, 14, 7, 15], [6, 16, 6, 17, 1, 16, 1, 17, 1, 18, 1, 19], [2, 16, 2, 17, 2, 14, 2, 15, 5, 14, 5, 15], [4, 16, 4, 17, 3, 16, 3, 17, 3, 18, 3, 19], [5, 17, 5, 18, 6, 17, 6, 18], [13, 17, 13, 18, 14, 17, 14, 18], [1, 17, 1, 18, 0, 17, 0, 18, 0, 19, 0, 20], [7, 17, 7, 18, 7, 15, 7, 16, 6, 15, 6, 16], [9, 17, 9, 18, 8, 17, 8, 18, 8, 19, 8, 20], [15, 17, 15, 18, 15, 15, 15, 16, 14, 15, 14, 16], [4, 18, 4, 19, 11, 18, 11, 19], [6, 18, 6, 19, 9, 18, 9, 19], [12, 18, 12, 19, 12, 16, 12, 17, 11, 16, 11, 17], [10, 18, 10, 19, 13, 18, 13, 19, 13, 20, 13, 21], [14, 18, 14, 19, 14, 16, 14, 17, 9, 16, 9, 17], [8, 18, 8, 19, 15, 18, 15, 19, 15, 20, 15, 21], [1, 19, 1, 20, 2, 19, 2, 20], [9, 19, 9, 20, 10, 19, 10, 20], [3, 19, 3, 20, 3, 17, 3, 18, 2, 17, 2, 18], [5, 19, 5, 20, 4, 19, 4, 20, 4, 21, 4, 22], [11, 19, 11, 20, 11, 17, 11, 18, 10, 17, 10, 18], [13, 19, 13, 20, 12, 19, 12, 20, 12, 21, 12, 22], [8, 20, 8, 21, 7, 20, 7, 21], [10, 20, 10, 21, 5, 20, 5, 21], [0, 20, 0, 21, 0, 18, 0, 19, 7, 18, 7, 19], [6, 20, 6, 21, 1, 20, 1, 21, 1, 22, 1, 23], [2, 20, 2, 21, 2, 18, 2, 19, 5, 18, 5, 19], [4, 20, 4, 21, 3, 20, 3, 21, 3, 22, 3, 23], [5, 21, 5, 22, 6, 21, 6, 22], [13, 21, 13, 22, 14, 21, 14, 22], [1, 21, 1, 22, 0, 21, 0, 22, 0, 23, 0, 24], [7, 21, 7, 22, 7, 19, 7, 20, 6, 19, 6, 20], [9, 21, 9, 22, 8, 21, 8, 22, 8, 23, 8, 24], [15, 21, 15, 22, 15, 19, 15, 20, 14, 19, 14, 20], [4, 22, 4, 23, 11, 22, 11, 23], [6, 22, 6, 23, 9, 22, 9, 23], [12, 22, 12, 23, 12, 20, 12, 21, 11, 20, 11, 21], [10, 22, 10, 23, 13, 22, 13, 23, 13, 24, 13, 25], [14, 22, 14, 23, 14, 20, 14, 21, 9, 20, 9, 21], [8, 22, 8, 23, 15, 22, 15, 23, 15, 24, 15, 25], [1, 23, 1, 24, 2, 23, 2, 24], [9, 23, 9, 24, 10, 23, 10, 24], [3, 23, 3, 24, 3, 21, 3, 22, 2, 21, 2, 22], [5, 23, 5, 24, 4, 23, 4, 24, 4, 25, 4, 26], [11, 23, 11, 24, 11, 21, 11, 22, 10, 21, 10, 22], [13, 23, 13, 24, 12, 23, 12, 24, 12, 25, 12, 26], [8, 24, 8, 25, 7, 24, 7, 25], [10, 24, 10, 25, 5, 24, 5, 25], [0, 24, 0, 25, 0, 22, 0, 23, 7, 22, 7, 23], [6, 24, 6, 25, 1, 24, 1, 25, 1, 26, 1, 27], [2, 24, 2, 25, 2, 22, 2, 23, 5, 22, 5, 23], [4, 24, 4, 25, 3, 24, 3, 25, 3, 26, 3, 27], [5, 25, 5, 26, 6, 25, 6, 26], [13, 25, 13, 26, 14, 25, 14, 26], [1, 25, 1, 26, 0, 25, 0, 26, 0, 27, 0, 28], [7, 25, 7, 26, 7, 23, 7, 24, 6, 23, 6, 24], [9, 25, 9, 26, 8, 25, 8, 26, 8, 27, 8, 28], [15, 25, 15, 26, 15, 23, 15, 24, 14, 23, 14, 24], [4, 26, 4, 27, 11, 26, 11, 27], [6, 26, 6, 27, 9, 26, 9, 27], [12, 26, 12, 27, 12, 24, 12, 25, 11, 24, 11, 25], [10, 26, 10, 27, 13, 26, 13, 27, 13, 28, 13, 29], [14, 26, 14, 27, 14, 24, 14, 25, 9, 24, 9, 25], [8, 26, 8, 27, 15, 26, 15, 27, 15, 28, 15, 29], [1, 27, 1, 28, 2, 27, 2, 28], [9, 27, 9, 28, 10, 27, 10, 28], [3, 27, 3, 28, 3, 25, 3, 26, 2, 25, 2, 26], [5, 27, 5, 28, 4, 27, 4, 28, 4, 29, 4, 30], [11, 27, 11, 28, 11, 25, 11, 26, 10, 25, 10, 26], [13, 27, 13, 28, 12, 27, 12, 28, 12, 29, 12, 30], [8, 28, 8, 29, 7, 28, 7, 29], [10, 28, 10, 29, 5, 28, 5, 29], [0, 28, 0, 29, 0, 26, 0, 27, 7, 26, 7, 27], [6, 28, 6, 29, 1, 28, 1, 29, 1, 30, 1, 31], [2, 28, 2, 29, 2, 26, 2, 27, 5, 26, 5, 27], [4, 28, 4, 29, 3, 28, 3, 29, 3, 30, 3, 31], [5, 29, 5, 30, 6, 29, 6, 30], [13, 29, 13, 30, 14, 29, 14, 30], [1, 29, 1, 30, 0, 29, 0, 30, 0, 31, 0, 32], [7, 29, 7, 30, 7, 27, 7, 28, 6, 27, 6, 28], [9, 29, 9, 30, 8, 29, 8, 30, 8, 31, 8, 32], [15, 29, 15, 30, 15, 27, 15, 28, 14, 27, 14, 28], [4, 30, 4, 31, 11, 30, 11, 31], [6, 30, 6, 31, 9, 30, 9, 31], [12, 30, 12, 31, 12, 28, 12, 29, 11, 28, 11, 29], [14, 30, 14, 31, 14, 28, 14, 29, 9, 28, 9, 29], [1, 31, 1, 32, 2, 31, 2, 32], [9, 31, 9, 32, 10, 31, 10, 32], [3, 31, 3, 32, 3, 29, 3, 30, 2, 29, 2, 30], [11, 31, 11, 32, 11, 29, 11, 30, 10, 29, 10, 30]

TABLE 18B

[10, 30, 10, 31, 13, 30, 13, 31, 13, 32, 0, 0], [8, 30, 8, 31, 15, 30, 15, 31, 15, 32, 0, 0], [5, 31, 5, 32, 4, 31, 4, 32], [7, 31, 7, 32, 6, 31, 6, 32], [13, 31, 13, 32, 12, 31, 12, 32], [15, 31, 15, 32, 14, 31, 14, 32], [4, 32, 0, 0, 3, 32, 0, 0], [6, 32, 0, 0, 1, 32, 0, 0], [8, 32, 0, 0, 7, 32, 0, 0], [10, 32, 0, 0, 5, 32, 0, 0], [12, 32, 0, 0, 11, 32, 0, 0], [14, 32, 0, 0, 9, 32, 0, 0], [0, 32, 0, 0, 0, 30, 0, 31, 7, 30, 7, 31], [2, 32, 0, 0, 2, 30, 2, 31, 5, 30, 5, 31]

The core oligonucleotide sequences used to produce 4H×4H×512B nucleic acid structures of the invention are designated SEQ ID NOs. 3249-3632, and the corresponding voxel coordinates are shown respectively in Table 19A. The end oligonucleotide sequences used to produce 4H×4H× 512B nucleic acid structures of the invention are designated SEQ ID NOs. 3689-3702, and the corresponding voxel coordinates are shown respectively in Table 19B. (See also Appendix, Table 8 of U.S. provisional application No. 61/675,309, filed Jul. 24, 2012, incorporated by reference herein.)

TABLE 19A

[0, 0, 0, 1, 0, 0, 0, 0], [0, 0, 2, 1, 0, 0, 0, 0], [0, 0, 13, 1, 0, 0, 0, 0], [0, 0, 15, 1, 0, 0, 0, 0], [0, 0, 8, 1, 0, 0, 7, 1], [0, 0, 10, 1, 0, 0, 5, 1], [0, 0, 6, 1, 0, 0, 1, 1, 2, 1, 3], [0, 0, 4, 1, 0, 0, 3, 1, 3, 2, 3], [4, 1, 4, 2, 0, 0, 0, 0], [7, 1, 7, 2, 0, 0, 0, 0], [12, 1, 12, 2, 0, 0, 0, 0], [15, 1, 15, 2, 0, 0, 0, 0], [5, 1, 5, 2, 6, 1, 6, 2], [13, 1, 13, 2, 14, 1, 14, 2], [1, 1, 1, 2, 0, 1, 0, 2, 0, 3, 0, 4], [9, 1, 9, 2, 8, 1, 8, 2, 8, 3, 8, 4], [4, 2, 4, 3, 11, 2, 11, 3], [6, 2, 6, 3, 9, 2, 9, 3], [12, 2, 12, 3, 0, 0, 12, 1, 0, 0, 11, 1], [14, 2, 14, 3, 0, 0, 14, 1, 0, 0, 9, 1], [1, 3, 1, 4, 2, 3, 2, 4], [9, 3, 9, 4, 10, 3, 10, 4], [3, 3, 3, 4, 3, 1, 3, 2, 2, 1, 2, 2], [11, 3, 11, 4, 11, 1, 11, 2, 10, 1, 10, 2], [10, 2, 10, 3, 13, 2, 13, 3, 13, 4, 13, 5], [8, 2, 8, 3, 15, 2, 15, 3, 15, 4, 15, 5], [5, 3, 5, 4, 4, 3, 4, 4, 4, 4, 5, 4, 6], [13, 3, 13, 4, 12, 3, 12, 4, 12, 5, 12, 6], [8, 4, 8, 5, 7, 4, 7, 5], [10, 4, 10, 5, 5, 4, 5, 5], [0, 4, 0, 5, 0, 2, 0, 3, 7, 2, 7, 3], [6, 4, 6, 5, 1, 4, 1, 5, 1, 6, 1, 7], [2, 4, 2, 5, 2, 2, 2, 3, 5, 2, 5, 3], [4, 4, 4, 5, 3, 4, 3, 5, 3, 6, 3, 7], [5, 5, 5, 6, 6, 5, 6, 6], [13, 5, 13, 6, 14, 5, 14, 6], [1, 5, 1, 6, 0, 5, 0, 6, 0, 7, 0, 8], [7, 5, 7, 6, 7, 3, 7, 4, 6, 3, 6, 4], [9, 5, 9, 6, 8, 5, 8, 6, 8, 7, 8, 8], [15, 5, 15, 6, 15, 3, 15, 4, 14, 3, 14, 4], [4, 6, 4, 7, 11, 6, 11, 7], [6, 6, 6, 7, 9, 6, 9, 7], [12, 6, 12, 7, 12, 4, 12, 5, 11, 4, 11, 5], [14, 6, 14, 7, 14, 4, 14, 5, 9, 4, 9, 5], [1, 7, 1, 8, 2, 7, 2, 8], [9, 7, 9, 8, 10, 7, 10, 8], [3, 7, 3, 8, 3, 5, 3, 6, 2, 5, 2, 6], [11, 7, 11, 8, 11, 5, 11, 6, 10, 5, 10, 6], [10, 6, 10, 7, 13, 6, 13, 7, 13, 8, 13, 9], [8, 6, 8, 7, 15, 6, 15, 7, 15, 8, 15, 9], [5, 7, 5, 8, 4, 7, 4, 8, 4, 9, 4, 10], [13, 7, 13, 8, 12, 7, 12, 8, 12, 9, 12, 10], [8, 8, 8, 9, 7, 8, 7, 9], [10, 8, 10, 9, 5, 8, 5, 9], [0, 8, 0, 9, 0, 6, 0, 7, 7, 6, 7, 7], [6, 8, 6, 9, 1, 8, 1, 9, 1, 10, 1, 11], [2, 8, 2, 9, 2, 6, 2, 7, 5, 6, 5, 7], [4, 8, 4, 9, 3, 8, 3, 9, 3, 10, 3, 11], [5, 9, 5, 10, 6, 9, 6, 10], [13, 9, 13, 10, 14, 9, 14, 10], [1, 9, 1, 10, 0, 9, 0, 10, 0, 11, 0, 12], [7, 9, 7, 10, 7, 7, 7, 8, 6, 7, 6, 8], [9, 9, 9, 10, 8, 9, 8, 10, 8, 11, 8, 12], [15, 9, 15, 10, 15, 7, 15, 8, 14, 7, 14, 8], [4, 10, 4, 11, 11, 10, 11, 11], [6, 10, 6, 11, 9, 10, 9, 11], [12, 10, 12, 11, 12, 8, 12, 9, 11, 8, 11, 9], [10, 10, 10, 11, 13, 10, 13, 11, 13, 12, 13, 13], [14, 10, 14, 11, 14, 8, 14, 9, 9, 8, 9, 9], [8, 10, 8, 11, 15, 10, 15, 11, 15, 12, 15, 13], [1, 11, 1, 12, 2, 11, 2, 12], [9, 11, 9, 12, 10, 11, 10, 12], [3, 11, 3, 12, 3, 9, 3, 10, 2, 9, 2, 10], [5, 11, 5, 12, 4, 11, 4, 12, 4, 13, 4, 14], [1, 1, 11, 11, 12, 11, 9, 11, 10, 10, 9, 10, 10], [13, 11, 13, 12, 12, 11, 12, 12, 12, 13, 12, 14], [8, 12, 8, 13, 7, 12, 7, 13], [10, 12, 10, 13, 5, 12, 5, 13], [0, 12, 0, 13, 0, 10, 0, 11, 7, 10, 7, 11], [6, 12, 6, 13, 1, 12, 1, 13, 1, 14, 1, 15], [2, 12, 2, 13, 2, 10, 2, 11, 5, 10, 5, 11], [4, 12, 4, 13, 3, 12, 3, 13, 3, 14, 3, 15], [5, 13, 5, 14, 6, 13, 6, 14], [13, 13, 13, 14, 14, 13, 14, 14], [1, 13, 1, 14, 0, 13, 0, 14, 0, 15, 0, 16], [7, 13, 7, 14, 7, 11, 7, 12, 6, 11, 6, 12], [9, 13, 9, 14, 8, 13, 8, 14, 8, 15, 8, 16], [15, 13, 15, 14, 15, 11, 15, 12, 14, 11, 14, 12], [4, 14, 4, 15, 11, 14, 11, 15], [6, 14, 6, 15, 9, 14, 9, 15], [12, 14, 12, 15, 12, 12, 12, 13, 11, 12, 11, 13], [14, 14, 14, 15, 14, 12, 14, 13, 9, 12, 9, 13], [1, 15, 1, 16, 2, 15, 2, 16], [9, 15, 9, 16, 10, 15, 10, 16], [3, 15, 3, 16, 3, 13, 3, 14, 2, 13, 2, 14], [11, 15, 11, 16, 11, 13, 11, 14, 10, 13, 10, 14], [10, 14, 10, 15, 13, 14, 13, 15, 13, 16, 13, 17], [8, 14, 8, 15, 15, 14, 15, 15, 15, 16, 15, 17], [5, 15, 5, 16, 4, 15, 4, 16, 4, 17, 4, 18], [13, 15, 13, 16, 12, 15, 12, 16, 12, 17, 12, 18], [8, 16, 8, 17, 7, 16, 7, 17], [10, 16, 10, 17, 5, 16, 5, 17], [0, 16, 0, 17, 0, 14, 0, 15, 7, 14, 7, 15], [6, 16, 6, 17, 1, 16, 1, 17, 1, 18, 1, 19], [2, 16, 2, 17, 2, 14, 2, 15, 5, 14, 5, 15], [4, 16, 4, 17, 3, 16, 3, 17, 3, 18, 3, 19], [5, 17, 5, 18, 6, 17, 6, 18], [13, 17, 13, 18, 14, 17, 14, 18], [1, 17, 1, 18, 0, 17, 0, 18, 0, 19, 0, 20], [7, 17, 7, 18, 7, 15, 7, 16, 6, 15, 6, 16], [9, 17, 9, 18, 8, 17, 8, 18, 8, 19, 8, 20], [15, 17, 15, 18, 15, 15, 15, 16, 14, 15, 14, 16], [4, 18, 4, 19, 11, 18, 11, 19], [6, 18, 6, 19, 9, 18, 9, 19], [12, 18, 12, 19, 12, 16, 12, 17, 11, 16, 11, 17], [10, 18, 10, 19, 13, 18, 13, 19, 13, 20, 13, 21], [14, 18, 14, 19, 14, 16, 14, 17, 9, 16, 9, 17], [8, 18, 8, 19, 15, 18, 15, 19, 15, 20, 15, 21], [1, 19, 1, 20, 2, 19, 2, 20], [9, 19, 9, 20, 10, 19, 10, 20], [3, 19, 3, 20, 3, 17, 3, 18, 2, 17, 2, 18], [5, 19, 5, 20, 4, 19, 4, 20, 4, 21, 4, 22], [11, 19, 11, 20, 11, 17, 17, 10, 18], [10, 19, 10, 20, 13, 19, 13, 20, 12, 19, 12, 20, 22], [8, 20, 8, 21, 7, 20, 7, 21], [10, 20, 10, 21, 5, 20, 5, 21], [0, 20, 0, 21, 0, 18, 0, 19, 7, 18, 7, 19], [6, 20, 6, 21, 1, 20, 1, 21, 1, 22, 1, 23], [2, 20, 2, 21, 2, 18, 2, 19, 5, 18, 5, 19], [4, 20, 4, 21, 3, 20, 3, 21, 3, 22, 3, 23], [5, 21, 5, 22, 6, 21, 6, 22], [13, 21, 13, 22, 14, 21, 14, 22], [1, 21, 1, 22, 0, 21, 0, 22, 0, 23, 0, 24], [7, 21, 7, 22, 7, 19, 7, 20, 6, 19, 6, 20], [9, 21, 9, 22, 8, 21, 8, 22, 8, 23, 8, 24], [15, 21, 15, 22, 15, 19, 15, 20, 14, 19, 14, 20], [4, 22, 4, 23, 11, 22, 11, 23], [6, 22, 6, 23, 9, 22, 9, 23], [12, 22, 12, 23, 12, 20, 12, 21, 11, 20, 11, 21], [10, 22, 10, 23, 13, 22, 13, 23, 13, 24, 13, 25], [14, 22, 14, 23, 14, 20, 14, 21, 9, 20, 9, 21], [8, 22, 8, 23, 15, 22, 15, 23, 15, 24, 15, 25], [1, 23, 1, 24, 2, 23, 2, 24], [9, 23, 9, 24, 10, 23, 10, 24], [3, 23, 3, 24, 3, 21, 3, 22, 2, 21, 2, 22], [5, 23, 5, 24, 4, 23, 4, 24, 4, 25, 4, 26], [11, 23, 11, 24, 11, 21, 11, 22, 10, 21, 10, 22], [13, 23, 13, 24, 12, 23, 12, 24, 12, 25, 12, 26], [8, 24, 8, 25, 7, 24, 7, 25], [10, 24, 10, 25, 5, 24, 5, 25], [0, 24, 0, 25, 0, 22, 0, 23, 7, 22, 7, 23], [6, 24, 6, 25, 1, 24, 1, 25, 1, 26, 1, 27], [2, 24, 2, 25, 2, 22, 2, 23, 5, 22, 5, 23], [4, 24, 4, 25, 3, 24, 3, 25, 3, 26, 3, 27], [5, 25, 5, 26, 6, 25, 6, 26], [13, 25, 13, 26, 14, 25, 14, 26], [1, 25, 1, 26, 0, 25, 0, 26, 0, 27, 0, 28], [7, 25, 7, 26, 7, 23, 7, 24, 6, 23, 6, 24], [9, 25, 9, 26, 8, 25, 8, 26, 8, 27, 8, 28], [15, 25, 15, 26, 15, 23, 15, 24, 14, 23, 14, 24], [4, 26, 4, 27, 11, 26, 11, 27], [6, 26, 6, 27, 9, 26, 9, 27], [12, 26, 12, 27, 12, 24, 12, 25, 11, 24, 11, 25], [10, 26, 10, 27, 13, 26, 13, 27, 13, 28, 13, 29], [14, 26, 14, 27, 14, 24, 14, 25, 9, 24, 9, 25], [8, 26, 8, 27, 15, 26, 15, 27, 15, 28, 15, 29], [1, 27, 1, 28, 2, 27, 2, 28], [9, 27, 9, 28, 10, 27, 10, 28], [3, 27, 3, 28, 3, 25, 3, 26, 2, 25, 2, 26], [5, 27, 5, 28, 4, 27, 4, 28, 4, 29, 4, 30], [11, 27, 11, 28, 11, 25, 11, 26, 10, 25, 10, 26], [13, 27, 13, 28, 12, 27, 12, 28, 12, 29, 12, 30], [8, 28, 8, 29, 7, 28, 7, 29], [10, 28, 10, 29, 5, 28, 5, 29], [0, 28, 0, 29, 0, 26, 0, 27, 7, 26, 7, 27], [6, 28, 6, 29, 1, 28, 1, 29, 1, 30, 1, 31], [2, 28, 2, 29, 2, 26, 2, 27, 5, 26, 5, 27], [4, 28, 4, 29, 3, 28, 3, 29, 3, 30, 3, 31], [5, 29, 5, 30, 6, 29, 6, 30], [13, 29, 13, 30, 14, 29, 14, 30], [1, 29, 1, 30, 0, 29, 0, 30, 0, 31, 0, 32], [7, 29, 7, 30, 7, 27, 7, 28, 6, 27, 6, 28], [9, 29, 9, 30, 8, 29, 8, 30, 8, 31, 8, 32], [15, 29, 15, 30, 15, 27, 15, 28, 14, 27, 14, 28], [4, 30, 4, 31, 11, 30, 11, 31], [6, 30, 6, 31, 9, 30, 9, 31], [12, 30, 12, 31, 12, 28, 12, 29, 11, 28, 11, 29], [14, 30, 14, 31, 14, 28, 14, 29, 9, 28, 9, 29], [1, 31, 1, 32, 2, 31, 2, 32], [9, 31, 9, 32, 10, 31, 10, 32], [3, 31, 3, 32, 3, 29, 3, 30, 2, 29, 2, 30], [11, 31, 11, 32, 11, 29, 11, 30, 10, 29, 10, 30], [10, 30, 10, 31, 13, 30, 13, 31, 13, 32, 13, 33], [8, 30, 8, 31, 15, 30, 15, 31, 15, 32, 15, 33], [5, 31, 5, 32, 4, 31, 4, 32, 4, 33, 4, 34], [13, 31, 13, 32, 12, 31, 12, 32, 12, 33, 12, 34], [8, 32, 8, 33, 7, 32, 7, 33], [10, 32, 10, 33, 5, 32, 5, 33], [0, 32, 0, 33, 0, 30, 0, 31, 7, 30, 7, 31], [6, 32, 6, 33, 1, 32, 1, 33, 1, 34, 1, 35], [2, 32, 2, 33, 2, 30, 2, 31, 5, 30, 5, 31], [4, 32, 4, 33, 3, 32, 3, 33, 3, 34, 3, 35], [5, 33, 5, 34, 6, 33, 6, 34], [13, 33, 13, 34, 14, 33, 14, 34], [1, 33, 1, 34, 0, 33, 0, 34, 0, 35, 0, 36], [7, 33, 7, 34, 7, 31, 7, 32, 6, 31, 6, 32], [9, 33, 9, 34, 8, 33, 8, 34, 8, 35, 8, 36], [15, 33, 15, 34, 15, 31, 15, 32, 14, 31, 14, 32], [4, 34, 4, 35, 11, 34, 11, 35], [6, 34, 6, 35, 9, 34, 9, 35], [12, 34, 12, 35, 12, 32, 12, 33, 11, 32, 11, 33], [10, 34, 10, 35, 13, 34, 13, 35, 13, 36, 13, 37], [14, 34, 14, 35, 14, 32, 14, 33, 9, 32, 9, 33], [8, 34, 8, 35, 15, 34, 15, 35, 15, 36, 15, 37], [1, 35, 1, 36, 2, 35, 2, 36], [9, 35, 9, 36, 10, 35, 10, 36], [3, 35, 3, 36, 3, 33, 3, 34, 2, 33, 2, 34], [5, 35, 5, 36, 4, 35, 4, 36, 4, 37, 4, 38], [1 1, 35, 11, 36, 11, 33, 11, 34, 10, 33, 10, 34], [13, 35, 13, 36, 12, 35, 12, 36, 12, 37, 12, 38], [8, 36, 8, 37, 7, 36, 7, 37], [10, 36, 10, 37, 5, 36, 5, 37], [0, 36, 0, 37, 0, 34, 0, 35, 7, 34, 7, 35], [6, 36, 6, 37, 1, 36, 1, 37, 1, 38, 1, 39], [2, 36, 2, 37, 2, 34, 2, 35, 5, 34, 5, 35], [4, 36, 4, 37, 3, 36, 3, 37, 3, 38, 3, 39], [5, 37, 5, 38, 6, 37, 6, 38], [13, 37, 13, 38, 14, 37, 14, 38], [1, 37, 1, 38, 0, 37, 0, 38, 0, 39, 0, 40], [7, 37, 7, 38, 7, 35, 7, 36, 6, 35, 6, 36], [9, 37, 9, 38, 8, 37, 8, 38, 8, 39, 8, 40], [15, 37, 15, 38, 15, 35, 15, 36, 14, 35, 14, 36], [4, 38, 4, 39, 11, 38, 11, 39], [6, 38, 6, 39, 9, 38, 9, 39], [12, 38, 12, 39, 12, 36, 12, 37, 11, 36, 11, 37], [10, 38, 10, 39, 13, 38, 13, 39, 13, 40, 13, 41], [14, 38, 14, 39, 14, 36, 14, 37, 9, 36, 9, 37], [8, 38, 8, 39, 15, 38, 15, 39, 15, 40, 15, 41], [1, 39, 1, 40, 2, 39, 2, 40], [9, 39, 9, 40, 10, 39, 10, 40], [3, 39, 3, 40, 3, 37, 3, 38, 2, 37, 2, 38], [5, 39, 5, 40, 4, 39, 4, 40, 4, 41, 4, 42], [1 1, 39, 11, 40, 11, 37, 11, 38, 10, 37, 10, 38], [13, 39, 13, 40, 12, 39, 12, 40, 12, 41, 12, 42], [8, 40, 8, 41, 7, 40, 7, 41], [10, 40, 10, 41, 5, 40, 5, 41], [0, 40, 0, 41, 0, 38, 0, 39, 7, 38, 7, 39], [6, 40, 6, 41, 1, 40, 1, 41, 1, 42, 1, 43], [2, 40, 2, 41, 2, 38, 2, 39, 5, 38, 5, 39], [4, 40, 4, 41, 3,

TABLE 19A-continued 40, 3, 41, 3, 42, 3, 43], [5, 41, 5, 42, 6, 41, 6, 42], [13, 41, 13, 42, 14, 41, 14, 42], [1, 41, 1, 42, 0, 41, 0, 42, 0, 43, 0, 44], [7, 41, 7, 42, 7, 39, 7, 40, 6, 39, 6, 40], [9, 41, 9, 42, 8, 41, 8, 42, 8, 43, 8, 44], [15, 41, 15, 42, 15, 39, 15, 40, 14, 39, 14, 40], [4, 42, 4, 43, 11, 42, 11, 43], [6, 42, 6, 43, 9, 42, 9, 43], [12, 42, 12, 43, 12, 40, 12, 41, 11, 40, 11, 41], [10, 42, 10, 43, 13, 42, 13, 43, 13, 44, 13, 45], [14, 42, 14, 43, 14, 40, 14, 41, 9, 40, 9, 41], [8, 42, 8, 43, 15, 42, 15, 43, 15, 44, 15, 45], [1, 43, 1, 44, 2, 43, 2, 44], [9, 43, 9, 44, 10, 43, 10, 44], [3, 43, 3, 44, 3, 41, 3, 42, 2, 41, 2, 42], [5, 43, 5, 44, 4, 43, 4, 44, 4, 45, 4, 46], [11, 43, 11, 44, 11, 41, 11, 42, 10, 41, 10, 42], [13, 43, 13, 44, 12, 43, 12, 44, 12, 45, 12, 46], [8, 44, 8, 45, 7, 44, 7, 45], [10, 44, 10, 45, 5, 44, 5, 45], [0, 44, 0, 45, 0, 42, 0, 43, 7, 42, 7, 43], [6, 44, 6, 45, 1, 44, 1, 45, 1, 46, 1, 47], [2, 44, 2, 45, 2, 42, 2, 43, 5, 42, 5, 43], [4, 44, 4, 45, 3, 44, 3, 45, 3, 46, 3, 47], [5, 45, 5, 46, 6, 45, 6, 46], [13, 45, 13, 46, 14, 45, 14, 46], [1, 45, 1, 46, 0, 45, 0, 46, 0, 47, 0, 48], [7, 45, 7, 46, 7, 43, 7, 44, 6, 43, 6, 44], [9, 45, 9, 46, 8, 45, 8, 46, 8, 47, 8, 48], [15, 45, 15, 46, 15, 43, 15, 44, 14, 43, 14, 44], [4, 46, 4, 47, 11, 46, 11, 47], [6, 46, 6, 47, 9, 46, 9, 47], [12, 46, 12, 47, 12, 44, 12, 45, 11, 44, 11, 45], [10, 46, 10, 47, 13, 46, 13, 47, 13, 48, 13, 49], [14, 46, 14, 47, 14, 44, 14, 45, 9, 44, 9, 45], [8, 46, 8, 47, 15, 46, 15, 47, 15, 48, 15, 49], [1, 47, 1, 48, 2, 47, 2, 48], [9, 47, 9, 48, 10, 47, 10, 48], [3, 47, 3, 48, 3, 45, 3, 46, 2, 45, 2, 46], [5, 47, 5, 48, 4, 47, 4, 48, 4, 49, 4, 50], [1 1, 47, 11, 48, 11, 45, 11, 46, 10, 45, 10, 46], [13, 47, 13, 48, 12, 47, 12, 48, 12, 49, 12, 50], [8, 48, 8, 49, 7, 48, 7, 49], [10, 48, 10, 49, 5, 48, 5, 49], [0, 48, 0, 49, 0, 46, 0, 47, 7, 46, 7, 47], [6, 48, 6, 49, 1, 48, 1, 49, 1, 50, 1, 51], [2, 48, 2, 49, 2, 46, 2, 47, 5, 46, 5, 47], [4, 48, 4, 49, 3, 48, 3, 49, 3, 50, 3, 51], [5, 49, 5, 50, 6, 49, 6, 50], [13, 49, 13, 50, 14, 49, 14, 50], [1, 49, 1, 50, 0, 49, 0, 50, 0, 51, 0, 52], [7, 49, 7, 50, 7, 47, 7, 48, 6, 47, 6, 48], [9, 49, 9, 50, 8, 49, 8, 50, 8, 51, 8, 52], [15, 49, 15, 50, 15, 47, 15, 48, 14, 47, 14, 48], [4, 50, 4, 51, 11, 50, 11, 51], [6, 50, 6, 51, 9, 50, 9, 51], [12, 50, 12, 51, 12, 48, 12, 49, 11, 48, 11, 49], [10, 50, 10, 51, 13, 50, 13, 51, 13, 52, 13, 53], [14, 50, 14, 51, 14, 48, 14, 49, 9, 48, 9, 49], [8, 50, 8, 51, 15, 50, 15, 51, 15, 52, 15, 53], [1, 51, 1, 52, 2, 51, 2, 52], [9, 51, 9, 52, 10, 51, 10, 52], [3, 51, 3, 52, 3, 49, 3, 50, 2, 49, 2, 50], [5, 51, 5, 52, 4, 51, 4, 52, 4, 53, 4, 54], [11, 51, 11, 52, 11, 49, 11, 50, 10, 49, 10, 50], [13, 51, 13, 52, 12, 51, 12, 52, 12, 53, 12, 54], [8, 52, 8, 53, 7, 52, 7, 53], [10, 52, 10, 53, 5, 52, 5, 53], [0, 52, 0, 53, 0, 50, 0, 51, 7, 50, 7, 51], [6, 52, 6, 53, 1, 52, 1, 53, 1, 54, 1, 55], [2, 52, 2, 53, 2, 50, 2, 51, 5, 50, 5, 51], [4, 52, 4, 53, 3, 52, 3, 53, 3, 54, 3, 55], [5, 53, 5, 54, 6, 53, 6, 54], [13, 53, 13, 54, 14, 53, 14, 54], [1, 53, 1, 54, 0, 53, 0, 54, 0, 55, 0, 56], [7, 53, 7, 54, 7, 51, 7, 52, 6, 51, 6, 52], [9, 53, 9, 54, 8, 53, 8, 54, 8, 55, 8, 56], [15, 53, 15, 54, 15, 51, 15, 52, 14, 51, 14, 52], [4, 54, 4, 55, 11, 54, 11, 55], [6, 54, 6, 55, 9, 54, 9, 55], [12, 54, 12, 55, 12, 52, 12, 53, 11, 52, 11, 53], [10, 54, 10, 55, 13, 54, 13, 55, 13, 56, 13, 57], [14, 54, 14, 55, 14, 52, 14, 53, 9, 52, 9, 53], [8, 54, 8, 55, 15, 54, 15, 55, 15, 56, 15, 57], [1, 55, 1, 56, 2, 55, 2, 56], [9, 55, 9, 56, 10, 55, 10, 56], [3, 55, 3, 56, 3, 53, 3, 54, 2, 53, 2, 54], [5, 55, 5, 56, 4, 55, 4, 56, 4, 57, 4, 58], [11, 55, 11, 56, 11, 53, 11, 54, 10, 53, 10, 54], [13, 55, 13, 56, 12, 55, 12, 56, 12, 57, 12, 58], [8, 56, 8, 57, 7, 56, 7, 57], [10, 56, 10, 57, 5, 56, 5, 57], [0, 56, 0, 57, 0, 54, 0, 55, 7, 54, 7, 55], [6, 56, 6, 57, 1, 56, 1, 57, 1, 58, 1, 59], [2, 56, 2, 57, 2, 54, 2, 55, 5, 54, 5, 55], [4, 56, 4, 57, 3, 56, 3, 57, 3, 58, 3, 59], [5, 57, 5, 58, 6, 57, 6, 58], [13, 57, 13, 58, 14, 57, 14, 58], [1, 57, 1, 58, 0, 57, 0, 58, 0, 59, 0, 60], [7, 57, 7, 58, 7, 55, 7, 56, 6, 55, 6, 56], [9, 57, 9, 58, 8, 57, 8, 58, 8, 59, 8, 60], [15, 57, 15, 58, 15, 55, 15, 56, 14, 55, 14, 56], [4, 58,4, 59, 11, 58, 11, 59], [6, 58, 6, 59, 9, 58, 9, 59], [12, 58, 12, 59, 12, 56, 12, 57, 11, 56, 11, 57], [10, 58, 10, 59, 13, 58, 13, 59, 13, 60, 13, 61], [14, 58, 14, 59, 14, 56, 14, 57, 9, 56, 9, 57], [8, 58, 8, 59, 15, 58, 15, 59, 15, 60, 15, 61], [1, 59, 1, 60, 2, 59, 2, 60], [9, 59, 9, 60, 10, 59, 10, 60], [3, 59, 3, 60, 3, 57, 3, 58, 2, 57, 2, 58], [5, 59, 5, 60, 4, 59, 4, 60, 4, 61, 4, 62], [11, 59, 11, 60, 11, 57, 11, 58, 10, 57, 10, 58], [13, 59, 13, 60, 12, 59, 12, 60, 12, 61, 12, 62], [8, 60, 8, 61, 7, 60, 7, 61], [10, 60, 10, 61, 5, 60, 5, 61], [0, 60, 0, 61, 0, 58, 0, 59, 7, 58, 7, 59], [6, 60, 6, 61, 1, 60, 1, 61, 1, 62, 1, 63], [2, 60, 2, 61, 2, 58, 2, 59, 5, 58, 5, 59], [4, 60, 4, 61, 3, 60, 3, 61, 3, 62, 3, 63], [5, 61, 5, 62, 6, 61, 6, 62], [13, 61, 13, 62, 14, 61, 14, 62], [1, 61, 1, 62, 0, 61, 0, 62, 0, 63, 0, 64], [7, 61, 7, 62, 7, 59, 7, 60, 6, 59, 6, 60], [9, 61, 9, 62, 8, 61, 8, 62, 8, 63, 8, 64], [15, 61, 15, 62, 15, 59, 15, 60, 14, 59, 14, 60], [4, 62, 4, 63, 11, 62, 11, 63], [6, 62, 6, 63, 9, 62, 9, 63], [12, 62, 12, 63, 12, 60, 12, 61, 11, 60, 11, 61], [14, 62, 14, 63, 14, 60, 14, 61, 9, 60, 9, 61], [1, 63, 1, 64, 2, 63, 2, 64], [9, 63, 9, 64, 10, 63, 10, 64], [3, 63, 3, 64, 3, 61, 3, 62, 2, 61, 2, 62], [11, 63, 11, 64, 11, 61, 11, 62, 10, 61, 10, 62].

TABLE 19B

[10, 62, 10, 63, 13, 62, 13, 63, 13, 64, 0, 0], [8, 62, 8, 63, 15, 62, 15, 63, 15, 64, 0, 0], [5, 63, 5, 64, 4, 63, 4, 64], [7, 63, 7, 64, 6, 63, 6, 64], [13, 63, 13, 64, 12, 63, 12, 64], [15, 63, 15, 64, 14, 63, 14, 64], [4, 64, 0, 0, 3, 64, 0, 0], [6, 64, 0, 0, 1, 64, 0, 0], [8, 64, 0, 0, 7, 64, 0, 0], [10, 64, 0, 0, 5, 64, 0, 0], [12, 64, 0, 0, 11, 64, 0, 0], [14, 64, 0, 0, 9, 64, 0, 0], [0, 64, 0, 0, 0, 62, 0, 63, 7, 62, 7, 63], [2, 64, 0, 0, 2, 62, 2, 63, 5, 62, 5, 63]

The core oligonucleotide sequences used to produce 6H×6H×32B nucleic acid structures of the invention are designated SEQ ID NOs. 3703-3762, and the corresponding voxel coordinates are shown respectively in Table 20A. The end oligonucleotide sequences used to produce 6H×6H×32B nucleic acid structures of the invention are designated SEQ ID NOs. 4183-4209, and the corresponding voxel coordinates are shown respectively in Table 20B. (See also Appendix, Table 9 of U.S. provisional application No. 61/675,309, filed Jul. 24, 2012, incorporated by reference herein.)

TABLE 20A

[0, 0, 0, 1, 0, 0, 0, 0], [0, 0, 2, 1, 0, 0, 0, 0], [0, 0, 4, 1, 0, 0, 0, 0], [0, 0, 31, 1, 0, 0, 0, 0], [0, 0, 33, 1, 0, 0, 0, 0], [0, 0, 35, 1, 0, 0, 0, 0], [0, 0, 12, 1, 0, 0, 11, 1], [0, 0, 14, 1, 0, 0, 9, 1], [0, 0, 16, 1, 0, 0, 7, 1], [0, 0, 18, 1, 0, 0, 17, 1], [0, 0, 20, 1, 0, 0, 15, 1], [0, 0, 22, 1, 0, 0, 13, 1], [0, 0, 24, 1, 0, 0, 23, 1], [0, 0, 26, 1, 0, 0, 21, 1], [0, 0, 28, 1, 0, 0, 19, 1], [0, 0, 10, 1, 0, 0, 1, 1, 1, 2, 1, 3], [0, 0, 8, 1, 0, 0, 3, 1, 3, 2, 3, 3], [0, 0, 6, 1, 0, 0, 5, 1, 5, 2, 5, 3], [6, 1, 6, 2, 0, 0, 0, 0], [1 1, 1, 11, 2, 0, 0, 0, 0], [18, 1, 18, 2, 0, 0, 0, 0], [23, 1, 23, 2, 0, 0, 0, 01, [30, 1, 30, 2, 0, 0, 0, 0], [35, 1, 35, 2, 0, 0, 0, 0], [3, 1, 3, 2, 2, 1, 2, 2], [7, 1, 7, 2, 8, 1, 8, 2], [9, 1, 9, 2, 10, 1, 10, 2], [15, 1, 15, 2, 14, 1, 14, 2], [19, 1, 19, 2, 20, 1, 20, 2], [21, 1, 21, 2, 22, 1, 22, 2], [27, 1, 27, 2, 26, 1, 26, 2], [31, 1, 31, 2, 32, 1, 32, 2], [33, 1, 33, 2, 34, 1, 34, 2], [1, 1, 1, 2, 0, 1, 0, 2, 0, 3, 0, 4], [13, 1, 13, 2, 12, 1, 12, 2, 12, 3, 12, 4], [25, 1, 25, 2, 24, 1, 24, 2, 24, 3, 24, 4], [6, 2, 6, 3, 17, 2, 17, 3], [8, 2, 8, 3, 15, 2, 15, 3], [10, 2, 10, 3, 13, 2, 13, 3], [12, 2, 12, 3, 23, 2, 23, 3], [14, 2, 14, 3, 21, 2, 21, 3], [16, 2, 16, 3, 19, 2, 19, 3], [18, 2, 18, 3, 29, 2, 29, 3], [20, 2, 20, 3, 27, 2, 27, 3], [22, 2, 22, 3, 25, 2, 25, 3], [30, 2, 30, 3, 0, 0, 30, 1, 0, 0, 29, 1], [32, 2, 32, 3, 0, 0, 32, 1, 0, 0, 27, 1], [34, 2, 34, 3, 0, 0, 34, 1, 0, 0, 25, 1], [1, 3, 1, 4, 2, 3, 2, 4], [3, 3, 3, 4, 4, 3, 4, 4], [9, 3, 9, 4, 8, 3, 8, 4], [13, 3, 13, 4, 14, 3, 14, 4], [15, 3, 15, 4, 16, 3, 16, 4], [21, 3, 21, 4, 20, 3, 20, 4], [25, 3, 25, 4, 26, 3, 26, 4], [27, 3, 27, 4, 28, 3, 28, 4], [33, 3, 33, 4, 32, 3, 32, 4], [5, 3, 5, 4, 5, 1, 5, 2, 4, 1, 4, 2], [17, 3, 17, 4, 17, 1, 17, 2, 16, 1, 16, 2], [29, 3, 29, 4, 29, 1, 29, 2, 28, 1, 28, 2].

TABLE 20B

[28, 2, 28, 3, 31, 2, 31, 3, 31, 4, 0, 0], [26, 2, 26, 3, 33, 2, 33, 3, 33, 4, 0, 0], [24, 2, 24, 3, 35, 2, 35, 3, 35, 4, 0, 0], [7, 3, 7, 4, 6, 3, 6, 4], [11, 3, 11, 4, 10, 3, 10, 4], [19, 3, 19, 4, 18, 3, 18, 4], [23, 3, 23, 4, 22, 3, 22, 4], [31, 3, 31, 4, 30, 3, 30, 4], [35, 3, 35, 4, 34, 3, 34, 4], [6, 4, 0, 0, 5, 4, 0, 0], [8, 4, 0, 0, 3, 4, 0, 0], [10, 4, 0, 0, 1, 4, 0, 0], [12, 4, 0, 0, 11, 4, 0, 0], [14, 4, 0, 0, 9, 4, 0, 0], [16, 4, 0, 0, 7, 4, 0, 0], [18, 4, 0, 0, 17, 4, 0, 0], [20, 4, 0, 0, 15, 4, 0, 0], [22, 4, 0, 0, 13, 4, 0, 0], [24, 4, 0, 0, 23, 4, 0, 0], [26, 4, 0, 0, 21, 4, 0, 0],

TABLE 20B-continued

[28, 4, 0, 0, 19, 4, 0, 0], [30, 4, 0, 0, 29, 4, 0, 0], [32, 4, 0, 0, 27, 4, 0, 0], [34, 4, 0, 0, 25, 4, 0, 0], [0, 4, 0, 0, 0, 2, 0, 3, 11, 2, 11, 3], [2, 4, 0, 0, 2, 2, 2, 3, 9, 2, 9, 3], [4, 4, 0, 0, 4, 2, 4, 3, 7, 2, 7, 3]

The core oligonucleotide sequences used to produce 6H×6H×64B nucleic acid structures of the invention are designated SEQ ID NOs. 3703-3822, and the corresponding voxel coordinates are shown respectively in Table 21A. The end oligonucleotide sequences used to produce 6H×6H×64B nucleic acid structures of the invention are designated SEQ ID NOs. 4210-4236, and the corresponding voxel coordinates are shown respectively in Table 21B. (See also Appendix, Table 9 of U.S. provisional application No. 61/675,309, filed Jul. 24, 2012, incorporated by reference herein.)

TABLE 21A

[0, 0, 0, 1, 0, 0, 0, 0], [0, 0, 2, 1, 0, 0, 0, 0], [0, 0, 4, 1, 0, 0, 0, 0], [0, 0, 31, 1, 0, 0, 0, 0], [0, 0, 33, 1, 0, 0, 0, 0], [0, 0, 35, 1, 0, 0, 0, 0], [0, 0, 12, 1, 0, 0, 11, 1], [0, 0, 14, 1, 0, 0, 9, 1], [0, 0, 16, 1, 0, 0, 7, 1], [0, 0, 18, 1, 0, 0, 17, 1], [0, 0, 20, 1, 0, 0, 15, 1], [0, 0, 22, 1, 0, 0, 13, 1], [0, 0, 24, 1, 0, 0, 23, 1], [0, 0, 26, 1, 0, 0, 21, 1], [0, 0, 28, 1, 0, 0, 19, 1], [0, 0, 10, 1, 0, 0, 1, 1, 1, 2, 1, 3], [0, 0, 8, 1, 0, 0, 3, 1, 3, 2, 3, 3], [0, 0, 6, 1, 0, 0, 5, 1, 5, 2, 5, 3], [6, 1, 6, 2, 0, 0, 0, 0], [1 1, 1, 11, 2, 0, 0, 0, 0], [18, 1, 18, 2, 0, 0, 0, 0], [23, 1, 23, 2, 0, 0, 0, 0], [30, 1, 30, 2, 0, 0, 0, 0], [35, 1, 35, 2, 0, 0, 0, 0], [3, 1, 3, 2, 2, 1, 2, 2], [7, 1, 7, 2, 8, 1, 8, 2], [9, 1, 9, 2, 10, 1, 10, 2], [15, 1, 15, 2, 14, 1, 14, 2], [19, 1, 19, 2, 20, 1, 20, 2], [21, 1, 21, 2, 22, 1, 22, 2], [27, 1, 27, 2, 26, 1, 26, 2], [31, 1, 31, 2, 32, 1, 32, 2], [33, 1, 33, 2, 34, 1, 34, 2], [1, 1, 1, 2, 0, 1, 0, 2, 0, 3, 0, 4], [13, 1, 13, 2, 12, 1, 12, 2, 12, 3, 12, 4], [25, 1, 25, 2, 24, 1, 24, 2, 24, 3, 24, 4], [6, 2, 6, 3, 17, 2, 17, 3], [8, 2, 8, 3, 15, 2, 15, 3], [10, 2, 10, 3, 13, 2, 13, 3], [12, 2, 12, 3, 23, 2, 23, 3], [14, 2, 14, 3, 21, 2, 21, 3], [16, 2, 16, 3, 19, 2, 19, 3], [18, 2, 18, 3, 29, 2, 29, 3], [20, 2, 20, 3, 27, 2, 27, 3], [22, 2, 22, 3, 25, 2, 25, 3], [30, 2, 30, 3, 0, 0, 30, 1, 0, 0, 29, 1], [32, 2, 32, 3, 0, 0, 32, 1, 0, 0, 27, 1], [34, 2, 34, 3, 0, 0, 34, 1, 0, 0, 25, 1], [1, 3, 1, 4, 2, 3, 2, 4], [3, 3, 3, 4, 4, 3, 4, 4], [9, 3, 9, 4, 8, 3, 8, 4], [13, 3, 13, 4, 14, 3, 14, 4], [15, 3, 15, 4, 16, 3, 16, 4], [21, 3, 21, 4, 20, 3, 20, 4], [25, 3, 25, 4, 26, 3, 26, 4], [27, 3, 27, 4, 28, 3, 28, 4], [33, 3, 33, 4, 32, 3, 32, 4], [5, 3, 5, 4, 5, 1, 5, 2, 4, 1, 4, 2], [17, 3, 17, 4, 17, 1, 17, 2, 16, 1, 16, 2], [29, 3, 29, 4, 29, 1, 29, 2, 28, 1, 28, 2], [28, 2, 28, 3, 31, 2, 31, 3, 31, 4, 31, 5], [26, 2, 26, 3, 33, 2, 33, 3, 33, 4, 33, 5], [24, 2, 24, 3, 35, 2, 35, 3, 35, 4, 35, 5], [7, 3, 7, 4, 6, 3, 6, 4, 6, 5, 6, 6], [19, 3, 19, 4, 18, 3, 18, 4, 18, 5, 18, 6], [31, 3, 31, 4, 30, 3, 30, 4, 30, 5, 30, 6], [12, 4, 12, 5, 11, 4, 11, 5], [14, 4, 14, 5, 9, 4, 9, 5], [16, 4, 16, 5, 7, 4, 7, 5], [18, 4, 18, 5, 17, 4, 17, 5], [20, 4, 20, 5, 15, 4, 15, 5], [22, 4, 22, 5, 13, 4, 13, 5], [24, 4, 24, 5, 23, 4, 23, 5], [26, 4, 26, 5, 21, 4, 21, 5], [28, 4, 28, 5, 19, 4, 19, 5], [0, 4, 0, 5, 0, 2, 0, 3, 11, 2, 11, 3], [10, 4, 10, 5, 1, 4, 1, 5, 1, 6, 1, 7], [2, 4, 2, 5, 2, 2, 2, 3, 9, 2, 9, 3], [8, 4, 8, 5, 3, 4, 3, 5, 3, 6, 3, 7], [4, 4, 4, 5, 4, 2, 4, 3, 7, 2, 7, 3], [6, 4, 6, 5, 5, 4, 5, 5, 5, 6, 5, 7], [3, 5, 3, 6, 2, 5, 2, 6], [7, 5, 7, 6, 8, 5, 8, 6], [9, 5, 9, 6, 10, 5, 10, 6], [15, 5, 15, 6, 14, 5, 14, 6], [19, 5, 19, 6, 20, 5, 20, 6], [21, 5, 21, 6, 22, 5, 22, 6], [27, 5, 27, 6, 26, 5, 26, 6], [31, 5, 31, 6, 32, 5, 32, 6], [33, 5, 33, 6, 34, 5, 34, 6], [1, 5, 1, 6, 0, 5, 0, 6, 0, 7, 0, 8], [11, 5, 11, 6, 11, 3, 11, 4, 10, 3, 10, 4], [13, 5, 13, 6, 12, 5, 12, 6, 12, 7, 12, 8], [23, 5, 23, 6, 23, 3, 23, 4, 22, 3, 22, 4], [25, 5, 25, 6, 24, 5, 24, 6, 24, 7, 24, 8], [35, 5, 35, 6, 35, 3, 35, 4, 34, 3, 34, 4], [6, 6, 6, 7, 17, 6, 17, 7], [8, 6, 8, 7, 15, 6, 15, 7], [12, 6, 12, 7, 23, 6, 23, 7], [14, 6, 14, 7, 21, 6, 21, 7], [16, 6, 16, 7, 19, 6, 19, 7], [18, 6, 18, 7, 29, 6, 29, 7], [20, 6, 20, 7, 27, 6, 27, 7], [22, 6, 22, 7, 25, 6, 25, 7], [30, 6, 30, 7, 30, 4, 30, 5, 29, 4, 29, 5], [32, 6, 32, 7, 32, 4, 32, 5, 27, 4, 27, 5], [34, 6, 34, 7, 34, 4, 34, 5, 25, 4, 25, 5], [1, 7, 1, 8, 2, 7, 2, 8], [3, 7, 3, 8, 4, 7, 4, 8], [9, 7, 9, 8, 8, 7, 8, 8], [13, 7, 13, 8, 14, 7, 14, 8], [15, 7, 15, 8, 16, 7, 16, 8], [21, 7, 21, 8, 20, 7, 20, 8], [25, 7, 25, 8, 26, 7, 26, 8], [27, 7, 27, 8, 28, 7, 28, 8], [33, 7, 33, 8, 32, 7, 32, 8], [5, 7, 5, 8, 5, 5, 5, 6, 4, 5, 4, 6], [17, 7, 17, 8, 17, 5, 17, 6, 16, 5, 16, 6], [29, 7, 29, 8, 29, 5, 29, 6, 28, 5, 28, 6].

TABLE 21B

[28, 6, 28, 7, 31, 6, 31, 7, 31, 8, 0, 0],
[26, 6, 26, 7, 33, 6, 33, 7, 33, 8, 0, 0],
[24, 6, 24, 7, 35, 6, 35, 7, 35, 8, 0, 0], [7, 7, 7, 8, 6, 7, 6, 8],
[11, 7, 11, 8, 10, 7, 10, 8], [19, 7, 19, 8, 18, 7, 18, 8], [23, 7, 23, 8, 22, 7, 22, 8], [31, 7, 31, 8, 30, 7, 30, 8], [35, 7, 35, 8, 34, 7, 34, 8],
[6, 8, 0, 0, 5, 8, 0, 0], [8, 8, 0, 0, 3, 8, 0, 0], [10, 8, 0, 0, 1, 8, 0, 0],
[12, 8, 0, 0, 11, 8, 0, 0], [14, 8, 0, 0, 9, 8, 0, 0], [16, 8, 0, 0, 7, 8, 0, 0], [18, 8, 0, 0, 17, 8, 0, 0], [20, 8, 0, 0, 15, 8, 0, 0],
[22, 8, 0, 0, 13, 8, 0, 0],
[24, 8, 0, 0, 23, 8, 0, 0], [26, 8, 0, 0, 21, 8, 0, 0], [28, 8, 0, 0, 19, 8, 0, 0], [30, 8, 0, 0, 29, 8, 0, 0], [32, 8, 0, 0, 27, 8, 0, 0],
[34, 8, 0, 0, 25, 8, 0, 0],
[0, 8, 0, 0, 0, 6, 0, 7, 11, 6, 11, 7], [2, 8, 0, 0, 2, 6, 2, 7, 9, 6, 9, 7], [4, 8, 0, 0, 4, 6, 4, 7, 7, 6, 7, 7]

The core oligonucleotide sequences used to produce 6H×6H×128B nucleic acid structures of the invention are designated SEQ ID NOs. 3703-3942, and the corresponding voxel coordinates are shown respectively in Table 22A. The end oligonucleotide sequences used to produce 6H×6H×128B nucleic acid structures of the invention are designated SEQ ID NOs. 4237-4263, and the corresponding voxel coordinates are shown respectively in Table 22B. (See also Appendix, Table 9 of U.S. provisional application No. 61/675,309, filed Jul. 24, 2012, incorporated by reference herein.)

TABLE 22A

[0, 0, 0, 1, 0, 0, 0, 0], [0, 0, 2, 1, 0, 0, 0, 0], [0, 0, 4, 1, 0, 0, 0, 0], [0, 0, 31, 1, 0, 0, 0, 0], [0, 0, 33, 1, 0, 0, 0, 0], [0, 0, 35, 1, 0, 0, 0, 0], [0, 0, 12, 1, 0, 0, 11, 1], [0, 0, 14, 1, 0, 0, 9, 1], [0, 0, 16, 1, 0, 0, 7, 1], [0, 0, 18, 1, 0, 0, 17, 1], [0, 0, 20, 1, 0, 0, 15, 1], [0, 0, 22, 1, 0, 0, 13, 1], [0, 0, 24, 1, 0, 0, 23, 1], [0, 0, 26, 1, 0, 0, 21, 1], [0, 0, 28, 1, 0, 0, 19, 1], [0, 0, 10, 1, 0, 0, 1, 1, 1, 2, 1, 3], [0, 0, 8, 1, 0, 0, 3, 1, 3, 2, 3, 3], [0, 0, 6, 1, 0, 0, 5, 1, 5, 2, 5, 3], [6, 1, 6, 2, 0, 0, 0, 0], [11, 1, 11, 2, 0, 0, 0, 0], [18, 1, 18, 2, 0, 0, 0, 0], [23, 1, 23, 2, 0, 0, 0, 0], [30, 1, 30, 2, 0, 0, 0, 0], [35, 1, 35, 2, 0, 0, 0, 0], [3, 1, 3, 2, 2, 1, 2, 2], [7, 1, 7, 2, 8, 1, 8, 2], [9, 1, 9, 2, 10, 1, 10, 2], [15, 1, 15, 2, 14, 1, 14, 2], [19, 1, 19, 2, 20, 1, 20, 2], [21, 1, 21, 2, 22, 1, 22, 2], [27, 1, 27, 2, 26, 1, 26, 2], [31, 1, 31, 2, 32, 1, 32, 2], [33, 1, 33, 2, 34, 1, 34, 2], [1, 1, 1, 2, 0, 1, 0, 2, 0, 3, 0, 4], [13, 1, 13, 2, 12, 1, 12, 2, 12, 3, 12, 4], [25, 1, 25, 2, 24, 1, 24, 2, 24, 3, 24, 4], [6, 2, 6, 3, 17, 2, 17, 3], [8, 2, 8, 3, 15, 2, 15, 3], [10, 2, 10, 3, 13, 2, 13, 3], [12, 2, 12, 3, 23, 2, 23, 3], [14, 2, 14, 3, 21, 2, 21, 3], [16, 2, 16, 3, 19, 2, 19, 3], [18, 2, 18, 3, 29, 2, 29, 3], [20, 2, 20, 3, 27, 2, 27, 3], [22, 2, 22, 3, 25, 2, 25, 3], [30, 2, 30, 3, 0, 0, 30, 1, 0, 0, 29, 1], [32, 2,

TABLE 22A-continued 32, 3, 0, 0, 32, 1, 0, 0, 27, 1], [34, 2, 34, 3, 0, 0, 34, 1, 0, 0, 25, 1], [1, 3, 1, 4, 2, 3, 2, 4], [3, 3, 3, 4, 4, 3, 4, 4], [9, 3, 9, 4, 8, 3, 8, 4], [13, 3, 13, 4, 14, 3, 14, 4], [15, 3, 15, 4, 16, 3, 16, 4], [21, 3, 21, 4, 20, 3, 20, 4], [25, 3, 25, 4, 26, 3, 26, 4], [27, 3, 27, 4, 28, 3, 28, 4], [33, 3, 33, 4, 32, 3, 32, 4], [5, 3, 5, 4, 5, 1, 5, 2, 4, 1, 4, 2], [17, 3, 17, 4, 17, 1, 17, 2, 16, 1, 16, 2], [29, 3, 29, 4, 29, 1, 29, 2, 28, 1, 28, 2], [28, 2, 28, 3, 31, 2, 31, 3, 31, 4, 31, 5], [26, 2, 26, 3, 33, 2, 33, 3, 33, 4, 33, 5], [24, 2, 24, 3, 35, 2, 35, 3, 35, 4, 35, 5], [7, 3, 7, 4, 6, 3, 6, 4, 6, 5, 6, 6], [19, 3, 19, 4, 18, 3, 18, 4, 18, 5, 18, 6], [31, 3, 31, 4, 30, 3, 30, 4, 30, 5, 30, 6], [12, 4, 12, 5, 11, 4, 11, 5], [14, 4, 14, 5, 9, 4, 9, 5], [16, 4, 16, 5, 7, 4, 7, 5], [18, 4, 18, 5, 17, 4, 17, 5], [20, 4, 20, 5, 15, 4, 15, 5], [22, 4, 22, 5, 13, 4, 13, 5], [24, 4, 24, 5, 23, 4, 23, 5], [26, 4, 26, 5, 21, 4, 21, 5], [28, 4, 28, 5, 19, 4, 19, 5], [0, 4, 0, 5, 0, 2, 0, 3, 11, 2, 11, 3], [10, 4, 10, 5, 1, 4, 1, 5, 1, 6, 1, 7], [2, 4, 2, 5, 2, 2, 2, 3, 9, 2, 9, 3], [8, 4, 8, 5, 3, 4, 3, 5, 3, 6, 3, 7], [4, 4, 4, 5, 4, 2, 4, 3, 7, 2, 7, 3], [6, 4, 6, 5, 5, 4, 5, 5, 5, 6, 5, 7], [3, 5, 3, 6, 2, 5, 2, 6], [7, 5, 7, 6, 8, 5, 8, 6], [9, 5, 9, 6, 10, 5, 10, 6], [15, 5, 15, 6, 14, 5, 14, 6], [19, 5, 19, 6, 20, 5, 20, 6], [21, 5, 21, 6, 22, 5, 22, 6], [27, 5, 27, 6, 26, 5, 26, 6], [31, 5, 31, 6, 32, 5, 32, 6], [33, 5, 33, 6, 34, 5, 34, 6], [1, 5, 1, 6, 0, 5, 0, 6, 0, 7, 0, 8], [11, 5, 11, 6, 11, 3, 11, 4, 10, 3, 10, 4], [13, 5, 13, 6, 12, 5, 12, 6, 12, 7, 12, 8], [23, 5, 23, 6, 23, 3, 23, 4, 22, 3, 22, 4], [25, 5, 25, 6, 24, 5, 24, 6, 24, 7, 24, 8], [35, 5, 35, 6, 35, 3, 35, 4, 34, 3, 34, 4], [6, 6, 6, 7, 17, 6, 17, 7], [8, 6, 8, 7, 15, 6, 15, 7], [10, 6, 10, 7, 13, 6, 13, 7], [12, 6, 12, 7, 23, 6, 23, 7], [14, 6, 14, 7, 21, 6, 21, 7], [16, 6, 16, 7, 19, 6, 19, 7], [18, 6, 18, 7, 29, 6, 29, 7], [20, 6, 20, 7, 27, 6, 27, 7], [22, 6, 22, 7, 25, 6, 25, 7], [30, 6, 30, 7, 30, 4, 30, 5, 29, 4, 29, 5], [32, 6, 32, 7, 32, 4, 32, 5, 27, 4, 27, 5], [34, 6, 34, 7, 34, 4, 34, 5, 25, 4, 25, 5], [1, 7, 1, 8, 2, 7, 2, 8], [3, 7, 3, 8, 4, 7, 4, 8], [9, 7, 9, 8, 8, 7, 8, 8], [13, 7, 13, 8, 14, 7, 14, 8], [15, 7, 15, 8, 16, 7, 16, 8], [21, 7, 21, 8, 20, 7, 20, 8], [25, 7, 25, 8, 26, 7, 26, 8], [27, 7, 27, 8, 28, 7, 28, 8], [33, 7, 33, 8, 32, 7, 32, 8], [5, 7, 5, 8, 5, 5, 5, 6, 4, 5, 4, 6], [17, 7, 17, 8, 17, 5, 17, 6, 16, 5, 16, 6], [29, 7, 29, 8, 29, 5, 29, 6, 28, 5, 28, 6], [28, 6, 28, 7, 31, 6, 31, 7, 31, 8, 31, 9], [26, 6, 26, 7, 33, 6, 33, 7, 33, 8, 33, 9], [24, 6, 24, 7, 35, 6, 35, 7, 35, 8, 35, 9], [7, 7, 7, 8, 6, 7, 6, 8, 6, 9, 6, 10], [19, 7, 19, 8, 18, 7, 18, 8, 18, 9, 18, 10], [31, 7, 31, 8, 30, 7, 30, 8, 30, 9, 30, 10], [12, 8, 12, 9, 11, 8, 11, 9], [14, 8, 14, 9, 9, 8, 9, 9], [16, 8, 16, 9, 7, 8, 7, 9], [18, 8, 18, 9, 17, 8, 17, 9], [20, 8, 20, 9, 15, 8, 15, 9], [22, 8, 22, 9, 13, 8, 13, 9], [24, 8, 24, 9, 23, 8, 23, 9], [26, 8, 26, 9, 21, 8, 21, 9], [28, 8, 28, 9, 19, 8, 19, 9], [0, 8, 0, 9, 0, 6, 0, 7, 11, 6, 11, 7], [10, 8, 10, 9, 1, 8, 1, 9, 1, 10, 1, 11], [2, 8, 2, 9, 2, 6, 2, 7, 9, 6, 9, 7], [8, 8, 8, 9, 3, 8, 3, 9, 3, 10, 3, 11], [4, 8, 4, 9, 4, 6, 4, 7, 7, 6, 7, 7], [6, 8, 6, 9, 5, 8, 5, 9, 5, 10, 5, 11], [3, 9, 3, 10, 2, 9, 2, 10], [7, 9, 7, 10, 8, 9, 8, 10], [9, 9, 9, 10, 10, 9, 10, 10], [15, 9, 15, 10, 14, 9, 14, 10], [19, 9, 19, 10, 20, 9, 20, 10], [21, 9, 21, 10, 22, 9, 22, 10], [27, 9, 27, 10, 26, 9, 26, 10], [31, 9, 31, 10, 32, 9, 32, 10], [33, 9, 33, 10, 34, 9, 34, 10], [1, 9, 1, 10, 0, 9, 0, 10, 0, 11, 0, 12], [11, 9, 11, 10, 11, 7, 11, 8, 10, 7, 10, 8], [13, 9, 13, 10, 12, 9, 12, 10, 12, 11, 12, 12], [23, 9, 23, 10, 23, 7, 23, 8, 22, 7, 22, 8], [25, 9, 25, 10, 24, 9, 24, 10, 24, 11, 24, 12], [35, 9, 35, 10, 35, 7, 35, 8, 34, 7, 34, 8], [6, 10, 6, 11, 17, 10, 17, 11], [8, 10, 8, 11, 15, 10, 15, 11], [10, 10, 10, 11, 13, 10, 13, 11], [12, 10, 12, 11, 23, 10, 23, 11], [14, 10, 14, 11, 21, 10, 21, 11], [16, 10, 16, 11, 19, 10, 19, 11], [18, 10, 18, 11, 29, 10, 29, 11], [20, 10, 20, 11, 27, 10, 27, 11], [22, 10, 22, 11, 25, 10, 25, 11], [30, 10, 30, 11, 30, 8, 30, 9, 29, 8, 29, 9], [28, 10, 28, 11, 31, 10, 31, 11, 31, 12, 31, 13], [32, 10, 32, 11, 32, 8, 32, 9, 27, 8, 27, 9], [26, 10, 26, 11, 33, 10, 33, 11, 33, 12, 33, 13], [34, 10, 34, 11, 34, 8, 34, 9, 25, 8, 25, 9], [24, 10, 24, 11, 35, 10, 35, 11, 35, 12, 35, 13], [1, 11, 1, 12, 2, 11, 2, 12], [3, 11, 3, 12, 4, 11, 4, 12], [9, 11, 9, 12, 8, 11, 8, 12], [13, 11, 13, 12, 14, 11, 14, 12], [15, 11, 15, 12, 16, 11, 16, 12], [21, 11, 21, 12, 20, 11, 20, 12], [25, 11, 25, 12, 26, 11, 26, 12], [27, 11, 27, 12, 28, 11, 28, 12], [33, 11, 33, 12, 32, 11, 32, 12], [5, 11, 5, 12, 5, 9, 5, 10, 4, 9, 4, 10], [7, 11, 7, 12, 6, 11, 6, 12, 6, 13, 6, 14], [17, 11, 17, 12, 17, 9, 17, 10, 16, 9, 16, 10], [19, 11, 19, 12, 18, 11, 18, 12, 18, 13, 18, 14], [29, 11, 29, 12, 29, 9, 29, 10, 28, 9, 28, 10], [31, 11, 31, 12, 30, 11, 30, 12, 30, 13, 30, 14], [12, 12, 12, 13, 11, 12, 11, 13], [14, 12, 14, 13, 9, 12, 9, 13], [16, 12, 16, 13, 7, 12, 7, 13], [18, 12, 18, 13, 17, 12, 17, 13], [20, 12, 20, 13, 15, 12, 15, 13], [22, 12, 22, 13, 13, 12, 13, 13], [24, 12, 24, 13, 23, 12, 23, 13], [26, 12, 26, 13, 21, 12, 21, 13], [28, 12, 28, 13, 19, 12, 19, 13], [0, 12, 0, 13, 0, 10, 0, 11, 11, 10, 11, 11], [10, 12, 10, 13, 1, 12, 1, 13, 1, 14, 1, 15], [2, 12, 2, 13, 2, 10, 2, 11, 9, 10, 9, 11], [8, 12, 8, 13, 3, 12, 3, 13, 3, 14, 3, 15], [4, 12, 4, 13, 4, 10, 4, 11, 7, 10, 7, 11], [6, 12, 6, 13, 5, 12, 5, 13, 5, 14, 5, 15], [3, 13, 3, 14, 2, 13, 2, 14], [7, 13, 7, 14, 8, 13, 8, 14], [9, 13, 9, 14, 10, 13, 10, 14], [15, 13, 15, 14, 14, 13, 14, 14], [19, 13, 19, 14, 20, 13, 20, 14], [21, 13, 21, 14, 22, 13, 22, 14], [27, 13, 27, 14, 26, 13, 26, 14], [31, 13, 31, 14, 32, 13, 32, 14], [33, 13, 33, 14, 34, 13, 34, 14], [1, 13, 1, 14, 0, 13, 0, 14, 0, 15, 0, 16], [11, 13, 11, 14, 11, 11, 11, 12, 10, 11, 10, 12], [13, 13, 13, 14, 12, 13, 12, 14, 12, 15, 12, 16], [23, 13, 23, 14, 23, 11, 23, 12, 22, 11, 22, 12], [25, 13, 25, 14, 24, 13, 24, 14, 24, 15, 24, 16], [35, 13, 35, 14, 35, 11, 35, 12, 34, 11, 34, 12], [6, 14, 6, 15, 17, 14, 17, 15], [8, 14, 8, 15, 15, 14, 15, 15], [10, 14, 10, 15, 13, 14, 13, 15], [12, 14, 12, 15, 23, 14, 23, 15], [14, 14, 14, 15, 21, 14, 21, 15], [16, 14, 16, 15, 19, 14, 19, 15], [18, 14, 18, 15, 29, 14, 29, 15], [20, 14, 20, 15, 27, 14, 27, 15], [22, 14, 22, 15, 25, 14, 25, 15], [30, 14, 30, 15, 30, 12, 30, 13, 29, 12, 29, 13], [32, 14, 32, 15, 32, 12, 32, 13, 27, 12, 27, 13], [34, 14, 34, 15, 34, 12, 34, 13, 25, 12, 25, 13], [1, 15, 1, 16, 2, 15, 2, 16], [3, 15, 3, 16, 4, 15, 4, 16], [9, 15, 9, 16, 8, 15, 8, 16], [13, 15, 13, 16, 14, 15, 14, 16], [15, 15, 15, 16, 16, 15, 16, 16], [21, 15, 21, 16, 20, 15, 20, 16], [25, 15, 25, 16, 26, 15, 26, 16], [27, 15, 27, 16, 28, 15, 28, 16], [33, 15, 33, 16, 32, 15, 32, 16], [5, 15, 5, 16, 5, 13, 5, 14, 4, 13, 4, 14], [17, 15, 17, 16, 17, 13, 17, 14, 16, 13, 16, 14], [29, 15, 29, 16, 29, 13, 29, 14, 28, 13, 28, 14]

TABLE 22B

[28, 14, 28, 15, 31, 14, 31, 15, 31, 16, 0, 0], [26, 14, 26, 15, 33, 14, 33, 15, 33, 16, 0, 0], [24, 14, 24, 15, 35, 14, 35, 15, 35, 16, 0, 0], [7, 15, 7, 16, 6, 15, 6, 16], [11, 15, 11, 16, 10, 15, 10, 16], [19, 15, 19, 16, 18, 15, 18, 16], [23, 15, 23, 16, 22, 15, 22, 16], [31, 15, 31, 16, 30, 15, 30, 16], [35, 15, 35, 16, 34, 15, 34, 16], [6, 16, 0, 0, 5, 16, 0, 0], [8, 16, 0, 0, 3, 16, 0, 0], [10, 16, 0, 0, 1, 16, 0, 0], [12, 16, 0, 0, 11, 16, 0, 0], [14, 16, 0, 0, 9, 16, 0, 0], [16, 16, 0, 0, 7, 16, 0, 0], [18, 16, 0, 0, 17, 16, 0, 0], [20, 16, 0, 0, 15, 16, 0, 0], [22, 16, 0, 0, 13, 16, 0, 0], [24, 16, 0, 0, 23, 16, 0, 0], [26, 16, 0, 0, 21, 16, 0, 0], [28, 16, 0, 0, 19, 16, 0, 0], [30, 16, 0, 0, 29, 16, 0, 0], [32, 16, 0, 0, 27, 16, 0, 0], [34, 16, 0, 0, 25, 16, 0, 0], [0, 16, 0, 0, 14, 0, 15, 11, 14, 11, 15], [2, 16, 0, 0, 2, 14, 2, 15, 9, 14, 9, 15], [4, 16, 0, 0, 4, 14, 4, 15, 7, 14, 7, 15]

The core oligonucleotide sequences used to produce 6H×6H×256B nucleic acid structures of the invention are designated SEQ ID NOs. 3703-4182, and the corresponding voxel coordinates are shown respectively in Table 23A. The end oligonucleotide sequences used to produce 6H×6H×256B nucleic acid structures of the invention are designated SEQ ID NOs. 4264-4290, and the corresponding voxel coordinates are shown respectively in Table 23B. (See also Appendix, Table 9 of U.S. provisional application No. 61/675,309, filed Jul. 24, 2012, incorporated by reference herein.)

TABLE 23A

[0, 0, 0, 1, 0, 0, 0, 0], [0, 0, 2, 1, 0, 0, 0, 0], [0, 0, 4, 1, 0, 0, 0, 0], [0, 0, 31, 1, 0, 0, 0, 0], [0, 0, 33, 1, 0, 0, 0, 0], [0, 0, 35, 1, 0, 0, 0, 0], [0, 0, 12, 1, 0, 0, 11, 1], [0, 0, 14, 1, 0, 0, 9, 1], [0, 0, 16, 1, 0, 0, 7, 1], [0, 0, 18, 1, 0, 0, 17, 1], [0, 0, 20, 1, 0, 0, 15, 1], [0, 0, 22, 1, 0, 0, 13, 1], [0, 0, 24, 1, 0, 0, 23, 1], [0, 0, 26, 1, 0, 0, 21, 1], [0, 0, 28, 1, 0, 0, 19, 1], [0, 0, 10, 1, 0, 0, 1, 1, 1, 2, 1, 3], [0, 0, 8, 1, 0, 0, 3, 1, 3, 2, 3, 3], [0, 0, 6, 1, 0, 0, 5, 1, 5, 2, 5, 3], [6, 1, 6, 2, 0, 0, 0, 0], [11, 1, 11, 2, 0, 0, 0, 0], [18, 1, 18, 2, 0, 0, 0, 0], [23, 1, 23, 2, 0, 0, 0, 0], [30, 1, 30, 2, 0, 0, 0, 0], [35, 1, 35, 2, 0, 0, 0, 0], [3, 1, 3, 2, 2, 1, 2, 2], [7, 1, 7, 2, 8, 1, 8, 2], [9, 1, 9, 2, 10, 1, 10, 2], [15, 1, 15, 2, 14, 1, 14, 2], [19, 1, 19, 2, 20, 1, 20, 2], [21, 1, 21, 2, 22, 1, 22, 2], [27, 1, 27, 2, 26, 1, 26, 2], [31, 1, 31, 2, 32, 1, 32, 2], [33, 1, 33, 2,

TABLE 23A-continued 34, 1, 34, 2], [1, 1, 1, 2, 0, 1, 0, 2, 0, 3, 0, 4], [13, 1, 13, 2, 12, 1, 12, 2, 12, 3, 12, 4], [25, 1, 25, 2, 24, 1, 24, 2, 24, 3, 24, 4], [6, 2, 6, 3, 17, 2, 17, 3], [8, 2, 8, 3, 15, 2, 15, 3], [10, 2, 10, 3, 13, 2, 13, 3], [12, 2, 12, 3, 23, 2, 23, 3], [14, 2, 14, 3, 21, 2, 21, 3], [16, 2, 16, 3, 19, 2, 19, 3], [18, 2, 18, 3, 29, 2, 29, 3], [20, 2, 20, 3, 27, 2, 27, 3], [22, 2, 22, 3, 25, 2, 25, 3], [30, 2, 30, 3, 0, 0, 30, 1, 0, 0, 29, 1], [32, 2, 32, 3, 0, 0, 32, 1, 0, 0, 27, 1], [34, 2, 34, 3, 0, 0, 34, 1, 0, 0, 25, 1], [1, 3, 1, 4, 2, 3, 2, 4], [3, 3, 3, 4, 4, 3, 4, 4], [9, 3, 9, 4, 8, 3, 8, 4], [13, 3, 13, 4, 14, 3, 14, 4], [15, 3, 15, 4, 16, 3, 16, 4], [21, 3, 21, 4, 20, 3, 20, 4], [25, 3, 25, 4, 26, 3, 26, 4], [27, 3, 27, 4, 28, 3, 28, 4], [33, 3, 33, 4, 32, 3, 32, 4], [5, 3, 5, 4, 5, 1, 5, 2, 4, 1, 4, 2], [17, 3, 17, 4, 17, 1, 17, 2, 16, 1, 16, 2], [29, 3, 29, 4, 29, 1, 29, 2, 28, 1, 28, 2], [28, 2, 28, 3, 31, 2, 31, 3, 31, 4, 31, 5], [26, 2, 26, 3, 33, 2, 33, 3, 33, 4, 33, 5], [24, 2, 24, 3, 35, 2, 35, 3, 35, 4, 35, 5], [7, 3, 7, 4, 6, 3, 6, 4, 6, 5, 6, 6], [19, 3, 19, 4, 18, 3, 18, 4, 18, 5, 18, 6], [31, 3, 31, 4, 30, 3, 30, 4, 30, 5, 30, 6], [12, 4, 12, 5, 11, 4, 11, 5], [14, 4, 14, 5, 9, 4, 9, 5], [16, 4, 16, 5, 7, 4, 7, 5], [18, 4, 18, 5, 17, 4, 17, 5], [20, 4, 20, 5, 15, 4, 15, 5], [22, 4, 22, 5, 13, 4, 13, 5], [24, 4, 24, 5, 23, 4, 23, 5], [26, 4, 26, 5, 21, 4, 21, 5], [28, 4, 28, 5, 19, 4, 19, 5], [0, 4, 0, 5, 0, 2, 0, 3, 11, 2, 11, 3], [10, 4, 10, 5, 1, 4, 1, 5, 1, 6, 1, 7], [2, 4, 2, 5, 2, 2, 2, 3, 9, 2, 9, 3], [8, 4, 8, 5, 3, 4, 3, 5, 3, 6, 3, 7], [4, 4, 4, 5, 4, 2, 4, 3, 7, 2, 7, 3], [6, 4, 6, 5, 5, 4, 5, 5, 5, 6, 5, 7], [3, 5, 3, 6, 2, 5, 2, 6], [7, 5, 7, 6, 8, 5, 8, 6], [9, 5, 9, 6, 10, 5, 10, 6], [15, 5, 15, 6, 14, 5, 14, 6], [19, 5, 19, 6, 20, 5, 20, 6], [21, 5, 21, 6, 22, 5, 22, 6], [27, 5, 27, 6, 26, 5, 26, 6], [31, 5, 31, 6, 32, 5, 32, 6], [33, 5, 33, 6, 34, 5, 34, 6], [1, 5, 1, 6, 0, 5, 0, 6, 0, 7, 0, 8], [11, 5, 11, 6, 11, 3, 11, 4, 10, 3, 10, 4], [13, 5, 13, 6, 12, 5, 12, 6, 12, 7, 12, 8], [23, 5, 23, 6, 23, 3, 23, 4, 22, 3, 22, 4], [25, 5, 25, 6, 24, 5, 24, 6, 24, 7, 24, 8], [35, 5, 35, 6, 35, 3, 35, 4, 34, 3, 34, 4], [6, 6, 6, 7, 17, 6, 17, 7], [8, 6, 8, 7, 15, 6, 15, 7], [10, 6, 10, 7, 13, 6, 13, 7], [12, 6, 12, 7, 23, 6, 23, 7], [14, 6, 14, 7, 21, 6, 21, 7], [16, 6, 16, 7, 19, 6, 19, 7], [18, 6, 18, 7, 29, 6, 29, 7], [20, 6, 20, 7, 27, 6, 27, 7], [22, 6, 22, 7, 25, 6, 25, 7], [30, 6, 30, 7, 30, 4, 30, 5, 29, 4, 29, 5], [32, 6, 32, 7, 32, 4, 32, 5, 27, 4, 27, 5], [34, 6, 34, 7, 34, 4, 34, 5, 25, 4, 25, 5], [1, 7, 1, 8, 2, 7, 2, 8], [3, 7, 3, 8, 4, 7, 4, 8], [9, 7, 9, 8, 8, 7, 8, 8], [13, 7, 13, 8, 14, 7, 14, 8], [15, 7, 15, 8, 16, 7, 16, 8], [21, 7, 21, 8, 20, 7, 20, 8], [25, 7, 25, 8, 26, 7, 26, 8], [27, 7, 27, 8, 28, 7, 28, 8], [33, 7, 33, 8, 32, 7, 32, 8], [5, 7, 5, 8, 5, 5, 5, 6, 4, 5, 4, 6], [17, 7, 17, 8, 17, 5, 17, 6, 16, 5, 16, 6], [29, 7, 29, 8, 29, 5, 29, 6, 28, 5, 28, 6], [28, 6, 28, 7, 31, 6, 31, 7, 31, 8, 31, 9], [26, 6, 26, 7, 33, 6, 33, 7, 33, 8, 33, 9], [24, 6, 24, 7, 35, 6, 35, 7, 35, 8, 35, 9], [7, 7, 7, 8, 6, 7, 6, 8, 6, 9, 6, 10], [19, 7, 19, 8, 18, 7, 18, 8, 18, 9, 18, 10], [31, 7, 31, 8, 30, 7, 30, 8, 30, 9, 30, 10], [12, 8, 12, 9, 11, 8, 11, 9], [14, 8, 14, 9, 9, 8, 9, 9], [16, 8, 16, 9, 7, 8, 7, 9], [18, 8, 18, 9, 17, 8, 17, 9], [20, 8, 20, 9, 15, 8, 15, 9], [22, 8, 22, 9, 13, 8, 13, 9], [24, 8, 24, 9, 23, 8, 23, 9], [26, 8, 26, 9, 21, 8, 21, 9], [28, 8, 28, 9, 19, 8, 19, 9], [0, 8, 0, 9, 0, 6, 0, 7, 11, 6, 11, 7], [10, 8, 10, 9, 1, 8, 1, 9, 1, 10, 1, 11], [2, 8, 2, 9, 2, 6, 2, 7, 9, 6, 9, 7], [8, 8, 8, 9, 3, 8, 3, 9, 3, 10, 3, 11], [4, 8, 4, 9, 4, 6, 4, 7, 7, 6, 7, 7], [6, 8, 6, 9, 5, 8, 5, 9, 5, 10, 5, 11], [7, 9, 7, 10, 8, 9, 8, 10], [9, 9, 9, 10, 10, 9, 10, 10], [15, 9, 15, 10, 14, 9, 14, 10], [19, 9, 19, 10, 20, 9, 20, 10], [21, 9, 21, 10, 22, 9, 22, 10], [27, 9, 27, 10, 26, 9, 26, 10], [31, 9, 31, 10, 32, 9, 32, 10], [33, 9, 33, 10, 34, 9, 34, 10], [1, 9, 1, 10, 0, 9, 0, 10, 0, 11, 0, 12], [11, 9, 11, 10, 11, 7, 11, 8, 10, 7, 10, 8], [13, 9, 13, 10, 12, 9, 12, 10, 12, 11, 12, 12], [23, 9, 23, 10, 23, 7, 23, 8, 22, 7, 22, 8], [25, 9, 25, 10, 24, 9, 24, 10, 24, 11, 24, 12], [35, 9, 35, 10, 35, 7, 35, 8, 34, 7, 34, 8], [6, 10, 6, 11, 17, 10, 17, 11], [8, 10, 8, 11, 15, 10, 15, 11], [10, 10, 10, 11, 13, 10, 13, 11], [12, 10, 12, 11, 23, 10, 23, 11], [14, 10, 14, 11, 21, 10, 21, 11], [16, 10, 16, 11, 19, 10, 19, 11], [18, 10, 18, 11, 29, 10, 29, 11], [20, 10, 20, 11, 27, 10, 27, 11], [22, 10, 22, 11, 25, 10, 25, 11], [30, 10, 30, 11, 30, 8, 30, 9, 29, 8, 29, 9], [28, 10, 28, 11, 31, 10, 31, 11, 31, 12, 31, 13], [32, 10, 32, 11, 32, 8, 32, 9, 27, 8, 27, 9], [26, 10, 26, 11, 33, 10, 33, 11, 33, 12, 33, 13], [34, 10, 34, 11, 34, 8, 34, 9, 25, 8, 25, 9], [24, 10, 24, 11, 35, 10, 35, 11, 35, 12, 35, 13], [1, 11, 1, 12, 2, 11, 2, 12], [3, 11, 3, 12, 4, 11, 4, 12], [9, 11, 9, 12, 8, 11, 8, 12], [13, 11, 13, 12, 14, 11, 14, 12], [15, 11, 15, 12, 16, 11, 16, 12], [21, 11, 21, 12, 20, 11, 20, 12], [25, 11, 25, 12, 26, 11, 26, 12], [27, 11, 27, 12, 28, 11, 28, 12], [33, 11, 33, 12, 32, 11, 32, 12], [5, 11, 5, 12, 5, 9, 5, 10, 4, 9, 4, 10], [7, 11, 7, 12, 6, 11, 6, 12, 6, 13, 6, 14], [17, 11, 17, 12, 17, 9, 17, 10, 16, 9, 16, 10], [19, 11, 19, 12, 18, 11, 18, 12, 18, 13, 18, 14], [29, 11, 29, 12, 29, 9, 29, 10, 28, 9, 28, 10], [31, 11, 31, 12, 30, 11, 30, 12, 30, 13, 30, 14], [12, 12, 12, 13, 11, 12, 11, 13], [14, 12, 14, 13, 9, 12, 9, 13], [16, 12, 16, 13, 7, 12, 7, 13], [18, 12, 18, 13, 17, 12, 17, 13], [20, 12, 20, 13, 15, 12, 15, 13], [22, 12, 22, 13, 13, 12, 13, 13], [26, 12, 26, 13, 21, 12, 21, 13], [28, 12, 28, 13, 19, 12, 19, 13], [0, 12, 0, 13, 0, 10, 0, 11, 11, 10, 11, 11], [10, 12, 10, 13, 1, 12, 1, 13, 1, 14, 1, 15], [2, 12, 2, 13, 2, 10, 2, 11, 9, 10, 9, 11], [8, 12, 8, 13, 3, 12, 3, 13, 3, 14, 3, 15], [4, 12, 4, 13, 4, 10, 4, 11, 7, 10, 7, 11], [6, 12, 6, 13, 5, 12, 5, 13, 5, 14, 5, 15], [3, 13, 3, 14, 2, 13, 2, 14], [7, 13, 7, 14, 8, 13, 8, 14], [9, 13, 9, 14, 10, 13, 10, 14], [15, 13, 15, 14, 14, 13, 14, 14], [19, 13, 19, 14, 20, 13, 20, 14], [21, 13, 21, 14, 22, 13, 22, 14], [27, 13, 27, 14, 26, 13, 26, 14], [31, 13, 31, 14, 32, 13, 32, 14], [33, 13, 33, 14, 34, 13, 34, 14], [1, 13, 1, 14, 0, 13, 0, 14, 0, 15, 0, 16], [11, 13, 11, 14, 11, 11, 11, 12, 10, 11, 10, 12], [13, 13, 13, 14, 12, 13, 12, 14, 12, 15, 12, 16], [23, 13, 23, 14, 23, 11, 23, 12, 22, 11, 22, 12], [25, 13, 25, 14, 24, 13, 24, 14, 24, 15, 24, 16], [35, 13, 35, 14, 35, 11, 35, 12, 34, 11, 34, 12], [6, 14, 6, 15, 17, 14, 17, 15], [8, 14, 8, 15, 15, 14, 15, 15], [10, 14, 10, 15, 13, 14, 13, 15], [12, 14, 12, 15, 23, 14, 23, 15], [14, 14, 14, 15, 21, 14, 21, 15], [16, 14, 16, 15, 19, 14, 19, 15], [18, 14, 18, 15, 29, 14, 29, 15], [22, 14, 22, 15, 25, 14, 25, 15], [30, 14, 30, 15, 30, 12, 30, 13, 29, 12, 29, 13], [32, 14, 32, 15, 32, 12, 32, 13, 27, 12, 27, 13], [34, 14, 34, 15, 34, 12, 34, 13, 25, 12, 25, 13], [1, 15, 1, 16, 2, 15, 2, 16], [3, 15, 3, 16, 4, 15, 4, 16], [9, 15, 9, 16, 8, 15, 8, 16], [13, 15, 13, 16, 14, 15, 14, 16], [15, 15, 15, 16, 16, 15, 16, 16], [21, 15, 21, 16, 20, 15, 20, 16], [25, 15, 25, 16, 26, 15, 26, 16], [27, 15, 27, 16, 28, 15, 28, 16], [33, 15, 33, 16, 32, 15, 32, 16], [5, 15, 5, 16, 5, 13, 5, 14, 4, 13, 4, 14], [17, 15, 17, 16, 17, 13, 17, 14, 16, 13, 16, 14], [29, 15, 29, 16, 29, 13, 29, 14, 28, 13, 28, 14], [28, 14, 28, 15, 31, 14, 31, 15, 31, 16, 31, 17], [26, 14, 26, 15, 33, 14, 33, 15, 33, 16, 33, 17], [24, 14, 24, 15, 35, 14, 35, 15, 35, 16, 35, 17], [7, 15, 7, 16, 6, 15, 6, 16, 6, 17, 6, 18], [19, 15, 19, 16, 18, 15, 18, 16, 18, 17, 18, 18], [31, 15, 31, 16, 30, 15, 30, 16, 30, 17, 30, 18], [12, 16, 12, 17, 11, 16, 11, 17], [14, 16, 14, 17, 9, 16, 9, 17], [16, 16, 16, 17, 7, 16, 7, 17], [18, 16, 18, 17, 17, 16, 17, 17], [20, 16, 20, 17, 15, 16, 15, 17], [22, 16, 22, 17, 13, 16, 13, 17], [24, 16, 24, 17, 23, 16, 23, 17], [26, 16, 26, 17, 21, 16, 21, 17], [28, 16, 28, 17, 19, 16, 19, 17], [0, 16, 0, 17, 0, 14, 0, 15, 11, 14, 11, 15], [10, 16, 10, 17, 1, 16, 1, 17, 1, 18, 1, 19], [2, 16, 2, 17, 2, 14, 2, 15, 9, 14, 9, 15], [8, 16, 8, 17, 3, 16, 3, 17, 3, 18, 3, 19], [4, 16, 4, 17, 4, 14, 4, 15, 7, 14, 7, 15], [6, 16, 6, 17, 5, 16, 5, 17, 5, 18, 5, 19], [3, 17, 3, 18, 2, 17, 2, 18], [7, 17, 7, 18, 8, 17, 8, 18], [9, 17, 9, 18, 10, 17, 10, 18], [15, 17, 15, 18, 14, 17, 14, 18], [19, 17, 19, 18, 20, 17, 20, 18], [21, 17, 21, 18, 22, 17, 22, 18], [27, 17, 27, 18, 26, 17, 26, 18], [31, 17, 31, 18, 32, 17, 32, 18], [33, 17, 33, 18, 34, 17, 34, 18], [1, 17, 1, 18, 0, 17, 0, 18, 0, 19, 0, 20], [11, 17, 11, 18, 11, 15, 11, 16, 10, 15, 10, 16], [13, 17, 13, 18, 12, 17, 12, 18, 12, 19, 12, 20], [23, 17, 23, 18, 23, 15, 23, 16, 22, 15, 22, 16], [25, 17, 25, 18, 24, 17, 24, 18, 24, 19, 24, 20], [35, 17, 35, 18, 35, 15, 35, 16, 34, 15, 34, 16], [6, 18, 6, 19, 17, 18, 17, 19], [8, 18, 8, 19, 15, 18, 15, 19], [10, 18, 10, 19, 13, 18, 13, 19], [12, 18, 12, 19, 23, 18, 23, 19], [14, 18, 14, 19, 21, 18, 21, 19], [16, 18, 16, 19, 19, 18, 19, 19], [18, 18, 18, 19, 29, 18, 29, 19], [20, 18, 20, 19, 27, 18, 27, 19], [22, 18, 22, 19, 25, 18, 25, 19], [30, 18, 30, 19, 30, 16, 30, 17, 29, 16, 29, 17], [28, 18, 28, 19, 31, 18, 31, 19, 31, 20, 31, 21], [32, 18, 32, 19, 32, 16, 32, 17, 27, 16, 27, 17], [26, 18, 26, 19, 33, 18, 33, 19, 33, 20, 33, 21], [34, 18, 34, 19, 34, 16, 34, 17, 25, 16, 25, 17], [24, 18, 24, 19, 35, 18, 35, 19, 35, 20, 35, 21], [1, 19, 1, 20, 2, 19, 2, 20], [3, 19, 3, 20, 4, 19, 4, 20], [9, 19, 9, 20, 8, 19, 8, 20], [13, 19, 13, 20, 14, 19, 14, 20], [15, 19, 15, 20, 16, 19, 16, 20], [21, 19, 21, 20, 20, 19, 20, 20], [25, 19, 25, 20, 26, 19, 26, 20], [27, 19, 27, 20, 28, 19, 28, 20], [33, 19, 33, 20, 32, 19, 32, 20], [5, 19, 5, 20, 5, 17, 5, 18, 4, 17, 4, 18], [7, 19, 7, 20, 6, 19, 6, 20, 6, 21, 6, 22], [17, 19, 17, 20, 17, 17, 17, 18, 16, 17, 16, 18], [19, 19, 19, 20, 18, 19, 18, 20, 18, 21, 18, 22], [29, 19, 29, 20, 29, 17, 29, 18, 28, 17, 28, 18], [31, 19, 31, 20, 30, 19, 30, 20, 30, 21, 30, 22], [12, 20, 12, 21, 11, 20, 11, 21], [14, 20, 14, 21, 9, 20, 9, 21], [16, 20, 16, 21, 7, 20, 7, 21], [18, 20, 18, 21, 17, 20, 17, 21], [20, 20, 20, 21, 15, 20, 15, 21], [22, 20, 22, 21, 13, 20, 13, 21], [24, 20, 24, 21, 23, 20, 23, 21], [26, 20, 26, 21, 21, 20, 21, 21], [28, 20, 28, 21, 19, 20, 19, 21], [0, 20, 0, 21, 0, 18, 0, 19, 11, 18, 11, 19], [10, 20, 10, 21, 1, 20, 1, 21, 1, 22, 1, 23], [2, 20, 2, 21, 2, 18, 2, 19, 9, 18, 9, 19], [8, 20, 8, 21, 3, 20, 3, 21, 3, 22, 3, 23], [4, 20, 4, 21, 4, 18, 4, 19, 7, 18, 7, 19], [6, 20, 6, 21, 5, 20, 5, 21, 5, 22, 5, 23], [3, 21, 3, 22, 2, 21, 2, 22], [7, 21, 7, 22, 8, 21, 8, 22], [9, 21, 9, 22, 10, 21, 10, 22], [15, 21, 15, 22, 14, 21, 14, 22], [19, 21, 19, 22, 20, 21, 20, 22], [21, 21, 21, 22, 22, 21, 22, 22], [27, 21, 27, 22, 26, 21, 26, 22], [31, 21, 31, 22, 32, 21, 32, 22], [33, 21, 33, 22, 34, 21, 34, 22], [1, 21, 1, 22, 0, 21, 0, 22, 0, 23, 0, 24], [11, 21, 11, 22, 11, 19, 11, 20, 10, 19, 10, 20], [13, 21, 13, 22, 12, 21, 12, 22, 12, 23, 12, 24], [23, 21, 23, 22, 23, 19, 23, 20, 22, 19, 22, 20], [25, 21, 25, 22, 24, 21, 24, 22, 24, 23, 24, 24], [35, 21, 35, 22, 35, 19, 35, 20, 34, 19, 34, 20], [6, 22, 6, 23, 17, 22, 17, 23], [8, 22, 8, 23, 15, 22, 15, 23], [10, 22, 10, 23, 13, 22, 13, 23], [12, 22, 12, 23, 23, 22, 23, 23], [14, 22, 14, 23, 21, 22, 21, 23], [16, 22, 16, 23, 19, 22, 19, 23], [18, 22, 18, 23, 29, 22, 29, 23], [20, 22, 20, 23, 27, 22, 27, 23], [22, 22, 22, 23, 25, 22, 25, 23], [30, 22, 30, 23, 30, 20, 30, 21, 29, 20, 29, 2 1], [28, 22, 28, 23, 31, 22, 31, 23, 31, 24, 31, 25], [32, 22, 32, 23, 32, 20, 32, 21, 27, 20, 27, 21], [26, 22, 26, 23, 33, 22, 33, 23, 33, 24, 33,

TABLE 23A-continued

25], [34, 22, 34, 23, 34, 20, 34, 21, 25, 20, 25, 21], [24, 22, 24, 23, 35, 22, 35, 23, 35, 24, 35, 25], [1, 23, 1, 24, 2, 23, 2, 24], [3, 23, 3, 24, 4, 23, 4, 24], [9, 23, 9, 24, 8, 23, 8, 24], [13, 23, 13, 24, 14, 23, 14, 24], [15, 23, 15, 24, 16, 23, 16, 24], [21, 23, 21, 24, 20, 23, 20, 24], [25, 23, 25, 24, 26, 23, 26, 24], [27, 23, 27, 24, 28, 23, 28, 24], [33, 23, 33, 24, 32, 23, 32, 24], [5, 23, 5, 24, 5, 21, 5, 22, 4, 21, 4 , 22], [7, 23, 7, 24, 6, 23, 6, 24, 6, 25, 6, 26], [17, 23, 17, 24, 17, 21, 17, 22, 16, 21, 16, 22], [19, 23, 19, 24, 18, 23, 18, 24, 18, 25, 18, 26], [29, 23, 29, 24, 29, 21, 29, 22, 28, 21, 28, 22], [31, 23, 31, 24, 30, 23, 30, 24, 30, 25, 30, 26], [12, 24, 12, 25, 11, 24, 11, 25], [14, 24, 14, 25, 9, 24, 9, 25], [16, 24, 16, 25, 7, 24, 7, 25], [18, 24, 18, 25, 17, 24, 17, 25], [20, 24, 20, 25, 15, 24, 15, 25], [22, 24, 22, 25, 13, 24, 13, 25], [24, 24, 24, 25, 23, 24, 23, 25], [26, 24, 26, 25, 21, 24, 21, 25], [28, 24, 28, 25, 19, 24, 19, 25], [0, 24, 0, 25, 0, 22, 0, 23, 11, 22, 11, 23], [10, 24, 10, 25, 1, 24, 1, 25, 1, 26, 1, 27], [2, 24, 2, 25, 2, 22, 2, 23, 9, 22, 9, 23], [8, 24, 8, 25, 3, 24, 3, 25, 3, 26, 3, 27], [4, 24, 4, 25, 4, 22, 4, 23, 7, 22, 7, 23], [6, 24, 6, 25, 5, 24, 5, 25, 5, 26, 5, 27], [3, 25, 3, 26, 2, 25, 2, 26], [7, 25, 7, 26, 8, 25, 8, 26], [9, 25, 9, 26, 10, 25, 10, 26], [15, 25, 15, 26, 14, 25, 14, 26], [19, 25, 19, 26, 20, 25, 20, 26], [21, 25, 21, 26, 22, 25, 22, 26], [27, 25, 27, 26, 26, 25, 26, 26], [31, 25, 31, 26, 32, 25, 32, 26], [33, 25, 33, 26, 34, 25, 34, 26], [1, 25, 1, 26, 0, 25, 0, 26, 0, 27, 0, 28], [11, 25, 11, 26, 11, 23, 11, 24, 10, 23, 10, 24], [13, 25, 13, 26, 12, 25, 12, 26, 12, 27, 12, 28], [23, 25, 23, 26, 23, 23, 23, 24, 22, 23, 22, 24], [25, 25, 25, 26, 24, 25, 24, 26, 24, 27, 24, 28], [35, 25, 35, 26, 35, 23, 35, 24, 34, 23, 34, 24], [6, 26, 6, 27, 17, 26, 17, 27], [8, 26, 8, 27, 15, 26, 15, 27], [10, 26, 10, 27, 13, 26, 13, 27], [12, 26, 12, 27, 23, 26, 23, 27], [14, 26, 14, 27, 21, 26, 21, 27], [16, 26, 16, 27, 19, 26, 19, 27], [18, 26, 18, 27, 29, 26, 29, 27], [20, 26, 20, 27, 27, 26, 27, 27], [22, 26, 22, 27, 25, 26, 25, 27], [30, 26, 30, 27, 30, 24, 30, 25, 29, 24, 29, 25], [28, 26, 28, 27, 31, 26, 31, 27, 31, 28, 31, 29], [32, 26, 32, 27, 32, 24, 32, 25, 27, 24, 27, 25], [26, 26, 26, 27, 33, 26, 33, 27, 33, 28, 33, 29], [34, 26, 34, 27, 34, 24, 34, 25, 25, 24, 25, 25], [24, 26, 24, 27, 35, 26, 35, 27, 35, 28, 35, 29], [1, 27, 1, 28, 2, 27, 2, 28], [3, 27, 3, 28, 4, 27, 4, 28], [9, 27, 9, 28, 8, 27, 8, 28], [13, 27, 13, 28, 14, 27, 14, 28], [15, 27, 15, 28, 16, 27, 16, 28], [21, 27, 21, 28, 20, 27, 20, 28], [25, 27, 25, 28, 26, 27, 26, 28], [27, 27, 27, 28, 28, 27, 28, 28], [33, 27, 33, 28, 32, 27, 32, 28], [5, 27, 5, 28, 5, 25, 5, 26, 4, 25, 4, 26], [7, 27, 7, 28, 6, 27, 6, 28, 6, 29, 6, 30], [17, 27, 17, 28, 17, 25, 17, 26, 16, 25, 16, 26], [19, 27, 19, 28, 18, 27, 18, 28, 18, 29, 18, 30], [29, 27, 29, 28, 29, 25, 29, 26, 28, 25, 28, 26], [31, 27, 31, 28, 30, 27, 30, 28, 30, 29, 30, 30], [12, 28, 12, 29, 11, 28, 11, 29], [14, 28, 14, 29, 9, 28, 9, 29], [16, 28, 16, 29, 7, 28, 7, 29], [18, 28, 18, 29, 17, 28, 17, 29], [20, 28, 20, 29, 15, 28, 15, 29], [22, 28, 22, 29, 13, 28, 13, 29], [24, 28, 24, 29, 23, 28, 23, 29], [26, 28, 26, 29, 21, 28, 21, 29], [28, 28, 28, 29, 19, 28, 19, 29], [0, 28, 0, 29, 0, 26, 0, 27, 11, 26, 11, 27], [10, 28, 10, 29, 1, 28, 1, 29, 1, 30, 1, 31], [2, 28, 2, 29, 2, 26, 2, 27, 9, 26, 9, 27], [8, 28, 8, 29, 3, 28, 3, 29, 3, 30, 3, 31], [4, 28, 4, 29, 4, 26, 4, 27, 7, 26, 7, 27], [6, 28, 6, 29, 5, 28, 5, 29, 5, 30, 5, 31], [3, 29, 3, 30, 2, 29, 2, 30], [7, 29, 7, 30, 8, 29, 8, 30], [9, 29, 9, 30, 10, 29, 10, 30], [15, 29, 15, 30, 14, 29, 14, 30], [19, 29, 19, 30, 20, 29, 20, 30], [21, 29, 21, 30, 22, 29, 22, 30], [27, 29, 27, 30, 26, 29, 26, 30], [31, 29, 31, 30, 32, 29, 32, 30], [33, 29, 33, 30, 34, 29, 34, 30], [1, 29, 1, 30, 0, 29, 0, 30, 0, 31, 0, 32], [11, 29, 11, 30, 11, 27, 11, 28, 10, 27, 10, 28], [13, 29, 13, 30, 12, 29, 12, 30, 12, 31, 12, 32], [23, 29, 23, 30, 23, 27, 23, 28, 22, 27, 22, 28], [25, 29, 25, 30, 24, 29, 24, 30, 24, 31, 24, 32], [35, 29, 35, 30, 35, 27, 35, 28, 34, 27, 34, 28], [6, 30, 6, 31, 17, 30, 17, 31], [8, 30, 8, 31, 15, 30, 15, 31], [10, 30, 10, 31, 13, 30, 13, 31], [12, 30, 12, 31, 23, 30, 23, 31], [14, 30, 14, 31, 21, 30, 21, 31], [16, 30, 16, 31, 19, 30, 19, 31], [18, 30, 18, 31, 29, 30, 29, 31], [20, 30, 20, 31, 27, 30, 27, 31], [22, 30, 22, 31, 25, 30, 25, 31], [30, 30, 30, 31, 30, 28, 30, 29, 29, 28, 29, 29], [32, 30, 32, 31, 32, 28, 32, 29, 27, 28, 27, 29], [34, 30, 34, 31, 34, 28, 34, 29, 25, 28, 25, 29], [1, 31, 1, 32, 2, 31, 2, 32], [3, 31, 3, 32, 4, 31, 4, 32], [9, 31, 9, 32, 8, 31, 8, 32], [13, 31, 13, 32, 14, 31, 14, 32], [15, 31, 15, 32, 16, 31, 16, 32], [21, 31, 21, 32, 20, 31, 20, 32], [25, 31, 25, 32, 26, 31, 26, 32], [27, 31, 27, 32, 28, 31, 28, 32], [33, 31, 33, 32, 32, 31, 32, 32], [5, 31, 5, 32, 5, 29, 5, 30, 4, 29, 4, 30], [17, 31, 17, 32, 17, 29, 17, 30, 16, 29, 16, 30], [29, 31, 29, 32, 29, 29, 29, 30, 28, 29, 28, 30]

TABLE 23B

[28, 30, 28, 31, 31, 30, 31, 31, 31, 32, 0, 0], [26, 30, 26, 31, 33, 30, 33, 31, 33, 32, 0, 0], [24, 30, 24, 31, 35, 30, 35, 31, 35, 32, 0, 0], [7, 31, 7, 32, 6, 31, 6, 32], [11, 31, 11, 32, 10, 31, 10, 32], [19, 31, 19, 32, 18, 31, 18, 32], [23, 31, 23, 32, 22, 31, 22, 32], [31, 31, 31, 32, 30, 31, 30, 32], [35, 31, 35, 32, 34, 31, 34, 32], [6, 32, 0, 0, 5, 32, 0, 0], [8, 32, 0, 0, 3, 32, 0, 0], [10, 32, 0, 0, 1, 32, 0, 0], [12, 32, 0, 0, 11, 32, 0, 0], [14, 32, 0, 0, 9, 32, 0, 0], [16, 32, 0, 0, 7, 32, 0, 0], [18, 32, 0, 0, 17, 32, 0, 0], [20, 32, 0, 0, 15, 32, 0, 0], [22, 32, 0, 0, 13, 32, 0, 0], [24, 32, 0, 0, 23, 32, 0, 0], [26, 32, 0, 0, 21, 32, 0, 0], [28, 32, 0, 0, 19, 32, 0, 0], [30, 32, 0, 0, 29, 32, 0, 0], [32, 32, 0, 0, 27, 32, 0, 0], [34, 32, 0, 0, 25, 32, 0, 0], [0, 32, 0, 0, 0, 30, 0, 31, 11, 30, 11, 31],
[2, 32, 0, 0, 2, 30, 2, 31, 9, 30, 9, 31], [4, 32, 0, 0, 4, 30, 4, 31, 7, 30, 7, 31]

The core oligonucleotide sequences used to produce 6H×10H×32B nucleic acid structures of the invention are designated SEQ ID NOs. 4291-4394, and the corresponding voxel coordinates are shown respectively in Table 24A. The end oligonucleotide sequences used to produce 6H×10H×32B nucleic acid structures of the invention are designated SEQ ID NOs. 4707-4749, and the corresponding voxel coordinates are shown respectively in Table 24B. (See also Appendix, Table 10 of U.S. provisional application No. 61/675,309, filed Jul. 24, 2012, incorporated by reference herein.)

TABLE 24A

[0, 0, 0, 1, 0, 0, 0, 0], [0, 0, 2, 1, 0, 0, 0, 0], [0, 0, 4, 1, 0, 0, 0, 0], [0, 0, 55, 1, 0, 0, 0, 0], [0, 0, 57, 1, 0, 0, 0, 0], [0, 0, 59, 1, 0, 0, 0, 0], [0, 0, 12, 1, 0, 0, 11, 1], [0, 0, 14, 1, 0, 0, 9, 1], [0, 0, 16, 1, 0, 0, 7, 1], [0, 0, 18, 1, 0, 0, 17, 1], [0, 0, 20, 1, 0, 0, 15, 1], [0, 0, 22, 1, 0, 0, 13, 1], [0, 0, 24, 1, 0, 0, 23, 1], [0, 0, 26, 1, 0, 0, 21, 1], [0, 0, 28, 1, 0, 0, 19, 1], [0, 0, 30, 1, 0, 0, 29, 1], [0, 0, 32, 1, 0, 0, 27, 1], [0, 0, 34, 1, 0, 0, 25, 1], [0, 0, 36, 1, 0, 0, 35, 1], [0, 0, 38, 1, 0, 0, 33, 1], [0, 0, 40, 1, 0, 0, 31, 1], [0, 0, 42, 1, 0, 0, 41, 1], [0, 0, 44, 1, 0, 0, 39, 1], [0, 0, 46, 1, 0, 0, 37, 1], [0, 0, 48, 1, 0, 0, 47, 1], [0, 0, 50, 1, 0, 0, 45, 1], [0, 0, 52, 1, 0, 0, 43, 1], [0, 0, 10, 1, 0, 0, 1, 1, 2, 1, 3], [0, 0, 8, 1, 0, 0, 3, 1, 3, 2, 3, 3], [0, 0, 6, 1, 0, 0, 5, 1, 5, 2, 5, 3], [6, 1, 6, 2, 0, 0, 0, 0], [11, 1, 11, 2, 0, 0, 0, 0], [18, 1, 18, 2, 0, 0, 0, 0], [23, 1, 23, 2, 0, 0, 0, 0], [30, 1, 30, 2, 0, 0, 0, 0], [35, 1, 35, 2, 0, 0, 0, 0], [42, 1, 42, 2, 0, 0, 0, 0], [47, 1, 47, 2, 0, 0, 0, 0], [54, 1, 54, 2, 0, 0, 0, 0], [59, 1, 59, 2, 0, 0, 0, 0], [3, 1, 3, 2, 2, 1, 2, 2], [7, 1, 7, 2, 8, 1, 8, 2], [9, 1, 9, 2, 10, 1, 10, 2], [15, 1, 15, 2, 14, 1, 14, 2], [19, 1, 19, 2, 20, 1, 20, 2], [21, 1, 21, 2, 22, 1, 22, 2], [27, 1, 27, 2, 26, 1, 26, 2], [31, 1, 31, 2, 32, 1, 32, 2], [33, 1, 33, 2, 34, 1, 34, 2], [39, 1, 39, 2, 38, 1, 38, 2], [43, 1, 43, 2, 44, 1, 44, 2], [45, 1, 45, 2, 46, 1, 46, 2], [51, 1, 51, 2, 50, 1, 50, 2], [55, 1, 55, 2, 56, 1, 56, 2], [57, 1, 57, 2, 58, 1, 58, 2], [1, 1, 1, 2, 0, 1, 0, 2, 0, 3, 0, 4], [13, 1, 13, 2, 12, 1, 12, 2, 12, 3, 12, 4], [25, 1, 25, 2, 24, 1, 24, 2, 24, 3, 24, 4], [37, 1, 37, 2, 36, 1, 36, 2, 36, 3, 36, 4], [49, 1, 49, 2, 48, 1, 48, 2, 48, 3, 48, 4], [6, 2, 6, 3, 17, 2, 17, 3], [8, 2, 8, 3, 15, 2, 15, 3], [10, 2, 10, 3, 13, 2, 13, 3], [12, 2, 12, 3, 23, 2, 23, 3], [14, 2, 14, 3, 21, 2, 21, 3], [16, 2, 16, 3, 19, 2, 19, 3], [18, 2, 18, 3, 29, 2, 29, 3], [20, 2, 20, 3, 27, 2, 27, 3], [22, 2, 22, 3, 25, 2, 25, 3], [24, 2, 24, 3, 35, 2, 35, 3], [26, 2, 26, 3, 33, 2, 33, 3], [28, 2, 28, 3, 31, 2, 31, 3], [30, 2, 30, 3, 41, 2, 41, 3], [32, 2, 32, 3, 39, 2, 39, 3], [34, 2, 34, 3, 37, 2, 37, 3], [36, 2, 36, 3, 47, 2, 47, 3], [38, 2, 38, 3, 45, 2, 45, 3], [40, 2, 40, 3, 43, 2, 43, 3], [42, 2, 42, 3, 53, 2, 53, 3], [44, 2, 44, 3, 51, 2, 51, 3], [46, 2, 46, 3, 49, 2, 49, 3], [54, 2, 54, 3, 0, 0, 54, 1, 0, 0, 53, 1], [56, 2, 56, 3, 0, 0, 56, 1, 0, 0, 51, 1], [58, 2, 58, 3, 0, 0, 58, 1, 0, 0, 49, 1], [1, 3, 1, 4, 2, 3, 2, 4], [3, 3, 3, 4, 4, 3, 4, 4], [9, 3, 9, 4, 8, 3, 8, 4], [13, 3, 13, 4, 14, 3, 14, 4], [15, 3, 15, 4, 16, 3, 16, 4], [21, 3, 21, 4, 20, 3, 20, 4], [25, 3, 25, 4, 26, 3, 26, 4], [27, 3, 27, 4, 28, 3, 28, 4], [33, 3, 33, 4, 32, 3, 32, 4], [37, 3, 37, 4, 38, 3, 38, 4], [39, 3, 39, 4, 40, 3, 40, 4], [45, 3, 45, 4, 44, 3, 44, 4], [49, 3, 49, 4, 50, 3,

TABLE 24A-continued 50, 4], [51, 3, 51, 4, 52, 3, 52, 4], [57, 3, 57, 4, 56, 3, 56, 4], [5, 3, 5, 4, 5, 1, 5, 2, 4, 1, 4, 2], [17, 3, 17, 4, 17, 1, 17, 2, 16, 1, 16, 2], [29, 3, 29, 4, 29, 1, 29, 2, 28, 1, 28, 2], [41, 3, 41, 4, 41, 1, 41, 2, 40, 1, 40, 2], [53, 3, 53, 4, 53, 1, 53, 2, 52, 1, 52, 2]

TABLE 24B

[52, 2, 52, 3, 55, 2, 55, 3, 55, 4, 0, 0], [50, 2, 50, 3, 57, 2, 57, 3, 57, 4, 0, 0], [48, 2, 48, 3, 59, 2, 59, 3, 59, 4, 0, 0], [7, 3, 7, 4, 6, 3, 6, 4], [11, 3, 11, 4, 10, 3, 10, 4], [19, 3, 19, 4, 18, 3, 18, 4], [23, 3, 23, 4, 22, 3, 22, 4], [31, 3, 31, 4, 30, 3, 30, 4], [35, 3, 35, 4, 34, 3, 34, 4], [43, 3, 43, 4, 42, 3, 42, 4], [47, 3, 47, 4, 46, 3, 46, 4], [55, 3, 55, 4, 54, 3, 54, 4], [59, 3, 59, 4, 58, 3, 58, 4], [6, 4, 0, 0, 5, 4, 0, 0], [8, 4, 0, 0, 3, 4, 0, 0], [10, 4, 0, 0, 1, 4, 0, 0], [12, 4, 0, 0, 11, 4, 0, 0], [14, 4, 0, 0, 9, 4, 0, 0], [16, 4, 0, 0, 7, 4, 0, 0], [18, 4, 0, 0, 17, 4, 0, 0], [20, 4, 0, 0, 15, 4, 0, 0], [22, 4, 0, 0, 13, 4, 0, 0], [24, 4, 0, 0, 23, 4, 0, 0], [26, 4, 0, 0, 21, 4, 0, 0], [28, 4, 0, 0, 19, 4, 0, 0], [30, 4, 0, 0, 29, 4, 0, 0], [32, 4, 0, 0, 27, 4, 0, 0], [34, 4, 0, 0, 25, 4, 0, 0], [36, 4, 0, 0, 35, 4, 0, 0], [38, 4, 0, 0, 33, 4, 0, 0], [40, 4, 0, 0, 31, 4, 0, 0], [42, 4, 0, 0, 41, 4, 0, 0], [44, 4, 0, 0, 39, 4, 0, 0], [46, 4, 0, 0, 37, 4, 0, 0], [48, 4, 0, 0, 47, 4, 0, 0], [50, 4, 0, 0, 45, 4, 0, 0], [52, 4, 0, 0, 43, 4, 0, 0], [54, 4, 0, 0, 53, 4, 0, 0], [56, 4, 0, 0, 51, 4, 0, 0], [58, 4, 0, 0, 49, 4, 0, 0], [0, 4, 0, 0, 0, 2, 0, 3, 11, 2, 11, 3], [2, 4, 0, 0, 2, 2, 2, 3, 9, 2, 9, 3], [4, 4, 0, 0, 4, 2, 4, 3, 7, 2, 7, 3]

The core oligonucleotide sequences used to produce 6H×10H×64B nucleic acid structures of the invention are designated SEQ ID NOs. 4291-4498, and the corresponding voxel coordinates are shown respectively in Table 25A. The end oligonucleotide sequences used to produce 6H×10H× 64B nucleic acid structures of the invention are designated SEQ ID NOs. 4750-4792, and the corresponding voxel coordinates are shown respectively in Table 25B. (See also Appendix, Table 10 of U.S. provisional application No. 61/675,309, filed Jul. 24, 2012, incorporated by reference herein.)

TABLE 25A

[0, 0, 0, 1, 0, 0, 0, 0], [0, 0, 2, 1, 0, 0, 0, 0], [0, 0, 4, 1, 0, 0, 0, 0], [0, 0, 55, 1, 0, 0, 0, 0], [0, 0, 57, 1, 0, 0, 0, 0], [0, 0, 59, 1, 0, 0, 0, 0], [0, 0, 12, 1, 0, 0, 11, 1], [0, 0, 14, 1, 0, 0, 9, 1], [0, 0, 16, 1, 0, 0, 7, 1], [0, 0, 18, 1, 0, 0, 17, 1], [0, 0, 20, 1, 0, 0, 15, 1], [0, 0, 22, 1, 0, 0, 13, 1], [0, 0, 24, 1, 0, 0, 23, 1], [0, 0, 26, 1, 0, 0, 21, 1], [0, 0, 28, 1, 0, 0, 19, 1], [0, 0, 30, 1, 0, 0, 29, 1], [0, 0, 32, 1, 0, 0, 27, 1], [0, 0, 34, 1, 0, 0, 25, 1], [0, 0, 36, 1, 0, 0, 35, 1], [0, 0, 38, 1, 0, 0, 33, 1], [0, 0, 40, 1, 0, 0, 31, 1], [0, 0, 42, 1, 0, 0, 41, 1], [0, 0, 44, 1, 0, 0, 39, 1], [0, 0, 46, 1, 0, 0, 37, 1], [0, 0, 48, 1, 0, 0, 47, 1], [0, 0, 50, 1, 0, 0, 45, 1], [0, 0, 52, 1, 0, 0, 43, 1], [0, 0, 10, 1, 0, 0, 1, 1, 1, 2, 1, 3], [0, 0, 8, 1, 0, 0, 3, 1, 3, 2, 3, 3], [0, 0, 6, 1, 0, 0, 5, 1, 5, 2, 5, 3], [6, 1, 6, 2, 0, 0, 0, 0], [11, 1, 11, 2, 0, 0, 0, 0], [18, 1, 18, 2, 0, 0, 0, 0], [23, 1, 23, 2, 0, 0, 0, 0], [30, 1, 30, 2, 0, 0, 0, 0], [35, 1, 35, 2, 0, 0, 0, 0], [42, 1, 42, 2, 0, 0, 0, 0], [47, 1, 47, 2, 0, 0, 0, 0], [54, 1, 54, 2, 0, 0, 0, 0], [59, 1, 59, 2, 0, 0, 0, 0], [3, 1, 3, 2, 2, 1, 2, 2], [7, 1, 7, 2, 8, 1, 8, 2], [9, 1, 9, 2, 10, 1, 10, 2], [15, 1, 15, 2, 14, 1, 14, 2], [19, 1, 19, 2, 20, 1, 20, 2], [21, 1, 21, 2, 22, 1, 22, 2], [27, 1, 27, 2, 26, 1, 26, 2], [31, 1, 31, 2, 32, 1, 32, 2], [33, 1, 33, 2, 34, 1, 34, 2], [39, 1, 39, 2, 38, 1, 38, 2], [43, 1, 43, 2, 44, 1, 44, 2], [45, 1, 45, 2, 46, 1, 46, 2], [51, 1, 51, 2, 50, 1, 50, 2], [55, 1, 55, 2, 56, 1, 56, 2], [57, 1, 57, 2, 58, 1, 58, 2], [1, 1, 1, 2, 0, 1, 0, 2, 0, 3, 0, 4], [13, 1, 13, 2, 12, 1, 12, 2, 12, 3, 12, 4], [25, 1, 25, 2, 24, 1, 24, 2, 24, 3, 24, 4], [37, 1, 37, 2, 36, 1, 36, 2, 36, 3, 36, 4], [49, 1, 49, 2, 48, 1, 48, 2, 48, 3, 48, 4], [6, 2, 6, 3, 17, 2, 17, 3], [8, 2, 8, 3, 15, 2, 15, 3], [10, 2, 10, 3, 13, 2, 13, 3], [12, 2, 12, 3, 23, 2, 23, 3], [14, 2, 14, 3, 21, 2, 21, 3], [16, 2, 16, 3, 19, 2, 19, 3], [18, 2, 18, 3, 29, 2, 29, 3], [20, 2, 20, 3, 27, 2, 27, 3], [22, 2, 22, 3, 25, 2, 25, 3], [24, 2, 24, 3, 35, 2, 35, 3], [26, 2, 26, 3, 33, 2, 33, 3], [28, 2, 28, 3, 31, 2, 31, 3], [30, 2, 30, 3, 41, 2, 41, 3], [32, 2, 32, 3, 39, 2, 39, 3], [34, 2, 34, 3, 37, 2, 37, 3], [36, 2, 36, 3, 47, 2, 47, 3], [38, 2, 38, 3, 45, 2, 45, 3], [40, 2, 40, 3, 43, 2, 43, 3], [42, 2, 42, 3, 53, 2, 53, 3], [44, 2, 44, 3, 51, 2, 51, 3], [46, 2, 46, 3, 49, 2, 49, 3], [54, 2, 54, 3, 0, 0, 54, 1, 0, 0, 53, 1], [56, 2, 56, 3, 0, 0, 56, 1, 0, 0, 51, 1], [58, 2, 58, 3, 0, 0, 58, 1, 0, 0, 49, 1], [1, 3, 1, 4, 2, 3, 2, 4], [3, 3, 3, 4, 4, 3, 4, 4], [9, 3, 9, 4, 8, 3, 8, 4], [13, 3, 13, 4, 14, 3, 14, 4], [15, 3, 15, 4, 16, 3, 16, 4], [21, 3, 21, 4, 20, 3, 20, 4], [25, 3, 25, 4, 26, 3, 26, 4], [27, 3, 27, 4, 28, 3, 28, 4], [33, 3, 33, 4, 32, 3, 32, 4], [37, 3, 37, 4, 38, 3, 38, 4], [39, 3, 39, 4, 40, 3, 40, 4], [45, 3, 45, 4, 44, 3, 44, 4], [49, 3, 49, 4, 50, 3, 50, 4], [51, 3, 51, 4, 52, 3, 52, 4], [57, 3, 57, 4, 56, 3, 56, 4], [5, 3, 5, 4, 5, 1, 5, 2, 4, 1, 4, 2], [17, 3, 17, 4, 17, 1, 17, 2, 16, 1, 16, 2], [29, 3, 29, 4, 29, 1, 29, 2, 28, 1, 28, 2], [41, 3, 41, 4, 41, 1, 41, 2, 40, 1, 40, 2], [53, 3, 53, 4, 53, 1, 53, 2, 52, 1, 52, 2], [52, 2, 52, 3, 55, 2, 55, 3, 55, 4, 55, 5], [50, 2, 50, 3, 57, 2, 57, 3, 57, 4, 57, 5], [48, 2, 48, 3, 59, 2, 59, 3, 59, 4, 59, 5], [7, 3, 7, 4, 6, 3, 6, 4, 6, 5, 6, 6], [19, 3, 19, 4, 18, 3, 18, 4, 18, 5, 18, 6], [31, 3, 31, 4, 30, 3, 30, 4, 30, 5, 30, 6], [43, 3, 43, 4, 42, 3, 42, 4, 42, 5, 42, 6], [55, 3, 55, 4, 54, 3, 54, 4, 54, 5, 54, 6], [12, 4, 12, 5, 11, 4, 11, 5], [14, 4, 14, 5, 9, 4, 9, 5], [16, 4, 16, 5, 7, 4, 7, 5], [18, 4, 18, 5, 17, 4, 17, 5], [20, 4, 20, 5, 15, 4, 15, 5], [22, 4, 22, 5, 13, 4, 13, 5], [24, 4, 24, 5, 23, 4, 23, 5], [26, 4, 26, 5, 21, 4, 21, 5], [28, 4, 28, 5, 19, 4, 19, 5], [30, 4, 30, 5, 29, 4, 29, 5], [32, 4, 32, 5, 27, 4, 27, 5], [34, 4, 34, 5, 25, 4, 25, 5], [36, 4, 36, 5, 35, 4, 35, 5], [38, 4, 38, 5, 33, 4, 33, 5], [40, 4, 40, 5, 31, 4, 31, 5], [42, 4, 42, 5, 41, 4, 41, 5], [44, 4, 44, 5, 39, 4, 39, 5], [46, 4, 46, 5, 37, 4, 37, 5], [48, 4, 48, 5, 47, 4, 47, 5], [50, 4, 50, 5, 45, 4, 45, 5], [52, 4, 52, 5, 43, 4, 43, 5], [0, 4, 0, 5, 0, 2, 0, 3, 11, 2, 11, 3], [10, 4, 10, 5, 1, 4, 1, 5, 1, 6, 1, 7], [2, 4, 2, 5, 2, 2, 2, 3, 9, 2, 9, 3], [8, 4, 8, 5, 3, 4, 3, 5, 3, 6, 3, 7], [4, 4, 4, 5, 4, 2, 4, 3, 7, 2, 7, 3], [6, 4, 6, 5, 5, 4, 5, 5, 5, 6, 5, 7], [3, 5, 3, 6, 2, 5, 2, 6], [7, 5, 7, 6, 8, 5, 8, 6], [9, 5, 9, 6, 10, 5, 10, 6], [15, 5, 15, 6, 14, 5, 14, 6], [19, 5, 19, 6, 20, 5, 20, 6], [21, 5, 21, 6, 22, 5, 22, 6], [27, 5, 27, 6, 26, 5, 26, 6], [31, 5, 31, 6, 32, 5, 32, 6], [33, 5, 33, 6, 34, 5, 34, 6], [39, 5, 39, 6, 38, 5, 38, 6], [43, 5, 43, 6, 44, 5, 44, 6], [45, 5, 45, 6, 46, 5, 46, 6], [51, 5, 51, 6, 50, 5, 50, 6], [55, 5, 55, 6, 56, 5, 56, 6], [57, 5, 57, 6, 58, 5, 58, 6], [1, 5, 1, 6, 0, 5, 0, 6, 0, 7, 0, 8], [11, 5, 11, 6, 11, 3, 11, 4, 10, 3, 10, 4], [13, 5, 13, 6, 12, 5, 12, 6, 12, 7, 12, 8], [23, 5, 23, 6, 23, 3, 23, 4, 22, 3, 22, 4], [25, 5, 25, 6, 24, 5, 24, 6, 24, 7, 24, 8], [35, 5, 35, 6, 35, 3, 35, 4, 34, 3, 34, 4], [37, 5, 37, 6, 36, 5, 36, 6, 36, 7, 36, 8], [47, 5, 47, 6, 47, 3, 47, 4, 46, 3, 46, 4], [49, 5, 49, 6, 48, 5, 48, 6, 48, 7, 48, 8], [59, 5, 59, 6, 59, 3, 59, 4, 58, 3, 58, 4], [6, 6, 6, 7, 17, 6, 17, 7], [8, 6, 8, 7, 15, 6, 15, 7], [10, 6, 10, 7, 13, 6, 13, 7], [12, 6, 12, 7, 23, 6, 23, 7], [14, 6, 14, 7, 21, 6, 21, 7], [16, 6, 16, 7, 19, 6, 19, 7], [18, 6, 18, 7, 29, 6, 29, 7], [20, 6, 20, 7, 27, 6, 27, 7], [22, 6, 22, 7, 25, 6, 25, 7], [24, 6, 24, 7, 35, 6, 35, 7], [26, 6, 26, 7, 33, 6, 33, 7], [28, 6, 28, 7, 31, 6, 31, 7], [30, 6, 30, 7, 41, 6, 41, 7], [32, 6, 32, 7, 39, 6, 39, 7], [34, 6, 34, 7, 37, 6, 37, 7], [36, 6, 36, 7, 47, 6, 47, 7], [38, 6, 38, 7, 45, 6, 45, 7], [40, 6, 40, 7, 43, 6, 43, 7], [42, 6, 42, 7, 53, 6, 53, 7], [44, 6, 44, 7, 51, 6, 51, 7], [46, 6, 46, 7, 49, 6, 49, 7], [54, 6, 54, 7, 54, 4, 54, 5, 53, 4, 53, 5], [56, 6, 56, 7, 56, 4, 56, 5, 51, 4, 51, 5], [58, 6, 58, 7, 58, 4, 58, 5, 49, 4, 49, 5], [1, 7, 1, 8, 2, 7, 2, 8], [3, 7, 3, 8, 4, 7, 4, 8], [9, 7, 9, 8, 8, 7, 8, 8], [13, 7, 13, 8, 14, 7, 14, 8], [15, 7, 15, 8, 16, 7, 16, 8], [21, 7, 21, 8, 20, 7, 20, 8], [25, 7, 25, 8, 26, 7, 26, 8], [27, 7, 27, 8, 28, 7, 28, 8], [33, 7, 33, 8, 32, 7, 32, 8], [37, 7, 37, 8, 38, 7, 38, 8], [39, 7, 39, 8, 40, 7, 40, 8], [45, 7, 45, 8, 44, 7, 44, 8], [49, 7, 49, 8, 50, 7, 50, 8], [51, 7, 51, 8, 52, 7, 52, 8], [57, 7, 57, 8, 56, 7, 56, 8], [5, 7, 5, 8, 5, 5, 5, 6, 4, 5, 4, 6], [17, 7, 17, 8, 17, 5, 17, 6, 16, 5, 16, 6], [29, 7, 29, 8, 29, 5, 29, 6, 28, 5, 28, 6], [41, 7, 41, 8, 41, 5, 41, 6, 40, 5, 40, 6], [53, 7, 53, 8, 53, 5, 53, 6, 52, 5, 52, 6]

TABLE 25B

[52, 6, 52, 7, 55, 6, 55, 7, 55, 8, 0, 0], [50, 6, 50, 7, 57, 6, 57, 7, 57, 8, 0, 0], [48, 6, 48, 7, 59, 6, 59, 7, 59, 8, 0, 0],
[7, 7, 7, 8, 6, 7, 6, 8],
[11, 7, 11, 8, 10, 7, 10, 8], [19, 7, 19, 8, 18, 7, 18, 8], [23, 7, 23, 8, 22, 7, 22, 8], [31, 7, 31, 8, 30, 7, 30, 8], [35, 7, 35, 8, 34, 7, 34, 8],
[43, 7, 43, 8, 42, 7, 42, 8], [47, 7, 47, 8, 46, 7, 46, 8], [55, 7, 55, 8, 54, 7, 54, 8], [59, 7, 59, 8, 58, 7, 58, 8], [6, 8, 0, 0, 5, 8, 0, 0], [8, 8,
0, 0, 3, 8, 0, 0], [10, 8, 0, 0, 1, 8, 0, 0], [12, 8, 0, 0, 11, 8, 0, 0], [14, 8, 0, 0, 9, 8, 0, 0], [16, 8, 0, 0, 7, 8, 0, 0], [18, 8, 0, 0, 17, 8, 0, 0],
[20, 8, 0, 0, 15, 8, 0, 0], [22, 8, 0, 0, 13, 8, 0, 0], [24, 8, 0, 0, 23, 8, 0, 0], [26, 8, 0, 0, 21, 8, 0, 0], [28, 8, 0, 0, 19, 8, 0, 0], [30, 8, 0, 0,
29, 8, 0, 0], [32, 8, 0, 0, 27, 8, 0, 0], [34, 8, 0, 0, 25, 8, 0, 0], [36, 8, 0, 0, 35, 8, 0, 0], [38, 8, 0, 0, 33, 8, 0, 0], [40, 8, 0, 0, 31, 8, 0, 0],
[42, 8, 0, 0, 41, 8, 0, 0], [44, 8, 0, 0, 39, 8, 0, 0], [46, 8, 0, 0, 37, 8, 0, 0], [48, 8, 0, 0, 47, 8, 0, 0], [50, 8, 0, 0, 45, 8, 0, 0], [52, 8, 0, 0,
43, 8, 0, 0], [54, 8, 0, 0, 53, 8, 0, 0], [56, 8, 0, 0, 51, 8, 0, 0], [58, 8, 0, 0, 49, 8, 0, 0], [0, 8, 0, 0, 0, 6, 0, 7, 11, 6, 11, 7],
[2, 8, 0, 0, 2, 6, 2, 7, 9, 6, 9, 7], [4, 8, 0, 0, 4, 6, 4, 7, 7, 6, 7, 7]

The core oligonucleotide sequences used to produce 6H×10H×128B nucleic acid structures of the invention are designated SEQ ID NOs. 4291-4706, and the corresponding voxel coordinates are shown respectively in Table 26A. The end oligonucleotide sequences used to produce 6H×10H×128B nucleic acid structures of the invention are designated SEQ ID NOs. 4793-4835, and the corresponding voxel coordinates are shown respectively in Table 26B. (See also Appendix, Table 10 of U.S. provisional application No. 61/675,309, filed Jul. 24, 2012, incorporated by reference herein.)

TABLE 26A

[53, 7, 53, 8, 53, 5, 53, 6, 52, 5, 52, 6], [52, 6, 52, 7, 55, 6, 55, 7, 55, 8, 55, 9], [50, 6, 50, 7, 57, 6, 57, 7, 57, 8, 57, 9], [48, 6, 48, 7, 59,
6, 59, 7, 59, 8, 59, 9], [7, 7, 7, 8, 6, 7, 6, 8, 6, 9, 6, 10], [19, 7, 19, 8, 18, 7, 18, 8, 18, 9, 18, 10], [31, 7, 31, 8, 30, 7, 30, 8, 30, 9, 30,
10], [43, 7, 43, 8, 42, 7, 42, 8, 42, 9, 42, 10], [55, 7, 55, 8, 54, 7, 54, 8, 54, 9, 54, 10], [12, 8, 12, 9, 11, 8, 11, 9], [14, 8, 14, 9, 9, 8, 9,
9], [16, 8, 16, 9, 7, 8, 7, 9], [18, 8, 18, 9, 17, 8, 17, 9], [20, 8, 20, 9, 15, 8, 15, 9], [22, 8, 22, 9, 13, 8, 13, 9], [24, 8, 24, 9, 23, 8, 23, 9],
[26, 8, 26, 9, 21, 8, 21, 9], [28, 8, 28, 9, 19, 8, 19, 9], [30, 8, 30, 9, 29, 8, 29, 9], [32, 8, 32, 9, 27, 8, 27, 9], [34, 8, 34, 9, 25, 8, 25, 9],
[36, 8, 36, 9, 35, 8, 35, 9], [38, 8, 38, 9, 33, 8, 33, 9], [40, 8, 40, 9, 31, 8, 31, 9], [42, 8, 42, 9, 41, 8, 41, 9], [44, 8, 44, 9, 39, 8, 39, 9],
[46, 8, 46, 9, 37, 8, 37, 9], [48, 8, 48, 9, 47, 8, 47, 9], [50, 8, 50, 9, 45, 8, 45, 9], [52, 8, 52, 9, 43, 8, 43, 9], [0, 8, 0, 9, 0, 6, 0, 7, 11, 6,
11, 7], [10, 8, 10, 9, 1, 8, 1, 9, 1, 10, 1, 11], [2, 8, 2, 9, 2, 6, 2, 7, 9, 6, 9, 7], [8, 8, 8, 9, 3, 8, 3, 9, 3, 10, 3, 11], [4, 8, 4, 9, 4, 6, 4, 7, 7, 6,
7, 7], [6, 8, 6, 9, 5, 8, 5, 9, 5, 10, 5, 11], [3, 9, 3, 10, 2, 9, 2, 10], [7, 9, 7, 10, 8, 9, 8, 10], [9, 9, 9, 10, 10, 9, 10, 10], [15, 9, 15, 10, 14,
9, 14, 10], [19, 9, 19, 10, 20, 9, 20, 10], [21, 9, 21, 10, 22, 9, 22, 10], [27, 9, 27, 10, 26, 9, 26, 10], [31, 9, 31, 10, 32, 9, 32, 10], [33, 9,
33, 10, 34, 9, 34, 10], [39, 9, 39, 10, 38, 9, 38, 10], [43, 9, 43, 10, 44, 9, 44, 10], [45, 9, 45, 10, 46, 9, 46, 10], [51, 9, 51, 10, 50, 9, 50,
10], [55, 9, 55, 10, 56, 9, 56, 10], [57, 9, 57, 10, 58, 9, 58, 10], [1, 9, 1, 10, 0, 9, 0, 10, 0, 11, 0, 12], [11, 9, 11, 10, 11, 7, 11, 8, 10, 7,
10, 8], [13, 9, 13, 10, 12, 9, 12, 10, 12, 11, 12, 12], [23, 9, 23, 10, 23, 7, 23, 8, 22, 7, 22, 8], [25, 9, 25, 10, 24, 9, 24, 10, 24, 11, 24,
12], [35, 9, 35, 10, 35, 7, 35, 8, 34, 7, 34, 8], [37, 9, 37, 10, 36, 9, 36, 10, 36, 11, 36, 12], [47, 9, 47, 10, 47, 7, 47, 8, 46, 7, 46, 8], [49,
9, 49, 10, 48, 9, 48, 10, 48, 11, 48, 12], [59, 9, 59, 10, 59, 7, 59, 8, 58, 7, 58, 8], [6, 10, 6, 11, 17, 10, 17, 11], [8, 10, 8, 11, 15, 10, 15,
11], [10, 10, 10, 11, 13, 10, 13, 11], [12, 10, 12, 11, 23, 10, 23, 11], [14, 10, 14, 11, 21, 10, 21, 11], [16, 10, 16, 11, 19, 10, 19, 11],
[18, 10, 18, 11, 29, 10, 29, 11], [20, 10, 20, 11, 27, 10, 27, 11], [22, 10, 22, 11, 25, 10, 25, 11], [24, 10, 24, 11, 35, 10, 35, 11], [26, 10,
26, 11, 33, 10, 33, 11], [28, 10, 28, 11, 31, 10, 31, 11], [30, 10, 30, 11, 41, 10, 41, 11], [32, 10, 32, 11, 39, 10, 39, 11], [34, 10, 34, 11,
37, 10, 37, 11], [36, 10, 36, 11, 47, 10, 47, 11], [38, 10, 38, 11, 45, 10, 45, 11], [40, 10, 40, 11, 43, 10, 43, 11], [42, 10, 42, 11, 53, 10,
53, 11], [44, 10, 44, 11, 51, 10, 51, 11], [46, 10, 46, 11, 49, 10, 49, 11], [54, 10, 54, 11, 54, 8, 54, 9, 53, 8, 53, 9], [52, 10, 52, 11, 55,
10, 55, 11, 55, 12, 55, 13], [56, 10, 56, 11, 56, 8, 56, 9, 51, 8, 51, 9], [50, 10, 50, 11, 57, 10, 57, 11, 57, 12, 57, 13], [58, 10, 58, 11, 58,
8, 58, 9, 49, 8, 49, 9], [48, 10, 48, 11, 59, 10, 59, 11, 59, 12, 59, 13], [1, 11, 1, 12, 2, 11, 2, 12], [3, 11, 3, 12, 4, 11, 4, 12], [9, 11, 9, 12,
8, 11, 8, 12], [13, 11, 13, 12, 14, 11, 14, 12], [15, 11, 15, 12, 16, 11, 16, 12], [21, 11, 21, 12, 20, 11, 20, 12], [25, 11, 25, 12, 26, 11, 26,
12], [27, 11, 27, 12, 28, 11, 28, 12], [33, 11, 33, 12, 32, 11, 32, 12], [37, 11, 37, 12, 38, 11, 38, 12], [39, 11, 39, 12, 40, 11, 40, 12],
[45, 11, 45, 12, 44, 11, 44, 12], [49, 11, 49, 12, 50, 11, 50, 12], [51, 11, 51, 12, 52, 11, 52, 12], [57, 11, 57, 12, 56, 11, 56, 12], [5, 11,
5, 12, 5, 9, 5, 10, 4, 9, 4, 10], [7, 11, 7, 12, 6, 11, 6, 12, 6, 13, 6, 14], [17, 11, 17, 12, 17, 9, 17, 10, 16, 9, 16, 10], [19, 11, 19, 12, 18,
11, 18, 12, 18, 13, 18, 14], [29, 11, 29, 12, 29, 9, 29, 10, 28, 9, 28, 10], [31, 11, 31, 12, 30, 11, 30, 12, 30, 13, 30, 14], [41, 11, 41, 12,
41, 9, 41, 10, 40, 9, 40, 10], [43, 11, 43, 12, 42, 11, 42, 12, 42, 13, 42, 14], [53, 11, 53, 12, 53, 9, 53, 10, 52, 9, 52, 10], [55, 11, 55, 12,
54, 11, 54, 12, 54, 13, 54, 14], [12, 12, 12, 13, 11, 12, 11, 13], [14, 12, 14, 13, 9, 12, 9, 13], [16, 12, 16, 13, 7, 12, 7, 13], [18, 12, 18,
13, 17, 12, 17, 13], [20, 12, 20, 13, 15, 12, 15, 13], [22, 12, 22, 13, 13, 12, 13, 13], [24, 12, 24, 13, 23, 12, 23, 13], [26, 12, 26, 13, 21,
12, 21, 13], [28, 12, 28, 13, 19, 12, 19, 13], [30, 12, 30, 13, 29, 12, 29, 13], [32, 12, 32, 13, 27, 12, 27, 13], [34, 12, 34, 13, 25, 12, 25,
13], [36, 12, 36, 13, 35, 12, 35, 13], [38, 12, 38, 13, 33, 12, 33, 13], [40, 12, 40, 13, 31, 12, 31, 13], [42, 12, 42, 13, 41, 12, 41, 13],
[44, 12, 44, 13, 39, 12, 39, 13], [46, 12, 46, 13, 37, 12, 37, 13], [48, 12, 48, 13, 47, 12, 47, 13], [50, 12, 50, 13, 45, 12, 45, 13], [52, 12,
52, 13, 43, 12, 43, 13], [0, 12, 0, 13, 0, 10, 0, 11, 11, 10, 11, 11], [10, 12, 10, 13, 1, 12, 1, 13, 1, 14, 1, 15], [2, 12, 2, 13, 2, 10, 2, 11, 9,
10, 9, 11], [8, 12, 8, 13, 3, 12, 3, 13, 3, 14, 3, 15], [4, 12, 4, 13, 4, 10, 4, 11, 7, 10, 7, 11], [6, 12, 6, 13, 5, 12, 5, 13, 5, 14, 5, 15], [3, 13,
3, 14, 2, 13, 2, 14], [7, 13, 7, 14, 8, 13, 8, 14], [9, 13, 9, 14, 10, 13, 10, 14], [15, 13, 15, 14, 14, 13, 14, 14], [19, 13, 19, 14, 20, 13, 20,
14], [21, 13, 21, 14, 22, 13, 22, 14], [27, 13, 27, 14, 26, 13, 26, 14], [31, 13, 31, 14, 32, 13, 32, 14], [33, 13, 33, 14, 34, 13, 34, 14],
[39, 13, 39, 14, 38, 13, 38, 14], [43, 13, 43, 14, 44, 13, 44, 14], [45, 13, 45, 14, 46, 13, 46, 14], [51, 13, 51, 14, 50, 13, 50, 14], [55, 13,
55, 14, 56, 13, 56, 14], [57, 13, 57, 14, 58, 13, 58, 14], [1, 13, 1, 14, 0, 13, 0, 14, 0, 15, 0, 16], [11, 13, 11, 14, 11, 11, 11, 12, 10, 11,
10, 12], [13, 13, 13, 14, 12, 13, 12, 14, 12, 15, 12, 16], [23, 13, 23, 14, 23, 11, 23, 12, 22, 11, 22, 12], [25, 13, 25, 14, 24, 13, 24, 14,
24, 15, 24, 16], [35, 13, 35, 14, 35, 11, 35, 12, 34, 11, 34, 12], [37, 13, 37, 14, 36, 13, 36, 14, 36, 15, 36, 16], [47, 13, 47, 14, 47, 11,
47, 12, 46, 11, 46, 12], [49, 13, 49, 14, 48, 13, 48, 14, 48, 15, 48, 16], [59, 13, 59, 14, 59, 11, 59, 12, 58, 11, 58, 12], [6, 14, 6, 15, 17,
14, 17, 15], [8, 14, 8, 15, 15, 14, 15, 15], [10, 14, 10, 15, 13, 14, 13, 15], [12, 14, 12, 15, 23, 14, 23, 15], [14, 14, 14, 15, 21, 14, 21,
15], [16, 14, 16, 15, 19, 14, 19, 15], [18, 14, 18, 15, 29, 14, 29, 15], [20, 14, 20, 15, 27, 14, 27, 15], [22, 14, 22, 15, 25, 14, 25, 15],
[24, 14, 24, 15, 35, 14, 35, 15], [26, 14, 26, 15, 33, 14, 33, 15], [28, 14, 28, 15, 31, 14, 31, 15], [30, 14, 30, 15, 41, 14, 41, 15], [32, 14,
32, 15, 39, 14, 39, 15], [34, 14, 34, 15, 37, 14, 37, 15], [36, 14, 36, 15, 47, 14, 47, 15], [38, 14, 38, 15, 45, 14, 45, 15], [40, 14, 40, 15,
43, 14, 43, 15], [42, 14, 42, 15, 53, 14, 53, 15], [44, 14, 44, 15, 51, 14, 51, 15], [46, 14, 46, 15, 49, 14, 49, 15], [54, 14, 54, 15, 54, 12,
54, 13, 53, 12, 53, 13], [56, 14, 56, 15, 56, 12, 56, 13, 51, 12, 51, 13], [58, 14, 58, 15, 58, 12, 58, 13, 49, 12, 49, 13], [1, 15, 1, 16, 2,
15, 2, 16], [3, 15, 3, 16, 4, 15, 4, 16], [9, 15, 9, 16, 8, 15, 8, 16], [15, 15, 15, 16, 14, 15, 14, 16], [15, 15, 15, 16, 14, 15, 14, 16], [21,
15, 21, 16, 20, 15, 20, 16], [25, 15, 25, 16, 26, 15, 26, 16], [27, 15, 27, 16, 28, 15, 28, 16], [33, 15, 33, 16, 32, 15, 32, 16], [37, 15, 37,
16, 38, 15, 38, 16], [39, 15, 39, 16, 40, 15, 40, 16], [45, 15, 45, 16, 44, 15, 44, 16], [49, 15, 49, 16, 50, 15, 50, 16], [51, 15, 51, 16, 52,
15, 52, 16], [57, 15, 57, 16, 56, 15, 56, 16], [5, 15, 5, 16, 5, 13, 5, 14, 4, 13, 4, 14], [17, 15, 17, 16, 17, 13, 17, 14, 16, 13, 16, 14], [29,
15, 29, 16, 29, 13, 29, 14, 28, 13, 28, 14], [41, 15, 41, 16, 41, 13, 41, 14, 40, 13, 40, 14], [53, 15, 53, 16, 53, 13, 53, 14, 52, 13, 52, 14]

TABLE 26B

[52, 14, 52, 15, 55, 14, 55, 15, 55, 16, 0, 0], [50, 14, 50, 15, 57, 14, 57, 15, 57, 16, 0, 0], [48, 14, 48, 15, 59, 14, 59, 15, 59, 16, 0, 0], [7, 15, 7, 16, 6, 15, 6, 16], [11, 15, 11, 16, 10, 15, 10, 16], [19, 15, 19, 16, 18, 15, 18, 16], [23, 15, 23, 16, 22, 15, 22, 16], [31, 15, 31, 16, 30, 15, 30, 16], [35, 15, 35, 16, 34, 15, 34, 16], [43, 15, 43, 16, 42, 15, 42, 16], [47, 15, 47, 16, 46, 15, 46, 16], [55, 15, 55, 16, 54, 15, 54, 16], [59, 15, 59, 16, 58, 15, 58, 16], [6, 16, 0, 0, 5, 16, 0, 0], [8, 16, 0, 0, 3, 16, 0, 0], [10, 16, 0, 0, 1, 16, 0, 0], [12, 16, 0, 0, 11, 16, 0, 0], [14, 16, 0, 0, 9, 16, 0, 0], [16, 16, 0, 0, 7, 16, 0, 0], [18, 16, 0, 0, 17, 16, 0, 0], [20, 16, 0, 0, 15, 16, 0, 0], [22, 16, 0, 0, 13, 16, 0, 0], [24, 16, 0, 0, 23, 16, 0, 0], [26, 16, 0, 0, 21, 16, 0, 0], [28, 16, 0, 0, 19, 16, 0, 0], [30, 16, 0, 0, 29, 16, 0, 0], [32, 16, 0, 0, 27, 16, 0, 0], [34, 16, 0, 0, 25, 16, 0, 0], [36, 16, 0, 0, 35, 16, 0, 0], [38, 16, 0, 0, 33, 16, 0, 0], [40, 16, 0, 0, 31, 16, 0, 0], [42, 16, 0, 0, 41, 16, 0, 0], [44, 16, 0, 0, 39, 16, 0, 0], [46, 16, 0, 0, 37, 16, 0, 0], [48, 16, 0, 0, 47, 16, 0, 0], [50, 16, 0, 0, 45, 16, 0, 0], [52, 16, 0, 0, 43, 16, 0, 0], [54, 16, 0, 0, 53, 16, 0, 0], [56, 16, 0, 0, 51, 16, 0, 0], [58, 16, 0, 0, 49, 16, 0, 0], [0, 16, 0, 0, 0, 14, 0, 15, 11, 14, 11, 15], [2, 16, 0, 0, 2, 14, 2, 15, 9, 14, 9, 15], [4, 16, 0, 0, 4, 14, 4, 15, 7, 14, 7, 15]

The core oligonucleotide sequences used to produce 8H×12H×32B nucleic acid structures of the invention are designated SEQ ID NOs. 4836-5007, and the corresponding voxel coordinates are shown respectively in Table 27A. The end oligonucleotide sequences used to produce 8H×12H×32B nucleic acid structures of the invention are designated SEQ ID NOs. 5482-5545, and the corresponding voxel coordinates are shown respectively in Table 27B. (See also Appendix, Table 11 of U.S. provisional application No. 61/675,309, filed Jul. 24, 2012, incorporated by reference herein.)

TABLE 27A

[0, 0, 0, 1, 0, 0, 0, 0], [0, 0, 2, 1, 0, 0, 0, 0], [0, 0, 4, 1, 0, 0, 0, 0], [0, 0, 6, 1, 0, 0, 0, 0], [0, 0, 89, 1, 0, 0, 0, 0], [0, 0, 91, 1, 0, 0, 0, 0], [0, 0, 93, 1, 0, 0, 0, 0], [0, 0, 95, 1, 0, 0, 0, 0], [0, 0, 16, 1, 0, 0, 15, 1], [0, 0, 18, 1, 0, 0, 13, 1], [0, 0, 20, 1, 0, 0, 11, 1], [0, 0, 22, 1, 0, 0, 9, 1], [0, 0, 24, 1, 0, 0, 23, 1], [0, 0, 26, 1, 0, 0, 21, 1], [0, 0, 28, 1, 0, 0, 19, 1], [0, 0, 30, 1, 0, 0, 17, 1], [0, 0, 32, 1, 0, 0, 31, 1], [0, 0, 34, 1, 0, 0, 29, 1], [0, 0, 36, 1, 0, 0, 27, 1], [0, 0, 38, 1, 0, 0, 25, 1], [0, 0, 40, 1, 0, 0, 39, 1], [0, 0, 42, 1, 0, 0, 37, 1], [0, 0, 44, 1, 0, 0, 35, 1], [0, 0, 46, 1, 0, 0, 33, 1], [0, 0, 48, 1, 0, 0, 47, 1], [0, 0, 50, 1, 0, 0, 45, 1], [0, 0, 52, 1, 0, 0, 43, 1], [0, 0, 54, 1, 0, 0, 41, 1], [0, 0, 56, 1, 0, 0, 55, 1], [0, 0, 58, 1, 0, 0, 53, 1], [0, 0, 60, 1, 0, 0, 51, 1], [0, 0, 62, 1, 0, 0, 49, 1], [0, 0, 64, 1, 0, 0, 63, 1], [0, 0, 66, 1, 0, 0, 61, 1], [0, 0, 68, 1, 0, 0, 59, 1], [0, 0, 70, 1, 0, 0, 57, 1], [0, 0, 72, 1, 0, 0, 71, 1], [0, 0, 74, 1, 0, 0, 69, 1], [0, 0, 76, 1, 0, 0, 67, 1], [0, 0, 78, 1, 0, 0, 65, 1], [0, 0, 80, 1, 0, 0, 79, 1], [0, 0, 82, 1, 0, 0, 77, 1], [0, 0, 84, 1, 0, 0, 75, 1], [0, 0, 86, 1, 0, 0, 73, 1], [0, 0, 14, 1, 0, 0, 1, 1, 1, 2, 1, 3], [0, 0, 12, 1, 0, 0, 3, 1, 3, 2, 3, 3], [0, 0, 10, 1, 0, 0, 5, 1, 5, 2, 5, 3], [0, 0, 8, 1, 0, 0, 7, 1, 7, 2, 7, 3], [8, 1, 8, 2, 0, 0, 0, 0], [15, 1, 15, 2, 0, 0, 0, 0], [24, 1, 24, 2, 0, 0, 0, 0], [31, 1, 31, 2, 0, 0, 0, 0], [40, 1, 40, 2, 0, 0, 0, 0], [47, 1, 47, 2, 0, 0, 0, 0], [56, 1, 56, 2, 0, 0, 0, 0], [63, 1, 63, 2, 0, 0, 0, 0], [72, 1, 72, 2, 0, 0, 0, 0], [79, 1, 79, 2, 0, 0, 0, 0], [88, 1, 88, 2, 0, 0, 0, 0], [95, 1, 95, 2, 0, 0, 0, 0], [3, 1, 3, 2, 2, 1, 2, 2], [5, 1, 5, 2, 4, 1, 4, 2], [9, 1, 9, 2, 10, 1, 10, 2], [11, 1, 11, 2, 12, 1, 12, 2], [13, 1, 13, 2, 14, 1, 14, 2], [19, 1, 19, 2, 18, 1, 18, 2], [21, 1, 21, 2, 20, 1, 20, 2], [25, 1, 25, 2, 26, 1, 26, 2], [27, 1, 27, 2, 28, 1, 28, 2], [29, 1, 29, 2, 30, 1, 30, 2], [35, 1, 35, 2, 34, 1, 34, 2], [37, 1, 37, 2, 36, 1, 36, 2], [41, 1, 41, 2, 42, 1, 42, 2], [43, 1, 43, 2, 44, 1, 44, 2], [45, 1, 45, 2, 46, 1, 46, 2], [51, 1, 51, 2, 50, 1, 50, 2], [53, 1, 53, 2, 52, 1, 52, 2], [57, 1, 57, 2, 58, 1, 58, 2], [59, 1, 59, 2, 60, 1, 60, 2], [61, 1, 61, 2, 62, 1, 62, 2], [67, 1, 67, 2, 66, 1, 66, 2], [69, 1, 69, 2, 68, 1, 68, 2], [73, 1, 73, 2, 74, 1, 74, 2], [75, 1, 75, 2, 76, 1, 76, 2], [77, 1, 77, 2, 78, 1, 78, 2], [83, 1, 83, 2, 82, 1, 82, 2], [85, 1, 85, 2, 84, 1, 84, 2], [89, 1, 89, 2, 90, 1, 90, 2], [91, 1, 91, 2, 92, 1, 92, 2], [93, 1, 93, 2, 94, 1, 94, 2], [1, 1, 1, 2, 0, 1, 0, 2, 0, 3, 0, 4], [17, 1, 17, 2, 16, 1, 16, 2, 16, 3, 16, 4], [33, 1, 33, 2, 32, 1, 32, 2, 32, 3, 32, 4], [49, 1, 49, 2, 48, 1, 48, 2, 48, 3, 48, 4], [65, 1, 65, 2, 64, 1, 64, 2, 64, 3, 64, 4], [81, 1, 81, 2, 80, 1, 80, 2, 80, 3, 80, 4], [8, 2, 8, 3, 23, 2, 23, 3], [10, 2, 10, 3, 21, 2, 21, 3], [12, 2, 12, 3, 19, 2, 19, 3], [14, 2, 14, 3, 17, 2, 17, 3], [16, 2, 16, 3, 31, 2, 31, 3], [18, 2, 18, 3, 29, 2, 29, 3], [20, 2, 20, 3, 27, 2, 27, 3], [22, 2, 22, 3, 25, 2, 25, 3], [24, 2, 24, 3, 39, 2, 39, 3], [26, 2, 26, 3, 37, 2, 37, 3], [28, 2, 28, 3, 35, 2, 35, 3], [30, 2, 30, 3, 33, 2, 33, 3], [32, 2, 32, 3, 47, 2, 47, 3], [34, 2, 34, 3, 45, 2, 45, 3], [36, 2, 36, 3, 43, 2, 43, 3], [38, 2, 38, 3, 41, 2, 41, 3], [40, 2, 40, 3, 55, 2, 55, 3], [42, 2, 42, 3, 53, 2, 53, 3], [44, 2, 44, 3, 51, 2, 51, 3], [46, 2, 46, 3, 49, 2, 49, 3], [50, 2, 50, 3, 61, 2, 61, 3], [52, 2, 52, 3, 59, 2, 59, 3], [54, 2, 54, 3, 57, 2, 57, 3], [56, 2, 56, 3, 71, 2, 71, 3], [58, 2, 58, 3, 69, 2, 69, 3], [60, 2, 60, 3, 67, 2, 67, 3], [62, 2, 62, 3, 65, 2, 65, 3], [64, 2, 64, 3, 79, 2, 79, 3], [66, 2, 66, 3, 77, 2, 77, 3], [68, 2, 68, 3, 75, 2, 75, 3], [70, 2, 70, 3, 73, 2, 73, 3], [72, 2, 72, 3, 87, 2, 87, 3], [74, 2, 74, 3, 85, 2, 85, 3], [76, 2, 76, 3, 83, 2, 83, 3], [78, 2, 78, 3, 81, 2, 81, 3], [88, 2, 88, 3, 0, 0, 88, 1, 0, 0, 87, 1], [90, 2, 90, 3, 0, 0, 90, 1, 0, 0, 85, 1], [92, 2, 92, 3, 0, 0, 92, 1, 0, 0, 83, 1], [94, 2, 94, 3, 0, 0, 94, 1, 0, 0, 81, 1], [1, 3, 1, 4, 2, 3, 2, 4], [3, 3, 3, 4, 4, 3, 4, 4], [5, 3, 5, 4, 6, 3, 6, 4], [11, 3, 11, 4, 10, 3, 10, 4], [13, 3, 13, 4, 12, 3, 12, 4], [17, 3, 17, 4, 18, 3, 18, 4], [19, 3, 19, 4, 20, 3, 20, 4], [21, 3, 21, 4, 22, 3, 22, 4], [27, 3, 27, 4, 26, 3, 26, 4], [29, 3, 29, 4, 28, 3, 28, 4], [33, 3, 33, 4, 34, 3, 34, 4], [35, 3, 35, 4, 36, 3, 36, 4], [37, 3, 37, 4, 38, 3, 38, 4], [43, 3, 43, 4, 42, 3, 42, 4], [45, 3, 45, 4, 44, 3, 44, 4], [49, 3, 49, 4, 50, 3, 50, 4], [51, 3, 51, 4, 52, 3, 52, 4], [53, 3, 53, 4, 54, 3, 54, 4], [59, 3, 59, 4, 58, 3, 58, 4], [61, 3, 61, 4, 60, 3, 60, 4], [65, 3, 65, 4, 66, 3, 66, 4], [67, 3, 67, 4, 68, 3, 68, 4], [69, 3, 69, 4, 70, 3, 70, 4], [75, 3, 75, 4, 74, 3, 74, 4], [77, 3, 77, 4, 76, 3, 76, 4], [81, 3, 81, 4, 82, 3, 82, 4], [83, 3, 83, 4, 84, 3, 84, 4], [85, 3, 85, 4, 86, 3, 86, 4], [91, 3, 91, 4, 90, 3, 90, 4], [93, 3, 93, 4, 92, 3, 92, 4], [7, 3, 7, 4, 7, 1, 7, 2, 6, 1, 6, 2], [23, 3, 23, 4, 23, 1, 23, 2, 22, 1, 22, 2], [39, 3, 39, 4, 39, 1, 39, 2, 38, 1, 38, 2], [55, 3, 55, 4, 55, 1, 55, 2, 54, 1, 54, 2], [71, 3, 71, 4, 71, 1, 71, 2, 70, 1, 70, 2], [87, 3, 87, 4, 87, 1, 87, 2, 86, 1, 86, 2]

TABLE 27B

[86, 2, 86, 3, 89, 2, 89, 3, 89, 4, 0, 0], [84, 2, 84, 3, 91, 2, 91, 3, 91, 4, 0, 0], [82, 2, 82, 3, 93, 2, 93, 3, 93, 4, 0, 0], [80, 2, 80, 3, 95, 2, 95, 3, 95, 4, 0, 0], [9, 3, 9, 4, 8, 3, 8, 4], [15, 3, 15, 4, 14, 3, 14, 4], [25, 3, 25, 4, 24, 3, 24, 4], [31, 3, 31, 4, 30, 3, 30, 4], [41, 3, 41, 4, 40, 3, 40, 4], [47, 3, 47, 4, 46, 3, 46, 4], [57, 3, 57, 4, 56, 3, 56, 4], [63, 3, 63, 4, 62, 3, 62, 4], [73, 3, 73, 4, 72, 3, 72, 4], [79, 3, 79, 4, 78, 3, 78, 4], [89, 3, 89, 4, 88, 3, 88, 4], [95, 3, 95, 4, 94, 3, 94, 4], [8, 4, 0, 0, 7, 4, 0, 0], [10, 4, 0, 0, 5, 4, 0, 0], [12, 4, 0, 0, 3, 4, 0, 0], [14, 4, 0, 0, 1, 4, 0, 0], [16, 4, 0, 0, 15, 4, 0, 0], [18, 4, 0, 0, 13, 4, 0, 0], [20, 4, 0, 0, 11, 4, 0, 0], [22, 4, 0, 0, 9, 4, 0, 0], [24, 4, 0, 0, 23, 4, 0, 0], [26, 4, 0, 0, 21, 4, 0, 0], [28, 4, 0, 0, 19, 4, 0, 0], [30, 4, 0, 0, 17, 4, 0, 0], [32, 4, 0, 0, 31, 4, 0, 0], [34, 4, 0, 0, 29, 4, 0, 0], [36, 4, 0, 0, 27, 4, 0, 0], [38, 4, 0, 0, 25, 4, 0, 0], [40, 4, 0, 0, 39, 4, 0, 0], [42, 4, 0, 0, 37, 4, 0, 0], [44, 4, 0, 0, 35, 4, 0, 0], [46, 4, 0, 0, 33, 4, 0, 0], [48, 4, 0, 0, 47, 4, 0, 0], [50, 4, 0, 0, 45, 4, 0, 0], [52, 4, 0, 0, 43, 4, 0, 0], [54, 4, 0, 0, 41, 4, 0, 0], [56, 4, 0, 0, 55, 4, 0, 0], [58, 4, 0, 0, 53, 4, 0, 0], [60, 4, 0, 0, 51, 4, 0, 0], [62, 4, 0, 0, 49, 4, 0, 0], [64, 4, 0, 0, 63, 4, 0, 0], [66, 4, 0, 0, 61, 4, 0, 0], [68, 4, 0, 0, 59, 4, 0, 0], [70, 4, 0, 0, 57, 4, 0, 0], [72, 4, 0, 0, 71, 4, 0, 0], [74, 4, 0, 0, 69, 4, 0, 0], [76, 4, 0, 0, 67, 4, 0, 0], [78, 4, 0, 0, 65, 4, 0, 0], [80, 4, 0, 0, 79, 4, 0, 0], [82, 4, 0, 0, 77, 4, 0, 0], [84, 4, 0, 0, 75, 4, 0, 0], [86, 4, 0, 0, 73, 4, 0, 0], [88, 4, 0, 0, 87, 4, 0, 0], [90, 4, 0, 0, 85, 4, 0, 0], [92, 4, 0, 0, 83, 4, 0, 0], [94, 4, 0, 0, 81, 4, 0, 0], [0, 4, 0, 0, 0, 2, 0, 3, 15, 2, 15, 3], [2, 4, 0, 0, 2, 2, 2, 3, 13, 2, 13, 3], [4, 4, 0, 0, 4, 2, 4, 3, 11, 2, 11, 3], [6, 4, 0, 0, 6, 2, 6, 3, 9, 2, 9, 3]

The core oligonucleotide sequences used to produce 8H×12H×64B nucleic acid structures of the invention are designated SEQ ID NOs. 4836-5179, and the corresponding voxel coordinates are shown respectively in Table 28A. The end oligonucleotide sequences used to produce 8H×12H×64B nucleic acid structures of the invention are designated SEQ ID NOs. 5546-5609, and the corresponding voxel coordinates are shown respectively in Table 28B. (See also Appendix, Table 11 of U.S. provisional application No. 61/675,309, filed Jul. 24, 2012, incorporated by reference herein.)

TABLE 28A

[0, 0, 0, 1, 0, 0, 0, 0], [0, 0, 2, 1, 0, 0, 0, 0], [0, 0, 4, 1, 0, 0, 0, 0], [0, 0, 6, 1, 0, 0, 0, 0], [0, 0, 89, 1, 0, 0, 0, 0], [0, 0, 91, 1, 0, 0, 0, 0], [0, 0, 93, 1, 0, 0, 0, 0], [0, 0, 95, 1, 0, 0, 0, 0], [0, 0, 16, 1, 0, 0, 15, 1], [0, 0, 18, 1, 0, 0, 13, 1], [0, 0, 20, 1, 0, 0, 11, 1], [0, 0, 22, 1, 0, 0, 9, 1], [0, 0, 24, 1, 0, 0, 23, 1], [0, 0, 26, 1, 0, 0, 21, 1], [0, 0, 28, 1, 0, 0, 19, 1], [0, 0, 30, 1, 0, 0, 17, 1], [0, 0, 32, 1, 0, 0, 31, 1], [0, 0, 34, 1, 0, 0, 29, 1], [0, 0, 36, 1, 0, 0, 27, 1], [0, 0, 38, 1, 0, 0, 25, 1], [0, 0, 40, 1, 0, 0, 39, 1], [0, 0, 42, 1, 0, 0, 37, 1], [0, 0, 44, 1, 0, 0, 35, 1], [0, 0, 46, 1, 0, 0, 33, 1], [0, 0, 48, 1, 0, 0, 47, 1], [0, 0, 50, 1, 0, 0, 45, 1], [0, 0, 52, 1, 0, 0, 43, 1], [0, 0, 54, 1, 0, 0, 41, 1], [0, 0, 56, 1, 0, 0, 55, 1], [0, 0, 58, 1, 0, 0, 53, 1], [0, 0, 60, 1, 0, 0, 51, 1], [0, 0, 62, 1, 0, 0, 49, 1], [0, 0, 64, 1, 0, 0, 63, 1], [0, 0, 66, 1, 0, 0, 61, 1], [0, 0, 68, 1, 0, 0, 59, 1], [0, 0, 70, 1, 0, 0, 57, 1], [0, 0, 72, 1, 0, 0, 71, 1], [0, 0, 74, 1, 0, 0, 69, 1], [0, 0, 76, 1, 0, 0, 67, 1], [0, 0, 78, 1, 0, 0, 65, 1], [0, 0, 80, 1, 0, 0, 79, 1], [0, 0, 82, 1, 0, 0, 77, 1], [0, 0, 84, 1, 0, 0, 75, 1], [0, 0, 86, 1, 0, 0, 73, 1], [0, 0, 14, 1, 0, 0, 1, 1, 1, 2, 1, 3], [0, 0, 12, 1, 0, 0, 3, 1, 3, 2, 3], [0, 0, 10, 1, 0, 0, 5, 1, 5, 2, 5, 3], [0, 0, 8, 1, 0, 0, 7, 1, 7, 2, 7, 3], [8, 1, 8, 2, 0, 0, 0, 0], [15, 1, 15, 2, 0, 0, 0, 0], [24, 1, 24, 2, 0, 0, 0, 0], [31, 1, 31, 2, 0, 0, 0, 0], [40, 1, 40, 2, 0, 0, 0, 0], [47, 1, 47, 2, 0, 0, 0, 0], [56, 1, 56, 2, 0, 0, 0, 0], [63, 1, 63, 2, 0, 0, 0, 0], [72, 1, 72, 2, 0, 0, 0, 0], [79, 1, 79, 2, 0, 0, 0, 0], [88, 1, 88, 2, 0, 0, 0, 0], [95, 1, 95, 2, 0, 0, 0, 0], [3, 1, 3, 2, 1, 2], [5, 1, 5, 2, 4, 1, 4, 2], [9, 1, 9, 2, 10, 1, 10, 2], [11, 1, 11, 2, 12, 1, 12, 2], [13, 1, 13, 2, 14, 1, 14, 2], [19, 1, 19, 2, 18, 1, 18, 2], [21, 1, 21, 2, 20, 1, 20, 2], [25, 1, 25, 2, 26, 1, 26, 2], [27, 1, 27, 2, 28, 1, 28, 2], [29, 1, 29, 2, 30, 1, 30, 2], [35, 1, 35, 2, 34, 1, 34, 2], [37, 1, 37, 2, 36, 1, 36, 2], [41, 1, 41, 2, 42, 1, 42, 2], [43, 1, 43, 2, 44, 1, 44, 2], [45, 1, 45, 2, 46, 1, 46, 2], [51, 1, 51, 2, 50, 1, 50, 2], [53, 1, 53, 2, 52, 1, 52, 2], [57, 1, 57, 2, 58, 1, 58, 2], [59, 1, 59, 2, 60, 1, 60, 2], [61, 1, 61, 2, 62, 1, 62, 2], [67, 1, 67, 2, 66, 1, 66, 2], [69, 1, 69, 2, 68, 1, 68, 2], [73, 1, 73, 2, 74, 1, 74, 2], [75, 1, 75, 2, 76, 1, 76, 2], [77, 1, 77, 2, 78, 1, 78, 2], [83, 1, 83, 2, 82, 1, 82, 2], [85, 1, 85, 2, 84, 1, 84, 2], [89, 1, 89, 2, 90, 1, 90, 2], [91, 1, 91, 2, 92, 1, 92, 2], [93, 1, 93, 2, 94, 1, 94, 2], [1, 1, 1, 2, 0, 1, 0, 2, 0, 3, 0, 4], [17, 1, 17, 2, 16, 1, 16, 2, 16, 3, 16, 4], [33, 1, 33, 2, 32, 1, 32, 2, 32, 3, 32, 4], [49, 1, 49, 2, 48, 1, 48, 2, 48, 3, 48, 4], [65, 1, 65, 2, 64, 1, 64, 2, 64, 3, 64, 4], [81, 1, 81, 2, 80, 1, 80, 2, 80, 3, 80, 4], [8, 2, 8, 3, 23, 2, 23, 3], [10, 2, 10, 3, 21, 2, 21, 3], [12, 2, 12, 3, 19, 2, 19, 3], [14, 2, 14, 3, 17, 2, 17, 3], [16, 2, 16, 3, 31, 2, 31, 3], [18, 2, 18, 3, 29, 2, 29, 3], [20, 2, 20, 3, 27, 2, 27, 3], [22, 2, 22, 3, 25, 2, 25, 3], [24, 2, 24, 3, 39, 2, 39, 3], [26, 2, 26, 3, 37, 2, 37, 3], [28, 2, 28, 3, 35, 2, 35, 3], [30, 2, 30, 3, 33, 2, 33, 3], [32, 2, 32, 3, 47, 2, 47, 3], [34, 2, 34, 3, 45, 2, 45, 3], [36, 2, 36, 3, 43, 2, 43, 3], [38, 2, 38, 3, 41, 2, 41, 3], [40, 2, 40, 3, 55, 2, 55, 3], [42, 2, 42, 3, 53, 2, 53, 3], [44, 2, 44, 3, 51, 2, 51, 3], [46, 2, 46, 3, 49, 2, 49, 3], [48, 2, 48, 3, 63, 2, 63, 3], [50, 2, 50, 3, 61, 2, 61, 3], [52, 2, 52, 3, 59, 2, 59, 3], [54, 2, 54, 3, 57, 2, 57, 3], [56, 2, 56, 3, 71, 2, 71, 3], [58, 2, 58, 3, 69, 2, 69, 3], [60, 2, 60, 3, 67, 2, 67, 3], [62, 2, 62, 3, 65, 2, 65, 3], [64, 2, 64, 3, 79, 2, 79, 3], [66, 2, 66, 3, 77, 2, 77, 3], [68, 2, 68, 3, 75, 2, 75, 3], [70, 2, 70, 3, 73, 2, 73, 3], [72, 2, 72, 3, 87, 2, 87, 3], [74, 2, 74, 3, 85, 2, 85, 3], [76, 2, 76, 3, 83, 2, 83, 3], [78, 2, 78, 3, 81, 2, 81, 3], [88, 2, 88, 3, 0, 0, 88, 1, 0, 0, 87, 1], [90, 2, 90, 3, 0, 0, 90, 1, 0, 0, 85, 1], [92, 2, 92, 3, 0, 0, 92, 1, 0, 0, 83, 1], [94, 2, 94, 3, 0, 0, 94, 1, 0, 0, 81, 1], [1, 3, 1, 4, 2, 3, 2, 4], [3, 3, 3, 4, 4, 3, 4, 4], [5, 3, 5, 4, 6, 3, 6, 4], [11, 3, 11, 4, 10, 3, 10, 4], [13, 3, 13, 4, 12, 3, 12, 4], [17, 3, 17, 4, 18, 3, 18, 4], [19, 3, 19, 4, 20, 3, 20, 4], [21, 3, 21, 4, 22, 3, 22, 4], [27, 3, 27, 4, 26, 3, 26, 4], [29, 3, 29, 4, 28, 3, 28, 4], [33, 3, 33, 4, 34, 3, 34, 4], [35, 3, 35, 4, 36, 3, 36, 4], [37, 3, 37, 4, 38, 3, 38, 4], [43, 3, 43, 4, 42, 3, 42, 4], [45, 3, 45, 4, 44, 3, 44, 4], [49, 3, 49, 4, 50, 3, 50, 4], [51, 3, 51, 4, 52, 3, 52, 4], [53, 3, 53, 4, 54, 3, 54, 4], [59, 3, 59, 4, 58, 3, 58, 4], [61, 3, 61, 4, 60, 3, 60, 4], [65, 3, 65, 4, 66, 3, 66, 4], [67, 3, 67, 4, 68, 3, 68, 4], [69, 3, 69, 4, 70, 3, 70, 4], [75, 3, 75, 4, 74, 3, 74, 4], [77, 3, 77, 4, 76, 3, 76, 4], [81, 3, 81, 4, 82, 3, 82, 4], [83, 3, 83, 4, 84, 3, 84, 4], [85, 3, 85, 4, 86, 3, 86, 4], [91, 3, 91, 4, 90, 3, 90, 4], [93, 3, 93, 4, 92, 3, 92, 4], [7, 3, 7, 4, 7, 1, 7, 2, 6, 1, 6, 2], [23, 3, 23, 4, 23, 1, 23, 2, 22, 1, 22, 2], [39, 3, 39, 4, 39, 1, 39, 2, 38, 1, 38, 2], [55, 3, 55, 4, 55, 1, 55, 2, 54, 1, 54, 2], [71, 3, 71, 4, 71, 1, 71, 2, 70, 1, 70, 2], [87, 3, 87, 4, 87, 1, 87, 2, 86, 1, 86, 2], [86, 2, 86, 3, 89, 2, 89, 3, 89, 4, 89, 5], [84, 2, 84, 3, 91, 2, 91, 3, 91, 4, 91, 5], [82, 2, 82, 3, 93, 2, 93, 3, 93, 4, 93, 5], [80, 2, 80, 3, 95, 2, 95, 3, 95, 4, 95, 5], [9, 3, 9, 4, 8, 3, 8, 4, 8, 5, 8, 6], [25, 3, 25, 4, 24, 3, 24, 4, 24, 5, 24, 6], [41, 3, 41, 4, 40, 3, 40, 4, 40, 5, 40, 6], [57, 3, 57, 4, 56, 3, 56, 4, 56, 5, 56, 6], [73, 3, 73, 4, 72, 3, 72, 4, 72, 5, 72, 6], [89, 3, 89, 4, 88, 3, 88, 4, 88, 5, 88, 6], [16, 4, 16, 5, 15, 4, 15, 5], [18, 4, 18, 5, 13, 4, 13, 5], [20, 4, 20, 5, 11, 4, 11, 5], [22, 4, 22, 5, 9, 4, 9, 5], [24, 4, 24, 5, 23, 4, 23, 5], [26, 4, 26, 5, 21, 4, 21, 5], [28, 4, 28, 5, 19, 4, 19, 5], [30, 4, 30, 5, 17, 4, 17, 5], [32, 4, 32, 5, 31, 4, 31, 5], [34, 4, 34, 5, 29, 4, 29, 5], [36, 4, 36, 5, 27, 4, 27, 5], [38, 4, 38, 5, 25, 4, 25, 5], [40, 4, 40, 5, 39, 4, 39, 5], [42, 4, 42, 5, 37, 4, 37, 5], [44, 4, 44, 5, 35, 4, 35, 5], [46, 4, 46, 5, 33, 4, 33, 5], [48, 4, 48, 5, 47, 4, 47, 5], [50, 4, 50, 5, 45, 4, 45, 5], [52, 4, 52, 5, 43, 4, 43, 5], [54, 4, 54, 5, 41, 4, 41, 5], [56, 4, 56, 5, 55, 4, 55, 5], [58, 4, 58, 5, 53, 4, 53, 5], [60, 4, 60, 5, 51, 4, 51, 5], [62, 4, 62, 5, 49, 4, 49, 5], [64, 4, 64, 5, 63, 4, 63, 5], [66, 4, 66, 5, 61, 4, 61, 5], [68, 4, 68, 5, 59, 4, 59, 5], [70, 4, 70, 5, 57, 4, 57, 5], [72, 4, 72, 5, 71, 4, 71, 5], [74, 4, 74, 5, 69, 4, 69, 5], [76, 4, 76, 5, 67, 4, 67, 5], [78, 4, 78, 5, 65, 4, 65, 5], [80, 4, 80, 5, 79, 4, 79, 5], [82, 4, 82, 5, 77, 4, 77, 5], [84, 4, 84, 5, 75, 4, 75, 5], [86, 4, 86, 5, 73, 4, 73, 5], [0, 4, 0, 5, 0, 2, 0, 3, 15, 2, 15, 3], [14, 4, 14, 5, 1, 4, 1, 5, 1, 6, 1, 7], [2, 4, 2, 5, 2, 2, 2, 3, 13, 2, 13, 3], [12, 4, 12, 5, 3, 4, 3, 5, 3, 6, 3, 7], [4, 4, 4, 5, 4, 2, 4, 3, 11, 2, 11, 3], [10, 4, 10, 5, 5, 4, 5, 5, 5, 6, 5, 7], [6, 4, 6, 5, 6, 2, 6, 3, 9, 2, 9, 3], [8, 4, 8, 5, 7, 4, 7, 5, 7, 6, 7, 7], [3, 5, 3, 6, 2, 5, 2, 6], [5, 5, 5, 6, 4, 5, 4, 6], [9, 5, 9, 6, 10, 5, 10, 6], [11, 5, 11, 6, 12, 5, 12, 6], [13, 5, 13, 6, 14, 5, 14, 6], [19, 5, 19, 6, 18, 5, 18, 6], [21, 5, 21, 6, 20, 5, 20, 6], [25, 5, 25, 6, 26, 5, 26, 6], [27, 5, 27, 6, 28, 5, 28, 6], [29, 5, 29, 6, 30, 5, 30, 6], [35, 5, 35, 6, 34, 5, 34, 6], [37, 5, 37, 6, 36, 5, 36, 6], [41, 5, 41, 6, 42, 5, 42, 6], [43, 5, 43, 6, 44, 5, 44, 6], [45, 5, 45, 6, 46, 5, 46, 6], [51, 5, 51, 6, 50, 5, 50, 6], [53, 5, 53, 6, 52, 5, 52, 6], [57, 5, 57, 6, 58, 5, 58, 6], [59, 5, 59, 6, 60, 5, 60, 6], [61, 5, 61, 6, 62, 5, 62, 6], [67, 5, 67, 6, 66, 5, 66, 6], [69, 5, 69, 6, 68, 5, 68, 6], [73, 5, 73, 6, 74, 5, 74, 6], [75, 5, 75, 6, 76, 5, 76, 6], [77, 5, 77, 6, 78, 5, 78, 6], [83, 5, 83, 6, 82, 5, 82, 6], [85, 5, 85, 6, 84, 5, 84, 6], [89, 5, 89, 6, 90, 5, 90, 6], [91, 5, 91, 6, 92, 5, 92, 6], [93, 5, 93, 6, 94, 5, 94, 6], [1, 5, 1, 6, 0, 5, 0, 6, 0, 7, 0, 8], [15, 5, 15, 6, 15, 3, 15, 4, 14, 3, 14, 4], [17, 5, 17, 6, 16, 5, 16, 6, 16, 7, 16, 8], [31, 5, 31, 6, 31, 3, 31, 4, 30, 3, 30, 4], [33, 5, 33, 6, 32, 5, 32, 6, 32, 7, 32, 8], [47, 5, 47, 6, 47, 3, 47, 4, 46, 3, 46, 4], [49, 5, 49, 6, 48, 5, 48, 6, 48, 7, 48, 8], [63, 5, 63, 6, 63, 3, 63, 4, 62, 3, 62, 4], [65, 5, 65, 6, 64, 5, 64, 6, 64, 7, 64, 8], [79, 5, 79, 6, 79, 3, 79, 4, 78, 3, 78, 4], [81, 5, 81, 6, 80, 5, 80, 6, 80, 7, 80, 8], [95, 5, 95, 6, 95, 3, 95, 4, 94, 3, 94, 4], [8, 6, 8, 7, 23, 6, 23, 7], [10, 6, 10, 7, 21, 6, 21, 7], [12, 6, 12, 7, 19, 6, 19, 7], [14, 6, 14, 7, 17, 6, 17, 7], [16, 6, 16, 7, 31, 6, 31, 7], [18, 6, 18, 7, 29, 6, 29, 7], [20, 6, 20, 7, 27, 6, 27, 7], [22, 6, 22, 7, 25, 6, 25, 7], [24, 6, 24, 7, 39, 6, 39, 7], [26, 6, 26, 7, 37, 6, 37, 7], [28, 6, 28, 7, 35, 6, 35, 7], [30, 6, 30, 7, 33, 6, 33, 7], [32, 6, 32, 7, 47, 6, 47, 7], [34, 6, 34, 7, 45, 6, 45, 7], [36, 6, 36, 7, 43, 6, 43, 7], [38, 6, 38, 7, 41, 6, 41, 7], [40, 6, 40, 7, 55, 6, 55, 7], [42, 6, 42, 7, 53, 6, 53, 7], [44, 6, 44, 7, 51, 6, 51, 7], [46, 6, 46, 7, 49, 6, 49, 7], [48, 6, 48, 7, 63, 6, 63, 7], [50, 6, 50, 7, 61, 6, 61, 7], [52, 6, 52, 7, 59, 6, 59, 7], [54, 6, 54, 7, 57, 6, 57, 7], [56, 6, 56, 7, 71, 6, 71, 7], [58, 6, 58, 7, 69, 6, 69, 7], [60, 6, 60, 7, 67, 6, 67, 7], [62, 6, 62, 7, 65, 6, 65, 7], [64, 6, 64, 7, 79, 6, 79, 7], [66, 6, 66, 7, 77, 6, 77, 7], [68, 6, 68, 7, 75, 6, 75, 7], [70, 6, 70, 7, 73, 6, 73, 7], [72, 6, 72, 7, 87, 6, 87, 7], [74, 6, 74, 7, 85, 6, 85, 7], [76, 6, 76, 7, 83, 6, 83, 7], [78, 6, 78, 7, 81, 6, 81, 7], [88, 6, 88, 7, 88, 4, 88, 5, 87, 4, 87, 5], [90, 6, 90, 7, 90, 4, 90, 5, 85, 4, 85, 5], [92, 6, 92, 7, 92, 4, 92, 5, 83, 4, 83, 5], [94, 6, 94, 7, 94, 4, 94, 5, 81, 4, 81, 5], [1, 7, 1, 8, 2, 7, 2, 8], [3, 7, 3, 8, 4, 7, 4, 8], [5, 7, 5, 8, 6, 7, 6, 8], [11, 7, 11, 8, 10, 7, 10, 8], [13, 7, 13, 8, 12, 7, 12, 8], [17, 7, 17, 8, 18, 7, 18, 8], [19, 7, 19, 8, 20, 7, 20, 8], [21, 7, 21, 8, 22, 7, 22, 8], [27, 7, 27, 8, 26, 7, 26, 8], [29, 7, 29, 8, 28, 7, 28, 8], [33, 7, 33, 8, 34, 7, 34, 8], [35, 7, 35, 8, 36, 7, 36, 8], [37, 7, 37, 8, 38, 7, 38, 8], [43, 7, 43, 8, 42, 7, 42, 8], [45, 7, 45, 8, 44, 7, 44, 8], [49, 7, 49, 8, 50, 7, 50, 8], [51, 7, 51, 8, 52, 7, 52, 8], [53, 7, 53, 8, 54, 7, 54, 8], [59, 7, 59, 8, 58, 7, 58, 8], [61, 7, 61, 8, 60, 7, 60, 8], [65, 7, 65, 8, 66, 7, 66, 8], [67, 7, 67, 8, 68, 7, 68, 8], [69, 7, 69, 8, 70, 7, 70, 8], [75, 7, 75, 8, 74, 7, 74, 8], [77, 7, 77, 8, 76, 7, 76,

TABLE 28A-continued

8], [81, 7, 81, 8, 82, 7, 82, 8], [83, 7, 83, 8, 84, 7, 84, 8], [85, 7, 85, 8, 86, 7, 86, 8], [91, 7, 91, 8, 90, 7, 90, 8], [93, 7, 93, 8, 92, 7, 92, 8], [7, 7, 7, 8, 7, 5, 7, 6, 6, 5, 6, 6], [23, 7, 23, 8, 23, 5, 23, 6, 22, 5, 22, 6], [39, 7, 39, 8, 39, 5, 39, 6, 38, 5, 38, 6], [55, 7, 55, 8, 55, 5, 55, 6, 54, 5, 54, 6], [71, 7, 71, 8, 71, 5, 71, 6, 70, 5, 70, 6], [87, 7, 87, 8, 87, 5, 87, 6, 86, 5, 86, 6]

TABLE 28B

[86, 6, 86, 7, 89, 6, 89, 7, 89, 8, 0, 0], [84, 6, 84, 7, 91, 6, 91, 7, 91, 8, 0, 0], [82, 6, 82, 7, 93, 6, 93, 7, 93, 8, 0, 0], [80, 6, 80, 7, 95, 6, 95, 7, 95, 8, 0, 0], [9, 7, 9, 8, 8, 7, 8, 8], [15, 7, 15, 8, 14, 7, 14, 8], [25, 7, 25, 8, 24, 7, 24, 8], [31, 7, 31, 8, 30, 7, 30, 8], [41, 7, 41, 8, 40, 7, 40, 8], [47, 7, 47, 8, 46, 7, 46, 8], [57, 7, 57, 8, 56, 7, 56, 8], [63, 7, 63, 8, 62, 7, 62, 8], [73, 7, 73, 8, 72, 7, 72, 8], [79, 7, 79, 8, 78, 7, 78, 8], [89, 7, 89, 8, 88, 7, 88, 8], [95, 7, 95, 8, 94, 7, 94, 8], [8, 8, 0, 0, 7, 8, 0, 0], [10, 8, 0, 0, 5, 8, 0, 0], [12, 8, 0, 0, 3, 8, 0, 0], [14, 8, 0, 0, 1, 8, 0, 0], [16, 8, 0, 0, 15, 8, 0, 0], [18, 8, 0, 0, 13, 8, 0, 0], [20, 8, 0, 0, 11, 8, 0, 0], [22, 8, 0, 0, 9, 8, 0, 0], [24, 8, 0, 0, 23, 8, 0, 0], [26, 8, 0, 0, 21, 8, 0, 0], [28, 8, 0, 0, 19, 8, 0, 0], [30, 8, 0, 0, 17, 8, 0, 0], [32, 8, 0, 0, 31, 8, 0, 0], [34, 8, 0, 0, 29, 8, 0, 0], [36, 8, 0, 0, 27, 8, 0, 0], [38, 8, 0, 0, 25, 8, 0, 0], [40, 8, 0, 0, 39, 8, 0, 0], [42, 8, 0, 0, 37, 8, 0, 0], [44, 8, 0, 0, 35, 8, 0, 0], [46, 8, 0, 0, 33, 8, 0, 0], [48, 8, 0, 0, 47, 8, 0, 0],
[50, 8, 0, 0, 45, 8, 0, 0], [52, 8, 0, 0, 43, 8, 0, 0], [54, 8, 0, 0, 41, 8, 0, 0], [56, 8, 0, 0, 55, 8, 0, 0], [58, 8, 0, 0, 53, 8, 0, 0], [60, 8, 0, 0, 51, 8, 0, 0], [62, 8, 0, 0, 49, 8, 0, 0], [64, 8, 0, 0, 63, 8, 0, 0], [66, 8, 0, 0, 61, 8, 0, 0], [68, 8, 0, 0, 59, 8, 0, 0], [70, 8, 0, 0, 57, 8, 0, 0], [72, 8, 0, 0, 71, 8, 0, 0], [74, 8, 0, 0, 69, 8, 0, 0], [76, 8, 0, 0, 67, 8, 0, 0], [78, 8, 0, 0, 65, 8, 0, 0], [80, 8, 0, 0, 79, 8, 0, 0], [82, 8, 0, 0, 77, 8, 0, 0], [84, 8, 0, 0, 75, 8, 0, 0], [86, 8, 0, 0, 73, 8, 0, 0], [88, 8, 0, 0, 87, 8, 0, 0], [90, 8, 0, 0, 85, 8, 0, 0], [92, 8, 0, 0, 83, 8, 0, 0], [94, 8, 0, 0, 81, 8, 0, 0], [0, 8, 0, 0, 0, 6, 0, 7, 15, 6, 15, 7], [2, 8, 0, 0, 2, 6, 2, 7, 13, 6, 13, 7], [4, 8, 0, 0, 4, 6, 4, 7, 11, 6, 11, 7], [6, 8, 0, 0, 6, 6, 6, 7, 9, 6, 9, 7]

The core oligonucleotide sequences used to produce 8H×12H×128B nucleic acid structures of the invention are designated SEQ ID NOs. 4836-5481, and the corresponding voxel coordinates are shown respectively in Table 29A. The end oligonucleotide sequences used to produce 8H×12H×128B nucleic acid structures of the invention are designated SEQ ID NOs. 5610-5671, and the corresponding voxel coordinates are shown respectively in Table 29B. (See also Appendix, Table 11 of U.S. provisional application No. 61/675,309, filed Jul. 24, 2012, incorporated by reference herein.)

TABLE 29A

[0, 0, 0, 1, 0, 0, 0, 0], [0, 0, 2, 1, 0, 0, 0, 0], [0, 0, 4, 1, 0, 0, 0, 0], [0, 0, 6, 1, 0, 0, 0, 0], [0, 0, 89, 1, 0, 0, 0, 0], [0, 0, 91, 1, 0, 0, 0, 0], [0, 0, 93, 1, 0, 0, 0, 0], [0, 0, 95, 1, 0, 0, 0, 0], [0, 0, 16, 1, 0, 0, 15, 1], [0, 0, 18, 1, 0, 0, 13, 1], [0, 0, 20, 1, 0, 0, 11, 1], [0, 0, 22, 1, 0, 0, 9, 1], [0, 0, 24, 1, 0, 0, 23, 1], [0, 0, 26, 1, 0, 0, 21, 1], [0, 0, 28, 1, 0, 0, 19, 1], [0, 0, 30, 1, 0, 0, 17, 1], [0, 0, 32, 1, 0, 0, 31, 1], [0, 0, 34, 1, 0, 0, 29, 1], [0, 0, 36, 1, 0, 0, 27, 1], [0, 0, 38, 1, 0, 0, 25, 1], [0, 0, 40, 1, 0, 0, 39, 1], [0, 0, 42, 1, 0, 0, 37, 1], [0, 0, 44, 1, 0, 0, 35, 1], [0, 0, 46, 1, 0, 0, 33, 1], [0, 0, 48, 1, 0, 0, 47, 1], [0, 0, 50, 1, 0, 0, 45, 1], [0, 0, 52, 1, 0, 0, 43, 1], [0, 0, 54, 1, 0, 0, 41, 1], [0, 0, 56, 1, 0, 0, 55, 1], [0, 0, 58, 1, 0, 0, 53, 1], [0, 0, 60, 1, 0, 0, 51, 1], [0, 0, 62, 1, 0, 0, 49, 1], [0, 0, 64, 1, 0, 0, 63, 1], [0, 0, 66, 1, 0, 0, 61, 1], [0, 0, 68, 1, 0, 0, 59, 1], [0, 0, 70, 1, 0, 0, 57, 1], [0, 0, 72, 1, 0, 0, 71, 1], [0, 0, 74, 1, 0, 0, 69, 1], [0, 0, 76, 1, 0, 0, 67, 1], [0, 0, 78, 1, 0, 0, 65, 1], [0, 0, 80, 1, 0, 0, 79, 1], [0, 0, 82, 1, 0, 0, 77, 1], [0, 0, 84, 1, 0, 0, 75, 1], [0, 0, 86, 1, 0, 0, 73, 1], [0, 0, 14, 1, 0, 0, 1, 1, 1, 2, 1, 3], [0, 0, 12, 1, 0, 0, 3, 1, 3, 2, 3, 3], [0, 0, 10, 1, 0, 0, 5, 1, 5, 2, 5, 3], [0, 0, 8, 1, 0, 0, 7, 1, 7, 2, 7, 3], [8, 1, 8, 2, 0, 0, 0, 0], [15, 1, 15, 2, 0, 0, 0, 0], [24, 1, 24, 2, 0, 0, 0, 0], [31, 1, 31, 2, 0, 0, 0, 0], [40, 1, 40, 2, 0, 0, 0, 0], [47, 1, 47, 2, 0, 0, 0, 0], [56, 1, 56, 2, 0, 0, 0, 0], [63, 1, 63, 2, 0, 0, 0, 0], [72, 1, 72, 2, 0, 0, 0, 0], [79, 1, 79, 2, 0, 0, 0, 0], [88, 1, 88, 2, 0, 0, 0, 0], [95, 1, 95, 2, 0, 0, 0, 0], [3, 1, 3, 2, 2, 1, 2, 2], [5, 1, 5, 2, 4, 1, 4, 2], [9, 1, 9, 2, 10, 1, 10, 2], [11, 1, 11, 2, 12, 1, 12, 2], [13, 1, 13, 2, 14, 1, 14, 2], [19, 1, 19, 2, 18, 1, 18, 2], [21, 1, 21, 2, 20, 1, 20, 2], [25, 1, 25, 2, 26, 1, 26, 2], [27, 1, 27, 2, 28, 1, 28, 2], [29, 1, 29, 2, 30, 1, 30, 2], [35, 1, 35, 2, 34, 1, 34, 2], [37, 1, 37, 2, 36, 1, 36, 2], [41, 1, 41, 2, 42, 1, 42, 2], [43, 1, 43, 2, 44, 1, 44, 2], [45, 1, 45, 2, 46, 1, 46, 2], [51, 1, 51, 2, 50, 1, 50, 2], [53, 1, 53, 2, 52, 1, 52, 2], [57, 1, 57, 2, 58, 1, 58, 2], [59, 1, 59, 2, 60, 1, 60, 2], [61, 1, 61, 2, 62, 1, 62, 2], [67, 1, 67, 2, 66, 1, 66, 2], [69, 1, 69, 2, 68, 1, 68, 2], [73, 1, 73, 2, 74, 1, 74, 2], [75, 1, 75, 2, 76, 1, 76, 2], [77, 1, 77, 2, 78, 1, 78, 2], [83, 1, 83, 2, 82, 1, 82, 2], [85, 1, 85, 2, 84, 1, 84, 2], [89, 1, 89, 2, 90, 1, 90, 2], [91, 1, 91, 2, 92, 1, 92, 2], [93, 1, 93, 2, 94, 1, 94, 2], [1, 1, 1, 2, 0, 1, 0, 2, 0, 3, 0, 4], [17, 1, 17, 2, 16, 1, 16, 2, 16, 3, 16, 4], [33, 1, 33, 2, 32, 1, 32, 2, 32, 3, 32, 4], [49, 1, 49, 2, 48, 1, 48, 2, 48, 3, 48, 4], [65, 1, 65, 2, 64, 1, 64, 2, 64, 3, 64, 4], [81, 1, 81, 2, 80, 1, 80, 2, 80, 3, 80, 4], [8, 2, 8, 3, 23, 2, 23, 3], [10, 2, 10, 3, 21, 2, 21, 3], [12, 2, 12, 3, 19, 2, 19, 3], [14, 2, 14, 3, 17, 2, 17, 3], [16, 2, 16, 3, 31, 2, 31, 3], [18, 2, 18, 3, 29, 2, 29, 3], [20, 2, 20, 3, 27, 2, 27, 3], [22, 2, 22, 3, 25, 2, 25, 3], [24, 2, 24, 3, 39, 2, 39, 3], [26, 2, 26, 3, 37, 2, 37, 3], [28, 2, 28, 3, 35, 2, 35, 3], [30, 2, 30, 3, 33, 2, 33, 3], [32, 2, 32, 3, 47, 2, 47, 3], [34, 2, 34, 3, 45, 2, 45, 3], [36, 2, 36, 3, 43, 2, 43, 3], [38, 2, 38, 3, 41, 2, 41, 3], [40, 2, 40, 3, 55, 2, 55, 3], [42, 2, 42, 3, 53, 2, 53, 3], [44, 2, 44, 3, 51, 2, 51, 3], [46, 2, 46, 3, 49, 2, 49, 3], [48, 2, 48, 3, 63, 2, 63, 3], [50, 2, 50, 3, 61, 2, 61, 3], [52, 2, 52, 3, 59, 2, 59, 3], [54, 2, 54, 3, 57, 2, 57, 3], [56, 2, 56, 3, 71, 2, 71, 3], [58, 2, 58, 3, 69, 2, 69, 3], [60, 2, 60, 3, 67, 2, 67, 3], [62, 2, 62, 3, 65, 2, 65, 3], [64, 2, 64, 3, 79, 2, 79, 3], [66, 2, 66, 3, 77, 2, 77, 3], [68, 2, 68, 3, 75, 2, 75, 3], [70, 2, 70, 3, 73, 2, 73, 3], [72, 2, 72, 3, 87, 2, 87, 3], [74, 2, 74, 3, 85, 2, 85, 3], [76, 2, 76, 3, 83, 2, 83, 3], [78, 2, 78, 3, 81, 2, 81, 3], [88, 2, 88, 3, 0, 0, 88, 1, 0, 0, 87, 1], [90, 2, 90, 3, 0, 0, 90, 1, 0, 0, 85, 1], [92, 2, 92, 3, 0, 0, 92, 1, 0, 0, 83, 1], [94, 2, 94, 3, 0, 0, 94, 1, 0, 0, 81, 1], [1, 3, 1, 4, 2, 3, 2, 4], [3, 3, 3, 4, 4, 3, 4, 4], [5, 3, 5, 4, 6, 3, 6, 4], [11, 3, 11, 4, 10, 3, 10, 4], [13, 3, 13, 4, 12, 3, 12, 4], [17, 3, 17, 4, 18, 3, 18, 4], [19, 3, 19, 4, 20, 3, 20, 4], [21, 3, 21, 4, 22, 3, 22, 4], [27, 3, 27, 4, 26, 3, 26, 4], [29, 3, 29, 4, 28, 3, 28, 4], [33, 3, 33, 4, 34, 3, 34, 4], [35, 3, 35, 4, 36, 3, 36, 4], [37, 3, 37, 4, 38, 3, 38, 4], [43, 3, 43, 4, 42, 3, 42, 4], [45, 3, 45, 4, 44, 3, 44, 4], [49, 3, 49, 4, 50, 3, 50, 4], [51, 3, 51, 4, 52, 3, 52, 4], [53, 3, 53, 4, 54, 3, 54, 4], [59, 3, 59, 4, 58, 3, 58, 4], [61, 3, 61, 4, 60, 3, 60, 4], [65, 3, 65, 4, 66, 3, 66, 4], [67, 3, 67, 4, 68, 3, 68, 4], [69, 3, 69, 4, 70, 3, 70, 4], [75, 3, 75, 4, 74, 3, 74, 4], [77, 3, 77, 4, 76, 3, 76, 4], [81, 3, 81, 4, 82, 3, 82, 4], [83, 3, 83, 4, 84, 3, 84, 4], [85, 3, 85, 4, 86, 3, 86, 4], [91, 3, 91, 4, 90, 3, 90, 4], [93, 3, 93, 4, 92, 3, 92, 4], [7, 3, 7, 4, 7, 1, 7, 2, 6, 1, 6, 2], [23, 3, 23, 4, 23, 1, 23, 2, 22, 1, 22, 2], [39, 3, 39, 4, 39, 1, 39, 2, 38, 1, 38, 2], [55, 3, 55, 4, 55, 1, 55, 2, 54, 1, 54, 2], [71, 3, 71, 4, 71, 1, 71, 2, 70, 1, 70, 2], [87, 3, 87, 4, 87, 1, 87, 2, 86, 1, 86, 2], [86, 2, 86, 3, 89, 2, 89, 3, 89, 4, 89, 5], [84, 2, 84, 3, 91, 2, 91, 3, 91, 4, 91, 5], [82, 2, 82, 3, 93, 2, 93, 3, 93, 4, 93, 5], [80, 2, 80, 3, 95, 2, 95, 3, 95, 4, 95, 5], [9, 3, 9, 4, 8, 3, 8, 4, 8, 5, 8, 6], [25, 3, 25, 4, 24, 3, 24, 4, 24, 5, 24, 6], [41, 3, 41, 4, 40, 3, 40, 4, 40, 5, 40, 6], [57, 3, 57, 4, 56, 3, 56, 4, 56, 5, 56, 6], [73, 3, 73, 4, 72, 3, 72, 4, 72, 5, 72, 6], [89, 3, 89, 4, 88, 3, 88, 4, 88, 5, 88, 6], [16, 4, 16, 5, 15, 4, 15, 5], [18, 4, 18, 5, 13, 4, 13, 5], [20, 4, 20, 5, 11, 4, 11, 5], [22, 4, 22, 5, 9, 4, 9, 5], [24, 4, 24, 5, 23, 4, 23, 5], [26, 4, 26, 5, 21, 4, 21, 5], [28, 4, 28, 5, 19, 4, 19, 5], [30, 4, 30, 5, 17, 4, 17, 5], [32, 4, 32, 5, 31, 4, 31, 5], [34, 4, 34, 5, 29, 4, 29, 5], [36, 4, 36, 5, 27, 4, 27, 5], [38, 4, 38, 5, 25, 4, 25, 5], [40, 4, 40, 5, 39, 4, 39, 5], [42, 4, 42, 5, 37, 4, 37, 5], [44, 4, 44, 5, 35, 4, 35, 5], [46, 4, 46, 5, 33, 4, 33, 5], [48, 4, 48, 5, 47, 4, 47, 5], [50, 4, 50, 5, 45, 4, 45, 5], [52, 4, 52, 5, 43, 4, 43, 5], [54, 4, 54, 5, 41, 4, 41, 5], [56, 4, 56, 5, 55, 4, 55, 5], [58, 4, 58, 5, 53, 4, 53, 5], [60, 4, 60, 5, 51, 4, 51, 5], [62, 4, 62, 5, 49, 4, 49, 5], [64, 4, 64, 5, 63, 4, 63, 5], [66, 4, 66, 5, 61, 4, 61, 5], [68, 4, 68, 5, 59, 4, 59, 5], [70, 4, 70, 5, 57, 4, 57, 5], [72, 4, 72, 5, 71, 4, 71, 5], [74, 4, 74, 5, 69, 4, 69, 5], [76, 4, 76, 5, 67, 4, 67, 5], [78, 4, 78, 5, 65, 4, 65, 5], [80, 4, 80, 5, 79, 4, 79, 5], [82, 4, 82, 5, 77, 4,

TABLE 29A-continued 77, 5], [84, 4, 84, 5, 75, 4, 75, 5], [86, 4, 86, 5, 73, 4, 73, 5], [0, 4, 0, 5, 0, 2, 0, 3, 15, 2, 15, 3], [14, 4, 14, 5, 1, 4, 1, 5, 1, 6, 1, 7], [2, 4, 2, 5, 2, 2, 2, 3, 13, 2, 13, 3], [12, 4, 12, 5, 3, 4, 3, 5, 3, 6, 3, 7], [4, 4, 4, 5, 4, 2, 4, 3, 11, 2, 11, 3], [10, 4, 10, 5, 5, 4, 5, 5, 5, 6, 5, 7], [6, 4, 6, 5, 6, 2, 6, 3, 9, 2, 9, 3], [8, 4, 8, 5, 7, 4, 7, 5, 7, 6, 7, 7], [3, 5, 3, 6, 2, 5, 2, 6], [5, 5, 5, 6, 4, 5, 4, 6], [9, 5, 9, 6, 10, 5, 10, 6], [11, 5, 11, 6, 12, 5, 12, 6], [13, 5, 13, 6, 14, 5, 14, 6], [19, 5, 19, 6, 18, 5, 18, 6], [21, 5, 21, 6, 20, 5, 20, 6], [25, 5, 25, 6, 26, 5, 26, 6], [27, 5, 27, 6, 28, 5, 28, 6], [29, 5, 29, 6, 30, 5, 30, 6], [35, 5, 35, 6, 34, 5, 34, 6], [37, 5, 37, 6, 36, 5, 36, 6], [41, 5, 41, 6, 42, 5, 42, 6], [43, 5, 43, 6, 44, 5, 44, 6], [45, 5, 45, 6, 46, 5, 46, 6], [51, 5, 51, 6, 50, 5, 50, 6], [53, 5, 53, 6, 52, 5, 52, 6], [57, 5, 57, 6, 58, 5, 58, 6], [59, 5, 59, 6, 60, 5, 60, 6], [61, 5, 61, 6, 62, 5, 62, 6], [67, 5, 67, 6, 66, 5, 66, 6], [69, 5, 69, 6, 68, 5, 68, 6], [73, 5, 73, 6, 74, 5, 74, 6], [75, 5, 75, 6, 76, 5, 76, 6], [77, 5, 77, 6, 78, 5, 78, 6], [83, 5, 83, 6, 82, 5, 82, 6], [85, 5, 85, 6, 84, 5, 84, 6], [89, 5, 89, 6, 90, 5, 90, 6], [91, 5, 91, 6, 92, 5, 92, 6], [93, 5, 93, 6, 94, 5, 94, 6], [1, 5, 1, 6, 0, 5, 0, 6, 0, 7, 0, 8], [15, 5, 15, 6, 15, 3, 15, 4, 14, 3, 14, 4], [17, 5, 17, 6, 16, 5, 16, 6, 16, 7, 16, 8], [31, 5, 31, 6, 31, 3, 31, 4, 30, 3, 30, 4], [33, 5, 33, 6, 32, 5, 32, 6, 32, 7, 32, 8], [47, 5, 47, 6, 47, 3, 47, 4, 46, 3, 46, 4], [49, 5, 49, 6, 48, 5, 48, 6, 48, 7, 48, 8], [63, 5, 63, 6, 63, 3, 63, 4, 62, 3, 62, 4], [65, 5, 65, 6, 64, 5, 64, 6, 64, 7, 64, 8], [79, 5, 79, 6, 79, 3, 79, 4, 78, 3, 78, 4], [81, 5, 81, 6, 80, 5, 80, 6, 80, 7, 80, 8], [95, 5, 95, 6, 95, 3, 95, 4, 94, 3, 94, 4], [8, 6, 8, 7, 23, 6, 23, 7], [10, 6, 10, 7, 21, 6, 21, 7], [12, 6, 12, 7, 19, 6, 19, 7], [14, 6, 14, 7, 17, 6, 17, 7], [16, 6, 16, 7, 31, 6, 31, 7], [18, 6, 18, 7, 29, 6, 29, 7], [20, 6, 20, 7, 27, 6, 27, 7], [22, 6, 22, 7, 25, 6, 25, 7], [24, 6, 24, 7, 39, 6, 39, 7], [26, 6, 26, 7, 37, 6, 37, 7], [28, 6, 28, 7, 35, 6, 35, 7], [30, 6, 30, 7, 33, 6, 33, 7], [32, 6, 32, 7, 47, 6, 47, 7], [34, 6, 34, 7, 45, 6, 45, 7], [36, 6, 36, 7, 43, 6, 43, 7], [38, 6, 38, 7, 41, 6, 41, 7], [40, 6, 40, 7, 55, 6, 55, 7], [42, 6, 42, 7, 53, 6, 53, 7], [44, 6, 44, 7, 51, 6, 51, 7], [46, 6, 46, 7, 49, 6, 49, 7], [48, 6, 48, 7, 63, 6, 63, 7], [50, 6, 50, 7, 61, 6, 61, 7], [52, 6, 52, 7, 59, 6, 59, 7], [54, 6, 54, 7, 57, 6, 57, 7], [56, 6, 56, 7, 71, 6, 71, 7], [58, 6, 58, 7, 69, 6, 69, 7], [60, 6, 60, 7, 67, 6, 67, 7], [62, 6, 62, 7, 65, 6, 65, 7], [64, 6, 64, 7, 79, 6, 79, 7], [66, 6, 66, 7, 77, 6, 77, 7], [68, 6, 68, 7, 75, 6, 75, 7], [70, 6, 70, 7, 73, 6, 73, 7], [72, 6, 72, 7, 87, 6, 87, 7], [74, 6, 74, 7, 85, 6, 85, 7], [76, 6, 76, 7, 83, 6, 83, 7], [78, 6, 78, 7, 81, 6, 81, 7], [88, 6, 88, 7, 88, 4, 88, 5, 87, 4, 87, 5], [90, 6, 90, 7, 90, 4, 90, 5, 85, 4, 85, 5], [92, 6, 92, 7, 92, 4, 92, 5, 83, 4, 83, 5], [94, 6, 94, 7, 94, 4, 94, 5, 81, 4, 81, 5], [1, 7, 1, 8, 2, 7, 2, 8], [3, 7, 3, 8, 4, 7, 4, 8], [5, 7, 5, 8, 6, 7, 6, 8], [11, 7, 11, 8, 10, 7, 10, 8], [13, 7, 13, 8, 12, 7, 12, 8], [17, 7, 17, 8, 18, 7, 18, 8], [19, 7, 19, 8, 20, 7, 20, 8], [21, 7, 21, 8, 22, 7, 22, 8], [27, 7, 27, 8, 26, 7, 26, 8], [29, 7, 29, 8, 28, 7, 28, 8], [33, 7, 33, 8, 34, 7, 34, 8], [35, 7, 35, 8, 36, 7, 36, 8], [37, 7, 37, 8, 38, 7, 38, 8], [43, 7, 43, 8, 42, 7, 42, 8], [45, 7, 45, 8, 44, 7, 44, 8], [49, 7, 49, 8, 50, 7, 50, 8], [51, 7, 51, 8, 52, 7, 52, 8], [53, 7, 53, 8, 54, 7, 54, 8], [59, 7, 59, 8, 58, 7, 58, 8], [61, 7, 61, 8, 60, 7, 60, 8], [65, 7, 65, 8, 66, 7, 66, 8], [67, 7, 67, 8, 68, 7, 68, 8], [69, 7, 69, 8, 70, 7, 70, 8], [75, 7, 75, 8, 74, 7, 74, 8], [77, 7, 77, 8, 76, 7, 76, 8], [81, 7, 81, 8, 82, 7, 82, 8], [83, 7, 83, 8, 84, 7, 84, 8], [85, 7, 85, 8, 86, 7, 86, 8], [91, 7, 91, 8, 90, 7, 90, 8], [93, 7, 93, 8, 92, 7, 92, 8], [7, 7, 7, 8, 7, 5, 7, 6, 6, 5, 6, 6], [23, 7, 23, 8, 23, 5, 23, 6, 22, 5, 22, 6], [39, 7, 39, 8, 39, 5, 39, 6, 38, 5, 38, 6], [55, 7, 55, 8, 55, 5, 55, 6, 54, 5, 54, 6], [71, 7, 71, 8, 71, 5, 71, 6, 70, 5, 70, 6], [87, 7, 87, 8, 87, 5, 87, 6, 86, 5, 86, 6], [86, 6, 86, 7, 89, 6, 89, 7, 89, 8, 89, 9], [84, 6, 84, 7, 91, 6, 91, 7, 91, 8, 91, 9], [82, 6, 82, 7, 93, 6, 93, 7, 93, 8, 93, 9], [80, 6, 80, 7, 95, 6, 95, 7, 95, 8, 95, 9], [9, 7, 9, 8, 8, 7, 8, 8, 8, 9, 8, 10], [25, 7, 25, 8, 24, 7, 24, 8, 24, 9, 24, 10], [41, 7, 41, 8, 40, 7, 40, 8, 40, 9, 40, 10], [57, 7, 57, 8, 56, 7, 56, 8, 56, 9, 56, 10], [73, 7, 73, 8, 72, 7, 72, 8, 72, 9, 72, 10], [89, 7, 89, 8, 88, 7, 88, 8, 88, 9, 88, 10], [16, 8, 16, 9, 15, 8, 15, 9], [18, 8, 18, 9, 13, 8, 13, 9], [20, 8, 20, 9, 11, 8, 11, 9], [22, 8, 22, 9, 9, 8, 9, 9], [24, 8, 24, 9, 23, 8, 23, 9], [26, 8, 26, 9, 21, 8, 21, 9], [28, 8, 28, 9, 19, 8, 19, 9], [30, 8, 30, 9, 17, 8, 17, 9], [32, 8, 32, 9, 31, 8, 31, 9], [34, 8, 34, 9, 29, 8, 29, 9], [36, 8, 36, 9, 27, 8, 27, 9], [38, 8, 38, 9, 25, 8, 25, 9], [40, 8, 40, 9, 39, 8, 39, 9], [42, 8, 42, 9, 37, 8, 37, 9], [44, 8, 44, 9, 35, 8, 35, 9], [46, 8, 46, 9, 33, 8, 33, 9], [48, 8, 48, 9, 47, 8, 47, 9], [50, 8, 50, 9, 45, 8, 45, 9], [52, 8, 52, 9, 43, 8, 43, 9], [54, 8, 54, 9, 41, 8, 41, 9], [56, 8, 56, 9, 55, 8, 55, 9], [58, 8, 58, 9, 53, 8, 53, 9], [60, 8, 60, 9, 51, 8, 51, 9], [62, 8, 62, 9, 49, 8, 49, 9], [64, 8, 64, 9, 63, 8, 63, 9], [66, 8, 66, 9, 61, 8, 61, 9], [68, 8, 68, 9, 59, 8, 59, 9], [70, 8, 70, 9, 57, 8, 57, 9], [72, 8, 72, 9, 71, 8, 71, 9], [74, 8, 74, 9, 69, 8, 69, 9], [76, 8, 76, 9, 67, 8, 67, 9], [78, 8, 78, 9, 65, 8, 65, 9], [80, 8, 80, 9, 79, 8, 79, 9], [82, 8, 82, 9, 77, 8, 77, 9], [86, 8, 86, 9, 73, 8, 73, 9], [0, 8, 0, 9, 0, 6, 0, 7, 15, 6, 15, 7], [14, 8, 14, 9, 1, 8, 1, 9, 1, 10, 1, 11], [2, 8, 2, 9, 2, 6, 2, 7, 13, 6, 13, 7], [12, 8, 12, 9, 3, 8, 3, 9, 3, 10, 3, 11], [4, 8, 4, 9, 4, 6, 4, 7, 11, 6, 11, 7], [10, 8, 10, 9, 5, 8, 5, 9, 5, 10, 5, 11], [6, 8, 6, 9, 6, 6, 6, 7, 9, 6, 9, 7], [8, 8, 8, 9, 7, 8, 7, 9, 7, 10, 7, 11], [3, 9, 3, 10, 2, 9, 2, 10], [5, 9, 5, 10, 4, 9, 4, 10], [9, 9, 9, 10, 10, 9, 10, 10], [11, 9, 11, 10, 12, 9, 12, 10], [13, 9, 13, 10, 14, 9, 14, 10], [19, 9, 19, 10, 18, 9, 18, 10], [21, 9, 21, 10, 20, 9, 20, 10], [25, 9, 25, 10, 26, 9, 26, 10], [27, 9, 27, 10, 28, 9, 28, 10], [29, 9, 29, 10, 30, 9, 30, 10], [35, 9, 35, 10, 34, 9, 34, 10], [37, 9, 37, 10, 36, 9, 36, 10], [41, 9, 41, 10, 42, 9, 42, 10], [43, 9, 43, 10, 44, 9, 44, 10], [45, 9, 45, 10, 46, 9, 46, 10], [51, 9, 51, 10, 50, 9, 50, 10], [53, 9, 53, 10, 52, 9, 52, 10], [57, 9, 57, 10, 58, 9, 58, 10], [59, 9, 59, 10, 60, 9, 60, 10], [61, 9, 61, 10, 62, 9, 62, 10], [67, 9, 67, 10, 66, 9, 66, 10], [69, 9, 69, 10, 68, 9, 68, 10], [73, 9, 73, 10, 74, 9, 74, 10], [75, 9, 75, 10, 76, 9, 76, 10], [77, 9, 77, 10, 78, 9, 78, 10], [83, 9, 83, 10, 82, 9, 82, 10], [85, 9, 85, 10, 84, 9, 84, 10], [89, 9, 89, 10, 90, 9, 90, 10], [91, 9, 91, 10, 92, 9, 92, 10], [93, 9, 93, 10, 94, 9, 94, 10], [1, 9, 1, 10, 0, 9, 0, 10, 0, 11, 0, 12], [15, 9, 15, 10, 15, 7, 15, 8, 14, 7, 14, 8], [17, 9, 17, 10, 16, 9, 16, 10, 16, 11, 16, 12], [31, 9, 31, 10, 31, 7, 31, 8, 30, 7, 30, 8], [33, 9, 33, 10, 32, 9, 32, 10, 32, 11, 32, 12], [47, 9, 47, 10, 47, 7, 47, 8, 46, 7, 46, 8], [49, 9, 49, 10, 48, 9, 48, 10, 48, 11, 48, 12], [63, 9, 63, 10, 63, 7, 63, 8, 62, 7, 62, 8], [65, 9, 65, 10, 64, 9, 64, 10, 64, 11, 64, 12], [79, 9, 79, 10, 79, 7, 79, 8, 78, 7, 78, 8], [81, 9, 81, 10, 80, 9, 80, 10, 80, 11, 80, 12], [95, 9, 95, 10, 95, 7, 95, 8, 94, 7, 94, 8], [8, 10, 8, 11, 23, 10, 23, 11], [10, 10, 10, 11, 21, 10, 21, 11], [12, 10, 12, 11, 19, 10, 19, 11], [14, 10, 14, 11, 17, 10, 17, 11], [16, 10, 16, 11, 31, 10, 31, 11], [18, 10, 18, 11, 29, 10, 29, 11], [20, 10, 20, 11, 27, 10, 27, 11], [22, 10, 22, 11, 25, 10, 25, 11], [24, 10, 24, 11, 39, 10, 39, 11], [26, 10, 26, 11, 37, 10, 37, 11], [28, 10, 28, 11, 35, 10, 35, 11], [30, 10, 30, 11, 33, 10, 33, 11], [32, 10, 32, 11, 47, 10, 47, 11], [34, 10, 34, 11, 45, 10, 45, 11], [36, 10, 36, 11, 43, 10, 43, 11], [38, 10, 38, 11, 41, 10, 41, 11], [40, 10, 40, 11, 55, 10, 55, 11], [42, 10, 42, 11, 53, 10, 53, 11], [44, 10, 44, 11, 51, 10, 51, 11], [46, 10, 46, 11, 49, 10, 49, 11], [48, 10, 48, 11, 63, 10, 63, 11], [50, 10, 50, 11, 61, 10, 61, 11], [52, 10, 52, 11, 59, 10, 59, 11], [54, 10, 54, 11, 57, 10, 57, 11], [56, 10, 56, 11, 71, 10, 71, 11], [58, 10, 58, 11, 69, 10, 69, 11], [60, 10, 60, 11, 67, 10, 67, 11], [62, 10, 62, 11, 65, 10, 65, 11], [64, 10, 64, 11, 79, 10, 79, 11], [66, 10, 66, 11, 77, 10, 77, 11], [68, 10, 68, 11, 75, 10, 75, 11], [70, 10, 70, 11, 73, 10, 73, 11], [72, 10, 72, 11, 87, 10, 87, 11], [74, 10, 74, 11, 85, 10, 85, 11], [76, 10, 76, 11, 83, 10, 83, 11], [78, 10, 78, 11, 81, 10, 81, 11], [88, 10, 88, 11, 88, 9, 88, 7, 87, 9], [86, 10, 86, 11, 89, 10, 89, 11, 89, 12, 89, 13], [90, 10, 90, 11, 90, 8, 90, 9, 85, 8, 85, 9], [84, 10, 84, 11, 91, 10, 91, 11, 91, 12, 91, 13], [92, 10, 92, 11, 92, 8, 92, 9, 83, 8, 83, 9], [82, 10, 82, 11, 93, 10, 93, 11, 93, 12, 93, 13], [94, 10, 94, 11, 94, 8, 94, 9, 81, 8, 81, 9], [80, 10, 80, 11, 95, 10, 95, 11, 95, 12, 95, 13], [1, 11, 1, 2, 2, 11, 2, 12], [3, 11, 3, 12, 4, 11, 4, 12], [5, 11, 5, 12, 6, 11, 6, 12], [11, 11, 11, 12, 10, 11, 10, 12], [13, 11, 13, 12, 12, 11, 12, 12], [17, 11, 17, 12, 18, 11, 18, 12], [19, 11, 19, 12, 20, 11, 20, 12], [21, 11, 21, 12, 22, 11, 22, 12], [27, 11, 27, 12, 26, 11, 26, 12], [29, 11, 29, 12, 28, 11, 28, 12], [33, 11, 33, 12, 34, 11, 34, 12], [35, 11, 35, 12, 36, 11, 36, 12], [37, 11, 37, 12, 38, 11, 38, 12], [43, 11, 43, 12, 42, 11, 42, 12], [45, 11, 45, 12, 44, 11, 44, 12], [49, 11, 49, 12, 50, 11, 50, 12], [51, 11, 51, 12, 52, 11, 52, 12], [53, 11, 53, 12, 54, 11, 54, 12], [59, 11, 59, 12, 58, 11, 58, 12], [61, 11, 61, 12, 60, 11, 60, 12], [65, 11, 65, 12, 66, 11, 66, 12], [67, 11, 67, 12, 68, 11, 68, 12], [69, 11, 69, 12, 70, 11, 70, 12], [75, 11, 75, 12, 74, 11, 74, 12], [77, 11, 77, 12, 76, 11, 76, 12], [81, 11, 81, 12, 82, 11, 82, 12], [83, 11, 83, 12, 84, 11, 84, 12], [85, 11, 85, 12, 86, 11, 86, 12], [91, 11, 91, 12, 90, 11, 90, 12], [93, 11, 93, 12, 92, 11, 92, 12], [7, 11, 7, 12, 7, 9, 7, 10, 6, 9, 6, 10], [9, 11, 9, 12, 8, 11, 8, 12, 8, 13, 8, 14], [23, 11, 23, 12, 23, 9, 23, 10, 22, 9, 22, 10], [25, 11, 25, 12, 24, 11, 24, 12, 24, 13, 24, 14], [39, 11, 39, 12, 39, 9, 39, 10, 38, 9, 38, 10], [41, 11, 41, 12, 40, 11, 40, 12, 40, 13, 40, 14], [55, 11, 55, 12, 55, 9, 55, 10, 54, 9, 54, 10], [57, 11, 57, 12, 56, 12, 56, 13, 56, 14], [71, 11, 71, 12, 71, 9, 71, 10, 70, 9, 70, 10], [73, 11, 73, 12, 72, 11, 72, 12, 72, 13, 72, 14], [87, 11, 87, 12, 87, 9, 87, 10, 86, 9, 86, 10], [89, 11, 89, 12, 88, 11, 88, 12, 88, 13, 88, 14], [16, 12, 16, 13, 15, 12, 15, 13], [18, 12, 18, 13, 13, 12, 13, 13], [20, 12, 20, 13, 11, 12, 11, 13], [22, 12, 22, 13, 9, 12, 9, 13], [24, 12, 24, 13, 23, 12, 23, 13], [26, 12, 26, 13, 21, 12, 21, 13], [28, 12, 28, 13, 19, 12, 19, 13], [30, 12, 30, 13, 17, 12, 17, 13], [32, 12, 32, 13, 31, 12, 31, 13], [34, 12, 34, 13, 29, 12, 29, 13], [36, 12, 36, 13, 27, 12, 27, 13], [38, 12, 38, 13, 25, 12, 25, 13], [40, 12, 40, 13, 39, 12, 39, 13], [42, 12, 42, 13, 37, 12, 37, 13], [44, 12, 44, 13, 35, 12, 35, 13], [46, 12, 46, 13, 33, 12, 33, 13], [48, 12, 48, 13, 47, 12, 47, 13], [50, 12, 50, 13, 45, 12, 45, 13], [52, 12, 52, 13, 43, 12, 43, 13], [54, 12, 54, 13, 41, 12, 41, 13], [56, 12, 56, 13, 55, 12, 55, 13], [58, 12, 58, 13, 53, 12, 53, 13], [60, 12, 60, 13, 51, 12, 51, 13], [62, 12, 62, 13, 49, 12, 49, 13], [64, 12, 64, 13, 63, 12, 63, 13], [66, 12, 66, 13, 61, 12, 61, 13], [68, 12, 68, 13, 59, 12, 59, 13], [70, 12, 70, 13, 57, 12, 57, 13], [72, 12, 72, 13, 71, 12, 71, 13], [74, 12, 74, 13, 69, 12, 69, 13], [76, 12, 76, 13, 67, 12, 67, 13], [78, 12, 78, 13, 65, 12, 65, 13], [80, 12, 80, 13, 79, 12, 79, 13], [82, 12, 82, 13,

TABLE 29A-continued 77, 12, 77, 13], [84, 12, 84, 13, 75, 12, 75, 13], [86, 12, 86, 13, 73, 12, 73, 13], [0, 12, 0, 13, 0, 10, 0, 11, 15, 10, 15, 11], [14, 12, 14, 13, 1, 12, 1, 13, 1, 14, 1, 15], [2, 12, 2, 13, 2, 10, 2, 11, 13, 10, 13, 11], [12, 12, 12, 13, 3, 12, 3, 13, 3, 14, 3, 15], [4, 12, 4, 13, 4, 10, 4, 11, 11, 10, 11, 11], [10, 12, 10, 13, 5, 12, 5, 13, 5, 14, 5, 15], [6, 12, 6, 13, 6, 10, 6, 11, 9, 10, 9, 11], [8, 12, 8, 13, 7, 12, 7, 13, 7, 14, 7, 15], [3, 13, 3, 14, 2, 13, 2, 14], [5, 13, 5, 14, 4, 13, 4, 14], [9, 13, 9, 14, 10, 13, 10, 14], [11, 13, 11, 14, 12, 13, 12, 14], [13, 13, 13, 14, 14, 13, 14, 14], [19, 13, 19, 14, 18, 13, 18, 14], [21, 13, 21, 14, 20, 13, 20, 14], [25, 13, 25, 14, 26, 13, 26, 14], [27, 13, 27, 14, 28, 13, 28, 14], [29, 13, 29, 14, 30, 13, 30, 14], [35, 13, 35, 14, 34, 13, 34, 14], [37, 13, 37, 14, 36, 13, 36, 14], [41, 13, 41, 14, 42, 13, 42, 14], [43, 13, 43, 14, 44, 13, 44, 14], [45, 13, 45, 14, 46, 13, 46, 14], [51, 13, 51, 14, 50, 13, 50, 14], [53, 13, 53, 14, 52, 13, 52, 14], [57, 13, 57, 14, 58, 13, 58, 14], [59, 13, 59, 14, 60, 13, 60, 14], [61, 13, 61, 14, 62, 13, 62, 14], [67, 13, 67, 14, 66, 13, 66, 14], [69, 13, 69, 14, 68, 13, 68, 14], [73, 13, 73, 14, 74, 13, 74, 14], [75, 13, 75, 14, 76, 13, 76, 14], [77, 13, 77, 14, 78, 13, 78, 14], [83, 13, 83, 14, 82, 13, 82, 14], [85, 13, 85, 14, 84, 13, 84, 14], [89, 13, 89, 14, 90, 13, 90, 14], [91, 13, 91, 14, 92, 13, 92, 14], [93, 13, 93, 14, 94, 13, 94, 14], [15, 13, 15, 14, 15, 11, 15, 12, 14, 11, 14, 12], [31, 13, 31, 14, 31, 11, 31, 12, 30, 11, 30, 12], [47, 13, 47, 14, 47, 11, 47, 12, 46, 11, 46, 12], [63, 13, 63, 14, 63, 11, 63, 12, 62, 11, 62, 12], [79, 13, 79, 14, 79, 11, 79, 12, 78, 11, 78, 12], [95, 13, 95, 14, 95, 11, 95, 12, 94, 11, 94, 12], [8, 14, 8, 15, 23, 14, 23, 15], [10, 14, 10, 15, 21, 14, 21, 15], [12, 14, 12, 15, 19, 14, 19, 15], [14, 14, 14, 15, 17, 14, 17, 15], [16, 14, 16, 15, 31, 14, 31, 15], [18, 14, 18, 15, 29, 14, 29, 15], [20, 14, 20, 15, 27, 14, 27, 15], [22, 14, 22, 15, 25, 14, 25, 15], [24, 14, 24, 15, 39, 14, 39, 15], [26, 14, 26, 15, 37, 14, 37, 15], [28, 14, 28, 15, 35, 14, 35, 15], [30, 14, 30, 15, 33, 14, 33, 15], [32, 14, 32, 15, 47, 14, 47, 15], [34, 14, 34, 15, 45, 14, 45, 15], [36, 14, 36, 15, 43, 14, 43, 15], [38, 14, 38, 15, 41, 14, 41, 15], [40, 14, 40, 15, 55, 14, 55, 15], [42, 14, 42, 15, 53, 14, 53, 15], [44, 14, 44, 15, 51, 14, 51, 15], [46, 14, 46, 15, 49, 14, 49, 15], [48, 14, 48, 15, 63, 14, 63, 15], [50, 14, 50, 15, 61, 14, 61, 15], [52, 14, 52, 15, 59, 14, 59, 15], [54, 14, 54, 15, 57, 14, 57, 15], [56, 14, 56, 15, 71, 14, 71, 15], [58, 14, 58, 15, 69, 14, 69, 15], [60, 14, 60, 15, 67, 14, 67, 15], [62, 14, 62, 15, 65, 14, 65, 15], [64, 14, 64, 15, 79, 14, 79, 15], [66, 14, 66, 15, 77, 14, 77, 15], [68, 14, 68, 15, 75, 14, 75, 15], [70, 14, 70, 15, 73, 14, 73, 15], [72, 14, 72, 15, 87, 14, 87, 15], [74, 14, 74, 15, 85, 14, 85, 15], [76, 14, 76, 15, 83, 14, 83, 15], [78, 14, 78, 15, 81, 14, 81, 15], [88, 14, 88, 15, 88, 12, 88, 13, 87, 12, 87, 13], [90, 14, 90, 15, 90, 12, 90, 13, 85, 12, 85, 13], [92, 14, 92, 15, 92, 12, 92, 13, 83, 12, 83, 13], [94, 14, 94, 15, 94, 12, 94, 13, 81, 12, 81, 13]

TABLE 29B

[1, 13, 1, 14, 0, 13, 0, 14, 0, 15, 0, 0], [17, 13, 17, 14, 16, 13, 16, 14, 16, 15, 0, 0], [33, 13, 33, 14, 32, 13, 32, 14, 32, 15, 0, 0], [49, 13, 49, 14, 48, 13, 48, 14, 48, 15, 0, 0], [65, 13, 65, 14, 64, 13, 64, 14, 64, 15, 0, 0], [81, 13, 81, 14, 80, 13, 80, 14, 80, 15, 0, 0], [0, 14, 0, 15, 15, 14, 15, 15], [2, 14, 2, 15, 13, 14, 13, 15], [4, 14, 4, 15, 11, 14, 11, 15], [6, 14, 6, 15, 9, 14, 9, 15], [80, 14, 80, 15, 95, 14, 95, 15], [82, 14, 82, 15, 93, 14, 93, 15], [84, 14, 84, 15, 91, 14, 91, 15], [86, 14, 86, 15, 89, 14, 89, 15], [1, 15, 0, 0, 2, 15, 0, 0], [3, 15, 0, 0, 4, 15, 0, 0], [5, 15, 0, 0, 6, 15, 0, 0], [9, 15, 0, 0, 8, 15, 0, 0], [11, 15, 0, 0, 10, 15, 0, 0], [13, 15, 0, 0, 12, 15, 0, 0], [15, 15, 0, 0, 14, 15, 0, 0], [17, 15, 0, 0, 18, 15, 0, 0], [19, 15, 0, 0, 20, 15, 0, 0], [21, 15, 0, 0, 22, 15, 0, 0], [25, 15, 0, 0, 24, 15, 0, 0], [27, 15, 0, 0, 26, 15, 0, 0], [29, 15, 0, 0, 28, 15, 0, 0], [31, 15, 0, 0, 30, 15, 0, 0], [33, 15, 0, 0, 34, 15, 0, 0], [35, 15, 0, 0, 36, 15, 0, 0], [37, 15, 0, 0, 38, 15, 0, 0], [41, 15, 0, 0, 40, 15, 0, 0], [43, 15, 0, 0, 42, 15, 0, 0], [45, 15, 0, 0, 44, 15, 0, 0], [47, 15, 0, 0, 46, 15, 0, 0], [49, 15, 0, 0, 50, 15, 0, 0], [51, 15, 0, 0, 52, 15, 0, 0], [53, 15, 0, 0, 54, 15, 0, 0], [57, 15, 0, 0, 56, 15, 0, 0], [59, 15, 0, 0, 58, 15, 0, 0], [61, 15, 0, 0, 60, 15, 0, 0], [63, 15, 0, 0, 62, 15, 0, 0], [65, 15, 0, 0, 66, 15, 0, 0], [67, 15, 0, 0, 68, 15, 0, 0], [69, 15, 0, 0, 70, 15, 0, 0], [73, 15, 0, 0, 72, 15, 0, 0], [75, 15, 0, 0, 74, 15, 0, 0], [77, 15, 0, 0, 76, 15, 0, 0], [79, 15, 0, 0, 78, 15, 0, 0], [81, 15, 0, 0, 82, 15, 0, 0], [83, 15, 0, 0, 84, 15, 0, 0], [85, 15, 0, 0, 86, 15, 0, 0], [89, 15, 0, 0, 88, 15, 0, 0], [91, 15, 0, 0, 90, 15, 0, 0], [93, 15, 0, 0, 92, 15, 0, 0], [95, 15, 0, 0, 94, 15, 0, 0], [7, 15, 0, 0, 7, 13, 7, 14, 6, 13, 6, 14], [23, 15, 0, 0, 23, 13, 23, 14, 22, 13, 22, 14], [39, 15, 0, 0, 39, 13, 39, 14, 38, 13, 38, 14], [55, 15, 0, 0, 55, 13, 55, 14, 54, 13, 54, 14], [71, 15, 0, 0, 71, 13, 71, 14, 70, 13, 70, 14], [87, 15, 0, 0, 87, 13, 87, 14, 86, 13, 86, 14]

The oligonucleotide sequences used to produce 4H×24H×120B nucleic acid structures of the invention are designated SEQ ID NOs. 5672-6355, and the corresponding 5' end coordinates are shown respectively in Table 30. (See also Appendix, Table 12 of U.S. provisional application No. 61/675,309, filed Jul. 24, 2012, incorporated by reference herein.)

TABLE 30

[1, 23], [1, 39], [1, 55], [1, 71], [1, 87], [1, 103], [1, 119], [1, 135], [3, 39], [3, 71], [3, 103], [3, 135], [4, 8], [5, 23], [5, 39], [5, 55], [5, 71], [5, 87], [5, 103], [5, 119], [5, 135], [7, 23], [7, 55], [7, 87], [7, 119], [7, 135], [9, 23], [9, 39], [9, 55], [9, 71], [9, 87], [9, 103], [9, 119], [9, 135], [11, 39], [11, 71], [11, 103], [11, 135], [12, 8], [13, 23], [13, 39], [13, 55], [13, 71], [13, 87], [13, 103], [13, 119], [13, 135], [15, 23], [15, 55], [15, 87], [15, 119], [15, 135], [17, 23], [17, 39], [17, 55], [17, 71], [17, 87], [17, 103], [17, 119], [17, 135], [19, 39], [19, 71], [19, 103], [19, 135], [20, 8], [21, 23], [21, 39], [21, 55], [21, 71], [21, 87], [21, 103], [21, 119], [21, 135], [23, 23], [23, 55], [23, 87], [23, 119], [23, 135], [25, 23], [25, 39], [25, 55], [25, 71], [25, 87], [25, 103], [25, 119], [25, 135], [27, 39], [27, 71], [27, 103], [27, 135], [28, 8], [29, 23], [29, 39], [29, 55], [29, 71], [29, 87], [29, 103], [29, 119], [29, 135], [31, 23], [31, 55], [31, 87], [31, 119], [31, 135], [33, 23], [33, 39], [33, 55], [33, 71], [33, 87], [33, 103], [33, 119], [33, 135], [35, 39], [35, 71], [35, 103], [35, 135], [36, 8], [37, 23], [37, 39], [37, 55], [37, 71], [37, 87], [37, 103], [37, 119], [37, 135], [39, 23], [39, 55], [39, 87], [39, 119], [39, 135], [41, 23], [41, 39], [41, 55], [41, 71], [41, 87], [41, 103], [41, 119], [41, 135], [43, 39], [43, 71], [43, 103], [43, 135], [44, 8], [45, 23], [45, 39], [45, 55], [45, 71], [45, 87], [45, 103], [45, 119], [45, 135], [47, 23], [47, 55], [47, 87], [47, 119], [47, 135], [49, 23], [49, 39], [49, 55], [49, 71], [49, 87], [49, 103], [49, 119], [49, 135], [51, 39], [51, 71], [51, 103], [51, 135], [52, 8], [53, 23], [53, 39], [53, 55], [53, 71], [53, 87], [53, 103], [53, 119], [53, 135], [55, 23], [55, 55], [55, 87], [55, 119], [55, 135], [57, 23], [57, 39], [57, 55], [57, 71], [57, 87], [57, 103], [57, 119], [57, 135], [59, 39], [59, 71], [59, 103], [59, 135], [60, 8], [61, 23], [61, 39], [61, 55], [61, 71], [61, 87], [61, 103], [61, 119], [61, 135], [63, 23], [63, 55], [63, 87], [63, 119], [63, 135], [65, 23], [65, 39], [65, 55], [65, 71], [65, 87], [65, 103], [65, 119], [65, 135], [67, 39], [67, 71], [67, 103], [67, 135], [68, 8], [69, 23], [69, 39], [69, 55], [69, 71], [69, 87], [69, 103], [69, 119], [69, 135], [71, 23], [71, 55], [71, 87], [71, 119], [71, 135], [73, 23], [73, 39], [73, 55], [73, 71], [73, 87], [73, 103], [73, 119], [73, 135], [75, 39], [75, 71], [75, 103], [75, 135], [76, 8], [77, 23], [77, 39], [77, 55], [77, 71], [77, 87], [77, 103], [77, 119], [77, 135], [79, 23], [79, 55], [79, 87], [79, 119], [79, 135], [81, 23], [81, 39], [81, 55], [81, 71], [81, 87], [81, 103], [81, 119], [81, 135], [83, 39], [83, 71], [83, 103], [83, 135], [84, 8], [85, 23], [85, 39], [85, 55], [85, 71], [85, 87], [85, 103], [85, 119], [85, 135], [87, 23], [87, 55], [87, 87], [87, 119], [87, 135], [89, 23], [89, 39], [89, 55], [89, 71], [89, 87], [89, 103], [89, 119], [89, 135], [91, 39], [91, 71], [91, 103], [91, 135], [92, 8], [93, 23], [93, 39], [93, 55], [93, 71], [93, 87], [93, 103], [93, 119], [93, 135], [95, 23], [95, 55], [95, 87], [95, 119], [95, 135], [0, 47], [0, 79], [0, 111], [0, 143], [1, 16], [2, 47], [2, 79], [2, 111], [2, 143], [3, 16], [4, 31], [4, 47], [4, 63], [4, 79], [4, 95], [4, 111], [4, 127], [4, 143], [6, 31], [6, 47], [6, 63], [6, 79], [6, 95], [6, 111], [6, 127], [6, 143], [8, 31], [8, 47], [8, 63], [8, 79], [8, 95], [8, 111], [8, 127], [8, 143], [10, 31], [10, 47], [10, 63], [10, 79], [10, 95], [10, 111], [10, 127], [10, 143], [12, 31], [12, 47], [12,

TABLE 30-continued

63], [12, 79], [12, 95], [12, 111], [12, 127], [12, 143], [14, 31], [14, 47], [14, 63], [14, 79], [14, 95], [14, 111], [14, 127], [14, 143], [16, 31], [16, 47], [16, 63], [16, 79], [16, 95], [16, 111], [16, 127], [16, 143], [18, 31], [18, 47], [18, 63], [18, 79], [18, 95], [18, 111], [18, 127], [18, 143], [20, 31], [20, 47], [20, 63], [20, 79], [20, 95], [20, 111], [20, 127], [20, 143], [22, 31], [22, 47], [22, 63], [22, 79], [22, 95], [22, 111], [22, 127], [22, 143], [24, 31], [24, 47], [24, 63], [24, 79], [24, 95], [24, 111], [24, 127], [24, 143], [26, 31], [26, 47], [26, 63], [26, 79], [26, 95], [26, 111], [26, 127], [26, 143], [28, 31], [28, 47], [28, 63], [28, 79], [28, 95], [28, 111], [28, 127], [28, 143], [30, 31], [30, 47], [30, 63], [30, 79], [30, 95], [30, 111], [30, 127], [30, 143], [32, 31], [32, 47], [32, 63], [32, 79], [32, 95], [32, 111], [32, 127], [32, 143], [34, 31], [34, 47], [34, 63], [34, 79], [34, 95], [34, 111], [34, 127], [34, 143], [36, 31], [36, 47], [36, 63], [36, 79], [36, 95], [36, 111], [36, 127], [36, 143], [38, 31], [38, 47], [38, 63], [38, 79], [38, 95], [38, 111], [38, 127], [38, 143], [40, 31], [40, 47], [40, 63], [40, 79], [40, 95], [40, 111], [40, 127], [40, 143], [42, 31], [42, 47], [42, 63], [42, 79], [42, 95], [42, 111], [42, 127], [42, 143], [44, 31], [44, 47], [44, 63], [44, 79], [44, 95], [44, 111], [44, 127], [44, 143], [46, 31], [46, 47], [46, 63], [46, 79], [46, 95], [46, 111], [46, 127], [46, 143], [48, 31], [48, 47], [48, 63], [48, 79], [48, 95], [48, 111], [48, 127], [48, 143], [50, 31], [50, 47], [50, 63], [50, 79], [50, 95], [50, 111], [50, 127], [50, 143], [52, 31], [52, 47], [52, 63], [52, 79], [52, 95], [52, 111], [52, 127], [52, 143], [54, 31], [54, 47], [54, 63], [54, 79], [54, 95], [54, 111], [54, 127], [54, 143], [56, 31], [56, 47], [56, 63], [56, 79], [56, 95], [56, 111], [56, 127], [56, 143], [58, 31], [58, 47], [58, 63], [58, 79], [58, 95], [58, 111], [58, 127], [58, 143], [60, 31], [60, 47], [60, 63], [60, 79], [60, 95], [60, 111], [60, 127], [60, 143], [62, 31], [62, 47], [62, 63], [62, 79], [62, 95], [62, 111], [62, 127], [62, 143], [64, 31], [64, 47], [64, 63], [64, 79], [64, 95], [64, 111], [64, 127], [64, 143], [66, 31], [66, 47], [66, 63], [66, 79], [66, 95], [66, 111], [66, 127], [66, 143], [68, 31], [68, 47], [68, 63], [68, 79], [68, 95], [68, 111], [68, 127], [68, 143], [70, 31], [70, 47], [70, 63], [70, 79], [70, 95], [70, 111], [70, 127], [70, 143], [72, 31], [72, 47], [72, 63], [72, 79], [72, 95], [72, 111], [72, 127], [72, 143], [74, 31], [74, 47], [74, 63], [74, 79], [74, 95], [74, 111], [74, 127], [74, 143], [76, 31], [76, 47], [76, 63], [76, 79], [76, 95], [76, 111], [76, 127], [76, 143], [78, 31], [78, 47], [78, 63], [78, 79], [78, 95], [78, 111], [78, 127], [78, 143], [80, 31], [80, 47], [80, 63], [80, 79], [80, 95], [80, 111], [80, 127], [80, 143], [82, 31], [82, 47], [82, 63], [82, 79], [82, 95], [82, 111], [82, 127], [82, 143], [84, 31], [84, 47], [84, 63], [84, 79], [84, 95], [84, 111], [84, 127], [84, 143], [86, 31], [86, 47], [86, 63], [86, 79], [86, 95], [86, 111], [86, 127], [86, 143], [88, 31], [88, 47], [88, 63], [88, 79], [88, 95], [88, 111], [88, 127], [88, 143], [90, 31], [90, 47], [90, 63], [90, 79], [90, 95], [90, 111], [90, 127], [90, 143], [92, 31], [92, 63], [92, 95], [92, 127], [92, 143], [94, 31], [94, 63], [94, 95], [94, 127], [94, 143]

The oligonucleotide sequences used to produce 12H×12H×48B nucleic acid structures of the invention are designated SEQ ID NOs. 6356-6841, and the corresponding 5' coordinates are shown respectively in Table 31. (See also Appendix, Table 13 of U.S. provisional application No. 61/675,309, filed Jul. 24, 2012, incorporated by reference herein.)

The oligonucleotide sequences used to produce the shapes of FIG. 3E from a 10×10×10 voxel 3D canvas are designated SEQ ID NOs. 6842-11296 (strands 0-4454, respectively), and the corresponding voxel coordinates are shown respectively in Table 32. (See also Appendix, Table 14 of U.S. provisional application No. 61/675,309, filed Jul. 24, 2012, incorporated by reference herein.)

TABLE 31

[1, 23], [1, 55], [1, 39], [3, 23], [3, 55], [3, 39], [5, 23], [5, 55], [5, 39], [7, 23], [7, 55], [7, 39], [9, 23], [9, 55], [9, 39], [11, 39], [11, 55], [12, 8], [13, 39], [13, 23], [13, 55], [15, 39], [15, 23], [15, 55], [17, 39], [17, 23], [17, 55], [19, 39], [19, 23], [19, 55], [21, 39], [21, 23], [21, 55], [23, 55], [23, 23], [25, 23], [25, 55], [25, 39], [27, 23], [27, 55], [27, 39], [29, 23], [29, 55], [29, 39], [31, 23], [31, 55], [31, 39], [33, 23], [33, 55], [33, 39], [35, 39], [35, 55], [36, 8], [37, 39], [37, 23], [37, 55], [39, 39], [39, 23], [39, 55], [41, 39], [41, 23], [41, 55], [43, 39], [43, 23], [43, 55], [45, 39], [45, 23], [45, 55], [47, 55], [47, 23], [49, 23], [49, 55], [49, 39], [51, 23], [51, 55], [51, 39], [53, 23], [53, 55], [53, 39], [55, 23], [55, 55], [55, 39], [57, 23], [57, 55], [57, 39], [59, 39], [59, 55], [60, 8], [61, 39], [61, 23], [61, 55], [63, 39], [63, 23], [63, 55], [65, 39], [65, 23], [65, 55], [67, 39], [67, 23], [67, 55], [69, 39], [69, 23], [69, 55], [71, 55], [71, 23], [73, 23], [73, 55], [73, 39], [75, 23], [75, 55], [75, 39], [77, 23], [77, 55], [77, 39], [79, 23], [79, 55], [79, 39], [81, 23], [81, 55], [81, 39], [83, 39], [83, 55], [84, 8], [85, 39], [85, 23], [85, 55], [87, 39], [87, 23], [87, 55], [89, 39], [89, 23], [89, 55], [91, 39], [91, 23], [91, 55], [93, 39], [93, 23], [93, 55], [95, 55], [95, 23], [97, 23], [97, 55], [97, 39], [99, 23], [99, 55], [99, 39], [101, 23], [101, 55], [101, 39], [103, 23], [103, 55], [103, 39], [105, 23], [105, 55], [105, 39], [107, 39], [107, 55], [108, 8], [109, 39], [109, 23], [109, 55], [111, 39], [111, 23], [111, 55], [113, 39], [113, 23], [113, 55], [115, 39], [115, 23], [115, 55], [117, 39], [117, 23], [117, 55], [119, 55], [119, 23], [121, 23], [121, 55], [121, 39], [123, 23], [123, 55], [123, 39], [125, 23], [125, 55], [125, 39], [127, 23], [127, 55], [127, 39], [129, 23], [129, 55], [129, 39], [131, 39], [131, 55], [132, 8], [133, 39], [133, 23], [133, 55], [135, 39], [135, 23], [135, 55], [137, 39], [137, 23], [137, 55], [139, 39], [139, 23], [139, 55], [141, 39], [141, 23], [141, 55], [143, 55], [143, 23], [0, 15], [2, 15], [4, 15], [6, 15], [8, 15], [10, 15], [0, 47], [0, 63], [2, 47], [2, 63], [4, 47], [4, 63], [6, 47], [6, 63], [8, 47], [8, 63], [10, 47], [10, 63], [12, 15], [12, 47], [14, 15], [14, 47], [16, 15], [16, 47], [18, 15], [18, 47], [20, 15], [20, 47], [22, 15], [22, 47], [12, 31], [12, 63], [14, 31], [14, 63], [16, 31], [16, 63], [18, 31], [18, 63], [20, 31], [20, 63], [22, 31], [22, 63], [24, 15], [24, 47], [26, 15], [26, 47], [28, 15], [28, 47], [30, 15], [30, 47], [32, 15], [32, 47], [34, 15], [34, 47], [24, 31], [24, 63], [26, 31], [26, 63], [28, 31], [28, 63], [30, 31], [30, 63], [32, 31], [32, 63], [34, 31], [34, 63], [36, 15], [36, 47], [38, 15], [38, 47], [40, 15], [40, 47], [42, 15], [42, 47], [44, 15], [44, 47], [46, 15], [46, 47], [36, 31], [36, 63], [38, 31], [38, 63], [40, 31], [40, 63], [42, 31], [42, 63], [44, 31], [44, 63], [46, 31], [46, 63], [48, 15], [48, 47], [50, 15], [50, 47], [52, 15], [52, 47], [54, 15], [54, 47], [56, 15], [56, 47], [58, 15], [58, 47], [48, 31], [48, 63], [50, 31], [50, 63], [52, 31], [52, 63], [54, 31], [54, 63], [56, 31], [56, 63], [58, 31], [58, 63], [60, 15], [60, 47], [62, 15], [62, 47], [64, 15], [64, 47], [66, 15], [66, 47], [68, 15], [68, 47], [70, 15], [70, 47], [60, 31], [60, 63], [62, 31], [62, 63], [64, 31], [64, 63], [66, 31], [66, 63], [68, 31], [68, 63], [70, 31], [70, 63], [72, 15], [72, 47], [74, 15], [74, 47], [76, 15], [76, 47], [78, 15], [78, 47], [80, 15], [80, 47], [82, 15], [82, 47], [72, 31], [72, 63], [74, 31], [74, 63], [76, 31], [76, 63], [78, 31], [78, 63], [80, 31], [80, 63], [82, 31], [82, 63], [84, 15], [84, 47], [86, 15], [86, 47], [88, 15], [88, 47], [90, 15], [90, 47], [92, 15], [92, 47], [94, 15], [94, 47], [84, 31], [84, 63], [86, 31], [86, 63], [88, 31], [88, 63], [90, 31], [90, 63], [92, 31], [92, 63], [94, 31], [94, 63], [96, 15], [96, 47], [98, 15], [98, 47], [100, 15], [100, 47], [102, 15], [102, 47], [104, 15], [104, 47], [106, 15], [106, 47], [96, 31], [96, 63], [98, 31], [98, 63], [100, 31], [100, 63], [102, 31], [102, 63], [104, 31], [104, 63], [106, 31], [106, 63], [108, 15], [108, 47], [110, 15], [110, 47], [112, 15], [112, 47], [114, 15], [114, 47], [116, 15], [116, 47], [118, 15], [118, 47], [108, 31], [108, 63], [110, 31], [110, 63], [112, 31], [112, 63], [114, 31], [114, 63], [116, 31], [116, 63], [118, 31], [118, 63], [120, 15], [120, 47], [122, 15], [122, 47], [124, 15], [124, 47], [126, 15], [126, 47], [128, 15], [128, 47], [130, 15], [130, 47], [120, 31], [120, 63], [122, 31], [122, 63], [124, 31], [124, 63], [126, 31], [126, 63], [128, 31], [128, 63], [130, 31], [130, 63], [132, 31], [132, 63], [134, 31], [134, 63], [136, 31], [136, 63], [138, 31], [138, 63], [140, 31], [140, 63], [142, 31], [142, 63], [133, 0], [135, 0], [137, 0], [139, 0], [141, 0], [143, 0]

TABLE 32

[1, 1, 1, 2, 0, 1, 0, 2], [1, 3, 1, 4, 2, 3, 2, 4], [1, 5, 1, 6, 0, 5, 0, 6], [1, 7, 1, 8, 2, 7, 2, 8], [1, 9, 1, 10, 0, 9, 0, 10], [3, 1, 3, 2, 2, 1, 2, 2], [3, 3, 3, 4, 4, 3, 4, 4], [3, 5, 3, 6, 2, 5, 2, 6], [3, 7, 3, 8, 4, 7, 4, 8], [3, 9, 3, 10, 2, 9, 2, 10], [5, 1, 5, 2, 4, 1, 4, 2], [5, 3, 5, 4, 6, 3, 6, 4], [5, 5, 5, 6, 4, 5, 4, 6], [5, 7, 5, 8, 6, 7, 6, 8], [5, 9, 5, 10, 4, 9, 4, 10], [7, 1, 7, 2, 6, 1, 6, 2], [7, 3, 7, 4, 8, 3, 8, 4], [7, 5, 7, 6, 6, 5, 6, 6], [7, 7, 7, 8, 8, 7, 8, 8], [7, 9, 7, 10, 6, 9, 6, 10], [9, 1, 9, 2, 8, 1, 8, 2], [9, 5, 9, 6, 8, 5, 8, 6], [9, 9, 9, 10, 8, 9, 8, 10], [11, 1, 11, 2, 12, 1, 12, 2], [11, 3, 11, 4, 10, 3, 10, 4], [11, 5, 11, 6, 12, 5, 12, 6], [11, 7, 11, 8, 10, 7, 10, 8], [11, 9, 11, 10, 12, 9, 12, 10], [13, 1, 13, 2, 14, 1, 14, 2], [13, 3, 13, 4, 12, 3, 12, 4], [13, 5, 13, 6, 14, 5, 14, 6], [13, 7, 13, 8, 12, 7, 12, 8], [13, 9, 13, 10, 14, 9, 14, 10], [15, 1, 15, 2, 16, 1, 16, 2], [15, 3, 15, 4, 14, 3, 14, 4], [15, 5, 15, 6, 16, 5, 16, 6], [15, 7, 15, 8, 14, 7, 14, 8], [15, 9, 15, 10, 16, 9, 16, 10], [17, 1, 17, 2, 18, 1, 18, 2], [17, 3, 17, 4, 16, 3, 16, 4], [17, 5, 17, 6, 18, 5, 18, 6], [17, 7, 17, 8, 16, 7, 16, 8], [17, 9, 17, 10, 18, 9, 18, 10], [19, 3, 19, 4, 18, 3, 18, 4], [19, 7, 19, 8, 18, 7, 18, 8], [21, 1, 21, 2, 20, 1, 20, 2], [21, 3, 21, 4, 22, 3, 22, 4], [21, 5, 21, 6, 20, 5, 20, 6], [21, 7, 21, 8, 22, 7, 22, 8], [21, 9, 21, 10, 20, 9, 20, 10], [23, 1, 23, 2, 22, 1, 22, 2], [23, 3, 23, 4, 24, 3, 24, 4], [23, 5, 23, 6, 22, 5, 22, 6], [23, 7, 23, 8, 24, 7, 24, 8], [23, 9, 23, 10, 22, 9, 22, 10], [25, 1, 25, 2, 24, 1, 24, 2], [25, 3, 25, 4, 26, 3, 26, 4], [25, 5, 25, 6, 24, 5, 24, 6], [25, 7, 25, 8, 26, 7, 26, 8], [25, 9, 25, 10, 24, 9, 24, 10], [27, 1, 27, 2, 26, 1, 26, 2], [27, 3, 27, 4, 28, 3, 28, 4], [27, 5, 27, 6, 26, 5, 26, 6], [27, 7, 27, 8, 28, 7, 28, 8], [27, 9, 27, 10, 26, 9, 26, 10], [29, 1, 29, 2, 28, 1, 28, 2], [29, 5, 29, 6, 28, 5, 28, 6], [29, 9, 29, 10, 28, 9, 28, 10], [31, 1, 31, 2, 32, 1, 32, 2], [31, 3, 31, 4, 30, 3, 30, 4], [31, 5, 31, 6, 32, 5, 32, 6], [31, 7, 31, 8, 30, 7, 30, 8], [31, 9, 31, 10, 32, 9, 32, 10], [33, 1, 33, 2, 34, 1, 34, 2], [33, 3, 33, 4, 32, 3, 32, 4], [33, 5, 33, 6, 34, 5, 34, 6], [33, 7, 33, 8, 32, 7, 32, 8], [33, 9, 33, 10, 34, 9, 34, 10], [35, 1, 35, 2, 36, 1, 36, 2], [35, 3, 35, 4, 34, 3, 34, 4], [35, 5, 35, 6, 36, 5, 36, 6], [35, 7, 35, 8, 34, 7, 34, 8], [35, 9, 35, 10, 36, 9, 36, 10], [37, 1, 37, 2, 38, 1, 38, 2], [37, 3, 37, 4, 36, 3, 36, 4], [37, 5, 37, 6, 38, 5, 38, 6], [37, 7, 37, 8, 36, 7, 36, 8], [37, 9, 37, 10, 38, 9, 38, 10], [39, 3, 39, 4, 38, 3, 38, 4], [39, 7, 39, 8, 38, 7, 38, 8], [41, 1, 41, 2, 40, 1, 40, 2], [41, 3, 41, 4, 42, 3, 42, 4], [41, 5, 41, 6, 40, 5, 40, 6], [41, 7, 41, 8, 42, 7, 42, 8], [41, 9, 41, 10, 40, 9, 40, 10], [43, 1, 43, 2, 42, 1, 42, 2], [43, 3, 43, 4, 44, 3, 44, 4], [43, 5, 43, 6, 42, 5, 42, 6], [43, 7, 43, 8, 44, 7, 44, 8], [43, 9, 43, 10, 42, 9, 42, 10], [45, 1, 45, 2, 44, 1, 44, 2], [45, 3, 45, 4, 46, 3, 46, 4], [45, 5, 45, 6, 44, 5, 44, 6], [45, 7, 45, 8, 46, 7, 46, 8], [45, 9, 45, 10, 44, 9, 44, 10], [47, 1, 47, 2, 46, 1, 46, 2], [47, 3, 47, 4, 48, 3, 48, 4], [47, 5, 47, 6, 46, 5, 46, 6], [47, 7, 47, 8, 48, 7, 48, 8], [47, 9, 47, 10, 46, 9, 46, 10], [49, 1, 49, 2, 48, 1, 48, 2], [49, 5, 49, 6, 48, 5, 48, 6], [49, 9, 49, 10, 48, 9, 48, 10], [51, 1, 51, 2, 52, 1, 52, 2], [51, 3, 51, 4, 50, 3, 50, 4], [51, 5, 51, 6, 52, 5, 52, 6], [51, 7, 51, 8, 50, 7, 50, 8], [51, 9, 51, 10, 52, 9, 52, 10], [53, 1, 53, 2, 54, 1, 54, 2], [53, 3, 53, 4, 52, 3, 52, 4], [53, 5, 53, 6, 54, 5, 54, 6], [53, 7, 53, 8, 52, 7, 52, 8], [53, 9, 53, 10, 54, 9, 54, 10], [55, 1, 55, 2, 56, 1, 56, 2], [55, 3, 55, 4, 54, 3, 54, 4], [55, 5, 55, 6, 56, 5, 56, 6], [55, 7, 55, 8, 54, 7, 54, 8], [55, 9, 55, 10, 56, 9, 56, 10], [57, 1, 57, 2, 58, 1, 58, 2], [57, 3, 57, 4, 56, 3, 56, 4], [57, 5, 57, 6, 58, 5, 58, 6], [57, 7, 57, 8, 56, 7, 56, 8], [57, 9, 57, 10, 58, 9, 58, 10], [59, 3, 59, 4, 58, 3, 58, 4], [59, 7, 59, 8, 58, 7, 58, 8], [61, 1, 61, 2, 60, 1, 60, 2], [61, 3, 61, 4, 62, 3, 62, 4], [61, 5, 61, 6, 60, 5, 60, 6], [61, 7, 61, 8, 62, 7, 62, 8], [61, 9, 61, 10, 60, 9, 60, 10], [63, 1, 63, 2, 62, 1, 62, 2], [63, 3, 63, 4, 64, 3, 64, 4], [63, 5, 63, 6, 62, 5, 62, 6], [63, 7, 63, 8, 64, 7, 64, 8], [63, 9, 63, 10, 62, 9, 62, 10], [65, 1, 65, 2, 64, 1, 64, 2], [65, 3, 65, 4, 66, 3, 66, 4], [65, 5, 65, 6, 64, 5, 64, 6], [65, 7, 65, 8, 66, 7, 66, 8], [65, 9, 65, 10, 64, 9, 64, 10], [67, 1, 67, 2, 66, 1, 66, 2], [67, 3, 67, 4, 68, 3, 68, 4], [67, 5, 67, 6, 66, 5, 66, 6], [67, 7, 67, 8, 68, 7, 68, 8], [67, 9, 67, 10, 66, 9, 66, 10], [69, 1, 69, 2, 68, 1, 68, 2], [69, 5, 69, 6, 68, 5, 68, 6], [69, 9, 69, 10, 68, 9, 68, 10], [71, 1, 71, 2, 72, 1, 72, 2], [71, 3, 71, 4, 70, 3, 70, 4], [71, 5, 71, 6, 72, 5, 72, 6], [71, 7, 71, 8, 70, 7, 70, 8], [71, 9, 71, 10, 72, 9, 72, 10], [73, 1, 73, 2, 74, 1, 74, 2], [73, 3, 73, 4, 72, 3, 72, 4], [73, 5, 73, 6, 74, 5, 74, 6], [73, 7, 73, 8, 72, 7, 72, 8], [73, 9, 73, 10, 74, 9, 74, 10], [75, 1, 75, 2, 76, 1, 76, 2], [75, 3, 75, 4, 74, 3, 74, 4], [75, 5, 75, 6, 76, 5, 76, 6], [75, 7, 75, 8, 74, 7, 74, 8], [75, 9, 75, 10, 76, 9, 76, 10], [77, 1, 77, 2, 78, 1, 78, 2], [77, 3, 77, 4, 76, 3, 76, 4], [77, 5, 77, 6, 78, 5, 78, 6], [77, 7, 77, 8, 76, 7, 76, 8], [77, 9, 77, 10, 78, 9, 78, 10], [79, 3, 79, 4, 78, 3, 78, 4], [79, 7, 79, 8, 78, 7, 78, 8], [81, 1, 81, 2, 80, 1, 80, 2], [81, 3, 81, 4, 82, 3, 82, 4], [81, 5, 81, 6, 80, 5, 80, 6], [81, 7, 81, 8, 82, 7, 82, 8], [81, 9, 81, 10, 80, 9, 80, 10], [83, 1, 83, 2, 82, 1, 82, 2], [83, 3, 83, 4, 84, 3, 84, 4], [83, 5, 83, 6, 82, 5, 82, 6], [83, 7, 83, 8, 84, 7, 84, 8], [83, 9, 83, 10, 82, 9, 82, 10], [85, 1, 85, 2, 84, 1, 84, 2], [85, 3, 85, 4, 86, 3, 86, 4], [85, 5, 85, 6, 84, 5, 84, 6], [85, 7, 85, 8, 86, 7, 86, 8], [85, 9, 85, 10, 84, 9, 84, 10], [87, 1, 87, 2, 86, 1, 86, 2], [87, 3, 87, 4, 88, 3, 88, 4], [87, 5, 87, 6, 86, 5, 86, 6], [87, 7, 87, 8, 88, 7, 88, 8], [87, 9, 87, 10, 86, 9, 86, 10], [89, 1, 89, 2, 88, 1, 88, 2], [89, 5, 89, 6, 88, 5, 88, 6], [89, 9, 89, 10, 88, 9, 88, 10], [91, 1, 91, 2, 92, 1, 92, 2], [91, 3, 91, 4, 90, 3, 90, 4], [91, 5, 91, 6, 92, 5, 92, 6], [91, 7, 91, 8, 90, 7, 90, 8], [91, 9, 91, 10, 92, 9, 92, 10], [93, 1, 93, 2, 94, 1, 94, 2], [93, 3, 93, 4, 92, 3, 92, 4], [93, 5, 93, 6, 94, 5, 94, 6], [93, 7, 93, 8, 92, 7, 92, 8], [93, 9, 93, 10, 94, 9, 94, 10], [95, 1, 95, 2, 96, 1, 96, 2], [95, 3, 95, 4, 94, 3, 94, 4], [95, 5, 95, 6, 96, 5, 96, 6], [95, 7, 95, 8, 94, 7, 94, 8], [95, 9, 95, 10, 96, 9, 96, 10], [97, 1, 97, 2, 98, 1, 98, 2], [97, 3, 97, 4, 96, 3, 96, 4], [97, 5, 97, 6, 98, 5, 98, 6], [97, 7, 97, 8, 96, 7, 96, 8], [97, 9, 97, 10, 98, 9, 98, 10], [99, 3, 99, 4, 98, 3, 98, 4], [99, 7, 99, 8, 98, 7, 98, 8], [0, 2, 0, 3, 19, 2, 19, 3], [0, 6, 0, 7, 19, 6, 19, 7], [2, 2, 2, 3, 17, 2, 17, 3], [2, 6, 2, 7, 17, 6, 17, 7], [2, 10, 0, 0, 17, 10, 0, 0], [4, 2, 4, 3, 15, 2, 15, 3], [4, 6, 4, 7, 15, 6, 15, 7], [4, 10, 0, 0, 15, 10, 0, 0], [6, 2, 6, 3, 13, 2, 13, 3], [6, 6, 6, 7, 13, 6, 13, 7], [6, 10, 0, 0, 13, 10, 0, 0], [8, 2, 8, 3, 11, 2, 11, 3], [8, 6, 8, 7, 11, 6, 11, 7], [8, 10, 0, 0, 11, 10, 0, 0], [0, 0, 10, 1, 0, 0, 9, 1], [10, 2, 10, 3, 29, 2, 29, 3], [10, 4, 10, 5, 9, 4, 9, 5], [10, 6, 10, 7, 29, 6, 29, 7], [10, 8, 10, 9, 9, 8, 9, 9], [10, 10, 0, 0, 29, 10, 0, 0], [0, 0, 12, 1, 0, 0, 7, 1], [12, 2, 12, 3, 27, 2, 27, 3], [12, 4, 12, 5, 7, 4, 7, 5], [12, 6, 12, 7, 27, 6, 27, 7], [12, 8, 12, 9, 7, 8, 7, 9], [12, 10, 0, 0, 27, 10, 0, 0], [0, 0, 14, 1, 0, 0, 5, 1], [14, 2, 14, 3, 25, 2, 25, 3], [14, 4, 14, 5, 5, 4, 5, 5], [14, 6, 14, 7, 25, 6, 25, 7], [14, 8, 14, 9, 5, 8, 5, 9], [14, 10, 0, 0, 25, 10, 0, 0], [0, 0, 16, 1, 0, 0, 3, 1], [16, 2, 16, 3, 23, 2, 23, 3], [16, 4, 16, 5, 3, 4, 3, 5], [16, 6, 16, 7, 23, 6, 23, 7], [16, 8, 16, 9, 3, 8, 3, 9], [16, 10, 0, 0, 23, 10, 0, 0], [0, 0, 18, 1, 0, 0, 1, 1], [18, 2, 18, 3, 21, 2, 21, 3], [18, 4, 18, 5, 1, 4, 1, 5], [18, 6, 18, 7, 21, 6, 21, 7], [18, 8, 18, 9, 1, 8, 1, 9], [18, 10, 0, 0, 21, 10, 0, 0], [0, 0, 20, 1, 0, 0, 19, 1], [20, 2, 20, 3, 39, 2, 39, 3], [20, 4, 20, 5, 19, 4, 19, 5], [20, 6, 20, 7, 39, 6, 39, 7], [20, 8, 20, 9, 19, 8, 19, 9], [20, 10, 0, 0, 39, 10, 0, 0], [0, 0, 22, 1, 0, 0, 17, 1], [22, 2, 22, 3, 37, 2, 37, 3], [22, 4, 22, 5, 17, 4, 17, 5], [22, 6, 22, 7, 37, 6, 37, 7], [22, 8, 22, 9, 17, 8, 17, 9], [22, 10, 0, 0, 37, 10, 0, 0], [0, 0, 24, 1, 0, 0, 15, 1], [24, 2, 24, 3, 35, 2, 35, 3], [24, 4, 24, 5, 15, 4, 15, 5], [24, 6, 24, 7, 35, 6, 35, 7], [24, 8, 24, 9, 15, 8, 15, 9], [24, 10, 0, 0, 35, 10, 0, 0], [0, 0, 26, 1, 0, 0, 13, 1], [26, 2, 26, 3, 33, 2, 33, 3], [26, 4, 26, 5, 13, 4, 13, 5], [26, 6, 26, 7, 33, 6, 33, 7], [26, 8, 26, 9, 13, 8, 13, 9], [26, 10, 0, 0, 33, 10, 0, 0], [0, 0, 28, 1, 0, 0, 11, 1], [28, 2, 28, 3, 31, 2, 31, 3], [28, 4, 28, 5, 11, 4, 11, 5], [28, 6, 28, 7, 31, 6, 31, 7], [28, 8, 28, 9, 11, 8, 11, 9], [28, 10, 0, 0, 31, 10, 0, 0], [0, 0, 30, 1, 0, 0, 29, 1], [30, 2, 30, 3, 49, 2, 49, 3], [30, 4, 30, 5, 29, 4, 29, 5], [30, 6, 30, 7, 49, 6, 49, 7], [30, 8, 30, 9, 29, 8, 29, 9], [30, 10, 0, 0, 49, 10, 0, 0], [0, 0, 32, 1, 0, 0, 27, 1], [32, 2, 32, 3, 47, 2, 47, 3], [32, 4, 32, 5, 27, 4, 27, 5], [32, 6, 32, 7, 47, 6, 47, 7], [32, 8, 32, 9, 27, 8, 27, 9], [32, 10, 0, 0, 47, 10, 0, 0], [0, 0, 34, 1, 0, 0, 25, 1], [34, 2, 34, 3, 45, 2, 45, 3], [34, 4, 34, 5, 25, 4, 25, 5], [34, 6, 34, 7, 45, 6, 45, 7], [34, 8, 34, 9, 25, 8, 25, 9], [34, 10, 0, 0, 45, 10, 0, 0], [0, 0, 36, 1, 0, 0, 23, 1], [36, 2, 36, 3, 43, 2, 43, 3], [36, 4, 36, 5, 23, 4, 23, 5], [36, 6, 36, 7, 43, 6, 43, 7], [36, 8, 36, 9, 23, 8, 23, 9], [36, 10, 0, 0, 43, 10, 0, 0], [0, 0, 38, 1, 0, 0, 21, 1], [38, 2, 38, 3, 41, 2, 41, 3], [38, 4, 38, 5, 21, 4, 21, 5], [38, 6, 38, 7, 41, 6, 41, 7], [38, 8, 38, 9, 21, 8, 21, 9], [38, 10, 0, 0, 41, 10, 0, 0], [0, 0, 40, 1, 0, 0, 39, 1], [40, 2, 40, 3, 59, 2, 59, 3], [40, 4, 40, 5, 39, 4, 39, 5], [40, 6, 40, 7, 59, 6, 59, 7], [40, 8, 40, 9, 39, 8, 39, 9], [40, 10, 0, 0, 59, 10, 0, 0], [0, 0, 42, 1, 0, 0, 37, 1], [42, 2, 42, 3, 57, 2, 57, 3], [42, 4, 42, 5, 37, 4, 37, 5], [42, 6, 42, 7, 57, 6, 57, 7], [42, 8, 42, 9, 37, 8, 37, 9], [42, 10, 0, 0, 57, 10, 0, 0], [0, 0, 44, 1, 0, 0, 35, 1], [44, 2, 44, 3, 55, 2, 55, 3], [44, 4, 44, 5, 35, 4, 35, 5], [44, 6, 44, 7, 55, 6, 55, 7], [44, 8, 44, 9, 35, 8, 35, 9], [44, 10, 0, 0, 55, 10, 0, 0], [0, 0, 46, 1, 0, 0, 33, 1], [46, 2, 46, 3, 53, 2, 53, 3], [46, 4, 46, 5, 33, 4, 33, 5], [46, 6, 46, 7, 53, 6, 53, 7], [46, 8, 46, 9, 33, 8, 33, 9], [46, 10, 0, 0, 53, 10, 0, 0], [0, 0, 48, 1, 0, 0, 31, 1], [48, 2, 48, 3, 51, 2, 51, 3], [48, 4, 48, 5, 31, 4, 31, 5], [48, 6, 48, 7, 51, 6, 51, 7], [48, 8, 48, 9, 31, 8, 31, 9], [48, 10, 0, 0, 51, 10, 0, 0], [0, 0, 50, 1, 0, 0, 49, 1], [50, 2, 50, 3, 69, 2, 69, 3], [50, 4, 50, 5, 49, 4, 49, 5], [50, 6, 50, 7, 69, 6, 69, 7], [50, 8, 50, 9, 49, 8, 49, 9], [50, 10, 0, 0, 69, 10, 0, 0], [0, 0, 52, 1, 0, 0, 47, 1], [52, 2, 52, 3, 67, 2, 67, 3], [52, 4, 52, 5, 47, 4, 47, 5], [52, 6, 52, 7, 67, 6, 67, 7], [52, 8, 52, 9, 47, 8, 47, 9], [52, 10, 0, 0, 67, 10, 0, 0], [0, 0, 54, 1, 0, 0, 45, 1], [54, 2, 54, 3, 65, 2, 65, 3], [54, 4, 54, 5, 45, 4, 45, 5], [54, 6, 54, 7, 65, 6, 65, 7], [54, 8, 54, 9, 45, 8, 45, 9], [54, 10, 0, 0, 65, 10, 0, 0], [0, 0, 56, 1, 0, 0, 43, 1], [56, 2, 56, 3, 63, 2, 63, 3], [56, 4, 56, 5, 43, 4, 43, 5], [56, 6, 56, 7, 63, 6, 63, 7], [56, 8, 56, 9, 43, 8, 43, 9], [56, 10, 0, 0, 63, 10, 0, 0], [0, 0, 58, 1, 0, 0, 41, 1], [58, 2, 58, 3, 61, 2, 61, 3], [58, 4, 58, 5, 41, 4, 41, 5], [58, 6, 58, 7, 61, 6, 61, 7], [58, 8, 58, 9, 41, 8, 41, 9], [58, 10, 0, 0, 61, 10, 0, 0], [0, 0, 60, 1, 0, 0, 59, 1], [60, 2, 60, 3, 79, 2, 79, 3], [60, 4, 60, 5, 59, 4, 59, 5], [60, 6, 60, 7, 79, 6, 79, 7], [60, 8, 60, 9, 59, 8, 59, 9], [60, 10, 0, 0, 79, 10, 0, 0], [0, 0, 62, 1, 0, 0, 57, 1], [62, 2, 62, 3, 77, 2, 77, 3], [62, 4, 62, 5, 57, 4, 57, 5], [62, 6, 62, 7, 77, 6, 77, 7], [62, 8, 62, 9, 57, 8, 57, 9], [62, 10, 0, 0, 77, 10, 0, 0], [0, 0, 64, 1, 0, 0, 55, 1], [64, 2, 64, 3, 75, 2, 75, 3], [64, 4, 64, 5, 55,

TABLE 32-continued 4, 55, 5], [64, 6, 64, 7, 75, 6, 75, 7], [64, 8, 64, 9, 55, 8, 55, 9], [64, 10, 0, 0, 75, 10, 0, 0], [0, 0, 66, 1, 0, 0, 53, 1], [66, 2, 66, 3, 73, 2, 73, 3], [66, 4, 66, 5, 53, 4, 53, 5], [66, 6, 66, 7, 73, 6, 73, 7], [66, 8, 66, 9, 53, 8, 53, 9], [66, 10, 0, 0, 73, 10, 0, 0], [0, 0, 68, 1, 0, 0, 51, 1], [68, 2, 68, 3, 71, 2, 71, 3], [68, 4, 68, 5, 51, 4, 51, 5], [68, 6, 68, 7, 71, 6, 71, 7], [68, 8, 68, 9, 51, 8, 51, 9], [68, 10, 0, 0, 71, 10, 0, 0], [0, 0, 70, 1, 0, 0, 69, 1], [70, 2, 70, 3, 89, 2, 89, 3], [70, 4, 70, 5, 69, 4, 69, 5], [70, 6, 70, 7, 89, 6, 89, 7], [70, 8, 70, 9, 69, 8, 69, 9], [70, 10, 0, 0, 89, 10, 0, 0], [0, 0, 72, 1, 0, 0, 67, 1], [72, 2, 72, 3, 87, 2, 87, 3], [72, 4, 72, 5, 67, 4, 67, 5], [72, 6, 72, 7, 87, 6, 87, 7], [72, 8, 72, 9, 67, 8, 67, 9], [72, 10, 0, 0, 87, 10, 0, 0], [0, 0, 74, 1, 0, 0, 65, 1], [74, 2, 74, 3, 85, 2, 85, 3], [74, 4, 74, 5, 65, 4, 65, 5], [74, 6, 74, 7, 85, 6, 85, 7], [74, 8, 74, 9, 65, 8, 65, 9], [74, 10, 0, 0, 85, 10, 0, 0], [0, 0, 76, 1, 0, 0, 63, 1], [76, 2, 76, 3, 83, 2, 83, 3], [76, 4, 76, 5, 63, 4, 63, 5], [76, 6, 76, 7, 83, 6, 83, 7], [76, 8, 76, 9, 63, 8, 63, 9], [76, 10, 0, 0, 83, 10, 0, 0], [0, 0, 78, 1, 0, 0, 61, 1], [78, 2, 78, 3, 81, 2, 81, 3], [78, 4, 78, 5, 61, 4, 61, 5], [78, 6, 78, 7, 81, 6, 81, 7], [78, 8, 78, 9, 61, 8, 61, 9], [78, 10, 0, 0, 81, 10, 0, 0], [0, 0, 80, 1, 0, 0, 79, 1], [80, 2, 80, 3, 99, 2, 99, 3], [80, 4, 80, 5, 79, 4, 79, 5], [80, 6, 80, 7, 99, 6, 99, 7], [80, 8, 80, 9, 79, 8, 79, 9], [80, 10, 0, 0, 99, 10, 0, 0], [0, 0, 82, 1, 0, 0, 77, 1], [82, 2, 82, 3, 97, 2, 97, 3], [82, 4, 82, 5, 77, 4, 77, 5], [82, 6, 82, 7, 97, 6, 97, 7], [82, 8, 82, 9, 77, 8, 77, 9], [82, 10, 0, 0, 97, 10, 0, 0], [0, 0, 84, 1, 0, 0, 75, 1], [84, 2, 84, 3, 95, 2, 95, 3], [84, 4, 84, 5, 75, 4, 75, 5], [84, 6, 84, 7, 95, 6, 95, 7], [84, 8, 84, 9, 75, 8, 75, 9], [84, 10, 0, 0, 95, 10, 0, 0], [0, 0, 86, 1, 0, 0, 73, 1], [86, 2, 86, 3, 93, 2, 93, 3], [86, 4, 86, 5, 73, 4, 73, 5], [86, 6, 86, 7, 93, 6, 93, 7], [86, 8, 86, 9, 73, 8, 73, 9], [86, 10, 0, 0, 93, 10, 0, 0], [0, 0, 88, 1, 0, 0, 71, 1], [88, 2, 88, 3, 91, 2, 91, 3], [88, 4, 88, 5, 71, 4, 71, 5], [88, 6, 88, 7, 91, 6, 91, 7], [88, 8, 88, 9, 71, 8, 71, 9], [88, 10, 0, 0, 91, 10, 0, 0], [0, 0, 90, 1, 0, 0, 89, 1], [90, 4, 90, 5, 89, 4, 89, 5], [90, 8, 90, 9, 89, 8, 89, 9], [0, 0, 92, 1, 0, 0, 87, 1], [92, 4, 92, 5, 87, 4, 87, 5], [92, 8, 92, 9, 87, 8, 87, 9], [0, 0, 94, 1, 0, 0, 85, 1], [94, 4, 94, 5, 85, 4, 85, 5], [94, 8, 94, 9, 85, 8, 85, 9], [0, 0, 96, 1, 0, 0, 83, 1], [96, 4, 96, 5, 83, 4, 83, 5], [96, 8, 96, 9, 83, 8, 83, 9], [0, 0, 98, 1, 0, 0, 81, 1], [98, 4, 98, 5, 81, 4, 81, 5], [98, 8, 98, 9, 81, 8, 81, 9], [1, 1, 1, 2, 0, 0, 0, 0], [0, 1, 0, 2, 0, 0, 0, 0], [1, 3, 1, 4, 0, 0, 0, 0], [2, 3, 2, 4, 0, 0, 0, 0], [1, 5, 1, 6, 0, 0, 0, 0], [0, 5, 0, 6, 0, 0, 0, 0], [1, 7, 1, 8, 0, 0, 0, 0], [2, 7, 2, 8, 0, 0, 0, 0], [1, 9, 1, 10, 0, 0, 0, 0], [0, 9, 0, 10, 0, 0, 0, 0], [3, 1, 3, 2, 0, 0, 0, 0], [2, 1, 2, 2, 0, 0, 0, 0], [3, 3, 3, 4, 0, 0, 0, 0], [4, 3, 4, 4, 0, 0, 0, 0], [3, 5, 3, 6, 0, 0, 0, 0], [2, 5, 2, 6, 0, 0, 0, 0], [3, 7, 3, 8, 0, 0, 0, 0], [4, 7, 4, 8, 0, 0, 0, 0], [3, 9, 3, 10, 0, 0, 0, 0], [2, 9, 2, 10, 0, 0, 0, 0], [5, 1, 5, 2, 0, 0, 0, 0], [4, 1, 4, 2, 0, 0, 0, 0], [5, 3, 5, 4, 0, 0, 0, 0], [6, 3, 6, 4, 0, 0, 0, 0], [5, 5, 5, 6, 0, 0, 0, 0], [4, 5, 4, 6, 0, 0, 0, 0], [5, 7, 5, 8, 0, 0, 0, 0], [6, 7, 6, 8, 0, 0, 0, 0], [5, 9, 5, 10, 0, 0, 0, 0], [4, 9, 4, 10, 0, 0, 0, 0], [7, 1, 7, 2, 0, 0, 0, 0], [6, 1, 6, 2, 0, 0, 0, 0], [7, 3, 7, 4, 0, 0, 0, 0], [8, 3, 8, 4, 0, 0, 0, 0], [7, 5, 7, 6, 0, 0, 0, 0], [6, 5, 6, 6, 0, 0, 0, 0], [7, 7, 7, 8, 0, 0, 0, 0], [8, 7, 8, 8, 0, 0, 0, 0], [7, 9, 7, 10, 0, 0, 0, 0], [6, 9, 6, 10, 0, 0, 0, 0], [9, 1, 9, 2, 0, 0, 0, 0], [8, 1, 8, 2, 0, 0, 0, 0], [9, 5, 9, 6, 0, 0, 0, 0], [8, 5, 8, 6, 0, 0, 0, 0], [9, 9, 9, 10, 0, 0, 0, 0], [8, 9, 8, 10, 0, 0, 0, 0], [11, 1, 11, 2, 0, 0, 0, 0], [12, 1, 12, 2, 0, 0, 0, 0], [11, 3, 11, 4, 0, 0, 0, 0], [10, 3, 10, 4, 0, 0, 0, 0], [11, 5, 11, 6, 0, 0, 0, 0], [12, 5, 12, 6, 0, 0, 0, 0], [11, 7, 11, 8, 0, 0, 0, 0], [10, 7, 10, 8, 0, 0, 0, 0], [11, 9, 11, 10, 0, 0, 0, 0], [12, 9, 12, 10, 0, 0, 0, 0], [13, 1, 13, 2, 0, 0, 0, 0], [14, 1, 14, 2, 0, 0, 0, 0], [13, 3, 13, 4, 0, 0, 0, 0], [12, 3, 12, 4, 0, 0, 0, 0], [13, 5, 13, 6, 0, 0, 0, 0], [14, 5, 14, 6, 0, 0, 0, 0], [13, 7, 13, 8, 0, 0, 0, 0], [12, 7, 12, 8, 0, 0, 0, 0], [13, 9, 13, 10, 0, 0, 0, 0], [14, 9, 14, 10, 0, 0, 0, 0], [15, 1, 15, 2, 0, 0, 0, 0], [16, 1, 16, 2, 0, 0, 0, 0], [15, 3, 15, 4, 0, 0, 0, 0], [14, 3, 14, 4, 0, 0, 0, 0], [15, 5, 15, 6, 0, 0, 0, 0], [16, 5, 16, 6, 0, 0, 0, 0], [15, 7, 15, 8, 0, 0, 0, 0], [14, 7, 14, 8, 0, 0, 0, 0], [15, 9, 15, 10, 0, 0, 0, 0], [16, 9, 16, 10, 0, 0, 0, 0], [17, 1, 17, 2, 0, 0, 0, 0], [18, 1, 18, 2, 0, 0, 0, 0], [17, 3, 17, 4, 0, 0, 0, 0], [16, 3, 16, 4, 0, 0, 0, 0], [17, 5, 17, 6, 0, 0, 0, 0], [18, 5, 18, 6, 0, 0, 0, 0], [17, 7, 17, 8, 0, 0, 0, 0], [16, 7, 16, 8, 0, 0, 0, 0], [17, 9, 17, 10, 0, 0, 0, 0], [18, 9, 18, 10, 0, 0, 0, 0], [19, 3, 19, 4, 0, 0, 0, 0], [18, 3, 18, 4, 0, 0, 0, 0], [19, 7, 19, 8, 0, 0, 0, 0], [18, 7, 18, 8, 0, 0, 0, 0], [21, 1, 21, 2, 0, 0, 0, 0], [20, 1, 20, 2, 0, 0, 0, 0], [21, 3, 21, 4, 0, 0, 0, 0], [22, 3, 22, 4, 0, 0, 0, 0], [21, 5, 21, 6, 0, 0, 0, 0], [20, 5, 20, 6, 0, 0, 0, 0], [21, 7, 21, 8, 0, 0, 0, 0], [22, 7, 22, 8, 0, 0, 0, 0], [21, 9, 21, 10, 0, 0, 0, 0], [20, 9, 20, 10, 0, 0, 0, 0], [23, 1, 23, 2, 0, 0, 0, 0], [22, 1, 22, 2, 0, 0, 0, 0], [23, 3, 23, 4, 0, 0, 0, 0], [24, 3, 24, 4, 0, 0, 0, 0], [23, 5, 23, 6, 0, 0, 0, 0], [22, 5, 22, 6, 0, 0, 0, 0], [23, 7, 23, 8, 0, 0, 0, 0], [24, 7, 24, 8, 0, 0, 0, 0], [23, 9, 23, 10, 0, 0, 0, 0], [22, 9, 22, 10, 0, 0, 0, 0], [25, 1, 25, 2, 0, 0, 0, 0], [24, 1, 24, 2, 0, 0, 0, 0], [25, 3, 25, 4, 0, 0, 0, 0], [26, 3, 26, 4, 0, 0, 0, 0], [25, 5, 25, 6, 0, 0, 0, 0], [24, 5, 24, 6, 0, 0, 0, 0], [25, 7, 25, 8, 0, 0, 0, 0], [26, 7, 26, 8, 0, 0, 0, 0], [25, 9, 25, 10, 0, 0, 0, 0], [24, 9, 24, 10, 0, 0, 0, 0], [27, 1, 27, 2, 0, 0, 0, 0], [26, 1, 26, 2, 0, 0, 0, 0], [27, 3, 27, 4, 0, 0, 0, 0], [28, 3, 28, 4, 0, 0, 0, 0], [27, 5, 27, 6, 0, 0, 0, 0], [26, 5, 26, 6, 0, 0, 0, 0], [27, 7, 27, 8, 0, 0, 0, 0], [28, 7, 28, 8, 0, 0, 0, 0], [27, 9, 27, 10, 0, 0, 0, 0], [26, 9, 26, 10, 0, 0, 0, 0], [29, 1, 29, 2, 0, 0, 0, 0], [28, 1, 28, 2, 0, 0, 0, 0], [29, 5, 29, 6, 0, 0, 0, 0], [28, 5, 28, 6, 0, 0, 0, 0], [29, 9, 29, 10, 0, 0, 0, 0], [28, 9, 28, 10, 0, 0, 0, 0], [31, 1, 31, 2, 0, 0, 0, 0], [32, 1, 32, 2, 0, 0, 0, 0], [31, 3, 31, 4, 0, 0, 0, 0], [30, 3, 30, 4, 0, 0, 0, 0], [31, 5, 31, 6, 0, 0, 0, 0], [32, 5, 32, 6, 0, 0, 0, 0], [31, 7, 31, 8, 0, 0, 0, 0], [30, 7, 30, 8, 0, 0, 0, 0], [31, 9, 31, 10, 0, 0, 0, 0], [32, 9, 32, 10, 0, 0, 0, 0], [33, 1, 33, 2, 0, 0, 0, 0], [34, 1, 34, 2, 0, 0, 0, 0], [33, 3, 33, 4, 0, 0, 0, 0], [32, 3, 32, 4, 0, 0, 0, 0], [33, 5, 33, 6, 0, 0, 0, 0], [34, 5, 34, 6, 0, 0, 0, 0], [33, 7, 33, 8, 0, 0, 0, 0], [32, 7, 32, 8, 0, 0, 0, 0], [33, 9, 33, 10, 0, 0, 0, 0], [34, 9, 34, 10, 0, 0, 0, 0], [35, 1, 35, 2, 0, 0, 0, 0], [36, 1, 36, 2, 0, 0, 0, 0], [35, 3, 35, 4, 0, 0, 0, 0], [34, 3, 34, 4, 0, 0, 0, 0], [35, 5, 35, 6, 0, 0, 0, 0], [36, 5, 36, 6, 0, 0, 0, 0], [35, 7, 35, 8, 0, 0, 0, 0], [34, 7, 34, 8, 0, 0, 0, 0], [35, 9, 35, 10, 0, 0, 0, 0], [36, 9, 36, 10, 0, 0, 0, 0], [37, 1, 37, 2, 0, 0, 0, 0], [38, 1, 38, 2, 0, 0, 0, 0], [37, 3, 37, 4, 0, 0, 0, 0], [36, 3, 36, 4, 0, 0, 0, 0], [37, 5, 37, 6, 0, 0, 0, 0], [38, 5, 38, 6, 0, 0, 0, 0], [37, 7, 37, 8, 0, 0, 0, 0], [36, 7, 36, 8, 0, 0, 0, 0], [37, 9, 37, 10, 0, 0, 0, 0], [38, 9, 38, 10, 0, 0, 0, 0], [39, 3, 39, 4, 0, 0, 0, 0], [38, 3, 38, 4, 0, 0, 0, 0], [39, 7, 39, 8, 0, 0, 0, 0], [38, 7, 38, 8, 0, 0, 0, 0], [41, 1, 41, 2, 0, 0, 0, 0], [40, 1, 40, 2, 0, 0, 0, 0], [41, 3, 41, 4, 0, 0, 0, 0], [42, 3, 42, 4, 0, 0, 0, 0], [41, 5, 41, 6, 0, 0, 0, 0], [40, 5, 40, 6, 0, 0, 0, 0], [41, 7, 41, 8, 0, 0, 0, 0], [42, 7, 42, 8, 0, 0, 0, 0], [41, 9, 41, 10, 0, 0, 0, 0], [40, 9, 40, 10, 0, 0, 0, 0], [43, 1, 43, 2, 0, 0, 0, 0], [42, 1, 42, 2, 0, 0, 0, 0], [43, 3, 43, 4, 0, 0, 0, 0], [44, 3, 44, 4, 0, 0, 0, 0], [43, 5, 43, 6, 0, 0, 0, 0], [42, 5, 42, 6, 0, 0, 0, 0], [43, 7, 43, 8, 0, 0, 0, 0], [44, 7, 44, 8, 0, 0, 0, 0], [43, 9, 43, 10, 0, 0, 0, 0], [42, 9, 42, 10, 0, 0, 0, 0], [45, 1, 45, 2, 0, 0, 0, 0], [44, 1, 44, 2, 0, 0, 0, 0], [45, 3, 45, 4, 0, 0, 0, 0], [46, 3, 46, 4, 0, 0, 0, 0], [45, 5, 45, 6, 0, 0, 0, 0], [44, 5, 44, 6, 0, 0, 0, 0], [45, 7, 45, 8, 0, 0, 0, 0], [46, 7, 46, 8, 0, 0, 0, 0], [45, 9, 45, 10, 0, 0, 0, 0], [44, 9, 44, 10, 0, 0, 0, 0], [47, 1, 47, 2, 0, 0, 0, 0], [46, 1, 46, 2, 0, 0, 0, 0], [47, 3, 47, 4, 0, 0, 0, 0], [48, 3, 48, 4, 0, 0, 0, 0], [47, 5, 47, 6, 0, 0, 0, 0], [46, 5, 46, 6, 0, 0, 0, 0], [47, 7, 47, 8, 0, 0, 0, 0], [48, 7, 48, 8, 0, 0, 0, 0], [47, 9, 47, 10, 0, 0, 0, 0], [46, 9, 46, 10, 0, 0, 0, 0], [49, 1, 49, 2, 0, 0, 0, 0], [48, 1, 48, 2, 0, 0, 0, 0], [49, 5, 49, 6, 0, 0, 0, 0], [48, 5, 48, 6, 0, 0, 0, 0], [49, 9, 49, 10, 0, 0, 0, 0], [48, 9, 48, 10, 0, 0, 0, 0], [51, 1, 51, 2, 0, 0, 0, 0], [52, 1, 52, 2, 0, 0, 0, 0], [51, 3, 51, 4, 0, 0, 0, 0], [50, 3, 50, 4, 0, 0, 0, 0], [51, 5, 51, 6, 0, 0, 0, 0], [52, 5, 52, 6, 0, 0, 0, 0], [51, 7, 51, 8, 0, 0, 0, 0], [50, 7, 50, 8, 0, 0, 0, 0], [51, 9, 51, 10, 0, 0, 0, 0], [52, 9, 52, 10, 0, 0, 0, 0], [53, 1, 53, 2, 0, 0, 0, 0], [54, 1, 54, 2, 0, 0, 0, 0], [53, 3, 53, 4, 0, 0, 0, 0], [52, 3, 52, 4, 0, 0, 0, 0], [53, 5, 53, 6, 0, 0, 0, 0], [54, 5, 54, 6, 0, 0, 0, 0], [53, 7, 53, 8, 0, 0, 0, 0], [52, 7, 52, 8, 0, 0, 0, 0], [53, 9, 53, 10, 0, 0, 0, 0], [54, 9, 54, 10, 0, 0, 0, 0], [55, 1, 55, 2, 0, 0, 0, 0], [56, 1, 56, 2, 0, 0, 0, 0], [55, 3, 55, 4, 0, 0, 0, 0], [54, 3, 54, 4, 0, 0, 0, 0], [55, 5, 55, 6, 0, 0, 0, 0], [56, 5, 56, 6, 0, 0, 0, 0], [55, 7, 55, 8, 0, 0, 0, 0], [54, 7, 54, 8, 0, 0, 0, 0], [55, 9, 55, 10, 0, 0, 0, 0], [56, 9, 56, 10, 0, 0, 0, 0], [57, 1, 57, 2, 0, 0, 0, 0], [58, 1, 58, 2, 0, 0, 0, 0], [57, 3, 57, 4, 0, 0, 0, 0], [56, 3, 56, 4, 0, 0, 0, 0], [57, 5, 57, 6, 0, 0, 0, 0], [58, 5, 58, 6, 0, 0, 0, 0], [57, 7, 57, 8, 0, 0, 0, 0], [56, 7, 56, 8, 0, 0, 0, 0], [57, 9, 57, 10, 0, 0, 0, 0], [58, 9, 58, 10, 0, 0, 0, 0], [59, 3, 59, 4, 0, 0, 0, 0], [58, 3, 58, 4, 0, 0, 0, 0], [59, 7, 59, 8, 0, 0, 0, 0], [58, 7, 58, 8, 0, 0, 0, 0], [61, 1, 61, 2, 0, 0, 0, 0], [60, 1, 60, 2, 0, 0, 0, 0], [61, 3, 61, 4, 0, 0, 0, 0], [62, 3, 62, 4, 0, 0, 0, 0], [61, 5, 61, 6, 0, 0, 0, 0], [60, 5, 60, 6, 0, 0, 0, 0], [61, 7, 61, 8, 0, 0, 0, 0], [62, 7, 62, 8, 0, 0, 0, 0], [61, 9, 61, 10, 0, 0, 0, 0], [60, 9, 60, 10, 0, 0, 0, 0], [63, 1, 63, 2, 0, 0, 0, 0], [62, 1, 62, 2, 0, 0, 0, 0], [63, 3, 63, 4, 0, 0, 0, 0], [64, 3, 64, 4, 0, 0, 0, 0], [63, 5, 63, 6, 0, 0, 0, 0], [62, 5, 62, 6, 0, 0, 0, 0], [63, 7, 63, 8, 0, 0, 0, 0], [64, 7, 64, 8, 0, 0, 0, 0], [63, 9, 63, 10, 0, 0, 0, 0], [62, 9, 62, 10, 0, 0, 0, 0], [65, 1, 65, 2, 0, 0, 0, 0], [64, 1, 64, 2, 0, 0, 0, 0], [65, 3, 65, 4, 0, 0, 0, 0], [66, 3, 66, 4, 0, 0, 0, 0], [65, 5, 65, 6, 0, 0, 0, 0], [64, 5, 64, 6, 0, 0, 0, 0], [65, 7, 65, 8, 0, 0, 0, 0], [66, 7, 66, 8, 0, 0, 0, 0], [65, 9, 65, 10, 0, 0, 0, 0], [64, 9, 64, 10, 0, 0, 0, 0], [67, 1, 67, 2, 0, 0, 0, 0], [66, 1, 66, 2, 0, 0, 0, 0], [67, 3, 67, 4, 0, 0, 0, 0], [68, 3, 68, 4, 0, 0, 0, 0], [67, 5, 67, 6, 0, 0, 0, 0], [66, 5, 66, 6, 0, 0, 0, 0], [67, 7, 67, 8, 0, 0, 0, 0], [68, 7, 68, 8, 0, 0, 0, 0], [67, 9, 67, 10, 0, 0, 0, 0], [66, 9, 66, 10, 0, 0, 0, 0], [69, 1, 69, 2, 0, 0, 0, 0], [68, 1, 68, 2, 0, 0, 0, 0], [69, 5, 69, 6, 0, 0, 0, 0], [68, 5, 68, 6, 0, 0, 0, 0], [69, 9, 69, 10, 0, 0, 0, 0], [68, 9, 68, 10, 0, 0, 0, 0], [71, 1, 71, 2, 0, 0, 0, 0], [72, 1, 72, 2, 0, 0, 0, 0], [71, 3, 71, 4, 0, 0, 0, 0], [70, 3, 70, 4, 0, 0, 0, 0], [71, 5, 71, 6, 0, 0, 0, 0], [72, 5, 72, 6, 0, 0, 0, 0], [71, 7, 71, 8, 0, 0, 0, 0], [70, 7, 70, 8, 0, 0, 0, 0], [71, 9, 71, 10, 0, 0, 0, 0], [72, 9, 72, 10, 0, 0, 0, 0], [73, 1, 73, 2, 0, 0, 0, 0], [74, 1, 74, 2, 0, 0, 0, 0], [73, 3, 73, 4, 0, 0, 0, 0], [72, 3, 72, 4, 0, 0, 0, 0], [73, 5, 73, 6, 0, 0, 0, 0], [74, 5, 74, 6, 0, 0, 0, 0], [73, 7, 73, 8, 0, 0, 0, 0], [72, 7, 72, 8, 0, 0, 0, 0], [73, 9, 73, 10, 0, 0, 0, 0], [74, 9, 74, 10, 0, 0, 0, 0], [75, 1, 75, 2, 0, 0, 0, 0], [76, 1, 76, 2, 0, 0, 0, 0], [75, 3, 75, 4, 0, 0, 0, 0], [74, 3, 74, 4, 0, 0, 0, 0], [75, 5, 75, 6, 0, 0, 0, 0], [76, 5, 76, 6, 0, 0, 0, 0], [75, 7, 75, 8, 0, 0, 0, 0], [74, 7, 74, 8, 0, 0, 0, 0], [75, 9, 75, 10, 0, 0, 0, 0], [76, 9, 76, 10, 0, 0, 0, 0], [77, 1, 77, 2, 0, 0, 0, 0], TABLE 32-continued

[78, 1, 78, 2, 0, 0, 0, 0], [77, 3, 77, 4, 0, 0, 0, 0], [76, 3, 76, 4, 0, 0, 0, 0], [77, 5, 77, 6, 0, 0, 0, 0], [78, 5, 78, 6, 0, 0, 0, 0], [77, 7, 77, 8, 0, 0, 0, 0], [76, 7, 76, 8, 0, 0, 0, 0], [77, 9, 77, 10, 0, 0, 0, 0], [78, 9, 78, 10, 0, 0, 0, 0], [79, 3, 79, 4, 0, 0, 0, 0], [78, 3, 78, 4, 0, 0, 0, 0], [79, 7, 79, 8, 0, 0, 0, 0], [78, 7, 78, 8, 0, 0, 0, 0], [81, 1, 81, 2, 0, 0, 0, 0], [80, 1, 80, 2, 0, 0, 0, 0], [81, 3, 81, 4, 0, 0, 0, 0], [82, 3, 82, 4, 0, 0, 0, 0], [81, 5, 81, 6, 0, 0, 0, 0], [80, 5, 80, 6, 0, 0, 0, 0], [81, 7, 81, 8, 0, 0, 0, 0], [82, 7, 82, 8, 0, 0, 0, 0], [81, 9, 81, 10, 0, 0, 0, 0], [80, 9, 80, 10, 0, 0, 0, 0], [83, 1, 83, 2, 0, 0, 0, 0], [82, 1, 82, 2, 0, 0, 0, 0], [83, 3, 83, 4, 0, 0, 0, 0], [84, 3, 84, 4, 0, 0, 0, 0], [83, 5, 83, 6, 0, 0, 0, 0], [82, 5, 82, 6, 0, 0, 0, 0], [83, 7, 83, 8, 0, 0, 0, 0], [84, 7, 84, 8, 0, 0, 0, 0], [83, 9, 83, 10, 0, 0, 0, 0], [82, 9, 82, 10, 0, 0, 0, 0], [85, 1, 85, 2, 0, 0, 0, 0], [84, 1, 84, 2, 0, 0, 0, 0], [85, 3, 85, 4, 0, 0, 0, 0], [86, 3, 86, 4, 0, 0, 0, 0], [85, 5, 85, 6, 0, 0, 0, 0], [84, 5, 84, 6, 0, 0, 0, 0], [85, 7, 85, 8, 0, 0, 0, 0], [86, 7, 86, 8, 0, 0, 0, 0], [85, 9, 85, 10, 0, 0, 0, 0], [84, 9, 84, 10, 0, 0, 0, 0], [87, 1, 87, 2, 0, 0, 0, 0], [86, 1, 86, 2, 0, 0, 0, 0], [87, 3, 87, 4, 0, 0, 0, 0], [88, 3, 88, 4, 0, 0, 0, 0], [87, 5, 87, 6, 0, 0, 0, 0], [86, 5, 86, 6, 0, 0, 0, 0], [87, 7, 87, 8, 0, 0, 0, 0], [88, 7, 88, 8, 0, 0, 0, 0], [87, 9, 87, 10, 0, 0, 0, 0], [86, 9, 86, 10, 0, 0, 0, 0], [89, 1, 89, 2, 0, 0, 0, 0], [88, 1, 88, 2, 0, 0, 0, 0], [89, 5, 89, 6, 0, 0, 0, 0], [88, 5, 88, 6, 0, 0, 0, 0], [89, 9, 89, 10, 0, 0, 0, 0], [88, 9, 88, 10, 0, 0, 0, 0], [91, 1, 91, 2, 0, 0, 0, 0], [92, 1, 92, 2, 0, 0, 0, 0], [91, 3, 91, 4, 0, 0, 0, 0], [90, 3, 90, 4, 0, 0, 0, 0], [91, 5, 91, 6, 0, 0, 0, 0], [92, 5, 92, 6, 0, 0, 0, 0], [91, 7, 91, 8, 0, 0, 0, 0], [90, 7, 90, 8, 0, 0, 0, 0], [91, 9, 91, 10, 0, 0, 0, 0], [92, 9, 92, 10, 0, 0, 0, 0], [93, 1, 93, 2, 0, 0, 0, 0], [94, 1, 94, 2, 0, 0, 0, 0], [93, 3, 93, 4, 0, 0, 0, 0], [92, 3, 92, 4, 0, 0, 0, 0], [93, 5, 93, 6, 0, 0, 0, 0], [94, 5, 94, 6, 0, 0, 0, 0], [93, 7, 93, 8, 0, 0, 0, 0], [92, 7, 92, 8, 0, 0, 0, 0], [93, 9, 93, 10, 0, 0, 0, 0], [94, 9, 94, 10, 0, 0, 0, 0], [95, 1, 95, 2, 0, 0, 0, 0], [96, 1, 96, 2, 0, 0, 0, 0], [95, 3, 95, 4, 0, 0, 0, 0], [94, 3, 94, 4, 0, 0, 0, 0], [95, 5, 95, 6, 0, 0, 0, 0], [96, 5, 96, 6, 0, 0, 0, 0], [95, 7, 95, 8, 0, 0, 0, 0], [94, 7, 94, 8, 0, 0, 0, 0], [95, 9, 95, 10, 0, 0, 0, 0], [96, 9, 96, 10, 0, 0, 0, 0], [97, 1, 97, 2, 0, 0, 0, 0], [98, 1, 98, 2, 0, 0, 0, 0], [97, 3, 97, 4, 0, 0, 0, 0], [96, 3, 96, 4, 0, 0, 0, 0], [97, 5, 97, 6, 0, 0, 0, 0], [98, 5, 98, 6, 0, 0, 0, 0], [97, 7, 97, 8, 0, 0, 0, 0], [96, 7, 96, 8, 0, 0, 0, 0], [97, 9, 97, 10, 0, 0, 0, 0], [98, 9, 98, 10, 0, 0, 0, 0], [99, 3, 99, 4, 0, 0, 0, 0], [98, 3, 98, 4, 0, 0, 0, 0], [99, 7, 99, 8, 0, 0, 0, 0], [98, 7, 98, 8, 0, 0, 0, 0], [0, 2, 0, 3, 0, 0, 0, 0], [19, 2, 19, 3, 0, 0, 0, 0], [0, 6, 0, 7, 0, 0, 0, 0], [19, 6, 19, 7, 0, 0, 0, 0], [2, 2, 2, 3, 0, 0, 0, 0], [17, 2, 17, 3, 0, 0, 0, 0], [2, 6, 2, 7, 0, 0, 0, 0], [17, 6, 17, 7, 0, 0, 0, 0], [4, 2, 4, 3, 0, 0, 0, 0], [15, 2, 15, 3, 0, 0, 0, 0], [4, 6, 4, 7, 0, 0, 0, 0], [15, 6, 15, 7, 0, 0, 0, 0], [6, 2, 6, 3, 0, 0, 0, 0], [13, 2, 13, 3, 0, 0, 0, 0], [6, 6, 6, 7, 0, 0, 0, 0], [13, 6, 13, 7, 0, 0, 0, 0], [8, 2, 8, 3, 0, 0, 0, 0], [11, 2, 11, 3, 0, 0, 0, 0], [8, 6, 8, 7, 0, 0, 0, 0], [11, 6, 11, 7, 0, 0, 0, 0], [10, 2, 10, 3, 0, 0, 0, 0], [29, 2, 29, 3, 0, 0, 0, 0], [10, 4, 10, 5, 0, 0, 0, 0], [9, 4, 9, 5, 0, 0, 0, 0], [10, 6, 10, 7, 0, 0, 0, 0], [29, 6, 29, 7, 0, 0, 0, 0], [10, 8, 10, 9, 0, 0, 0, 0], [9, 8, 9, 9, 0, 0, 0, 0], [12, 2, 12, 3, 0, 0, 0, 0], [27, 2, 27, 3, 0, 0, 0, 0], [12, 4, 12, 5, 0, 0, 0, 0], [7, 4, 7, 5, 0, 0, 0, 0], [12, 6, 12, 7, 0, 0, 0, 0], [27, 6, 27, 7, 0, 0, 0, 0], [12, 8, 12, 9, 0, 0, 0, 0], [7, 8, 7, 9, 0, 0, 0, 0], [14, 2, 14, 3, 0, 0, 0, 0], [25, 2, 25, 3, 0, 0, 0, 0], [14, 4, 14, 5, 0, 0, 0, 0], [5, 4, 5, 5, 0, 0, 0, 0], [14, 6, 14, 7, 0, 0, 0, 0], [25, 6, 25, 7, 0, 0, 0, 0], [14, 8, 14, 9, 0, 0, 0, 0], [5, 8, 5, 9, 0, 0, 0, 0], [16, 2, 16, 3, 0, 0, 0, 0], [23, 2, 23, 3, 0, 0, 0, 0], [16, 4, 16, 5, 0, 0, 0, 0], [3, 4, 3, 5, 0, 0, 0, 0], [16, 6, 16, 7, 0, 0, 0, 0], [23, 6, 23, 7, 0, 0, 0, 0], [16, 8, 16, 9, 0, 0, 0, 0], [3, 8, 3, 9, 0, 0, 0, 0], [18, 2, 18, 3, 0, 0, 0, 0], [21, 2, 21, 3, 0, 0, 0, 0], [18, 4, 18, 5, 0, 0, 0, 0], [1, 4, 1, 5, 0, 0, 0, 0], [18, 6, 18, 7, 0, 0, 0, 0], [21, 6, 21, 7, 0, 0, 0, 0], [18, 8, 18, 9, 0, 0, 0, 0], [1, 8, 1, 9, 0, 0, 0, 0], [20, 2, 20, 3, 0, 0, 0, 0], [39, 2, 39, 3, 0, 0, 0, 0], [20, 4, 20, 5, 0, 0, 0, 0], [19, 4, 19, 5, 0, 0, 0, 0], [20, 6, 20, 7, 0, 0, 0, 0], [39, 6, 39, 7, 0, 0, 0, 0], [20, 8, 20, 9, 0, 0, 0, 0], [19, 8, 19, 9, 0, 0, 0, 0], [22, 2, 22, 3, 0, 0, 0, 0], [37, 2, 37, 3, 0, 0, 0, 0], [22, 4, 22, 5, 0, 0, 0, 0], [17, 4, 17, 5, 0, 0, 0, 0], [22, 6, 22, 7, 0, 0, 0, 0], [37, 6, 37, 7, 0, 0, 0, 0], [22, 8, 22, 9, 0, 0, 0, 0], [17, 8, 17, 9, 0, 0, 0, 0], [24, 2, 24, 3, 0, 0, 0, 0], [35, 2, 35, 3, 0, 0, 0, 0], [24, 4, 24, 5, 0, 0, 0, 0], [15, 4, 15, 5, 0, 0, 0, 0], [24, 6, 24, 7, 0, 0, 0, 0], [35, 6, 35, 7, 0, 0, 0, 0], [24, 8, 24, 9, 0, 0, 0, 0], [15, 8, 15, 9, 0, 0, 0, 0], [26, 2, 26, 3, 0, 0, 0, 0], [33, 2, 33, 3, 0, 0, 0, 0], [26, 4, 26, 5, 0, 0, 0, 0], [13, 4, 13, 5, 0, 0, 0, 0], [26, 6, 26, 7, 0, 0, 0, 0], [33, 6, 33, 7, 0, 0, 0, 0], [26, 8, 26, 9, 0, 0, 0, 0], [13, 8, 13, 9, 0, 0, 0, 0], [28, 2, 28, 3, 0, 0, 0, 0], [31, 2, 31, 3, 0, 0, 0, 0], [28, 4, 28, 5, 0, 0, 0, 0], [11, 4, 11, 5, 0, 0, 0, 0], [28, 6, 28, 7, 0, 0, 0, 0], [31, 6, 31, 7, 0, 0, 0, 0], [28, 8, 28, 9, 0, 0, 0, 0], [11, 8, 11, 9, 0, 0, 0, 0], [30, 2, 30, 3, 0, 0, 0, 0], [49, 2, 49, 3, 0, 0, 0, 0], [30, 4, 30, 5, 0, 0, 0, 0], [29, 4, 29, 5, 0, 0, 0, 0], [30, 6, 30, 7, 0, 0, 0, 0], [49, 6, 49, 7, 0, 0, 0, 0], [30, 8, 30, 9, 0, 0, 0, 0], [29, 8, 29, 9, 0, 0, 0, 0], [32, 2, 32, 3, 0, 0, 0, 0], [47, 2, 47, 3, 0, 0, 0, 0], [32, 4, 32, 5, 0, 0, 0, 0], [27, 4, 27, 5, 0, 0, 0, 0], [32, 6, 32, 7, 0, 0, 0, 0], [47, 6, 47, 7, 0, 0, 0, 0], [32, 8, 32, 9, 0, 0, 0, 0], [27, 8, 27, 9, 0, 0, 0, 0], [34, 2, 34, 3, 0, 0, 0, 0], [45, 2, 45, 3, 0, 0, 0, 0], [34, 4, 34, 5, 0, 0, 0, 0], [25, 4, 25, 5, 0, 0, 0, 0], [34, 6, 34, 7, 0, 0, 0, 0], [45, 6, 45, 7, 0, 0, 0, 0], [34, 8, 34, 9, 0, 0, 0, 0], [25, 8, 25, 9, 0, 0, 0, 0], [36, 2, 36, 3, 0, 0, 0, 0], [43, 2, 43, 3, 0, 0, 0, 0], [36, 4, 36, 5, 0, 0, 0, 0], [23, 4, 23, 5, 0, 0, 0, 0], [36, 6, 36, 7, 0, 0, 0, 0], [43, 6, 43, 7, 0, 0, 0, 0], [36, 8, 36, 9, 0, 0, 0, 0], [23, 8, 23, 9, 0, 0, 0, 0], [38, 2, 38, 3, 0, 0, 0, 0], [41, 2, 41, 3, 0, 0, 0, 0], [38, 4, 38, 5, 0, 0, 0, 0], [21, 4, 21, 5, 0, 0, 0, 0], [38, 6, 38, 7, 0, 0, 0, 0], [41, 6, 41, 7, 0, 0, 0, 0], [38, 8, 38, 9, 0, 0, 0, 0], [21, 8, 21, 9, 0, 0, 0, 0], [40, 2, 40, 3, 0, 0, 0, 0], [59, 2, 59, 3, 0, 0, 0, 0], [40, 4, 40, 5, 0, 0, 0, 0], [39, 4, 39, 5, 0, 0, 0, 0], [40, 6, 40, 7, 0, 0, 0, 0], [59, 6, 59, 7, 0, 0, 0, 0], [40, 8, 40, 9, 0, 0, 0, 0], [39, 8, 39, 9, 0, 0, 0, 0], [42, 2, 42, 3, 0, 0, 0, 0], [57, 2, 57, 3, 0, 0, 0, 0], [42, 4, 42, 5, 0, 0, 0, 0], [37, 4, 37, 5, 0, 0, 0, 0], [42, 6, 42, 7, 0, 0, 0, 0], [57, 6, 57, 7, 0, 0, 0, 0], [42, 8, 42, 9, 0, 0, 0, 0], [37, 8, 37, 9, 0, 0, 0, 0], [44, 2, 44, 3, 0, 0, 0, 0], [55, 2, 55, 3, 0, 0, 0, 0], [44, 4, 44, 5, 0, 0, 0, 0], [35, 4, 35, 5, 0, 0, 0, 0], [44, 6, 44, 7, 0, 0, 0, 0], [55, 6, 55, 7, 0, 0, 0, 0], [44, 8, 44, 9, 0, 0, 0, 0], [35, 8, 35, 9, 0, 0, 0, 0], [46, 2, 46, 3, 0, 0, 0, 0], [53, 2, 53, 3, 0, 0, 0, 0], [46, 4, 46, 5, 0, 0, 0, 0], [33, 4, 33, 5, 0, 0, 0, 0], [46, 6, 46, 7, 0, 0, 0, 0], [53, 6, 53, 7, 0, 0, 0, 0], [46, 8, 46, 9, 0, 0, 0, 0], [33, 8, 33, 9, 0, 0, 0, 0], [48, 2, 48, 3, 0, 0, 0, 0], [51, 2, 51, 3, 0, 0, 0, 0], [48, 4, 48, 5, 0, 0, 0, 0], [31, 4, 31, 5, 0, 0, 0, 0], [48, 6, 48, 7, 0, 0, 0, 0], [51, 6, 51, 7, 0, 0, 0, 0], [48, 8, 48, 9, 0, 0, 0, 0], [31, 8, 31, 9, 0, 0, 0, 0], [50, 2, 50, 3, 0, 0, 0, 0], [69, 2, 69, 3, 0, 0, 0, 0], [50, 4, 50, 5, 0, 0, 0, 0], [49, 4, 49, 5, 0, 0, 0, 0], [50, 6, 50, 7, 0, 0, 0, 0], [69, 6, 69, 7, 0, 0, 0, 0], [50, 8, 50, 9, 0, 0, 0, 0], [49, 8, 49, 9, 0, 0, 0, 0], [52, 2, 52, 3, 0, 0, 0, 0], [67, 2, 67, 3, 0, 0, 0, 0], [52, 4, 52, 5, 0, 0, 0, 0], [47, 4, 47, 5, 0, 0, 0, 0], [52, 6, 52, 7, 0, 0, 0, 0], [67, 6, 67, 7, 0, 0, 0, 0], [52, 8, 52, 9, 0, 0, 0, 0], [47, 8, 47, 9, 0, 0, 0, 0], [54, 2, 54, 3, 0, 0, 0, 0], [65, 2, 65, 3, 0, 0, 0, 0], [54, 4, 54, 5, 0, 0, 0, 0], [45, 4, 45, 5, 0, 0, 0, 0], [54, 6, 54, 7, 0, 0, 0, 0], [65, 6, 65, 7, 0, 0, 0, 0], [54, 8, 54, 9, 0, 0, 0, 0], [45, 8, 45, 9, 0, 0, 0, 0], [56, 2, 56, 3, 0, 0, 0, 0], [63, 2, 63, 3, 0, 0, 0, 0], [56, 4, 56, 5, 0, 0, 0, 0], [43, 4, 43, 5, 0, 0, 0, 0], [56, 6, 56, 7, 0, 0, 0, 0], [63, 6, 63, 7, 0, 0, 0, 0], [56, 8, 56, 9, 0, 0, 0, 0], [43, 8, 43, 9, 0, 0, 0, 0], [58, 2, 58, 3, 0, 0, 0, 0], [61, 2, 61, 3, 0, 0, 0, 0], [58, 4, 58, 5, 0, 0, 0, 0], [41, 4, 41, 5, 0, 0, 0, 0], [58, 6, 58, 7, 0, 0, 0, 0], [61, 6, 61, 7, 0, 0, 0, 0], [58, 8, 58, 9, 0, 0, 0, 0], [41, 8, 41, 9, 0, 0, 0, 0], [60, 2, 60, 3, 0, 0, 0, 0], [79, 2, 79, 3, 0, 0, 0, 0], [60, 4, 60, 5, 0, 0, 0, 0], [59, 4, 59, 5, 0, 0, 0, 0], [60, 6, 60, 7, 0, 0, 0, 0], [79, 6, 79, 7, 0, 0, 0, 0], [60, 8, 60, 9, 0, 0, 0, 0], [59, 8, 59, 9, 0, 0, 0, 0], [62, 2, 62, 3, 0, 0, 0, 0], [77, 2, 77, 3, 0, 0, 0, 0], [62, 4, 62, 5, 0, 0, 0, 0], [57, 4, 57, 5, 0, 0, 0, 0], [62, 6, 62, 7, 0, 0, 0, 0], [77, 6, 77, 7, 0, 0, 0, 0], [62, 8, 62, 9, 0, 0, 0, 0], [57, 8, 57, 9, 0, 0, 0, 0], [64, 2, 64, 3, 0, 0, 0, 0], [75, 2, 75, 3, 0, 0, 0, 0], [64, 4, 64, 5, 0, 0, 0, 0], [55, 4, 55, 5, 0, 0, 0, 0], [64, 6, 64, 7, 0, 0, 0, 0], [75, 6, 75, 7, 0, 0, 0, 0], [64, 8, 64, 9, 0, 0, 0, 0], [55, 8, 55, 9, 0, 0, 0, 0], [66, 2, 66, 3, 0, 0, 0, 0], [73, 2, 73, 3, 0, 0, 0, 0], [66, 4, 66, 5, 0, 0, 0, 0], [53, 4, 53, 5, 0, 0, 0, 0], [66, 6, 66, 7, 0, 0, 0, 0], [73, 6, 73, 7, 0, 0, 0, 0], [66, 8, 66, 9, 0, 0, 0, 0], [53, 8, 53, 9, 0, 0, 0, 0], [68, 2, 68, 3, 0, 0, 0, 0], [71, 2, 71, 3, 0, 0, 0, 0], [68, 4, 68, 5, 0, 0, 0, 0], [51, 4, 51, 5, 0, 0, 0, 0], [68, 6, 68, 7, 0, 0, 0, 0], [71, 6, 71, 7, 0, 0, 0, 0], [68, 8, 68, 9, 0, 0, 0, 0], [51, 8, 51, 9, 0, 0, 0, 0], [70, 2, 70, 3, 0, 0, 0, 0], [89, 2, 89, 3, 0, 0, 0, 0], [70, 4, 70, 5, 0, 0, 0, 0], [69, 4, 69, 5, 0, 0, 0, 0], [70, 6, 70, 7, 0, 0, 0, 0], [89, 6, 89, 7, 0, 0, 0, 0], [70, 8, 70, 9, 0, 0, 0, 0], [69, 8, 69, 9, 0, 0, 0, 0], [72, 2, 72, 3, 0, 0, 0, 0], [87, 2, 87, 3, 0, 0, 0, 0], [72, 4, 72, 5, 0, 0, 0, 0], [67, 4, 67, 5, 0, 0, 0, 0], [72, 6, 72, 7, 0, 0, 0, 0], [87, 6, 87, 7, 0, 0, 0, 0], [72, 8, 72, 9, 0, 0, 0, 0], [67, 8, 67, 9, 0, 0, 0, 0], [74, 2, 74, 3, 0, 0, 0, 0], [85, 2, 85, 3, 0, 0, 0, 0], [74, 4, 74, 5, 0, 0, 0, 0], [65, 4, 65, 5, 0, 0, 0, 0], [74, 6, 74, 7, 0, 0, 0, 0], [85, 6, 85, 7, 0, 0, 0, 0], [74, 8, 74, 9, 0, 0, 0, 0], [65, 8, 65, 9, 0, 0, 0, 0], [76, 2, 76, 3, 0, 0, 0, 0], [83, 2, 83, 3, 0, 0, 0, 0], [76, 4, 76, 5, 0, 0, 0, 0], [63, 4, 63, 5, 0, 0, 0, 0], [76, 6, 76, 7, 0, 0, 0, 0], [83, 6, 83, 7, 0, 0, 0, 0], [76, 8, 76, 9, 0, 0, 0, 0], [63, 8, 63, 9, 0, 0, 0, 0], [78, 2, 78, 3, 0, 0, 0, 0], [81, 2, 81, 3, 0, 0, 0, 0], [78, 4, 78, 5, 0, 0, 0, 0], [61, 4, 61, 5, 0, 0, 0, 0], [78, 6, 78, 7, 0, 0, 0, 0], [81, 6, 81, 7, 0, 0, 0, 0], [78, 8, 78, 9, 0, 0, 0, 0], [61, 8, 61, 9, 0, 0, 0, 0], [80, 2, 80, 3, 0, 0, 0, 0], [99, 2, 99, 3, 0, 0, 0, 0], [80, 4, 80, 5, 0, 0, 0, 0], [79, 4, 79, 5, 0, 0, 0, 0], [80, 6, 80, 7, 0, 0, 0, 0], [99, 6, 99, 7, 0, 0, 0, 0], [80, 8, 80, 9, 0, 0, 0, 0], [79, 8, 79, 9, 0, 0, 0, 0], [82, 2, 82, 3, 0, 0, 0, 0], [97, 2, 97, 3, 0, 0, 0, 0], [82, 4, 82, 5, 0, 0, 0, 0], [77, 4, 77, 5, 0, 0, 0, 0], [82, 6, 82, 7, 0, 0, 0, 0], [97, 6, 97, 7, 0, 0, 0, 0], [82, 8, 82, 9, 0, 0, 0, 0], [77, 8, 77, 9, 0, 0, 0, 0], [84, 2, 84, 3, 0, 0, 0, 0], [95, 2, 95, 3, 0, 0, 0, 0], [84, 4, 84, 5, 0, 0, 0, 0], [75, 4, 75, 5, 0, 0, 0, 0], [84, 6, 84, 7, 0, 0, 0, 0], [95, 6, 95, 7, 0, 0, 0, 0], [84, 8, 84, 9, 0, 0, 0, 0], [75, 8, 75, 9, 0, 0, 0, 0], [86, 2, 86, 3, 0, 0, 0, 0], [93, 2, 93, 3, 0, 0, 0, 0], [86, 4, 86, 5, 0, 0, 0, 0], [73, 4, 73, 5, 0, 0, 0, 0], [86, 6, 86, 7, 0, 0, 0, 0], [93, 6, 93, 7, 0, 0, 0, 0], [86, 8, 86, 9, 0, 0, 0, 0], [73, 8, 73, 9, 0, 0, 0, 0], [88, 2, 88, 3, 0, 0, 0, 0], [91, 2, 91, 3, 0, 0, 0, 0], [88, 4, 88, 5, 0, 0, 0, 0], [71, 4, 71, 5, 0, 0, 0, 0], [88, 6, 88, 7, 0, 0, 0, 0], [91, 6, 91, 7, 0, 0, 0, 0], [88, 8, 88, 9, 0, 0, 0, 0], [71, 8, 71, 9, 0, 0, 0, 0],

TABLE 32-continued

[90, 4, 90, 5, 0, 0, 0, 0], [89, 4, 89, 5, 0, 0, 0, 0], [90, 8, 90, 9, 0, 0, 0, 0], [89, 8, 89, 9, 0, 0, 0, 0], [92, 4, 92, 5, 0, 0, 0, 0], [87, 4, 87, 5, 0, 0, 0, 0], [92, 8, 92, 9, 0, 0, 0, 0], [87, 8, 87, 9, 0, 0, 0, 0], [94, 4, 94, 5, 0, 0, 0, 0], [85, 4, 85, 5, 0, 0, 0, 0], [94, 8, 94, 9, 0, 0, 0, 0], [85, 8, 85, 9, 0, 0, 0, 0], [96, 4, 96, 5, 0, 0, 0, 0], [83, 4, 83, 5, 0, 0, 0, 0], [96, 8, 96, 9, 0, 0, 0, 0], [83, 8, 83, 9, 0, 0, 0, 0], [98, 4, 98, 5, 0, 0, 0, 0], [81, 4, 81, 5, 0, 0, 0, 0], [98, 8, 98, 9, 0, 0, 0, 0], [81, 8, 81, 9, 0, 0, 0, 0], [0, 3, 0, 4, 0, 0, 0, 0], [0, 7, 0, 8, 0, 0, 0, 0], [9, 3, 9, 4, 0, 0, 0, 0], [9, 7, 9, 8, 0, 0, 0, 0], [10, 1, 10, 2, 0, 0, 0, 0], [10, 5, 10, 6, 0, 0, 0, 0], [10, 9, 10, 10, 0, 0, 0, 0], [19, 1, 19, 2, 0, 0, 0, 0], [19, 5, 19, 6, 0, 0, 0, 0], [19, 9, 19, 10, 0, 0, 0, 0], [20, 3, 20, 4, 0, 0, 0, 0], [20, 7, 20, 8, 0, 0, 0, 0], [29, 3, 29, 4, 0, 0, 0, 0], [29, 7, 29, 8, 0, 0, 0, 0], [30, 1, 30, 2, 0, 0, 0, 0], [30, 5, 30, 6, 0, 0, 0, 0], [30, 9, 30, 10, 0, 0, 0, 0], [39, 1, 39, 2, 0, 0, 0, 0], [39, 5, 39, 6, 0, 0, 0, 0], [39, 9, 39, 10, 0, 0, 0, 0], [40, 3, 40, 4, 0, 0, 0, 0], [40, 7, 40, 8, 0, 0, 0, 0], [49, 3, 49, 4, 0, 0, 0, 0], [49, 7, 49, 8, 0, 0, 0, 0], [50, 1, 50, 2, 0, 0, 0, 0], [50, 5, 50, 6, 0, 0, 0, 0], [50, 9, 50, 10, 0, 0, 0, 0], [59, 1, 59, 2, 0, 0, 0, 0], [59, 5, 59, 6, 0, 0, 0, 0], [59, 9, 59, 10, 0, 0, 0, 0], [60, 3, 60, 4, 0, 0, 0, 0], [60, 7, 60, 8, 0, 0, 0, 0], [69, 3, 69, 4, 0, 0, 0, 0], [69, 7, 69, 8, 0, 0, 0, 0], [70, 1, 70, 2, 0, 0, 0, 0], [70, 5, 70, 6, 0, 0, 0, 0], [70, 9, 70, 10, 0, 0, 0, 0], [79, 1, 79, 2, 0, 0, 0, 0], [79, 5, 79, 6, 0, 0, 0, 0], [79, 9, 79, 10, 0, 0, 0, 0], [80, 3, 80, 4, 0, 0, 0, 0], [80, 7, 80, 8, 0, 0, 0, 0], [89, 3, 89, 4, 0, 0, 0, 0], [89, 7, 89, 8, 0, 0, 0, 0], [90, 1, 90, 2, 0, 0, 0, 0], [90, 5, 90, 6, 0, 0, 0, 0], [90, 9, 90, 10, 0, 0, 0, 0], [99, 1, 99, 2, 0, 0, 0, 0], [99, 5, 99, 6, 0, 0, 0, 0], [99, 9, 99, 10, 0, 0, 0, 0], [0, 4, 0, 5, 0, 0, 0, 0], [0, 8, 0, 9, 0, 0, 0, 0], [1, 2, 1, 3, 0, 0, 0, 0], [1, 6, 1, 7, 0, 0, 0, 0], [2, 4, 2, 5, 0, 0, 0, 0], [2, 8, 2, 9, 0, 0, 0, 0], [3, 2, 3, 3, 0, 0, 0, 0], [3, 6, 3, 7, 0, 0, 0, 0], [4, 4, 4, 5, 0, 0, 0, 0], [4, 8, 4, 9, 0, 0, 0, 0], [5, 2, 5, 3, 0, 0, 0, 0], [5, 6, 5, 7, 0, 0, 0, 0], [6, 4, 6, 5, 0, 0, 0, 0], [6, 8, 6, 9, 0, 0, 0, 0], [7, 2, 7, 3, 0, 0, 0, 0], [7, 6, 7, 7, 0, 0, 0, 0], [8, 4, 8, 5, 0, 0, 0, 0], [8, 8, 8, 9, 0, 0, 0, 0], [9, 2, 9, 3, 0, 0, 0, 0], [9, 6, 9, 7, 0, 0, 0, 0], [90, 2, 90, 3, 0, 0, 0, 0], [90, 6, 90, 7, 0, 0, 0, 0], [91, 4, 91, 5, 0, 0, 0, 0], [91, 8, 91, 9, 0, 0, 0, 0], [92, 2, 92, 3, 0, 0, 0, 0], [92, 6, 92, 7, 0, 0, 0, 0], [93, 4, 93, 5, 0, 0, 0, 0], [93, 8, 93, 9, 0, 0, 0, 0], [94, 2, 94, 3, 0, 0, 0, 0], [94, 6, 94, 7, 0, 0, 0, 0], [95, 4, 95, 5, 0, 0, 0, 0], [95, 8, 95, 9, 0, 0, 0, 0], [96, 2, 96, 3, 0, 0, 0, 0], [96, 6, 96, 7, 0, 0, 0, 0], [97, 4, 97, 5, 0, 0, 0, 0], [97, 8, 97, 9, 0, 0, 0, 0], [98, 2, 98, 3, 0, 0, 0, 0], [98, 6, 98, 7, 0, 0, 0, 0], [99, 4, 99, 5, 0, 0, 0, 0], [99, 8, 99, 9, 0, 0, 0, 0], [1, 1, 0, 0, 0, 1, 0, 0], [0, 0, 1, 2, 0, 0, 0, 2], [1, 3, 0, 0, 0, 2, 3, 0, 0], [0, 0, 1, 4, 0, 0, 2, 4], [1, 5, 0, 0, 0, 5, 0, 0], [0, 0, 1, 6, 0, 0, 0, 6], [1, 7, 0, 0, 2, 7, 0, 0], [0, 0, 1, 8, 0, 0, 2, 8], [1, 9, 0, 0, 0, 9, 0, 0], [0, 0, 1, 10, 0, 0, 0, 10], [3, 1, 0, 0, 2, 1, 0, 0], [0, 0, 3, 2, 0, 0, 2, 2], [3, 3, 0, 0, 0, 4, 3, 0, 0], [0, 0, 3, 4, 0, 0, 4, 4], [3, 5, 0, 0, 2, 5, 0, 0], [0, 0, 3, 6, 0, 0, 2, 6], [3, 7, 0, 0, 4, 7, 0, 0], [0, 0, 3, 8, 0, 0, 4, 8], [3, 9, 0, 0, 0, 2, 9, 0, 0], [0, 0, 3, 10, 0, 0, 2, 10], [5, 1, 0, 0, 4, 1, 0, 0], [0, 0, 5, 2, 0, 0, 4, 2], [5, 3, 0, 0, 6, 3, 0, 0], [0, 0, 5, 4, 0, 0, 6, 4], [5, 5, 0, 0, 4, 5, 0, 0], [0, 0, 5, 6, 0, 0, 4, 6], [5, 7, 0, 0, 6, 7, 0, 0], [0, 0, 5, 8, 0, 0, 6, 8], [5, 9, 0, 0, 4, 9, 0, 0], [0, 0, 5, 10, 0, 0, 4, 10], [7, 1, 0, 0, 6, 1, 0, 0], [0, 0, 7, 2, 0, 0, 6, 2], [7, 3, 0, 0, 8, 3, 0, 0], [0, 0, 7, 4, 0, 0, 8, 4], [7, 5, 0, 0, 6, 5, 0, 0], [0, 0, 7, 6, 0, 0, 6, 6], [7, 7, 0, 0, 8, 7, 0, 0], [0, 0, 7, 8, 0, 0, 8, 8], [7, 9, 0, 0, 6, 9, 0, 0], [0, 0, 7, 10, 0, 0, 6, 10], [9, 1, 0, 0, 8, 1, 0, 0], [0, 0, 9, 2, 0, 0, 8, 2], [9, 5, 0, 0, 8, 5, 0, 0], [0, 0, 9, 6, 0, 0, 8, 6], [9, 9, 0, 0, 8, 9, 0, 0], [0, 0, 9, 10, 0, 0, 8, 10], [11, 1, 0, 0, 12, 1, 0, 0], [0, 0, 11, 2, 0, 0, 12, 2], [11, 3, 0, 0, 10, 3, 0, 0], [0, 0, 11, 4, 0, 0, 10, 4], [11, 5, 0, 0, 12, 5, 0, 0], [0, 0, 11, 6, 0, 0, 12, 6], [11, 7, 0, 0, 10, 7, 0, 0], [0, 0, 11, 8, 0, 0, 10, 8], [11, 9, 0, 0, 12, 9, 0, 0], [0, 0, 11, 10, 0, 0, 12, 10], [13, 1, 0, 0, 14, 1, 0, 0], [0, 0, 13, 2, 0, 0, 14, 2], [13, 3, 0, 0, 12, 3, 0, 0], [0, 0, 13, 4, 0, 0, 12, 4], [13, 5, 0, 0, 14, 5, 0, 0], [0, 0, 13, 6, 0, 0, 14, 6], [13, 7, 0, 0, 12, 7, 0, 0], [0, 0, 13, 8, 0, 0, 12, 8], [13, 9, 0, 0, 14, 9, 0, 0], [0, 0, 13, 10, 0, 0, 14, 10], [15, 1, 0, 0, 16, 1, 0, 0], [0, 0, 15, 2, 0, 0, 16, 2], [15, 3, 0, 0, 14, 3, 0, 0], [0, 0, 15, 4, 0, 0, 14, 4], [15, 5, 0, 0, 16, 5, 0, 0], [0, 0, 15, 6, 0, 0, 16, 6], [15, 7, 0, 0, 14, 7, 0, 0], [0, 0, 15, 8, 0, 0, 14, 8], [15, 9, 0, 0, 16, 9, 0, 0], [0, 0, 15, 10, 0, 0, 16, 10], [17, 1, 0, 0, 18, 1, 0, 0], [0, 0, 17, 2, 0, 0, 18, 2], [17, 3, 0, 0, 16, 3, 0, 0], [0, 0, 17, 4, 0, 0, 16, 4], [17, 5, 0, 0, 18, 5, 0, 0], [0, 0, 17, 6, 0, 0, 18, 6], [17, 7, 0, 0, 16, 7, 0, 0], [0, 0, 17, 8, 0, 0, 16, 8], [17, 9, 0, 0, 18, 9, 0, 0], [0, 0, 17, 10, 0, 0, 18, 10], [19, 3, 0, 0, 18, 3, 0, 0], [0, 0, 19, 4, 0, 0, 18, 4], [19, 7, 0, 0, 18, 7, 0, 0], [0, 0, 19, 8, 0, 0, 18, 8], [21, 1, 0, 0, 20, 1, 0, 0], [0, 0, 21, 2, 0, 0, 20, 2], [21, 3, 0, 0, 22, 3, 0, 0], [0, 0, 21, 4, 0, 0, 22, 4], [21, 5, 0, 0, 20, 5, 0, 0], [0, 0, 21, 6, 0, 0, 20, 6], [21, 7, 0, 0, 22, 7, 0, 0], [0, 0, 21, 8, 0, 0, 22, 8], [21, 9, 0, 0, 20, 9, 0, 0], [0, 0, 21, 10, 0, 0, 20, 10], [23, 1, 0, 0, 22, 1, 0, 0], [0, 0, 23, 2, 0, 0, 22, 2], [23, 3, 0, 0, 24, 3, 0, 0], [0, 0, 23, 4, 0, 0, 24, 4], [23, 5, 0, 0, 22, 5, 0, 0], [0, 0, 23, 6, 0, 0, 22, 6], [23, 7, 0, 0, 24, 7, 0, 0], [0, 0, 23, 8, 0, 0, 24, 8], [23, 9, 0, 0, 22, 9, 0, 0], [0, 0, 23, 10, 0, 0, 22, 10], [25, 1, 0, 0, 24, 1, 0, 0], [0, 0, 25, 2, 0, 0, 24, 2], [25, 3, 0, 0, 26, 3, 0, 0], [0, 0, 25, 4, 0, 0, 26, 4], [25, 5, 0, 0, 24, 5, 0, 0], [0, 0, 25, 6, 0, 0, 24, 6], [25, 7, 0, 0, 26, 7, 0, 0], [0, 0, 25, 8, 0, 0, 26, 8], [25, 9, 0, 0, 24, 9, 0, 0], [0, 0, 25, 10, 0, 0, 24, 10], [27, 1, 0, 0, 26, 1, 0, 0], [0, 0, 27, 2, 0, 0, 26, 2], [27, 3, 0, 0, 28, 3, 0, 0], [0, 0, 27, 4, 0, 0, 28, 4], [27, 5, 0, 0, 26, 5, 0, 0], [0, 0, 27, 6, 0, 0, 26, 6], [27, 7, 0, 0, 28, 7, 0, 0], [0, 0, 27, 8, 0, 0, 28, 8], [27, 9, 0, 0, 26, 9, 0, 0], [0, 0, 27, 10, 0, 0, 26, 10], [29, 1, 0, 0, 28, 1, 0, 0], [0, 0, 29, 2, 0, 0, 28, 2], [29, 5, 0, 0, 28, 5, 0, 0], [0, 0, 29, 6, 0, 0, 28, 6], [29, 9, 0, 0, 28, 9, 0, 0], [0, 0, 29, 10, 0, 0, 28, 10], [31, 1, 0, 0, 32, 1, 0, 0], [0, 0, 31, 2, 0, 0, 32, 2], [31, 3, 0, 0, 30, 3, 0, 0], [0, 0, 31, 4, 0, 0, 30, 4], [31, 5, 0, 0, 32, 5, 0, 0], [0, 0, 31, 6, 0, 0, 32, 6], [31, 7, 0, 0, 30, 7, 0, 0], [0, 0, 31, 8, 0, 0, 30, 8], [31, 9, 0, 0, 32, 9, 0, 0], [0, 0, 31, 10, 0, 0, 32, 10], [33, 1, 0, 0, 34, 1, 0, 0], [0, 0, 33, 2, 0, 0, 34, 2], [33, 3, 0, 0, 32, 3, 0, 0], [0, 0, 33, 4, 0, 0, 32, 4], [33, 5, 0, 0, 34, 5, 0, 0], [0, 0, 33, 6, 0, 0, 34, 6], [33, 7, 0, 0, 32, 7, 0, 0], [0, 0, 33, 8, 0, 0, 32, 8], [33, 9, 0, 0, 34, 9, 0, 0], [0, 0, 33, 10, 0, 0, 34, 10], [35, 1, 0, 0, 36, 1, 0, 0], [0, 0, 35, 2, 0, 0, 36, 2], [35, 3, 0, 0, 34, 3, 0, 0], [0, 0, 35, 4, 0, 0, 34, 4], [35, 5, 0, 0, 36, 5, 0, 0], [0, 0, 35, 6, 0, 0, 36, 6], [35, 7, 0, 0, 34, 7, 0, 0], [0, 0, 35, 8, 0, 0, 34, 8], [35, 9, 0, 0, 36, 9, 0, 0], [0, 0, 35, 10, 0, 0, 36, 10], [37, 1, 0, 0, 38, 1, 0, 0], [0, 0, 37, 2, 0, 0, 38, 2], [37, 3, 0, 0, 36, 3, 0, 0], [0, 0, 37, 4, 0, 0, 36, 4], [37, 5, 0, 0, 38, 5, 0, 0], [0, 0, 37, 6, 0, 0, 38, 6], [37, 7, 0, 0, 36, 7, 0, 0], [0, 0, 37, 8, 0, 0, 36, 8], [37, 9, 0, 0, 38, 9, 0, 0], [0, 0, 37, 10, 0, 0, 38, 10], [39, 3, 0, 0, 38, 3, 0, 0], [0, 0, 39, 4, 0, 0, 38, 4], [39, 7, 0, 0, 38, 7, 0, 0], [0, 0, 39, 8, 0, 0, 38, 8], [41, 1, 0, 0, 40, 1, 0, 0], [0, 0, 41, 2, 0, 0, 40, 2], [41, 3, 0, 0, 42, 3, 0, 0], [0, 0, 41, 4, 0, 0, 42, 4], [41, 5, 0, 0, 40, 5, 0, 0], [0, 0, 41, 6, 0, 0, 40, 6], [41, 7, 0, 0, 42, 7, 0, 0], [0, 0, 41, 8, 0, 0, 42, 8], [41, 9, 0, 0, 40, 9, 0, 0], [0, 0, 41, 10, 0, 0, 40, 10], [43, 1, 0, 0, 42, 1, 0, 0], [0, 0, 43, 2, 0, 0, 42, 2], [43, 3, 0, 0, 44, 3, 0, 0], [0, 0, 43, 4, 0, 0, 44, 4], [43, 5, 0, 0, 42, 5, 0, 0], [0, 0, 43, 6, 0, 0, 42, 6], [43, 7, 0, 0, 44, 7, 0, 0], [0, 0, 43, 8, 0, 0, 44, 8], [43, 9, 0, 0, 42, 9, 0, 0], [0, 0, 43, 10, 0, 0, 42, 10], [45, 1, 0, 0, 44, 1, 0, 0], [0, 0, 45, 2, 0, 0, 44, 2], [45, 3, 0, 0, 46, 3, 0, 0], [0, 0, 45, 4, 0, 0, 46, 4], [45, 5, 0, 0, 44, 5, 0, 0], [0, 0, 45, 6, 0, 0, 44, 6], [45, 7, 0, 0, 46, 7, 0, 0], [0, 0, 45, 8, 0, 0, 46, 8], [45, 9, 0, 0, 44, 9, 0, 0], [0, 0, 45, 10, 0, 0, 44, 10], [47, 1, 0, 0, 46, 1, 0, 0], [0, 0, 47, 2, 0, 0, 46, 2], [47, 3, 0, 0, 48, 3, 0, 0], [0, 0, 47, 4, 0, 0, 48, 4], [47, 5, 0, 0, 46, 5, 0, 0], [0, 0, 47, 6, 0, 0, 46, 6], [47, 7, 0, 0, 48, 7, 0, 0], [0, 0, 47, 8, 0, 0, 48, 8], [47, 9, 0, 0, 46, 9, 0, 0], [0, 0, 47, 10, 0, 0, 46, 10], [49, 1, 0, 0, 48, 1, 0, 0], [0, 0, 49, 2, 0, 0, 48, 2], [49, 5, 0, 0, 48, 5, 0, 0], [0, 0, 49, 6, 0, 0, 48, 6], [49, 9, 0, 0, 48, 9, 0, 0], [0, 0, 49, 10, 0, 0, 48, 10], [51, 1, 0, 0, 52, 1, 0, 0], [0, 0, 51, 2, 0, 0, 52, 2], [51, 3, 0, 0, 50, 3, 0, 0], [0, 0, 51, 4, 0, 0, 50, 4], [51, 5, 0, 0, 52, 5, 0, 0], [0, 0, 51, 6, 0, 0, 52, 6], [51, 7, 0, 0, 50, 7, 0, 0], [0, 0, 51, 8, 0, 0, 50, 8], [51, 9, 0, 0, 52, 9, 0, 0], [0, 0, 51, 10, 0, 0, 52, 10], [53, 1, 0, 0, 54, 1, 0, 0], [0, 0, 53, 2, 0, 0, 54, 2], [53, 3, 0, 0, 52, 3, 0, 0], [0, 0, 53, 4, 0, 0, 52, 4], [53, 5, 0, 0, 54, 5, 0, 0], [0, 0, 53, 6, 0, 0, 54, 6], [53, 7, 0, 0, 52, 7, 0, 0], [0, 0, 53, 8, 0, 0, 52, 8], [53, 9, 0, 0, 54, 9, 0, 0], [0, 0, 53, 10, 0, 0, 54, 10], [55, 1, 0, 0, 56, 1, 0, 0], [0, 0, 55, 2, 0, 0, 56, 2], [55, 3, 0, 0, 54, 3, 0, 0], [0, 0, 55, 4, 0, 0, 54, 4], [55, 5, 0, 0, 56, 5, 0, 0], [0, 0, 55, 6, 0, 0, 56, 6], [55, 7, 0, 0, 54, 7, 0, 0], [0, 0, 55, 8, 0, 0, 54, 8], [55, 9, 0, 0, 56, 9, 0, 0], [0, 0, 55, 10, 0, 0, 56, 10], [57, 1, 0, 0, 58, 1, 0, 0], [0, 0, 57, 2, 0, 0, 58, 2], [57, 3, 0, 0, 56, 3, 0, 0], [0, 0, 57, 4, 0, 0, 56, 4], [57, 5, 0, 0, 58, 5, 0, 0], [0, 0, 57, 6, 0, 0, 58, 6], [57, 7, 0, 0, 56, 7, 0, 0], [0, 0, 57, 8, 0, 0, 56, 8], [57, 9, 0, 0, 58, 9, 0, 0], [0, 0, 57, 10, 0, 0, 58, 10], [59, 3, 0, 0, 58, 3, 0, 0], [0, 0, 59, 4, 0, 0, 58, 4], [59, 7, 0, 0, 58, 7, 0, 0], [0, 0, 59, 8, 0, 0, 58, 8], [61, 1, 0, 0, 60, 1, 0, 0], [0, 0, 61, 2, 0, 0, 60, 2], [61, 3, 0, 0, 62, 3, 0, 0], [0, 0, 61, 4, 0, 0, 62, 4], [61, 5, 0, 0, 60, 5, 0, 0], [0, 0, 61, 6, 0, 0, 60, 6], [61, 7, 0, 0, 62, 7, 0, 0], [0, 0, 61, 8, 0, 0, 62, 8], [61, 9, 0, 0, 60, 9, 0, 0], [0, 0, 61, 10, 0, 0, 60, 10], [63, 1, 0, 0, 62, 1, 0, 0], [0, 0, 63, 2, 0, 0, 62, 2], [63, 3, 0, 0, 64, 3, 0, 0], [0, 0, 63, 4, 0, 0, 64, 4], [63, 5, 0, 0, 62, 5, 0, 0], [0, 0, 63, 6, 0, 0, 62, 6], [63, 7, 0, 0, 64, 7, 0, 0], [0, 0, 63, 8, 0, 0, 64, 8], [63, 9, 0, 0, 62, 9, 0, 0], [0, 0, 63, 10, 0, 0, 62, 10], [65, 1, 0, 0, 64, 1, 0, 0], [0, 0, 65, 2, 0, 0, 64, 2], [65, 3, 0, 0, 66, 3, 0, 0], [0, 0, 65, 4, 0, 0, 66, 4], [65, 5, 0, 0, 64, 5, 0, 0], [0, 0, 65, 6, 0, 0, 64, 6], [65, 7, 0, 0, 66, 7, 0, 0], [0, 0, 65, 8, 0, 0, 66, 8], [65, 9, 0, 0, 64, 9, 0, 0], [0, 0, 65, 10, 0, 0, 64, 10], [67, 1, 0, 0, 66, 1, 0, 0], [0, 0, 67, 2, 0, 0, 66, 2], [67, 3, 0, 0, 68, 3, 0, 0], [0, 0, 67, 4, 0, 0, 68, 4], [67, 5, 0, 0, 66, 5, 0, 0], [0, 0, 67, 6, 0, 0, 66, 6], [67, 7, 0, 0, 68, 7, 0, 0], [0, 0, 67, 8, 0, 0, 68, 8], [67, 9, 0, 0, 66, 9, 0, 0], [0, 0, 67, 10, 0, 0, 66, 10], [69, 1, 0, 0, 68, 1, 0, 0], [0, 0, 69, 2, 0, 0, 68, 2], [69, 5, 0, 0, 68, 5, 0, 0], [0, 0, 69, 6, 0, 0, 68, 6], [69, 9, 0, 0, 68, 9, 0, 0], [0, 0, 69, 10, 0, 0, 68, 10], [71, 1, 0, 0, 72, 1, 0, 0], [0, 0, 71, 2, 0, 0, 72, 2], [71, 3, 0, 0, 70, 3, 0, 0], [0, 0, 71, 4, 0, 0, 70, 4], [71, 5, 0, 0, 72, 5, 0, 0], [0, 0, 71, 6, 0, 0, 72, 6], [71, 7, 0, 0, 70, 7, 0, 0], [0, 0, 71, 8, 0, 0, 70, 8], [71, 9, 0, 0, 72, 9, 0, 0], [0, 0, 71, 10, 0, 0, 72, 10], [73, 1, 0, 0, 74, 1, 0, 0], [0, 0, 73, 2, 0, 0, 74, 2], [73, 3, 0, 0, 72, 3, 0, 0], [0, 0, 73, 4, 0, 0, 72, 4], [73, 5, 0, 0, 74, 5, 0, 0], [0, 0, 73, 6, 0, 0, 74, 6], [73, 7, 0, 0, 72, 7, 0, 0], [0, 0, 73, 8, 0, 0, 72, 8], [73, 9, 0, 0, 74, 9, 0, 0], [0, 0, 73, 10, 0, 0, 74, 10], [75, 1, 0, 0, 76, 1, 0, 0], [0, 0, 75, 2,

TABLE 32-continued 0, 0, 76, 2], [75, 3, 0, 0, 74, 3, 0, 0], [0, 0, 75, 4, 0, 0, 74, 4], [75, 5, 0, 0, 76, 5, 0, 0], [0, 0, 75, 6, 0, 0, 76, 6], [75, 7, 0, 0, 74, 7, 0, 0], [0, 0, 75, 8, 0, 0, 74, 8], [75, 9, 0, 0, 76, 9, 0, 0], [0, 0, 75, 10, 0, 0, 76, 10], [77, 1, 0, 0, 78, 1, 0, 0], [0, 0, 77, 2, 0, 0, 78, 2], [77, 3, 0, 0, 76, 3, 0, 0], [0, 0, 77, 4, 0, 0, 76, 4], [77, 5, 0, 0, 78, 5, 0, 0], [0, 0, 77, 6, 0, 0, 78, 6], [77, 7, 0, 0, 76, 7, 0, 0], [0, 0, 77, 8, 0, 0, 76, 8], [77, 9, 0, 0, 78, 9, 0, 0], [0, 0, 77, 10, 0, 0, 78, 10], [79, 3, 0, 0, 78, 3, 0, 0], [0, 0, 79, 4, 0, 0, 78, 4], [79, 7, 0, 0, 78, 7, 0, 0], [0, 0, 79, 8, 0, 0, 78, 8], [81, 1, 0, 0, 80, 1, 0, 0], [0, 0, 81, 2, 0, 0, 80, 2], [81, 3, 0, 0, 82, 3, 0, 0], [0, 0, 81, 4, 0, 0, 82, 4], [81, 5, 0, 0, 80, 5, 0, 0], [0, 0, 81, 6, 0, 0, 80, 6], [81, 7, 0, 0, 82, 7, 0, 0], [0, 0, 81, 8, 0, 0, 82, 8], [81, 9, 0, 0, 80, 9, 0, 0], [0, 0, 81, 10, 0, 0, 80, 10], [83, 1, 0, 0, 82, 1, 0, 0], [0, 0, 83, 2, 0, 0, 82, 2], [83, 3, 0, 0, 84, 3, 0, 0], [0, 0, 83, 4, 0, 0, 84, 4], [83, 5, 0, 0, 82, 5, 0, 0], [0, 0, 83, 6, 0, 0, 82, 6], [83, 7, 0, 0, 84, 7, 0, 0], [0, 0, 83, 8, 0, 0, 84, 8], [83, 9, 0, 0, 82, 9, 0, 0], [0, 0, 83, 10, 0, 0, 82, 10], [85, 1, 0, 0, 84, 1, 0, 0], [0, 0, 85, 2, 0, 0, 84, 2], [85, 3, 0, 0, 86, 3, 0, 0], [0, 0, 85, 4, 0, 0, 86, 4], [85, 5, 0, 0, 84, 5, 0, 0], [0, 0, 85, 6, 0, 0, 84, 6], [85, 7, 0, 0, 86, 7, 0, 0], [0, 0, 85, 8, 0, 0, 86, 8], [85, 9, 0, 0, 84, 9, 0, 0], [0, 0, 85, 10, 0, 0, 84, 10], [87, 1, 0, 0, 86, 1, 0, 0], [0, 0, 87, 2, 0, 0, 86, 2], [87, 3, 0, 0, 88, 3, 0, 0], [0, 0, 87, 4, 0, 0, 88, 4], [87, 5, 0, 0, 86, 5, 0, 0], [0, 0, 87, 6, 0, 0, 86, 6], [87, 7, 0, 0, 88, 7, 0, 0], [0, 0, 87, 8, 0, 0, 88, 8], [87, 9, 0, 0, 86, 9, 0, 0], [0, 0, 87, 10, 0, 0, 86, 10], [89, 1, 0, 0, 88, 1, 0, 0], [0, 0, 89, 2, 0, 0, 88, 2], [89, 5, 0, 0, 88, 5, 0, 0], [0, 0, 89, 6, 0, 0, 88, 6], [89, 9, 0, 0, 88, 9, 0, 0], [0, 0, 89, 10, 0, 0, 88, 10], [91, 1, 0, 0, 92, 1, 0, 0], [0, 0, 91, 2, 0, 0, 92, 2], [91, 3, 0, 0, 90, 3, 0, 0], [0, 0, 91, 4, 0, 0, 90, 4], [91, 5, 0, 0, 92, 5, 0, 0], [0, 0, 91, 6, 0, 0, 92, 6], [91, 7, 0, 0, 90, 7, 0, 0], [0, 0, 91, 8, 0, 0, 90, 8], [91, 9, 0, 0, 92, 9, 0, 0], [0, 0, 91, 10, 0, 0, 92, 10], [93, 1, 0, 0, 94, 1, 0, 0], [0, 0, 93, 2, 0, 0, 94, 2], [93, 3, 0, 0, 92, 3, 0, 0], [0, 0, 93, 4, 0, 0, 92, 4], [93, 5, 0, 0, 94, 5, 0, 0], [0, 0, 93, 6, 0, 0, 94, 6], [93, 7, 0, 0, 92, 7, 0, 0], [0, 0, 93, 8, 0, 0, 92, 8], [93, 9, 0, 0, 94, 9, 0, 0], [0, 0, 93, 10, 0, 0, 94, 10], [95, 1, 0, 0, 96, 1, 0, 0], [0, 0, 95, 2, 0, 0, 96, 2], [95, 3, 0, 0, 94, 3, 0, 0], [0, 0, 95, 4, 0, 0, 94, 4], [95, 5, 0, 0, 96, 5, 0, 0], [0, 0, 95, 6, 0, 0, 96, 6], [95, 7, 0, 0, 94, 7, 0, 0], [0, 0, 95, 8, 0, 0, 94, 8], [95, 9, 0, 0, 96, 9, 0, 0], [0, 0, 95, 10, 0, 0, 96, 10], [97, 1, 0, 0, 98, 1, 0, 0], [0, 0, 97, 2, 0, 0, 98, 2], [97, 3, 0, 0, 96, 3, 0, 0], [0, 0, 97, 4, 0, 0, 96, 4], [97, 5, 0, 0, 98, 5, 0, 0], [0, 0, 97, 6, 0, 0, 98, 6], [97, 7, 0, 0, 96, 7, 0, 0], [0, 0, 97, 8, 0, 0, 96, 8], [97, 9, 0, 0, 98, 9, 0, 0], [0, 0, 97, 10, 0, 0, 98, 10], [99, 3, 0, 0, 98, 3, 0, 0], [0, 0, 99, 4, 0, 0, 98, 4], [99, 7, 0, 0, 98, 7, 0, 0], [0, 0, 99, 8, 0, 0, 98, 8], [2, 2, 0, 0, 19, 2, 0, 0], [0, 0, 3, 0, 0, 19, 3], [6, 6, 0, 0, 19, 6, 0, 0], [0, 0, 7, 0, 0, 19, 7], [2, 2, 0, 0, 17, 2, 0, 0], [0, 0, 2, 3, 0, 0, 17, 3], [2, 6, 0, 0, 17, 6, 0, 0], [0, 0, 2, 7, 0, 0, 17, 7], [4, 2, 0, 0, 15, 2, 0, 0], [0, 0, 4, 3, 0, 0, 15, 3], [4, 6, 0, 0, 15, 6, 0, 0], [0, 0, 4, 7, 0, 0, 15, 7], [6, 2, 0, 0, 13, 2, 0, 0], [0, 0, 6, 3, 0, 0, 13, 3], [6, 6, 0, 0, 13, 6, 0, 0], [0, 0, 6, 7, 0, 0, 13, 7], [8, 2, 0, 0, 11, 2, 0, 0], [0, 0, 8, 3, 0, 0, 11, 3], [8, 6, 0, 0, 11, 6, 0, 0], [0, 0, 8, 7, 0, 0, 11, 7], [10, 2, 0, 0, 29, 2, 0, 0], [0, 0, 10, 3, 0, 0, 29, 3], [10, 4, 0, 0, 9, 4, 0, 0], [0, 0, 10, 5, 0, 0, 9, 5], [10, 6, 0, 0, 29, 6, 0, 0], [0, 0, 10, 7, 0, 0, 29, 7], [10, 8, 0, 0, 9, 8, 0, 0], [0, 0, 10, 9, 0, 0, 9, 9], [12, 2, 0, 0, 27, 2, 0, 0], [0, 0, 12, 3, 0, 0, 27, 3], [12, 4, 0, 0, 7, 4, 0, 0], [0, 0, 12, 5, 0, 0, 7, 5], [12, 6, 0, 0, 27, 6, 0, 0], [0, 0, 12, 7, 0, 0, 27, 7], [12, 8, 0, 0, 7, 8, 0, 0], [0, 0, 12, 9, 0, 0, 7, 9], [14, 2, 0, 0, 25, 2, 0, 0], [0, 0, 14, 3, 0, 0, 25, 3], [14, 4, 0, 0, 5, 4, 0, 0], [0, 0, 14, 5, 0, 0, 5, 5], [14, 6, 0, 0, 25, 6, 0, 0], [0, 0, 14, 7, 0, 0, 25, 7], [14, 8, 0, 0, 5, 8, 0, 0], [0, 0, 14, 9, 0, 0, 5, 9], [16, 2, 0, 0, 23, 2, 0, 0], [0, 0, 16, 3, 0, 0, 23, 3], [16, 4, 0, 0, 3, 4, 0, 0], [0, 0, 16, 5, 0, 0, 3, 5], [16, 6, 0, 0, 23, 6, 0, 0], [0, 0, 16, 7, 0, 0, 23, 7], [16, 8, 0, 0, 3, 8, 0, 0], [0, 0, 16, 9, 0, 0, 3, 9], [18, 2, 0, 0, 21, 2, 0, 0], [0, 0, 18, 3, 0, 0, 21, 3], [18, 4, 0, 0, 1, 4, 0, 0], [0, 0, 18, 5, 0, 0, 1, 5], [18, 6, 0, 0, 21, 6, 0, 0], [0, 0, 18, 7, 0, 0, 21, 7], [18, 8, 0, 0, 1, 8, 0, 0], [0, 0, 18, 9, 0, 0, 1, 9], [20, 2, 0, 0, 39, 2, 0, 0], [0, 0, 20, 3, 0, 0, 39, 3], [20, 4, 0, 0, 19, 4, 0, 0], [0, 0, 20, 5, 0, 0, 19, 5], [20, 6, 0, 0, 39, 6, 0, 0], [0, 0, 20, 7, 0, 0, 39, 7], [20, 8, 0, 0, 19, 8, 0, 0], [0, 0, 20, 9, 0, 0, 19, 9], [22, 2, 0, 0, 37, 2, 0, 0], [0, 0, 22, 3, 0, 0, 37, 3], [22, 4, 0, 0, 17, 4, 0, 0], [0, 0, 22, 5, 0, 0, 17, 5], [22, 6, 0, 0, 37, 6, 0, 0], [0, 0, 22, 7, 0, 0, 37, 7], [22, 8, 0, 0, 17, 8, 0, 0], [0, 0, 22, 9, 0, 0, 17, 9], [24, 2, 0, 0, 35, 2, 0, 0], [0, 0, 24, 3, 0, 0, 35, 3], [24, 4, 0, 0, 15, 4, 0, 0], [0, 0, 24, 5, 0, 0, 15, 5], [24, 6, 0, 0, 35, 6, 0, 0], [0, 0, 24, 7, 0, 0, 35, 7], [24, 8, 0, 0, 15, 8, 0, 0], [0, 0, 24, 9, 0, 0, 15, 9], [26, 2, 0, 0, 33, 2, 0, 0], [0, 0, 26, 3, 0, 0, 33, 3], [26, 4, 0, 0, 13, 4, 0, 0], [0, 0, 26, 5, 0, 0, 13, 5], [26, 6, 0, 0, 33, 6, 0, 0], [0, 0, 26, 7, 0, 0, 33, 7], [26, 8, 0, 0, 13, 8, 0, 0], [0, 0, 26, 9, 0, 0, 13, 9], [28, 2, 0, 0, 31, 2, 0, 0], [0, 0, 28, 3, 0, 0, 31, 3], [28, 4, 0, 0, 11, 4, 0, 0], [0, 0, 28, 5, 0, 0, 11, 5], [28, 6, 0, 0, 31, 6, 0, 0], [0, 0, 28, 7, 0, 0, 31, 7], [28, 8, 0, 0, 11, 8, 0, 0], [0, 0, 28, 9, 0, 0, 11, 9], [30, 2, 0, 0, 49, 2, 0, 0], [0, 0, 30, 3, 0, 0, 49, 3], [30, 4, 0, 0, 29, 4, 0, 0], [0, 0, 30, 5, 0, 0, 29, 5], [30, 6, 0, 0, 49, 6, 0, 0], [0, 0, 30, 7, 0, 0, 49, 7], [30, 8, 0, 0, 29, 8, 0, 0], [0, 0, 30, 9, 0, 0, 29, 9], [32, 2, 0, 0, 47, 2, 0, 0], [0, 0, 32, 3, 0, 0, 47, 3], [32, 4, 0, 0, 27, 4, 0, 0], [0, 0, 32, 5, 0, 0, 27, 5], [32, 6, 0, 0, 47, 6, 0, 0], [0, 0, 32, 7, 0, 0, 47, 7], [32, 8, 0, 0, 27, 8, 0, 0], [0, 0, 32, 9, 0, 0, 27, 9], [34, 2, 0, 0, 45, 2, 0, 0], [0, 0, 34, 3, 0, 0, 45, 3], [34, 4, 0, 0, 25, 4, 0, 0], [0, 0, 34, 5, 0, 0, 25, 5], [34, 6, 0, 0, 45, 6, 0, 0], [0, 0, 34, 7, 0, 0, 45, 7], [34, 8, 0, 0, 25, 8, 0, 0], [0, 0, 34, 9, 0, 0, 25, 9], [36, 2, 0, 0, 43, 2, 0, 0], [0, 0, 36, 3, 0, 0, 43, 3], [36, 4, 0, 0, 23, 4, 0, 0], [0, 0, 36, 5, 0, 0, 23, 5], [36, 6, 0, 0, 43, 6, 0, 0], [0, 0, 36, 7, 0, 0, 43, 7], [36, 8, 0, 0, 23, 8, 0, 0], [0, 0, 36, 9, 0, 0, 23, 9], [38, 2, 0, 0, 41, 2, 0, 0], [0, 0, 38, 3, 0, 0, 41, 3], [38, 4, 0, 0, 21, 4, 0, 0], [0, 0, 38, 5, 0, 0, 21, 5], [38, 6, 0, 0, 41, 6, 0, 0], [0, 0, 38, 7, 0, 0, 41, 7], [38, 8, 0, 0, 21, 8, 0, 0], [0, 0, 38, 9, 0, 0, 21, 9], [40, 2, 0, 0, 59, 2, 0, 0], [0, 0, 40, 3, 0, 0, 59, 3], [40, 4, 0, 0, 39, 4, 0, 0], [0, 0, 40, 5, 0, 0, 39, 5], [40, 6, 0, 0, 59, 6, 0, 0], [0, 0, 40, 7, 0, 0, 59, 7], [40, 8, 0, 0, 39, 8, 0, 0], [0, 0, 40, 9, 0, 0, 39, 9], [42, 2, 0, 0, 57, 2, 0, 0], [0, 0, 42, 3, 0, 0, 57, 3], [42, 4, 0, 0, 37, 4, 0, 0], [0, 0, 42, 5, 0, 0, 37, 5], [42, 6, 0, 0, 57, 6, 0, 0], [0, 0, 42, 7, 0, 0, 57, 7], [42, 8, 0, 0, 37, 8, 0, 0], [0, 0, 42, 9, 0, 0, 37, 9], [44, 2, 0, 0, 55, 2, 0, 0], [0, 0, 44, 3, 0, 0, 55, 3], [44, 4, 0, 0, 35, 4, 0, 0], [0, 0, 44, 5, 0, 0, 35, 5], [44, 6, 0, 0, 55, 6, 0, 0], [0, 0, 44, 7, 0, 0, 55, 7], [44, 8, 0, 0, 35, 8, 0, 0], [0, 0, 44, 9, 0, 0, 35, 9], [46, 2, 0, 0, 53, 2, 0, 0], [0, 0, 46, 3, 0, 0, 53, 3], [46, 4, 0, 0, 33, 4, 0, 0], [0, 0, 46, 5, 0, 0, 33, 5], [46, 6, 0, 0, 53, 6, 0, 0], [0, 0, 46, 7, 0, 0, 53, 7], [46, 8, 0, 0, 33, 8, 0, 0], [0, 0, 46, 9, 0, 0, 33, 9], [48, 2, 0, 0, 51, 2, 0, 0], [0, 0, 48, 3, 0, 0, 51, 3], [48, 4, 0, 0, 31, 4, 0, 0], [0, 0, 48, 5, 0, 0, 31, 5], [48, 6, 0, 0, 51, 6, 0, 0], [0, 0, 48, 7, 0, 0, 51, 7], [48, 8, 0, 0, 31, 8, 0, 0], [0, 0, 48, 9, 0, 0, 31, 9], [50, 2, 0, 0, 69, 2, 0, 0], [0, 0, 50, 3, 0, 0, 69, 3], [50, 4, 0, 0, 49, 4, 0, 0], [0, 0, 50, 5, 0, 0, 49, 5], [50, 6, 0, 0, 69, 6, 0, 0], [0, 0, 50, 7, 0, 0, 69, 7], [50, 8, 0, 0, 49, 8, 0, 0], [0, 0, 50, 9, 0, 0, 49, 9], [52, 2, 0, 0, 67, 2, 0, 0], [0, 0, 52, 3, 0, 0, 67, 3], [52, 4, 0, 0, 47, 4, 0, 0], [0, 0, 52, 5, 0, 0, 47, 5], [52, 6, 0, 0, 67, 6, 0, 0], [0, 0, 52, 7, 0, 0, 67, 7], [52, 8, 0, 0, 47, 8, 0, 0], [0, 0, 52, 9, 0, 0, 47, 9], [54, 2, 0, 0, 65, 2, 0, 0], [0, 0, 54, 3, 0, 0, 65, 3], [54, 4, 0, 0, 45, 4, 0, 0], [0, 0, 54, 5, 0, 0, 45, 5], [54, 6, 0, 0, 65, 6, 0, 0], [0, 0, 54, 7, 0, 0, 65, 7], [54, 8, 0, 0, 45, 8, 0, 0], [0, 0, 54, 9, 0, 0, 45, 9], [56, 2, 0, 0, 63, 2, 0, 0], [0, 0, 56, 3, 0, 0, 63, 3], [56, 4, 0, 0, 43, 4, 0, 0], [0, 0, 56, 5, 0, 0, 43, 5], [56, 6, 0, 0, 63, 6, 0, 0], [0, 0, 56, 7, 0, 0, 63, 7], [56, 8, 0, 0, 43, 8, 0, 0], [0, 0, 56, 9, 0, 0, 43, 9], [58, 2, 0, 0, 61, 2, 0, 0], [0, 0, 58, 3, 0, 0, 61, 3], [58, 4, 0, 0, 41, 4, 0, 0], [0, 0, 58, 5, 0, 0, 41, 5], [58, 6, 0, 0, 61, 6, 0, 0], [0, 0, 58, 7, 0, 0, 61, 7], [58, 8, 0, 0, 41, 8, 0, 0], [0, 0, 58, 9, 0, 0, 41, 9], [60, 2, 0, 0, 79, 2, 0, 0], [0, 0, 60, 3, 0, 0, 79, 3], [60, 4, 0, 0, 59, 4, 0, 0], [0, 0, 60, 5, 0, 0, 59, 5], [60, 6, 0, 0, 79, 6, 0, 0], [0, 0, 60, 7, 0, 0, 79, 7], [60, 8, 0, 0, 59, 8, 0, 0], [0, 0, 60, 9, 0, 0, 59, 9], [62, 2, 0, 0, 77, 2, 0, 0], [0, 0, 62, 3, 0, 0, 77, 3], [62, 4, 0, 0, 57, 4, 0, 0], [0, 0, 62, 5, 0, 0, 57, 5], [62, 6, 0, 0, 77, 6, 0, 0], [0, 0, 62, 7, 0, 0, 77, 7], [62, 8, 0, 0, 57, 8, 0, 0], [0, 0, 62, 9, 0, 0, 57, 9], [64, 2, 0, 0, 75, 2, 0, 0], [0, 0, 64, 3, 0, 0, 75, 3], [64, 4, 0, 0, 55, 4, 0, 0], [0, 0, 64, 5, 0, 0, 55, 5], [64, 6, 0, 0, 75, 6, 0, 0], [0, 0, 64, 7, 0, 0, 75, 7], [64, 8, 0, 0, 55, 8, 0, 0], [0, 0, 64, 9, 0, 0, 55, 9], [66, 2, 0, 0, 73, 2, 0, 0], [0, 0, 66, 3, 0, 0, 73, 3], [66, 4, 0, 0, 53, 4, 0, 0], [0, 0, 66, 5, 0, 0, 53, 5], [66, 6, 0, 0, 73, 6, 0, 0], [0, 0, 66, 7, 0, 0, 73, 7], [66, 8, 0, 0, 53, 8, 0, 0], [0, 0, 66, 9, 0, 0, 53, 9], [68, 2, 0, 0, 71, 2, 0, 0], [0, 0, 68, 3, 0, 0, 71, 3], [68, 4, 0, 0, 51, 4, 0, 0], [0, 0, 68, 5, 0, 0, 51, 5], [68, 6, 0, 0, 71, 6, 0, 0], [0, 0, 68, 7, 0, 0, 71, 7], [68, 8, 0, 0, 51, 8, 0, 0], [0, 0, 68, 9, 0, 0, 51, 9], [70, 2, 0, 0, 89, 2, 0, 0], [0, 0, 70, 3, 0, 0, 89, 3], [70, 4, 0, 0, 69, 4, 0, 0], [0, 0, 70, 5, 0, 0, 69, 5], [70, 6, 0, 0, 89, 6, 0, 0], [0, 0, 70, 7, 0, 0, 89, 7], [70, 8, 0, 0, 69, 8, 0, 0], [0, 0, 70, 9, 0, 0, 69, 9], [72, 2, 0, 0, 87, 2, 0, 0], [0, 0, 72, 3, 0, 0, 87, 3], [72, 4, 0, 0, 67, 4, 0, 0], [0, 0, 72, 5, 0, 0, 67, 5], [72, 6, 0, 0, 87, 6, 0, 0], [0, 0, 72, 7, 0, 0, 87, 7], [72, 8, 0, 0, 67, 8, 0, 0], [0, 0, 72, 9, 0, 0, 67, 9], [74, 2, 0, 0, 85, 2, 0, 0], [0, 0, 74, 3, 0, 0, 85, 3], [74, 4, 0, 0, 65, 4, 0, 0], [0, 0, 74, 5, 0, 0, 65, 5], [74, 6, 0, 0, 85, 6, 0, 0], [0, 0, 74, 7, 0, 0, 85, 7], [74, 8, 0, 0, 65, 8, 0, 0], [0, 0, 74, 9, 0, 0, 65, 9], [76, 2, 0, 0, 83, 2, 0, 0], [0, 0, 76, 3, 0, 0, 83, 3], [76, 4, 0, 0, 63, 4, 0, 0], [0, 0, 76, 5, 0, 0, 63, 5], [76, 6, 0, 0, 83, 6, 0, 0], [0, 0, 76, 7, 0, 0, 83, 7], [76, 8, 0, 0, 63, 8, 0, 0], [0, 0, 76, 9, 0, 0, 63, 9], [78, 2, 0, 0, 81, 2, 0, 0], [0, 0, 78, 3, 0, 0, 81, 3], [78, 4, 0, 0, 61, 4, 0, 0], [0, 0, 78, 5, 0, 0, 61, 5], [78, 6, 0, 0, 81, 6, 0, 0], [0, 0, 78, 7, 0, 0, 81, 7], [78, 8, 0, 0, 61, 8, 0, 0], [0, 0, 78, 9, 0, 0, 61, 9], [80, 2, 0, 0, 99, 2, 0, 0], [0, 0, 80, 3, 0, 0, 99, 3], [80, 4, 0, 0, 79, 4, 0, 0], [0, 0, 80, 5, 0, 0, 79, 5], [80, 6, 0, 0, 99, 6, 0, 0], [0, 0, 80, 7, 0, 0, 99, 7], [80, 8, 0, 0, 79, 8, 0, 0], [0, 0, 80, 9, 0, 0, 79, 9], [82, 2, 0, 0, 97, 2, 0, 0], [0, 0, 82, 3, 0, 0, 97, 3], [82, 4, 0, 0, 77, 4, 0, 0], [0, 0, 82, 5, 0, 0, 77, 5], [82, 6, 0, 0, 97, 6, 0, 0], [0, 0, 82, 7, 0, 0, 97, 7], [82, 8, 0, 0, 77, 8, 0, 0], [0, 0, 82, 9, 0, 0, 77, 9], [84, 2, 0, 0, 95, 2, 0, 0], [0, 0, 84, 3, 0, 0, 95, 3], [84, 4, 0, 0, 75, 4, 0, 0], [0, 0, 84, 5, 0, 0, 75, 5], [84, 6, 0, 0, 95, 6, 0, 0], [0, 0, 84, 7, 0, 0, 95, 7], [84, 8, 0, 0, 75, 8, 0, 0], [0, 0, 84, 9, 0, 0, 75, 9], [86, 2, 0, 0, 93, 2, 0, 0], [0, 0, 86, 3, 0, 0, 93, 3], [86, 4, 0, 0, 73, 4, 0, 0], [0, 0, 86, 5, 0, 0, 73, 5], [86, 6, 0, 0, 93, 6, 0, 0], [0, 0, 86, 7, 0, 0, 93, 7], [86, 8, 0, 0, 73, 8, 0, 0], [0, 0, 86, 9, 0, 0, 73, 9], [88, 2, TABLE 32-continued 0, 0, 91, 2, 0, 0], [0, 0, 88, 3, 0, 0, 91, 3], [88, 4, 0, 0, 71, 4, 0, 0], [0, 0, 88, 5, 0, 0, 71, 5], [88, 6, 0, 0, 91, 6, 0, 0], [0, 0, 88, 7, 0, 0, 91, 7], [88, 8, 0, 0, 71, 8, 0, 0], [0, 0, 88, 9, 0, 0, 71, 9], [90, 4, 0, 0, 89, 4, 0, 0], [0, 0, 90, 5, 0, 0, 89, 5], [90, 8, 0, 0, 89, 8, 0, 0], [0, 0, 90, 9, 0, 0, 89, 9], [92, 4, 0, 0, 87, 4, 0, 0], [0, 0, 92, 5, 0, 0, 87, 5], [92, 8, 0, 0, 87, 8, 0, 0], [0, 0, 92, 9, 0, 0, 87, 9], [94, 4, 0, 0, 85, 4, 0, 0], [0, 0, 94, 5, 0, 0, 85, 5], [94, 8, 0, 0, 85, 8, 0, 0], [0, 0, 94, 9, 0, 0, 85, 9], [96, 4, 0, 0, 83, 4, 0, 0], [0, 0, 96, 5, 0, 0, 83, 5], [96, 8, 0, 0, 83, 8, 0, 0], [0, 0, 96, 9, 0, 0, 83, 9], [98, 4, 0, 0, 81, 4, 0, 0], [0, 0, 98, 5, 0, 0, 81, 5], [98, 8, 0, 0, 81, 8, 0, 0], [0, 0, 98, 9, 0, 0, 81, 9], [1, 1, 0, 0, 0, 1, 0, 2], [0, 0, 1, 2, 0, 1, 0, 2], [1, 1, 1, 2, 0, 0, 0, 2], [1, 1, 1, 2, 0, 1, 0, 0], [1, 3, 0, 0, 2, 3, 2, 4], [0, 0, 1, 4, 2, 3, 2, 4], [1, 3, 1, 4, 0, 0, 2, 4], [1, 3, 1, 4, 2, 3, 0, 0], [1, 5, 0, 0, 0, 5, 0, 6], [0, 0, 1, 6, 0, 5, 0, 6], [1, 5, 1, 6, 0, 0, 0, 6], [1, 5, 1, 6, 0, 5, 0, 0], [1, 7, 0, 0, 2, 7, 2, 8], [0, 0, 1, 8, 2, 7, 2, 8], [1, 7, 1, 8, 0, 0, 2, 8], [1, 7, 1, 8, 2, 7, 0, 0], [1, 9, 0, 0, 0, 9, 0, 10], [0, 0, 1, 10, 0, 9, 0, 10], [1, 9, 1, 10, 0, 0, 0, 10], [1, 9, 1, 10, 0, 9, 0, 0], [3, 1, 0, 0, 2, 1, 2, 2], [0, 0, 3, 2, 2, 1, 2, 2], [3, 1, 3, 2, 0, 0, 2, 2], [3, 1, 3, 2, 2, 1, 0, 0], [3, 3, 0, 0, 4, 3, 4, 4], [0, 0, 3, 4, 4, 3, 4, 4], [3, 3, 3, 4, 0, 0, 4, 4], [3, 3, 3, 4, 4, 3, 0, 0], [3, 5, 0, 0, 2, 5, 2, 6], [0, 0, 3, 6, 2, 5, 2, 6], [3, 5, 3, 6, 0, 0, 2, 6], [3, 5, 3, 6, 2, 5, 0, 0], [3, 7, 0, 0, 4, 7, 4, 8], [0, 0, 3, 8, 4, 7, 4, 8], [3, 7, 3, 8, 0, 0, 4, 8], [3, 7, 3, 8, 4, 7, 0, 0], [3, 9, 0, 0, 2, 9, 2, 10], [0, 0, 3, 10, 2, 9, 2, 10], [3, 9, 3, 10, 0, 0, 2, 10], [3, 9, 3, 10, 2, 9, 0, 0], [5, 1, 0, 0, 4, 1, 4, 2], [0, 0, 5, 2, 4, 1, 4, 2], [5, 1, 5, 2, 0, 0, 4, 2], [5, 1, 5, 2, 4, 1, 0, 0], [5, 3, 0, 0, 6, 3, 6, 4], [0, 0, 5, 4, 6, 3, 6, 4], [5, 3, 5, 4, 0, 0, 6, 4], [5, 3, 5, 4, 6, 3, 0, 0], [5, 5, 0, 0, 4, 5, 4, 6], [0, 0, 5, 6, 4, 5, 4, 6], [5, 5, 5, 6, 0, 0, 4, 6], [5, 5, 5, 6, 4, 5, 0, 0], [5, 7, 0, 0, 6, 7, 6, 8], [0, 0, 5, 8, 6, 7, 6, 8], [5, 7, 5, 8, 0, 0, 6, 8], [5, 7, 5, 8, 6, 7, 0, 0], [5, 9, 0, 0, 4, 9, 4, 10], [0, 0, 5, 10, 4, 9, 4, 10], [5, 9, 5, 10, 0, 0, 4, 10], [5, 9, 5, 10, 4, 9, 0, 0], [7, 1, 0, 0, 6, 1, 6, 2], [0, 0, 7, 2, 6, 1, 6, 2], [7, 1, 7, 2, 0, 0, 6, 2], [7, 1, 7, 2, 6, 1, 0, 0], [7, 3, 0, 0, 8, 3, 8, 4], [0, 0, 7, 4, 8, 3, 8, 4], [7, 3, 7, 4, 0, 0, 8, 4], [7, 3, 7, 4, 8, 3, 0, 0], [7, 5, 0, 0, 6, 5, 6, 6], [0, 0, 7, 6, 6, 5, 6, 6], [7, 5, 7, 6, 0, 0, 6, 6], [7, 5, 7, 6, 6, 5, 0, 0], [7, 7, 0, 0, 8, 7, 8, 8], [0, 0, 7, 8, 8, 7, 8, 8], [7, 7, 7, 8, 0, 0, 8, 8], [7, 7, 7, 8, 8, 7, 0, 0], [7, 9, 0, 0, 6, 9, 6, 10], [0, 0, 7, 10, 6, 9, 6, 10], [7, 9, 7, 10, 0, 0, 6, 10], [7, 9, 7, 10, 6, 9, 0, 0], [9, 1, 0, 0, 8, 1, 8, 2], [0, 0, 9, 2, 8, 1, 8, 2], [9, 1, 9, 2, 0, 0, 8, 2], [9, 1, 9, 2, 8, 1, 0, 0], [9, 5, 0, 0, 8, 5, 8, 6], [0, 0, 9, 6, 8, 5, 8, 6], [9, 5, 9, 6, 0, 0, 8, 6], [9, 5, 9, 6, 8, 5, 0, 0], [9, 9, 0, 0, 8, 9, 8, 10], [0, 0, 9, 10, 8, 9, 8, 10], [9, 9, 9, 10, 0, 0, 8, 10], [9, 9, 9, 10, 8, 9, 0, 0], [11, 1, 0, 0, 12, 1, 12, 2], [0, 0, 11, 2, 12, 1, 12, 2], [11, 1, 11, 2, 0, 0, 12, 2], [11, 1, 11, 2, 12, 1, 0, 0], [11, 3, 0, 0, 10, 3, 10, 4], [0, 0, 11, 4, 10, 3, 10, 4], [11, 3, 11, 4, 0, 0, 10, 4], [11, 3, 11, 4, 10, 3, 0, 0], [11, 5, 0, 0, 12, 5, 12, 6], [0, 0, 11, 6, 12, 5, 12, 6], [11, 5, 11, 6, 0, 0, 12, 6], [11, 5, 11, 6, 12, 5, 0, 0], [11, 7, 0, 0, 10, 7, 10, 8], [0, 0, 11, 8, 10, 7, 10, 8], [11, 7, 11, 8, 0, 0, 10, 8], [11, 7, 11, 8, 10, 7, 0, 0], [11, 9, 0, 0, 12, 9, 12, 10], [0, 0, 11, 10, 12, 9, 12, 10], [11, 9, 11, 10, 0, 0, 12, 10], [11, 9, 11, 10, 12, 9, 0, 0], [13, 1, 0, 0, 14, 1, 14, 2], [0, 0, 13, 2, 14, 1, 14, 2], [13, 1, 13, 2, 0, 0, 14, 2], [13, 1, 13, 2, 14, 1, 0, 0], [13, 3, 0, 0, 12, 3, 12, 4], [0, 0, 13, 4, 12, 3, 12, 4], [13, 3, 13, 4, 0, 0, 12, 4], [13, 3, 13, 4, 12, 3, 0, 0], [13, 5, 0, 0, 14, 5, 14, 6], [0, 0, 13, 6, 14, 5, 14, 6], [13, 5, 13, 6, 0, 0, 14, 6], [13, 5, 13, 6, 14, 5, 0, 0], [13, 7, 0, 0, 12, 7, 12, 8], [0, 0, 13, 8, 12, 7, 12, 8], [13, 7, 13, 8, 0, 0, 12, 8], [13, 7, 13, 8, 12, 7, 0, 0], [13, 9, 0, 0, 14, 9, 14, 10], [0, 0, 13, 10, 14, 9, 14, 10], [13, 9, 13, 10, 0, 0, 14, 10], [13, 9, 13, 10, 14, 9, 0, 0], [15, 1, 0, 0, 16, 1, 16, 2], [0, 0, 15, 2, 16, 1, 16, 2], [15, 1, 15, 2, 0, 0, 16, 2], [15, 1, 15, 2, 16, 1, 0, 0], [15, 3, 0, 0, 14, 3, 14, 4], [0, 0, 15, 4, 14, 3, 14, 4], [15, 3, 15, 4, 0, 0, 14, 4], [15, 3, 15, 4, 14, 3, 0, 0], [15, 5, 0, 0, 16, 5, 16, 6], [0, 0, 15, 6, 16, 5, 16, 6], [15, 5, 15, 6, 0, 0, 16, 6], [15, 5, 15, 6, 16, 5, 0, 0], [15, 7, 0, 0, 14, 7, 14, 8], [0, 0, 15, 8, 14, 7, 14, 8], [15, 7, 15, 8, 0, 0, 14, 8], [15, 7, 15, 8, 14, 7, 0, 0], [15, 9, 0, 0, 16, 9, 16, 10], [0, 0, 15, 10, 16, 9, 16, 10], [15, 9, 15, 10, 0, 0, 16, 10], [15, 9, 15, 10, 16, 9, 0, 0], [17, 1, 0, 0, 18, 1, 18, 2], [0, 0, 17, 2, 18, 1, 18, 2], [17, 1, 17, 2, 0, 0, 18, 2], [17, 1, 17, 2, 18, 1, 0, 0], [17, 3, 0, 0, 16, 3, 16, 4], [0, 0, 17, 4, 16, 3, 16, 4], [17, 3, 17, 4, 0, 0, 16, 4], [17, 3, 17, 4, 16, 3, 0, 0], [17, 5, 0, 0, 18, 5, 18, 6], [0, 0, 17, 6, 18, 5, 18, 6], [17, 5, 17, 6, 0, 0, 18, 6], [17, 5, 17, 6, 18, 5, 0, 0], [17, 7, 0, 0, 16, 7, 16, 8], [0, 0, 17, 8, 16, 7, 16, 8], [17, 7, 17, 8, 0, 0, 16, 8], [17, 7, 17, 8, 16, 7, 0, 0], [17, 9, 0, 0, 18, 9, 18, 10], [0, 0, 17, 10, 18, 9, 18, 10], [17, 9, 17, 10, 0, 0, 18, 10], [17, 9, 17, 10, 18, 9, 0, 0], [19, 3, 0, 0, 18, 3, 18, 4], [0, 0, 19, 4, 18, 3, 18, 4], [19, 3, 19, 4, 0, 0, 18, 4], [19, 3, 19, 4, 18, 3, 0, 0], [19, 7, 0, 0, 18, 7, 18, 8], [0, 0, 19, 8, 18, 7, 18, 8], [19, 7, 19, 8, 0, 0, 18, 8], [19, 7, 19, 8, 18, 7, 0, 0], [21, 1, 0, 0, 20, 1, 20, 2], [0, 0, 21, 2, 20, 1, 20, 2], [21, 1, 21, 2, 0, 0, 20, 2], [21, 1, 21, 2, 20, 1, 0, 0], [21, 3, 0, 0, 22, 3, 22, 4], [0, 0, 21, 4, 22, 3, 22, 4], [21, 3, 21, 4, 0, 0, 22, 4], [21, 3, 21, 4, 22, 3, 0, 0], [21, 5, 0, 0, 20, 5, 20, 6], [0, 0, 21, 6, 20, 5, 20, 6], [21, 5, 21, 6, 0, 0, 20, 6], [21, 5, 21, 6, 20, 5, 0, 0], [21, 7, 0, 0, 22, 7, 22, 8], [0, 0, 21, 8, 22, 7, 22, 8], [21, 7, 21, 8, 0, 0, 22, 8], [21, 7, 21, 8, 22, 7, 0, 0], [21, 9, 0, 0, 20, 9, 20, 10], [0, 0, 21, 10, 20, 9, 20, 10], [21, 9, 21, 10, 0, 0, 20, 10], [21, 9, 21, 10, 20, 9, 0, 0], [23, 1, 0, 0, 22, 1, 22, 2], [0, 0, 23, 2, 22, 1, 22, 2], [23, 1, 23, 2, 0, 0, 22, 2], [23, 1, 23, 2, 22, 1, 0, 0], [23, 3, 0, 0, 24, 3, 24, 4], [0, 0, 23, 4, 24, 3, 24, 4], [23, 3, 23, 4, 0, 0, 24, 4], [23, 3, 23, 4, 24, 3, 0, 0], [23, 5, 0, 0, 22, 5, 22, 6], [0, 0, 23, 6, 22, 5, 22, 6], [23, 5, 23, 6, 0, 0, 22, 6], [23, 5, 23, 6, 22, 5, 0, 0], [23, 7, 0, 0, 24, 7, 24, 8], [0, 0, 23, 8, 24, 7, 24, 8], [23, 7, 23, 8, 0, 0, 24, 8], [23, 7, 23, 8, 24, 7, 0, 0], [23, 9, 0, 0, 22, 9, 22, 10], [0, 0, 23, 10, 22, 9, 22, 10], [23, 9, 23, 10, 0, 0, 22, 10], [23, 9, 23, 10, 22, 9, 0, 0], [25, 1, 0, 0, 24, 1, 24, 2], [0, 0, 25, 2, 24, 1, 24, 2], [25, 1, 25, 2, 0, 0, 24, 2], [25, 1, 25, 2, 24, 1, 0, 0], [25, 3, 0, 0, 26, 3, 26, 4], [0, 0, 25, 4, 26, 3, 26, 4], [25, 3, 25, 4, 0, 0, 26, 4], [25, 3, 25, 4, 26, 3, 0, 0], [25, 5, 0, 0, 24, 5, 24, 6], [0, 0, 25, 6, 24, 5, 24, 6], [25, 5, 25, 6, 0, 0, 24, 6], [25, 5, 25, 6, 24, 5, 0, 0], [25, 7, 0, 0, 26, 7, 26, 8], [0, 0, 25, 8, 26, 7, 26, 8], [25, 7, 25, 8, 0, 0, 26, 8], [25, 7, 25, 8, 26, 7, 0, 0], [25, 9, 0, 0, 24, 9, 24, 10], [0, 0, 25, 10, 24, 9, 24, 10], [25, 9, 25, 10, 0, 0, 24, 10], [25, 9, 25, 10, 24, 9, 0, 0], [27, 1, 0, 0, 26, 1, 26, 2], [0, 0, 27, 2, 26, 1, 26, 2], [27, 1, 27, 2, 0, 0, 26, 2], [27, 1, 27, 2, 26, 1, 0, 0], [27, 3, 0, 0, 28, 3, 28, 4], [0, 0, 27, 4, 28, 3, 28, 4], [27, 3, 27, 4, 0, 0, 28, 4], [27, 3, 27, 4, 28, 3, 0, 0], [27, 5, 0, 0, 26, 5, 26, 6], [0, 0, 27, 6, 26, 5, 26, 6], [27, 5, 27, 6, 0, 0, 26, 6], [27, 5, 27, 6, 26, 5, 0, 0], [27, 7, 0, 0, 28, 7, 28, 8], [0, 0, 27, 8, 28, 7, 28, 8], [27, 7, 27, 8, 0, 0, 28, 8], [27, 7, 27, 8, 28, 7, 0, 0], [27, 9, 0, 0, 26, 9, 26, 10], [0, 0, 27, 10, 26, 9, 26, 10], [27, 9, 27, 10, 0, 0, 26, 10], [27, 9, 27, 10, 26, 9, 0, 0], [29, 1, 0, 0, 28, 1, 28, 2], [0, 0, 29, 2, 28, 1, 28, 2], [29, 1, 29, 2, 0, 0, 28, 2], [29, 1, 29, 2, 28, 1, 0, 0], [29, 5, 0, 0, 28, 5, 28, 6], [0, 0, 29, 6, 28, 5, 28, 6], [29, 5, 29, 6, 0, 0, 28, 6], [29, 5, 29, 6, 28, 5, 0, 0], [29, 9, 0, 0, 28, 9, 28, 10], [0, 0, 29, 10, 28, 9, 28, 10], [29, 9, 29, 10, 0, 0, 28, 10], [29, 9, 29, 10, 28, 9, 0, 0], [31, 1, 0, 0, 32, 1, 32, 2], [0, 0, 31, 2, 32, 1, 32, 2], [31, 1, 31, 2, 0, 0, 32, 2], [31, 1, 31, 2, 32, 1, 0, 0], [31, 3, 0, 0, 30, 3, 30, 4], [0, 0, 31, 4, 30, 3, 30, 4], [31, 3, 31, 4, 0, 0, 30, 4], [31, 3, 31, 4, 30, 3, 0, 0], [31, 5, 0, 0, 32, 5, 32, 6], [0, 0, 31, 6, 32, 5, 32, 6], [31, 5, 31, 6, 0, 0, 32, 6], [31, 5, 31, 6, 32, 5, 0, 0], [31, 7, 0, 0, 30, 7, 30, 8], [0, 0, 31, 8, 30, 7, 30, 8], [31, 7, 31, 8, 0, 0, 30, 8], [31, 7, 31, 8, 30, 7, 0, 0], [31, 9, 0, 0, 32, 9, 32, 10], [0, 0, 31, 10, 32, 9, 32, 10], [31, 9, 31, 10, 0, 0, 32, 10], [31, 9, 31, 10, 32, 9, 0, 0], [33, 1, 0, 0, 34, 1, 34, 2], [0, 0, 33, 2, 34, 1, 34, 2], [33, 1, 33, 2, 0, 0, 34, 2], [33, 1, 33, 2, 34, 1, 0, 0], [33, 3, 0, 0, 32, 3, 32, 4], [0, 0, 33, 4, 32, 3, 32, 4], [33, 3, 33, 4, 0, 0, 32, 4], [33, 3, 33, 4, 32, 3, 0, 0], [33, 5, 0, 0, 34, 5, 34, 6], [0, 0, 33, 6, 34, 5, 34, 6], [33, 5, 33, 6, 0, 0, 34, 6], [33, 5, 33, 6, 34, 5, 0, 0], [33, 7, 0, 0, 32, 7, 32, 8], [0, 0, 33, 8, 32, 7, 32, 8], [33, 7, 33, 8, 0, 0, 32, 8], [33, 7, 33, 8, 32, 7, 0, 0], [33, 9, 0, 0, 34, 9, 34, 10], [0, 0, 33, 10, 34, 9, 34, 10], [33, 9, 33, 10, 0, 0, 34, 10], [33, 9, 33, 10, 34, 9, 0, 0], [35, 1, 0, 0, 36, 1, 36, 2], [0, 0, 35, 2, 36, 1, 36, 2], [35, 1, 35, 2, 0, 0, 36, 2], [35, 1, 35, 2, 36, 1, 0, 0], [35, 3, 0, 0, 34, 3, 34, 4], [0, 0, 35, 4, 34, 3, 34, 4], [35, 3, 35, 4, 0, 0, 34, 4], [35, 3, 35, 4, 34, 3, 0, 0], [35, 5, 0, 0, 36, 5, 36, 6], [0, 0, 35, 6, 36, 5, 36, 6], [35, 5, 35, 6, 0, 0, 36, 6], [35, 5, 35, 6, 36, 5, 0, 0], [35, 7, 0, 0, 34, 7, 34, 8], [0, 0, 35, 8, 34, 7, 34, 8], [35, 7, 35, 8, 0, 0, 34, 8], [35, 7, 35, 8, 34, 7, 0, 0], [35, 9, 0, 0, 36, 9, 36, 10], [0, 0, 35, 10, 36, 9, 36, 10], [35, 9, 35, 10, 0, 0, 36, 10], [35, 9, 35, 10, 36, 9, 0, 0], [37, 1, 0, 0, 38, 1, 38, 2], [0, 0, 37, 2, 38, 1, 38, 2], [37, 1, 37, 2, 0, 0, 38, 2], [37, 1, 37, 2, 38, 1, 0, 0], [37, 3, 0, 0, 36, 3, 36, 4], [0, 0, 37, 4, 36, 3, 36, 4], [37, 3, 37, 4, 0, 0, 36, 4], [37, 3, 37, 4, 36, 3, 0, 0], [37, 5, 0, 0, 38, 5, 38, 6], [0, 0, 37, 6, 38, 5, 38, 6], [37, 5, 37, 6, 0, 0, 38, 6], [37, 5, 37, 6, 38, 5, 0, 0], [37, 7, 0, 0, 36, 7, 36, 8], [0, 0, 37, 8, 36, 7, 36, 8], [37, 7, 37, 8, 0, 0, 36, 8], [37, 7, 37, 8, 36, 7, 0, 0], [37, 9, 0, 0, 38, 9, 38, 10], [0, 0, 37, 10, 38, 9, 38, 10], [37, 9, 37, 10, 0, 0, 38, 10], [37, 9, 37, 10, 38, 9, 0, 0], [39, 3, 0, 0, 38, 3, 38, 4], [0, 0, 39, 4, 38, 3, 38, 4], [39, 3, 39, 4, 0, 0, 38, 4], [39, 3, 39, 4, 38, 3, 0, 0], [39, 7, 0, 0, 38, 7, 38, 8], [0, 0, 39, 8, 38, 7, 38, 8], [39, 7, 39, 8, 0, 0, 38, 8], [39, 7, 39, 8, 38, 7, 0, 0], [41, 1, 0, 0, 40, 1, 40, 2], [0, 0, 41, 2, 40, 1, 40, 2], [41, 1, 41, 2, 0, 0, 40, 2], [41, 1, 41, 2, 40, 1, 0, 0], [41, 3, 0, 0, 42, 3, 42, 4], [0, 0, 41, 4, 42, 3, 42, 4], [41, 3, 41, 4, 0, 0, 42, 4], [41, 3, 41, 4, 42, 3, 0, 0], [41, 5, 0, 0, 40, 5, 40, 6], [0, 0, 41, 6, 40, 5, 40, 6], [41, 5, 41, 6, 0, 0, 40, 6], [41, 5, 41, 6, 40, 5, 0, 0], [41, 7, 0, 0, 42, 7, 42, 8], [0, 0, 41, 8, 42, 7, 42, 8], [41, 7, 41, 8, 0, 0, 42, 8], [41, 7, 41, 8, 42, 7, 0, 0], [41, 9, 0, 0, 40, 9, 40, 10], [0, 0, 41, 10, 40, 9, 40, 10], [41, 9, 41, 10, 0, 0, 40, 10], [41, 9, 41, 10, 40, 9, 0, 0], [43, 1, 0, 0, 42, 1, 42, 2], [0, 0, 43, 2, 42, 1, 42, 2], [43, 1, 43, 2, 0, 0, 42, 2], [43, 1, 43, 2, 42, 1, 0, 0], [43, 3, 0, 0, 44, 3, 44, 4], [0, 0, 43, 4, 44, 3, 44, 4], [43, 3, 43, 4, 0, 0, 44, 4], [43, 3, 43, 4, 44, 3, 0, 0], [43, 5, 0, 0, 42, 5, 42, 6], [0, 0, 43, 6, 42, 5, 42, 6], [43, 5, 43, 6, 0, 0, 42, 6], [43, 5, 43, 6, 42, 5, 0, 0], [43, 7, 0, 0, 44, 7, 44, 8], [0, 0, 43, 8, 44, 7, 44, 8], [43, 7, 43, 8, 0, 0, 44, 8], [43, 7, 43, 8, 44, 7, 0, 0], [43, 9, 0, 0, 42, 9, 42, 10], [0, 0, 43, 10, 42, 9, 42, 10], [43, 9, 43, 10, 0, 0, 42, 10], [43, 9, 43, 10, 42, 9, 0, 0], [45, 1, 0, 0, 44, 1, 44, 2], [0, 0, 45, 2, 44, 1, 44, 2], [45, 1, 45, 2, TABLE 32-continued 0, 0, 44, 2], [45, 1, 45, 2, 44, 1, 0, 0], [45, 3, 0, 0, 46, 3, 46, 4], [0, 0, 45, 4, 46, 3, 46, 4], [45, 3, 45, 4, 0, 0, 46, 4], [45, 3, 45, 4, 46, 3, 0, 0], [45, 5, 0, 0, 44, 5, 44, 6], [0, 0, 45, 6, 44, 5, 44, 6], [45, 5, 45, 6, 0, 0, 44, 6], [45, 5, 45, 6, 44, 5, 0, 0], [45, 7, 0, 0, 46, 7, 46, 8], [0, 0, 45, 8, 46, 7, 46, 8], [45, 7, 45, 8, 0, 0, 46, 8], [45, 7, 45, 8, 46, 7, 0, 0], [45, 9, 0, 0, 44, 9, 44, 10], [0, 0, 45, 10, 44, 9, 44, 10], [45, 9, 45, 10, 0, 0, 44, 10], [45, 9, 45, 10, 44, 9, 0, 0], [47, 1, 0, 0, 46, 1, 46, 2], [0, 0, 47, 2, 46, 1, 46, 2], [47, 1, 47, 2, 0, 0, 46, 2], [47, 1, 47, 2, 46, 1, 0, 0], [47, 3, 0, 0, 48, 3, 48, 4], [0, 0, 47, 4, 48, 3, 48, 4], [47, 3, 47, 4, 0, 0, 48, 4], [47, 3, 47, 4, 48, 3, 0, 0], [47, 5, 0, 0, 46, 5, 46, 6], [0, 0, 47, 6, 46, 5, 46, 6], [47, 5, 47, 6, 0, 0, 46, 6], [47, 5, 47, 6, 46, 5, 0, 0], [47, 7, 0, 0, 48, 7, 48, 8], [0, 0, 47, 8, 48, 7, 48, 8], [47, 7, 47, 8, 0, 0, 48, 8], [47, 7, 47, 8, 48, 7, 0, 0], [47, 9, 0, 0, 46, 9, 46, 10], [0, 0, 47, 10, 46, 9, 46, 10], [47, 9, 47, 10, 0, 0, 46, 10], [47, 9, 47, 10, 46, 9, 0, 0], [49, 1, 0, 0, 48, 1, 48, 2], [0, 0, 49, 2, 48, 1, 48, 2], [49, 1, 49, 2, 0, 0, 48, 2], [49, 1, 49, 2, 48, 1, 0, 0], [49, 5, 0, 0, 48, 5, 48, 6], [0, 0, 49, 6, 48, 5, 48, 6], [49, 5, 49, 6, 0, 0, 48, 6], [49, 5, 49, 6, 48, 5, 0, 0], [49, 9, 0, 0, 48, 9, 48, 10], [0, 0, 49, 10, 48, 9, 48, 10], [49, 9, 49, 10, 0, 0, 48, 10], [49, 9, 49, 10, 48, 9, 0, 0], [51, 1, 0, 0, 52, 1, 52, 2], [0, 0, 51, 2, 52, 1, 52, 2], [51, 1, 51, 2, 0, 0, 52, 2], [51, 1, 51, 2, 52, 1, 0, 0], [51, 3, 0, 0, 50, 3, 50, 4], [0, 0, 51, 4, 50, 3, 50, 4], [51, 3, 51, 4, 0, 0, 50, 4], [51, 3, 51, 4, 50, 3, 0, 0], [51, 5, 0, 0, 52, 5, 52, 6], [0, 0, 51, 6, 52, 5, 52, 6], [51, 5, 51, 6, 0, 0, 52, 6], [51, 5, 51, 6, 52, 5, 0, 0], [51, 7, 0, 0, 50, 7, 50, 8], [0, 0, 51, 8, 50, 7, 50, 8], [51, 7, 51, 8, 0, 0, 50, 8], [51, 7, 51, 8, 50, 7, 0, 0], [51, 9, 0, 0, 52, 9, 52, 10], [0, 0, 51, 10, 52, 9, 52, 10], [51, 9, 51, 10, 0, 0, 52, 10], [51, 9, 51, 10, 52, 9, 0, 0], [53, 1, 0, 0, 54, 1, 54, 2], [0, 0, 53, 2, 54, 1, 54, 2], [53, 1, 53, 2, 0, 0, 54, 2], [53, 1, 53, 2, 54, 1, 0, 0], [53, 3, 0, 0, 52, 3, 52, 4], [0, 0, 53, 4, 52, 3, 52, 4], [53, 3, 53, 4, 0, 0, 52, 4], [53, 3, 53, 4, 52, 3, 0, 0], [53, 5, 0, 0, 54, 5, 54, 6], [0, 0, 53, 6, 54, 5, 54, 6], [53, 5, 53, 6, 0, 0, 54, 6], [53, 5, 53, 6, 54, 5, 0, 0], [53, 7, 0, 0, 52, 7, 52, 8], [0, 0, 53, 8, 52, 7, 52, 8], [53, 7, 53, 8, 0, 0, 52, 8], [53, 7, 53, 8, 52, 7, 0, 0], [53, 9, 0, 0, 54, 9, 54, 10], [0, 0, 53, 10, 54, 9, 54, 10], [53, 9, 53, 10, 0, 0, 54, 10], [53, 9, 53, 10, 54, 9, 0, 0], [55, 1, 0, 0, 56, 1, 56, 2], [0, 0, 55, 2, 56, 1, 56, 2], [55, 1, 55, 2, 0, 0, 56, 2], [55, 1, 55, 2, 56, 1, 0, 0], [55, 3, 0, 0, 54, 3, 54, 4], [0, 0, 55, 4, 54, 3, 54, 4], [55, 3, 55, 4, 0, 0, 54, 4], [55, 3, 55, 4, 54, 3, 0, 0], [55, 5, 0, 0, 56, 5, 56, 6], [0, 0, 55, 6, 56, 5, 56, 6], [55, 5, 55, 6, 0, 0, 56, 6], [55, 5, 55, 6, 56, 5, 0, 0], [55, 7, 0, 0, 54, 7, 54, 8], [0, 0, 55, 8, 54, 7, 54, 8], [55, 7, 55, 8, 0, 0, 54, 8], [55, 7, 55, 8, 54, 7, 0, 0], [55, 9, 0, 0, 56, 9, 56, 10], [0, 0, 55, 10, 56, 9, 56, 10], [55, 9, 55, 10, 0, 0, 56, 10], [55, 9, 55, 10, 56, 9, 0, 0], [57, 1, 0, 0, 58, 1, 58, 2], [0, 0, 57, 2, 58, 1, 58, 2], [57, 1, 57, 2, 0, 0, 58, 2], [57, 1, 57, 2, 58, 1, 0, 0], [57, 3, 0, 0, 56, 3, 56, 4], [0, 0, 57, 4, 56, 3, 56, 4], [57, 3, 57, 4, 0, 0, 56, 4], [57, 3, 57, 4, 56, 3, 0, 0], [57, 5, 0, 0, 58, 5, 58, 6], [0, 0, 57, 6, 58, 5, 58, 6], [57, 5, 57, 6, 0, 0, 58, 6], [57, 5, 57, 6, 58, 5, 0, 0], [57, 7, 0, 0, 56, 7, 56, 8], [0, 0, 57, 8, 56, 7, 56, 8], [57, 7, 57, 8, 0, 0, 56, 8], [57, 7, 57, 8, 56, 7, 0, 0], [57, 9, 0, 0, 58, 9, 58, 10], [0, 0, 57, 10, 58, 9, 58, 10], [57, 9, 57, 10, 0, 0, 58, 10], [57, 9, 57, 10, 58, 9, 0, 0], [59, 3, 0, 0, 58, 3, 58, 4], [0, 0, 59, 4, 58, 3, 58, 4], [59, 3, 59, 4, 0, 0, 58, 4], [59, 3, 59, 4, 58, 3, 0, 0], [59, 7, 0, 0, 58, 7, 58, 8], [0, 0, 59, 8, 58, 7, 58, 8], [59, 7, 59, 8, 0, 0, 58, 8], [59, 7, 59, 8, 58, 7, 0, 0], [61, 1, 0, 0, 60, 1, 60, 2], [0, 0, 61, 2, 60, 1, 60, 2], [61, 1, 61, 2, 0, 0, 60, 2], [61, 1, 61, 2, 60, 1, 0, 0], [61, 3, 0, 0, 62, 3, 62, 4], [0, 0, 61, 4, 62, 3, 62, 4], [61, 3, 61, 4, 0, 0, 62, 4], [61, 3, 61, 4, 62, 3, 0, 0], [61, 5, 0, 0, 60, 5, 60, 6], [0, 0, 61, 6, 60, 5, 60, 6], [61, 5, 61, 6, 0, 0, 60, 6], [61, 5, 61, 6, 60, 5, 0, 0], [61, 7, 0, 0, 62, 7, 62, 8], [0, 0, 61, 8, 62, 7, 62, 8], [61, 7, 61, 8, 0, 0, 62, 8], [61, 7, 61, 8, 62, 7, 0, 0], [61, 9, 0, 0, 60, 9, 60, 10], [0, 0, 61, 10, 60, 9, 60, 10], [61, 9, 61, 10, 0, 0, 60, 10], [61, 9, 61, 10, 60, 9, 0, 0], [63, 1, 0, 0, 62, 1, 62, 2], [0, 0, 63, 2, 62, 1, 62, 2], [63, 1, 63, 2, 0, 0, 62, 2], [63, 1, 63, 2, 62, 1, 0, 0], [63, 3, 0, 0, 64, 3, 64, 4], [0, 0, 63, 4, 64, 3, 64, 4], [63, 3, 63, 4, 0, 0, 64, 4], [63, 3, 63, 4, 64, 3, 0, 0], [63, 5, 0, 0, 62, 5, 62, 6], [0, 0, 63, 6, 62, 5, 62, 6], [63, 5, 63, 6, 0, 0, 62, 6], [63, 5, 63, 6, 62, 5, 0, 0], [63, 7, 0, 0, 64, 7, 64, 8], [0, 0, 63, 8, 64, 7, 64, 8], [63, 7, 63, 8, 0, 0, 64, 8], [63, 7, 63, 8, 64, 7, 0, 0], [63, 9, 0, 0, 62, 9, 62, 10], [0, 0, 63, 10, 62, 9, 62, 10], [63, 9, 63, 10, 0, 0, 62, 10], [63, 9, 63, 10, 62, 9, 0, 0], [65, 1, 0, 0, 64, 1, 64, 2], [0, 0, 65, 2, 64, 1, 64, 2], [65, 1, 65, 2, 0, 0, 64, 2], [65, 1, 65, 2, 64, 1, 0, 0], [65, 3, 0, 0, 66, 3, 66, 4], [0, 0, 65, 4, 66, 3, 66, 4], [65, 3, 65, 4, 0, 0, 66, 4], [65, 3, 65, 4, 66, 3, 0, 0], [65, 5, 0, 0, 64, 5, 64, 6], [0, 0, 65, 6, 64, 5, 64, 6], [65, 5, 65, 6, 0, 0, 64, 6], [65, 5, 65, 6, 64, 5, 0, 0], [65, 7, 0, 0, 66, 7, 66, 8], [0, 0, 65, 8, 66, 7, 66, 8], [65, 7, 65, 8, 0, 0, 66, 8], [65, 7, 65, 8, 66, 7, 0, 0], [65, 9, 0, 0, 64, 9, 64, 10], [0, 0, 65, 10, 64, 9, 64, 10], [65, 9, 65, 10, 0, 0, 64, 10], [65, 9, 65, 10, 64, 9, 0, 0], [67, 1, 0, 0, 66, 1, 66, 2], [0, 0, 67, 2, 66, 1, 66, 2], [67, 1, 67, 2, 0, 0, 66, 2], [67, 1, 67, 2, 66, 1, 0, 0], [67, 3, 0, 0, 68, 3, 68, 4], [0, 0, 67, 4, 68, 3, 68, 4], [67, 3, 67, 4, 0, 0, 68, 4], [67, 3, 67, 4, 68, 3, 0, 0], [67, 5, 0, 0, 66, 5, 66, 6], [0, 0, 67, 6, 66, 5, 66, 6], [67, 5, 67, 6, 0, 0, 66, 6], [67, 5, 67, 6, 66, 5, 0, 0], [67, 7, 0, 0, 68, 7, 68, 8], [0, 0, 67, 8, 68, 7, 68, 8], [67, 7, 67, 8, 0, 0, 68, 8], [67, 7, 67, 8, 68, 7, 0, 0], [67, 9, 0, 0, 66, 9, 66, 10], [0, 0, 67, 10, 66, 9, 66, 10], [67, 9, 67, 10, 0, 0, 66, 10], [67, 9, 67, 10, 66, 9, 0, 0], [69, 1, 0, 0, 68, 1, 68, 2], [0, 0, 69, 2, 68, 1, 68, 2], [69, 1, 69, 2, 0, 0, 68, 2], [69, 1, 69, 2, 68, 1, 0, 0], [69, 5, 0, 0, 68, 5, 68, 6], [0, 0, 69, 6, 68, 5, 68, 6], [69, 5, 69, 6, 0, 0, 68, 6], [69, 5, 69, 6, 68, 5, 0, 0], [69, 9, 0, 0, 68, 9, 68, 10], [0, 0, 69, 10, 68, 9, 68, 10], [69, 9, 69, 10, 0, 0, 68, 10], [69, 9, 69, 10, 68, 9, 0, 0], [71, 1, 0, 0, 72, 1, 72, 2], [0, 0, 71, 2, 72, 1, 72, 2], [71, 1, 71, 2, 0, 0, 72, 2], [71, 1, 71, 2, 72, 1, 0, 0], [71, 3, 0, 0, 70, 3, 70, 4], [0, 0, 71, 4, 70, 3, 70, 4], [71, 3, 71, 4, 0, 0, 70, 4], [71, 3, 71, 4, 70, 3, 0, 0], [71, 5, 0, 0, 72, 5, 72, 6], [0, 0, 71, 6, 72, 5, 72, 6], [71, 5, 71, 6, 0, 0, 72, 6], [71, 5, 71, 6, 72, 5, 0, 0], [71, 7, 0, 0, 70, 7, 70, 8], [0, 0, 71, 8, 70, 7, 70, 8], [71, 7, 71, 8, 0, 0, 70, 8], [71, 7, 71, 8, 70, 7, 0, 0], [71, 9, 0, 0, 72, 9, 72, 10], [0, 0, 71, 10, 72, 9, 72, 10], [71, 9, 71, 10, 0, 0, 72, 10], [71, 9, 71, 10, 72, 9, 0, 0], [73, 1, 0, 0, 74, 1, 74, 2], [0, 0, 73, 2, 74, 1, 74, 2], [73, 1, 73, 2, 0, 0, 74, 2], [73, 1, 73, 2, 74, 1, 0, 0], [73, 3, 0, 0, 72, 3, 72, 4], [0, 0, 73, 4, 72, 3, 72, 4], [73, 3, 73, 4, 0, 0, 72, 4], [73, 3, 73, 4, 72, 3, 0, 0], [73, 5, 0, 0, 74, 5, 74, 6], [0, 0, 73, 6, 74, 5, 74, 6], [73, 5, 73, 6, 0, 0, 74, 6], [73, 5, 73, 6, 74, 5, 0, 0], [73, 7, 0, 0, 72, 7, 72, 8], [0, 0, 73, 8, 72, 7, 72, 8], [73, 7, 73, 8, 0, 0, 72, 8], [73, 7, 73, 8, 72, 7, 0, 0], [73, 9, 0, 0, 74, 9, 74, 10], [0, 0, 73, 10, 74, 9, 74, 10], [73, 9, 73, 10, 0, 0, 74, 10], [73, 9, 73, 10, 74, 9, 0, 0], [75, 1, 0, 0, 76, 1, 76, 2], [0, 0, 75, 2, 76, 1, 76, 2], [75, 1, 75, 2, 0, 0, 76, 2], [75, 1, 75, 2, 76, 1, 0, 0], [75, 3, 0, 0, 74, 3, 74, 4], [0, 0, 75, 4, 74, 3, 74, 4], [75, 3, 75, 4, 0, 0, 74, 4], [75, 3, 75, 4, 74, 3, 0, 0], [75, 5, 0, 0, 76, 5, 76, 6], [0, 0, 75, 6, 76, 5, 76, 6], [75, 5, 75, 6, 0, 0, 76, 6], [75, 5, 75, 6, 76, 5, 0, 0], [75, 7, 0, 0, 74, 7, 74, 8], [0, 0, 75, 8, 74, 7, 74, 8], [75, 7, 75, 8, 0, 0, 74, 8], [75, 7, 75, 8, 74, 7, 0, 0], [75, 9, 0, 0, 76, 9, 76, 10], [0, 0, 75, 10, 76, 9, 76, 10], [75, 9, 75, 10, 0, 0, 76, 10], [75, 9, 75, 10, 76, 9, 0, 0], [77, 1, 0, 0, 78, 1, 78, 2], [0, 0, 77, 2, 78, 1, 78, 2], [77, 1, 77, 2, 0, 0, 78, 2], [77, 1, 77, 2, 78, 1, 0, 0], [77, 3, 0, 0, 76, 3, 76, 4], [0, 0, 77, 4, 76, 3, 76, 4], [77, 3, 77, 4, 0, 0, 76, 4], [77, 3, 77, 4, 76, 3, 0, 0], [77, 5, 0, 0, 78, 5, 78, 6], [0, 0, 77, 6, 78, 5, 78, 6], [77, 5, 77, 6, 0, 0, 78, 6], [77, 5, 77, 6, 78, 5, 0, 0], [77, 7, 0, 0, 76, 7, 76, 8], [0, 0, 77, 8, 76, 7, 76, 8], [77, 7, 77, 8, 0, 0, 76, 8], [77, 7, 77, 8, 76, 7, 0, 0], [77, 9, 0, 0, 78, 9, 78, 10], [0, 0, 77, 10, 78, 9, 78, 10], [77, 9, 77, 10, 0, 0, 78, 10], [77, 9, 77, 10, 78, 9, 0, 0], [79, 3, 0, 0, 78, 3, 78, 4], [0, 0, 79, 4, 78, 3, 78, 4], [79, 3, 79, 4, 0, 0, 78, 4], [79, 3, 79, 4, 78, 3, 0, 0], [79, 7, 0, 0, 78, 7, 78, 8], [0, 0, 79, 8, 78, 7, 78, 8], [79, 7, 79, 8, 0, 0, 78, 8], [79, 7, 79, 8, 78, 7, 0, 0], [81, 1, 0, 0, 80, 1, 80, 2], [0, 0, 81, 2, 80, 1, 80, 2], [81, 1, 81, 2, 0, 0, 80, 2], [81, 1, 81, 2, 80, 1, 0, 0], [81, 3, 0, 0, 82, 3, 82, 4], [0, 0, 81, 4, 82, 3, 82, 4], [81, 3, 81, 4, 0, 0, 82, 4], [81, 3, 81, 4, 82, 3, 0, 0], [81, 5, 0, 0, 80, 5, 80, 6], [0, 0, 81, 6, 80, 5, 80, 6], [81, 5, 81, 6, 0, 0, 80, 6], [81, 5, 81, 6, 80, 5, 0, 0], [81, 7, 0, 0, 82, 7, 82, 8], [0, 0, 81, 8, 82, 7, 82, 8], [81, 7, 81, 8, 0, 0, 82, 8], [81, 7, 81, 8, 82, 7, 0, 0], [81, 9, 0, 0, 80, 9, 80, 10], [0, 0, 81, 10, 80, 9, 80, 10], [81, 9, 81, 10, 0, 0, 80, 10], [81, 9, 81, 10, 80, 9, 0, 0], [83, 1, 0, 0, 82, 1, 82, 2], [0, 0, 83, 2, 82, 1, 82, 2], [83, 1, 83, 2, 0, 0, 82, 2], [83, 1, 83, 2, 82, 1, 0, 0], [83, 3, 0, 0, 84, 3, 84, 4], [0, 0, 83, 4, 84, 3, 84, 4], [83, 3, 83, 4, 0, 0, 84, 4], [83, 3, 83, 4, 84, 3, 0, 0], [83, 5, 0, 0, 82, 5, 82, 6], [0, 0, 83, 6, 82, 5, 82, 6], [83, 5, 83, 6, 0, 0, 82, 6], [83, 5, 83, 6, 82, 5, 0, 0], [83, 7, 0, 0, 84, 7, 84, 8], [0, 0, 83, 8, 84, 7, 84, 8], [83, 7, 83, 8, 0, 0, 84, 8], [83, 7, 83, 8, 84, 7, 0, 0], [83, 9, 0, 0, 82, 9, 82, 10], [0, 0, 83, 10, 82, 9, 82, 10], [83, 9, 83, 10, 0, 0, 82, 10], [83, 9, 83, 10, 82, 9, 0, 0], [85, 1, 0, 0, 84, 1, 84, 2], [0, 0, 85, 2, 84, 1, 84, 2], [85, 1, 85, 2, 0, 0, 84, 2], [85, 1, 85, 2, 84, 1, 0, 0], [85, 3, 0, 0, 86, 3, 86, 4], [0, 0, 85, 4, 86, 3, 86, 4], [85, 3, 85, 4, 0, 0, 86, 4], [85, 3, 85, 4, 86, 3, 0, 0], [85, 5, 0, 0, 84, 5, 84, 6], [0, 0, 85, 6, 84, 5, 84, 6], [85, 5, 85, 6, 0, 0, 84, 6], [85, 5, 85, 6, 84, 5, 0, 0], [85, 7, 0, 0, 86, 7, 86, 8], [0, 0, 85, 8, 86, 7, 86, 8], [85, 7, 85, 8, 0, 0, 86, 8], [85, 7, 85, 8, 86, 7, 0, 0], [85, 9, 0, 0, 84, 9, 84, 10], [0, 0, 85, 10, 84, 9, 84, 10], [85, 9, 85, 10, 0, 0, 84, 10], [85, 9, 85, 10, 84, 9, 0, 0], [87, 1, 0, 0, 86, 1, 86, 2], [0, 0, 87, 2, 86, 1, 86, 2], [87, 1, 87, 2, 0, 0, 86, 2], [87, 1, 87, 2, 86, 1, 0, 0], [87, 3, 0, 0, 88, 3, 88, 4], [0, 0, 87, 4, 88, 3, 88, 4], [87, 3, 87, 4, 0, 0, 88, 4], [87, 3, 87, 4, 88, 3, 0, 0], [87, 5, 0, 0, 86, 5, 86, 6], [0, 0, 87, 6, 86, 5, 86, 6], [87, 5, 87, 6, 0, 0, 86, 6], [87, 5, 87, 6, 86, 5, 0, 0], [87, 7, 0, 0, 88, 7, 88, 8], [0, 0, 87, 8, 88, 7, 88, 8], [87, 7, 87, 8, 0, 0, 88, 8], [87, 7, 87, 8, 88, 7, 0, 0], [87, 9, 0, 0, 86, 9, 86, 10], [0, 0, 87, 10, 86, 9, 86, 10], [87, 9, 87, 10, 0, 0, 86, 10], [87, 9, 87, 10, 86, 9, 0, 0], [89, 1, 0, 0, 88, 1, 88, 2], [0, 0, 89, 2, 88, 1, 88, 2], [89, 1, 89, 2, 0, 0, 88, 2], [89, 1, 89, 2, 88, 1, 0, 0], [89, 5, 0, 0, 88, 5, 88, 6], [0, 0, 89, 6, 88, 5, 88, 6], [89, 5, 89, 6, 0, 0, 88, 6], [89, 5, 89, 6, 88, 5, 0, 0], [89, 9, 0, 0, 88, 9, 88, 10], [0, 0, 89, 10, 88, 9, 88, 10], [89, 9, 89, 10, 0, 0, 88, 10], [89, 9, 89, 10, 88, 9, 0, 0], [91, 1, 0, 0, 92, 1, 92, 2], [0, 0, 91, 2, 92, 1, 92, 2], [91, 1, 91, 2, 0, 0, 92, 2], [91, 1, 91, 2, 92, 1, 0, 0], [91, 3, 0, 0, 90, 3, 90, 4], [0, 0,

TABLE 32-continued 91, 4, 90, 3, 90, 4], [91, 3, 91, 4, 0, 0, 90, 4], [91, 3, 91, 4, 90, 3, 0, 0], [91, 5, 0, 0, 92, 5, 92, 6], [0, 0, 91, 6, 92, 5, 92, 6], [91, 5, 91, 6, 0, 0, 92, 6], [91, 5, 91, 6, 92, 5, 0, 0], [91, 7, 0, 0, 90, 7, 90, 8], [0, 0, 91, 8, 90, 7, 90, 8], [91, 7, 91, 8, 0, 0, 90, 8], [91, 7, 91, 8, 90, 7, 0, 0], [91, 9, 0, 0, 92, 9, 92, 10], [0, 0, 91, 10, 92, 9, 92, 10], [91, 9, 91, 10, 0, 0, 92, 10], [91, 9, 91, 10, 92, 9, 0, 0], [93, 1, 0, 0, 94, 1, 94, 2], [0, 0, 93, 2, 94, 1, 94, 2], [93, 1, 93, 2, 0, 0, 94, 2], [93, 1, 93, 2, 94, 1, 0, 0], [93, 3, 0, 0, 92, 3, 92, 4], [0, 0, 93, 4, 92, 3, 92, 4], [93, 3, 93, 4, 0, 0, 92, 4], [93, 3, 93, 4, 92, 3, 0, 0], [93, 5, 0, 0, 94, 5, 94, 6], [0, 0, 93, 6, 94, 5, 94, 6], [93, 5, 93, 6, 0, 0, 94, 6], [93, 5, 93, 6, 94, 5, 0, 0], [93, 7, 0, 0, 92, 7, 92, 8], [0, 0, 93, 8, 92, 7, 92, 8], [93, 7, 93, 8, 0, 0, 92, 8], [93, 7, 93, 8, 92, 7, 0, 0], [93, 9, 0, 0, 94, 9, 94, 10], [0, 0, 93, 10, 94, 9, 94, 10], [93, 9, 93, 10, 0, 0, 94, 10], [93, 9, 93, 10, 94, 9, 0, 0], [95, 1, 0, 0, 96, 1, 96, 2], [0, 0, 95, 2, 96, 1, 96, 2], [95, 1, 95, 2, 0, 0, 96, 2], [95, 1, 95, 2, 96, 1, 0, 0], [95, 3, 0, 0, 94, 3, 94, 4], [0, 0, 95, 4, 94, 3, 94, 4], [95, 3, 95, 4, 0, 0, 94, 4], [95, 3, 95, 4, 94, 3, 0, 0], [95, 5, 0, 0, 96, 5, 96, 6], [0, 0, 95, 6, 96, 5, 96, 6], [95, 5, 95, 6, 0, 0, 96, 6], [95, 5, 95, 6, 96, 5, 0, 0], [95, 7, 0, 0, 94, 7, 94, 8], [0, 0, 95, 8, 94, 7, 94, 8], [95, 7, 95, 8, 0, 0, 94, 8], [95, 7, 95, 8, 94, 7, 0, 0], [95, 9, 0, 0, 96, 9, 96, 10], [0, 0, 95, 10, 96, 9, 96, 10], [95, 9, 95, 10, 0, 0, 96, 10], [95, 9, 95, 10, 96, 9, 0, 0], [97, 1, 0, 0, 98, 1, 98, 2], [0, 0, 97, 2, 98, 1, 98, 2], [97, 1, 97, 2, 0, 0, 98, 2], [97, 1, 97, 2, 98, 1, 0, 0], [97, 3, 0, 0, 96, 3, 96, 4], [0, 0, 97, 4, 96, 3, 96, 4], [97, 3, 97, 4, 0, 0, 96, 4], [97, 3, 97, 4, 96, 3, 0, 0], [97, 5, 0, 0, 98, 5, 98, 6], [0, 0, 97, 6, 98, 5, 98, 6], [97, 5, 97, 6, 0, 0, 98, 6], [97, 5, 97, 6, 98, 5, 0, 0], [97, 7, 0, 0, 96, 7, 96, 8], [0, 0, 97, 8, 96, 7, 96, 8], [97, 7, 97, 8, 0, 0, 96, 8], [97, 7, 97, 8, 96, 7, 0, 0], [97, 9, 0, 0, 98, 9, 98, 10], [0, 0, 97, 10, 98, 9, 98, 10], [97, 9, 97, 10, 0, 0, 98, 10], [97, 9, 97, 10, 98, 9, 0, 0], [99, 3, 0, 0, 98, 3, 98, 4], [0, 0, 99, 4, 98, 3, 98, 4], [99, 3, 99, 4, 0, 0, 98, 4], [99, 3, 99, 4, 98, 3, 0, 0], [99, 7, 0, 0, 98, 7, 98, 8], [0, 0, 99, 8, 98, 7, 98, 8], [99, 7, 99, 8, 0, 0, 98, 8], [99, 7, 99, 8, 98, 7, 0, 0], [0, 2, 0, 0, 19, 2, 19, 3], [0, 0, 0, 3, 19, 2, 19, 3], [0, 2, 0, 3, 19, 2, 0, 0], [0, 6, 0, 0, 19, 6, 19, 7], [0, 0, 0, 7, 19, 6, 19, 7], [0, 6, 0, 7, 0, 0, 19, 7], [0, 6, 0, 7, 19, 6, 0, 0], [2, 2, 0, 0, 17, 2, 17, 3], [0, 0, 2, 3, 17, 2, 17, 3], [2, 2, 2, 3, 0, 0, 17, 3], [2, 2, 2, 3, 17, 2, 0, 0], [2, 6, 0, 0, 17, 6, 17, 7], [0, 0, 2, 7, 17, 6, 17, 7], [2, 6, 2, 7, 0, 0, 17, 7], [2, 6, 2, 7, 17, 6, 0, 0], [4, 2, 0, 0, 15, 2, 15, 3], [0, 0, 4, 3, 15, 2, 15, 3], [4, 2, 4, 3, 0, 0, 15, 3], [4, 2, 4, 3, 15, 2, 0, 0], [4, 6, 0, 0, 15, 6, 15, 7], [0, 0, 4, 7, 15, 6, 15, 7], [4, 6, 4, 7, 0, 0, 15, 7], [4, 6, 4, 7, 15, 6, 0, 0], [6, 2, 0, 0, 13, 2, 13, 3], [0, 0, 6, 3, 13, 2, 13, 3], [6, 2, 6, 3, 0, 0, 13, 3], [6, 2, 6, 3, 13, 2, 0, 0], [6, 6, 0, 0, 13, 6, 13, 7], [0, 0, 6, 7, 13, 6, 13, 7], [6, 6, 6, 7, 0, 0, 13, 7], [6, 6, 6, 7, 13, 6, 0, 0], [8, 2, 0, 0, 11, 2, 11, 3], [0, 0, 8, 3, 11, 2, 11, 3], [8, 2, 8, 3, 0, 0, 11, 3], [8, 2, 8, 3, 11, 2, 0, 0], [8, 6, 0, 0, 11, 6, 11, 7], [0, 0, 8, 7, 11, 6, 11, 7], [8, 6, 8, 7, 0, 0, 11, 7], [8, 6, 8, 7, 11, 6, 0, 0], [10, 2, 0, 0, 29, 2, 29, 3], [0, 0, 10, 3, 29, 2, 29, 3], [10, 2, 10, 3, 0, 0, 29, 3], [10, 2, 10, 3, 29, 2, 0, 0], [10, 4, 0, 0, 9, 4, 9, 5], [0, 0, 10, 5, 9, 4, 9, 5], [10, 4, 10, 5, 0, 0, 9, 5], [10, 4, 10, 5, 9, 4, 0, 0], [10, 6, 0, 0, 29, 6, 29, 7], [0, 0, 10, 7, 29, 6, 29, 7], [10, 6, 10, 7, 0, 0, 29, 7], [10, 6, 10, 7, 29, 6, 0, 0], [10, 8, 0, 0, 9, 8, 9, 9], [0, 0, 10, 9, 9, 8, 9, 9], [10, 8, 10, 9, 0, 0, 9, 9], [10, 8, 10, 9, 9, 8, 0, 0], [12, 2, 0, 0, 27, 2, 27, 3], [0, 0, 12, 3, 27, 2, 27, 3], [12, 2, 12, 3, 0, 0, 27, 3], [12, 2, 12, 3, 27, 2, 0, 0], [12, 4, 0, 0, 7, 4, 7, 5], [0, 0, 12, 5, 7, 4, 7, 5], [12, 4, 12, 5, 0, 0, 7, 5], [12, 4, 12, 5, 7, 4, 0, 0], [12, 6, 0, 0, 27, 6, 27, 7], [0, 0, 12, 7, 27, 6, 27, 7], [12, 6, 12, 7, 0, 0, 27, 7], [12, 6, 12, 7, 27, 6, 0, 0], [12, 8, 0, 0, 7, 8, 7, 9], [0, 0, 12, 9, 7, 8, 7, 9], [12, 8, 12, 9, 0, 0, 7, 9], [12, 8, 12, 9, 7, 8, 0, 0], [14, 2, 0, 0, 25, 2, 25, 3], [0, 0, 14, 3, 25, 2, 25, 3], [14, 2, 14, 3, 0, 0, 25, 3], [14, 2, 14, 3, 25, 2, 0, 0], [14, 4, 0, 0, 5, 4, 5, 5], [0, 0, 14, 5, 5, 4, 5, 5], [14, 4, 14, 5, 0, 0, 5, 5], [14, 4, 14, 5, 5, 4, 0, 0], [14, 6, 0, 0, 25, 6, 25, 7], [0, 0, 14, 7, 25, 6, 25, 7], [14, 6, 14, 7, 0, 0, 25, 7], [14, 6, 14, 7, 25, 6, 0, 0], [14, 8, 0, 0, 5, 8, 5, 9], [0, 0, 14, 9, 5, 8, 5, 9], [14, 8, 14, 9, 0, 0, 5, 9], [14, 8, 14, 9, 5, 8, 0, 0], [16, 2, 0, 0, 23, 2, 23, 3], [0, 0, 16, 3, 23, 2, 23, 3], [16, 2, 16, 3, 0, 0, 23, 3], [16, 2, 16, 3, 23, 2, 0, 0], [16, 4, 0, 0, 3, 4, 3, 5], [0, 0, 16, 5, 3, 4, 3, 5], [16, 4, 16, 5, 0, 0, 3, 5], [16, 4, 16, 5, 3, 4, 0, 0], [16, 6, 0, 0, 23, 6, 23, 7], [0, 0, 16, 7, 23, 6, 23, 7], [16, 6, 16, 7, 0, 0, 23, 7], [16, 6, 16, 7, 23, 6, 0, 0], [16, 8, 0, 0, 3, 8, 3, 9], [0, 0, 16, 9, 3, 8, 3, 9], [16, 8, 16, 9, 0, 0, 3, 9], [16, 8, 16, 9, 3, 8, 0, 0], [18, 2, 0, 0, 21, 2, 21, 3], [0, 0, 18, 3, 21, 2, 21, 3], [18, 2, 18, 3, 0, 0, 21, 3], [18, 2, 18, 3, 21, 2, 0, 0], [18, 4, 0, 0, 1, 4, 1, 5], [0, 0, 18, 5, 1, 4, 1, 5], [18, 4, 18, 5, 0, 0, 1, 5], [18, 4, 18, 5, 1, 4, 0, 0], [18, 6, 0, 0, 21, 6, 21, 7], [0, 0, 18, 7, 21, 6, 21, 7], [18, 6, 18, 7, 0, 0, 21, 7], [18, 6, 18, 7, 21, 6, 0, 0], [18, 8, 0, 0, 1, 8, 1, 9], [0, 0, 18, 9, 1, 8, 1, 9], [18, 8, 18, 9, 0, 0, 1, 9], [18, 8, 18, 9, 1, 8, 0, 0], [20, 2, 0, 0, 39, 2, 39, 3], [0, 0, 20, 3, 39, 2, 39, 3], [20, 2, 20, 3, 0, 0, 39, 3], [20, 2, 20, 3, 39, 2, 0, 0], [20, 4, 0, 0, 19, 4, 19, 5], [0, 0, 20, 5, 19, 4, 19, 5], [20, 4, 20, 5, 0, 0, 19, 5], [20, 4, 20, 5, 19, 4, 0, 0], [20, 6, 0, 0, 39, 6, 39, 7], [0, 0, 20, 7, 39, 6, 39, 7], [20, 6, 20, 7, 0, 0, 39, 7], [20, 6, 20, 7, 39, 6, 0, 0], [20, 8, 0, 0, 19, 8, 19, 9], [0, 0, 20, 9, 19, 8, 19, 9], [20, 8, 20, 9, 0, 0, 19, 9], [20, 8, 20, 9, 19, 8, 0, 0], [22, 2, 0, 0, 37, 2, 37, 3], [0, 0, 22, 3, 37, 2, 37, 3], [22, 2, 22, 3, 0, 0, 37, 3], [22, 2, 22, 3, 37, 2, 0, 0], [22, 4, 0, 0, 17, 4, 17, 5], [0, 0, 22, 5, 17, 4, 17, 5], [22, 4, 22, 5, 0, 0, 17, 5], [22, 4, 22, 5, 17, 4, 0, 0], [22, 6, 0, 0, 37, 6, 37, 7], [0, 0, 22, 7, 37, 6, 37, 7], [22, 6, 22, 7, 0, 0, 37, 7], [22, 6, 22, 7, 37, 6, 0, 0], [22, 8, 0, 0, 17, 8, 17, 9], [0, 0, 22, 9, 17, 8, 17, 9], [22, 8, 22, 9, 0, 0, 17, 9], [22, 8, 22, 9, 17, 8, 0, 0], [24, 2, 0, 0, 35, 2, 35, 3], [0, 0, 24, 3, 35, 2, 35, 3], [24, 2, 24, 3, 0, 0, 35, 3], [24, 2, 24, 3, 35, 2, 0, 0], [24, 4, 0, 0, 15, 4, 15, 5], [0, 0, 24, 5, 15, 4, 15, 5], [24, 4, 24, 5, 0, 0, 15, 5], [24, 4, 24, 5, 15, 4, 0, 0], [24, 6, 0, 0, 35, 6, 35, 7], [0, 0, 24, 7, 35, 6, 35, 7], [24, 6, 24, 7, 0, 0, 35, 7], [24, 6, 24, 7, 35, 6, 0, 0], [24, 8, 0, 0, 15, 8, 15, 9], [0, 0, 24, 9, 15, 8, 15, 9], [24, 8, 24, 9, 0, 0, 15, 9], [24, 8, 24, 9, 15, 8, 0, 0], [26, 2, 0, 0, 33, 2, 33, 3], [0, 0, 26, 3, 33, 2, 33, 3], [26, 2, 26, 3, 0, 0, 33, 3], [26, 2, 26, 3, 33, 2, 0, 0], [26, 4, 0, 0, 13, 4, 13, 5], [0, 0, 26, 5, 13, 4, 13, 5], [26, 4, 26, 5, 0, 0, 13, 5], [26, 4, 26, 5, 13, 4, 0, 0], [26, 6, 0, 0, 33, 6, 33, 7], [0, 0, 26, 7, 33, 6, 33, 7], [26, 6, 26, 7, 0, 0, 33, 7], [26, 6, 26, 7, 33, 6, 0, 0], [26, 8, 0, 0, 13, 8, 13, 9], [0, 0, 26, 9, 13, 8, 13, 9], [26, 8, 26, 9, 0, 0, 13, 9], [26, 8, 26, 9, 13, 8, 0, 0], [28, 2, 0, 0, 31, 2, 31, 3], [0, 0, 28, 3, 31, 2, 31, 3], [28, 2, 28, 3, 0, 0, 31, 3], [28, 2, 28, 3, 31, 2, 0, 0], [28, 4, 0, 0, 11, 4, 11, 5], [0, 0, 28, 5, 11, 4, 11, 5], [28, 4, 28, 5, 0, 0, 11, 5], [28, 4, 28, 5, 11, 4, 0, 0], [28, 6, 0, 0, 31, 6, 31, 7], [0, 0, 28, 7, 31, 6, 31, 7], [28, 6, 28, 7, 0, 0, 31, 7], [28, 6, 28, 7, 31, 6, 0, 0], [28, 8, 0, 0, 11, 8, 11, 9], [0, 0, 28, 9, 11, 8, 11, 9], [28, 8, 28, 9, 0, 0, 11, 9], [28, 8, 28, 9, 11, 8, 0, 0], [30, 2, 0, 0, 49, 2, 49, 3], [0, 0, 30, 3, 49, 2, 49, 3], [30, 2, 30, 3, 0, 0, 49, 3], [30, 2, 30, 3, 49, 2, 0, 0], [30, 4, 0, 0, 29, 4, 29, 5], [0, 0, 30, 5, 29, 4, 29, 5], [30, 4, 30, 5, 0, 0, 29, 5], [30, 4, 30, 5, 29, 4, 0, 0], [30, 6, 0, 0, 49, 6, 49, 7], [0, 0, 30, 7, 49, 6, 49, 7], [30, 6, 30, 7, 0, 0, 49, 7], [30, 6, 30, 7, 49, 6, 0, 0], [30, 8, 0, 0, 29, 8, 29, 9], [0, 0, 30, 9, 29, 8, 29, 9], [30, 8, 30, 9, 0, 0, 29, 9], [30, 8, 30, 9, 29, 8, 0, 0], [32, 2, 0, 0, 47, 2, 47, 3], [0, 0, 32, 3, 47, 2, 47, 3], [32, 2, 32, 3, 0, 0, 47, 3], [32, 2, 32, 3, 47, 2, 0, 0], [32, 4, 0, 0, 27, 4, 27, 5], [0, 0, 32, 5, 27, 4, 27, 5], [32, 4, 32, 5, 0, 0, 27, 5], [32, 4, 32, 5, 27, 4, 0, 0], [32, 6, 0, 0, 47, 6, 47, 7], [0, 0, 32, 7, 47, 6, 47, 7], [32, 6, 32, 7, 0, 0, 47, 7], [32, 6, 32, 7, 47, 6, 0, 0], [32, 8, 0, 0, 27, 8, 27, 9], [0, 0, 32, 9, 27, 8, 27, 9], [32, 8, 32, 9, 0, 0, 27, 9], [32, 8, 32, 9, 27, 8, 0, 0], [34, 2, 0, 0, 45, 2, 45, 3], [0, 0, 34, 3, 45, 2, 45, 3], [34, 2, 34, 3, 0, 0, 45, 3], [34, 2, 34, 3, 45, 2, 0, 0], [34, 4, 0, 0, 25, 4, 25, 5], [0, 0, 34, 5, 25, 4, 25, 5], [34, 4, 34, 5, 0, 0, 25, 5], [34, 4, 34, 5, 25, 4, 0, 0], [34, 6, 0, 0, 45, 6, 45, 7], [0, 0, 34, 7, 45, 6, 45, 7], [34, 6, 34, 7, 0, 0, 45, 7], [34, 6, 34, 7, 45, 6, 0, 0], [34, 8, 0, 0, 25, 8, 25, 9], [0, 0, 34, 9, 25, 8, 25, 9], [34, 8, 34, 9, 0, 0, 25, 9], [34, 8, 34, 9, 25, 8, 0, 0], [36, 2, 0, 0, 43, 2, 43, 3], [0, 0, 36, 3, 43, 2, 43, 3], [36, 2, 36, 3, 0, 0, 43, 3], [36, 2, 36, 3, 43, 2, 0, 0], [36, 4, 0, 0, 23, 4, 23, 5], [0, 0, 36, 5, 23, 4, 23, 5], [36, 4, 36, 5, 0, 0, 23, 5], [36, 4, 36, 5, 23, 4, 0, 0], [36, 6, 0, 0, 43, 6, 43, 7], [0, 0, 36, 7, 43, 6, 43, 7], [36, 6, 36, 7, 0, 0, 43, 7], [36, 6, 36, 7, 43, 6, 0, 0], [36, 8, 0, 0, 23, 8, 23, 9], [0, 0, 36, 9, 23, 8, 23, 9], [36, 8, 36, 9, 0, 0, 23, 9], [36, 8, 36, 9, 23, 8, 0, 0], [38, 2, 0, 0, 41, 2, 41, 3], [0, 0, 38, 3, 41, 2, 41, 3], [38, 2, 38, 3, 0, 0, 41, 3], [38, 2, 38, 3, 41, 2, 0, 0], [38, 4, 0, 0, 21, 4, 21, 5], [0, 0, 38, 5, 21, 4, 21, 5], [38, 4, 38, 5, 0, 0, 21, 5], [38, 4, 38, 5, 21, 4, 0, 0], [38, 6, 0, 0, 41, 6, 41, 7], [0, 0, 38, 7, 41, 6, 41, 7], [38, 6, 38, 7, 0, 0, 41, 7], [38, 6, 38, 7, 41, 6, 0, 0], [38, 8, 0, 0, 21, 8, 21, 9], [0, 0, 38, 9, 21, 8, 21, 9], [38, 8, 38, 9, 0, 0, 21, 9], [38, 8, 38, 9, 21, 8, 0, 0], [40, 2, 0, 0, 59, 2, 59, 3], [0, 0, 40, 3, 59, 2, 59, 3], [40, 2, 40, 3, 0, 0, 59, 3], [40, 2, 40, 3, 59, 2, 0, 0], [40, 4, 0, 0, 39, 4, 39, 5], [0, 0, 40, 5, 39, 4, 39, 5], [40, 4, 40, 5, 0, 0, 39, 5], [40, 4, 40, 5, 39, 4, 0, 0], [40, 6, 0, 0, 59, 6, 59, 7], [0, 0, 40, 7, 59, 6, 59, 7], [40, 6, 40, 7, 0, 0, 59, 7], [40, 6, 40, 7, 59, 6, 0, 0], [40, 8, 0, 0, 39, 8, 39, 9], [0, 0, 40, 9, 39, 8, 39, 9], [40, 8, 40, 9, 0, 0, 39, 9], [40, 8, 40, 9, 39, 8, 0, 0], [42, 2, 0, 0, 57, 2, 57, 3], [0, 0, 42, 3, 57, 2, 57, 3], [42, 2, 42, 3, 0, 0, 57, 3], [42, 2, 42, 3, 57, 2, 0, 0], [42, 4, 0, 0, 37, 4, 37, 5], [0, 0, 42, 5, 37, 4, 37, 5], [42, 4, 42, 5, 0, 0, 37, 5], [42, 4, 42, 5, 37, 4, 0, 0], [42, 6, 0, 0, 57, 6, 57, 7], [0, 0, 42, 7, 57, 6, 57, 7], [42, 6, 42, 7, 0, 0, 57, 7], [42, 6, 42, 7, 57, 6, 0, 0], [42, 8, 0, 0, 37, 8, 37, 9], [0, 0, 42, 9, 37, 8, 37, 9], [42, 8, 42, 9, 0, 0, 37, 9], [42, 8, 42, 9, 37, 8, 0, 0], [44, 2, 0, 0, 55, 2, 55, 3], [0, 0, 44, 3, 55, 2, 55, 3], [44, 2, 44, 3, 0, 0, 55, 3], [44, 2, 44, 3, 55, 2, 0, 0], [44, 4, 0, 0, 35, 4, 35, 5], [0, 0, 44, 5, 35, 4, 35, 5], [44, 4, 44, 5, 0, 0, 35, 5], [44, 4, 44, 5, 35, 4, 0, 0], [44, 6, 0, 0, 55, 6, 55, 7], [0, 0, 44, 7, 55, 6, 55, 7], [44, 6, 44, 7, 0, 0, 55, 7], [44, 6, 44, 7, 55, 6, 0, 0], [44, 8, 0, 0, 35, 8, 35, 9], [0, 0, 44, 9, 35, 8, 35, 9], [44, 8, 44, 9, 0, 0, 35, 9], [44, 8, 44, 9, 35, 8, 0, 0], [46, 2, 0, 0, 53, 2, 53, 3], [0, 0, 46, 3, 53, 2, 53, 3], [46, 2, 46, 3, 0, 0, 53, 3], [46, 2, 46, 3, 53, 2, 0, 0], [46, 4, 0, 0, 33, 4, 33, 5], [0, 0, 46, 5, 33, 4, 33, 5], [46, 4, 46, 5, 0, 0, 33, 5], [46, 4, 46, 5, 33, 4, 0, 0], [46, 6, 0, 0, 53, 6, 53, 7], [0, 0, 46, 7, 53, 6, 53, 7], [46, 6, 46, 7, 0, 0, 53, 7], [46, 6, 46, 7, 53, 6, 0, 0], [46, 8, 0, 0, 33, 8, 33, 9], [0, 0, 46, 9, 33, 8, 33, 9], [46, 8, 46, 9, 0, 0, 33, 9], TABLE 32-continued

[46, 8, 46, 9, 33, 8, 0, 0], [48, 2, 0, 0, 51, 2, 51, 3], [0, 0, 48, 3, 51, 2, 51, 3], [48, 2, 48, 3, 0, 0, 51, 3], [48, 2, 48, 3, 51, 2, 0, 0], [48, 4, 0, 0, 31, 4, 31, 5], [0, 0, 48, 5, 31, 4, 31, 5], [48, 4, 48, 5, 0, 0, 31, 5], [48, 4, 48, 5, 31, 4, 0, 0], [48, 6, 0, 0, 51, 6, 51, 7], [0, 0, 48, 7, 51, 6, 51, 7], [48, 6, 48, 7, 0, 0, 51, 7], [48, 6, 48, 7, 51, 6, 0, 0], [48, 8, 0, 0, 31, 8, 31, 9], [0, 0, 48, 9, 31, 8, 31, 9], [48, 8, 48, 9, 0, 0, 31, 9], [48, 8, 48, 9, 31, 8, 0, 0], [50, 2, 0, 0, 69, 2, 69, 3], [0, 0, 50, 3, 69, 2, 69, 3], [50, 2, 50, 3, 0, 0, 69, 3], [50, 2, 50, 3, 69, 2, 0, 0], [50, 4, 0, 0, 49, 4, 49, 5], [0, 0, 50, 5, 49, 4, 49, 5], [50, 4, 50, 5, 0, 0, 49, 5], [50, 4, 50, 5, 49, 4, 0, 0], [50, 6, 0, 0, 69, 6, 69, 7], [0, 0, 50, 7, 69, 6, 69, 7], [50, 6, 50, 7, 0, 0, 69, 7], [50, 6, 50, 7, 69, 6, 0, 0], [50, 8, 0, 0, 49, 8, 49, 9], [0, 0, 50, 9, 49, 8, 49, 9], [50, 8, 50, 9, 0, 0, 49, 9], [50, 8, 50, 9, 49, 8, 0, 0], [52, 2, 0, 0, 67, 2, 67, 3], [0, 0, 52, 3, 67, 2, 67, 3], [52, 2, 52, 3, 0, 0, 67, 3], [52, 2, 52, 3, 67, 2, 0, 0], [52, 4, 0, 0, 47, 4, 47, 5], [0, 0, 52, 5, 47, 4, 47, 5], [52, 4, 52, 5, 0, 0, 47, 5], [52, 4, 52, 5, 47, 4, 0, 0], [52, 6, 0, 0, 67, 6, 67, 7], [0, 0, 52, 7, 67, 6, 67, 7], [52, 6, 52, 7, 0, 0, 67, 7], [52, 6, 52, 7, 67, 6, 0, 0], [52, 8, 0, 0, 47, 8, 47, 9], [0, 0, 52, 9, 47, 8, 47, 9], [52, 8, 52, 9, 0, 0, 47, 9], [52, 8, 52, 9, 47, 8, 0, 0], [54, 2, 0, 0, 65, 2, 65, 3], [0, 0, 54, 3, 65, 2, 65, 3], [54, 2, 54, 3, 0, 0, 65, 3], [54, 2, 54, 3, 65, 2, 0, 0], [54, 4, 0, 0, 45, 4, 45, 5], [0, 0, 54, 5, 45, 4, 45, 5], [54, 4, 54, 5, 0, 0, 45, 5], [54, 4, 54, 5, 45, 4, 0, 0], [54, 6, 0, 0, 65, 6, 65, 7], [0, 0, 54, 7, 65, 6, 65, 7], [54, 6, 54, 7, 0, 0, 65, 7], [54, 6, 54, 7, 65, 6, 0, 0], [54, 8, 0, 0, 45, 8, 45, 9], [0, 0, 54, 9, 45, 8, 45, 9], [54, 8, 54, 9, 0, 0, 45, 9], [54, 8, 54, 9, 45, 8, 0, 0], [56, 2, 0, 0, 63, 2, 63, 3], [0, 0, 56, 3, 63, 2, 63, 3], [56, 2, 56, 3, 0, 0, 63, 3], [56, 2, 56, 3, 63, 2, 0, 0], [56, 4, 0, 0, 43, 4, 43, 5], [0, 0, 56, 5, 43, 4, 43, 5], [56, 4, 56, 5, 0, 0, 43, 5], [56, 4, 56, 5, 43, 4, 0, 0], [56, 6, 0, 0, 63, 6, 63, 7], [0, 0, 56, 7, 63, 6, 63, 7], [56, 6, 56, 7, 0, 0, 63, 7], [56, 6, 56, 7, 63, 6, 0, 0], [56, 8, 0, 0, 43, 8, 43, 9], [0, 0, 56, 9, 43, 8, 43, 9], [56, 8, 56, 9, 0, 0, 43, 9], [56, 8, 56, 9, 43, 8, 0, 0], [58, 2, 0, 0, 61, 2, 61, 3], [0, 0, 58, 3, 61, 2, 61, 3], [58, 2, 58, 3, 0, 0, 61, 3], [58, 2, 58, 3, 61, 2, 0, 0], [58, 4, 0, 0, 41, 4, 41, 5], [0, 0, 58, 5, 41, 4, 41, 5], [58, 4, 58, 5, 0, 0, 41, 5], [58, 4, 58, 5, 41, 4, 0, 0], [58, 6, 0, 0, 61, 6, 61, 7], [0, 0, 58, 7, 61, 6, 61, 7], [58, 6, 58, 7, 0, 0, 61, 7], [58, 6, 58, 7, 61, 6, 0, 0], [58, 8, 0, 0, 41, 8, 41, 9], [0, 0, 58, 9, 41, 8, 41, 9], [58, 8, 58, 9, 0, 0, 41, 9], [58, 8, 58, 9, 41, 8, 0, 0], [60, 2, 0, 0, 79, 2, 79, 3], [0, 0, 60, 3, 79, 2, 79, 3], [60, 2, 60, 3, 0, 0, 79, 3], [60, 2, 60, 3, 79, 2, 0, 0], [60, 4, 0, 0, 59, 4, 59, 5], [0, 0, 60, 5, 59, 4, 59, 5], [60, 4, 60, 5, 0, 0, 59, 5], [60, 4, 60, 5, 59, 4, 0, 0], [60, 6, 0, 0, 79, 6, 79, 7], [0, 0, 60, 7, 79, 6, 79, 7], [60, 6, 60, 7, 0, 0, 79, 7], [60, 6, 60, 7, 79, 6, 0, 0], [60, 8, 0, 0, 59, 8, 59, 9], [0, 0, 60, 9, 59, 8, 59, 9], [60, 8, 60, 9, 0, 0, 59, 9], [60, 8, 60, 9, 59, 8, 0, 0], [62, 2, 0, 0, 77, 2, 77, 3], [0, 0, 62, 3, 77, 2, 77, 3], [62, 2, 62, 3, 0, 0, 77, 3], [62, 2, 62, 3, 77, 2, 0, 0], [62, 4, 0, 0, 57, 4, 57, 5], [0, 0, 62, 5, 57, 4, 57, 5], [62, 4, 62, 5, 0, 0, 57, 5], [62, 4, 62, 5, 57, 4, 0, 0], [62, 6, 0, 0, 77, 6, 77, 7], [0, 0, 62, 7, 77, 6, 77, 7], [62, 6, 62, 7, 0, 0, 77, 7], [62, 6, 62, 7, 77, 6, 0, 0], [62, 8, 0, 0, 57, 8, 57, 9], [0, 0, 62, 9, 57, 8, 57, 9], [62, 8, 62, 9, 0, 0, 57, 9], [62, 8, 62, 9, 57, 8, 0, 0], [64, 2, 0, 0, 75, 2, 75, 3], [0, 0, 64, 3, 75, 2, 75, 3], [64, 2, 64, 3, 0, 0, 75, 3], [64, 2, 64, 3, 75, 2, 0, 0], [64, 4, 0, 0, 55, 4, 55, 5], [0, 0, 64, 5, 55, 4, 55, 5], [64, 4, 64, 5, 0, 0, 55, 5], [64, 4, 64, 5, 55, 4, 0, 0], [64, 6, 0, 0, 75, 6, 75, 7], [0, 0, 64, 7, 75, 6, 75, 7], [64, 6, 64, 7, 0, 0, 75, 7], [64, 6, 64, 7, 75, 6, 0, 0], [64, 8, 0, 0, 55, 8, 55, 9], [0, 0, 64, 9, 55, 8, 55, 9], [64, 8, 64, 9, 0, 0, 55, 9], [64, 8, 64, 9, 55, 8, 0, 0], [66, 2, 0, 0, 73, 2, 73, 3], [0, 0, 66, 3, 73, 2, 73, 3], [66, 2, 66, 3, 0, 0, 73, 3], [66, 2, 66, 3, 73, 2, 0, 0], [66, 4, 0, 0, 53, 4, 53, 5], [0, 0, 66, 5, 53, 4, 53, 5], [66, 4, 66, 5, 0, 0, 53, 5], [66, 4, 66, 5, 53, 4, 0, 0], [66, 6, 0, 0, 73, 6, 73, 7], [0, 0, 66, 7, 73, 6, 73, 7], [66, 6, 66, 7, 0, 0, 73, 7], [66, 6, 66, 7, 73, 6, 0, 0], [66, 8, 0, 0, 53, 8, 53, 9], [0, 0, 66, 9, 53, 8, 53, 9], [66, 8, 66, 9, 0, 0, 53, 9], [66, 8, 66, 9, 53, 8, 0, 0], [68, 2, 0, 0, 71, 2, 71, 3], [0, 0, 68, 3, 71, 2, 71, 3], [68, 2, 68, 3, 0, 0, 71, 3], [68, 2, 68, 3, 71, 2, 0, 0], [68, 4, 0, 0, 51, 4, 51, 5], [0, 0, 68, 5, 51, 4, 51, 5], [68, 4, 68, 5, 0, 0, 51, 5], [68, 4, 68, 5, 51, 4, 0, 0], [68, 6, 0, 0, 71, 6, 71, 7], [0, 0, 68, 7, 71, 6, 71, 7], [68, 6, 68, 7, 0, 0, 71, 7], [68, 6, 68, 7, 71, 6, 0, 0], [68, 8, 0, 0, 51, 8, 51, 9], [0, 0, 68, 9, 51, 8, 51, 9], [68, 8, 68, 9, 0, 0, 51, 9], [68, 8, 68, 9, 51, 8, 0, 0], [70, 2, 0, 0, 89, 2, 89, 3], [0, 0, 70, 3, 89, 2, 89, 3], [70, 2, 70, 3, 0, 0, 89, 3], [70, 2, 70, 3, 89, 2, 0, 0], [70, 4, 0, 0, 69, 4, 69, 5], [0, 0, 70, 5, 69, 4, 69, 5], [70, 4, 70, 5, 0, 0, 69, 5], [70, 4, 70, 5, 69, 4, 0, 0], [70, 6, 0, 0, 89, 6, 89, 7], [0, 0, 70, 7, 89, 6, 89, 7], [70, 6, 70, 7, 0, 0, 89, 7], [70, 6, 70, 7, 89, 6, 0, 0], [70, 8, 0, 0, 69, 8, 69, 9], [0, 0, 70, 9, 69, 8, 69, 9], [70, 8, 70, 9, 0, 0, 69, 9], [70, 8, 70, 9, 69, 8, 0, 0], [72, 2, 0, 0, 87, 2, 87, 3], [0, 0, 72, 3, 87, 2, 87, 3], [72, 2, 72, 3, 0, 0, 87, 3], [72, 2, 72, 3, 87, 2, 0, 0], [72, 4, 0, 0, 67, 4, 67, 5], [0, 0, 72, 5, 67, 4, 67, 5], [72, 4, 72, 5, 0, 0, 67, 5], [72, 4, 72, 5, 67, 4, 0, 0], [72, 6, 0, 0, 87, 6, 87, 7], [0, 0, 72, 7, 87, 6, 87, 7], [72, 6, 72, 7, 0, 0, 87, 7], [72, 6, 72, 7, 87, 6, 0, 0], [72, 8, 0, 0, 67, 8, 67, 9], [0, 0, 72, 9, 67, 8, 67, 9], [72, 8, 72, 9, 0, 0, 67, 9], [72, 8, 72, 9, 67, 8, 0, 0], [74, 2, 0, 0, 85, 2, 85, 3], [0, 0, 74, 3, 85, 2, 85, 3], [74, 2, 74, 3, 0, 0, 85, 3], [74, 2, 74, 3, 85, 2, 0, 0], [74, 4, 0, 0, 65, 4, 65, 5], [0, 0, 74, 5, 65, 4, 65, 5], [74, 4, 74, 5, 0, 0, 65, 5], [74, 4, 74, 5, 65, 4, 0, 0], [74, 6, 0, 0, 85, 6, 85, 7], [0, 0, 74, 7, 85, 6, 85, 7], [74, 6, 74, 7, 0, 0, 85, 7], [74, 6, 74, 7, 85, 6, 0, 0], [74, 8, 0, 0, 65, 8, 65, 9], [0, 0, 74, 9, 65, 8, 65, 9], [74, 8, 74, 9, 0, 0, 65, 9], [74, 8, 74, 9, 65, 8, 0, 0], [76, 2, 0, 0, 83, 2, 83, 3], [0, 0, 76, 3, 83, 2, 83, 3], [76, 2, 76, 3, 0, 0, 83, 3], [76, 2, 76, 3, 83, 2, 0, 0], [76, 4, 0, 0, 63, 4, 63, 5], [0, 0, 76, 5, 63, 4, 63, 5], [76, 4, 76, 5, 0, 0, 63, 5], [76, 4, 76, 5, 63, 4, 0, 0], [76, 6, 0, 0, 83, 6, 83, 7], [0, 0, 76, 7, 83, 6, 83, 7], [76, 6, 76, 7, 0, 0, 83, 7], [76, 6, 76, 7, 83, 6, 0, 0], [76, 8, 0, 0, 63, 8, 63, 9], [0, 0, 76, 9, 63, 8, 63, 9], [76, 8, 76, 9, 0, 0, 63, 9], [76, 8, 76, 9, 63, 8, 0, 0], [78, 2, 0, 0, 81, 2, 81, 3], [0, 0, 78, 3, 81, 2, 81, 3], [78, 2, 78, 3, 0, 0, 81, 3], [78, 2, 78, 3, 81, 2, 0, 0], [78, 4, 0, 0, 61, 4, 61, 5], [0, 0, 78, 5, 61, 4, 61, 5], [78, 4, 78, 5, 0, 0, 61, 5], [78, 4, 78, 5, 61, 4, 0, 0], [78, 6, 0, 0, 81, 6, 81, 7], [0, 0, 78, 7, 81, 6, 81, 7], [78, 6, 78, 7, 0, 0, 81, 7], [78, 6, 78, 7, 81, 6, 0, 0], [78, 8, 0, 0, 61, 8, 61, 9], [0, 0, 78, 9, 61, 8, 61, 9], [78, 8, 78, 9, 0, 0, 61, 9], [78, 8, 78, 9, 61, 8, 0, 0], [80, 2, 0, 0, 99, 2, 99, 3], [0, 0, 80, 3, 99, 2, 99, 3], [80, 2, 80, 3, 0, 0, 99, 3], [80, 2, 80, 3, 99, 2, 0, 0], [80, 4, 0, 0, 79, 4, 79, 5], [0, 0, 80, 5, 79, 4, 79, 5], [80, 4, 80, 5, 0, 0, 79, 5], [80, 4, 80, 5, 79, 4, 0, 0], [80, 6, 0, 0, 99, 6, 99, 7], [0, 0, 80, 7, 99, 6, 99, 7], [80, 6, 80, 7, 0, 0, 99, 7], [80, 6, 80, 7, 99, 6, 0, 0], [80, 8, 0, 0, 79, 8, 79, 9], [0, 0, 80, 9, 79, 8, 79, 9], [80, 8, 80, 9, 0, 0, 79, 9], [80, 8, 80, 9, 79, 8, 0, 0], [82, 2, 0, 0, 97, 2, 97, 3], [0, 0, 82, 3, 97, 2, 97, 3], [82, 2, 82, 3, 0, 0, 97, 3], [82, 2, 82, 3, 97, 2, 0, 0], [82, 4, 0, 0, 77, 4, 77, 5], [0, 0, 82, 5, 77, 4, 77, 5], [82, 4, 82, 5, 0, 0, 77, 5], [82, 4, 82, 5, 77, 4, 0, 0], [82, 6, 0, 0, 97, 6, 97, 7], [0, 0, 82, 7, 97, 6, 97, 7], [82, 6, 82, 7, 0, 0, 97, 7], [82, 6, 82, 7, 97, 6, 0, 0], [82, 8, 0, 0, 77, 8, 77, 9], [0, 0, 82, 9, 77, 8, 77, 9], [82, 8, 82, 9, 0, 0, 77, 9], [82, 8, 82, 9, 77, 8, 0, 0], [84, 2, 0, 0, 95, 2, 95, 3], [0, 0, 84, 3, 95, 2, 95, 3], [84, 2, 84, 3, 0, 0, 95, 3], [84, 2, 84, 3, 95, 2, 0, 0], [84, 4, 0, 0, 75, 4, 75, 5], [0, 0, 84, 5, 75, 4, 75, 5], [84, 4, 84, 5, 0, 0, 75, 5], [84, 4, 84, 5, 75, 4, 0, 0], [84, 6, 0, 0, 95, 6, 95, 7], [0, 0, 84, 7, 95, 6, 95, 7], [84, 6, 84, 7, 0, 0, 95, 7], [84, 6, 84, 7, 95, 6, 0, 0], [84, 8, 0, 0, 75, 8, 75, 9], [0, 0, 84, 9, 75, 8, 75, 9], [84, 8, 84, 9, 0, 0, 75, 9], [84, 8, 84, 9, 75, 8, 0, 0], [86, 2, 0, 0, 93, 2, 93, 3], [0, 0, 86, 3, 93, 2, 93, 3], [86, 2, 86, 3, 0, 0, 93, 3], [86, 2, 86, 3, 93, 2, 0, 0], [86, 4, 0, 0, 73, 4, 73, 5], [0, 0, 86, 5, 73, 4, 73, 5], [86, 4, 86, 5, 0, 0, 73, 5], [86, 4, 86, 5, 73, 4, 0, 0], [86, 6, 0, 0, 93, 6, 93, 7], [0, 0, 86, 7, 93, 6, 93, 7], [86, 6, 86, 7, 0, 0, 93, 7], [86, 6, 86, 7, 93, 6, 0, 0], [86, 8, 0, 0, 73, 8, 73, 9], [0, 0, 86, 9, 73, 8, 73, 9], [86, 8, 86, 9, 0, 0, 73, 9], [86, 8, 86, 9, 73, 8, 0, 0], [88, 2, 0, 0, 91, 2, 91, 3], [0, 0, 88, 3, 91, 2, 91, 3], [88, 2, 88, 3, 0, 0, 91, 3], [88, 2, 88, 3, 91, 2, 0, 0], [88, 4, 0, 0, 71, 4, 71, 5], [0, 0, 88, 5, 71, 4, 71, 5], [88, 4, 88, 5, 0, 0, 71, 5], [88, 4, 88, 5, 71, 4, 0, 0], [88, 6, 0, 0, 91, 6, 91, 7], [0, 0, 88, 7, 91, 6, 91, 7], [88, 6, 88, 7, 0, 0, 91, 7], [88, 6, 88, 7, 91, 6, 0, 0], [88, 8, 0, 0, 71, 8, 71, 9], [0, 0, 88, 9, 71, 8, 71, 9], [88, 8, 88, 9, 0, 0, 71, 9], [88, 8, 88, 9, 71, 8, 0, 0], [90, 4, 0, 0, 89, 4, 89, 5], [0, 0, 90, 5, 89, 4, 89, 5], [90, 4, 90, 5, 0, 0, 89, 5], [90, 4, 90, 5, 89, 4, 0, 0], [90, 8, 0, 0, 89, 8, 89, 9], [0, 0, 90, 9, 89, 8, 89, 9], [90, 8, 90, 9, 0, 0, 89, 9], [90, 8, 90, 9, 89, 8, 0, 0], [92, 4, 0, 0, 87, 4, 87, 5], [0, 0, 92, 5, 87, 4, 87, 5], [92, 4, 92, 5, 0, 0, 87, 5], [92, 4, 92, 5, 87, 4, 0, 0], [92, 8, 0, 0, 87, 8, 87, 9], [0, 0, 92, 9, 87, 8, 87, 9], [92, 8, 92, 9, 0, 0, 87, 9], [92, 8, 92, 9, 87, 8, 0, 0], [94, 4, 0, 0, 85, 4, 85, 5], [0, 0, 94, 5, 85, 4, 85, 5], [94, 4, 94, 5, 0, 0, 85, 5], [94, 4, 94, 5, 85, 4, 0, 0], [94, 8, 0, 0, 85, 8, 85, 9], [0, 0, 94, 9, 85, 8, 85, 9], [94, 8, 94, 9, 0, 0, 85, 9], [94, 8, 94, 9, 85, 8, 0, 0], [96, 4, 0, 0, 83, 4, 83, 5], [0, 0, 96, 5, 83, 4, 83, 5], [96, 4, 96, 5, 0, 0, 83, 5], [96, 4, 96, 5, 83, 4, 0, 0], [96, 8, 0, 0, 83, 8, 83, 9], [0, 0, 96, 9, 83, 8, 83, 9], [96, 8, 96, 9, 0, 0, 83, 9], [96, 8, 96, 9, 83, 8, 0, 0], [98, 4, 0, 0, 81, 4, 81, 5], [0, 0, 98, 5, 81, 4, 81, 5], [98, 4, 98, 5, 0, 0, 81, 5], [98, 4, 98, 5, 81, 4, 0, 0], [98, 8, 0, 0, 81, 8, 81, 9], [0, 0, 98, 9, 81, 8, 81, 9], [98, 8, 98, 9, 0, 0, 81, 9], [98, 8, 98, 9, 81, 8, 0, 0], [1, 1, 1, 2, 0, 1, 0, 2, 0, 3, 0, 4], [1, 5, 1, 6, 0, 5, 0, 6, 0, 7, 0, 8], [1, 3, 1, 4, 1, 1, 1, 2, 0, 1, 0, 2], [3, 1, 1, 3, 2, 2, 1, 2, 2, 2, 3, 2, 4], [1, 5, 1, 6, 1, 3, 1, 4, 2, 3, 2, 4], [1, 7, 1, 8, 1, 5, 1, 6, 0, 5, 0, 6], [3, 5, 3, 6, 2, 5, 2, 6, 2, 7, 2, 8], [1, 9, 1, 10, 1, 7, 1, 8, 2, 7, 2, 8], [3, 3, 3, 4, 3, 1, 3, 2, 2, 1, 2, 2], [5, 1, 5, 2, 4, 1, 4, 2, 4, 3, 4, 4], [1, 3, 1, 4, 2, 3, 2, 4, 2, 5, 2, 6], [3, 7, 3, 8, 3, 5, 3, 6, 3, 3, 3, 4, 4, 4], [3, 7, 3, 8, 3, 5, 3, 6, 5, 2, 5, 2, 6], [5, 5, 5, 6, 4, 5, 4, 6, 4, 7, 4, 8], [1, 7, 1, 8, 2, 7, 2, 8, 2, 9, 2, 10], [3, 9, 3, 10, 3, 7, 3, 8, 4, 7, 4, 8], [5, 3, 5, 4, 5, 1, 5, 2, 4, 1, 4, 2], [7, 1, 7, 2, 6, 1, 6, 2, 6, 3, 6, 4], [3, 3, 3, 4, 4, 3, 4, 4, 4, 5, 4, 6], [5, 5, 5, 6, 6, 5, 3, 5, 4, 6, 3, 6, 4], [5, 7, 5, 8, 5, 5, 5, 6, 4, 5, 4, 6], [7, 5, 7, 6, 6, 5, 6, 6, 6, 7, 6, 8], [3, 7, 3, 8, 4, 7, 4, 8, 4, 9, 4, 10], [5, 9, 5, 10, 5, 7, 5, 8, 6, 7, 6, 8], [7, 3, 7, 4, 7, 1, 7, 2, 6, 1, 6, 2], [9, 1, 9, 2, 8, 1, 8, 2, 8, 3, 8, 4], [5, 3, 5, 4, 6, 3, 6, 4, 6, 5, 6, 6], [7, 5, 7, 6, 7, 3, 7, 4, 8, 3, 8, 4], [7, 7, 7, 8, 7, 5, 7, 6, 6, 5, 6, 6], [9, 5, 9, 6, 8, 5, 8, 6, 8, 7, 8, 8], [5, 7, 5, 8, 6, 7, 8, 6, 8, 7, 8, 8], [5, 7, 5, 8, 6, 7, 6, 8, 6, 9, 6, 10], [7, 9, 7, 10, 7, 7, 7, 8, 8, 7, 8, 8], [9, 3, 9, 4, 9, 1, 9, 2, 8, 1, 8, 2], [7, 3, 7, 4, 8, 3, 8, 4, 8, 5, 8, 6], [9, 7, 9, 8, 9,

TABLE 32-continued 5, 9, 6, 8, 5, 8, 6], [7, 7, 7, 8, 8, 7, 8, 8, 8, 9, 8, 10], [11, 3, 11, 4, 10, 3, 10, 4, 10, 5, 10, 6], [11, 7, 11, 8, 10, 7, 10, 8, 10, 9, 10, 10], [11, 3, 11, 4, 11, 1, 11, 2, 12, 1, 12, 2], [11, 5, 11, 6, 11, 3, 11, 4, 10, 3, 10, 4], [13, 3, 13, 4, 12, 3, 12, 4, 12, 5, 12, 6], [11, 7, 11, 8, 11, 5, 11, 6, 12, 5, 12, 6], [11, 9, 11, 10, 11, 7, 11, 8, 10, 7, 10, 8], [13, 7, 13, 8, 12, 7, 12, 8, 12, 9, 12, 10], [11, 1, 11, 2, 12, 1, 12, 2, 12, 3, 12, 4], [13, 3, 13, 4, 13, 1, 13, 2, 14, 1, 14, 2], [13, 5, 13, 6, 13, 3, 13, 4, 12, 3, 12, 4], [15, 3, 15, 4, 14, 3, 14, 4, 14, 5, 14, 6], [11, 5, 11, 6, 12, 5, 12, 6, 12, 7, 12, 8], [13, 7, 13, 8, 13, 5, 13, 6, 14, 5, 14, 6], [13, 9, 13, 10, 13, 7, 13, 8, 12, 7, 12, 8], [15, 7, 15, 8, 14, 7, 14, 8, 14, 9, 14, 10], [13, 1, 13, 2, 14, 1, 14, 2, 14, 3, 14, 4], [15, 3, 15, 4, 15, 1, 15, 2, 16, 1, 16, 2], [15, 5, 15, 6, 15, 3, 15, 4, 14, 3, 14, 4], [17, 3, 17, 4, 16, 3, 16, 4, 16, 5, 16, 6], [13, 5, 13, 6, 14, 5, 14, 6, 14, 7, 14, 8], [15, 7, 15, 8, 15, 5, 15, 6, 16, 5, 16, 6], [15, 9, 15, 10, 15, 7, 15, 8, 14, 7, 14, 8], [17, 7, 17, 8, 16, 7, 16, 8, 16, 9, 16, 10], [15, 1, 15, 2, 16, 1, 16, 2, 16, 3, 16, 4], [17, 3, 17, 4, 17, 1, 17, 2, 18, 1, 18, 2], [17, 5, 17, 6, 17, 3, 17, 4, 16, 3, 16, 4], [19, 3, 19, 4, 18, 3, 18, 4, 18, 5, 18, 6], [15, 5, 15, 6, 16, 5, 16, 6, 16, 7, 16, 8], [17, 7, 17, 8, 17, 5, 17, 6, 18, 5, 18, 6], [17, 9, 17, 10, 17, 7, 17, 8, 16, 7, 16, 8], [19, 7, 19, 8, 18, 7, 18, 8, 18, 9, 18, 10], [17, 1, 17, 2, 18, 1, 18, 2, 18, 3, 18, 4], [19, 5, 19, 6, 19, 3, 19, 4, 18, 3, 18, 4], [17, 5, 17, 6, 18, 5, 18, 6, 18, 7, 18, 8], [19, 9, 19, 10, 19, 7, 19, 8, 18, 7, 18, 8], [21, 1, 21, 2, 20, 1, 20, 2, 20, 3, 20, 4], [21, 5, 21, 6, 20, 5, 20, 6, 20, 7, 20, 8], [21, 3, 21, 4, 21, 1, 21, 2, 20, 1, 20, 2], [23, 1, 23, 2, 22, 1, 22, 2, 22, 3, 22, 4], [21, 5, 21, 6, 21, 3, 21, 4, 22, 3, 22, 4], [21, 7, 21, 8, 21, 5, 21, 6, 20, 5, 20, 6], [23, 5, 23, 6, 22, 5, 22, 6, 22, 7, 22, 8], [21, 9, 21, 10, 21, 7, 21, 8, 22, 7, 22, 8], [23, 3, 23, 4, 23, 1, 23, 2, 22, 1, 22, 2], [25, 1, 25, 2, 24, 1, 24, 2, 24, 3, 24, 4], [21, 3, 21, 4, 22, 3, 22, 4, 22, 5, 22, 6], [23, 5, 23, 6, 23, 3, 23, 4, 23, 3, 24, 4], [23, 7, 23, 8, 23, 5, 23, 6, 22, 5, 22, 6], [25, 5, 25, 6, 24, 5, 24, 6, 24, 7, 24, 8], [21, 7, 21, 8, 22, 7, 22, 8, 22, 9, 22, 10], [23, 9, 23, 10, 23, 7, 23, 8, 24, 7, 24, 8], [25, 3, 25, 4, 25, 1, 25, 2, 24, 1, 24, 2], [27, 1, 27, 2, 26, 1, 26, 2, 26, 3, 26, 4], [23, 3, 23, 4, 24, 3, 24, 4, 24, 5, 24, 6], [25, 5, 25, 6, 25, 3, 25, 4, 26, 3, 26, 4], [25, 7, 25, 8, 25, 5, 25, 6, 24, 5, 24, 6], [27, 5, 27, 6, 26, 5, 26, 6, 26, 7, 26, 8], [23, 7, 23, 8, 24, 7, 24, 8, 24, 9, 24, 10], [25, 9, 25, 10, 25, 7, 25, 8, 26, 7, 26, 8], [27, 3, 27, 4, 27, 1, 27, 2, 26, 1, 26, 2], [29, 1, 29, 2, 28, 1, 28, 2, 28, 3, 28, 4], [25, 3, 25, 4, 26, 3, 26, 4, 26, 5, 26, 6], [27, 5, 27, 6, 27, 3, 27, 4, 28, 3, 28, 4], [27, 7, 27, 8, 27, 5, 27, 6, 26, 5, 26, 6], [29, 5, 29, 6, 28, 5, 28, 6, 28, 7, 28, 8], [25, 7, 25, 8, 26, 7, 26, 8, 26, 9, 26, 10], [27, 9, 27, 10, 27, 7, 27, 8, 28, 7, 28, 8], [29, 3, 29, 4, 29, 1, 29, 2, 28, 1, 28, 2], [27, 3, 27, 4, 28, 3, 28, 4, 28, 5, 28, 6], [29, 7, 29, 8, 29, 5, 29, 6, 28, 5, 28, 6], [27, 7, 27, 8, 28, 7, 28, 8, 28, 9, 28, 10], [31, 3, 31, 4, 30, 3, 30, 4, 30, 5, 30, 6], [31, 7, 31, 8, 30, 7, 30, 8, 30, 9, 30, 10], [31, 3, 31, 4, 31, 1, 31, 2, 32, 1, 32, 2], [31, 5, 31, 6, 31, 3, 31, 4, 30, 3, 30, 4], [33, 3, 33, 4, 32, 3, 32, 4, 32, 5, 32, 6], [31, 7, 31, 8, 31, 5, 31, 6, 32, 5, 32, 6], [31, 9, 31, 10, 31, 7, 31, 8, 30, 7, 30, 8], [33, 7, 33, 8, 32, 7, 32, 8, 32, 9, 32, 10], [31, 1, 31, 2, 32, 1, 32, 2, 32, 3, 32, 4], [33, 3, 33, 4, 33, 1, 33, 2, 34, 1, 34, 2], [33, 5, 33, 6, 33, 3, 33, 4, 32, 3, 32, 4], [35, 3, 35, 4, 34, 3, 34, 4, 34, 5, 34, 6], [31, 5, 31, 6, 32, 5, 32, 6, 32, 7, 32, 8], [33, 7, 33, 8, 33, 5, 33, 6, 34, 5, 34, 6], [33, 9, 33, 10, 33, 7, 33, 8, 32, 7, 32, 8], [35, 7, 35, 8, 34, 7, 34, 8, 34, 9, 34, 10], [33, 1, 33, 2, 34, 1, 34, 2, 34, 3, 34, 4], [35, 3, 35, 4, 35, 1, 35, 2, 36, 1, 36, 2], [35, 5, 35, 6, 35, 3, 35, 4, 34, 3, 34, 4], [37, 3, 37, 4, 36, 3, 36, 4, 36, 5, 36, 6], [33, 5, 33, 6, 34, 5, 34, 6, 34, 7, 34, 8], [35, 7, 35, 8, 35, 5, 35, 6, 36, 5, 36, 6], [35, 9, 35, 10, 35, 7, 35, 8, 34, 7, 34, 8], [37, 7, 37, 8, 36, 7, 36, 8, 36, 9, 36, 10], [35, 1, 35, 2, 36, 1, 36, 2, 36, 3, 36, 4], [37, 3, 37, 4, 37, 1, 37, 2, 38, 1, 38, 2], [37, 5, 37, 6, 37, 3, 37, 4, 36, 3, 36, 4], [39, 3, 39, 4, 38, 3, 38, 4, 38, 5, 38, 6], [35, 5, 35, 6, 36, 5, 36, 6, 36, 7, 36, 8], [37, 7, 37, 8, 37, 5, 37, 6, 38, 5, 38, 6], [37, 9, 37, 10, 37, 7, 37, 8, 36, 7, 36, 8], [39, 7, 39, 8, 38, 7, 38, 8, 38, 9, 38, 10], [37, 1, 37, 2, 38, 1, 38, 2, 38, 3, 38, 4], [39, 5, 39, 6, 39, 3, 39, 4, 38, 3, 38, 4], [37, 5, 37, 6, 38, 5, 38, 6, 38, 7, 38, 8], [39, 9, 39, 10, 39, 7, 39, 8, 38, 7, 38, 8], [41, 1, 41, 2, 40, 1, 40, 2, 40, 3, 40, 4], [41, 5, 41, 6, 40, 5, 40, 6, 40, 7, 40, 8], [41, 3, 41, 4, 41, 1, 41, 2, 40, 1, 40, 2], [43, 1, 43, 2, 42, 1, 42, 2, 42, 3, 42, 4], [41, 5, 41, 6, 41, 3, 41, 4, 42, 3, 42, 4], [41, 7, 41, 8, 41, 5, 41, 6, 40, 5, 40, 6], [43, 5, 43, 6, 42, 5, 42, 6, 42, 7, 42, 8], [41, 9, 41, 10, 41, 7, 41, 8, 42, 7, 42, 8], [43, 3, 43, 4, 43, 1, 43, 2, 42, 1, 42, 2], [45, 1, 45, 2, 44, 1, 44, 2, 44, 3, 44, 4], [41, 3, 41, 4, 42, 3, 42, 4, 42, 5, 42, 6], [43, 5, 43, 6, 43, 3, 43, 4, 44, 3, 44, 4], [43, 7, 43, 8, 43, 5, 43, 6, 42, 5, 42, 6], [45, 5, 45, 6, 44, 5, 44, 6, 44, 7, 44, 8], [41, 7, 41, 8, 42, 7, 42, 8, 42, 9, 42, 10], [43, 9, 43, 10, 43, 7, 43, 8, 44, 7, 44, 8], [45, 3, 45, 4, 45, 1, 45, 2, 44, 1, 44, 2], [47, 1, 47, 2, 46, 1, 46, 2, 46, 3, 46, 4], [43, 3, 43, 4, 44, 3, 44, 4, 44, 5, 44, 6], [45, 5, 45, 6, 45, 3, 45, 4, 46, 3, 46, 4], [45, 7, 45, 8, 45, 5, 45, 6, 44, 5, 44, 6], [47, 5, 47, 6, 46, 5, 46, 6, 46, 7, 46, 8], [43, 7, 43, 8, 44, 7, 44, 8, 44, 9, 44, 10], [45, 9, 45, 10, 45, 7, 45, 8, 46, 7, 46, 8], [47, 3, 47, 4, 47, 1, 47, 2, 46, 1, 46, 2], [49, 1, 49, 2, 48, 1, 48, 2, 48, 3, 48, 4], [45, 3, 45, 4, 46, 3, 46, 4, 46, 5, 46, 6], [47, 5, 47, 6, 47, 3, 47, 4, 48, 3, 48, 4], [47, 7, 47, 8, 47, 5, 47, 6, 46, 5, 46, 6], [49, 5, 49, 6, 48, 5, 48, 6, 48, 7, 48, 8], [45, 7, 45, 8, 46, 7, 46, 8, 46, 9, 46, 10], [47, 9, 47, 10, 47, 7, 47, 8, 48, 7, 48, 8], [49, 3, 49, 4, 49, 1, 49, 2, 48, 1, 48, 2], [47, 3, 47, 4, 48, 3, 48, 4, 48, 5, 48, 6], [49, 7, 49, 8, 49, 5, 49, 6, 48, 5, 48, 6], [47, 7, 47, 8, 48, 7, 48, 8, 48, 9, 48, 10], [51, 3, 51, 4, 50, 3, 50, 4, 50, 5, 50, 6], [51, 7, 51, 8, 50, 7, 50, 8, 50, 9, 50, 10], [51, 3, 51, 4, 51, 1, 51, 2, 52, 1, 52, 2], [51, 5, 51, 6, 51, 3, 51, 4, 50, 3, 50, 4], [53, 3, 53, 4, 52, 3, 52, 4, 52, 5, 52, 6], [51, 7, 51, 8, 51, 5, 51, 6, 52, 5, 52, 6], [51, 9, 51, 10, 51, 7, 51, 8, 50, 7, 50, 8], [53, 7, 53, 8, 52, 7, 52, 8, 52, 9, 52, 10], [51, 1, 51, 2, 52, 1, 52, 2, 52, 3, 52, 4], [53, 3, 53, 4, 53, 1, 53, 2, 54, 1, 54, 2], [53, 5, 53, 6, 53, 3, 53, 4, 52, 3, 52, 4], [55, 3, 55, 4, 54, 3, 54, 4, 54, 5, 54, 6], [51, 5, 51, 6, 52, 5, 52, 6, 52, 7, 52, 8], [53, 7, 53, 8, 53, 5, 53, 6, 54, 5, 54, 6], [53, 9, 53, 10, 53, 7, 53, 8, 52, 7, 52, 8], [55, 7, 55, 8, 54, 7, 54, 8, 54, 9, 54, 10], [53, 1, 53, 2, 54, 1, 54, 2, 54, 3, 54, 4], [55, 3, 55, 4, 55, 1, 55, 2, 56, 1, 56, 2], [55, 5, 55, 6, 55, 3, 55, 4, 54, 3, 54, 4], [57, 3, 57, 4, 56, 3, 56, 4, 56, 5, 56, 6], [53, 5, 53, 6, 54, 5, 54, 6, 54, 7, 54, 8], [55, 7, 55, 8, 55, 5, 55, 6, 56, 5, 56, 6], [55, 9, 55, 10, 55, 7, 55, 8, 56, 7, 56, 8], [57, 7, 57, 8, 56, 7, 56, 8, 56, 9, 56, 10], [55, 1, 55, 2, 56, 1, 56, 2, 56, 3, 56, 4], [57, 3, 57, 4, 57, 1, 57, 2, 58, 1, 58, 2], [57, 5, 57, 6, 57, 3, 57, 4, 56, 3, 56, 4], [59, 3, 59, 4, 58, 3, 58, 4, 58, 5, 58, 6], [55, 5, 55, 6, 56, 5, 56, 6, 56, 7, 56, 8], [57, 7, 57, 8, 57, 5, 57, 6, 58, 5, 58, 6], [57, 9, 57, 10, 57, 7, 57, 8, 56, 7, 56, 8], [59, 7, 59, 8, 58, 7, 58, 8, 58, 9, 58, 10], [57, 1, 57, 2, 58, 1, 58, 2, 58, 3, 58, 4], [59, 5, 59, 6, 59, 3, 59, 4, 58, 3, 58, 4], [57, 5, 57, 6, 58, 5, 58, 6, 58, 7, 58, 8], [59, 9, 59, 10, 59, 7, 59, 8, 58, 7, 58, 8], [61, 1, 61, 2, 60, 1, 60, 2, 60, 3, 60, 4], [61, 5, 61, 6, 60, 5, 60, 6, 60, 7, 60, 8], [61, 3, 61, 4, 61, 1, 61, 2, 60, 1, 60, 2], [63, 1, 63, 2, 62, 1, 62, 2, 62, 3, 62, 4], [61, 5, 61, 6, 61, 3, 61, 4, 62, 3, 62, 4], [61, 7, 61, 8, 61, 5, 61, 6, 60, 5, 60, 6], [63, 5, 63, 6, 62, 5, 62, 6, 62, 7, 62, 8], [61, 9, 61, 10, 61, 7, 61, 8, 62, 7, 62, 8], [63, 3, 63, 4, 63, 1, 63, 2, 62, 1, 62, 2], [65, 1, 65, 2, 64, 1, 64, 2, 64, 3, 64, 4], [61, 3, 61, 4, 62, 3, 62, 4, 62, 5, 62, 6], [63, 5, 63, 6, 63, 3, 63, 4, 64, 3, 64, 4], [63, 7, 63, 8, 63, 5, 63, 6, 62, 5, 62, 6], [65, 5, 65, 6, 64, 5, 64, 6, 64, 7, 64, 8], [61, 7, 61, 8, 62, 7, 62, 8, 62, 9, 62, 10], [63, 9, 63, 10, 63, 7, 63, 8, 64, 7, 64, 8], [65, 3, 65, 4, 65, 1, 65, 2, 64, 1, 64, 2], [67, 1, 67, 2, 66, 1, 66, 2, 66, 3, 66, 4], [63, 3, 63, 4, 64, 3, 64, 4, 64, 5, 64, 6], [65, 5, 65, 6, 65, 3, 65, 4, 66, 3, 66, 4], [65, 7, 65, 8, 65, 5, 65, 6, 64, 5, 64, 6], [67, 5, 67, 6, 66, 5, 66, 6, 66, 7, 66, 8], [63, 7, 63, 8, 64, 7, 64, 8, 64, 9, 64, 10], [65, 9, 65, 10, 65, 7, 65, 8, 66, 7, 66, 8], [67, 3, 67, 4, 67, 1, 67, 2, 66, 1, 66, 2], [69, 1, 69, 2, 68, 1, 68, 2, 68, 3, 68, 4], [65, 3, 65, 4, 66, 3, 66, 4, 66, 5, 66, 6], [67, 5, 67, 6, 67, 3, 67, 4, 68, 3, 68, 4], [67, 7, 67, 8, 67, 5, 67, 6, 66, 5, 66, 6], [69, 5, 69, 6, 68, 5, 68, 6, 68, 7, 68, 8], [65, 7, 65, 8, 66, 7, 66, 8, 66, 9, 66, 10], [67, 9, 67, 10, 67, 7, 67, 8, 68, 7, 68, 8], [69, 3, 69, 4, 69, 1, 69, 2, 68, 1, 68, 2], [67, 3, 67, 4, 68, 3, 68, 4, 68, 5, 68, 6], [69, 7, 69, 8, 69, 5, 69, 6, 68, 5, 68, 6], [67, 7, 67, 8, 68, 7, 68, 8, 68, 9, 68, 10], [71, 3, 71, 4, 70, 3, 70, 4, 70, 5, 70, 6], [71, 7, 71, 8, 70, 7, 70, 8, 70, 9, 70, 10], [71, 3, 71, 4, 71, 1, 71, 2, 72, 1, 72, 2], [71, 5, 71, 6, 71, 3, 71, 4, 70, 3, 70, 4], [73, 3, 73, 4, 72, 3, 72, 4, 72, 5, 72, 6], [71, 7, 71, 8, 71, 5, 71, 6, 72, 5, 72, 6], [71, 9, 71, 10, 71, 7, 71, 8, 70, 7, 70, 8], [73, 7, 73, 8, 72, 7, 72, 8, 72, 9, 72, 10], [71, 1, 71, 2, 72, 1, 72, 2, 72, 3, 72, 4], [73, 3, 73, 4, 73, 1, 73, 2, 74, 1, 74, 2], [73, 5, 73, 6, 73, 3, 73, 4, 72, 3, 72, 4], [75, 3, 75, 4, 74, 3, 74, 4, 74, 5, 74, 6], [71, 5, 71, 6, 72, 5, 72, 6, 72, 7, 72, 8], [73, 7, 73, 8, 73, 5, 73, 6, 74, 5, 74, 6], [73, 9, 73, 10, 73, 7, 73, 8, 72, 7, 72, 8], [75, 7, 75, 8, 74, 7, 74, 8, 74, 9, 74, 10], [73, 1, 73, 2, 74, 1, 74, 2, 74, 3, 74, 4], [75, 3, 75, 4, 75, 1, 75, 2, 76, 1, 76, 2], [75, 5, 75, 6, 75, 3, 75, 4, 74, 3, 74, 4], [77, 3, 77, 4, 76, 3, 76, 4, 76, 5, 76, 6], [73, 5, 73, 6, 74, 5, 74, 6, 74, 7, 74, 8], [75, 7, 75, 8, 75, 5, 75, 6, 76, 5, 76, 6], [75, 9, 75, 10, 75, 7, 75, 8, 74, 7, 74, 8], [77, 7, 77, 8, 76, 7, 76, 8, 76, 9, 76, 10], [75, 1, 75, 2, 76, 1, 76, 2, 76, 3, 76, 4], [77, 3, 77, 4, 77, 1, 77, 2, 78, 1, 78, 2], [77, 5, 77, 6, 77, 3, 77, 4, 76, 3, 76, 4], [79, 3, 79, 4, 78, 3, 78, 4, 78, 5, 78, 6], [75, 5, 75, 6, 76, 5, 76, 6, 76, 7, 76, 8], [77, 7, 77, 8, 77, 5, 77, 6, 78, 5, 78, 6], [77, 9, 77, 10, 77, 7, 77, 8, 76, 7, 76, 8], [79, 7, 79, 8, 78, 7, 78, 8, 78, 9, 78, 10], [77, 1, 77, 2, 78, 1, 78, 2, 78, 3, 78, 4], [79, 5, 79, 6, 79, 3, 79, 4, 78, 3, 78, 4], [77, 5, 77, 6, 78, 5, 78, 6, 78, 7, 78, 8], [79, 9, 79, 10, 79, 7, 79, 8, 78, 7, 78, 8], [81, 1, 81, 2, 80, 1, 80, 2, 80, 3, 80, 4], [81, 5, 81, 6, 80, 5, 80, 6, 80, 7, 80, 8], [81, 3, 81, 4, 81, 1, 81, 2, 80, 1, 80, 2], [83, 1, 83, 2, 82, 1, 82, 2, 82, 3, 82, 4], [81, 5, 81, 6, 81, 3, 81, 4, 82, 3, 82, 4], [81, 7, 81, 8, 81, 5, 81, 6, 80, 5, 80, 6], [83, 5, 83, 6, 82, 5, 82, 6, 82, 7, 82, 8], [81, 9, 81, 10, 81, 7, 81, 8, 82, 7, 82, 8], [83, 3, 83, 4, 83, 1, 83, 2, 82, 1, 82, 2], [85, 1, 85, 2, 84, 1, 84, 2, 84, 3, 84, 4], [81, 3, 81, 4, 82, 3, 82, 4, 82, 5, 82, 6], [83, 5, 83, 6, 83, 3, 83, 4, 84, 3, 84, 4], [83, 7, 83, 8, 83, 5, 83, 6, 82, 5, 82, 6], [85, 5, 85, 6, 84, 5, 84, 6, 84, 7, 84, 8], [81, 7, 81, 8, 82, 7, 82, 8, 82, 9, 82, 10], [83, 9, 83, 10, 83, 7, 83, 8, 84, 7, 84, 8], [85, 3, 85, 4, 85, 1, 85, 2, 84, 1, 84, 2], [87, 1, 87, 2, 86, 1, 86, 2, 86, 3, 86,

TABLE 32-continued

4], [83, 3, 83, 4, 84, 3, 84, 4, 84, 5, 84, 6], [85, 5, 85, 6, 85, 3, 85, 4, 86, 3, 86, 4], [85, 7, 85, 8, 85, 5, 85, 6, 84, 5, 84, 6], [87, 5, 87, 6, 86, 5, 86, 6, 86, 7, 86, 8], [83, 7, 83, 8, 84, 7, 84, 8, 84, 9, 84, 10], [85, 9, 85, 10, 85, 7, 85, 8, 86, 7, 86, 8], [87, 3, 87, 4, 87, 1, 87, 2, 86, 1, 86, 2], [89, 1, 89, 2, 88, 1, 88, 2, 88, 3, 88, 4], [85, 3, 85, 4, 86, 3, 86, 4, 86, 5, 86, 6], [87, 5, 87, 6, 87, 3, 87, 4, 88, 3, 88, 4], [87, 7, 87, 8, 87, 5, 87, 6, 86, 5, 86, 6], [89, 5, 89, 6, 88, 5, 88, 6, 88, 7, 88, 8], [85, 7, 85, 8, 86, 7, 86, 8, 86, 9, 86, 10], [87, 9, 87, 10, 87, 7, 87, 8, 88, 7, 88, 8], [89, 3, 89, 4, 89, 1, 89, 2, 88, 1, 88, 2], [87, 3, 87, 4, 88, 3, 88, 4, 88, 5, 88, 6], [89, 7, 89, 8, 89, 5, 89, 6, 88, 5, 88, 6], [87, 7, 87, 8, 88, 7, 88, 8, 88, 9, 88, 10], [91, 3, 91, 4, 90, 3, 90, 4, 90, 5, 90, 6], [91, 7, 91, 8, 90, 7, 90, 8, 90, 9, 90, 10], [91, 3, 91, 4, 91, 1, 91, 2, 92, 1, 92, 2], [91, 5, 91, 6, 91, 3, 91, 4, 90, 3, 90, 4], [93, 3, 93, 4, 92, 3, 92, 4, 92, 5, 92, 6], [91, 7, 91, 8, 91, 5, 91, 6, 92, 5, 92, 6], [91, 9, 91, 10, 91, 7, 91, 8, 90, 7, 90, 8], [93, 7, 93, 8, 92, 7, 92, 8, 92, 9, 92, 10], [91, 1, 91, 2, 92, 1, 92, 2, 92, 3, 92, 4], [93, 3, 93, 4, 93, 1, 93, 2, 94, 1, 94, 2], [93, 5, 93, 6, 93, 3, 93, 4, 92, 3, 92, 4], [95, 3, 95, 4, 94, 3, 94, 4, 94, 5, 94, 6], [91, 5, 91, 6, 92, 5, 92, 6, 92, 7, 92, 8], [93, 7, 93, 8, 93, 5, 93, 6, 94, 5, 94, 6], [93, 9, 93, 10, 93, 7, 93, 8, 92, 7, 92, 8], [95, 7, 95, 8, 94, 7, 94, 8, 94, 9, 94, 10], [93, 1, 93, 2, 94, 1, 94, 2, 94, 3, 94, 4], [95, 3, 95, 4, 95, 1, 95, 2, 96, 1, 96, 2], [95, 5, 95, 6, 95, 3, 95, 4, 94, 3, 94, 4], [97, 3, 97, 4, 96, 3, 96, 4, 96, 5, 96, 6], [93, 5, 93, 6, 94, 5, 94, 6, 94, 7, 94, 8], [95, 7, 95, 8, 95, 5, 95, 6, 95, 6, 96, 6], [95, 9, 95, 10, 95, 7, 95, 8, 94, 7, 94, 8], [97, 7, 97, 8, 96, 7, 96, 8, 96, 9, 96, 10], [95, 1, 95, 2, 96, 1, 96, 2, 96, 3, 96, 4], [97, 3, 97, 4, 97, 1, 97, 2, 98, 1, 98, 2], [97, 5, 97, 6, 97, 3, 97, 4, 96, 3, 96, 4], [99, 3, 99, 4, 98, 3, 98, 4, 98, 5, 98, 6], [95, 5, 95, 6, 96, 5, 96, 6, 96, 7, 96, 8], [97, 7, 97, 8, 97, 5, 97, 6, 98, 5, 98, 6], [97, 9, 97, 10, 97, 7, 97, 8, 96, 7, 96, 8], [99, 7, 99, 8, 98, 7, 98, 8, 98, 9, 98, 10], [97, 1, 97, 2, 98, 1, 98, 2, 98, 3, 98, 4], [99, 5, 99, 6, 99, 3, 99, 4, 98, 3, 98, 4], [97, 5, 97, 6, 98, 5, 98, 6, 98, 7, 98, 8], [99, 9, 99, 10, 99, 7, 99, 8, 98, 7, 98, 8], [0, 4, 0, 5, 0, 2, 0, 3, 19, 2, 19, 3], [20, 4, 20, 5, 19, 4, 19, 5, 19, 6, 19, 7], [0, 8, 0, 9, 0, 6, 0, 7, 19, 6, 19, 7], [18, 4, 18, 5, 1, 4, 1, 5, 1, 6, 1, 7], [2, 4, 2, 5, 2, 2, 2, 3, 17, 2, 17, 3], [22, 4, 22, 5, 17, 4, 17, 5, 17, 6, 17, 7], [2, 8, 2, 9, 2, 6, 2, 7, 17, 6, 17, 7], [16, 4, 16, 5, 3, 4, 3, 5, 3, 6, 3, 7], [4, 4, 4, 5, 4, 2, 4, 3, 15, 2, 15, 3], [24, 4, 24, 5, 15, 4, 15, 5, 15, 6, 15, 7], [4, 8, 4, 9, 4, 6, 4, 7, 15, 6, 15, 7], [14, 4, 14, 5, 5, 4, 5, 5, 5, 6, 5, 7], [6, 4, 6, 5, 6, 2, 6, 3, 13, 2, 13, 3], [26, 4, 26, 5, 13, 4, 13, 5, 13, 6, 13, 7], [6, 8, 6, 9, 6, 6, 6, 7, 13, 6, 13, 7], [12, 4, 12, 5, 7, 4, 7, 5, 7, 6, 7, 7], [8, 4, 8, 5, 8, 2, 8, 3, 11, 2, 11, 3], [28, 4, 28, 5, 11, 4, 11, 5, 11, 6, 11, 7], [8, 8, 8, 9, 8, 6, 8, 7, 11, 6, 11, 7], [10, 4, 10, 5, 9, 4, 9, 5, 9, 6, 9, 7], [10, 4, 10, 5, 10, 2, 10, 3, 29, 2, 29, 3], [10, 6, 10, 7, 10, 4, 10, 5, 9, 4, 9, 5], [30, 4, 30, 5, 29, 4, 29, 5, 29, 6, 29, 7], [10, 8, 10, 9, 10, 6, 10, 7, 29, 6, 29, 7], [12, 4, 12, 5, 12, 2, 12, 3, 27, 2, 27, 3], [12, 6, 12, 7, 12, 4, 12, 5, 7, 4, 7, 5], [32, 4, 32, 5, 27, 4, 27, 5, 27, 6, 27, 7], [12, 8, 12, 9, 12, 6, 12, 7, 27, 6, 27, 7], [14, 4, 14, 5, 14, 2, 14, 3, 25, 2, 25, 3], [14, 6, 14, 7, 14, 4, 14, 5, 4, 5, 5], [34, 4, 34, 5, 25, 4, 25, 5, 25, 6, 25, 7], [14, 8, 14, 9, 14, 6, 14, 7, 25, 6, 25, 7], [16, 4, 16, 5, 16, 2, 16, 3, 23, 2, 23, 3], [16, 6, 16, 7, 16, 4, 16, 5, 3, 4, 3, 5], [36, 4, 36, 5, 23, 4, 23, 5, 23, 6, 23, 7], [16, 8, 16, 9, 16, 6, 16, 7, 23, 6, 23, 7], [18, 4, 18, 5, 18, 2, 18, 3, 21, 2, 21, 3], [18, 6, 18, 7, 18, 4, 18, 5, 1, 4, 1, 5], [38, 4, 38, 5, 21, 4, 21, 5, 21, 6, 21, 7], [18, 8, 18, 9, 18, 6, 18, 7, 21, 6, 21, 7], [0, 2, 0, 3, 19, 2, 19, 3, 19, 4, 19, 5], [20, 4, 20, 5, 20, 2, 20, 3, 39, 2, 39, 3], [20, 6, 20, 7, 20, 4, 20, 5, 19, 4, 19, 5], [40, 4, 40, 5, 39, 4, 39, 5, 39, 6, 39, 7], [0, 6, 0, 7, 19, 6, 19, 7, 19, 8, 19, 9], [20, 8, 20, 9, 20, 6, 20, 7, 39, 6, 39, 7], [2, 2, 2, 3, 17, 2, 17, 3, 17, 4, 17, 5], [22, 4, 22, 5, 22, 2, 22, 3, 37, 2, 37, 3], [22, 6, 22, 7, 22, 4, 22, 5, 17, 4, 17, 5], [42, 4, 42, 5, 37, 4, 37, 5, 37, 6, 37, 7], [2, 6, 2, 7, 17, 6, 17, 7, 17, 8, 17, 9], [22, 8, 22, 9, 22, 6, 22, 7, 37, 6, 37, 7], [4, 2, 4, 3, 15, 2, 15, 3, 15, 4, 15, 5], [24, 4, 24, 5, 24, 2, 24, 3, 35, 2, 35, 3], [24, 6, 24, 7, 24, 4, 24, 5, 15, 4, 15, 5], [44, 4, 44, 5, 35, 4, 35, 5, 35, 6, 35, 7], [4, 6, 4, 7, 15, 6, 15, 7, 15, 8, 15, 9], [24, 8, 24, 9, 24, 6, 24, 7, 35, 6, 35, 7], [6, 2, 6, 3, 13, 2, 13, 3, 13, 4, 13, 5], [26, 4, 26, 5, 26, 2, 26, 3, 33, 2, 33, 3], [26, 6, 26, 7, 26, 4, 26, 5, 13, 4, 13, 5], [46, 4, 46, 5, 33, 4, 33, 5, 33, 6, 33, 7], [6, 6, 6, 7, 13, 6, 13, 7, 13, 8, 13, 9], [26, 8, 26, 9, 26, 6, 26, 7, 33, 6, 33, 7], [8, 2, 8, 3, 11, 2, 11, 3, 11, 4, 11, 5], [28, 4, 28, 5, 28, 2, 28, 3, 31, 2, 31, 3], [28, 6, 28, 7, 28, 4, 28, 5, 11, 4, 11, 5], [48, 4, 48, 5, 31, 4, 31, 5, 31, 6, 31, 7], [8, 6, 8, 7, 11, 6, 11, 7, 11, 8, 11, 9], [28, 8, 28, 9, 28, 6, 28, 7, 31, 6, 31, 7], [10, 2, 10, 3, 29, 2, 29, 3, 29, 4, 29, 5], [30, 4, 30, 5, 30, 2, 30, 3, 49, 2, 49, 3], [30, 6, 30, 7, 30, 4, 30, 5, 29, 4, 29, 5], [50, 4, 50, 5, 49, 4, 49, 5, 49, 6, 49, 7], [10, 6, 10, 7, 29, 6, 29, 7, 29, 8, 29, 9], [30, 8, 30, 9, 30, 6, 30, 7, 49, 6, 49, 7], [12, 2, 12, 3, 27, 2, 27, 3, 27, 4, 27, 5], [32, 4, 32, 5, 32, 2, 32, 3, 47, 2, 47, 3], [32, 6, 32, 7, 32, 4, 32, 5, 27, 4, 27, 5], [52, 4, 52, 5, 47, 4, 47, 5, 47, 6, 47, 7], [12, 6, 12, 7, 27, 6, 27, 7, 27, 8, 27, 9], [32, 8, 32, 9, 32, 6, 32, 7, 47, 6, 47, 7], [14, 2, 14, 3, 25, 2, 25, 3, 25, 4, 25, 5], [34, 4, 34, 5, 34, 2, 34, 3, 45, 2, 45, 3], [34, 6, 34, 7, 34, 4, 34, 5, 25, 4, 25, 5], [54, 4, 54, 5, 45, 4, 45, 5, 45, 6, 45, 7], [14, 6, 14, 7, 25, 6, 25, 7, 25, 8, 25, 9], [34, 8, 34, 9, 34, 6, 34, 7, 45, 6, 45, 7], [16, 2, 16, 3, 23, 2, 23, 3, 23, 4, 23, 5], [36, 4, 36, 5, 36, 2, 36, 3, 43, 2, 43, 3], [36, 6, 36, 7, 36, 4, 36, 5, 23, 4, 23, 5], [56, 4, 56, 5, 43, 4, 43, 5, 43, 6, 43, 7], [16, 6, 16, 7, 23, 6, 23, 7, 23, 8, 23, 9], [36, 8, 36, 9, 36, 6, 36, 7, 43, 6, 43, 7], [18, 2, 18, 3, 21, 2, 21, 3, 21, 4, 21, 5], [38, 4, 38, 5, 38, 2, 38, 3, 41, 2, 41, 3], [38, 6, 38, 7, 38, 4, 38, 5, 21, 4, 21, 5], [58, 4, 58, 5, 41, 4, 41, 5, 41, 6, 41, 7], [18, 6, 18, 7, 21, 6, 21, 7, 21, 8, 21, 9], [38, 8, 38, 9, 38, 6, 38, 7, 41, 6, 41, 7], [20, 2, 20, 3, 39, 2, 39, 3, 39, 4, 39, 5], [40, 4, 40, 5, 40, 2, 40, 3, 59, 2, 59, 3], [40, 6, 40, 7, 40, 4, 40, 5, 39, 4, 39, 5], [60, 4, 60, 5, 59, 4, 59, 5, 59, 6, 59, 7], [20, 6, 20, 7, 39, 6, 39, 7, 39, 8, 39, 9], [40, 8, 40, 9, 40, 6, 40, 7, 59, 6, 59, 7], [22, 2, 22, 3, 37, 2, 37, 3, 37, 4, 37, 5], [42, 4, 42, 5, 42, 2, 42, 3, 57, 2, 57, 3], [42, 6, 42, 7, 42, 4, 42, 5, 37, 4, 37, 5], [62, 4, 62, 5, 57, 4, 57, 5, 57, 6, 57, 7], [22, 6, 22, 7, 37, 6, 37, 7, 37, 8, 37, 9], [42, 8, 42, 9, 42, 6, 42, 7, 57, 6, 57, 7], [24, 2, 24, 3, 35, 2, 35, 3, 35, 4, 35, 5], [44, 4, 44, 5, 44, 2, 44, 3, 55, 2, 55, 3], [44, 6, 44, 7, 44, 4, 44, 5, 35, 4, 35, 5], [64, 4, 64, 5, 55, 4, 55, 5, 55, 6, 55, 7], [24, 6, 24, 7, 35, 6, 35, 7, 35, 8, 35, 9], [44, 8, 44, 9, 44, 6, 44, 7, 55, 6, 55, 7], [26, 2, 26, 3, 33, 2, 33, 3, 33, 4, 33, 5], [46, 4, 46, 5, 46, 2, 46, 3, 53, 2, 53, 3], [46, 6, 46, 7, 46, 4, 46, 5, 33, 4, 33, 5], [66, 4, 66, 5, 53, 4, 53, 5, 53, 6, 53, 7], [26, 6, 26, 7, 33, 6, 33, 7, 33, 8, 33, 9], [46, 8, 46, 9, 46, 6, 46, 7, 53, 6, 53, 7], [28, 2, 28, 3, 31, 2, 31, 3, 31, 4, 31, 5], [48, 4, 48, 5, 48, 2, 48, 3, 51, 2, 51, 3], [48, 6, 48, 7, 48, 4, 48, 5, 31, 4, 31, 5], [68, 4, 68, 5, 51, 4, 51, 5, 51, 6, 51, 7], [28, 6, 28, 7, 31, 6, 31, 7, 31, 8, 31, 9], [48, 8, 48, 9, 48, 6, 48, 7, 51, 6, 51, 7], [30, 2, 30, 3, 49, 2, 49, 3, 49, 4, 49, 5], [50, 4, 50, 5, 50, 2, 50, 3, 69, 2, 69, 3], [50, 6, 50, 7, 50, 4, 50, 5, 49, 4, 49, 5], [70, 4, 70, 5, 69, 4, 69, 5, 69, 6, 69, 7], [30, 6, 30, 7, 49, 6, 49, 7, 49, 8, 49, 9], [50, 8, 50, 9, 50, 6, 50, 7, 69, 6, 69, 7], [32, 2, 32, 3, 47, 2, 47, 3, 47, 4, 47, 5], [52, 4, 52, 5, 52, 2, 52, 3, 67, 2, 67, 3], [52, 6, 52, 7, 52, 4, 52, 5, 47, 4, 47, 5], [72, 4, 72, 5, 67, 4, 67, 5, 67, 6, 67, 7], [32, 6, 32, 7, 47, 6, 47, 7, 47, 8, 47, 9], [52, 8, 52, 9, 52, 6, 52, 7, 67, 6, 67, 7], [34, 2, 34, 3, 45, 2, 45, 3, 45, 4, 45, 5], [54, 4, 54, 5, 54, 2, 54, 3, 65, 2, 65, 3], [54, 6, 54, 7, 54, 4, 54, 5, 45, 4, 45, 5], [74, 4, 74, 5, 65, 4, 65, 5, 65, 6, 65, 7], [34, 6, 34, 7, 45, 6, 45, 7, 45, 8, 45, 9], [54, 8, 54, 9, 54, 6, 54, 7, 65, 6, 65, 7], [36, 2, 36, 3, 43, 2, 43, 3, 43, 4, 43, 5], [56, 4, 56, 5, 56, 2, 56, 3, 63, 2, 63, 3], [56, 6, 56, 7, 56, 4, 56, 5, 43, 4, 43, 5], [76, 4, 76, 5, 63, 4, 63, 5, 63, 6, 63, 7], [36, 6, 36, 7, 43, 6, 43, 7, 43, 8, 43, 9], [56, 8, 56, 9, 56, 6, 56, 7, 63, 6, 63, 7], [38, 2, 38, 3, 41, 2, 41, 3, 41, 4, 41, 5], [58, 4, 58, 5, 58, 2, 58, 3, 61, 2, 61, 3], [58, 6, 58, 7, 58, 4, 58, 5, 41, 4, 41, 5], [78, 4, 78, 5, 61, 4, 61, 5, 61, 6, 61, 7], [38, 6, 38, 7, 41, 6, 41, 7, 41, 8, 41, 9], [58, 8, 58, 9, 58, 6, 58, 7, 61, 6, 61, 7], [40, 2, 40, 3, 59, 2, 59, 3, 59, 4, 59, 5], [60, 4, 60, 5, 60, 2, 60, 3, 79, 2, 79, 3], [60, 6, 60, 7, 60, 4, 60, 5, 59, 4, 59, 5], [80, 4, 80, 5, 79, 4, 79, 5, 79, 6, 79, 7], [40, 6, 40, 7, 59, 6, 59, 7, 59, 8, 59, 9], [60, 8, 60, 9, 60, 6, 60, 7, 79, 6, 79, 7], [42, 2, 42, 3, 57, 2, 57, 3, 57, 4, 57, 5], [62, 4, 62, 5, 62, 2, 62, 3, 77, 2, 77, 3], [62, 6, 62, 7, 62, 4, 62, 5, 57, 4, 57, 5], [82, 4, 82, 5, 77, 4, 77, 5, 77, 6, 77, 7], [42, 6, 42, 7, 57, 6, 57, 7, 57, 8, 57, 9], [62, 8, 62, 9, 62, 6, 62, 7, 77, 6, 77, 7], [44, 2, 44, 3, 55, 2, 55, 3, 55, 4, 55, 5], [64, 4, 64, 5, 64, 2, 64, 3, 75, 2, 75, 3], [64, 6, 64, 7, 64, 4, 64, 5, 55, 4, 55, 5], [84, 4, 84, 5, 75, 4, 75, 5, 75, 6, 75, 7], [44, 6, 44, 7, 55, 6, 55, 7, 55, 8, 55, 9], [64, 8, 64, 9, 64, 6, 64, 7, 75, 6, 75, 7], [46, 2, 46, 3, 53, 2, 53, 3, 53, 4, 53, 5], [66, 4, 66, 5, 66, 2, 66, 3, 73, 2, 73, 3], [66, 6, 66, 7, 66, 4, 66, 5, 53, 4, 53, 5], [86, 4, 86, 5, 73, 4, 73, 5, 73, 6, 73, 7], [46, 6, 46, 7, 53, 6, 53, 7, 53, 8, 53, 9], [66, 8, 66, 9, 66, 6, 66, 7, 73, 6, 73, 7], [48, 2, 48, 3, 51, 2, 51, 3, 51, 4, 51, 5], [68, 4, 68, 5, 68, 2, 68, 3, 71, 2, 71, 3], [68, 6, 68, 7, 68, 4, 68, 5, 51, 4, 51, 5], [88, 4, 88, 5, 71, 4, 71, 5, 71, 6, 71, 7], [48, 6, 48, 7, 51, 6, 51, 7, 51, 8, 51, 9], [68, 8, 68, 9, 68, 6, 68, 7, 71, 6, 71, 7], [50, 2, 50, 3, 69, 2, 69, 3, 69, 4, 69, 5], [70, 4, 70, 5, 70, 2, 70, 3, 89, 2, 89, 3], [70, 6, 70, 7, 70, 4, 70, 5, 69, 4, 69, 5], [90, 4, 90, 5, 89, 4, 89, 5, 89, 6, 89, 7], [50, 6, 50, 7, 69, 6, 69, 7, 69, 8, 69, 9], [70, 8, 70, 9, 70, 6, 70, 7, 89, 6, 89, 7], [52, 2, 52, 3, 67, 2, 67, 3, 67, 4, 67, 5], [72, 4, 72, 5, 72, 2, 72, 3, 87, 2, 87, 3], [72, 6, 72, 7, 72, 4, 72, 5, 67, 4, 67, 5], [92, 4, 92, 5, 87, 4, 87, 5, 87, 6, 87, 7], [52, 6, 52, 7, 67, 6, 67, 7, 67, 8, 67, 9], [72, 8, 72, 9, 72, 6, 72, 7, 87, 6, 87, 7], [54, 2, 54, 3, 65, 2, 65, 3, 65, 4, 65, 5], [74, 4, 74, 5, 74, 2, 74, 3, 85, 2, 85, 3], [74, 6, 74, 7, 74, 4, 74, 5, 65, 4, 65, 5], [94, 4, 94, 5, 85, 4, 85, 5, 85, 6, 85, 7], [54, 6, 54, 7, 65, 6, 65, 7, 65, 8, 65, 9], [74, 8, 74, 9, 74, 6, 74, 7, 85, 6, 85, 7], [56, 2, 56, 3, 63, 2, 63, 3, 63, 4, 63, 5], [76, 4, 76, 5, 76, 2, 76, 3, 83, 2, 83, 3], [76, 6, 76, 7, 76, 4, 76, 5, 63, 4, 63, 5], [96, 4, 96, 5, 83, 4, 83, 5, 83, 6, 83, 7], [56, 6, 56, 7, 63, 6, 63, 7, 63, 8, 63, 9], [76, 8, 76, 9, 76, 6, 76, 7, 83, 6, 83, 7], [58, 2, 58, 3, 61, 2, 61, 3, 61, 4, 61, 5], [78, 4, 78, 5, 78, 2, 78, 3, 81, 2, 81, 3], [78, 6, 78, 7, 78, 4, 78, 5, 61, 4, 61, 5], [98, 4, 98, 5, 81, 4, 81, 5, 81, 6, 81, 7], [58, 6, 58, 7, 61, 6, 61, 7, 61, 8, 61, 9], [78, 8, 78, 9, 78, 6, 78, 7, 81, 6, 81, 7], [60, 2, 60, 3, 79, 2, 79, 3, 79, 4, 79, 5], [80, 4, 80, 5, 80, 2, 80, 3, 99, 2, 99, 3],

TABLE 32-continued

[80, 6, 80, 7, 80, 4, 80, 5, 79, 4, 79, 5], [60, 6, 60, 7, 79, 6, 79, 7, 79, 8, 79, 9], [80, 8, 80, 9, 80, 6, 80, 7, 99, 6, 99, 7], [62, 2, 62, 3, 77, 2, 77, 3, 77, 4, 77, 5], [82, 4, 82, 5, 82, 2, 82, 3, 97, 2, 97, 3], [82, 6, 82, 7, 82, 4, 82, 5, 77, 4, 77, 5], [62, 6, 62, 7, 77, 6, 77, 7, 77, 8, 77, 9], [82, 8, 82, 9, 82, 6, 82, 7, 97, 6, 97, 7], [64, 2, 64, 3, 75, 2, 75, 3, 75, 4, 75, 5], [84, 4, 84, 5, 84, 2, 84, 3, 95, 2, 95, 3], [84, 6, 84, 7, 84, 4, 84, 5, 75, 4, 75, 5], [64, 6, 64, 7, 75, 6, 75, 7, 75, 8, 75, 9], [84, 8, 84, 9, 84, 6, 84, 7, 95, 6, 95, 7], [66, 2, 66, 3, 73, 2, 73, 3, 73, 4, 73, 5], [86, 4, 86, 5, 86, 2, 86, 3, 93, 2, 93, 3], [86, 6, 86, 7, 86, 4, 86, 5, 73, 4, 73, 5], [66, 6, 66, 7, 73, 6, 73, 7, 73, 8, 73, 9], [86, 8, 86, 9, 86, 6, 86, 7, 93, 6, 93, 7], [68, 2, 68, 3, 71, 2, 71, 3, 71, 4, 71, 5], [88, 4, 88, 5, 88, 2, 88, 3, 91, 2, 91, 3], [88, 6, 88, 7, 88, 4, 88, 5, 71, 4, 71, 5], [68, 6, 68, 7, 71, 6, 71, 7, 71, 8, 71, 9], [88, 8, 88, 9, 88, 6, 88, 7, 91, 6, 91, 7], [70, 2, 70, 3, 89, 2, 89, 3, 89, 4, 89, 5], [90, 6, 90, 7, 90, 4, 90, 5, 89, 4, 89, 5], [70, 6, 70, 7, 89, 6, 89, 7, 89, 8, 89, 9], [88, 2, 88, 3, 91, 2, 91, 3, 91, 4, 91, 5], [88, 6, 88, 7, 91, 6, 91, 7, 91, 8, 91, 9], [72, 2, 72, 3, 87, 2, 87, 3, 87, 4, 87, 5], [92, 6, 92, 7, 92, 4, 92, 5, 87, 4, 87, 5], [72, 6, 72, 7, 87, 6, 87, 7, 87, 8, 87, 9], [86, 2, 86, 3, 93, 2, 93, 3, 93, 4, 93, 5], [86, 6, 86, 7, 93, 6, 93, 7, 93, 8, 93, 9], [74, 2, 74, 3, 85, 2, 85, 3, 85, 4, 85, 5], [94, 6, 94, 7, 94, 4, 94, 5, 85, 4, 85, 5], [74, 6, 74, 7, 85, 6, 85, 7, 85, 8, 85, 9], [84, 2, 84, 3, 95, 2, 95, 3, 95, 4, 95, 5], [84, 6, 84, 7, 95, 6, 95, 7, 95, 8, 95, 9], [76, 2, 76, 3, 83, 2, 83, 3, 83, 4, 83, 5], [96, 6, 96, 7, 96, 4, 96, 5, 83, 4, 83, 5], [76, 6, 76, 7, 83, 6, 83, 7, 83, 8, 83, 9], [82, 2, 82, 3, 97, 2, 97, 3, 97, 4, 97, 5], [82, 6, 82, 7, 97, 6, 97, 7, 97, 8, 97, 9], [78, 2, 78, 3, 81, 2, 81, 3, 81, 4, 81, 5], [98, 6, 98, 7, 98, 4, 98, 5, 81, 4, 81, 5], [78, 6, 78, 7, 81, 6, 81, 7, 81, 8, 81, 9], [80, 2, 80, 3, 99, 2, 99, 3, 99, 4, 99, 5], [80, 6, 80, 7, 99, 6, 99, 7, 99, 8, 99, 9]

The oligonucleotide sequences used to produce 30H×1H×126B nucleic acid structures of the invention are designated SEQ ID NOs. 11297-11502, and the corresponding 5' end coordinates are shown respectively in Table 33. (See also Appendix, Table 16 of U.S. provisional application No. 61/675,309, filed Jul. 24, 2012, incorporated by reference herein.)

TABLE 33

[1, 23], [1, 39], [1, 55], [1, 71], [1, 87], [1, 103], [1, 119], [1, 135], [3, 23], [3, 39], [3, 55], [3, 71], [3, 87], [3, 103], [3, 119], [3, 135], [5, 23], [5, 39], [5, 55], [5, 71], [5, 87], [5, 103], [5, 119], [5, 135], [7, 23], [7, 39], [7, 55], [7, 71], [7, 87], [7, 103], [7, 119], [7, 135], [9, 23], [9, 39], [9, 55], [9, 71], [9, 87], [9, 103], [9, 119], [9, 135], [11, 23], [11, 39], [11, 55], [11, 71], [11, 87], [11, 103], [11, 119], [11, 135], [13, 23], [13, 39], [13, 55], [13, 71], [13, 87], [13, 103], [13, 119], [13, 135], [15, 23], [15, 39], [15, 55], [15, 71], [15, 87], [15, 103], [15, 119], [15, 135], [17, 23], [17, 39], [17, 55], [17, 71], [17, 87], [17, 103], [17, 119], [17, 135], [19, 23], [19, 39], [19, 55], [19, 71], [19, 87], [19, 103], [19, 119], [19, 135], [21, 23], [21, 39], [21, 55], [21, 71], [21, 87], [21, 103], [21, 119], [21, 135], [23, 23], [23, 39], [23, 55], [23, 71], [23, 87], [23, 103], [23, 119], [23, 135], [25, 23], [25, 39], [25, 55], [25, 71], [25, 87], [25, 103], [25, 119], [25, 135], [27, 23], [27, 39], [27, 55], [27, 71], [27, 87], [27, 103], [27, 119], [27, 135], [29, 39], [29, 71], [29, 103], [29, 135], [0, 47], [0, 95], [0, 143], [1, 0], [1, 48], [1, 96], [2, 47], [2, 95], [2, 143], [3, 0], [3, 48], [3, 96], [4, 47], [4, 95], [4, 143], [5, 0], [5, 48], [5, 96], [6, 47], [6, 95], [6, 143], [7, 0], [7, 48], [7, 96], [8, 47], [8, 95], [8, 143], [9, 0], [9, 48], [9, 96], [10, 47], [10, 95], [10, 143], [11, 0], [11, 48], [11, 96], [12, 47], [12, 95], [12, 143], [13, 0], [13, 48], [13, 96], [14, 47], [14, 95], [14, 143], [15, 0], [15, 48], [15, 96], [16, 47], [16, 95], [16, 143], [17, 0], [17, 48], [17, 96], [18, 47], [18, 95], [18, 143], [19, 0], [19, 48], [19, 96], [20, 47], [20, 95], [20, 143], [21, 0], [21, 48], [21, 96], [22, 47], [22, 95], [22, 143], [23, 0], [23, 48], [23, 96], [24, 47], [24, 95], [24, 143], [25, 0], [25, 48], [25, 96], [26, 47], [26, 95], [26, 143], [27, 0], [27, 48], [27, 96], [28, 47], [28, 95], [28, 143], [29, 0], [29, 48], [29, 96]

The oligonucleotide sequences used to produce 6H×6H×84B-HC nucleic acid structures of the invention are designated SEQ ID NOs. 11503-11667, and the corresponding 5' end coordinates are shown respectively in Table 34. (See also Appendix, Table 17 of U.S. provisional application No. 61/675,309, filed Jul. 24, 2012, incorporated by reference herein.)

TABLE 34

[0, 47], [0, 89], [1, 46], [1, 64], [1, 88], [1, 106], [3, 46], [3, 64], [3, 88], [3, 106], [5, 46], [5, 64], [5, 88], [5, 106], [6, 23], [7, 46], [7, 64], [7, 88], [7, 106], [9, 46], [9, 64], [9, 88], [9, 106], [11, 46], [11, 88], [11, 106], [12, 47], [12, 89], [13, 46], [13, 64], [13, 88], [13, 106], [15, 46], [15, 64], [15, 88], [15, 106], [17, 46], [17, 64], [17, 88], [17, 106], [18, 23], [19, 46], [19, 64], [19, 88], [19, 106], [21, 46], [21, 64], [21, 88], [21, 106], [23, 46], [23, 88], [23, 106], [24, 47], [24, 89], [25, 46], [25, 64], [25, 88], [25, 106], [27, 46], [27, 64], [27, 88], [27, 106], [29, 46], [29, 64], [29, 88], [29, 106], [30, 23], [31, 46], [31, 64], [31, 88], [31, 106], [33, 46], [33, 64], [33, 88], [33, 106], [35, 46], [35, 88], [35, 106], [0, 55], [0, 111], [2, 55], [2, 111], [4, 55], [4, 111], [6, 34], [6, 55], [6, 76], [6, 97], [6, 118], [8, 34], [8, 55], [8, 76], [8, 97], [8, 118], [10, 34], [10, 55], [10, 76], [10, 97], [10, 118], [12, 34], [12, 55], [12, 76], [12, 97], [12, 118], [14, 34], [14, 55], [14, 76], [14, 97], [14, 118], [16, 34], [16, 55], [16, 76], [16, 97], [16, 118], [18, 34], [18, 55], [18, 76], [18, 97], [18, 118], [20, 34], [20, 55], [20, 76], [20, 97], [20, 118], [22, 34], [22, 55], [22, 76], [22, 97], [22, 118], [24, 34], [24, 55], [24, 76], [24, 97], [24, 118], [26, 34], [26, 55], [26, 76], [26, 97], [26, 118], [28, 34], [28, 55], [28, 76], [28, 97], [28, 118], [30, 34], [30, 55], [30, 76], [30, 97], [30, 118], [31, 14], [31, 56], [32, 34], [32, 55], [32, 76], [32, 97], [32, 118], [33, 14], [33, 56], [34, 34], [34, 55], [34, 76], [34, 97], [34, 118], [35, 14], [35, 56]

The oligonucleotide sequences used to produce 6H×7H×108B-HL nucleic acid structures of the invention are designated SEQ ID NOs. 11668-11935, and the corresponding 5' end coordinates are shown respectively in Table 35. (See also Appendix, Table 18 of U.S. provisional application No. 61/675,309, filed Jul. 24, 2012, incorporated by reference herein.)

TABLE 35

[0, 26], [0, 56], [0, 104], [1, 79], [1, 133], [2, 26], [2, 56], [2, 104], [3, 79], [3, 133], [4, 26], [4, 56], [4, 104], [5, 79], [5, 133], [6, 26], [6, 80], [7, 55], [7, 103], [7, 133], [8, 32], [8, 80], [9, 55], [9, 103], [9, 133], [10, 32], [10, 80], [11, 55], [11, 103], [11, 133], [12, 26], [12, 56], [12, 104], [13, 79], [13, 133], [14, 26], [14, 56], [14, 104], [15, 79], [15, 133], [16, 26], [16, 56], [16, 104], [17, 79], [17, 133], [18, 26], [18, 72], [18, 88], [19, 71], [19, 87], [19, 133], [20, 26], [20, 72], [20, 88], [21, 71], [21, 87], [21, 133], [22, 26], [22, 72], [22, 88], [23, 71], [23, 87], [23, 133], [24, 26], [24, 80], [25, 55], [25, 103], [25, 133], [26, 32], [26, 80], [27, 55], [27, 103], [27, 133], [28, 32], [28, 80], [29, 55], [29, 103], [29, 133], [30, 26], [30, 56], [30, 104], [31, 79], [31, 133], [32, 26], [32, 56], [32, 104], [33, 79], [33, 133], [34, 26], [34, 56], [34, 104], [35, 79], [35, 133], [36, 26], [36, 80], [37, 71], [37, 87], [37, 133], [38, 26], [38, 72], [38, 88], [39, 71], [39, 87], [39, 133], [40, 26], [40, 72], [40, 88], [41, 63], [41, 87], [41, 133], [0, 47], [0, 79], [0, 95], [0, 127], [1, 32], [2, 47], [2, 63], [2, 79], [2, 95], [2, 111], [2, 127], [3, 32], [4, 47], [4, 63], [4, 79], [4, 95], [4, 111], [4, 127], [5, 32], [5, 72], [6, 55], [6, 71], [6, 103], [6, 119], [6, 127], [8, 39], [8, 55], [8, 71], [8, 87], [8, 103], [8, 119], [8, 127], [10, 39], [10, 55], [10, 71], [10, 87], [10, 103], [10, 119], [10, 127], [12, 63], [12, 71], [12, 79], [12, 111], [12, 119], [12, 127], [13, 24], [14, 39], [14, 47], [14, 63], [14, 71], [14, 79], [14, 87], [14, 95], [14, 111], [14, 119], [14, 127], [15, 24], [16, 39], [16, 47], [16, 63], [16, 71], [16, 79], [16, 87], [16, 95], [16, 111], [16, 119], [16, 127], [17, 32], [18, 47], [18, 55], [18, 79], [18, 95], [18, 103], [18, 127], [20, 47], [20, 55], [20, 63], [20, 79], [20, 95], [20, 103], [20, 111], [20, 127], [22, 47], [22, 55], [22, 63], [22, 79], [22, 95], [22, 103], [22, 111], [22, 127], [24, 55], [24, 71], [24, 103], [24, 119], [24, 127], [26, 39], [26, 55], [26, 71], [26, 87], [26, 103], [26, 119], [26, 127], [28, 39], [28, 55], [28, 71], [28, 87], [28, 103], [28, 119], [28, 127], [30, 63], [30, 71], [30, 79], [30, 111], [30, 119], [30, 127], [31, 24], [32, 39], [32, 47], [32, 63], [32, 71], [32, 79], [32, 87], [32, 95], [32, 111], [32, 119], [32, 127], [33, 24], [34, 39], [34, 47], [34, 63], [34, 71], [34, 79], [34, 87], [34, 95], [34, 111], [34, 119], [34, 127], [35, 32], [36, 47], [36, 55], [36, 71], [36, 95], [36, 103], [36, 127], [38, 47], [38, 55], [38, 63], [38, 95], [38, 103], [38, 111], [38, 127], [40, 47], [40, 55], [40, 63], [40, 95], [40, 103], [40, 111], [40, 127]

The oligonucleotide sequences used to produce 6H×6H×64B (version 1) nucleic acid structures of the invention are designated SEQ ID NOs. 11936-12041, and the corresponding 5' end coordinates are shown respectively in Table 36. (See also Appendix, Table 19 of U.S. provisional application No. 61/675,309, filed Jul. 24, 2012, incorporated by reference herein.)

TABLE 36

[0, 26], [0, 85], [1, 58], [2, 43], [2, 85], [3, 58], [4, 40], [4, 85], [5, 75], [6, 52], [7, 43], [7, 84], [8, 59], [9, 41], [9, 84], [10, 59], [11, 41], [11, 100], [12, 26], [12, 85], [13, 58], [14, 43], [14, 85], [15, 58], [16, 43], [16, 85], [17, 67], [18, 43], [19, 58], [20, 44], [20, 85], [21, 58], [22, 44], [22, 85], [23, 51], [23, 100], [24, 26], [24, 85], [25, 58], [26, 43], [26, 85], [27, 58], [28, 43], [28, 85], [29, 67], [30,43], [31, 58], [32, 45], [32, 85], [33, 58], [34, 44], [34, 85], [35, 51], [35, 100], [0, 43], [0, 59], [1, 68], [1, 85], [2, 59], [2, 91], [3, 36],[3, 68], [4, 43], [4, 59], [4, 91], [5, 68], [6, 95], [11, 32], [12, 43], [12, 75], [13, 52], [13, 84], [14, 43], [14, 75], [15, 36], [15, 52], [15, 84], [16, 43], [16, 75], [17, 52], [17, 84], [18, 59], [18, 95], [19, 68], [20, 59], [21, 68], [21, 92], [22, 59], [23, 32], [23, 68], [26, 35], [27, 92], [30, 43], [30, 75], [30, 95], [31, 52], [31, 84], [32, 43], [32, 75], [33, 52], [33, 84], [34, 43], [34, 75], [35, 32], [35, 52], [35, 84]

The oligonucleotide sequences used to produce 6H×6H×64B (version 2) nucleic acid structures of the invention are designated SEQ ID NOs. 12042-12203, and the corresponding 5' end coordinates are shown respectively in Table 37. (See also Appendix, Table 20 of U.S. provisional application No. 61/675,309, filed Jul. 24, 2012, incorporated by reference herein.)

TABLE 37

[0, 28], [0, 60], [1, 35], [1, 67], [2, 28], [2, 60], [3, 35], [3, 67], [4, 28], [4, 60], [5, 35], [5, 67], [6, 12], [6, 44], [7, 19], [7, 51], [8, 44], [8, 76], [9, 19], [9, 51], [10, 44], [10, 76], [11, 51], [11, 83], [12, 28], [12, 60], [13, 35], [13, 67], [14, 28], [14, 60], [15, 35], [15, 67], [16, 28], [16, 60], [17, 35], [17, 67], [18, 12], [18, 44], [19, 19], [19, 51], [20, 44], [20, 76], [21, 19], [21, 51], [22, 44], [22, 76], [23, 51], [23, 83], [24, 28], [24, 60], [25, 35], [25, 67], [26, 28], [26, 60], [27, 35], [27, 67], [28, 28], [28, 60], [29, 35], [29, 67], [30, 12], [30, 44], [31, 19], [31, 51], [32, 44], [32, 76], [33, 19], [33, 51], [34, 44], [34, 76], [35, 51], [35, 83], [0, 43], [0, 75], [1, 20], [1, 52], [2, 43], [2, 75], [3, 20], [3, 52], [4, 43], [4, 75], [5, 20], [5, 52], [6, 27], [6, 59], [7, 36], [7, 68], [8, 27], [8, 59], [9, 36], [9, 68], [10, 27], [10, 59], [11, 36], [11, 68], [12, 11], [12, 43], [12, 75], [13, 20], [13, 52], [13, 84], [14, 11], [14, 43], [14, 75], [15, 20], [15, 52], [15, 84], [16, 11], [16, 43], [16, 75], [17, 20], [17, 52], [17, 84], [18, 27], [18, 59], [19, 68], [20, 27], [20, 59], [21, 36], [21, 68], [22, 27], [22, 59], [23, 36], [23, 68], [24, 11], [24, 43], [24, 75], [25, 20], [25, 52], [25, 84], [26, 11], [26, 43], [26, 75], [27, 20], [27, 52], [27, 84], [28, 11], [28, 43], [28, 75], [29, 20], [29, 52], [29, 84], [30, 27], [30, 59], [30, 91], [31, 4], [31, 36], [31, 68], [32, 27], [32, 59], [32, 91], [33, 4], [33, 36], [33, 68], [34, 27], [34, 59], [34, 91], [35, 4], [35, 36], [35, 68]

Single-Stranded Oligonucleotides

The nucleic acid structures of the invention are designed and made using a plurality of single-stranded oligonucleotides that anneal to each other in a sequence-specific manner. The oligonucleotides may be characterized by their length, their sequence, and their domain composition. The number and sequence of their domains governs the binding activity and location of each oligonucleotide. Their domain number typically governs the number of oligonucleotides each oligonucleotide will bind to in a structure.

In some instances, the oligonucleotides used to make a structure comprise an even number of domains. Each oligonucleotide typically comprises at least two domains. In some embodiments, oligonucleotides used to make a structure may be 2- and 4-domain oligonucleotides. It is also possible to form structures using other combinations of oligonucleotides including without limitation 2- and 6-domain oligonucleotides, 3- and 6-domain oligonucleotides, 2- and 8-domain oligonucleotides, 4- and 8-domain oligonucleotides, and the like.

A domain, as used herein, refers to a nucleotide sequence (i.e., a number of contiguous nucleotides or nucleotide analogs having the ability to bind in a sequence-specific manner to their complements). The domains in a plurality of oligonucleotides or in a nucleic acid structure are designed such that they anneal to domain in another oligonucleotide. The collective complementarity of all domains of an oligonucleotide facilitates the self-assembly of such oligonucleotides to form nucleic acid structures.

The domain length may vary. In situations where two contiguous domains from the same oligonucleotide are contributing to the same helix, the lengths of the two domains may be interrelated. As an example, one domain has a length of x and the other domain has a length of y, provided that x+y is about 16, provided that each of x and y is 1 or greater.

In some embodiments, two contiguous domains from the same oligonucleotide that contribute to the same helix may have a combined length of about 16+/−2 nucleotides in length. Thus, a single domain may have a length of, for example, 1, 2, 3, 4, 5, 6, 7, 8, 9, 10, 11, 12, 13, 14, 15, 16 or 17 nucleotides. Two contiguous domains may have a total combined length of, for example, 14, 15, 16, 17 or 18 nucleotides. A 2-domain oligonucleotide may have a length of, for example, 16+/−2 nucleotides. A 4-domain oligonucleotide may have a length of, for example, 32+/−4 nucleotides.

In some important embodiments, a domain has a length of 8 nucleotides, two contiguous domains have a length of 16 nucleotides, and a 4-domain oligonucleotide has a length of 32 nucleotides. It is to be understood that the invention contemplates oligonucleotides having two contiguous domains (both contributing to a single helix) that have a length that is a multiple of 16 nucleotides.

Typically in a given synthesis method or resultant structure, oligonucleotides having the same number of domains will also have the same length. As an example, in one embodiment, all 4-domain oligonucleotides will be the same length and all 2-domain oligonucleotides will be the same length (but that length will be different from that of the 4-domain oligonucleotides). More specifically, some embodiments will use 4-domain oligonucleotides that are one length (e.g., n nucleotides) and 2-domain oligonucleotides that are half that length (e.g., n/2 nucleotides).

The invention contemplates nucleic acid structures comprising any number of single-stranded oligonucleotides. As an example, the nucleic acid structures may comprise as few as 4 and as many as 1000 (or more) oligonucleotides, without limitation. Similarly, pluralities of oligonucleotides used to generate nucleic acid structures may comprise as few as 4 different types of oligonucleotides (as defined by nucleotide sequence) and as many as 1000 (or more) different oligonucleotide species (as defined by nucleotide sequence), without limitation. Thus, depending on the embodiment, the nucleic acid structure may comprise 4, 5, 6, 7, 8, 9, 10, 15, 10, 25, 50, 75, 100, 150, 200, 250, 300, 350, 400, 450, 500, 600, 700, 800, 900, 1000, 1100, 1200, 1300, 1400, 1500, or more oligonucleotides. Similarly, depending on the embodiment, a plurality of oligonucleotides used to generate nucleic acid structures may comprise 4, 5, 6, 7, 8, 9, 10, 15, 10, 25, 50, 75, 100, 150, 200, 250, 300, 350, 400, 450, 500, 600, 700, 800, 900, 1000, 1100, 1200, 1300, 1400, 1500, or more different oligonucleotides.

A variety of oligonucleotide sequences are provided herewith in the attached and incorporated appendix. The appendix illustrates the oligonucleotides required to form 3D canvases of various shapes and sizes, as described herein.

Oligonucleotides, in the context of the invention, include DNA such as D-form DNA and L-form DNA and RNA, as well as various modifications thereof. Modifications include base modifications, sugar modifications, and backbone modifications. Non-limiting examples of these are provided below.

Non-limiting examples of DNA variants that may be used in the invention are L-DNA (the backbone enantiomer of DNA, known in the literature), peptide nucleic acids (PNA) bisPNA clamp, a pseudocomplementary PNA, a locked nucleic acid (LNA), or co-nucleic acids of the above such as DNA-LNA co-nucleic acids. It is to be understood that the oligonucleotides used in products and methods of the invention may be homogeneous or heterogeneous in nature. As an example, they may be completely DNA in nature or they may be comprised of DNA and non-DNA (e.g., LNA) monomers or sequences. Thus, any combination of nucleic acid elements may be used. The oligonucleotide modification may render the oligonucleotide more stable and/or less susceptible to degradation under certain conditions. For example, in some instances, the oligonucleotides are nuclease-resistant.

The oligonucleotides may have a homogenous backbone (e.g., entirely phosphodiester or entirely phosphorothioate) or a heterogeneous (or chimeric) backbone. Phosphorothioate backbone modifications render an oligonucleotide less susceptible to nucleases and thus more stable (as compared to a native phosphodiester backbone nucleic acid) under certain conditions. Other linkages that may provide more stability to an oligonucleotide include without limitation phosphorodithioate linkages, methylphosphonate linkages, methylphosphorothioate linkages, boranophosphonate linkages, peptide linkages, alkyl linkages, dephospho type linkages, and the like. Thus, in some instances, the oligonucleotides have non-naturally occurring backbones.

Oligonucleotides may be synthesized in vitro. Methods for synthesizing nucleic acids, including automated nucleic acid synthesis, are also known in the art. Oligonucleotides having modified backbones, such as backbones comprising phosphorothioate linkages, and including those comprising chimeric modified backbones may be synthesized using automated techniques employing either phosphoramidate or H-phosphonate chemistries. (F. E. Eckstein, "Oligonucleotides and Analogues—A Practical Approach" *IRL Press*, Oxford, U K, 1991, and M. D. Matteucci and M. H. Caruthers, *Tetrahedron Lett*. 21, 719 (1980)) Aryl- and alkyl-phosphonate linkages can be made, e.g., as described in U.S. Pat. No. 4,469,863; and alkylphosphotriester linkages (in which the charged oxygen moiety is alkylated), e.g., as described in U.S. Pat. No. 5,023,243 and European Patent No. 092,574, can be prepared by automated solid phase synthesis using commercially available reagents. Methods for making other DNA backbone modifications and substitutions have been described. Uhlmann E et al. (1990) Chem Rev 90:544; Goodchild J (1990) Bioconjugate Chem 1:165; Crooke S T et al. (1996) Annu Rev Pharmacol Toxicol 36:107-129; and Hunziker J et al. (1995) Mod Synth Methods 7:331-417.

The oligonucleotides may additionally or alternatively comprise modifications in their sugars. For example, a β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, arabinose, 2'-F-arabinose, 2'-O—($C_1$-$C_6$)alkyl-ribose, preferably 2'-O—($C_1$-$C_6$) alkyl-ribose is 2'-O-methylribose, 2'-O—($C_2$-$C_6$)alkenyl-ribose, 2'-[O—($C_1$-$C_6$)alkyl-O—($C_1$-$C_6$)alkyl]-ribose, 2'-$NH_2$-2'-deoxyribose, 3-D-xylo-furanose, α-arabinofuranose, 2,4-dideoxy-β-D-erythro-hexo-pyranose, and carbocyclic (described, for example, in Froehler J (1992) Am Chem Soc 114:8320) and/or open-chain sugar analogs (described, for example, in Vandendriessche et al. (1993) Tetrahedron 49:7223) and/or bicyclosugar analogs (described, for example, in Tarkov M et al. (1993) Helv Chim Acta 76:481).

The oligonucleotides may comprise modifications in their bases. Modified bases include modified cytosines (such as 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil), modified guanines such as 7-deazaguanine, 7-deaza-7-substituted guanine (such as 7-deaza-7-(C2-C6)alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. The nucleic acids may comprise universal bases (e.g. 3-nitropyrrole, P-base, 4-methyl-indole, 5-nitro-indole, and K-base) and/or aromatic ring systems (e.g. fluorobenzene, difluorobenzene, benzimidazole or dichloro-benzimidazole, 1-methyl-1H-[1,2,4]triazole-3-carboxylic acid amide). A particular base pair that may be incorporated into the oligonucleotides of the invention is a dZ and dP non-standard nucleobase pair reported by Yang et al. NAR, 2006, 34(21):6095-6101. dZ, the pyrimidine analog, is 6-amino-5-nitro-3-(1'-β-D-2'-deoxyribofuranosyl)-2(1H)-pyridone, and its Watson-Crick complement dP, the purine analog, is 2-amino-8-(1'-β-D-1'-deoxyribofuranosyl)-imidazo[1,2-a]-1,3,5-triazin-4(8H)-one.

Methods of Synthesis

The invention contemplates synthesizing nucleic acid structures through annealing processes. In one approach, once the single-stranded oligonucleotides have been identified and synthesized (e.g., using commercial vendors such as Bioneer), they are combined, in a single vessel such as, but not limited to, a tube, a well, a vial, and the like. The molar amounts of oligonucleotides that are used will depend on the frequency of each oligonucleotide in the structures desired and the amount of structures desired. In some embodiments, the oligonucleotides may be present in equimolar concentrations. In some embodiments, each oligonucleotide may be present at a concentration of about 200 nM. The oligonucleotides are placed in a solution. Preferably the solution is buffered although the annealing reaction can also occur in the absence of buffer. The solution may further comprise divalent cations such as but not limited to $Mg^{2+}$. The cation or salt concentration may vary. An exemplary concentration is about 490 mM. The solution may also comprise EDTA or other nuclease inhibitors in order to prevent degradation of the oligonucleotides.

The annealing reaction is carried out by heating the solution and then allowing the solution to slowly cool down. The temperature of the reaction should be sufficiently high to melt any undesirable secondary structure such as hairpin structures and to ensure that the oligonucleotide species are not bound incorrectly to other non-complementary oligonucleotides. The temperature may therefore be initially raised to about 100° C., about 95° C., about 90° C., about 85° C., 80° C., 75° C., 70° C., 65° C. or 60° C. in some embodiments. The temperature may be raised by placing the vessel in a hot water bath or a heating block or a device capable of temperature control such as a PCR machine. The vessel may be kept in that environment for seconds or minutes. Typically, an incubation of about 1-10 minutes is sufficient.

Once the incubation at elevated temperature is complete, the temperature may be dropped in a number of ways. The temperature may be dropped in an automated manner using a computer algorithm that drops the temperature by a certain amount and maintains that temperature for a certain period of time before dropping the temperature again. Such automated methods may involve dropping the temperature by a degree in each step or by a number of degrees at each step. The vessel may thus be heated and cooled in the same device.

An exemplary process is provided. To effect a drop in temperature from about 80° C. to about 24° C., the temperature is changed from 80° C. to 61° C. in one degree increments at a rate of 3 minutes per degree (i.e., 80° C. for 3 minutes, 79° C. for 3 minutes, etc.). The temperature is then changed from 60° C. to 24° C. in one degree increments and at a rate of about 120 minutes per degree (i.e., 60° C. for 120 minutes, 59° C. for 210 minutes, etc.). The total annealing time for this process is about 17 hours. In accordance with the invention, under these conditions, the oligonucleotides self-assemble into a nucleic acid structure of predetermined and desired shape and size.

An example of a specific annealing process uses 100 200 nM oligonucleotides in a 5 mM Tris-1 mM EDTA (TE), 40 mM $MgCl_2$ solution and heating the solution to about 90° C. and then cooling the solution to about 24° C. over a period of about 73 hours, as described above with a 3 minute per degree drop between 80° C. and 61° C. and a 120 minute per degree drop between 60° C. and 24° C.

Composite Structures

The invention further contemplates that the nucleic acid structures described herein themselves may be used essentially as monomers or building blocks in order to form higher order or composite structures. The composite structures of the invention are comprised of nucleic acid structures linked to each other using spacer-linkers. The linkers are typically not integral to the nucleic acid structures although they may be attached to the structures via suitable functional groups. The ability to attach two or more nucleic acid structures together allows structures of greater size and complexity to be made.

The dimensions of these composite structures may range from 500 nm to 100 microns, or 1-1000 microns, without limitation.

Applications

The nucleic acid structures of the invention may be used in a variety of applications, including those that would benefit from the ability to precisely position and importantly arrange one or more moieties at a nanometer or micron scale.

As an example, the structures can be used as templates for arranging or patterning inorganic materials such as those useful in electronics, plasmonics, and quantum computing applications. Moieties that may be attached to the nucleic acid structures include metallic particles such as gold nanoparticles, quantum dots, carbon nanotubes, and the like. In this way, the nucleic acid structures provided by the invention act as scaffolds upon which other moieties may be arranged and/or other structures may be synthesized with nanometer precision and control. For example, carbon nanotubes can be organized into functional molecular electronics systems; tunable geometric arrangement of gold nanoparticles can be used to make functional molecular electronics circuits and novel plasmonics circuits; organized, predetermined arrangement of magnetic particles can be used to make nano-inductors or memory devices; and organized and predetermined arrangement of quantum dots can be used to make novel quantum computers.

In some embodiments, the moieties (e.g., gold nanoparticles) may be attached to nucleic acid structures of the invention through nucleotide base-pairing of complementary single-stranded oligonucleotides linked to the moieties and to the nucleic acid structure, as described, for example, in Example 5. Thus, in some embodiments, moieties such as gold nanoparticles may be arranged into discrete patterns as follows. Nucleic acid structures of the invention containing single-stranded poly-N oligonucleotide (e.g., a single-stranded poly-A oligonucleotide, or a single-stranded oligonucleotide comprising contiguous adenine nucleotides) at specific positions (e.g., within pores and/or channels) are contacted with moieties linked to (e.g., covalently, or non-covalently, attached to) a single-stranded poly-N oligonucleotide that is complementary to the single-stranded poly-N oligonucleotide of the nucleic acid structures (e.g., a single-stranded poly-T oligonucleotide, or a single-stranded oligonucleotide comprising contiguous thymidine nucleotides). In some embodiments, a single-stranded poly-N oligonucleotide is about 2 to about 15 nucleotides. In some embodiments, a single-stranded poly-N oligonucleotide is 2, 3, 4, 5, 6, 7, 8, 9, 10, 11, 12, 13, 14 or 15 nucleotides. In some embodiments, the single-stranded poly-N oligonucleotide is a single-stranded poly-A, single-stranded poly-T oligonucleotide, a single-stranded poly-G oligonucleotide, or a single-stranded poly-C oligonucleotide of about 10 nucleotides.

In other aspects, the invention contemplates that the nucleic acid structures of the invention may be metalized to make components for electronics. DNA tubes have been metalized into nanowires. Controlled metallization of the nucleic acid structures of the invention can be used to make, among other things, nano-wires with controlled diameters and hence controlled electronic properties. Further, novel molecular electronic components and circuits can be made through controlled metallization of the strut based nucleic acid structures provided by the invention.

The nucleic acid structures can also be used as templates for biological or organic molecules. Such templated molecules and systems may be useful, for example, in diagnostic and research applications. The biological or organic molecules include without limitation proteins and peptides such as antibodies and antibody fragments, enzymes and enzyme domains, receptors and receptor domains, biological ligands such as hormones and other signaling moieties, polysaccharides, cells, cell aggregates, and the like. Diverse strategies have been demonstrated for templating proteins on DNA lattices. Organization of proteins into prescribed geometric patterns with programmable nanometer precision can be used, for example, to study the cooperative behavior of biological motor proteins. Certain nucleic acid structures may also be used in cell or tissue culture. In these embodiments, as an example, the structures may be functionalized with biological moieties such as growth factors and extracellular matrix components. In this way, the functionalized structures may be arranged in culture to mimic a two or three-dimensional in vivo environment. As a further example, it is contemplated that higher order functionalize structures may be made that exhibit a concentration gradient for any particular biological moiety. These systems can then be used to study cellular development, differentiation and/or motion for any number of cell types. In still other instances, higher order structures of the invention can be used as scaffolds for cellular growth and differentiation in vitro or in vivo.

In various of these applications, the invention further contemplates that the nucleic acid scaffold comprised of the structures of the invention may be retained or it may be removed (e.g., through digestion or degradation) once it ceased being a template. For example, if the goal is to create a predetermined arrangement of gold particles and such particles are connect to each other as desired independently of the nucleic acid scaffold, the scaffold may be removed, leaving only the gold nanoparticle network.

Algorithms, Programs and Computer Systems

The invention contemplates algorithms for generating 3D nucleic acid structures of particular shape and size. These algorithms involve a starting point of a 3D canvas of sufficient size, wherein the oligonucleotides and domains contributing to any location in the canvas are known. The end user then defines within the canvas the desired structure and the algorithm identifies which oligonucleotides are to be included, which are to be excluded, and which are to be replaced in the generation of such a structure. Exemplary algorithm steps are shown in programs 1, 2 and 3 in FIG. 17. The invention contemplates that such algorithms may be performed manually or by computer means.

An illustrative implementation of a computer system that may be used in connection with some embodiments of the invention may include one or more processors and one or more computer-readable non-transitory storage media (e.g., memory and one or more non-volatile storage media). The processor may control writing data to and reading data from the memory and the non-volatile storage device in any suitable manner, as the aspects of the present invention described herein are not limited in this respect. To perform any of the functionality described herein, the processor may execute one or more instructions stored in one or more computer-readable storage media (e.g., the memory), which may serve as non-transitory computer-readable storage media storing instructions for execution by the processor.

Certain above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the present invention comprises at least one non-transitory computer-readable storage medium (e.g., a computer memory, a floppy disk, a compact disk, a tape, etc.) encoded with a computer program (e.g., a plurality of instructions), which, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

The following Examples are included for purposes of illustration and are not intended to limit the scope of the invention.

EXAMPLES

Example 1. Self-Assembly of 3D DNA-Block Nanostructures Across the Scale

To better understand our method and demonstrate its capability, 3D DNA-block nanostructures of a variety of sizes and aspect ratios were designed and tested (FIG. 2).

Random Sequence Design.

Figure 8A:
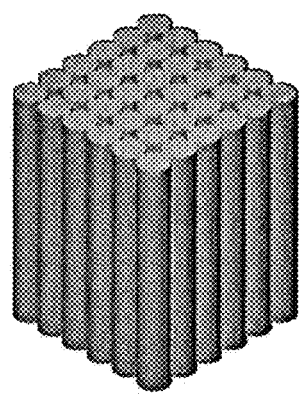
FIGS. 8A-8C show self-assembly of 6H×6H×64B cuboid with random sequence and designed sequence.
Figure 8B:
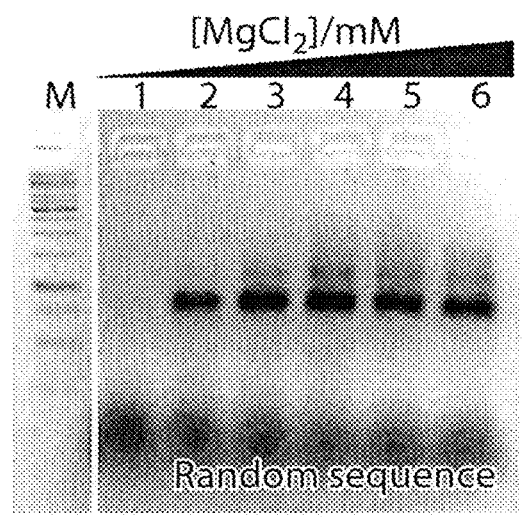
Figure 8C:
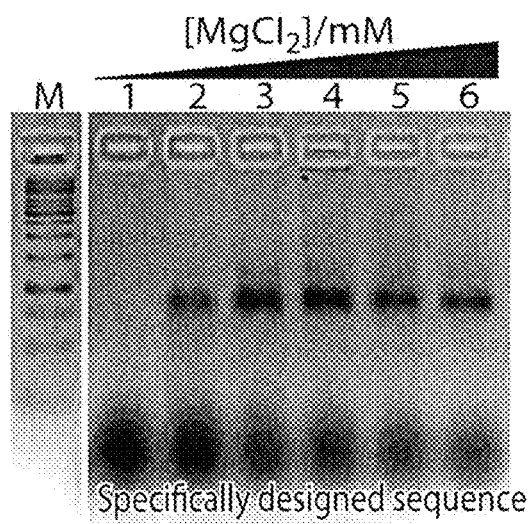

The sequences of oligonucleotides (also referred to as "DNA bricks") were designed by random assignments of base pairs (A-T, G-C) to 3D nanostructures. We first tested two versions of 6H×6H×64B with either random sequences or specially designed sequences and observed comparable self-assembly results (FIG. 8). We also tested three sets of random sequences on a 4H×12H×120B and also observed similar self-assembly yields (data not shown). Based on these results, we designed additional nanostructures using random sequences. The sequences were generated by a combination of a custom program and UNAfold, a program available at the mfold, rna, Albany website. Sequences of the first set of oligonucleotides (X-bricks) were first generated by taking the following three criteria into consideration: (1) smoothing binding energy of strands (each strand has similar GC content); (2) minimizing secondary structure of each strand; and (3) reducing sequence symmetry. The second set of oligonucleotides (Y-bricks) was then generated according to their complementarity to the first set. The product yields for structures assembled using random sequences and specifically designed sequences were similar. While the random sequence design strategy is used herein for synthesis of most nanostructures, the sequence design strategy may also be used and is being explored in ongoing studies.

Protector DNA Bricks.

Including unpaired single-strands at the ends of DNA duplex has proven to be effective for mitigating blunt-end stacking (P. W. K. Rothemund (2006)). An unpaired single-stranded 8 nt domain protrudes from every 5' or 3' end of all DNA duplexes in a 3D nanostructure (FIGS. 1C and 1D). Sequences of these 8 nt domains can be replaced with eight contiguous thymines to prevent undesired interactions. DNA blocks with modified head or tail domains are designated "head protectors" or "tail protectors," respectively.

Boundary DNA Bricks.

Figure 9A:
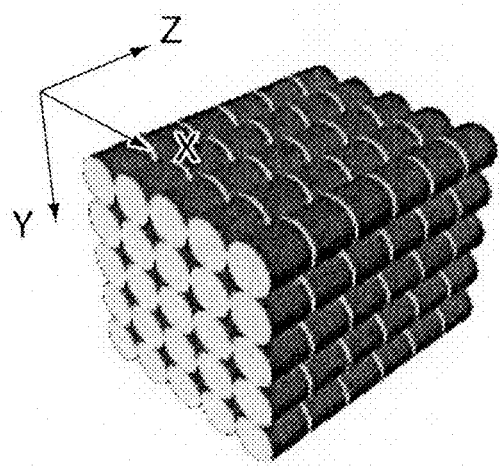
FIGS. 9A-9C show a 48 nucleotide boundary strand design.
Figure 9B:
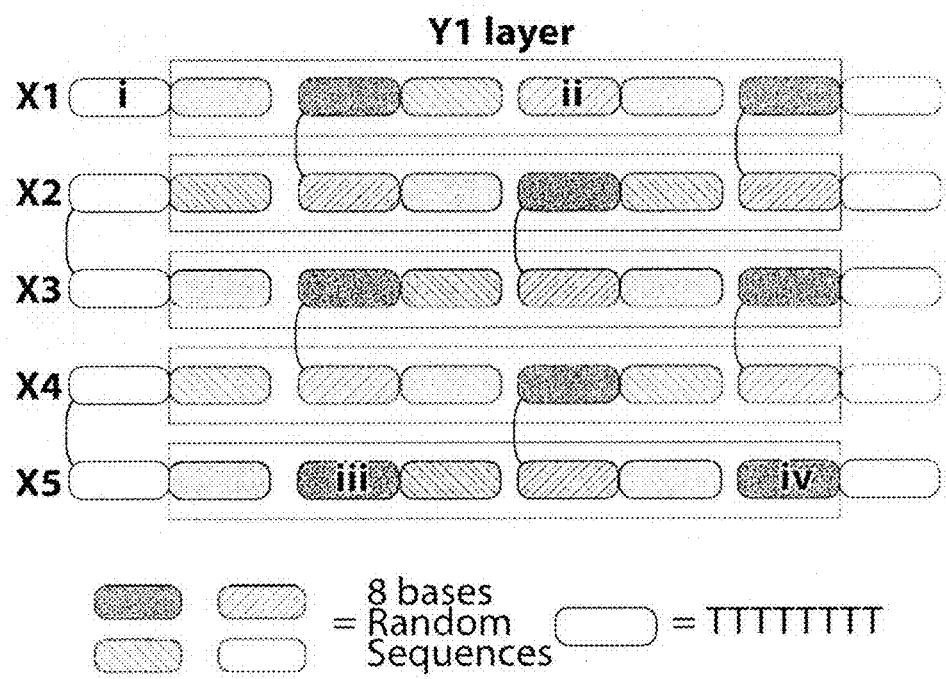
Figure 9C:
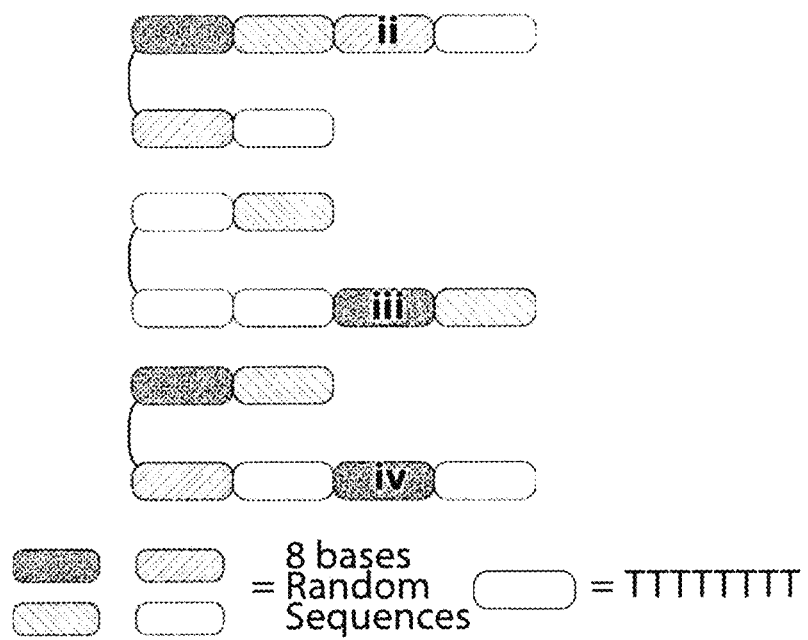
Figure 10A:
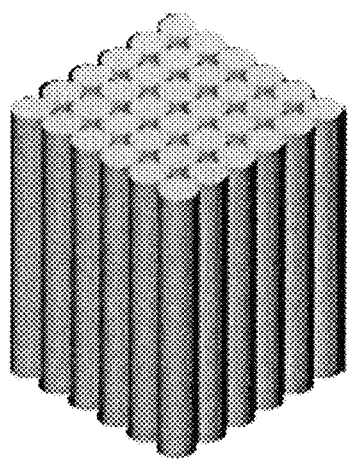
FIGS. 10A-10C show self-assembly of a 6H×6H×64B cuboid with 48 nucleotide boundary strand and without boundary strand.
Figure 10B:
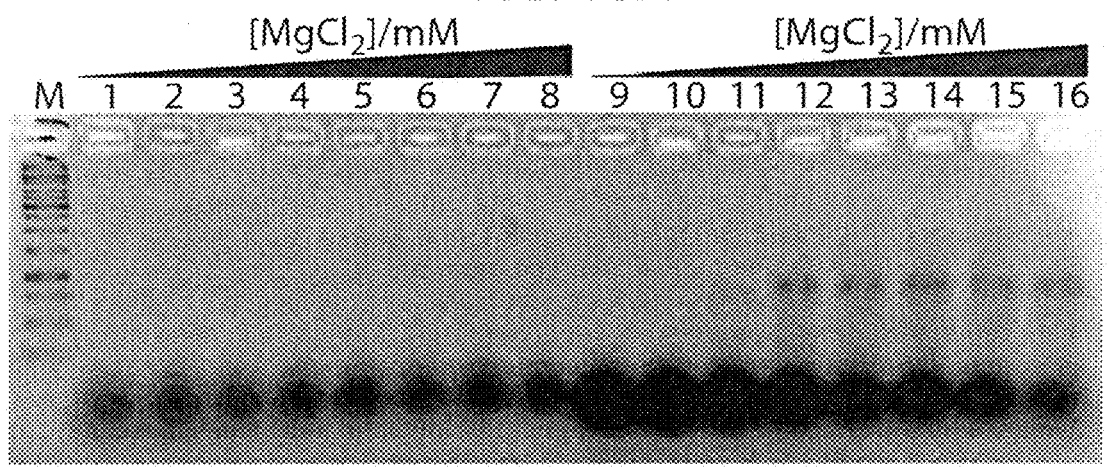
Figure 10C:
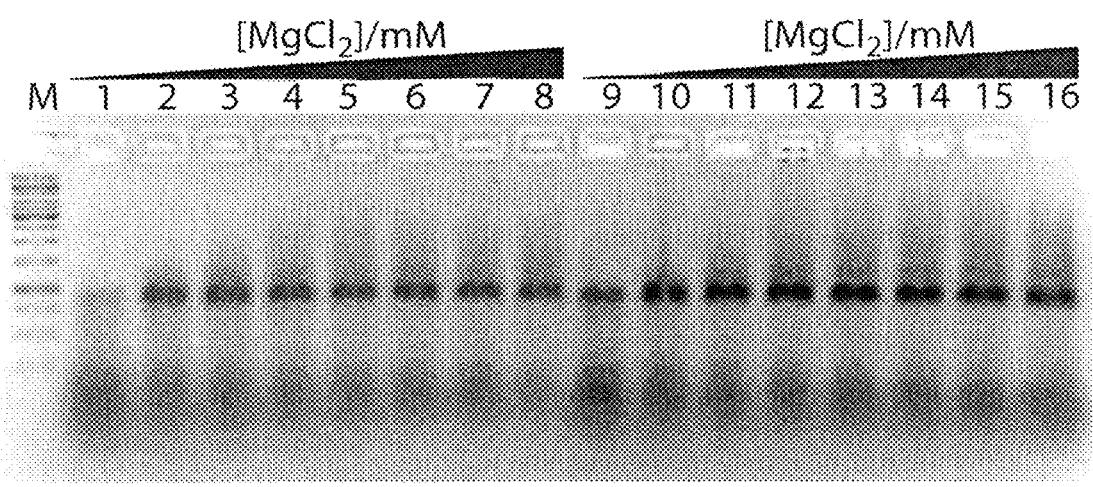

16 nt half-brick can be merged with a 32 nt full-brick that precedes along the direction of its helix, forming a 48 nt long boundary strand (FIGS. 9 and 10). We observed significant improvement of self-assembly for a 6H×6H×64B when the long boundary design was implemented, perhaps due to accelerated nucleation of target nanostructure formation. Hence, this merge strategy was applied to all 3D nanostructures.

Characterization of 6H×10H×128B.

Figure 11:
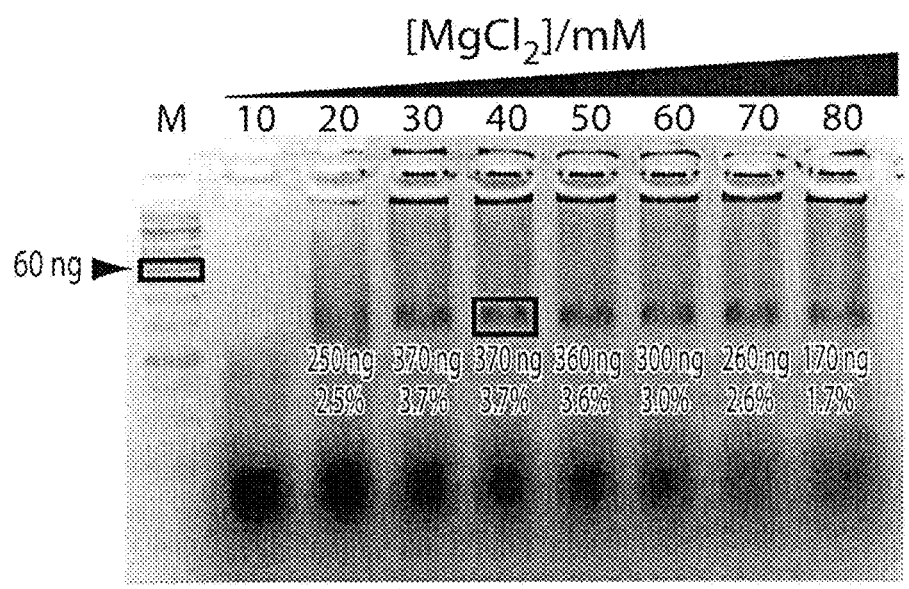
FIG. 11 shows yield analysis of a 6H×10H×128B structure based on agarose gel electrophoresis. 200 nM of each strand was self-assembled with a 72-hour annealing protocol and in 0.5×Tris buffer with 10, 20, 30, 40, 50, 60, 70, 80 mM MgCl$_2$, using a 72-hour annealing ramp. A 10 μL sample was loaded into each lane. Lane M shows the 1 kb ladder. The band in the light gray box on the left indicates the 3000 bp ladder band corresponding to 60 ng DNA. This band was used as a standard to measure the yield of products. Product band formed at 40 mM MgCl$_2$ is marked within a box. Below each product band, both the absolute mass value and percentage yield of the product band are shown.

We first constructed a 6H×10H×128B cuboid that consists of 459 strands (7680 bp, similar in size to an M13-based DNA origami, see FIGS. S11, S12 for design details). Unpurified DNA strands were mixed together at nominally equal ratios without careful adjustment of stoichiometry. To determine optimal annealing conditions, we tested two annealing ramps (24-hour annealing and 72-hour annealing), two strand concentrations (100 nM and 200 nM per strand), and eight MgCl$_2$ concentrations (10, 20, 30, 40, 50, 60, 70, 80 mM) for 6H×10H×128B self-assembly. Equal amounts of each samples (2 pmol per strand) were then subjected to ethidium bromide (EtBr)-stained 2% agarose gel electrophoresis (FIGS. 2B, 2C). The yields of 3D nanostructures were estimated using agarose gel electrophoresis. FIG. 11 demonstrates one example of such assays. Annealed samples were subjected to agarose gel electrophoresis to separate the product from free strands and unwanted aggregates. The yield of a product was estimated by comparing the fluorescence intensity of product band (marked in a black box) to the fluorescence intensity of the 3 k bp ladder band (marked in a gray box). Both fluorescence intensities were first subtracted by background noise, and then used for calculation. The intensities were measured using ImageJ software:

$$\text{Product mass} = \frac{\text{Fluorescence intensity of product band}}{\text{Fluorescence intensity of 3 kb ladder}} \times 60 \text{ ng}$$

Percentage yield is then calculated as:

$$\text{Percentage yield} = \frac{\text{Mass of product}}{\text{Mass of all strands}}$$

The efficiency of the EtBr staining may vary between the double-stranded 3 kbp ladder and our 3D structures. Therefore the absolute numbers of yield might vary. Nonetheless, this assay is especially useful for comparing self-assembly results between nanostructures and for screening optimal annealing conditions of 3D structures. Maximum yield (370 ng, or about 4%) was achieved at the following conditions: 200 nM per strand, 72-hour annealing, 40 mM MgCl$_2$. This yield is comparable to the previously reported 4% to 14% yield of 3D DNA origami of similar size and aspect ratio (a 10H×6H, an 8H×8H, a 6H×10H, and a 4H×16H) (S. Douglas, et al., Nucleic Acids Research 37, 5001 (2009)). It is worth noticing that the origami The origami yield is estimated as $$\text{Yield} = \frac{\text{Scaffold strands incorporated into product}}{\text{Total scaffold strands}}.$$

The loss of excessive staple strands (normally 5 to 10 fold more than the scaffold strand) is not taken into account. The optimal 40 mM MgCl$_2$ used herein is higher than the optimal 30 mM (or below) MgCl$_2$ concentration for 3D origami folding (S. M. Douglas, et al., Nature 459, 414 (2009)). Column-purified product (~50% recovery efficiency (FIG. 2D)) migrated as a single band by agarose gel electrophoresis and appeared under transmission electron microscopy (TEM) with expected morphology and measured dimensions of 0.34 nm (±0.01 nm SD) per base pair height and 2.5 nm (±0.2 nm SD) per helix width. After agarose gel purification of 6H×10H128B, yield was also calculated by counting the structures in the TEM images. This "TEM yield" is related to the stability of purified structures. The particles in TEM images were categorized as "good," "minor defect," or "major defect," depending upon the amount and degree of defects present. Final yields were determined by counting percentage of the good particle out of the total particles. Most minor defects occur at the locations close to the helix ends of structures, possibly indicating that strands are prone to dissociation at these locations. Additionally, these yields are generally indicative of the stability of the particles. It is worth noting that imaging bias the may affect accuracy of the measurements. An estimated 55% TEM yield was obtained by counting the percentage of intact particles in TEM images (FIG. 12). This TEM yield is comparable to the previously reported yields of 3D square-lattice DNA origami (27% yield for a 6H×12H×80B, 59% for an 8H×8H×96B) (Y. Ke, et al., *J. Am. Chem. Soc* 131, 15903 (2009)).

Figure 13A:
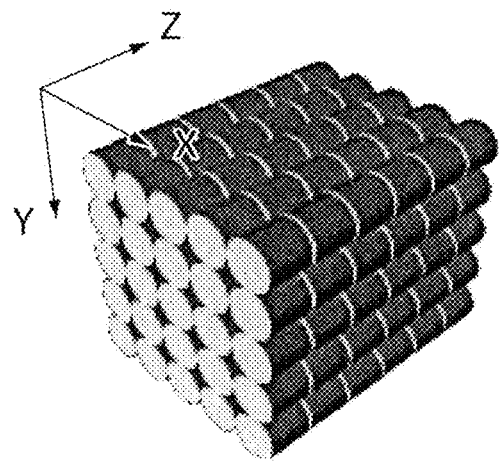
FIGS. 13A-13C show the design strategy for modified 3D structures.
Figure 13B:
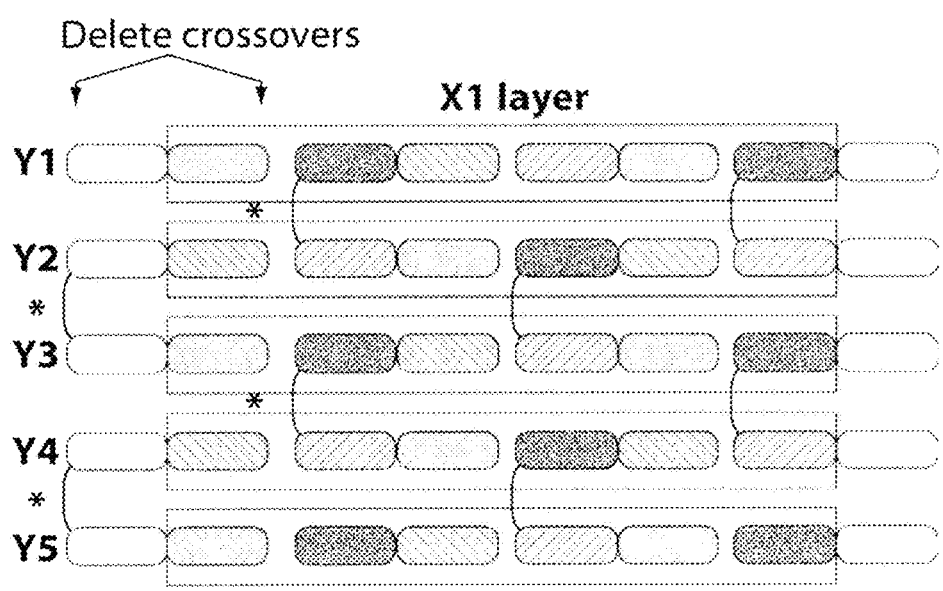
Figure 13C:
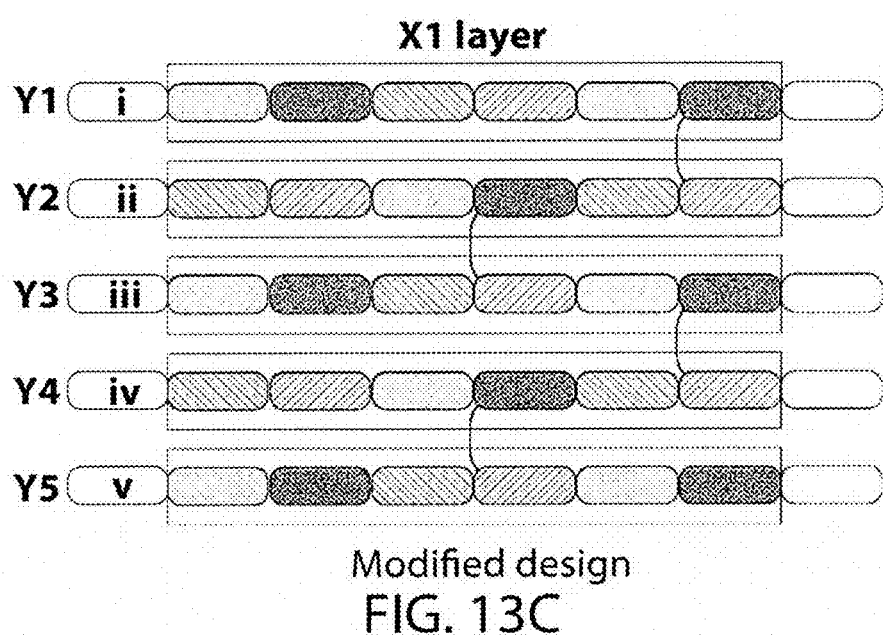
Figure 14A:
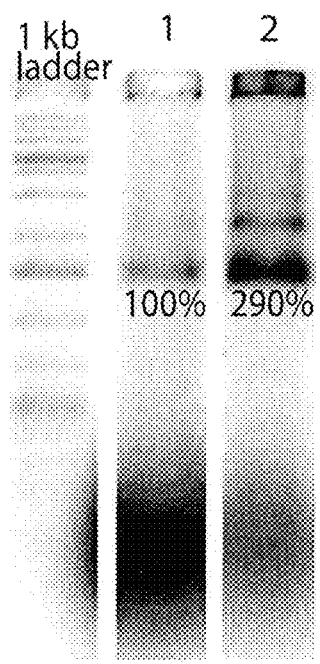
FIGS. 14A and 14B show agarose gel and TEM yields of 6H×10H×128B-M structures.
Figure 14B:
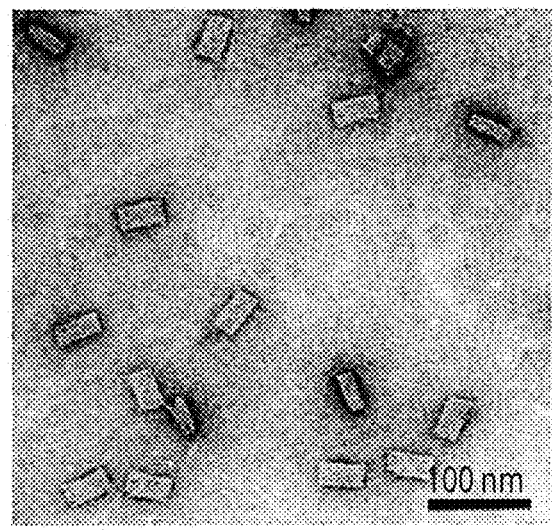

Strands that are located at the either ends of the DNA duplexes have only one or two 8 nt random-sequence segments, which are used to base-pair with other strands (FIG. 13B). Thus a reasonable assumption is that these "head" or "tail" strands are less likely to incorporate during the annealing and more prone to dissociation from an 3D structure after annealing, compared to strands that are located more deeply within a structure. It is conceivable that design strategies that increase the incorporation efficiency of these "head" or "tail" strands will favor the overall self-assembly quality of 3D structures. We tested this hypothesis with a modified design (FIG. 13C) to improve the incorporation efficiency of "head" strands. A similar modification can be applied to the "tail" strands as well. The design method includes two steps. (1) Deletion of crossovers: as indicated by the arrows (FIG. 13B), the first and second column of crossovers are removed. (2) Connection of strands: as shown in FIG. 13C, each pair of strands that are in the same duplex are merged together to form a longer single strand. These new strands are either 32 nt long with three random-sequence domains, or 48 nt long (boundary strand) with five random-sequence domains. By redesigning "head protectors" of 6H×10H×128B to merge them with their neighboring strands (FIG. 13), a modified version 6H×10H×128B-M showed 190% improvement of yield and 17% improvement of TEM yield, over the 6H×10H×128B (FIG. 14). Although the modification of "head" strands are expected to improve the self-assembly of SSD 3D structures, the deletion results in a lower crossover density that can create local deformation, especially for structures with shorter helices. Therefore, we only tried this modified version as a proof-of-concept that 3D structures can be stabilized by implementing special design rules. Other 3D structures used herein were designed using the original strategy. Other approaches, such as cross-linking (A. Rajendran, et al. *J. Am. Chem. Soc.* 133, 14488 (2011)), may prove to be more general methods for stabilizing 3D DNA nanostructures without sacrificing design flexibility.

Nanostructures of Different Sizes.

Figure 15A:
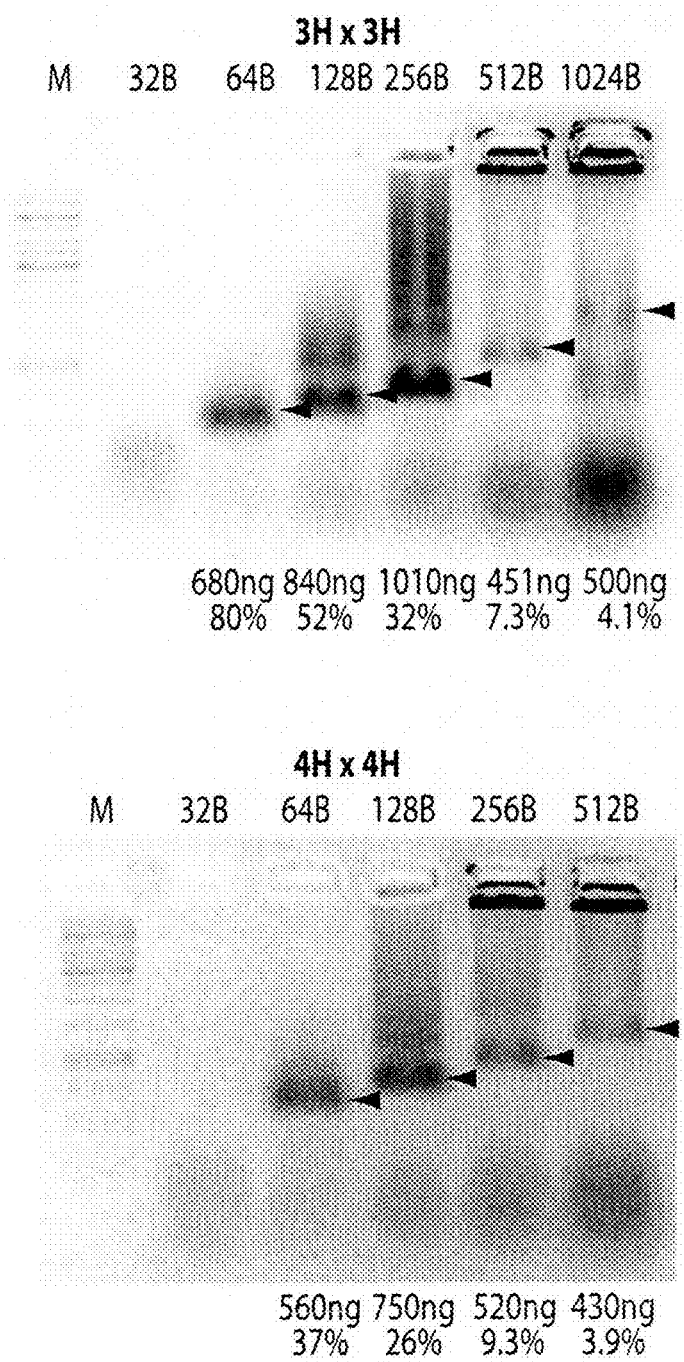
FIGS. 15A-15B show agarose gel yield analysis of 3H×3H, 4H×4H, 6H×6H, 6H×10H, and 8H×12H structures. The structures were self-assembled in 0.5×Tris buffer with 40 mM MgCl$_2$ using 72-hour annealing ramp. The concentration of each strand was 200 nM. A 10 μL sample was loaded into each lane. Lane M shows a 1 kb ladder. The 3000 base pair band corresponding to 60 ng of DNA was used as a standard to measure the yield of annealing products, which is indicated by the arrow. Below each product band, both the absolute mass value and percentage yield of the product band are shown.
Figure 15B:
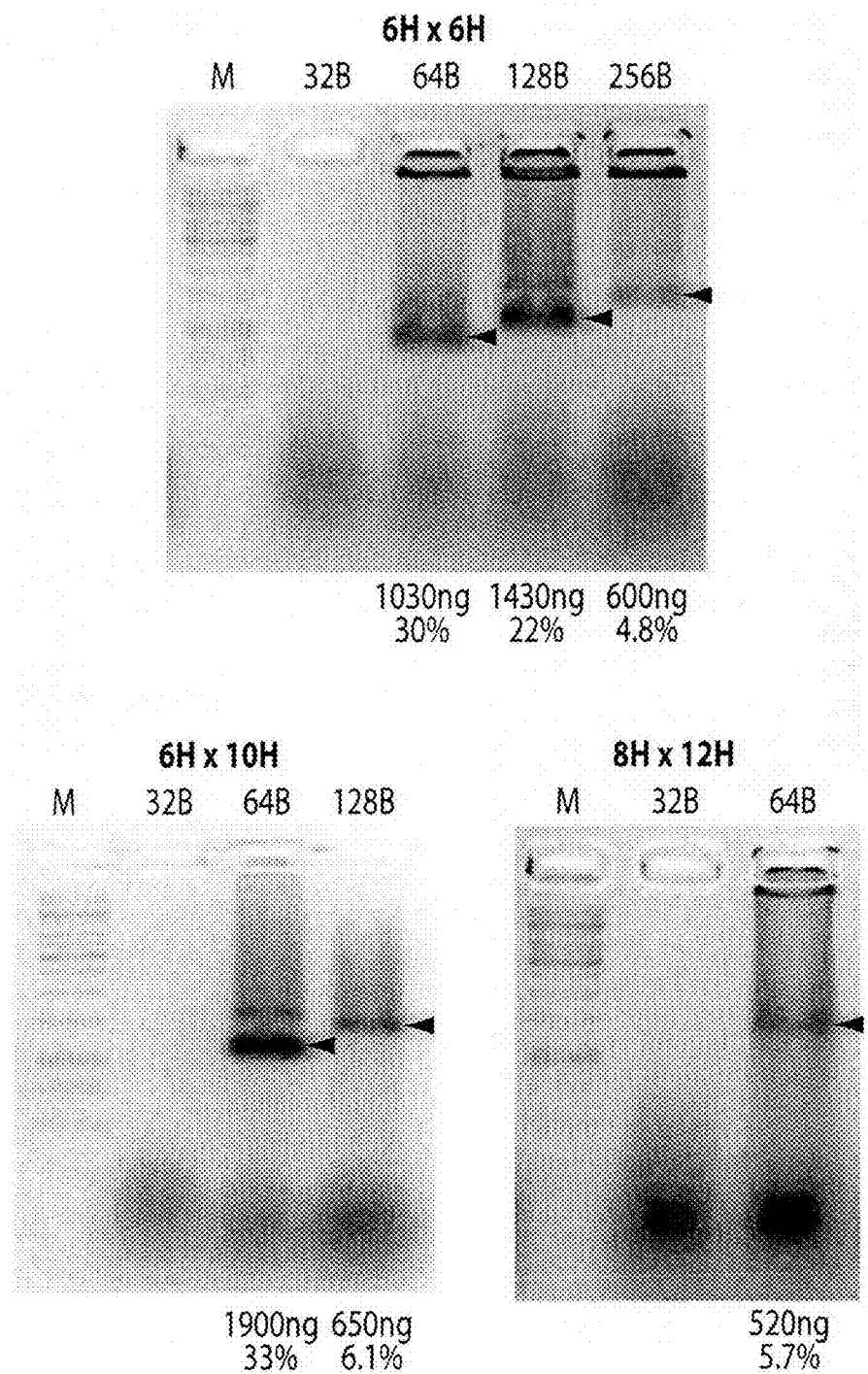

Six groups of nanostructures that contains 9 helices, 16 helices, 36 helices, 60 helices, 96 helices, and 144 helices were designed, then annealed using the optimal conditions previously identified for 6H×10H×128B self-assembly (data not shown). We observed correct product bands (FIGS. 2G and 15A-15B) for all designs except for those that are 32 bp in length (and that therefore contain one crossover between each pair of neighboring helices). Yields vary from lower than 1% to about 80% (FIGS. 15A-15B). Smaller designs exhibit higher percentage yields within each group, except for those that are 32 bp in length. The highest yield of all designs (80%) was observed for the smallest object 3H×3H×64B (1,296 nt or about 0.43 MDa). Lowest yields were observed for 8H×12H×120B, 4H×24H×120B, and 12H×12H×48B whose yields were too low (below 1%) to be measured accurately. Measured dimensions of intact particles for each nanostrutures are in agreement with our designs, suggesting 3D self-assembly of different sizes is successful (Table 1). The largest DNA structures assembled were 8H×12H×120B (formed by 728 strands) and 4H×24H×120B (formed by 710 strands), which were identical in molecular weight (24,576 nt, or about 8 MDa, 60% more massive than an M13-based DNA origami).

Example 2. Intricate Shapes Made from a 3D 10×10×10 Voxel Canvas

It is to be understood that based on the teachings provided herein, various canvases (and then structures) may be generated using the methods described herein. Accordingly this exemplification of one particular canvas is non-limiting.

The modularity of our approach is demonstrated via successful construction and characterization of 102 shapes made from a 10H×10H×80B cuboid (10×10×10 voxel) 3D canvas. (FIG. 3A and FIG. 16). Each voxel corresponds to an 8 bp (2.5 nm×2.5 nm×2.7 nm) formed by interaction of a pair of X and Y blocks.

TABLE 1

Statistics of 3H × 3H, 4H × 4H, 6H × 6H, 6H × 10H, 8H × 12H, 4H × 24H, 12H × 12H

| Nanostructure | 3H × 3H × 64B | 3H × 3H × 128B | 3H × 3H × 256B | 3H × 3H × 512B | 3H × 3H × 1024B |
|---|---|---|---|---|---|
| Number of strands | 33 | 57 | 105 | 201 | 393 |
| Number of nucleotides | 1296 | 2448 | 4752 | 9360 | 18576 |
| Measured X or Y dimension (nm) | 9 ± 0.3 | 9 ± 0.2 | 8 ± 0.2 | 8 ± 0.3 | 8 ± 0.4 |
| Measured Z dimension (nm) | 24 ± 0.4 | 45 ± 0.8 | 86 ± 1.2 | 170 ± 2 | 240 ± 10 |
| Agarose gel yield | 80% | 52% | 32% | 7.30% | 4.10% |

| Nanostructure | 4H × 4H × 64B | 4H × 4H × 128B | 4H × 4H × 256B | 4H × 4H × 512B |
|---|---|---|---|---|
| Number of strands | 62 | 110 | 206 | 398 |
| Number of nucleotides | 2304 | 4352 | 8448 | 16640 |
| Measured X or Y dimension (nm) | 11 ± 0.4 | 10 ± 0.4 | 11 ± 0.5 | 9 ± 0.3 |
| Measured Z dimension (nm) | 22 ± 0.3 | 46 ± 0.6 | 84 ± 1.1 | 170 ± 3 |
| Agarose gel yield | 37% | 26% | 9.30% | 3.90% |

TABLE 1-continued

Statistics of 3H × 3H, 4H × 4H, 6H × 6H, 6H × 10H, 8H × 12H, 4H × 24H, 12H × 12H

| Nanostructure | 6H × 6H × 64B | 6H × 6H × 128B | 6H × 6H × 256B | 12H × 12H × 48B |
|---|---|---|---|---|
| Number of strands | 147 | 267 | 507 | 486 |
| Number of nucleotides | 5,184 | 9,792 | 19,008 | 16128 |
| Measured X or Y dimension (nm) | 15 ± 0.7 | 16 ± 0.6 | 15 ± 0.6 | 31 ± 1.2 |
| Measured Z dimension (nm) | 22 ± 0.4 | 43 ± 0.8 | 86 ± 1.0 | 16 ± 0.2 |
| Agarose gel yield | 30% | 22% | 4.80% | N/A |

| Nanostructure | 6H × 10H × 64B | 6H × 10H × 128B | 8H × 12H × 64B | 8H × 12H × 120B | 4H × 24H × 120B |
|---|---|---|---|---|---|
| Number of strands | 251 | 459 | 408 | 728 | 710 |
| Number of nucleotides | 8640 | 16320 | 13824 | 24576 | 24576 |
| Measured X dimension (nm) | 16 ± 0.5 | 15 ± 0.6 | 22 ± 0.8 | 21 ± 0.7 | 11 ± 0.3 |
| Measured Y dimension (nm) | 24 ± 1.2 | 26 ± 1.0 | 29 ± 1.3 | 30 ± 1.4 | 57 ± 2.6 |
| Measured Z dimension (nm) | 22 ± 0.3 | 44 ± 0.7 | 22 ± 0.3 | 41 ± 0.6 | 41 ± 0.6 |
| Agarose gel yield | 33% | 6.1 | 5.7 | N/A | N/A |

DNA Bricks and Derivatives.

Any DNA brick in the 3D canvas can become either a boundary brick (i.e. exposed at the edges of a layer) or a protector brick (i.e. in the first or last layer), even both at same time, in an custom shape design. Thus, modified versions of each brick were generated with all combinations of domain-deletion (e.g., bisect to a half-brick), polythymidine-sequence-substitution (e.g., change to protector bricks), and boundary-brick-merger (e.g., change to 48 nt boundary bricks) to accommodate all possibilities (FIG. 16). Overall, 4455 strands (total 138,240 nt) were generated by a computer program, to guarantee that any shape can be assembled with head/tail protector and bricks long boundary bricks. Exemplary sequences are provided in the attached appendix submitted herewith and to be considered part of this disclosure.

Design Process.

Figure 17:
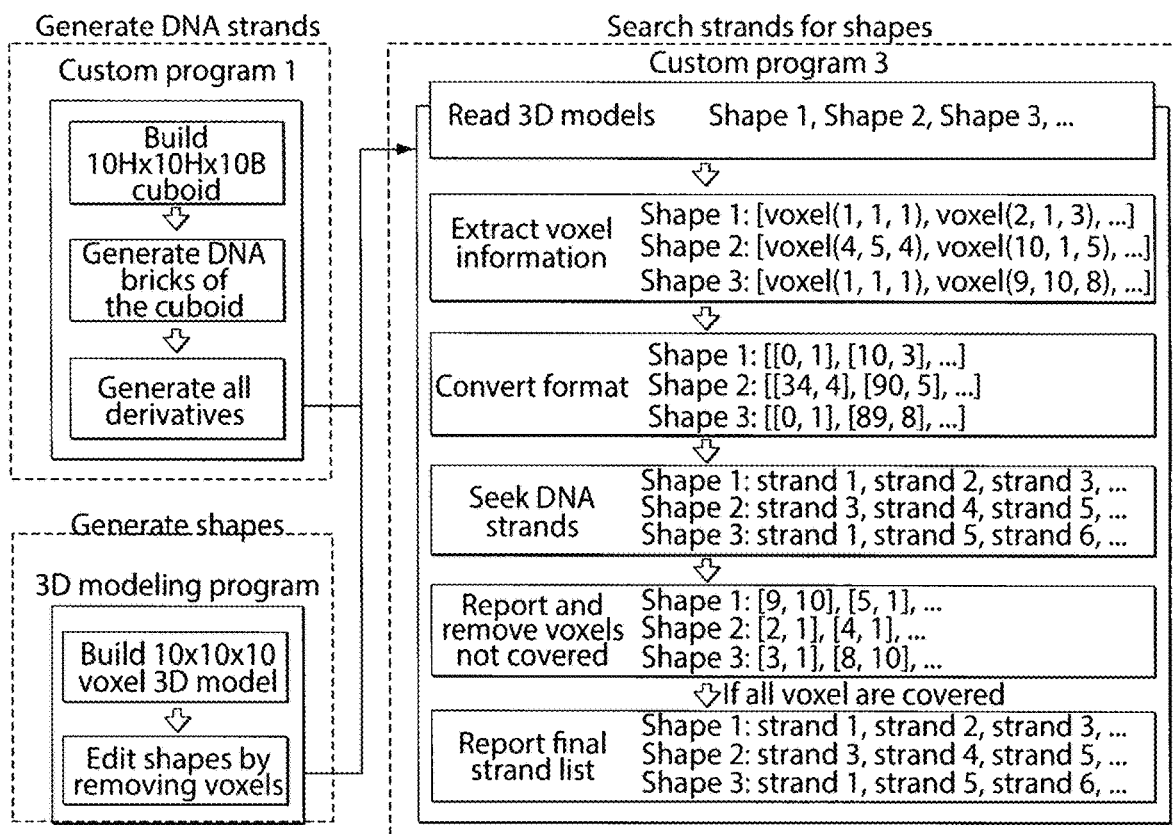
FIG. 17 shows a workflow diagram for designing 3D shapes.
Figure 18A:
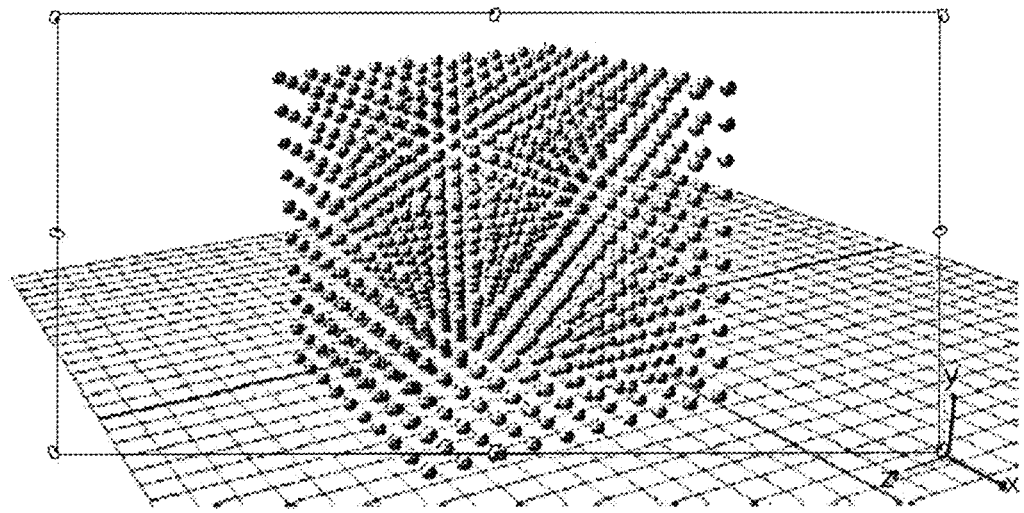
FIGS. 18A-18C show an illustration of 3D-shape-editing interface.
Figure 18B:
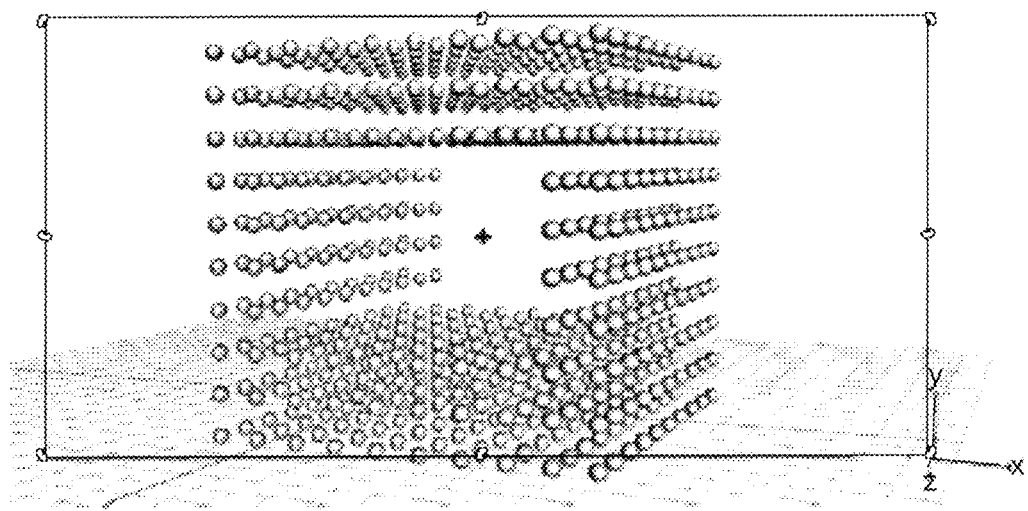
Figure 18C:
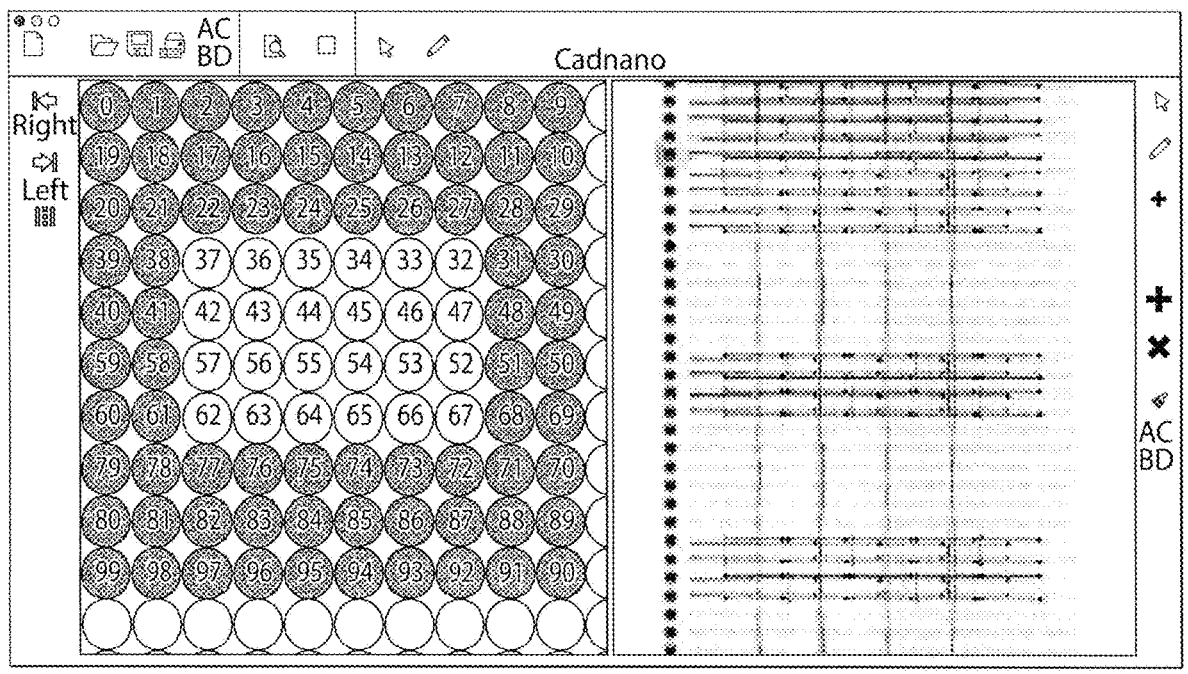

We first constructed the 10×10×10 voxel 3D canvas, where each XYZ voxel (where Z is in the helix direction) corresponds to an 8 bp duplex (2.5 nm×2.5 nm×2.7 nm). Shape design was mediated by selecting and removing particular sets of voxels. By rendering the 3D canvas using a 3D visualization software, it was possible to edit voxels on a graphical interface to design and visualize a shape (FIG. 3B and FIG. 17) with single voxel resolution. Then the voxel information of multiple shapes were interpreted by a custom program to generate a list of strands involved in the formation of each shape. This list was subsequently processed to direct a automated liquid handling robot to select DNA strands from source plates and pipette them to the wells of a product plate, mixing strands for many shapes in a high throughput manner. The complete design workflow is shown in FIGS. 17 and 18.

Design of 3D Shapes.

FIG. 16 demonstrates the 4-domain strands and their derivatives used for making arbitrary 3D shapes. Self-assembly of discrete DNA structures is often compromised by unwanted aggregation that occurs when a structure contains (1) unpaired single stranded domains, or (2) unprotected blunt ends of DNA duplexes. Different types of strands shown in C to E are designed to avoid these two situations by changing the DNA sequence of any unpaired single-stranded domain to eight consecutive Ts. This strategy leads to the presence of fourteen total types of derivatives of strands, to cover all possibilities when one, two, or three voxels is/are nonexistent for a arbitrary shape design.

If all fifteen types of strands (A to E) are included, any arbitrary shape can be designed with 8 bp (1 voxel) resolution.

Figure 16A:
FIGS. 16A-16G show designs of strands for making complex shapes from 3D canvas.
Figure 16A:
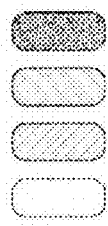
Figure 16A:
Figure 16B:
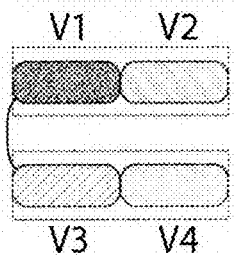
Figure 16C:
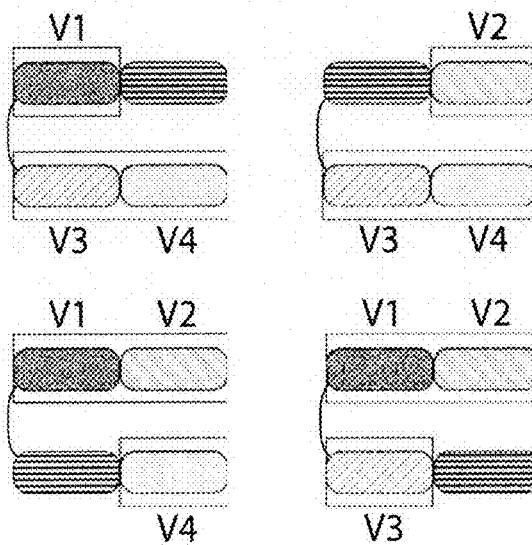
Figure 16D:
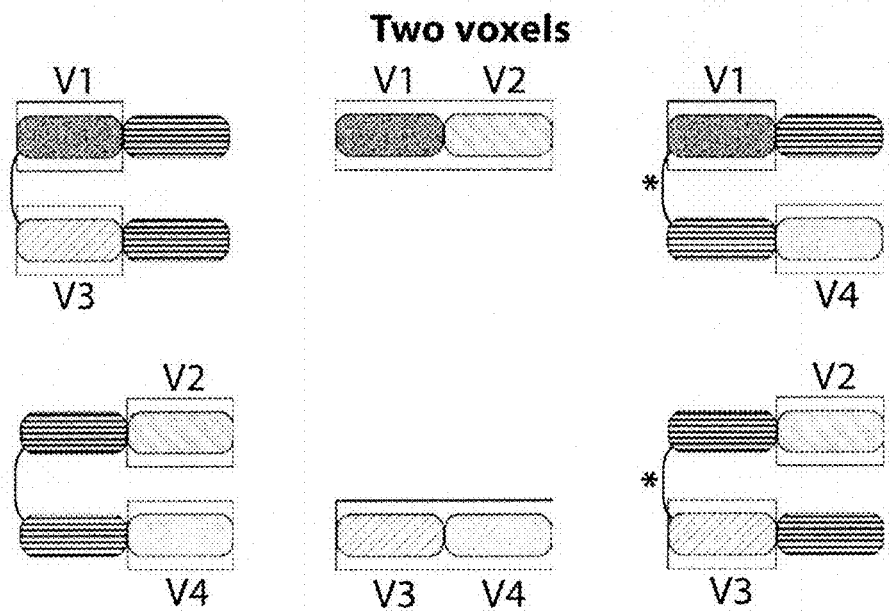
Figure 16E:
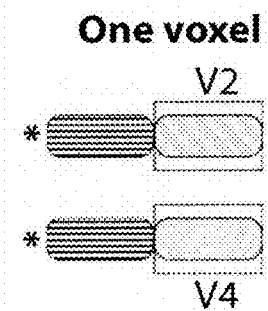
Figure 16E:
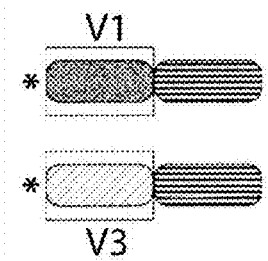

Of the fourteen derivatives of strands, only eight of them were actually implemented in the our designs and experiments. The other six derivatives (labeled with * in FIGS. 16D and 16E) types of strand are excluded. The two removed derivatives in FIG. 16D are considered to occur at low frequency for our designs of arbitrary shapes. The four removed derivatives in FIG. 16E consists of only one 8 nt random-sequence domain, so their incorporation to the DNA structures are considered less stable. We have redesigned two shapes (shape 45 and shape 55, see FIG. 3E for original shape) by incorporating more than one hundred "one voxel" derivatives for each shape. Both modified shapes failed to produce any target structures, as proven by the lack of product bands on agarose gels (data not shown). However, this simple experiment does not provide any clear indication about the incorporation efficiencies of individual "one voxel" derivatives. It is worth noting that these derivatives of strands only exist at the boundary of a shape. Exclusion of the six types of derivatives mentioned above actually appears to have little effect on the overall appearance of a shape.

We also included two types of 48 nt "boundary strands" (FIG. 10) to improve the self-assembly of the shapes. As described in the last section, each 48 nt "boundary" strand is used to substitute a 32 nt strand and a 16 nt strand. All together, for each strand, a total of (9+2)=11 original and derivatives were created for our design. Notice that strands located at the surface of a 3D canvas have fewer derivatives.

Figure 16F:
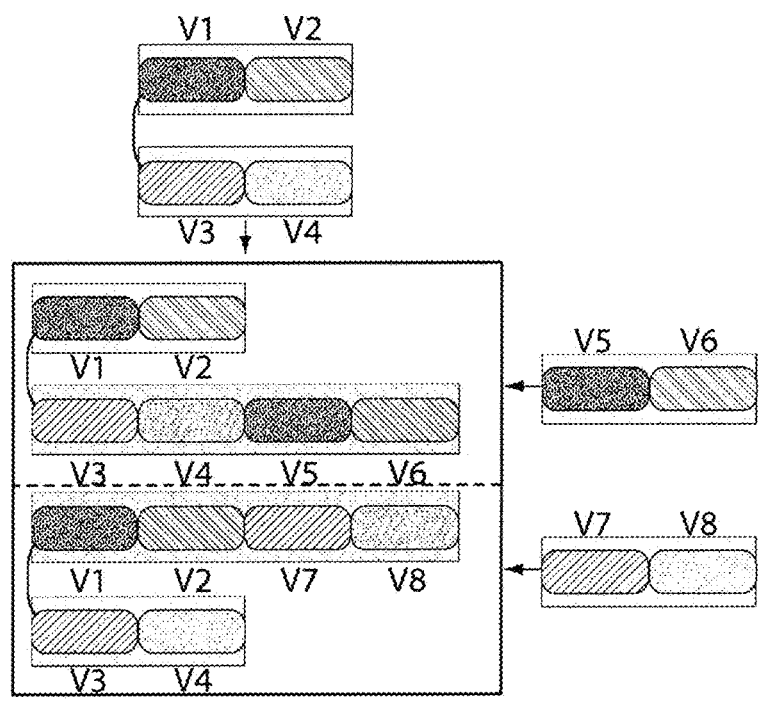
Figure 16G:
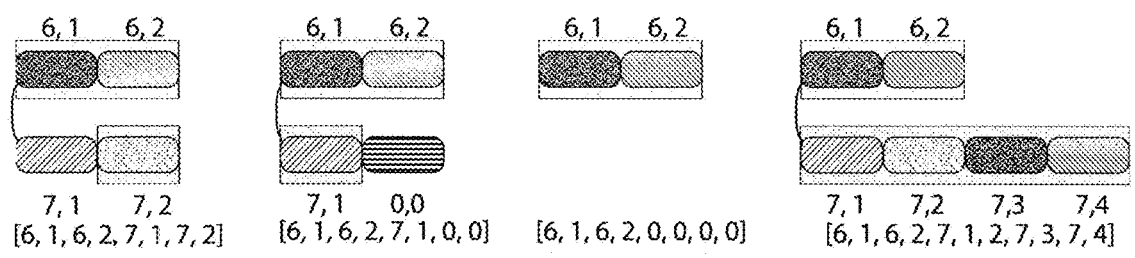

Each strand is named by the positions of the voxels it covers (FIG. 16G). Each pair of numbers represent one voxel. The first number indicates the helix and the second number indicate the voxel position on the helix. Numbers (0, 0) means a domain with eight consecutive Ts or a empty domain. The voxel information of strands is used to identify strands that can forma shape (FIG. 17).

An example of a method for designing 3D shapes is below.

Generate all DNA Strands:

(1) Build 3D canvas using a custom program (FIG. 6). We used a 10×10×10 voxel canvas herein, as an example. (2) A custom program generates strands and their derivatives (Section. S6.1.1) for self-assembly of arbitrary shapes that can be made from 10×10×10 voxel 3D canvas. All sequences and their corresponding voxel information are then stored in a single text file ALL-strand.txt. Total 4455 strands (138,240 nt) were generated for making arbitrary shapes.

Build 3D Model and Edit Shapes:

(3) Build a 3D model containing all 10×10×10 voxel using a commercial 3D modeling software (we used Strata™ 3D—at the Strata website). Each voxel is represented by a small sphere (FIG. 18A). Commercial modeling softwares provide convenient tools to remove/add voxels and visualize the shapes from different angles. (4) Design shapes by removing voxels from a 10×10×10 voxel 3D canvas, as shown in FIG. 18B. At this step, the shapes are designed with single voxel (8 bp) resolution. Each shape is stored in a single file with its voxel information.

Identify Strands for Each Shape Based on its Voxel Information:

(5) Our custom program reads out the voxel file. Based on the voxel information of the shape, the program searches the sequence file ALL-strand.txt and generates a list of strands for self-assembly of the designed shape. The program first searches for only the 32 nt and 16 nt strands to generate a shape. Then the program determines whether any pairs of 32 nt strands and 16 nt strands can be merged together to form a 48 nt "boundary" strand (FIG. 16F). If so, the program will substitute the 32 nt strand and 16 nt strand with a 48 nt "boundary" strand. (6) Because of our strand design described above, some voxel may not be covered by our strands in ALL-strand.txt. During this searching process, the program will automatically remove the voxels that cannot be covered and rerun the seeking-strand process. Notice that only a small number of voxels (on the boundary of a shape) will be removed from a shape, thus the deletions won't change the overall appearance of the shape. Note: the computer program can handle multiple shapes. So users can design all shapes first and use the computer program to generate lists of strands for all shapes at same time. (7) The program finishes searching strands, generates strand list of all shapes. It also reports voxels deleted from each shape. Users can check if there are mistakes or if too many voxels are removed. For example, the following output shows the 21 voxels removed from shape 23 (see FIG. 3E, for shapes): [[0, 1], [0, 10], [1, 10], [2, 1], [3, 10], [4, 1], [5, 10], [6, 1], [7, 10], [8, 1], [9, 10], [18, 10], [22, 10], [36, 10], [44, 10], [54, 10], [66, 10], [72, 10], [88, 10], [90, 9], [90, 10]].

Implementing this procedure, 102 distinct 3D shapes were assembled successfully (FIG. 3E). Shapes were annealed at the same annealing conditions (72-hour annealing in 0.5× TE, 40 mM $MgCl_2$ buffer) and characterized by agarose gel electrophoresis and TEM imaging (on unpurified samples).

Shape 1 to Shape 17.

The basic design constraints were studied using a group of shapes that each contains two 4H×10H×80B blocks connected by a middle two-layer "connecting block" (shape 2-17). The connecting blocks are systematically designed to possess decreasing numbers of voxels along Y-axis (shape 2-9) or Z-axis (shape 10-17). Eliminating voxels along the X axis should have the same impact as eliminating voxels along the Y-axis because of the shape symmetry. Agarose gel electrophoresis results revealed that shapes become less stable as the connecting block gets smaller for both systems (data not shown), but reducing the number of Z-axis connection appeared to have bigger effect on stability than reducing the number of Y-axis connection. Shape 9, having only a 2-voxel connection along the Y-axis, resulted in fewer than 50% broken nanostructures. In contrast, the majority of shape 17 (2 voxel along Z-axis) particles are broken, though agarose gel and TEM results do show that a small fraction of good particles were formed. Overall, these observations suggest a safe design criteria of at least two continuous X-axis or Y-axis voxels (2 helices) and three continuous Z-axis voxels (24 bp) for more stable features. However, as demonstrated in following experiments, smaller features (e.g., two continuous Z-axis voxels, shape 33 to 37) can stably exist in certain shapes where these features are presumably reinforced by voxels in close proximity.).

Solid Shape 18 to 31.

A number of solid shapes were designed including Z-direction extrusions of simple geometric shapes and more intricate objects. Formation yields and images of these objects provide more knowledge about the structural integrity of our methodology. In particular, shape 26 and 27, which both contain 3 helix thick appendages anchored only on one edge, are occasionally found without these protrusions or with them containing defects. Thus, such thin features, in spite of falling within our design criteria are less stable than more supported or thicker features.

Closed-Cavity Shape 32-42.

Previously, a few examples of 3D DNA origami with closed cavities were demonstrated, including a box (E. S. Andersen (2009)), a tetrahedron (Y. Ke (2009)), and a sphere and a ellipsoid (D. Han (2011)). Here, a series of "Empty boxes" with different sizes of cuboid cavity (shape 32 to 37) were created. Results herein also demonstrate that more complex cavity designs (e.g., square ring, cross, and triangle) are achievable (shape 38 to 42).

Open-Cavity Shape 43 to 62.

Shapes with a single cavity of varying width, depth and geometry (shape 43 to 53) and multiple-parallel cavities (shape 54 to 56) were constructed. Shapes with non-crossing perpendicular tunnels (shape 57), turning tunnels (shape 58), and crossing tunnels (shape 59 to 60) were also constructed. Furthermore, results showed the outer surface of the cuboid can be modified to create varying external views from different angles, as demonstrated by shapes 60 to 62. These shapes showcase the complexity achievable by the modular self-assembly presented herein.

Features-On-Solid-Base Shape 63 to 100.

Fine features or discrete features of 4-voxel thickness on a solid base of 10×10×6 voxel were designed. These included a full set of numerals (shape 65 to 74) and the latin alphabet (shape 75 to 100). The concentric ring structures (shape 63 and 64) showed that features as small as one voxel can be made. Such observations further show that the design criteria of 2 helix bundles by 24 bp are loosely dependent upon the surrounding environment of the structure. Because of the small number of voxel differences between the 2D features and the thickness of the solid base, the TEM images show low contrast between the two surfaces. Nonetheless, this method highlights the potential of using these 3D features to create multi-part extruded features that would otherwise be unattainable by a 2D surface.

For most shapes described herein, yields were between a few percent and 30 percent (yields of five 3D DNA origami nanostructures were reported as 7% to 44% (15)). Only five shapes had yields higher than 30 percent, and three shapes had yields lower than 1 percent. In spite of the success of making a variety of complex shapes, some shapes exhibited undesired properties. For example, complex shapes such as shape 60 to 62 showed a low percentage of intact particles in TEM images (less than 1%). Some fine features of a shape (e.g. the two wings of shapes 27) can be damaged or even totally removed if the shape is extracted from an agarose gel band. Four failed designs did not produce clear product bands on agarose gels (Fig. S55). Two other designs that had fine features on a solid base showed strong bands on agarose gels. Yet the features were unverifiable in TEM images. It is possible that self-assembly is successful for the last two shapes but the features are too small to be imaged.

Example 3. Generality of 3D DNA Modular Self-Assembly

To further explore versatility of modular DNA self-assembly, the following experiments were conducted: (1) designing of shapes with different lattice geometry, which have been demonstrated by DNA origami (P. W. K. Rothemund (2006); S. M. Douglas (2009); Y. Ke, et al. *J. Am. Chem. Soc* (2012)), and (2) testing 3D self-assembly using other types of modular DNA motifs.

Single-Layer (2D) Nanostructures.

Figure 4A:
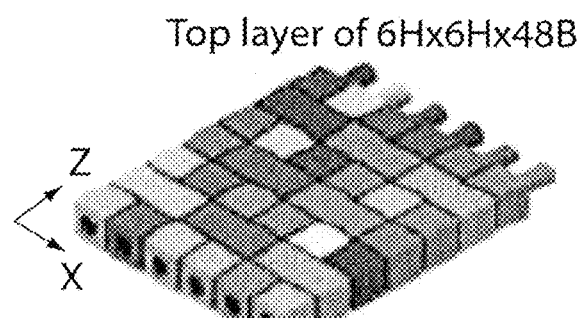
FIG. 4A is a schematic of DNA strands of the top of the 6H×6H×64B structure that is described in FIG. 1 with the crossovers to the layer below removed.
Figure 4B:
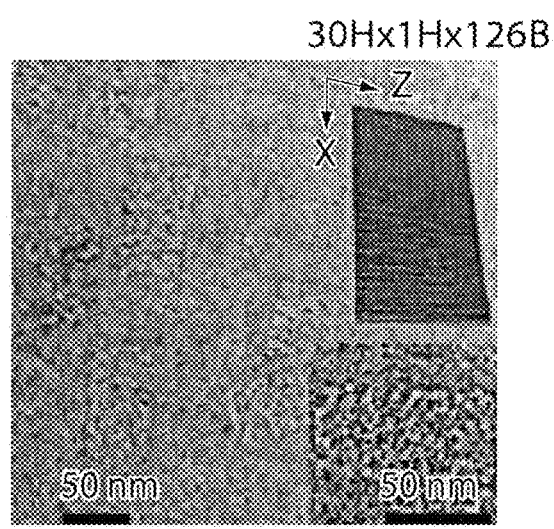
FIG. 4B shows a TEM image of a 30H×1H×126B structure. Top-right inset shows the model of the design. Bottom-right inset contains a higher magnification image of the nanostructure.
Figure 4C:
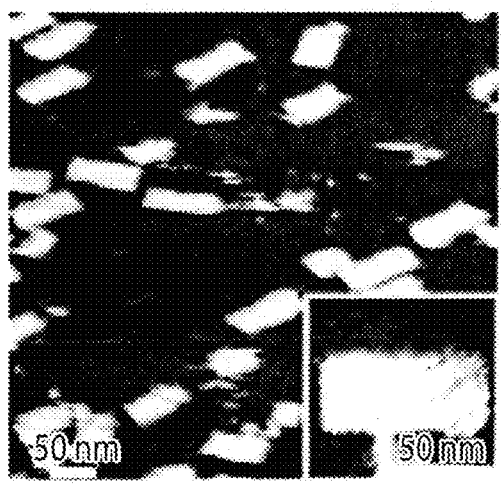
FIG. 4C shows atomic force microscopy (AFM) images of the 30H×1H×126B structure in FIG. 4B. Inset contains a higher magnification image of the structure.

Conceptually, a single layer (2D) DNA nanostructure can be constructed by "extraction" of a layer from a 3D DNA-block nanostructure (FIG. 4A). A 30H×1H×126B was tested (data not shown). It was intentionally modified to be 10.5 bp/turn instead of 10.67 bp/turn (for 3D design), in order to get a relatively flat nanostructure. Yield was estimated to be 18% based on result of agarose gel electrophoresis (data not shown). Dimensions of 30H×1H×126B were measured to be 0.31 nm (±0.01 nm SD) per bp, 2.6 nm (±0.3 nm SD) per helix, on basis of AFM images.

3D Honeycomb-Lattice Nanostructures.

Figure 4D:
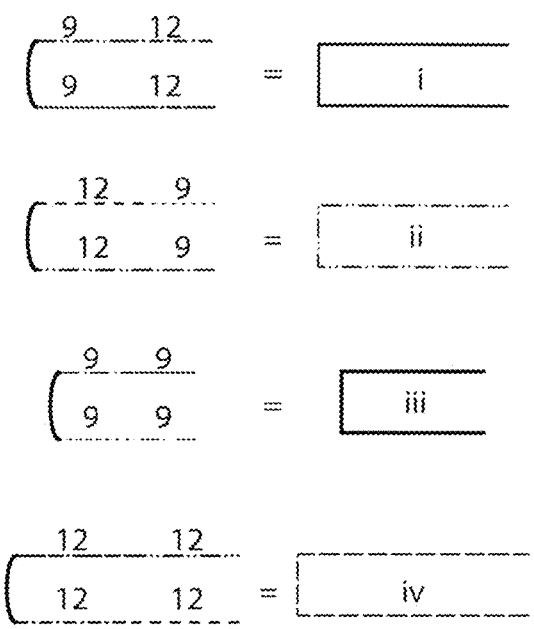
FIG. 4D is a schematic of the four types of strands designed for the formation of a honeycomb-lattice 3D DNA nanostructure.
Figure 4E:
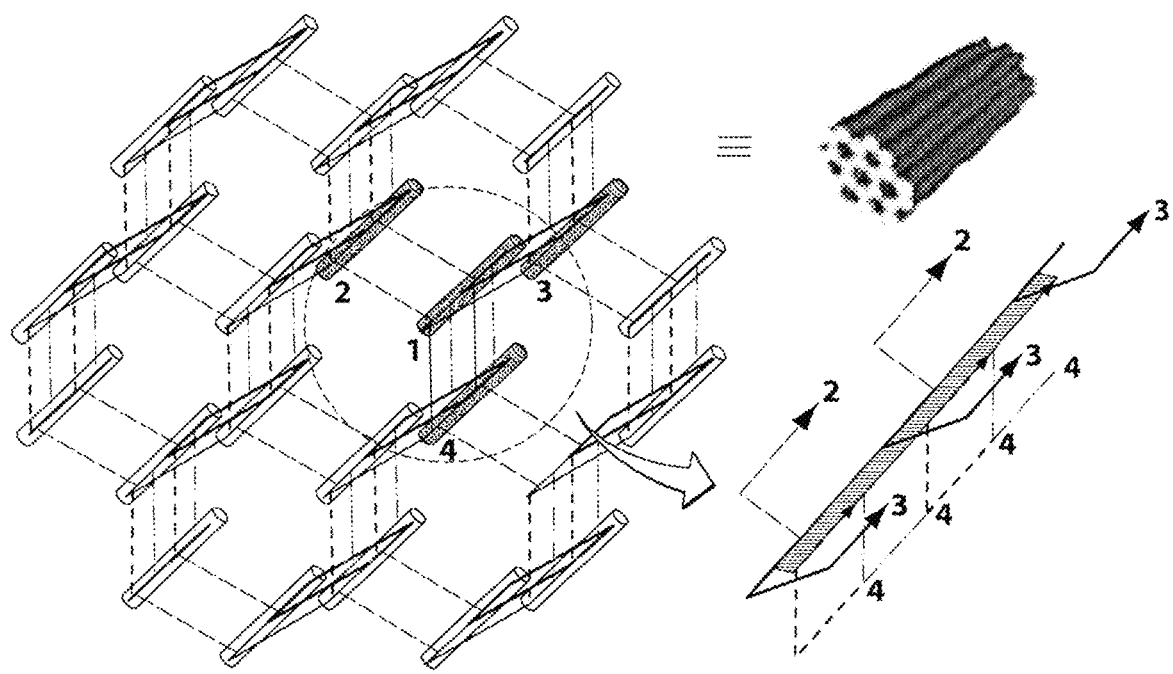
FIG. 4E is a schematic of a strand diagram of an 84 base pair 3D nanostructure. The right-bottom image depicts an enlarged image of the circled helix bundle.
Figure 4F:
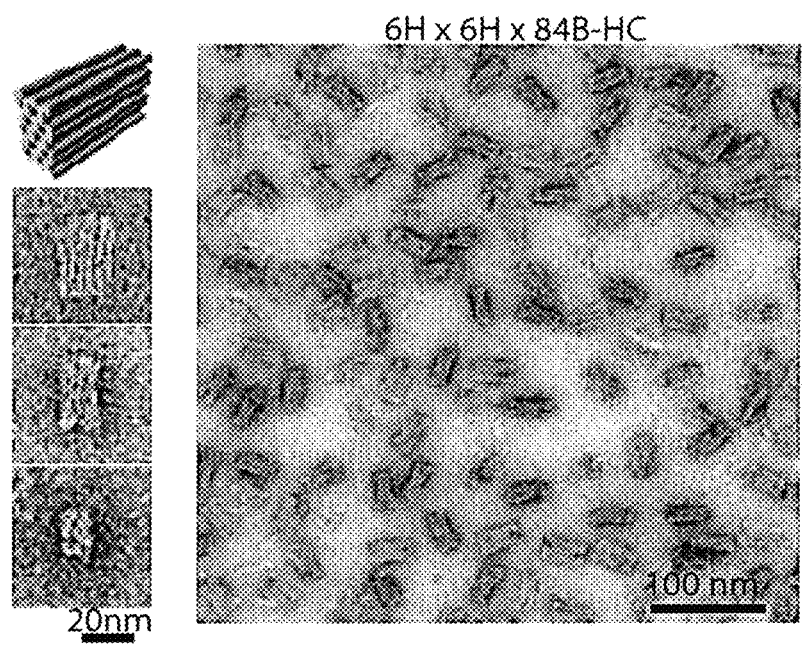
FIG. 4F shows TEM images of a 6H×6H×84B-HC (honeycomb lattice) 3D DNA nanostructure. Insets show enlarged images of different projections of the structures/particles.

We then created 10.8 bp/turn (33.3° twist per bp) 3D honeycomb-lattice and hexagonal-lattice DNA nanostructures. Four types of 4-domain DNA strands were designed for 3D honeycomb-lattice DNA nanostructures (FIGS. 4D, 4E). A 6H×6H×84B-HC nanostructure was successfully constructed and characterized (FIG. 4D, and data not shown). Particle in TEM images were measured to be 13 nm (±0.9 nm SD)×22 nm (±1.0 nm SD)×29 nm (±1.2 nm SD). Yield was estimated to be 30% (data not shown).

3D Hexagonal-Lattice DNA Nanostructures.

Figure 4G:
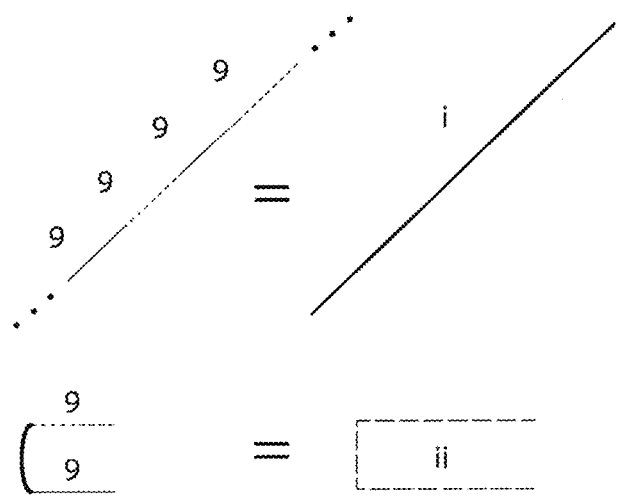
FIG. 4G is a schematic of two types of strands designed for formation of a hexagonal-lattice 3D DNA nanostructure.
Figure 4H:
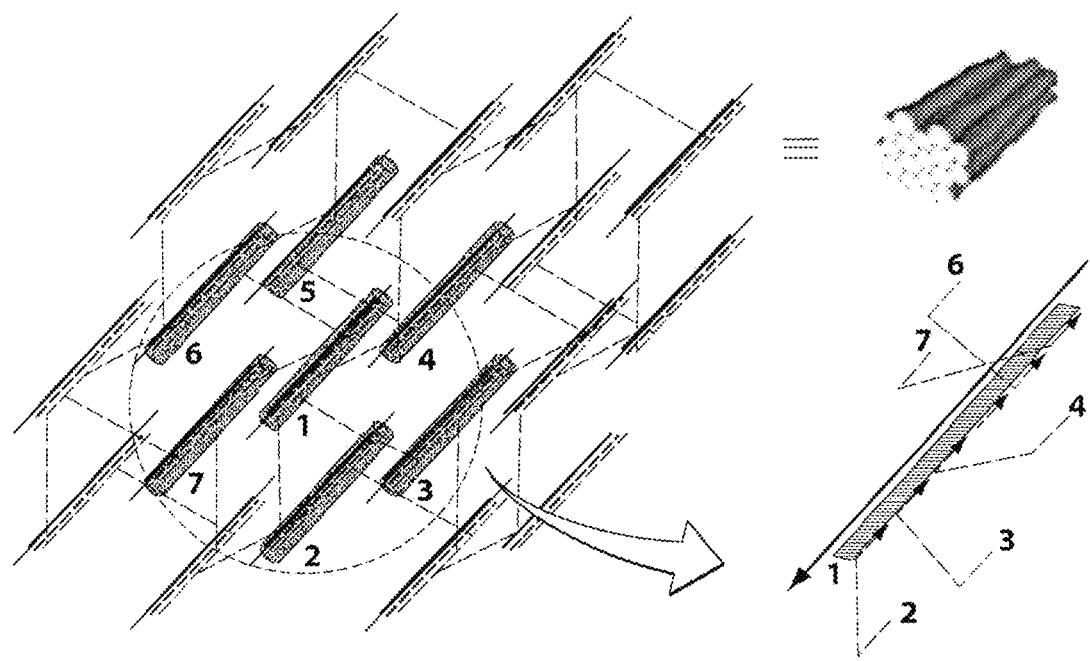
FIG. 4H is a schematic of a strand diagram of a 54 bp 3D nanostructure. The right-bottom image depicts an enlarged image of the circled helix bundle. Strand colors match those described in FIG. 4D.
Figure 4I:
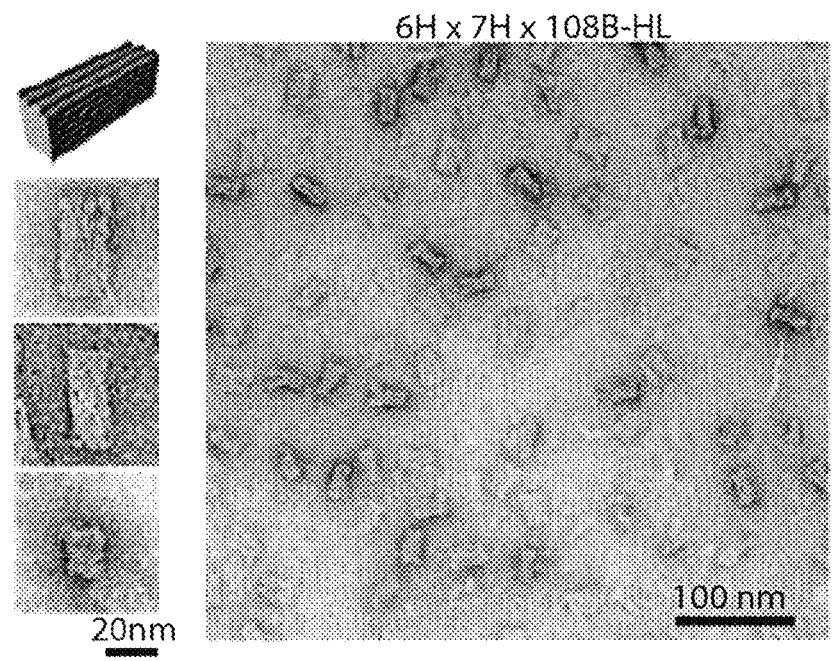
FIG. 4I shows TEM images of a 6H×7H×108B-HL (hexagonal lattice) 3D DNA nanostructure. Insets show enlarged images of the different projections of the structures/particles

Two types of strands are implemented to build a 3D hexagonal-lattice DNA nanostructure: a linear strand with multi 9 nt domains and an 18 nt strand with two 9 nt domains that are connected by a crossover (FIGS. 4G, 4H). A 6H×7H×108B-HL nanostructure was constructed and characterized (FIG. 4I, and data not shown). Particles in TEM images were measured to be 13 nm (±0.8 nm SD)×18 nm (±1.1 nm SD)×35 nm (±2.2 nm SD). Yield was estimated to be 26% (Fig. S64).

Other Motif Designs.

Figure 19A:
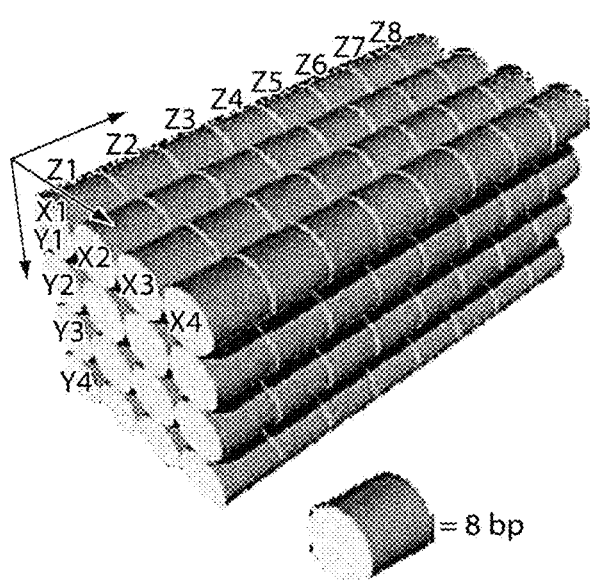
FIGS. 19A-19E show 3D structure design with alternating strands.
Figure 19B:
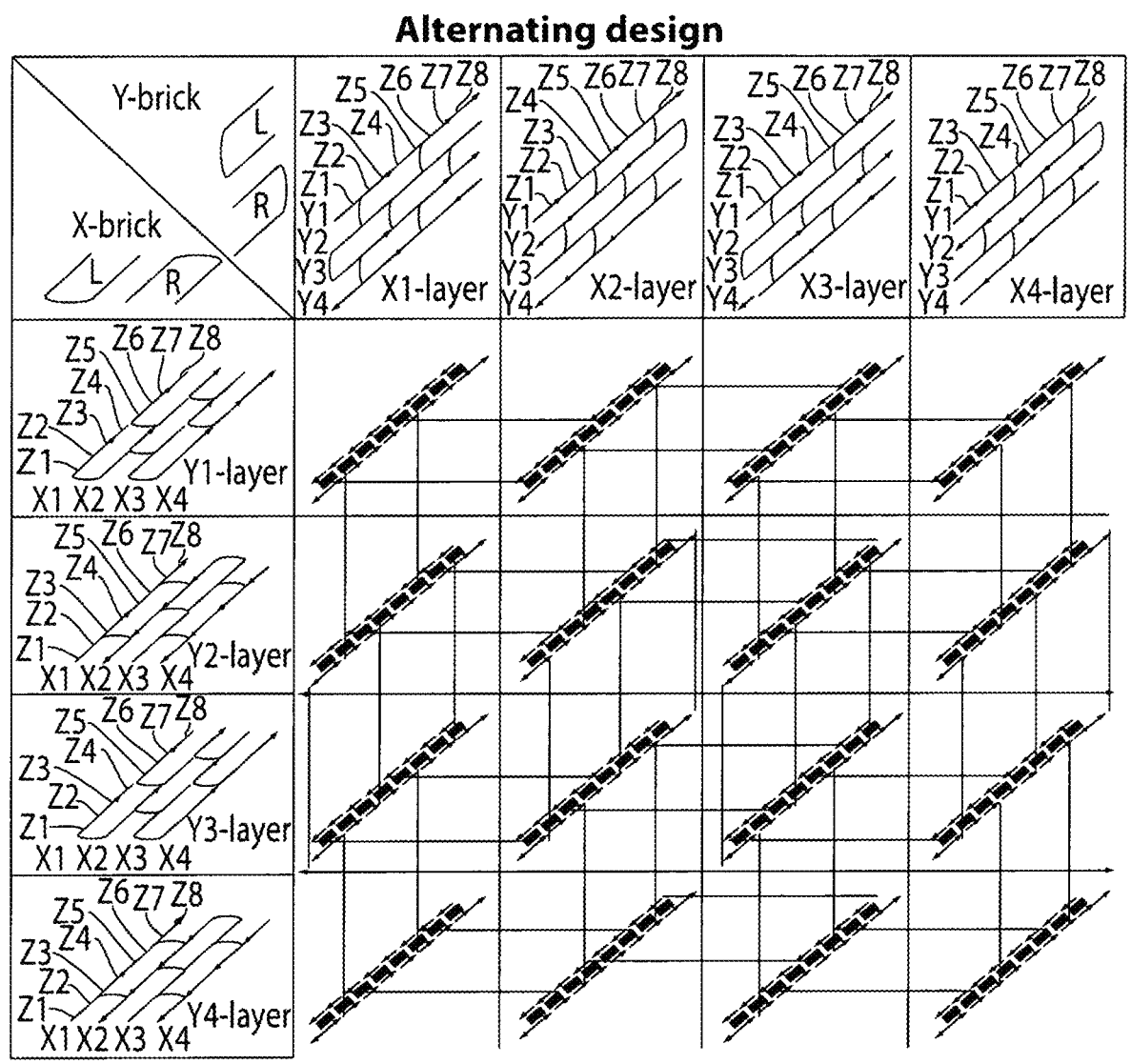
Figure 19C:
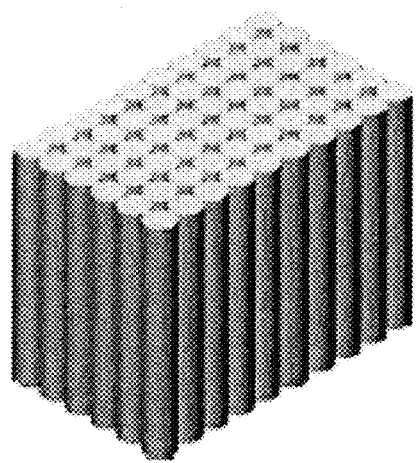
Figure 19D:
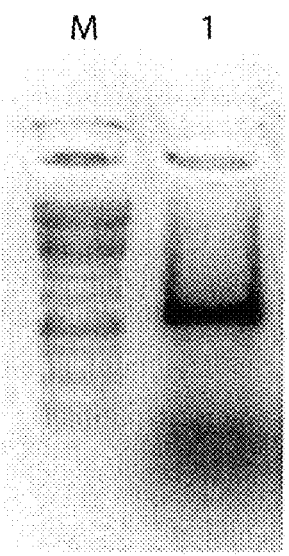
Figure 19E:
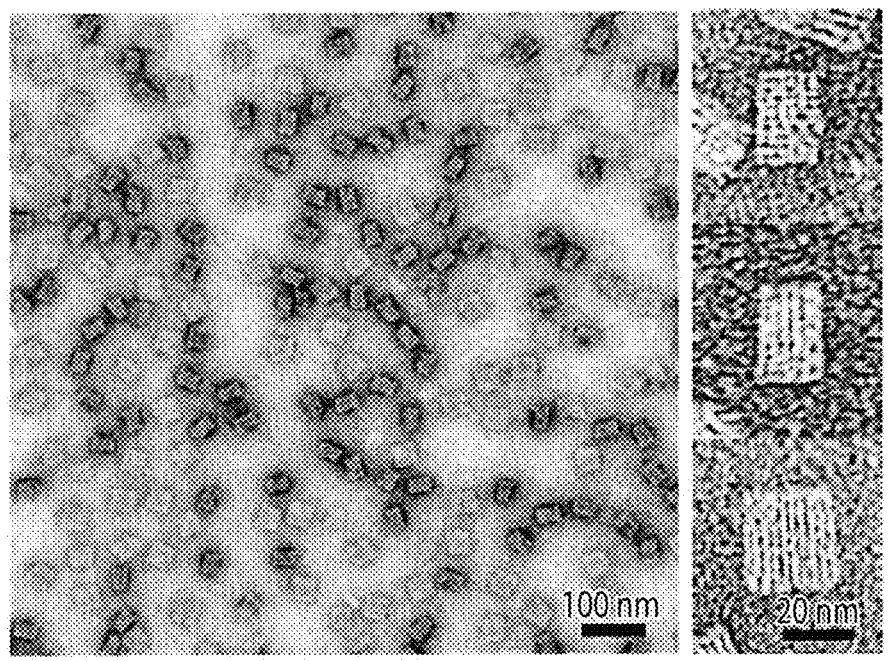

In contrast to the "unidirectional" design, strands can also be designed to point to opposite directions in a 3D nanostructure. Here we demonstrate a design strategy in which strands in odd number layers point in the Z− direction and strands in even number layers point in the Z+ direction (FIG. 19B). We designed and tested self-assembly of a 6H×6H×64B-A (alternating design), and two 6H×6H×64B nanostructures that implement two other DNA motif designs (data not shown). Successful self-assembly of 6H×6H×64B-A was confirmed by agarose gel electrophoresis and TEM imaging. Our results also demonstrated that strand design has much higher yield than the other two motif designs. Regardless of the sizes of nanostructures, crossovers are symmetrically arranged in such an alternating design. The success of these designs pictured a versatile methodology of modular DNA self assembly.

Example 4. DNA-Brick Crystals

Design of DNA brick crystals. All crystals were designed using 10.67 base-pair (bp)/turn twist density that is slightly departed from the 10.5 bp/turn twist density of natural B-form DNA. In an assembled structure, a DNA brick is a 32-nucleotide (nt) strand that can be depicted in a simple LEGO®-like brick model (FIG. 20A, top) containing four 8-nt binding domains. Many bricks—each with distinct sequences—assemble into a prescribed three-dimensional structure in a one-step annealing reaction (FIG. 20A, bottom).

Using "connecting" bricks between discrete three-dimensional DNA-brick structures yielded DNA-brick crystals. The design strategy was demonstrated on a small 6H (helix) by 6H (helix) by 24B (base pair) cuboid structure. The DNA bricks on the surfaces of a discrete DNA-brick design were modified to connect the individual structures and extend the growth of crystals along the X-axis, Y-axis and Z-axis individually to generate one-dimensional-growth crystals, or combinatorially to generate two-dimensional-growth crystals (FIG. 20D and FIGS. 24A-24C). In order to achieve multimerization along the Z-axis, the sequences of the first layer of domains were modified to be complementary to those in the last layer of domains. Multimerization along the X-axis or Y-axis was achieved by substituting the bricks on the boundary along X-axis or Y-axis with new 32-nt bricks. Each of these new 32-nt bricks contained two domains complementary to one side of the cuboid and another two domains complementary to the opposite side of the cuboid. Thus, these 32-nt bricks connect the cuboid monomers to achieve continuous growth.

Although the DNA-brick crystals were designed from repeating units, the connecting bricks were the same as the other bricks in size and function. Therefore, unlike the hierarchical growth of DNA-origami crystals, the growth of the DNA-brick crystals of the invention may be non-hierarchical (FIG. 20C, top). Bricks were incorporated individually into a crystal during its growth, without first forming the repeating fundamental unit. The informational hierarchy—sequence uniqueness of bricks in a repeating unit—was preserved in a final crystal structure. By contrast, DNA-origami crystallization is a hierarchical process in which origami structures have to form completely and then are incorporated into a crystal (FIG. 20C, bottom).

Using this design strategy, we constructed and tested three groups of crystals: (1) one-dimensional "DNA-bundle" crystals extending along the Z-axis (referred to as Z-crystals); (2) two-dimensional "DNA-multilayer" crystals extending along the Z-axis and the X-axis (referred to as ZX-crystals); and (3) two-dimensional "DNA-forest" crystals extending along the X-axis and Y-axis (referred to as XY-crystals) (FIGS. 20D and 20E). Using different designs of repeating units, DNA-brick crystals with prescribed dimension(s) and pattern(s) can be made (FIG. 20F). Accordingly, a crystal design is named as "[the growth direction(s)]-[the size of the repeating unit]-[basic feature of its shape]". Like the discrete DNA-brick structures, sequences of all DNA-brick crystals were randomly generated, as described herein.

A crystal was assembled by mixing all unpurified DNA bricks together at equimolar ratios (100 nM of each strand) in 1×TE/MgCl$_2$ (5 mM Tris, pH 7.9, 1 mM EDTA, 40 mM MgCl$_2$) buffer, without careful adjustment of stoichiometry. The mixture was then subjected to a single-step 72-hour or 168-hour thermal annealing, followed by TEM imaging without any purification. The effective diameter of each DNA helix was measured to be 2.5 nm in all 3D crystals.

One-Dimensional-Growth DNA-Bundle Crystals (Z Crystals).

Figure 21A:
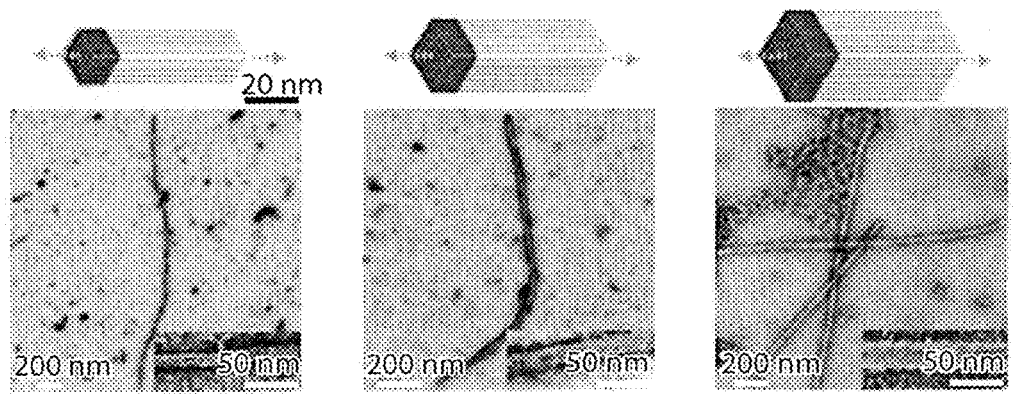
FIG. 21A shows models and TEM images of 6H×6H, an 8H×8H, and a 10H×10H DNA-bundle crystals, an 8H×8H DNA-bundle crystal with right-handed spiral channel, a 43H DNA-bundle crystal with triangle-shaped cross-section, and a 44H DNA-bundle crystal with hexagon-shaped cross-section.
Figure 21B:
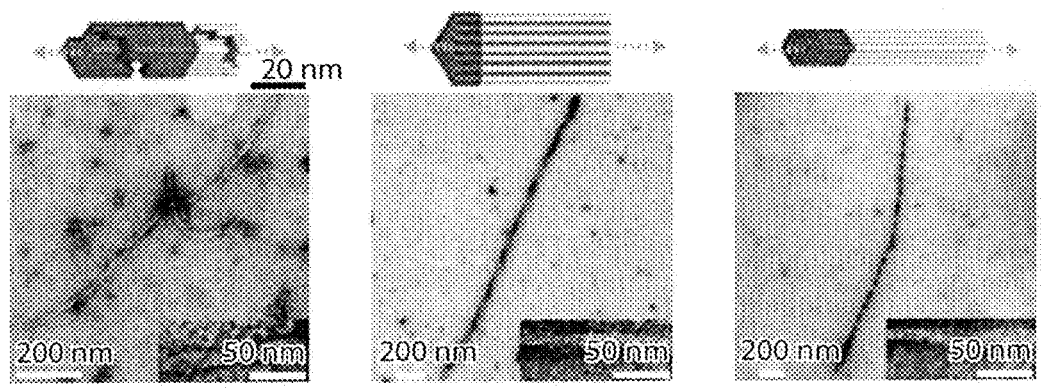
FIG. 21B shows models and TEM images of DNA-bundle crystals with tunnels: an 8H×8H DNA-bundle crystal with a 2H×4H tunnel, an 8H×8H DNA-bundle crystal with a 2H×2H tunnel and perpendicular 8H×2H×24B tunnels, a 12H×12H DNA-bundle crystal with a 6H×6H tunnel. The repeating units of each crystal are depicted as dark gray regions in the cylinder models.
Figure 21C:
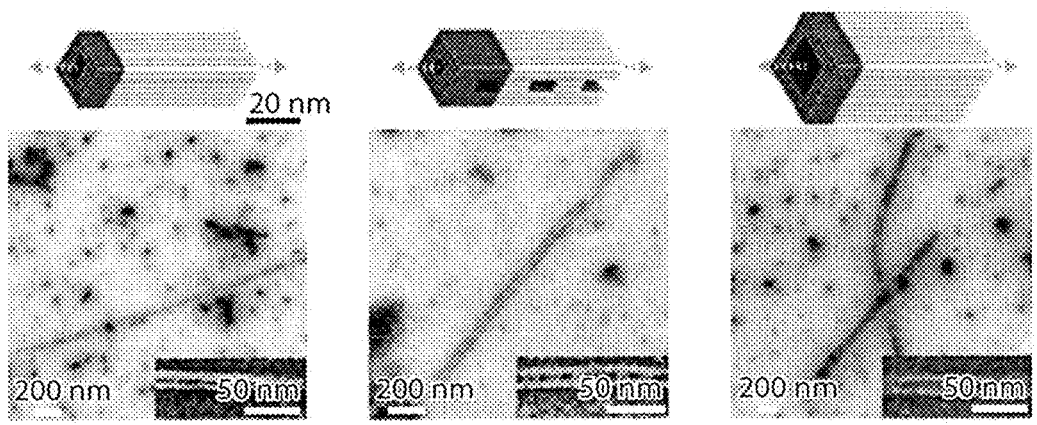
FIG. 21C shows additional models and TEM images of DNA-bundle crystals with tunnels.

We first made two groups of Z-crystals: (1) solid Z-crystals with different cross-sectional shapes, including a Z-6H×6H×32B, a Z-8H×8H×32B, and a Z-10H×10H×32B, a Z-8H×8H×128B-spiral, a Z-43H×32B-triangle, and a Z-44H×32B-hexagon (FIG. 21A); and (2) tube-shaped Z-crystals, a Z-56H×32B-tunnel, a Z-60H×64B-tunnel, and a Z-108H×32B-tunnel (FIG. 21B).

All Z-crystals exhibited global right handed twist in TEM images. The global twist is understood as a response to the stress generated by the 10.67 bp/turn underwinding design. The magnitude of twist was affected by the cross-sectional shapes of the Z-crystals. The Z-crystals formed easily. Most Z-crystals can grow to a few micrometers in length using a 24-hour annealing protocol. However, longer annealing protocols typically yield longer Z-crystals. Thus we used a 72-hour annealing protocol for all Z-crystals.

Three solid Z-crystals were designed using 32 bp repeating units. The square-shaped cross-sections of the Z-crystals contain a 6H×6H, 8H×8H, and 10H×10H cuboid, respectively. We then produced crystals with more complex cross-sectional shapes. A Z-8H×8H×128B-spiral crystal that displays a spiral channel along the Z-axis was successfully constructed. The channel is clearly visible in TEM images. We then constructed two simpler designs: a Z-43H×32B-triangle and a Z-44H×32B-hexagon. Both showed high assembly qualities comparable to the three square-shaped cross-section Z-crystals.

Three tube-shaped Z-crystals were then tested. The cross-section of the Z-56H×32B-tunnel is an 8H×8H square with a 2H×4H rectangle removed from the center. The cross-section of the Z-108H×32B-tunnel is a 12H×12H square with a 6H×6H square removed from the center. The Z-60H×64B-tunnel is the most complex design within this group. It contains a centered 2H×2H square tunnel along the Z-axis. In addition, 8H×2H×24B pores cross with the 2H×2H square tunnel in every 64 bp along the Z-axis. TEM images show many structures that appear to contain only half of the designed DNA helices. This may be due to the periodic 8H×2H×24B pores weakening the connections between the top half and the bottom half along the Y-axis.

Additional TEM images of the Z-crystals are shown in FIGS. 25A-25H.

Two-Dimensional-Growth DNA-Multilayer Crystals (ZX Crystals).

Figure 22A:
FIG. 22A shows cylinder models of a 4 layer, a 6 layer, a 10 layer and a 20 layer ZX-crystal.
Figure 22B:
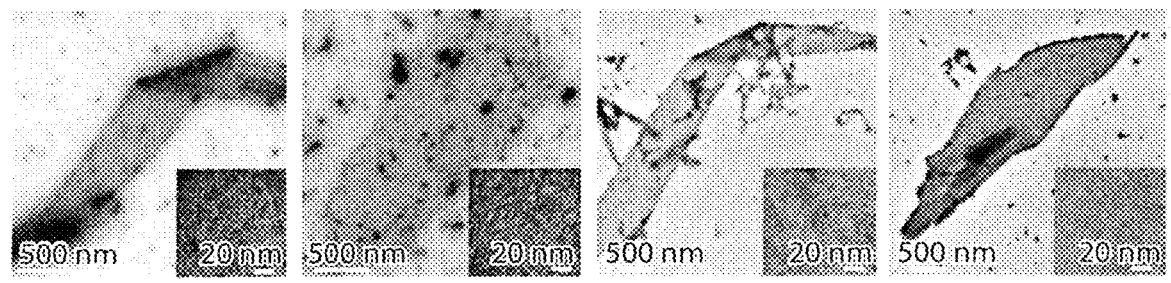
FIG. 22B shows TEM images of the ZX-crystals of FIG. 22A.
Figure 22C:
FIG. 22C shows TEM images of the folded crystals of FIGS. 21A and 21B. Arrows indicate the positions where the thicknesses of the crystals are measured.
Figure 22D:
FIG. 22D shows cylinder models of a 6 layer crystal with 2H×2H parallel channels: (left to right) a 6 layer crystal with two groups of crossing channels –2H×2H channels parallel to DNA helical axis and 2H×32B channels perpendicular to the DNA helical axis; a 6 layer crystal with 2H×6H×32B pores; a 10 layer crystal with two groups of no-contact tunnels –2H×2H tunnels parallel to DNA helical axis and 2H×24B tunnels perpendicular to the DNA helical axis. The two groups of tunnels are separated by two layers of DNA helices. The repeating units of each crystal are indicated as dark gray regions in the cylinder models.
Figure 22E:
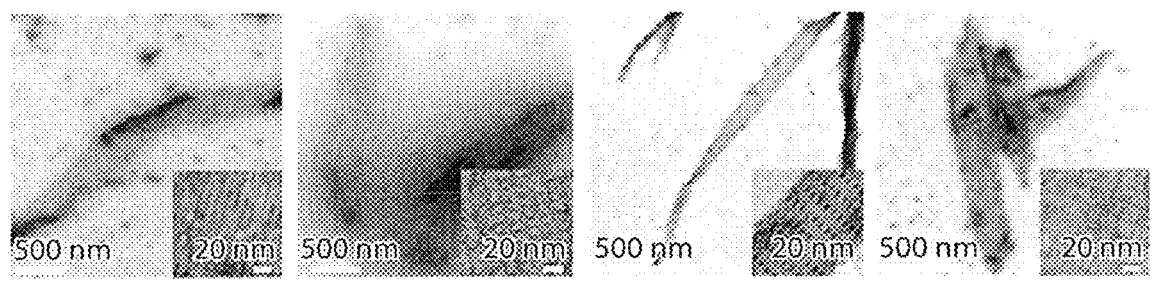
FIG. 22E shows TEM images of the crystals in FIG. 22D.

Two groups of ZX-crystals were then constructed: (1) solid ZX-crystals—ZX-4H×4H×32B-cuboid, a ZX-4H×6H×32B-cuboid, a ZX-4H×10H×32B-cuboid and a ZX-4H×20H×32B-cuboid that contains 4, 6, 10, and 20 layers of DNA helices, respectively (FIGS. 22A-22C); and (2) ZX-crystals with channels or pores—ZX-32H×64B-channels, ZX-32H×64B-cross-channels, ZX-6H×6H×64B-pores and ZX-96H×64B-cross-channels (FIGS. 22D and 22E).

We observed that all ZX-crystals grew faster along the Z-axis than the X-axis. In some cases (e.g., the X-6H×6H×64B-pore crystal), the growth along the Z-axis was much faster, resulting in the ribbon-like ZX-crystals that appear on the TEM images. This phenomenon suggests that crystal growth along the Z-axis (helical axis) is easier to realize than crystal growth along X-axis or Y-axis. This is possibly because of (1) Z-axis growth results in more pi-pi base stacking; and/or (2) X-axis or Y-axis growth needs to overcome the extra energy penalty for packing negative-charged DNA backbones close to each other. Most ZX-crystals were produced using 72-hour annealing protocol, except for the most complex ZX-crystal design, the ZX-96H×64B-cross-tunnels, which was annealed for 168 hours before imaging. All ZX-crystals showed small amounts of right-handed twist, which arises from the 10.67 bp/turn under-wound design. As a result, we observed that the crystals sometimes bend and land on top of themselves in TEM images. However, the magnitude of twist for ZX-crystals appeared to be much less than for the Z-crystals because the bending positions were typically observed a few micrometers apart on a ZX-crystal.

Four solid ZX-crystals were designed from 4H×4H×32B units that contained 4 layers, 6 layers, 10 layers, or 20 layers of helices. The thickness of a ZX-crystal was directly measured at the positions where the crystal folds in TEM images (FIG. 22C). The thicknesses of the 4 layer, 6 layer, 10 layer, and 20 layer ZX-crystals were measured as about 10 nm, 15 nm, 25 nm and 50 nm, respectively, showing that the crystals were completely formed, and each DNA helix was about 2.5 nm in diameter. We first designed three ZX-crystals from a 6H×6H×32B cuboid unit. Four helices were removed from the cuboid to generate the ZX-32H×64B channel design. The second ZX-32H×64B-cross-channel design was generated by removing a 2H×32B channel from the ZX-32H×64B-channel. The third ZX-6H×6H×64B pore design contained a 2H×4H×32B vertical pore along the Y-axis in each cuboid unit. This design yielded narrow and long crystals, likely due to less connection along the X-axis. The most complex ZX-crystal design was the ZX-96H×64B-cross-tunnel crystal. Its repeating unit can be considered as a 10H×10H×64B (6400 bp) cuboid with a 2H×2H×64B pore along the Z-axis and a 10H×2H×24B pore along the X-axis. Two groups of no-contact tunnels running perpendicular to each other were achieved. The two groups of tunnels were separated by two solid layers of DNA helices. Such rationally-designed 3D porous features were harder to achieve using conventional origami methods.

Additional TEM images of ZX-crystals are included in FIGS. 26A-26H.

Two-Dimensional-Growth DNA Forest Crystals (XY-Crystals).

Figures 23A, 23B, 23C, 23D:
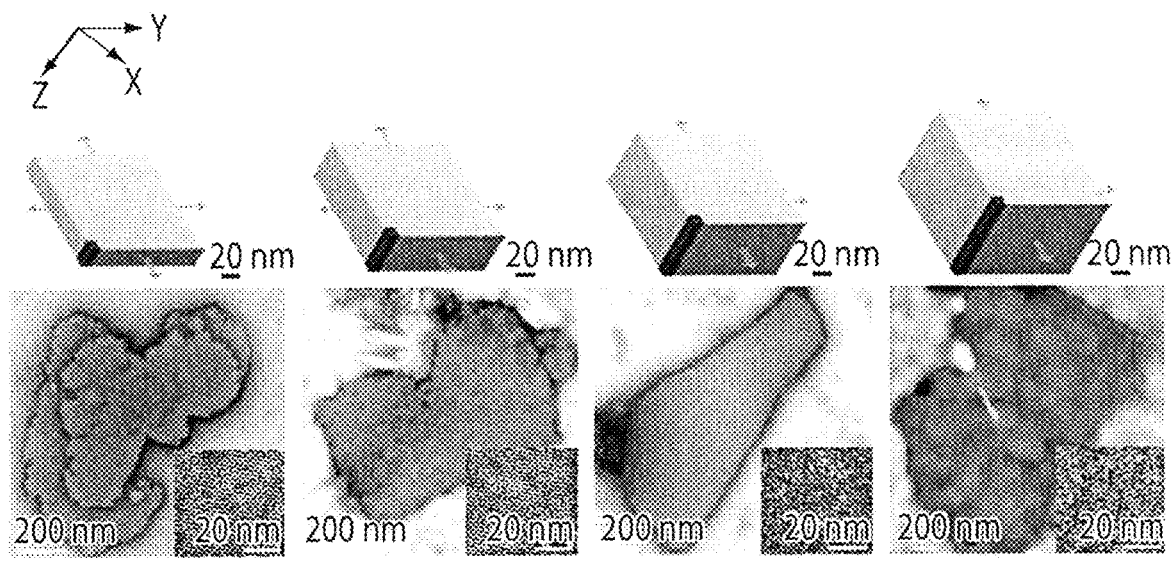
FIGS. 23A-23D show models of solid XY-crystals: 64 bp (A), 128 bp (B), 192 bp (C), and 256 bp (D). Cylinder models (top) and TEM images (bottom) are shown for each crystal.
Figures 23E, 23F:
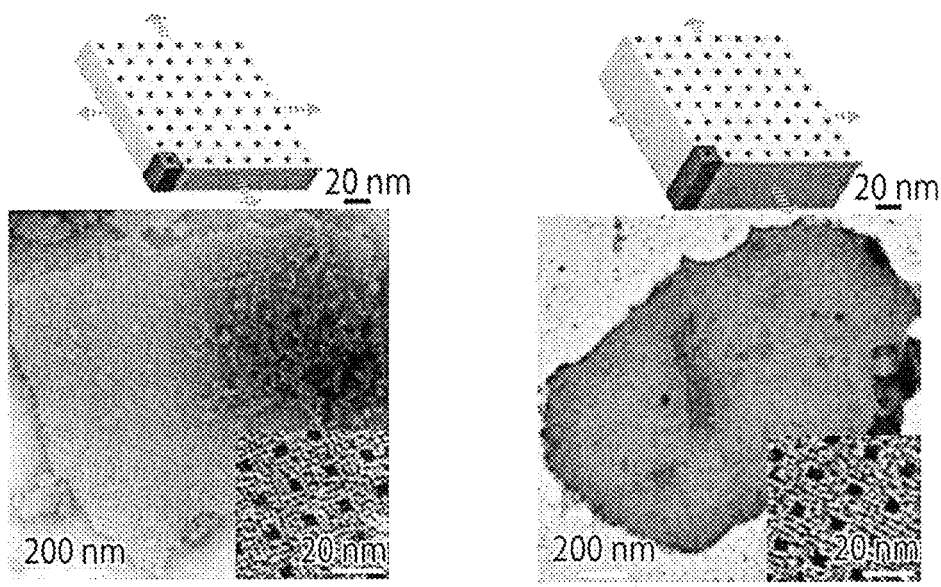
FIG. 23E shows a model of an XY-crystal with 2H×2H×64B parallel pores.
FIG. 23F shows a model of an XY-crystal with 2H×2H×128B parallel pores.
Figure 23G:
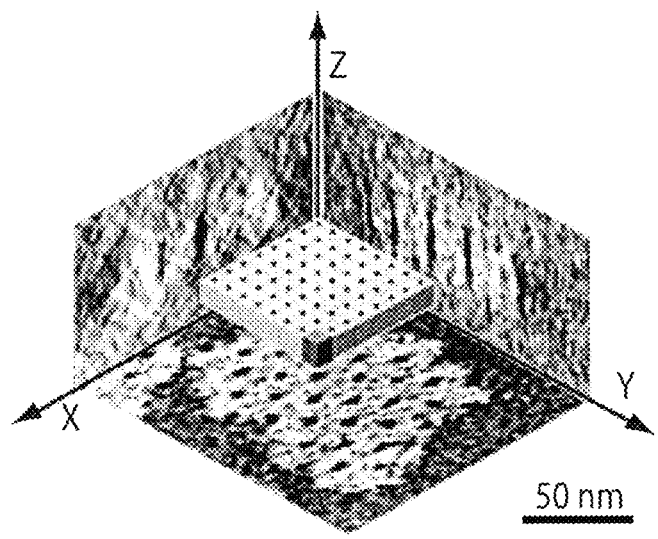
FIG. 23G shows a cryo-EM 3D reconstruction image of three projection views of a XY-32H×64B-pore crystal.
Figure 23H:
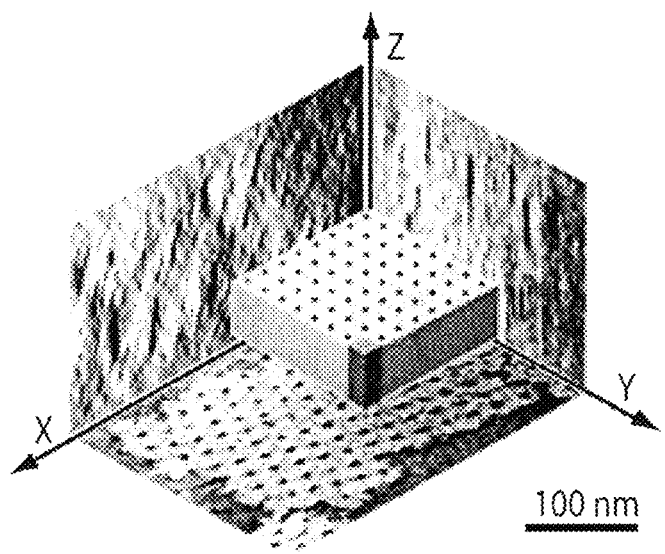
FIG. 23H shows a cryo-EM 3D reconstruction image of three projection views of a XY-32H×128B-pore crystal. Arrows indicate the positions where the thickness of the crystals is measured.
Figure 23I:
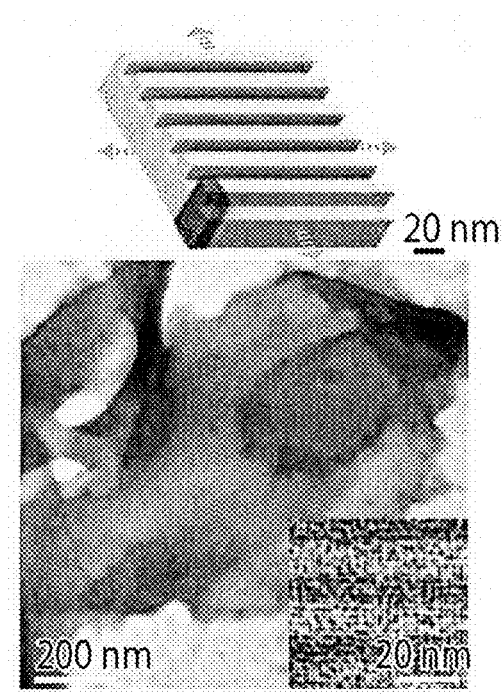
FIG. 23I shows a 96 bp crystal with 4H×32B parallel channels.
Figure 23J:
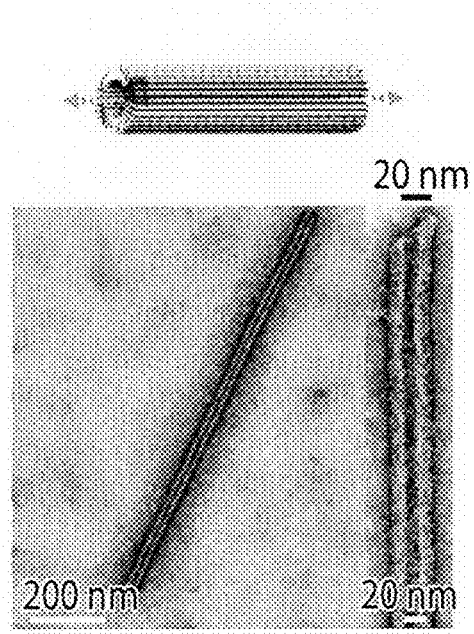
FIG. 23J shows a tube crystal formed by 32-bp helices that are perpendicular to the tube axis. Unit cells of crystals are denoted using dark-gray boxes.
Figure 24A:
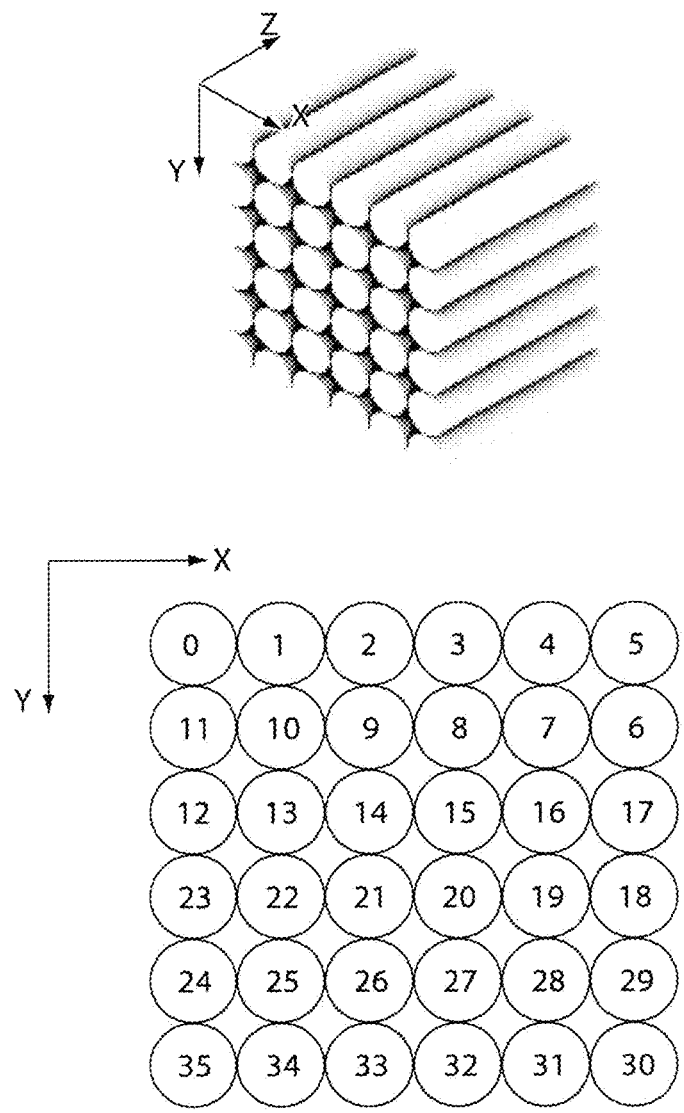
FIGS. 24A-24F show strand diagrams that show how the extended crystal is designed from a discrete object.
Figure 24B:
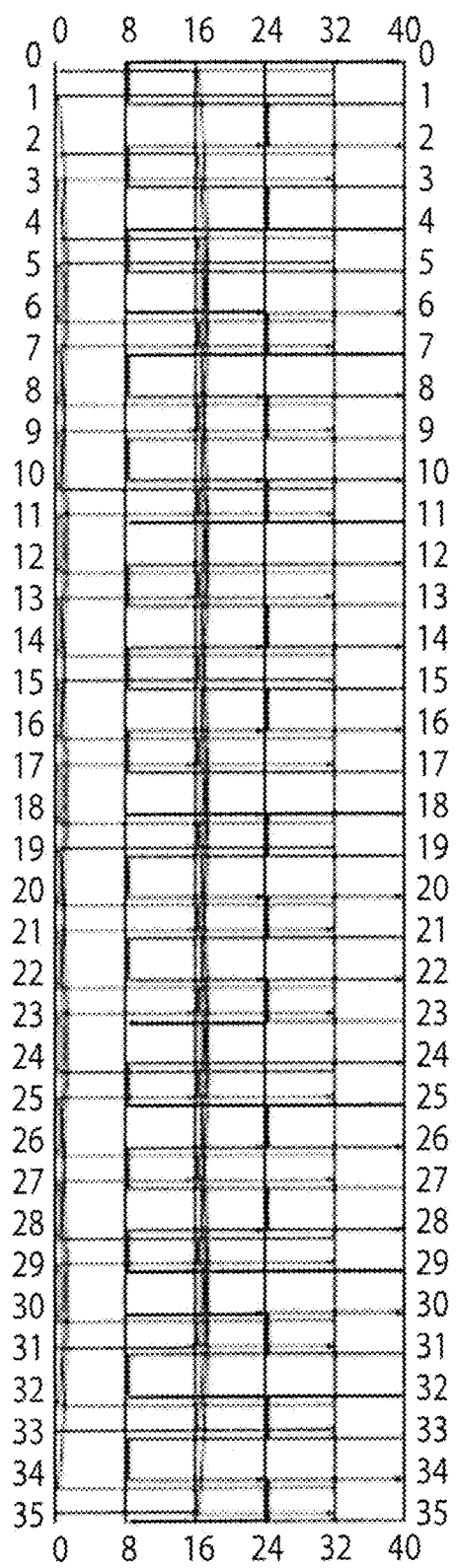
Figure 24C:
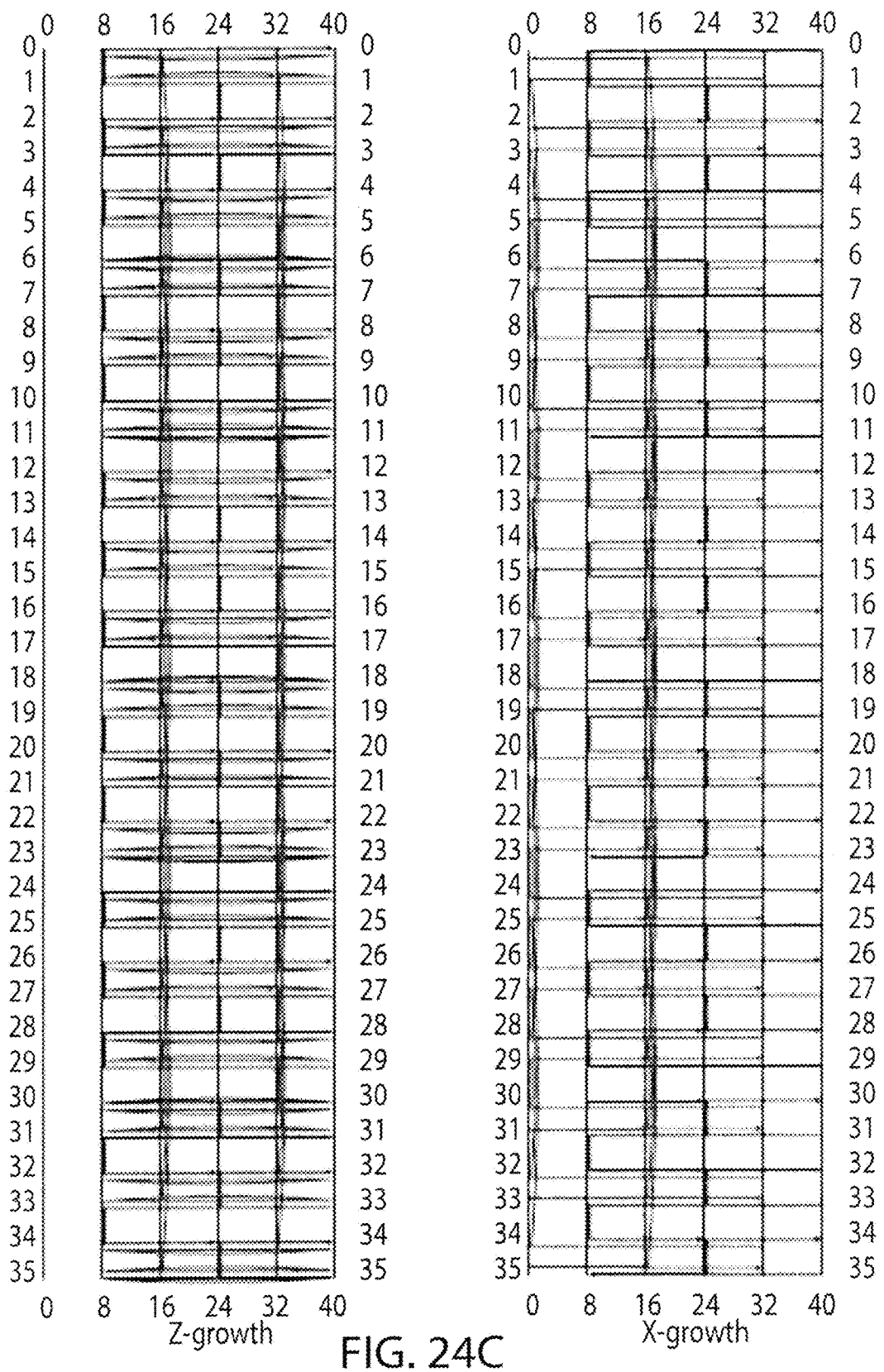
Figure 24D:
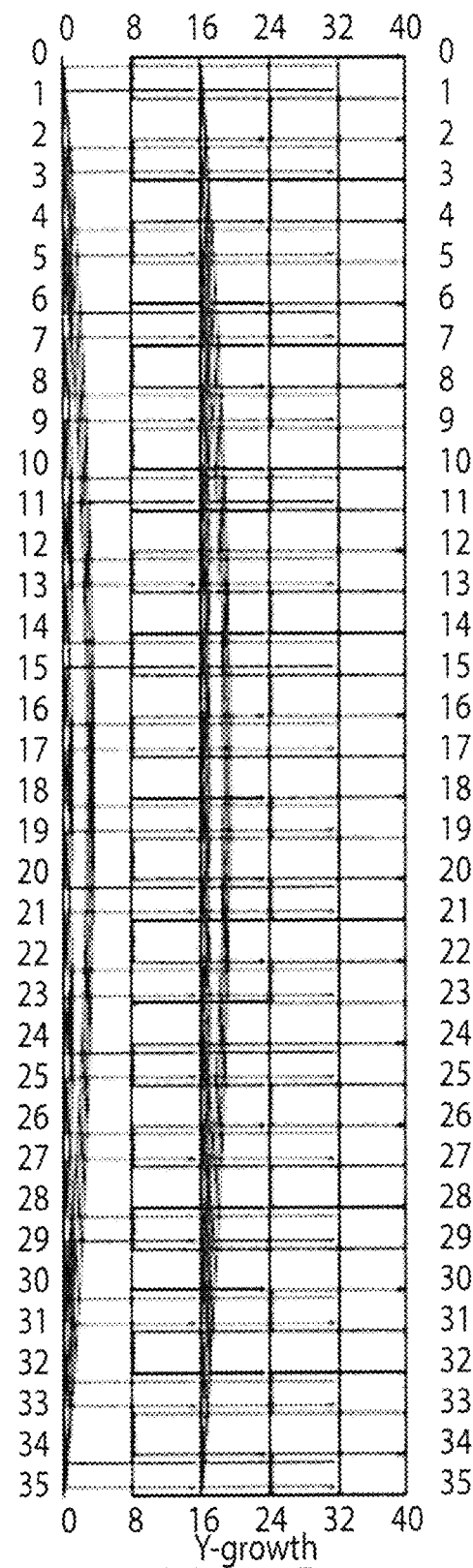
Figure 24E:
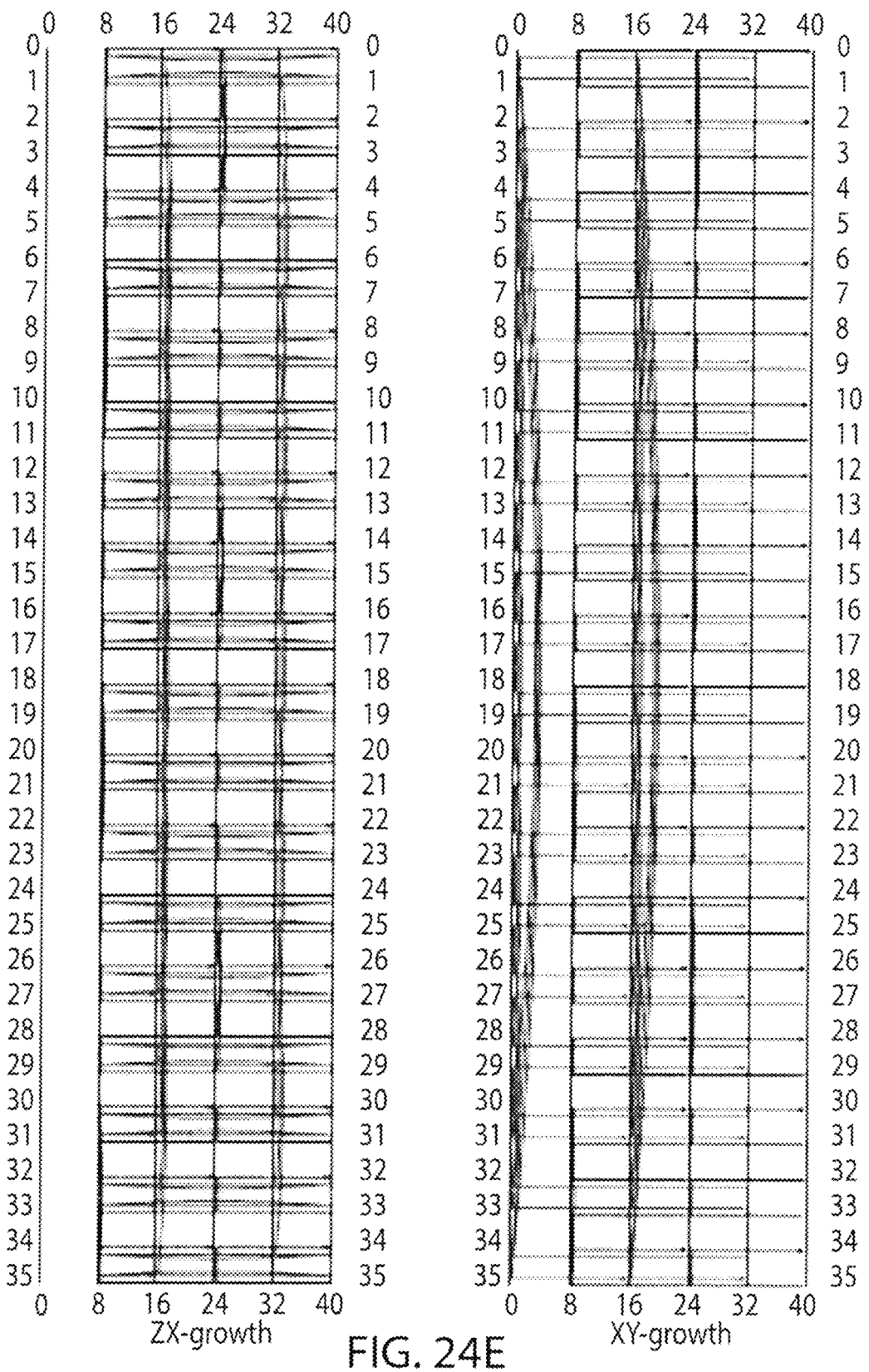
Figure 24F:
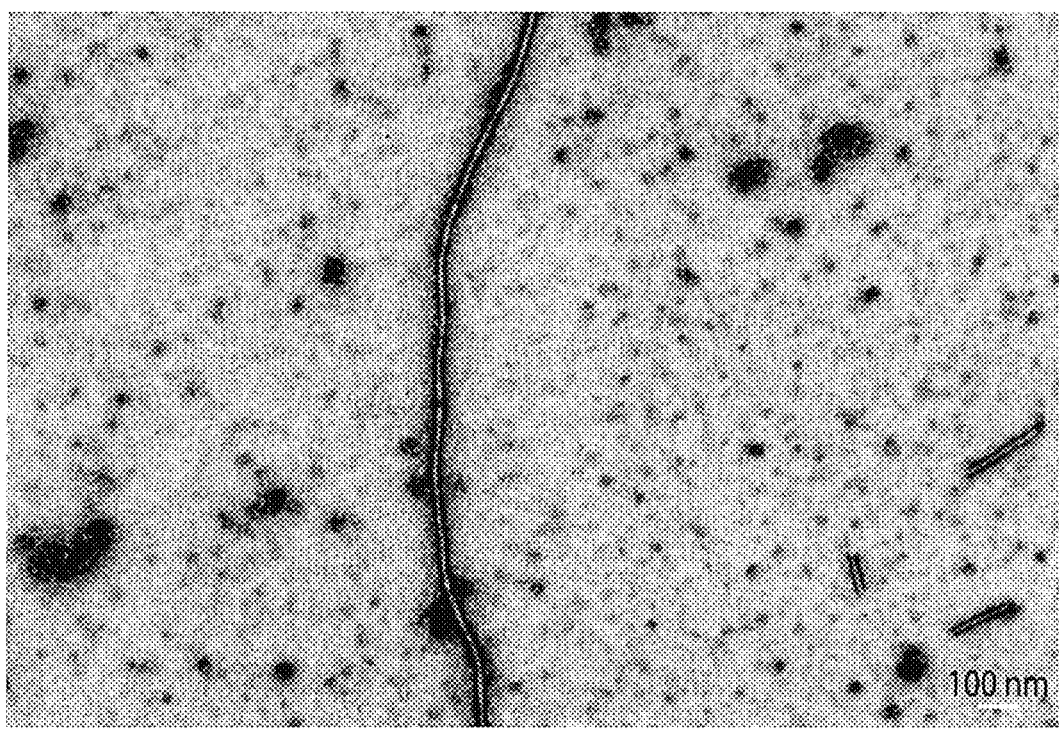
Figure 25A:
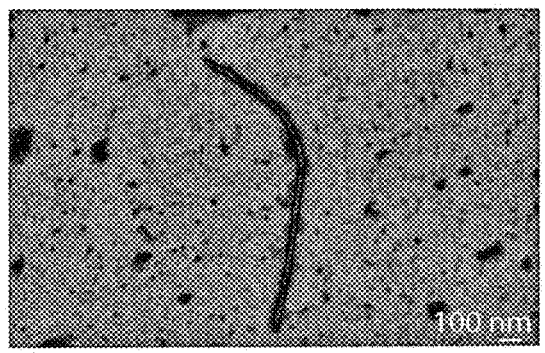
FIGS. 25A-25H show TEM images of Z-crystals. (A) Z-8H×8H×32B-cuboid crystal; (B) Z-10H×10H×32B-cuboid crystal; (C) Z-6H×6H×128B-spiral crystal; (D) Z-43H×32B-triangle crystal; (E) Z-44H×32B-hexagon crystal; (F) Z-56H×32B-tunnel crystal; (G) Z-60H×64B-tunnel crystal; and (H) Z-108H×32B-tunnel crystal.
Figure 25B:
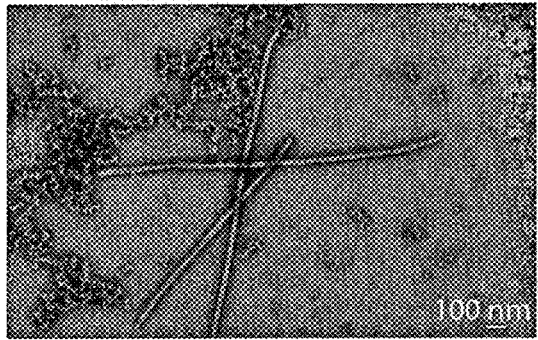
Figure 25C:
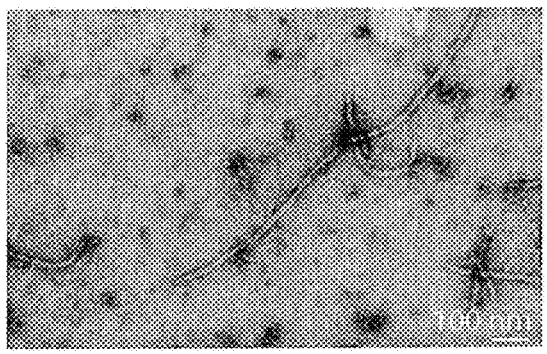
Figure 25D:
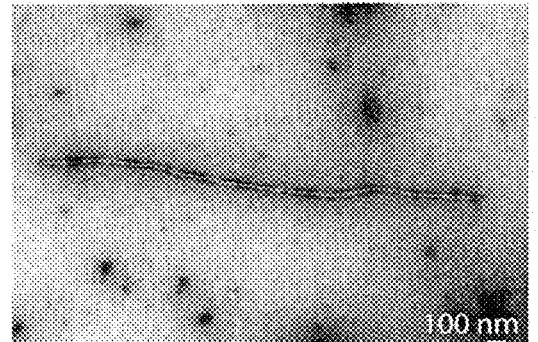
Figure 25E:
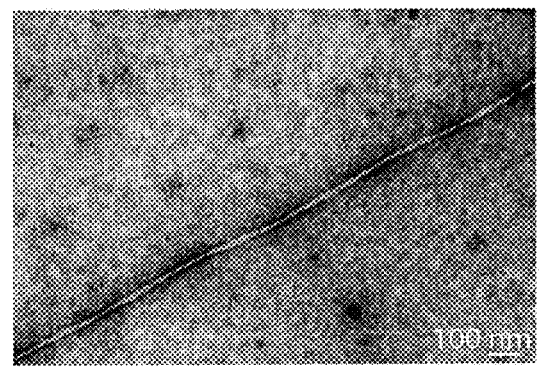
Figure 25F:
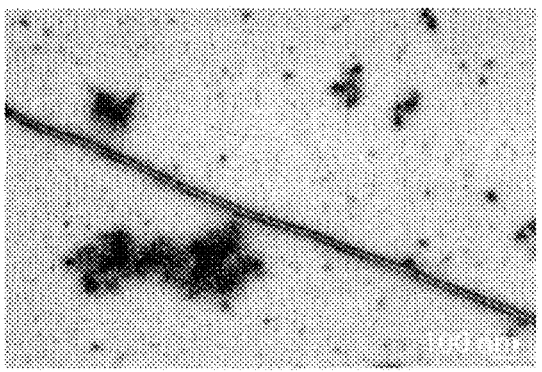
Figure 25G:
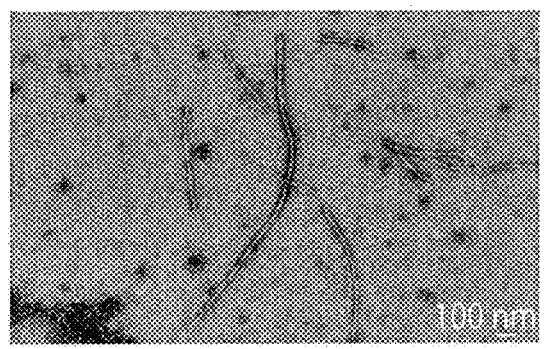
Figure 25H:
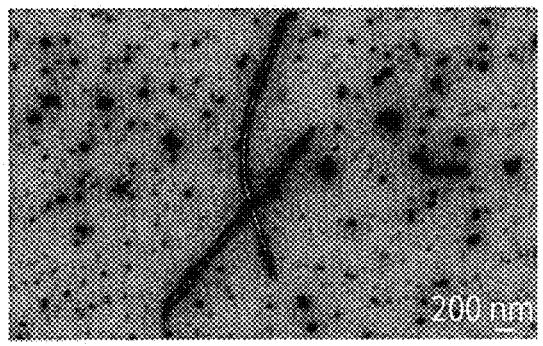
Figure 26A:
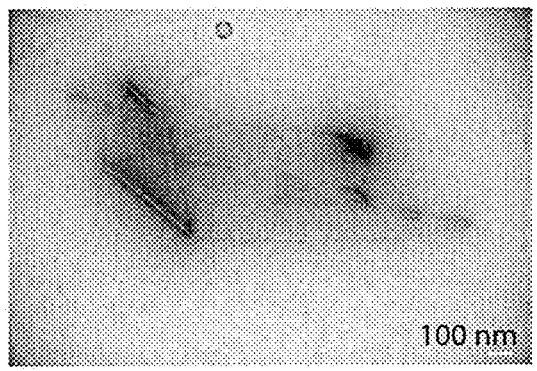
Figure 26B:
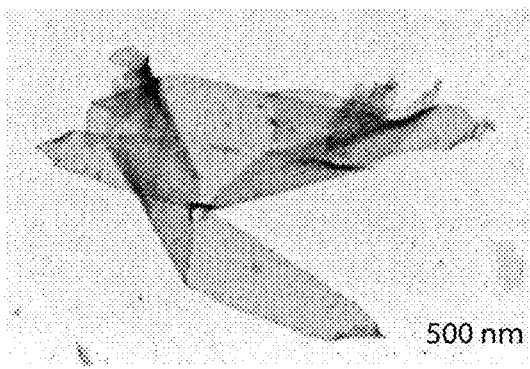
Figure 26C:
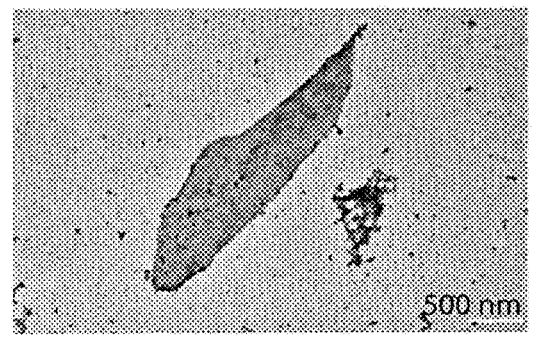
Figure 26D:
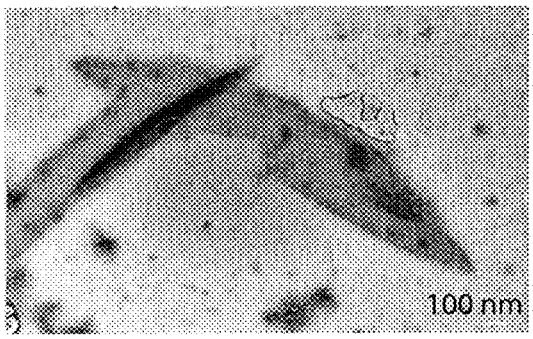
Figure 26E:
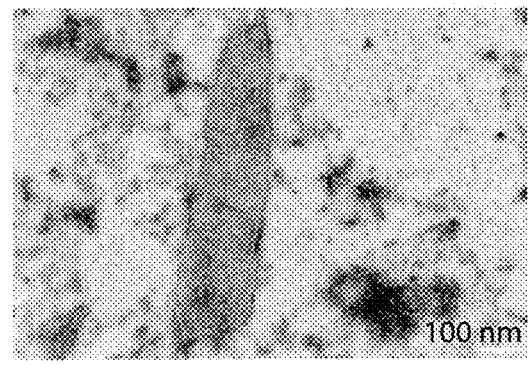
Figure 26F:
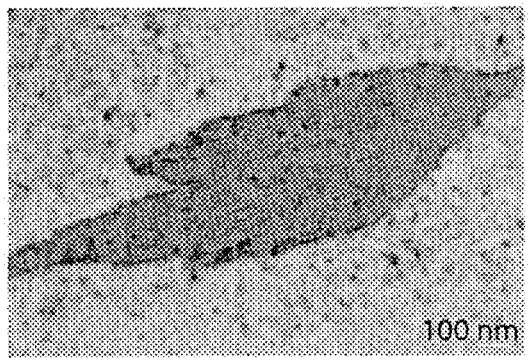
Figure 26G:
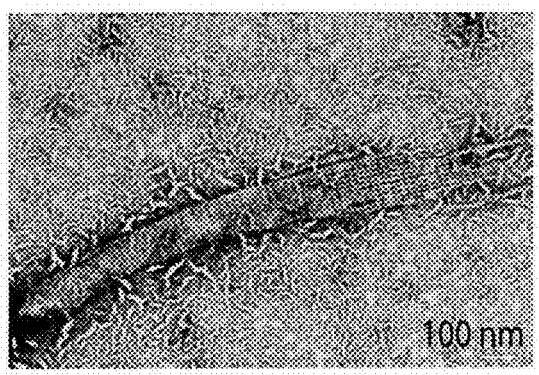
Figure 26H:
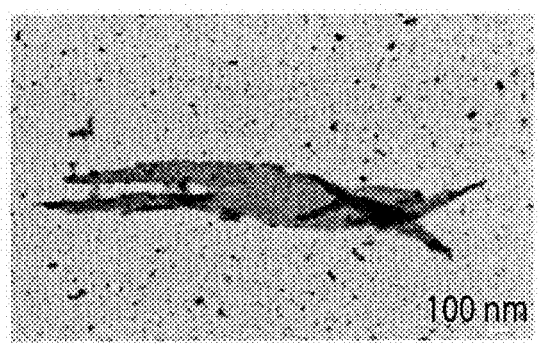
Figure 27A:
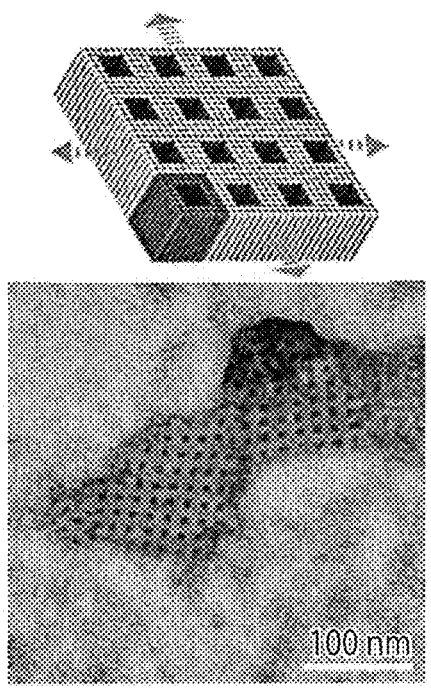
Figure 27B:
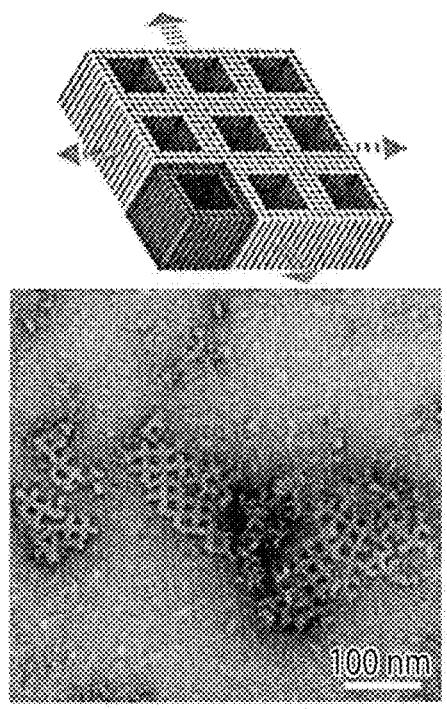
Figure 27C:
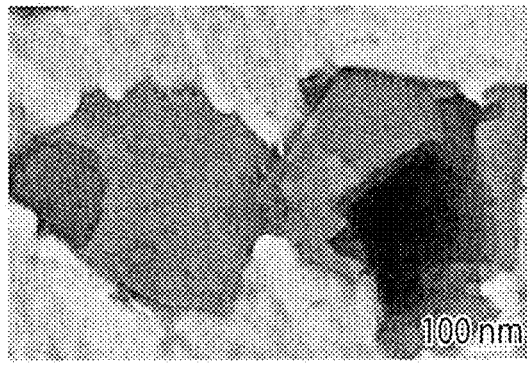
Figure 27D:
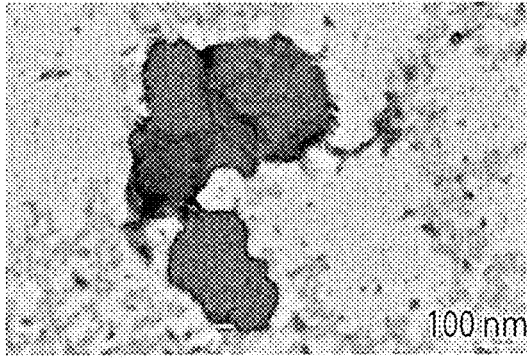
Figure 27E:
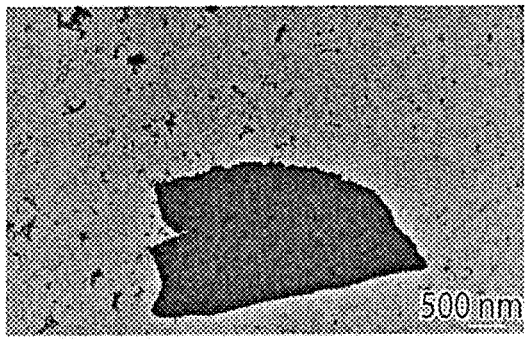
Figure 27F:
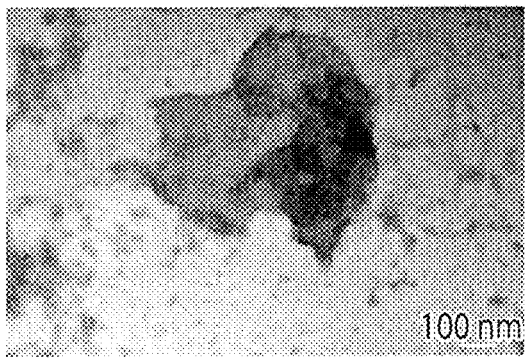
Figure 27G:
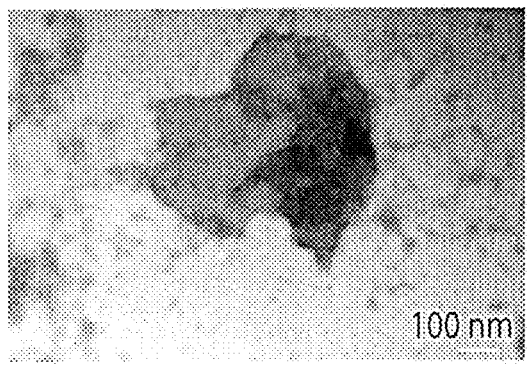
Figure 27H:
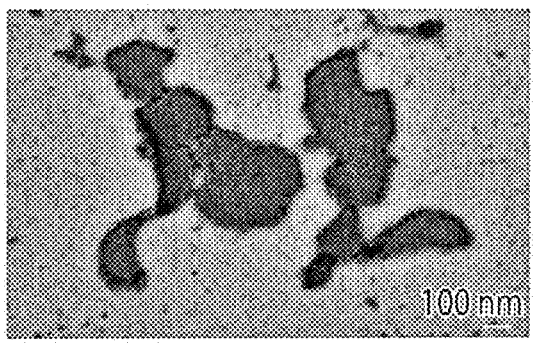
Figure 27I:
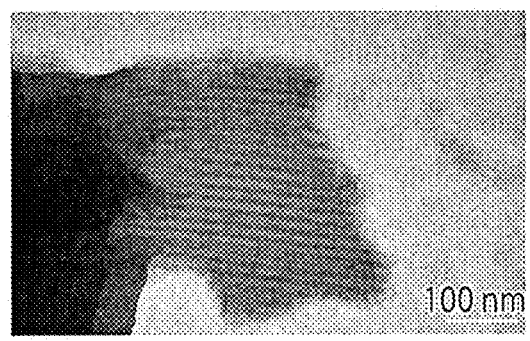

Lastly, we made two groups of XY-crystals: (1) solid XY-crystals—an XY-4H×4H×64B-cuboid, an XY-4H×4H×128B-cuboid, an XY-4H×4H×192B-cuboid, and an XY-4H×4H×256B-cuboid (FIGS. 23A and 23B); and (2) complex XY-crystals—an XY-32H×64B-pore, an XY-32H×128B-pore, an XY-4H×8H×96B-channel, and an XY-4H×4H×32B-tube (FIGS. 23C and 23D).

The XY-crystals are two-dimensional growth crystals that eliminate the growth along DNA helical axis. By contrast, all previous two-dimensional DNA crystals implement DNA-helical-axis growth. Because crystal growth along X-axis or Y-axis is harder than growth along Z-axis, a 72-hour annealing protocol often produces no XY-crystal or XY-crystals smaller than a few hundred nanometers along the X-axis or the Y-axis. Therefore, we used a 168-hour annealing protocol for all XY-crystals in FIG. 23. The growth of XY-crystals was isotropic and did not show apparent direction preference because the two growth directions (X-axis and Y-axis) were both perpendicular to the DNA helical axis.

The XY-crystals did not show any global right-handed twist in our images. In order to simplify the analysis, we assumed that an XY-crystal forms a perfect cylinder that contains n helices. The overall twist in radians of the cylinder $\theta = TL/JG$, where T is the applied torque resulting from the underwinding design, L is the length of a helix, G is the modulus rigidity of a helix, and J is the torsion constant. The first three parameters can be considered constants. The torsion constant J for a circle as a function of cross-sectional radius (XY-plane) can be approximated with the following formula: $J=\pi r^4/2$, where r is the circular cross-sectional radius. Thus, the θ is inversely proportional to $r^4$, or to $n^2$. When an XY-crystal grows and n approaches 1, the global twist is quickly mitigated and can no longer be observed.

The flatness of the surfaces of XY crystals is a desirable property for some applications because positions and orientations of guest molecules can be precisely controlled even in solution. By contrast, the conformation of a twisted structure (e.g., a ZX-crystal) or a flexible structure (e.g., a single-layer DNA-origami crystal) in solution is difficult to accurately predict. In addition, the XY-crystals provide easy platforms for arranging matter because the crystals expose a very large number of DNA helices on the surface. Functionalized materials can be conveniently connected to the ends of DNA helices, which are closely packed at 2.5 nm resolution in each dimension.

Solid XY-crystals of variable thicknesses were designed from a 4H×4H cuboid unit. Using different lengths of the 4H×4H cuboid unit, four XY-crystals that were 64 bp, 128 bp, 192 bp and 256 bp in thickness were generated. Thicknesses of these solid XY-crystals could not be directly measured from TEM imaging because they were perfectly flat. If each base pair corresponds to a standard 0.33 nm length in B-form DNA, the thickness of the four crystals should be about 21 nm, 42 nm, 63 nm and 84 nm, respectively.

An XY-32H×64B-pore and an XY-32H×128B-pore crystal were constructed. Both designs contained periodic 2H×2H (5 nm by 5 nm) pores that were separated by 4 helices (10 nm) in each dimension. The two crystal structures resembled a 21 nm and a 42 nm thick porous membrane structure. To demonstrate that non-porous structures with surface features can be constructed, we made an XY-4H×8H×96B-channel crystal. It contained a solid 64 bp (42 nm) tall base and parallel channels. The channels were 4 helices (10 nm) in width, 32 bp (21 nm) in height, and separated by 4 layers of helices.

Additional TEM images of XY-crystals are shown in FIG. 27A-27I.

Figure 28A:
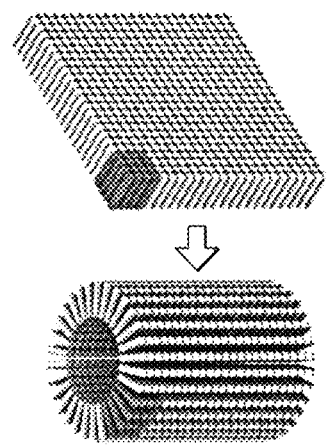
FIG. 28A shows a XY-4H×4H×32B-cuboid two-dimensional-growth crystal design (top) and how the structure can be used to form a tube (bottom).
Figure 28B:
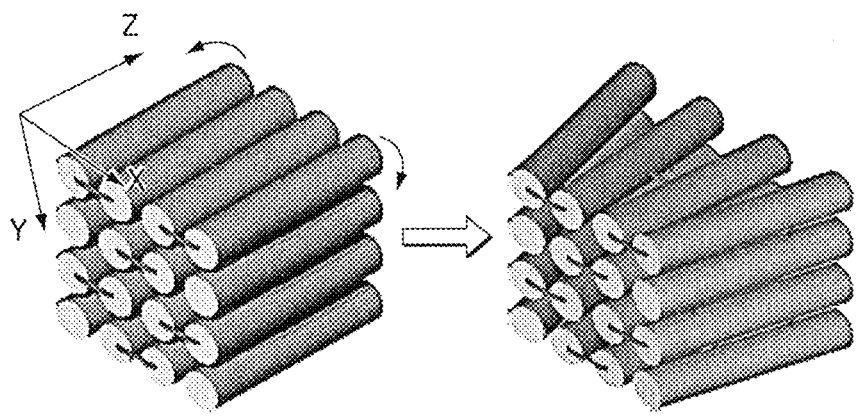
FIG. 28B shows a 4H×4H×32B-cuboid repeating unit expanded along the X-axis.
Figure 28C:
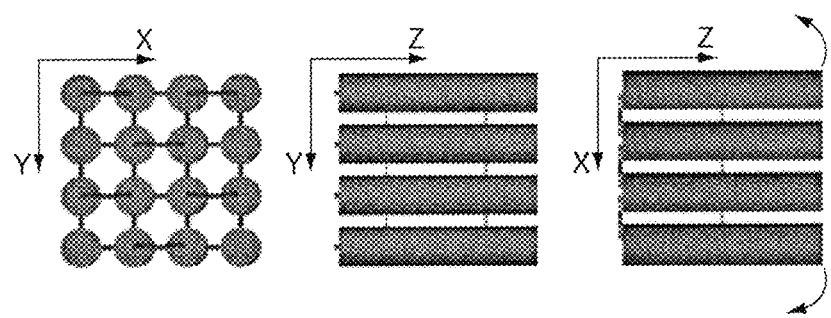
FIG. 28C shows projection views of a 4H×4H×32B-cuboid repeating unit. Along the Z-axis, the crossovers are asymmetrically distributed: half of the crossovers is located at the middle-point of the cuboid, and the other half is located at the left end of the cuboid.
Figure 29:
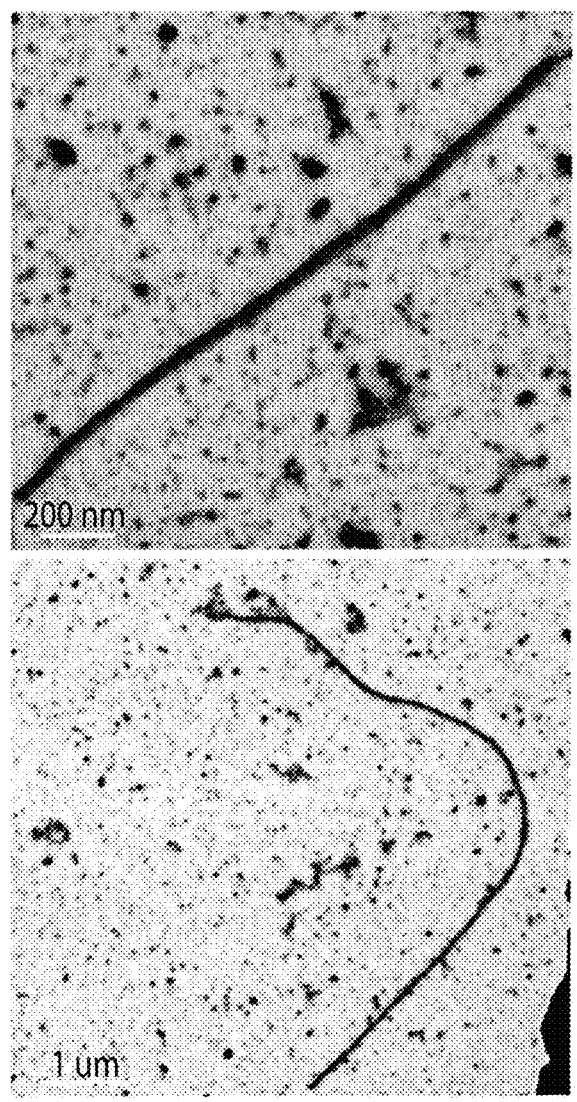
FIG. 29 shows TEM images of an XY-4H×4H×32B-tube crystal.
Figure 30:
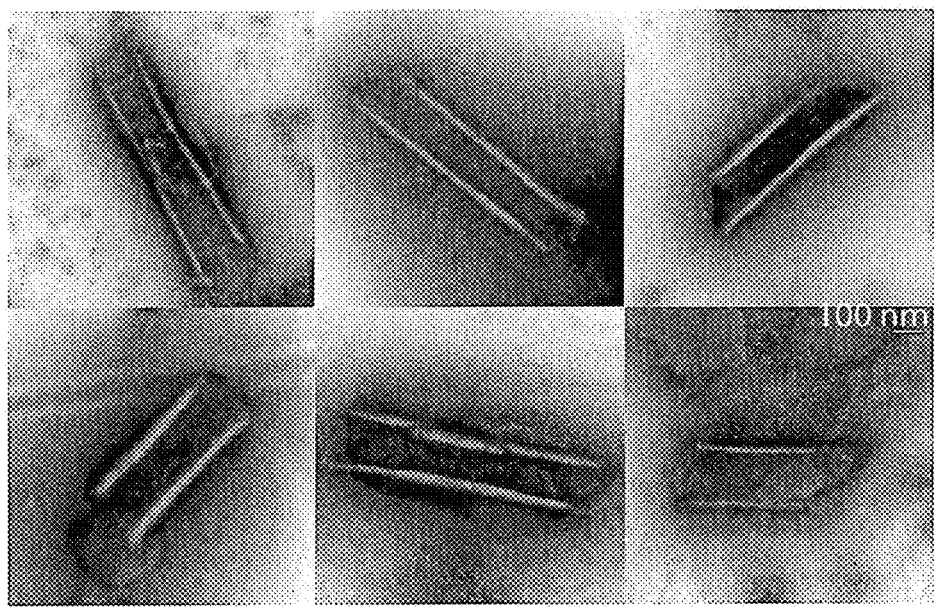
FIG. 30 shows TEM images of an XY-4H×4H×32B-tube crystal assembled in 60 mM of $MgCl_2$.
Figure 31:
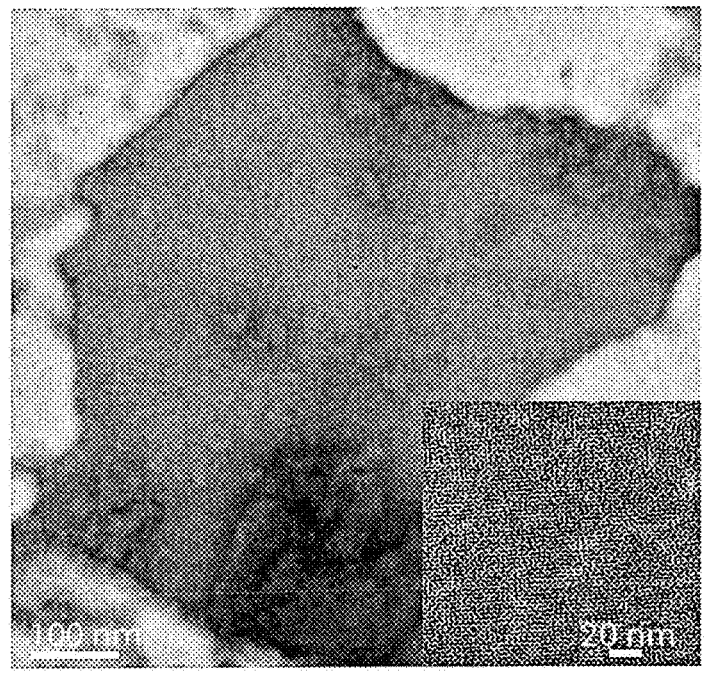
FIG. 31 shows TEM images of an XY-4H×4H×32B-cuboid crystal using alternating DNA-bricks.

A particularly interesting XY-crystal was the XY-4H×4H×32B-tube crystal. It was designed using same design strategy as other XY-crystals. This thin XY-crystal (32 bp, or 10.6 nm) formed a tube structure instead of a flat 2D crystal. Without being bound by theory, we hypothesize that the tube formation is due to the uneven distribution of connections between helices (FIGS. 28A-28C). Because helices in the XY-4H×4H×32B-tube are relatively short, there is only one connection between each pair of neighboring helices. The connections are evenly distributed along the Y-axis. Along the X-axis, half of the connections is located in the middle of the structure, and the other half is positioned at one side of the structure. Therefore, without being bound by theory, we hypothesize that the crystal expands at the opposite side and forms a tube. These tubes are narrow and can grow to several micrometers in length (FIG. 29). The diameters of tubes are about 14-20 nm with small variations. Annealing the XY-4H×4H×32B-tube in the presence of a higher $MgCl_2$ concentration can produce tubes with larger diameters because $Mg^{2+}$ can reduce the repulsion between negative-charged DNA helices. At 60 mM $MgCl_2$, we observed many tubes with diameters between 140 nm to 300 nm (FIG. 30). To further test our hypothesis, we designed an XY-4H×4H×32B-cuboid crystal in which the DNA bricks were arranged in an alternating fashion between layers. Connections between helices in this design were symmetrically distributed along both X-axis and Y-axis. TEM images demonstrated a flat crystal structure (FIG. 31). Thicker 64 bp, 128 bp, 192 bp and 256 bp XY-crystal designs had 2, 4, 6, and 8 connections between each pair of neighboring helices. No visible curvature was observed in TEM images for these designs.

Other DNA-Brick Crystals.

We further demonstrated that other types of DNA-brick crystals can be assembled from DNA bricks, including (1) two one-dimensional-growth crystals that extend along the X-axis and (2) a two-dimensional-growth crystal that implements an "offset" connection scheme.

Id X-Crystals.

Figure 32A:
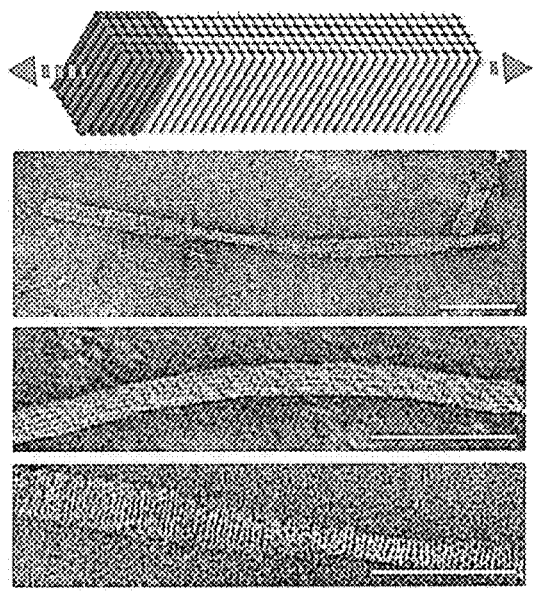
FIG. 32A shows an X-6H×6H×64B-cuboid crystal design and TEM images.
Figure 32B:
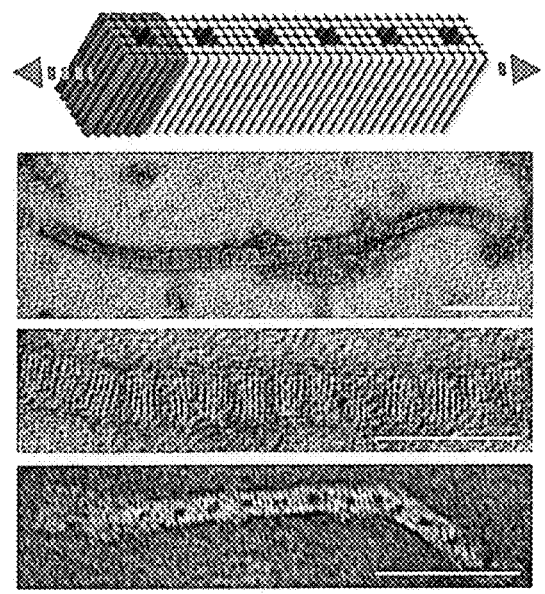
FIG. 32B shows an X-32H×64B-pore crystal design and TEM images. The dark regions represent repeating units.

Growing repeating units along the X-axis or Y-axis generated another type of one-dimensional-growth crystal. We designed and tested two X-crystals (note that X-crystals and Y-crystals should be very similar because of the symmetry of DNA-brick structures): a X-6H×6H×64B-cuboid crystal (FIG. 32A) and a X-32H×64B-pore crystal (FIG. 32B). The X-6H×6H×64B-cuboid crystal was designed based on a solid 6H×6H×64B cuboid unit. The X-32H×64B-pore crystal used a 6H×6H×64B cuboid unit with four helices removed from the center. Both crystals grew to a few hundred nanometers in length and appeared well-formed in TEM images. The average lengths of the two X-crystals were much shorter than the Z-crystals due to the close packing of large numbers of short DNA helices.

Offset 2D ZX-Crystals.

Figure 20B:
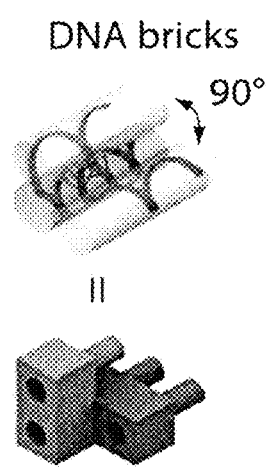
FIG. 20B shows a strand model (top) and a brick model (bottom) of a pair of 32-nucleotide single-stranded DNA bricks forming a 90° angle.
Figure 20C:
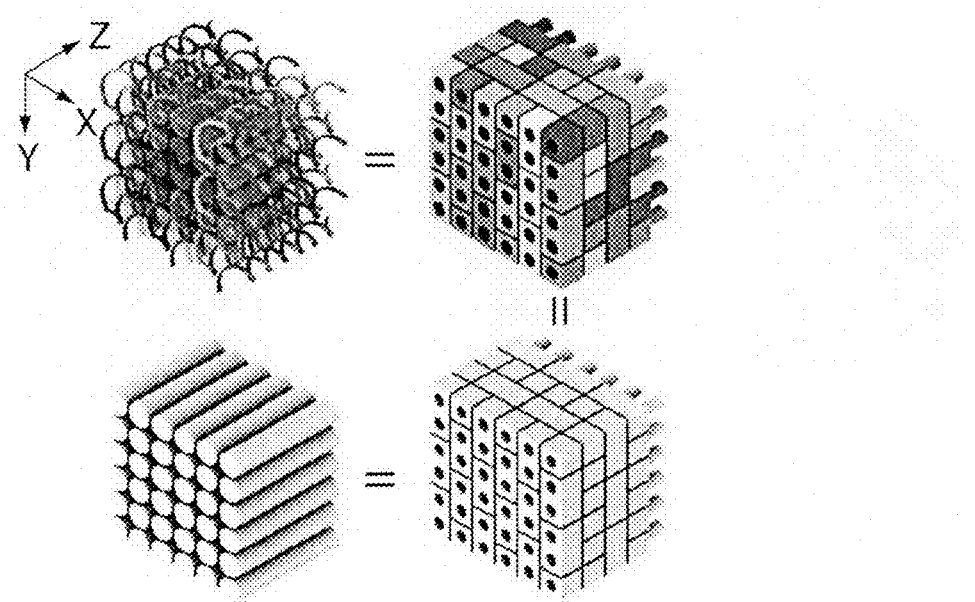
FIG. 20C, clockwise from the top-left, shows models of a 6H (helix)×6H×24B (base-pair) cuboid structure in order of most detailed to least detailed: a strand model in which bricks are labeled with different shades of gray, a brick model in which bricks are labeled with different shades of gray, a brick model in which all bricks are labeled with a light gray color, and a cylinder model that depicts DNA helices without showing bricks. Bricks have distinct sequences. The Z-axis is parallel to the DNA helices.
Figure 20D:
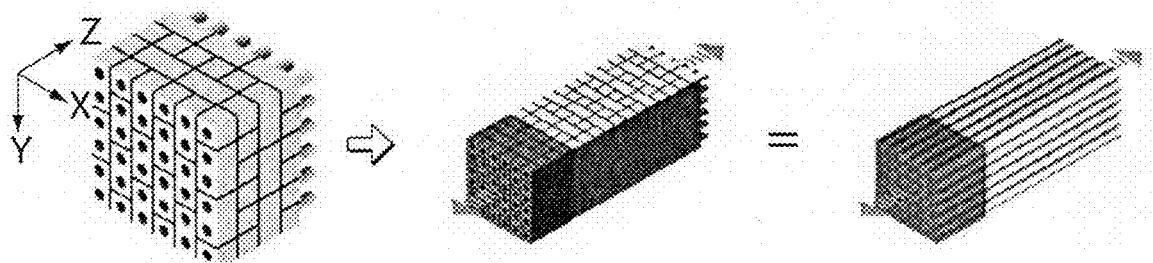
FIGS. 20D-20G show models of one-dimensional (1D), two-dimensional (2D) and three-dimensional (3D) DNA-brick crystals designed from the 6H×6H×24B cuboid.
Figure 20E:
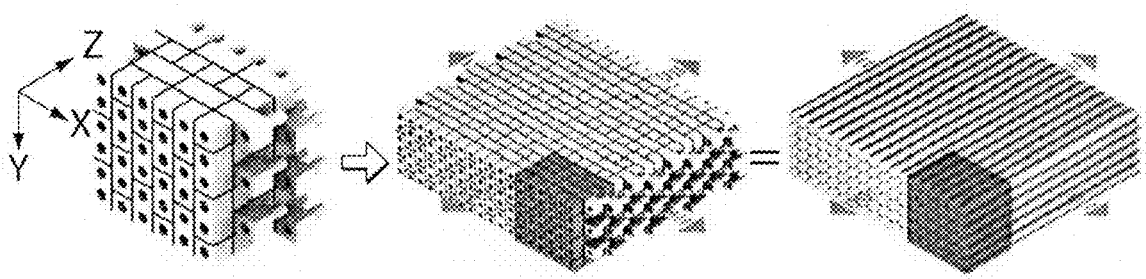
Figure 20F:
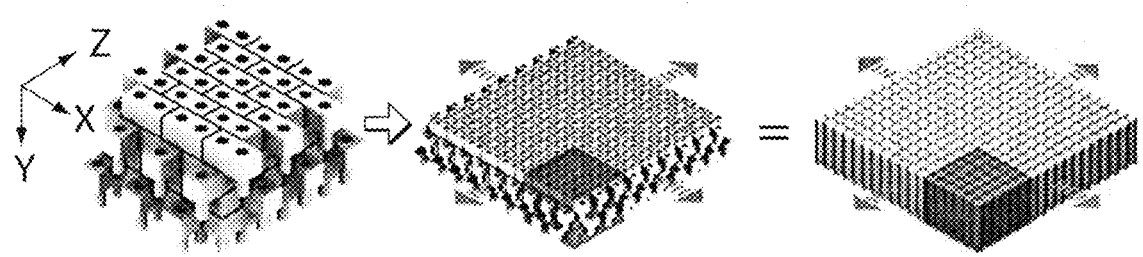
Figure 20G:
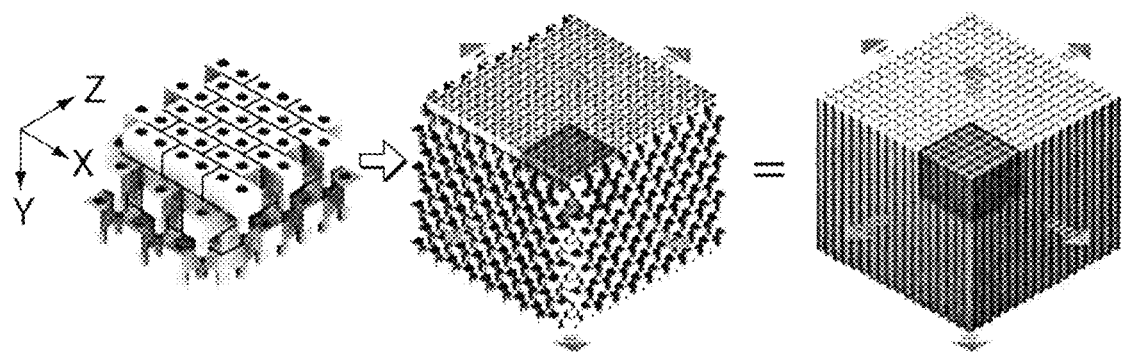
Figure 20H:
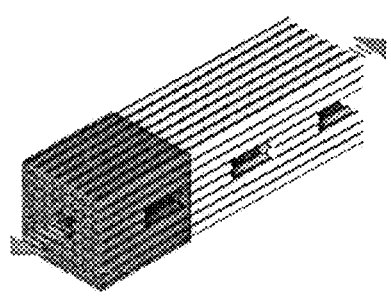
FIGS. 20H-20K show cylinder models of DNA crystals with channels, tunnels and cavities.
Figure 20I:
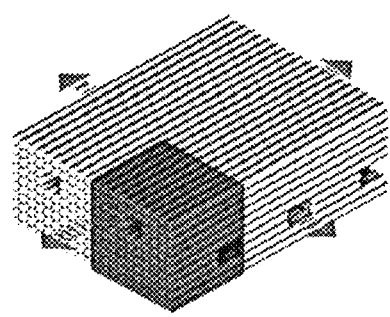
Figure 20J:
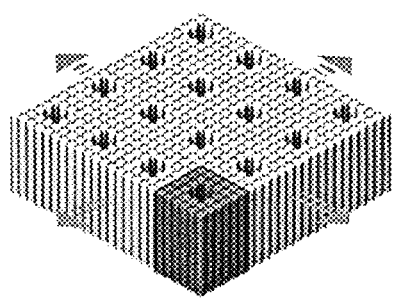
Figure 20K:
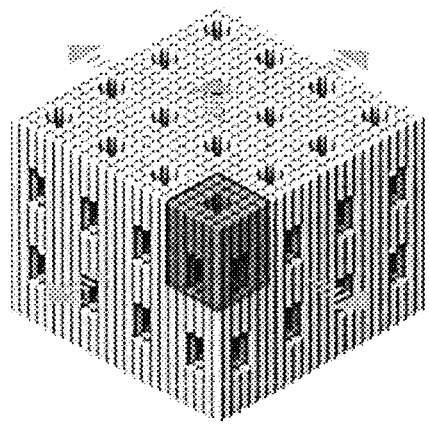
Figure 20L:
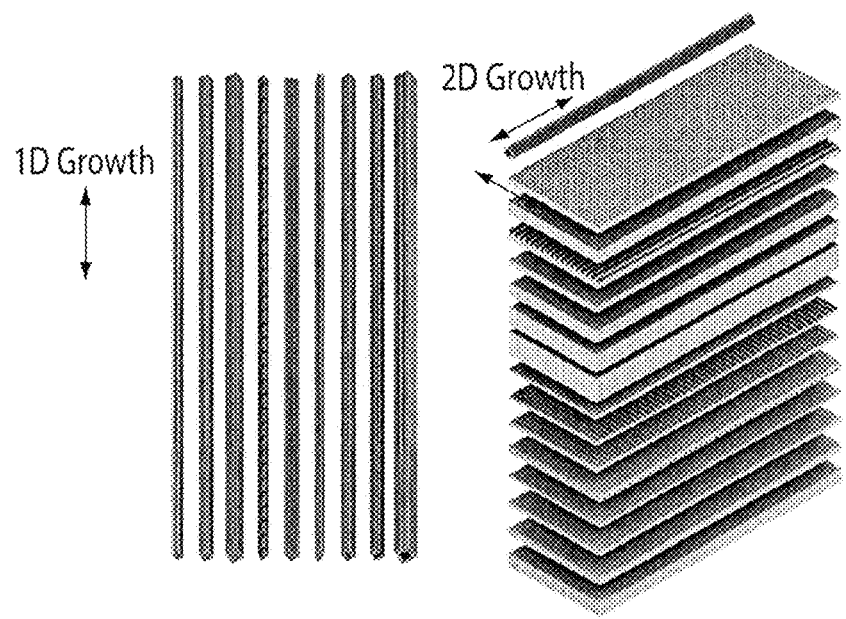
FIG. 20L shows complex DNA crystals in three-dimensional space.
Figure 20M:
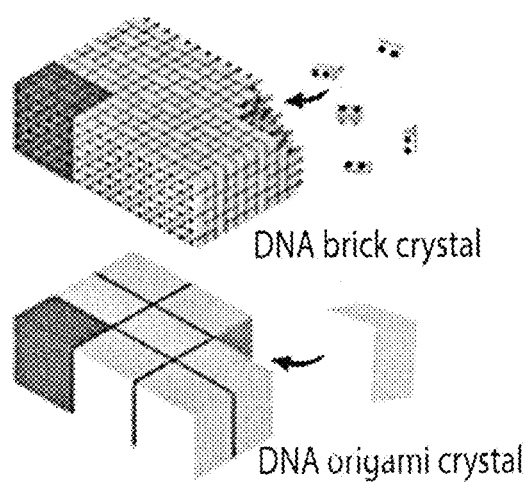
FIG. 20M shows a proposed assembly mechanism of a DNA-brick crystal of the invention compared to a proposed assembly mechanism of a DNA-origami crystal. Top: a 6H×6H×24B DNA-brick cuboid is extended to form a two-dimensional-growth crystal. Bricks are incorporated into the crystals individually. Bottom: a 6H×6H×24B DNA origami cuboid is extended to form a two-dimensional-growth crystal. Each cuboid needs to form correctly and then be incorporated into the crystal. The repeating informational units of both crystals are indicated in dark gray.
Figure 33A:
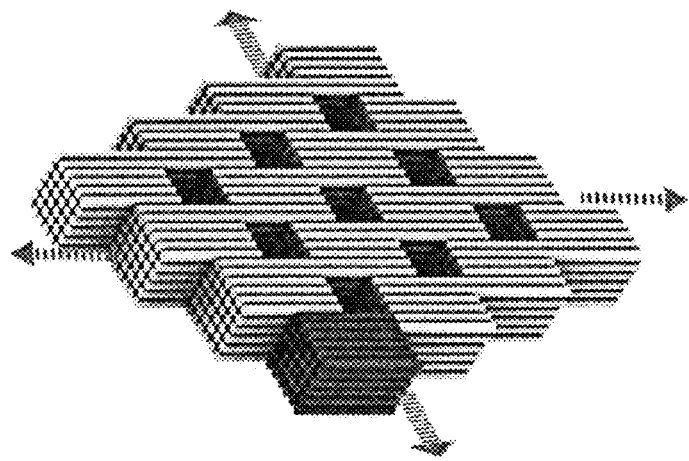
FIG. 33A shows the design of an offset-ZX-6H×6H×64B-cuboid crystal. The dark part represents a repeating unit.
Figure 33B:
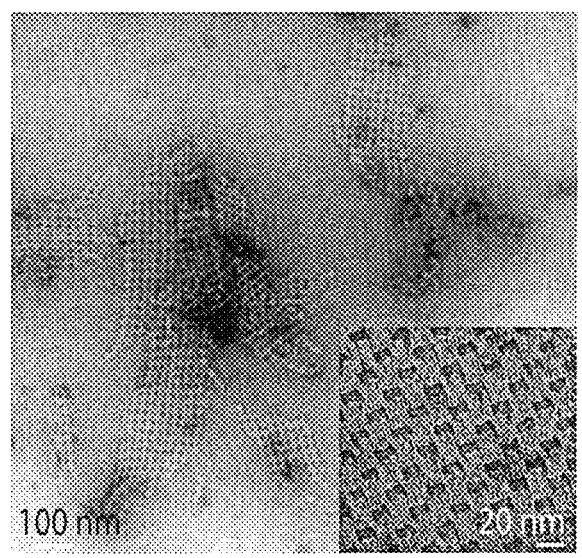
FIG. 33B shows TEM images of the offset-ZX-6H×6H×64B-cuboid crystal.
Figure 33C:
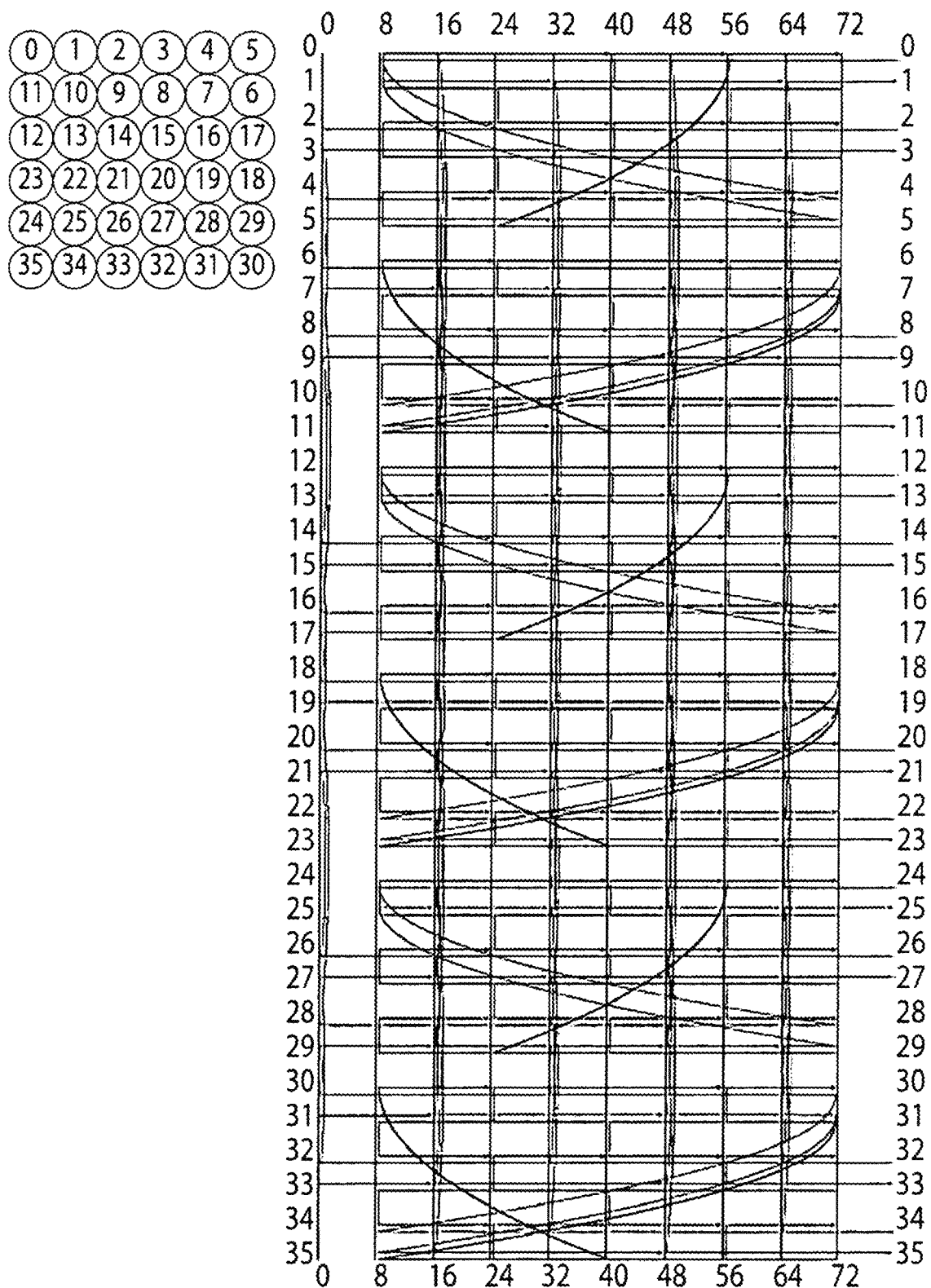
FIG. 33C shows a strand diagram of an offset-ZX-6H×6H×64B-cuboid crystal.

All of the foregoing crystals were designed using the connection scheme in FIG. 20B: extension of a structure was achieved by connecting the repeating units along an axis in a "perfect matching" fashion. For instance, in order to make a 6H×6H×32B-cuboid Z-axis crystal, every duplex in a repeating unit was designed to connect to the same duplex in the next repeating unit. However, connections along each axis can be shifted for generating "offset" crystals. Such strategy enables more crystal designs from a same basic repeating unit. We constructed a two-dimensional growth crystal that extended 6H×6H×64B-cuboid repeating units along the Z-axis and the X-axis using the offsetting scheme (FIGS. 33A-33C). In this design, the Z-axis extension of the crystal was shifted 4 duplexes along the X-axis; the X-axis extension of the crystal was shifted 32 bp along the Z-axis. The offset connections obeyed the following rules due to the periodicities of DNA-brick structures: shifting along X-axis or Y-axis occurred at 2-duplex intervals; and shifting along the Z-axis occurred at 32-bp intervals.

Example 5. Patterning Gold Nanoparticles

Figure 34A:
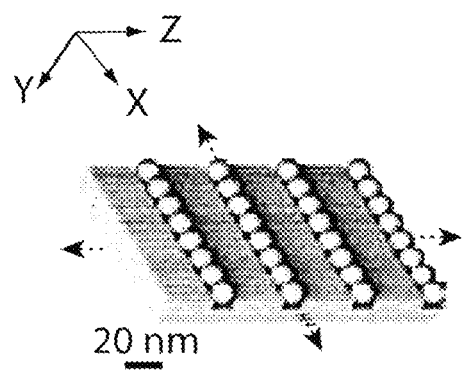
FIG. 34A shows a model of parallel lines of 10-nanometer gold nanoparticles closely packed on a ZX-4H×6H×96-channel crystal.
Figure 34B:
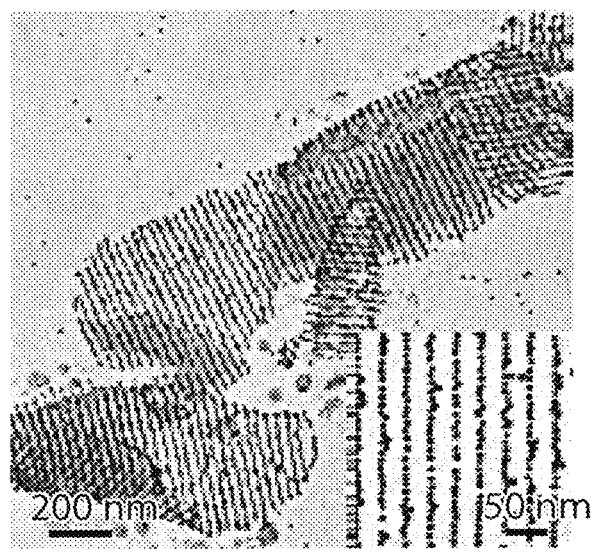
FIG. 34B shows a TEM image of parallel lines of 10-nanometer gold nanoparticles closely packed on a ZX-4H×6H×96-channel crystal.
Figure 34C:
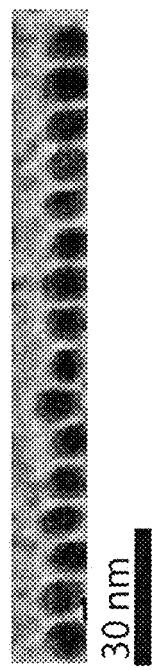
FIG. 34C shows a high-magnification TEM image of a single chain of gold nanoparticles.
Figure 34D:
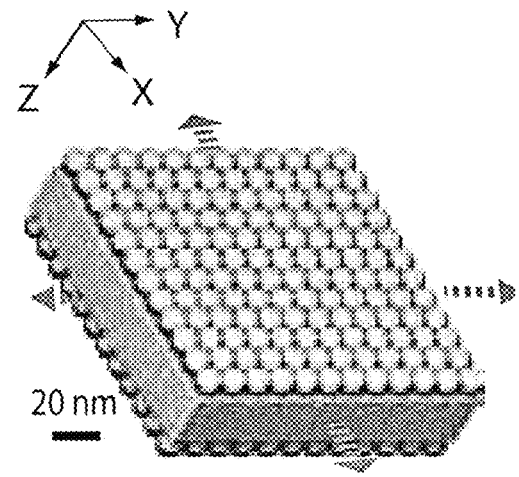
FIG. 34D shows a model of closely-packed gold nanoparticle monolayers that formed on the top surface and the bottom surface of a XY-4H×4H×64B-cuboid crystal.
Figure 34E:
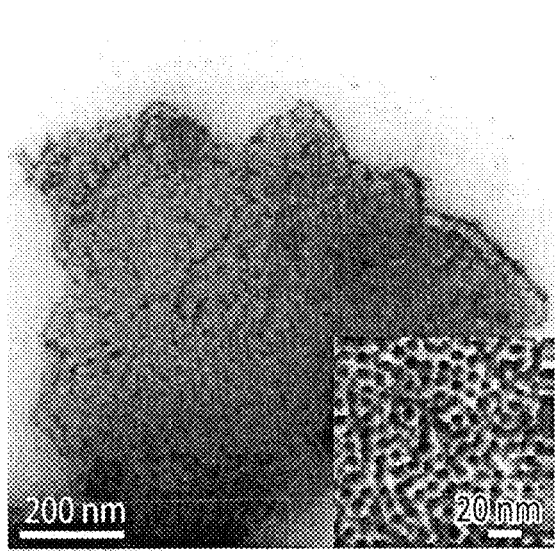
FIG. 34E shows a TEM image of closely-packed gold nanoparticle monolayers that formed on the top surface and the bottom surface of a XY-4H×4H×64B-cuboid crystal.
Figure 34F:
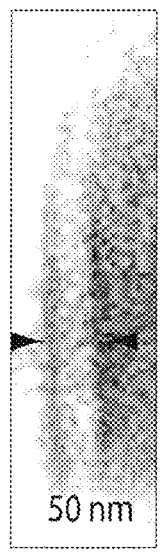
FIG. 34F shows a high-magnification TEM image a XY-4H×4H×64B-cuboid crystal with curvatures on the edge. Light gray arrows indicate curved positions where the two gold nanoparticle monolayers are visible.

Gold nanoparticles have been arranged into discrete patterns (Kuzyk, A. et al. *Nature* 483,311-314 (2012); Acuna, G P et al. *Science* 338,506-510 (2012); Aldaye, F A & Sleiman, H F. *Angew. Chem. Int. Ed.* 45,2204-2209 (2006)) and single-layer periodic patterns (Sharma, J. et al. *Science* 323,112-116 (2009)) using DNA structures as templates. However, it remains challenging to form closely-packed periodic patterns, especially multi-layer patterns, of gold nanoparticles. In order to demonstrate the use of the DNA-brick crystals for arranging materials, we designed and constructed closely-packed gold-nanoparticle structures: (1) a 2D arrangement of parallel gold-particle lines on a ZX-4H×6H×96-channel crystal (FIGS. 34A and 34B) and (2) a simple 3D arrangement of parallel gold-nanoparticle monolayers on the two surfaces of a XY-4H×4H×64-cuboid crystal (FIGS. 34C to 34E).

Figure 35A:
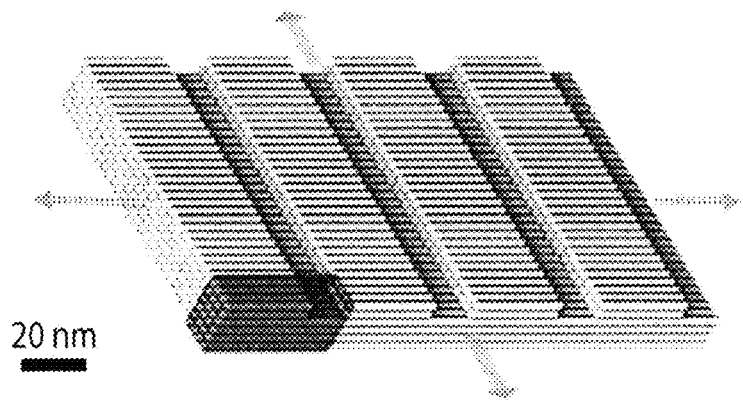
FIG. 35A shows the design of a ZX-4H×6H×96-channel crystal. The dark part represents a repeating unit.
Figure 35B:
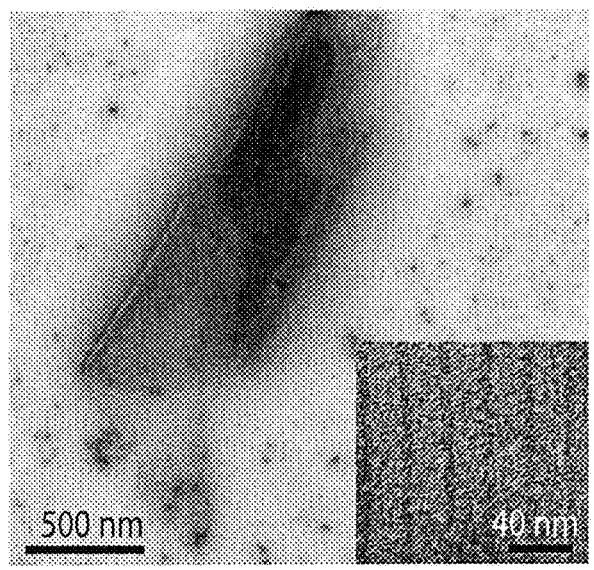
FIG. 35B shows a TEM image of the ZX-4H×6H×96-channel crystal.
Figure 35C:
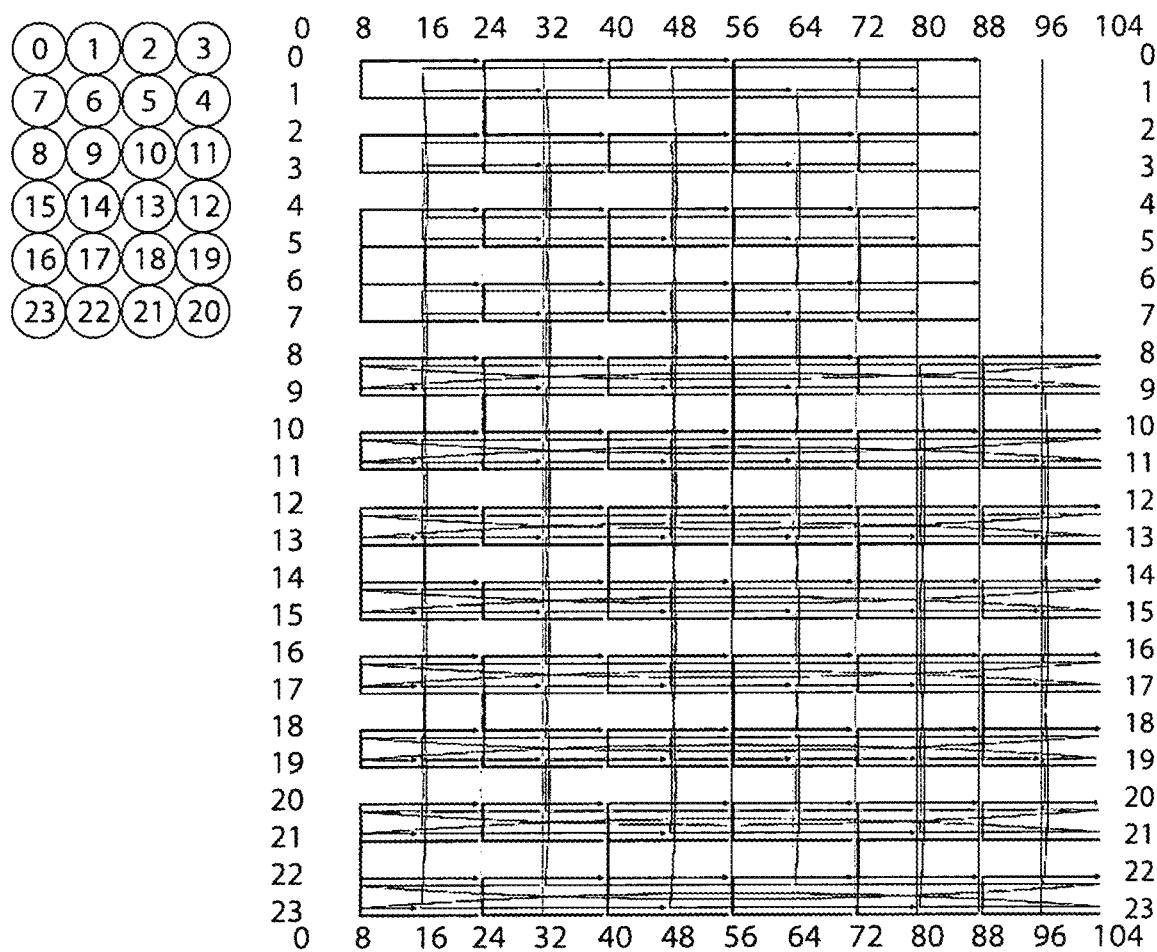
FIG. 35C shows a strand diagram of the ZX-4H×6H×96-channel crystal.

The design and TEM images of the ZX-4H×6H×96-channel crystal are shown in FIGS. 35A-35C. A channel is two-helix (5 nanometers) in depth and 32-bp (10.6 nanometers) in width. Neighboring parallel channels are separated by a 64-bp (21.2 nm) distance along the Z-axis. Gold nanoparticles functionalized with poly-A (ten consecutive adenine bases) DNA strands were arranged on the DNA crystals. Within the channels, every helix-end displays a poly-T single-stranded DNA for capturing the gold nanoparticles. The gold nanoparticles were successfully arranged into parallel lines consistent with our design. Within each line, a single chain of closely-packed gold nanoparticles was observed. The average distance between gold nanoparticles with a line is about 2 nanometers, except for some locations with clear defects (FIG. 34B). Two parallel gold-nanoparticle monolayers were assembled on the XY-4H×4H×64-cuboid crystal, as shown in FIG. 23C. The crystals displays poly-T sequences at each helix-end on both surfaces for capturing 10-nanometer gold nanoparticles functionalized with poly-A strands. The average distance between particles appeared to be about 1 to 2 nanometers (FIG. 34D). The structures sometimes curved on the edges (FIG. 34E). The edge-to-edge distance between the two monolayers of gold nanoparticles was measured to be about 25 nm, consistent with the designed crystal thickness.

Aligning gold nanoparticles into micron-scale ordered low-dimensional arrays is required in diverse plasmonic applica-tions (Melosh, N. A. et al. *Science* 300, 112-115 (2003); Qi, M. H. et al. *Nature* 429, 538-542 (2004)). In particular, nanoparticle arrays with less than 2 nm face-to-face spacing are expected to exhibit strong plasmonic coupling (Qi, M. H. et al., 2004). With DNA nanostructures as templates, gold nanoparticles have been arranged into chiral (Qi, M. H. et al., 2004), linear (Liu, N., et al. *Science* 332, 1407-1410 (2011); Tang, C. B., et al. *Science* 322, 429-432 (2008); Tavakkoli K. G., A. et al. *Science* 336, 1294-1298 (2012)), and branched patterns (Seeman, N.C. *J. Theor. Biol.* 99, 237-247 (1982); Chen, J. & Seeman, N. C. *Nature* 350, 631-633 (1991)). However, most of these structures are discrete sub-100 nm structures, which lack long-range ordering at micron scale. In addition, decreasing the interparticle spacing down to 2 nm is also challenging. Methods of producing DNA crystals of the invention provide a unique way to address these challenges. By varying the surface distribution of poly-T binding sites, gold nanoparticles were programmed with different 2D patterns at micron scale, from close-packing patterns to arrays of gold nanoparticle chain with 20-nm inter-chain spacing. The periodicity of poly-T binding site is 2.5 nm on DNA crystals, which reduced the inter-particle spacing to about 2 nm.

Our work presents generalized approaches to construct 3D square-lattice, honeycomb-lattice, and hexagonal-lattice DNA nanostructures from short synthetic DNA. Furthermore, we also demonstrated 102 intricate 3D shapes with diverse shapes and intricate features such as channels and pores. Our modular approach, accompanied by our simplified LEGO®-like model and computer-aided design process, provides a simple method for designing intricate 3D nanostructures. Because of the absence of the long scaffold strand, any voxel in a 3D canvas can be added or removed independently, allowing us to design shapes with 8 bp resolution. Taking advantage of the compactness and modularity of DNA bricks, we were able to assemble nanostructures with intricate features (such as thin cavities and passages) that may be difficult to achieve using DNA origami, where each staple strand component typically is much less compact and the scaffold is not modular at all. An 1000-voxel 3D DNA canvas provides up to $2^{1000}$~$10^{300}$ potential possibilities. However, each voxel must physically be connected to at least one of its neighboring voxels in order to self-assemble a complete shape. So the actual shapes that can be constructed are fewer.

We noticed that certain large or intricate designs may exhibit fragility. One example is the 3H×3H×1024B, which mostly broke into segments during TEM imaging after agarose-gel purification. One way to address this issue is through incorporation of longer synthetic DNA strands to some positions, especial to "weak points," of a nanostructure. These long strands may strengthen the shapes, like the scaffold strand does.

The ability to construct intricate 3D shapes will extend the range of challenges and applications that DNA nanotechnology can addresses, e.g. to make sophisticated DNA devices to mimic biosynthetic machineries, or to arrange guest molecules in 3D space to generate a variety of functional nanomaterials. In addition, 3D nanostructures made from synthetic DNA will allow researchers to design custom sequences tailored to their applications. Further, modular self-assembly using other synthetic informational polymers, including L-DNA, DNA with chemically modified backbones, DNA with artificial bases, and RNA may prove crucial for a variety of applications, such as drug delivery and therapeutic applications.

We have also provided a general methodology for constructing complex 3D DNA crystals with custom designed dimensions and nanoscale features. This is the first bottom-up self-assembly strategy that is capable of making genuine microscale 3D periodic structures, which can reach megadalton in size using repeating units that can be rationally designed at a few nanometers resolution. Using a variety of designs of periodic units—from a few hundred base pairs to several thousand base pairs—we constructed (1) 1D-growth DNA-bundle crystals that contain up to 108 parallel helices; (2) 2D-growth DNA multilayer crystals that are up to 20 layers (50 nm) in thickness; and (3) 2D-growth DNA-forest crystals that are up to 256 bp (84 nm) in height. Moreover, we demonstrated that complex nanometer scale surface features, channels, and porous patterns can be realized in the 3D crystals provided herein.

This assembly strategy is based on an understanding of DNA-origami and DNA-tile crystallization. Assembly of DNA-origami crystals herein may be carried out using a one-step-annealing reaction or a two-step-annealing reaction. In the one-annealing reaction, the scaffold, 5- to 10-fold staples, and connecting strands are annealed together. Without being bound by theory, it is believed that the DNA origami monomers have to formed correctly at earlier stages (at higher temperatures) of the annealing and then join with each other at later stages of annealing (at lower temperatures) to form crystals. The two-step-annealing reaction starts with an initial annealing of origami monomer excluding the connecting strands, followed by a purification step to obtain the origami monomers. The purified monomers are then mixed with connecting strands, and the mixture is subjected to a second annealing at a starting temperature lower than the first annealing step. In both cases, the assembly of DNA-origami crystals is a hierarchical process with two separate stages: monomer formation and crystallization of monomers.

Such a hierarchical crystallization may pose a few potential challenges. First, the formation of monomers and the crystallization may have to happen at two well-separated annealing stages. If the crystallization starts before the monomers are fully formed, it may be possible that defective monomers will compromise the growth of some well-ordered crystals. Second, the kinetics of incorporating a DNA origami monomer to a crystal may be slow because of the sheer size of the monomer and the large amount of negative charge of the monomer. These factors may prevent a crystal from reaching a large size within a reasonable annealing time. Third, successful crystallization may require some error-correction that involves re-occurring monomer incorporation and dissociation that eventually may result in the system reaching the lowest energy state. For a large origami monomer, the dissociation rate may be slow, which either may lead to defects in some crystals or may hinder crystal growth.

The DNA-brick crystal framework provided herein reveals a new perspective for making complex DNA crystals in three-dimensional space: fast kinetics during crystallization can be achieved without compromising informational complexity of the repeating units. Using a modular strategy that utilizes standardized components—like the DNA bricks—a repeating unit can contain thousands of base pairs, enabling complex designs in 3D space. Crystals grow through incorporation of individual bricks during DNA-brick crystallization, without the need to first form a multi-strand unit. Therefore, both the information complexity and fast kinetics for crystallization are realized in the modular DNA-brick crystals of the invention.

Rationally-designed, self-assembled DNA crystals of the invention may be used for templating functional moieties such as, but not limited to, proteins, nucleic acids, metallic particles, quantum dots, etc. Such a bottom-up approach can be used to fabricate micron-scaled periodic materials with nanoscale features. This technology facilitates arranging DNA crystals using top-down patterning, thus achieving one of the important goals of nanotechnology—combining efficient nanoscale DNA self-assembly with powerful top-down approaches for applications such as, for example, nanophotonics and nanoelectronics.

Methods and Materials

Sample Preparation.

DNA strands were synthesized by Integrated DNA Technology, Inc. or Bioneer Corporation. To assemble the structures, unpurified DNA strands were mixed to a final concentration of 100 nM or 200 nM per strand (for a nanostructure that contains more than 500 strands, an evaporation step was performed to achieve desired 200 nM concentration) in 0.5×TE buffer (5 mM Tris, pH 7.9, 1 mM EDTA) supplemented with 10 to 80 mM $MgCl_2$.

Annealing Ramps.

The strand mixture was then annealed in a PCR thermo cycler by a fast linear cooling step from 80° C. to 60° C. over 1 hour, then a 24 hour or 72 hour linear cooling ramp from 60° C. to 24° C. The annealing ramps were named according to length of the second cooling step, as 24-hour annealing or 72-hour annealing.

Agarose Gel Electrophoresis and Sample Purification.

Annealed samples were then subjected to 2 percent native agarose gel electrophoresis for 2 hours (gel prepared in 0.5×TBE buffer supplemented with 11 mM $MgCl_2$ and 0.005% (v/v) EtBr) in an ice water bath. Then, the target gel bands were excised and placed into a Freeze'N Squeeze column (Bio-Rad Laboratories, Inc.). The gel pieces were crushed into fine pieces by a microtube pestle in the column, and the column was then centrifuged at 7000 g for 5 minutes. Samples that were extracted through the column were collected for TEM or AFM imaging.

Robot Automation for Sample Preparation.

A Python program was designed to aid complex shapes design and automate strand mixing by using a liquid handling robot (Bravo, Agilent). For each shape, 4 µL of 10 µM of each strand in water solution was pipetted and mixed into a final volume of less than 2 mL (the exact volume was determined by the number of constituent strands for the target shape). The mixture was then vacufuge-dried (Savant Speedvac sc110) and resuspended in 200 µL 0.5×TE buffer with 40 mM $MgCl_2$. Each round of robot pipetting accommodated 48 shapes and took three to four days to complete.

Tem Imaging.

For imaging, 3.5 µL agarose-gel-purified or unpurified sample were adsorbed for 4 minutes onto glow discharged carbon-coated TEM grids and stained for 1 minute using a 2% aqueous uranyl formate solution containing 25 mM NaOH. Imaging was performed using a JEOL JEM-1400 operated at 80 kV.

AFM Imaging.

AFM images were obtained using an SPM Multimode with Digital Instruments Nanoscope V controller (Veeco). 5 µL of purified, annealed sample with purification followed by 40 µL of 0.5×TE (10 mM $MgCl_2$) was applied onto the surface of a freshly cleaved mica and left for approximately 2 minutes to allow for absorption. Dilution of the sample was sometimes performed to achieve the desired mica surface coverage. The AFM tips used were the short and thin cantilevers in the SNL-10 silicon nitride cantilever chip (Veeco Probes).

Methods and Materials for Crystal Growth Experiments.

Sample Preparation.

DNA strands were synthesized by Integrated DNA Technology, Inc. or Bioneer Corporation. To assemble the structures, unpurified DNA strands were mixed in an equimolar stoichiometric ratio to the highest possible concentration from a 100 µM stock in 0.5×TE buffer (5 mM Tris, pH 7.9, 1 mM EDTA) supplemented with 40 mM $MgCl_2$ or 60 mM $MgCl_2$.

Annealing Ramps.

The strand mixture was then annealed in a PCR thermo cycler by a fast linear cooling step from 80° C. to 60° C. over 1 hour, then a 72 hours or 168 hours linear cooling ramp from 60° C. to 24° C. The annealing ramps were named according to length of the second cooling step, as 72-hour annealing or 168-hour annealing.

Tem Imaging.

For imaging, 2.5 µL of annealed sample were adsorbed for 2 minutes onto glow-discharged, carbon-coated TEM grids. The grids were then stained for 10 seconds using a 2% aqueous uranyl formate solution containing 25 mM NaOH. Imaging was performed using a JEOL JEM-1400 TEM operated at 80 kV.

DNA-Decoration onto 10-nm Gold Nano-Particles.

Conjugation of thiolated DNA onto 10-nm gold nano-particles was achieved as previously described (Sharma, J. et al. *J. Am. Chem. Soc.* 130, 7820-7821, (2008)). In a typical experiment, 20 µL 2.5 µM phosphine-coated 10-nm gold nanoparticle was mixed with 0.5 µL 2 M NaNO3 and 0.65 µL 100 µM thiolated DNA in 0.25×TBE buffer. The reaction solution was incubated at room temperature for 36 hours in dark. After that, the reaction solution was loaded into 1% agarose gel containing 0.5×TBE buffer. The electrophoresis was running at 95 V for 1 hour in a gel box on an ice-water bath. The purple band was recovered by pestle crushing, followed by centrifugation for 3 min at 10,000 rpm at room temperature using "Freeze 'N Squeeze" DNA Gel Extraction spin columns (Bio-Rad). Recovered DNA molds were stored at 4° C. in the dark for further use. The sequence for the thiolated DNA was: 5'-AAAAAAAAAA-/3ThioMC3-D/.

Gold Nano Particle Decoration.

To 15 μL 400 mM NaCl solution, 0.8 μL (ZX-4H×6H×96B-channel crystal) or 0.6 μL (XY-4H×4H×64B-cuboid crystal) DNA samples were added. Then, 0.2 uL 95 nM 10 nm gold nanoparticles were introduced. After pipetting for 50 times, the reaction mixture was left at room temperature for three hours in the dark.

TABLE 2

List of strands for producing the nucleic acid structures of FIG. 3E. The individuals strands 0-4454 are designated as SEQ ID NOs. 6842-11296, respectively. See also Table 15 of U.S. provisional application number 61/675,309, filed Jul. 24, 2012, incorporated by reference herein.
Shape, total number of strands, [list of strands]

1, 517, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 68, 70, 72, 73, 74, 75, 76, 77, 78, 79, 80, 81, 82, 83, 84, 85, 86, 87, 91, 93, 94, 95, 96, 97, 98, 99, 100, 101, 102, 103, 104, 105, 106, 107, 108, 109, 112, 113, 115, 117, 118, 119, 120, 121, 122, 123, 124, 125, 126, 127, 128, 129, 130, 131, 132, 136, 138, 139, 140, 141, 142, 143, 144, 145, 146, 147, 148, 149, 150, 151, 152, 153, 154, 157, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 3018, 3036, 3038, 3056, 3058, 3076, 3078, 3096, 3707, 3789, 1305, 1307, 1309, 1312, 1319, 1322, 1329, 1332, 1339, 1342, 1349, 1357, 1361, 1365, 1369, 1373, 1375, 1379, 1383, 1387, 1391, 1393, 3826, 3859, 3861, 3862, 3894, 3896, 3897, 3898, 3929, 3931, 3933, 3934, 3966, 3968, 3969, 3970, 4001, 4003, 4005, 4006, 4038, 4040, 4041, 4042, 4073, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]

2, 504, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 68, 70, 72, 73, 74, 75, 76, 77, 78, 79, 80, 81, 82, 83, 84, 85, 86, 87, 95, 96, 97, 98, 99, 100, 101, 102, 103, 104, 105, 106, 107, 108, 109, 112, 113, 115, 117, 118, 119, 120, 121, 122, 123, 124, 125, 126, 127, 129, 131, 132, 136, 138, 139, 140, 141, 142, 143, 144, 145, 146, 147, 148, 149, 150, 151, 152, 153, 154, 157, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 272, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2747, 3018, 3036, 3038, 3056, 3058, 3076, 3078, 3096, 3227, 3707, 3789, 675, 1088, 1305, 1307, 1309, 1312, 1319, 1329, 1335, 1339, 1342, 1349, 1357, 1361, 1365, 1369, 1373, 1375, 1379, 1383, 1387, 1391, 1393, 3973, 3976, 4037, 4039, 4289, 4346, 4350, 3826, 3859, 3861, 3862, 3894, 3896, 3897, 3898, 3929, 3931, 3933, 3934, 3966, 3968, 4001, 4003, 4005, 4006, 4042, 4073, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]

3, 492, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 68, 70, 71, 72, 73, 74, 75, 76, 77, 78, 79, 80, 81, 82, 83, 84, 85, 86, 87, 95, 96, 97, 98, 99, 100, 101, 102, 103, 104, 105, 107, 109, 117, 118, 119, 120, 121, 122, 123, 124, 125, 126, 127, 129, 131, 132, 136, 138, 139, 140, 141, 142, 143, 144, 145, 146, 147, 148, 149, 150, 151, 152, 153, 154, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 272, 274, 275, 276, 277, 278, 279, 280, 281, 282, 283, 284, 285, 286, 287, 288, 289, 290, 291, 292, 293, 294, 295, 296, 297, 298, 299, 300, 306, 307, 308, 309, 310, 311, 312, 313, 314, 315, 316, 317, 318, 319, 320, 321, 322, 323, 324, 325, 326, 327, 328, 329, 336, 337, 338, 339, 340, 341, 342, 343, 344, 345, 346, 347, 348, 349, 350, 351, 352, 353, 354, 355, 356, 357, 358, 359, 366, 367, 368, 369, 370, 371, 372, 373, 374, 375, 376, 377, 378, 379, 380, 381, 382, 383, 384, 385, 386, 387, 388, 389, 395, 396, 397, 398, 399, 400, 401, 402, 403, 404, 405, 406, 407, 408, 409, 410, 411, 412, 413, 414, 415, 416, 417, 418, 419, 420, 421, 423, 424, 425, 426, 427, 428, 429, 430, 431, 432, 433, 434, 435, 436, 437, 438, 439, 440, 441, 442, 443, 444, 445, 446, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2747, 2833, 3018, 3036, 3038, 3056, 3058, 3076, 3078, 3096, 3227, 3317, 3707, 3789, 675, 716, 1045, 1088, 1126, 1305, 1307, 1309, 1312, 1319, 1335, 1339, 1342, 1349, 1357, 1361, 1365, 1369, 1373, 1375, 1379, 1383, 1387, 1391, 1393, 3973, 3976, 4002, 4004, 4007, 4010, 4037, 4039, 4257, 4289, 4318, 4346, 4350, 3826, 3859, 3861, 3862, 3894, 3896, 3897, 3898, 3929, 3931, 3933, 3966, 3968, 4042, 4073, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]

4, 480, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 68, 70, 71, 72, 73, 74, 75, 76, 77, 78, 79, 80, 81, 82, 83, 84, 85, 86, 96, 98, 99, 100, 101, 102, 103, 104, 105, 107, 109, 117, 118, 119, 120, 121, 122, 123, 124, 125, 126, 127, 136, 138, 140, 141, 142, 143, 144, 145, 146, 147, 148, 149, 150, 151, 152, 153, 154, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 272, 274, 275, 276, 277, 278, 279, 280, 281, 282, 283, 284, 285, 286, 287, 288, 289, 290, 291, 292, 293, 294, 295, 296, 297, 298, 299, 300, 306, 307, 308, 309, 310, 311, 312, 313, 314, 315, 316, 317, 318, 319, 320, 321, 322, 323, 324, 328, 336, 337, 338, 339, 340, 341, 342, 343, 344, 345, 346, 347, 348, 349, 350, 351, 352, 353, 354, 355, 356, 357, 358, 359, 366, 367, 368, 369, 370, 371, 372, 373, 374, 375, 376, 377, 378, 379, 380, 381, 382, 383, 395, 396, 397, 398, 399, 400, 401, 402, 403, 404, 405, 406, 407, 408, 409, 410, 411, 412, 413, 414, 415, 416, 417, 418, 419, 420, 421, 423, 424, 425, 426, 427, 428, 429, 430, 431, 432, 433, 434, 435, 436, 437, 438, 439, 440, 441, 442, 443, 444, 445, 447,

TABLE 2-continued

List of strands for producing the nucleic acid structures of FIG. 3E. The
individuals strands 0-4454 are designated as SEQ ID NOs. 6842-11296, respectively. See also
Table 15 of U.S. provisional application number 61/675,309, filed Jul. 24, 2012, incorporated
by reference herein.
Shape, total number of strands, [list of strands]

448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2556, 2747, 2761, 2833, 3018, 3036, 3038, 3056, 3058, 3076, 3078, 3096, 3227, 3317, 3707, 3789, 716, 751, 1045, 1077, 1088, 1126, 1158, 1305, 1307, 1309, 1312, 1319, 1335, 1339, 1342, 1349, 1357, 1361, 1365, 1369, 1373, 1375, 1379, 1383, 1387, 1391, 1393, 3972, 3975, 4002, 4004, 4007, 4010, 4031, 4035, 4257, 4281, 4289, 4318, 4342, 4346, 4350, 3826, 3859, 3861, 3862, 3894, 3896, 3897, 3898, 3929, 3931, 3933, 3966, 3968, 4042, 4073, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
5, 467, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 70, 71, 72, 73, 74, 75, 76, 77, 78, 79, 80, 81, 82, 83, 84, 85, 86, 96, 98, 99, 100, 101, 102, 103, 104, 109, 118, 120, 122, 123, 124, 125, 126, 127, 136, 138, 140, 141, 142, 143, 144, 145, 146, 147, 148, 149, 150, 151, 152, 153, 154, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 272, 274, 275, 276, 277, 278, 279, 280, 281, 282, 283, 284, 285, 286, 287, 288, 289, 290, 291, 292, 293, 294, 296, 298, 299, 300, 306, 307, 308, 309, 310, 311, 312, 313, 314, 315, 316, 317, 318, 319, 320, 321, 322, 323, 324, 328, 336, 337, 338, 339, 340, 341, 342, 343, 344, 345, 346, 347, 348, 349, 350, 351, 352, 353, 366, 367, 368, 369, 370, 371, 372, 373, 374, 375, 376, 377, 378, 379, 380, 381, 382, 383, 395, 396, 397, 398, 399, 400, 401, 402, 403, 404, 405, 406, 407, 408, 409, 410, 411, 412, 413, 419, 420, 421, 423, 424, 425, 426, 427, 428, 429, 430, 431, 432, 433, 434, 435, 436, 437, 438, 439, 440, 441, 442, 443, 444, 445, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2478, 2556, 2747, 2761, 2827, 2833, 3018, 3036, 3038, 3056, 3058, 3076, 3078, 3096, 3227, 3317, 3707, 3789, 722, 751, 1045, 1077, 1088, 1126, 1158, 1305, 1307, 1309, 1312, 1319, 1335, 1337, 1339, 1342, 1349, 1357, 1361, 1365, 1369, 1373, 1375, 1379, 1383, 1387, 1391, 1393, 3972, 3975, 3993, 3997, 4009, 4012, 4031, 4035, 4257, 4281, 4289, 4309, 4313, 4318, 4342, 4346, 4350, 4370, 4374, 3826, 3859, 3861, 3862, 3894, 3896, 3897, 3898, 3929, 3931, 3933, 3966, 3968, 4042, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
6, 453, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 70, 71, 72, 73, 74, 75, 76, 77, 78, 79, 80, 81, 82, 84, 85, 86, 100, 101, 102, 103, 104, 109, 118, 120, 122, 124, 126, 127, 136, 138, 141, 142, 143, 144, 145, 146, 147, 148, 149, 150, 151, 152, 153, 154, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 272, 274, 275, 276, 278, 280, 281, 282, 283, 284, 285, 286, 287, 288, 289, 290, 291, 292, 293, 294, 296, 298, 299, 300, 306, 307, 308, 309, 310, 311, 312, 313, 314, 315, 316, 317, 318, 319, 320, 321, 322, 323, 324, 328, 342, 343, 344, 345, 346, 347, 348, 349, 350, 351, 352, 353, 366, 367, 368, 369, 370, 371, 372, 373, 374, 375, 376, 377, 378, 379, 380, 381, 382, 383, 395, 401, 402, 403, 404, 405, 406, 407, 408, 409, 410, 411, 412, 413, 419, 420, 421, 423, 424, 425, 426, 427, 428, 429, 430, 431, 432, 433, 434, 435, 436, 437, 438, 439, 440, 441, 442, 443, 444, 445, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2478, 2538, 2556, 2747, 2761, 2767, 2827, 2833, 3018, 3036, 3038, 3056, 3058, 3076, 3078, 3096, 3227, 3317, 3707, 3789, 685, 722, 1045, 1077, 1088, 1126, 1158, 1305, 1307, 1309, 1312, 1319, 1335, 1337, 1339, 1342, 1349, 1357, 1361, 1365, 1369, 1373, 1375, 1379, 1383, 1387, 1391, 1393, 3980, 3984, 3993, 3997, 4009, 4012, 4029, 4033, 4257, 4281, 4289, 4291, 4295, 4309, 4313, 4318, 4342, 4346, 4350, 4352, 4356, 4370, 4374, 3826, 3859, 3861, 3862, 3894, 3896, 3897, 3898, 3929, 3931, 3933, 3966, 3968, 4042, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
7, 441, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 70, 71, 73, 74, 75, 76, 77, 78, 79, 80, 81, 82, 84, 85, 86, 100, 102, 104, 122, 124, 126, 127, 136, 138, 141, 142, 143, 144, 145, 146, 147, 148, 149, 150, 151, 152, 153, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 272, 274, 275, 276, 278, 280, 281, 282, 283, 284, 285, 286, 287, 288, 289, 290, 291, 292, 293, 294, 296, 298, 299, 300, 306, 310, 312, 313, 314, 315, 316, 317, 318, 319, 320, 321, 322, 323, 324, 328, 342, 343, 344, 345, 346, 347, 348, 349, 350, 351, 352, 353, 372, 373, 374, 375, 376, 377, 378, 379, 380, 381, 382, 383, 395, 401, 402, 403, 404, 405, 406, 407, 408, 409, 410, 411, 412, 413, 419, 420, 421, 423, 424, 425, 426, 427, 429, 430, 431, 432, 433, 434, 435, 436, 437, 438, 439, 440, 441, 442, 443, 444, 445, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2478, 2496, 2538, 2556, 2747, 2761, 2767, 2821, 2827, 2833, 3018, 3036, 3038, 3056, 3058, 3076, 3078, 3096, 3227, 3317, 3707, 3789, 685, 706, 1045, 1053, 1077, 1088, 1126, 1134, 1158, 1305, 1307, 1309, 1312, 1319, 1335, 1337, 1339, 1342, 1349, 1357, 1361, 1365, 1369, 1373, 1375, 1379, 1383, 1387, 1391, 1393, 3980, 3984, 3995, 3999, 4014, 4018, 4029, 4033, 4257, 4263, 4281, 4289, 4291, 4295, 4309, 4313, 4318, 4324, 4342, 4346, 4350, 4352, 4356, 4370, 4374, 3826, 3859, 3861, 3862, 3894, 3896, 3897, 3898, 3929, 3931, 3933, 3966, 3968, 4042, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
8, 429, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 70, 71, 73, 74, 75, 76, 77, 78, 79, 80, 81, 84, 85, 86, 104, 122, 136, 138, 141, 142, 143, 145, 146, 147, 148, 149, 150, 151, 152, 153, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 272, 274, 275, 276, 278, 280, 281, 282, 283, 284, 285, 286, 287, 288, 289, 290, 291, 292, 293, 294, 296, 298, 299, 300, 306, 310, 312, 313, 314, 315, 316, 317, 318, 322, 324, 328, 342, 343, 344, 345, 346, 347, 348, 349, 350, 351, 352, 353, 372, 373, 374, 375, 376, 377, 395, 401, 402, 403, 404, 405, 406, 407, 408, 409, 410, 411, 412, 413, 419, 420, 421, 423, 424, 425, 426, 427, 429, 430, 431, 432, 433, 434, 435, 436, 437, 438, 439, 441, 442, 443, 444, 445, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2478, 2496, 2536, 2538, 2556, 2747, 2761, 2767, 2781, 2821, 2827, 2833, 3018, 3036, 3038, 3056, 3058, 3076, 3078, 3096, 3227, 3317, 3707, 3789, 706, 741, 1045, 1053, 1069, 1077, 1088, 1126, 1134, 1150, 1158, 1305, 1307, 1309, 1312, 1319, 1335, 1337, 1339, 1342, 1349, 1357, 1361, 1365, 1369, 1373, 1375, 1379, 1383, 1387, 1391, 1393, 3978, 3982, 3995, 3999, 4014, 4018, 4023, 4027, 4257, 4263, 4275, 4281, 4289, 4291, 4295, 4309, 4313, 4318, 4324, 4336, 4342, 4346, 4350, 4352, 4356, 4370, 4374, 3826, 3859, 3861, 3862, 3894, 3896, 3897, 3898, 3929, 3931, 3933, 3966, 3968, 4042, 4075, 4077, 4078, 4110, 4112, 4113, 4114, 4145, 4147, 4149, 4182, 4184, 4185, 4187, 4188,

TABLE 2-continued

List of strands for producing the nucleic acid structures of FIG. 3E. The
individuals strands 0-4454 are designated as SEQ ID NOs. 6842-11296, respectively. See also
Table 15 of U.S. provisional application number 61/675,309, filed Jul. 24, 2012, incorporated
by reference herein.
Shape, total number of strands, [list of strands]

4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
9, 419, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 70, 71, 74, 75, 76, 77, 78, 79, 80, 81, 84, 85, 86, 104, 136, 138, 141, 142, 143, 145, 146, 147, 148, 149, 151, 152, 153, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 272, 274, 275, 276, 278, 280, 281, 282, 283, 284, 285, 286, 287, 288, 290, 292, 293, 294, 296, 298, 299, 300, 306, 310, 312, 313, 314, 315, 316, 317, 318, 322, 324, 328, 342, 343, 344, 345, 346, 347, 372, 373, 374, 375, 376, 377, 395, 401, 402, 403, 404, 405, 406, 407, 413, 419, 420, 421, 423, 424, 425, 426, 427, 429, 430, 431, 432, 433, 434, 435, 436, 437, 438, 439, 441, 442, 443, 444, 445, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2478, 2496, 2498, 2536, 2538, 2556, 2747, 2761, 2767, 2781, 2807, 2821, 2827, 2833, 3018, 3036, 3038, 3056, 3058, 3076, 3078, 3096, 3227, 3317, 3707, 3789, 697, 701, 732, 741, 745, 749, 1045, 1053, 1069, 1077, 1088, 1126, 1134, 1150, 1158, 1305, 1307, 1309, 1312, 1319, 1335, 1337, 1339, 1342, 1349, 1357, 1361, 1365, 1369, 1373, 1375, 1379, 1383, 1387, 1391, 1393, 1978, 3982, 4016, 4020, 4257, 4263, 4275, 4281, 4289, 4291, 4295, 4303, 4307, 4309, 4313, 4318, 4324, 4336, 4342, 4346, 4350, 4352, 4356, 4364, 4368, 4370, 4374, 3826, 3859, 3861, 3862, 3894, 3896, 3897, 3898, 3929, 3931, 3933, 3966, 3968, 4042, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
10, 503, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 70, 72, 74, 75, 76, 77, 79, 80, 81, 82, 84, 85, 86, 87, 91, 93, 94, 96, 97, 98, 99, 101, 102, 103, 104, 106, 107, 108, 109, 112, 115, 117, 119, 120, 121, 122, 124, 125, 126, 127, 129, 130, 131, 132, 136, 138, 139, 141, 142, 143, 144, 146, 147, 148, 149, 151, 152, 153, 154, 157, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 332, 333, 334, 335, 337, 338, 339, 340, 341, 343, 344, 345, 346, 347, 349, 350, 351, 352, 353, 355, 356, 357, 358, 359, 362, 363, 364, 365, 367, 368, 369, 370, 371, 373, 374, 375, 376, 377, 379, 380, 381, 382, 383, 385, 386, 387, 388, 389, 391, 392, 393, 394, 395, 397, 398, 399, 400, 401, 403, 404, 405, 406, 407, 409, 410, 411, 412, 413, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2478, 2498, 2518, 2538, 2747, 2767, 2787, 2807, 2827, 3018, 3036, 3038, 3056, 3058, 3076, 3078, 3096, 3227, 3387, 3466, 3707, 3789, 1305, 1307, 1309, 1312, 1319, 1325, 1327, 1335, 1337, 1339, 1342, 1349, 1357, 1361, 1365, 1369, 1373, 1375, 1379, 1383, 1387, 1391, 1393, 1576, 1586, 1596, 1606, 1616, 1622, 1632, 1642, 1652, 3826, 3859, 3861, 3862, 3894, 3896, 3897, 3898, 3929, 3931, 3933, 3934, 3966, 3968, 3970, 4003, 4005, 4006, 4038, 4040, 4042, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
11, 488, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 70, 71, 74, 75, 76, 79, 80, 81, 84, 85, 86, 91, 93, 96, 97, 98, 101, 102, 103, 106, 107, 108, 115, 116, 119, 120, 121, 124, 125, 126, 129, 130, 131, 134, 136, 138, 141, 142, 143, 146, 147, 148, 151, 152, 153, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 306, 307, 308, 309, 310, 312, 313, 314, 315, 316, 318, 319, 320, 321, 322, 324, 325, 326, 327, 328, 332, 333, 334, 337, 338, 339, 340, 343, 344, 345, 346, 349, 350, 351, 352, 355, 356, 357, 358, 362, 363, 367, 368, 369, 370, 373, 374, 375, 376, 379, 380, 381, 382, 385, 386, 387, 388, 391, 392, 393, 395, 397, 398, 399, 400, 401, 403, 404, 405, 406, 407, 409, 410, 411, 412, 413, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2478, 2496, 2498, 2516, 2518, 2536, 2538, 2556, 2747, 2761, 2767, 2781, 2787, 2801, 2807, 2821, 2827, 2833, 3018, 3036, 3038, 3056, 3058, 3076, 3078, 3096, 3227, 3317, 3387, 3466, 3477, 3560, 3707, 3789, 1305, 1307, 1309, 1312, 1319, 1325, 1327, 1335, 1337, 1339, 1342, 1349, 1357, 1361, 1365, 1369, 1373, 1375, 1383, 1387, 1391, 1393, 1576, 1583, 1586, 1593, 1596, 1603, 1606, 1613, 1616, 1619, 1622, 1629, 1632, 1639, 1642, 1649, 1652, 1659, 3826, 3859, 3861, 3862, 3894, 3896, 3897, 3898, 3929, 3931, 3933, 3966, 3968, 3970, 4003, 4005, 4038, 4042, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
12, 479, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 70, 71, 74, 75, 76, 79, 80, 81, 84, 85, 86, 91, 93, 96, 97, 98, 101, 102, 103, 106, 107, 108, 115, 116, 119, 120, 121, 124, 125, 126, 129, 130, 131, 134, 136, 138, 141, 142, 143, 146, 147, 148, 151, 152, 153, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 306, 307, 308, 309, 310, 312, 313, 314, 315, 316, 318, 319, 320, 321, 322, 324, 325, 326, 327, 328, 332, 333, 337, 338, 339, 343, 344, 345, 349, 350, 351, 355, 356, 357, 362, 363, 367, 368, 369, 373, 374, 375, 379, 380, 381, 385, 386, 387, 391, 392, 393, 395, 397, 398, 399, 400, 401, 403, 404, 405, 407, 409, 410, 411, 413, 415, 416, 417, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2478, 2496, 2498, 2516, 2518, 2536, 2538, 2556, 2747, 2761, 2767, 2781, 2787, 2801, 2807, 2821, 2827, 2833, 3018, 3036, 3038, 3056, 3058, 3076, 3078, 3096, 3227, 3317, 3387, 3397, 3413, 3429, 3445, 3461, 3466, 3560, 3576, 3592, 3608, 3624, 3707, 3789, 1305, 1307, 1309, 1312, 1319, 1325, 1327, 1335, 1337, 1339, 1342, 1349, 1357, 1361, 1365, 1369, 1373, 1375, 1379, 1383, 1387, 1391, 1393, 1576, 1586, 1596, 1606, 1616, 1622, 1632, 1642, 1652, 2031, 2039, 2047, 2055, 2063, 3826, 3859, 3861, 3862, 3894, 3896, 3897, 3898, 3929, 3931, 3933, 3966, 3968, 3970, 4003, 4005, 4038, 4042, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]

TABLE 2-continued

List of strands for producing the nucleic acid structures of FIG. 3E. The individuals strands 0-4454 are designated as SEQ ID NOs. 6842-11296, respectively. See also Table 15 of U.S. provisional application number 61/675,309, filed Jul. 24, 2012, incorporated by reference herein.
Shape, total number of strands, [list of strands]

13, 470, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 70, 71, 74, 75, 76, 79, 80, 81, 84, 85, 86, 91, 93, 96, 97, 98, 101, 102, 103, 106, 107, 108, 115, 116, 119, 120, 121, 124, 125, 126, 129, 130, 131, 134, 136, 138, 141, 142, 143, 146, 147, 148, 151, 152, 153, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 272, 273, 274, 275, 276, 277, 278, 279, 280, 281, 282, 283, 284, 285, 286, 287, 288, 289, 290, 291, 292, 293, 294, 295, 296, 297, 298, 299, 300, 302, 303, 306, 308, 309, 310, 312, 314, 315, 316, 318, 320, 321, 322, 324, 326, 327, 328, 332, 333, 338, 339, 344, 345, 350, 351, 356, 357, 362, 363, 368, 369, 374, 375, 380, 381, 386, 387, 391, 392, 393, 395, 397, 398, 399, 401, 403, 404, 405, 407, 409, 410, 411, 413, 415, 416, 417, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2478, 2496, 2498, 2516, 2518, 2536, 2538, 2556, 2747, 2761, 2767, 2781, 2787, 2801, 2807, 2821, 2827, 2833, 3018, 3036, 3038, 3056, 3058, 3076, 3078, 3096, 3227, 3307, 3317, 3323, 3339, 3355, 3371, 3397, 3413, 3429, 3445, 3461, 3466, 3482, 3498, 3514, 3530, 3560, 3576, 3592, 3608, 3624, 3707, 3789, 1305, 1307, 1309, 1312, 1319, 1325, 1327, 1335, 1337, 1339, 1342, 1349, 1357, 1361, 1365, 1369, 1373, 1375, 1379, 1383, 1387, 1391, 1393, 1986, 1994, 2002, 2010, 2018, 2031, 2039, 2047, 2055, 2063, 3826, 3859, 3861, 3862, 3894, 3896, 3897, 3898, 3929, 3931, 3933, 3966, 3968, 3970, 4003, 4005, 4038, 4042, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
14, 455, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 70, 71, 74, 75, 76, 79, 80, 81, 84, 85, 86, 91, 92, 96, 97, 101, 102, 106, 107, 111, 115, 119, 120, 124, 125, 129, 130, 136, 138, 141, 142, 143, 146, 147, 148, 151, 152, 153, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 272, 274, 275, 276, 277, 278, 280, 281, 282, 283, 284, 286, 287, 288, 289, 290, 292, 293, 294, 295, 296, 298, 299, 300, 302, 306, 308, 309, 310, 312, 314, 315, 316, 318, 320, 321, 322, 324, 326, 327, 328, 332, 338, 339, 344, 345, 350, 351, 356, 357, 362, 363, 368, 369, 374, 375, 380, 381, 386, 387, 391, 392, 395, 397, 398, 401, 403, 404, 407, 409, 410, 413, 415, 416, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2478, 2496, 2498, 2516, 2518, 2536, 2538, 2556, 2747, 2761, 2767, 2781, 2787, 2801, 2807, 2821, 2827, 2833, 3018, 3036, 3038, 3056, 3058, 3076, 3078, 3096, 3227, 3307, 3316, 3317, 3323, 3339, 3355, 3371, 3393, 3466, 3482, 3498, 3514, 3530, 3707, 3789, 1305, 1307, 1309, 1312, 1319, 1325, 1327, 1335, 1337, 1339, 1342, 1349, 1357, 1361, 1365, 1369, 1373, 1375, 1379, 1383, 1387, 1391, 1591, 1601, 1611, 1627, 1637, 1647, 1657, 1663, 1986, 1994, 2002, 2010, 2018, 4289, 4295, 4301, 4307, 4313, 4350, 4356, 4362, 4368, 4374, 3826, 3859, 3861, 3862, 3894, 3896, 3897, 3898, 3929, 3931, 3933, 3966, 3968, 4005, 4038, 4042, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
15, 450, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 70, 71, 74, 75, 76, 79, 80, 81, 84, 85, 86, 92, 97, 102, 107, 111, 115, 120, 125, 130, 136, 138, 141, 142, 143, 146, 147, 148, 151, 152, 153, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 272, 274, 275, 276, 277, 278, 280, 281, 282, 283, 284, 286, 287, 288, 289, 290, 292, 293, 294, 295, 296, 298, 299, 300, 302, 306, 308, 309, 310, 312, 314, 315, 316, 318, 320, 321, 322, 324, 326, 327, 328, 338, 339, 344, 345, 350, 351, 356, 357, 363, 368, 369, 374, 375, 380, 381, 386, 387, 391, 392, 395, 397, 398, 401, 403, 404, 407, 409, 410, 413, 415, 416, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2478, 2496, 2498, 2516, 2518, 2536, 2538, 2556, 2747, 2761, 2767, 2781, 2787, 2801, 2807, 2821, 2827, 2833, 3018, 3036, 3038, 3056, 3058, 3076, 3078, 3096, 3227, 3316, 3317, 3390, 3393, 3471, 3707, 3789, 1045, 1053, 1061, 1069, 1077, 1126, 1134, 1142, 1150, 1158, 1305, 1307, 1309, 1312, 1319, 1330, 1333, 1335, 1337, 1339, 1342, 1349, 1357, 1361, 1365, 1369, 1373, 1375, 1379, 1383, 1387, 1391, 1393, 1578, 1581, 1588, 1591, 1598, 1601, 1608, 1611, 1624, 1627, 1634, 1637, 1644, 1647, 1654, 1657, 1662, 1663, 4289, 4295, 4301, 4307, 4313, 4350, 4356, 4362, 4368, 4374, 3826, 3859, 3861, 3862, 3894, 3896, 3897, 3898, 3929, 3931, 3933, 3966, 3968, 4042, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
16, 441, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 70, 71, 74, 75, 76, 79, 80, 81, 84, 85, 86, 92, 97, 102, 107, 111, 115, 120, 125, 130, 136, 138, 141, 142, 143, 146, 147, 148, 151, 152, 153, 158, 160, 162, 163, 164, 165, 166, 167, 168, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 272, 274, 275, 276, 277, 278, 280, 281, 282, 283, 284, 286, 287, 288, 289, 290, 292, 293, 294, 295, 296, 298, 299, 300, 302, 306, 308, 309, 310, 312, 314, 315, 316, 318, 320, 321, 322, 324, 326, 327, 328, 339, 344, 345, 351, 357, 363, 369, 375, 381, 387, 391, 395, 397, 401, 403, 407, 409, 413, 415, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2478, 2496, 2498, 2516, 2518, 2536, 2538, 2556, 2747, 2761, 2767, 2781, 2787, 2801, 2807, 2821, 2827, 2833, 3018, 3036, 3038, 3056, 3058, 3076, 3078, 3096, 3227, 3316, 3317, 3390, 3393, 3406, 3422, 3438, 3454, 3551, 3567, 3583, 3599, 3615, 3707, 3789, 1045, 1053, 1061, 1069, 1077, 1126, 1134, 1142, 1150, 1158, 1305, 1307, 1309, 1312, 1319, 1330, 1333, 1335, 1337, 1339, 1342, 1349, 1357, 1361, 1365, 1369, 1373, 1375, 1379, 1383, 1387, 1391, 1393, 1581, 1591, 1601, 1611, 1627, 1637, 1647, 1657, 1663, 2028, 2036, 2044, 2052, 2060, 4289, 4295, 4301, 4307, 4313, 4350, 4356, 4362, 4368, 4374, 3826, 3859, 3861, 3862, 3894, 3896, 3897, 3898, 3929, 3931, 3933, 3966, 3968, 4042, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
17, 432, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 70, 71, 74, 75, 76, 79, 80, 81, 84, 85, 86, 92, 97, 102, 107, 111, 115, 120, 125, 130, 136, 138, 141, 142, 143, 146, 147, 148, 151, 152, 153, 158, 160, 162, 163, 164, 165, 166, 167, 168, 169, 170, 171, 172, 173, 174, 175, 176, 177, 181, 183,

TABLE 2-continued

List of strands for producing the nucleic acid structures of FIG. 3E. The
individuals strands 0-4454 are designated as SEQ ID NOs. 6842-11296, respectively. See also
Table 15 of U.S. provisional application number 61/675,309, filed Jul. 24, 2012, incorporated
by reference herein.
Shape, total number of strands, [list of strands]

184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 272, 274, 275, 276, 277, 278, 280, 281, 282, 283, 284, 286, 287, 288, 289, 290, 292, 293, 294, 295, 296, 298, 299, 300, 302, 306, 308, 310, 312, 314, 316, 318, 320, 322, 324, 326, 328, 391, 395, 397, 401, 403, 407, 409, 413, 415, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2478, 2496, 2498, 2516, 2518, 2536, 2538, 2556, 2747, 2761, 2767, 2781, 2787, 2801, 2807, 2821, 2827, 2833, 3018, 3036, 3038, 3056, 3058, 3076, 3078, 3096, 3227, 3316, 3317, 3332, 3348, 3364, 3380, 3390, 3406, 3422, 3438, 3454, 3473, 3489, 3505, 3521, 3537, 3551, 3567, 3583, 3599, 3615, 3707, 3789, 1045, 1053, 1061, 1069, 1077, 1126, 1134, 1142, 1150, 1158, 1305, 1307, 1309, 1312, 1319, 1330, 1333, 1335, 1337, 1339, 1342, 1349, 1357, 1361, 1365, 1369, 1373, 1375, 1379, 1383, 1387, 1391, 1393, 1989, 1997, 2005, 2013, 2021, 2028, 2036, 2044, 2052, 2060, 4289, 4295, 4301, 4307, 4313, 4350, 4356, 4362, 4368, 4374, 3826, 3859, 3861, 3862, 3894, 3896, 3897, 3898, 3929, 3931, 3933, 3966, 3968, 4042, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
18, 312, [6, 7, 11, 12, 29, 30, 33, 34, 35, 36, 39, 40, 71, 81, 89, 91, 96, 97, 98, 100, 101, 102, 106, 107, 108, 113, 115, 116, 119, 120, 123, 124, 125, 126, 129, 130, 134, 161, 171, 186, 187, 188, 190, 191, 192, 197, 198, 210, 214, 215, 232, 235, 246, 252, 253, 255, 258, 282, 283, 284, 285, 294, 295, 297, 300, 301, 303, 312, 313, 314, 315, 324, 325, 326, 327, 330, 331, 332, 333, 339, 342, 343, 344, 345, 351, 354, 355, 356, 357, 360, 361, 362, 363, 366, 372, 373, 374, 375, 378, 384, 385, 386, 387, 390, 392, 393, 402, 403, 404, 405, 414, 415, 416, 417, 420, 432, 433, 434, 435, 444, 446, 447, 459, 462, 464, 465, 471, 474, 483, 486, 489, 2227, 2240, 2247, 2260, 2267, 2318, 2329, 2369, 2387, 2580, 2587, 2620, 2627, 2678, 2689, 2718, 2729, 2921, 2947, 2980, 2987, 3038, 3049, 3058, 3069, 3089, 3117, 3217, 3233, 3547, 3691, 3723, 498, 527, 582, 587, 607, 611, 631, 642, 651, 655, 662, 787, 791, 811, 822, 831, 835, 842, 896, 902, 962, 966, 973, 989, 1054, 1070, 1133, 1137, 1149, 1153, 1176, 1192, 1205, 1214, 1230, 1248, 1255, 1277, 1302, 1315, 1317, 1318, 1319, 1320, 1322, 1323, 1329, 1332, 1335, 1336, 1337, 1338, 1339, 1340, 1343, 1359, 1361, 1362, 1365, 1367, 1369, 1370, 1379, 1380, 1381, 1383, 1387, 1388, 1389, 1472, 1761, 1879, 1887, 1895, 1927, 1943, 1951, 1967, 1983, 1991, 2007, 2023, 2031, 2039, 2047, 2055, 2063, 2071, 2087, 2103, 2111, 2127, 2143, 2167, 2183, 2191, 2195, 2199, 3853, 3863, 3866, 3902, 3906, 3910, 3922, 3926, 3936, 3944, 3960, 4043, 4046, 4050, 4054, 4066, 4070, 4080, 4088, 4104, 4117, 4146, 4153, 4175, 4202, 4207, 4210, 4218, 4221, 4226, 4231, 4243, 4264, 4276, 4292, 4304, 4377, 4384, 4396, 4421, 4427, 3969, 3970, 4001, 4003, 4005, 4038, 4193, 4196, 4441, 4443]
19, 147, [6, 7, 11, 12, 16, 17, 23, 25, 26, 28, 29, 30, 31, 33, 34, 35, 36, 39, 41, 48, 50, 51, 52, 53, 56, 57, 61, 62, 66, 86, 93, 229, 232, 235, 238, 240, 246, 249, 252, 255, 258, 259, 261, 264, 265, 267, 276, 277, 278, 279, 282, 288, 294, 318, 319, 320, 321, 324, 325, 326, 327, 336, 338, 339, 378, 384, 2220, 2227, 2240, 2247, 2260, 2267, 2280, 2287, 2426, 2437, 2446, 2457, 2466, 2718, 2729, 3156, 495, 585, 652, 675, 742, 762, 1021, 1029, 1037, 1149, 1157, 1307, 1309, 1317, 1357, 1361, 1365, 1369, 1373, 1871, 1879, 1887, 1895, 1903, 1919, 1927, 1935, 1943, 1975, 1983, 1999, 2055, 2063, 3829, 3893, 3895, 3901, 3942, 3952, 3965, 3967, 3973, 3977, 3981, 4024, 4039, 4239, 4245, 4251, 4255, 4261, 4267, 4335, 4341, 4351, 3859, 3861, 4188, 4189, 4192, 4193, 4196, 4197, 4200, 4201, 4204]
20, 144, [6, 7, 11, 12, 16, 17, 23, 25, 26, 28, 29, 30, 31, 33, 34, 35, 36, 39, 41, 51, 52, 55, 56, 57, 58, 61, 62, 66, 81, 103, 120, 229, 232, 235, 238, 240, 246, 249, 252, 253, 255, 258, 261, 264, 267, 276, 282, 283, 284, 285, 288, 289, 290, 291, 294, 312, 313, 314, 315, 342, 344, 345, 348, 350, 372, 2220, 2227, 2240, 2247, 2260, 2267, 2280, 2287, 2397, 2406, 2417, 2446, 2457, 2466, 2678, 2709, 3156, 3211, 3419, 3444, 495, 651, 706, 733, 1013, 1037, 1080, 1141, 1184, 1307, 1309, 1317, 1357, 1361, 1365, 1369, 1373, 1871, 1879, 1887, 1895, 1903, 1919, 1927, 1935, 1943, 1967, 2007, 2015, 2047, 3829, 3893, 3895, 3901, 3942, 3946, 3951, 3978, 3982, 3995, 4023, 4233, 4251, 4255, 4261, 4273, 4329, 4363, 3859, 3861, 4188, 4189, 4192, 4193, 4196, 4197, 4200, 4201, 4204]
21, 144, [12, 36, 58, 79, 80, 81, 84, 85, 93, 95, 96, 97, 98, 100, 102, 103, 120, 124, 125, 129, 131, 138, 176, 187, 235, 252, 253, 255, 282, 283, 284, 285, 288, 289, 290, 291, 312, 313, 314, 315, 321, 336, 337, 339, 342, 344, 345, 348, 350, 372, 378, 379, 380, 381, 384, 385, 386, 387, 396, 397, 398, 399, 438, 440, 444, 446, 447, 456, 2247, 2260, 2519, 2539, 2552, 2678, 2698, 2709, 2937, 2946, 3125, 3130, 3377, 3444, 3684, 3691, 508, 561, 616, 672, 675, 706, 733, 765, 832, 867, 1014, 1141, 1253, 1302, 1365, 1367, 1887, 1927, 1935, 1967, 1999, 2007, 2015, 2047, 2055, 2063, 2079, 2135, 2143, 2159, 3851, 3870, 3874, 3879, 3906, 3910, 3923, 3942, 3946, 3973, 3995, 4037, 4039, 4045, 4049, 4053, 4096, 4109, 4111, 4117, 4234, 4274, 4280, 4329, 4357, 4363, 4412, 4445, 4193, 4196]
22, 388, [8, 12, 28, 30, 32, 33, 34, 35, 36, 37, 41, 48, 50, 51, 52, 53, 54, 55, 56, 57, 58, 59, 60, 62, 64, 68, 70, 72, 73, 74, 75, 76, 77, 78, 79, 80, 81, 82, 83, 84, 85, 86, 87, 89, 91, 93, 94, 95, 96, 97, 98, 99, 100, 101, 102, 103, 104, 105, 106, 107, 108, 109, 112, 113, 115, 117, 118, 119, 120, 121, 122, 123, 124, 125, 126, 127, 128, 129, 130, 131, 132, 136, 138, 140, 141, 142, 143, 144, 145, 146, 147, 148, 149, 150, 151, 152, 153, 154, 157, 162, 163, 164, 165, 166, 167, 168, 169, 170, 171, 172, 174, 176, 186, 188, 190, 191, 192, 193, 194, 199, 214, 216, 233, 236, 251, 252, 253, 255, 256, 257, 258, 259, 261, 263, 276, 277, 279, 281, 282, 283, 284, 285, 286, 287, 288, 289, 290, 291, 292, 293, 299, 305, 306, 307, 308, 309, 310, 311, 312, 313, 314, 315, 316, 317, 318, 319, 320, 321, 322, 323, 324, 325, 327, 329, 330, 331, 333, 335, 336, 337, 338, 339, 340, 341, 342, 343, 344, 345, 346, 347, 348, 349, 350, 351, 352, 353, 354, 355, 356, 357, 358, 359, 360, 362, 364, 365, 366, 367, 368, 369, 370, 371, 372, 373, 374, 375, 376, 377, 378, 379, 380, 381, 382, 383, 384, 385, 386, 387, 388, 389, 390, 394, 396, 397, 398, 399, 400, 401, 402, 403, 404, 405, 406, 407, 408, 409, 410, 411, 412, 413, 414, 416, 418, 419, 426, 428, 430, 431, 432, 433, 434, 435, 436, 437, 438, 439, 440, 441, 442, 443, 444, 448, 456, 460, 462, 464, 466, 467, 468, 470, 472, 473, 486, 488, 489, 491, 2247, 2261, 2764, 2826, 2838, 2916, 2964, 2986, 3038, 3056, 3058, 3076, 3130, 3162, 3208, 3256, 3290, 3306, 3384, 3400, 505, 571, 585, 813, 887, 913, 934, 950, 975, 998, 1006, 1039, 1047, 1165, 1237, 1253, 1322, 1329, 1332, 1337, 1361, 1365, 1367, 1383, 1387, 3836, 3851, 3855, 3865, 3868, 3887, 3901, 3930, 3932, 4082, 4109, 4111, 4116, 4119, 4141, 4162, 4177, 4190, 4212, 4223, 4228, 4254, 4260, 4347, 4375, 4379, 4401, 4412, 4425, 4428, 4435, 4437, 3933, 3934, 3966, 3969, 3970, 4001, 4003, 4005, 4006, 4038, 4040, 4041, 4042, 4075, 4192, 4193, 4195, 4196, 4199, 4438, 4439, 4441, 4443, 4444, 4446]
23, 281, [1, 3, 6, 7, 8, 11, 12, 13, 16, 17, 18, 23, 25, 27, 28, 29, 30, 31, 32, 33, 34, 35, 36, 37, 39, 41, 51, 53, 55, 56, 57, 58, 59, 60, 61, 62, 63, 64, 67, 68, 70, 72, 73, 74, 75, 76, 77, 79, 81, 101, 103, 105, 106, 107, 108, 109, 112, 113, 115, 117, 119, 121, 151, 153, 157, 230, 233, 236, 239, 240, 241, 243, 244, 245, 246, 247, 249, 250, 251, 252, 253, 255, 256, 257, 258, 259, 261, 262, 263, 264, 268, 276, 280, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 322, 342, 346, 348, 349, 350, 351, 352, 353, 354, 355, 356, 357, 358, 359, 360, 361, 362, 363, 364, 365, 366, 367, 368, 369, 370, 371, 372, 376, 408, 412, 414, 415, 416, 417, 418, 419, 420, 421, 422, 423, 424, 425, 426, 430, 474, 478, 480, 2207, 2227, 2241, 2247, 2261, 2267, 2281, 2287, 2293, 2376, 2424, 2536, 2624, 2696, 2824, 2856, 3016, 3789, 904, 908, 945, 947, 997, 1013, 1069, 1101, 1141, 1189, 1213, 1277, 1305, 1307, 1309, 1319, 1329, 1339, 1347, 1348, 1349, 1350, 1355, 1356, 1357, 1358, 1361, 1365, 1369, 1373, 1375, 1403, 3893, 3895, 3900, 3903, 3957, 3961, 3978, 3982, 4021, 4025, 4058, 4062, 4085, 4089, 4138, 4142, 4222, 4233, 4275, 4299, 4329, 4365, 4383, 4427, 3826, 3859, 3861, 3862, 3929, 3931, 3933, 3934, 4001, 4003, 4005, 4006, 4073, 4075, 4077, 4078, 4189, 4191, 4192, 4193, 4195, 4196, 4197, 4199, 4200, 4201, 4203, 4204, 4431]
24, 189, [91, 95, 98, 99, 100, 101, 102, 103, 104, 109, 118, 119, 122, 123, 125, 126, 127, 129, 131, 132, 136, 140, 143, 144, 145, 146, 147, 148, 149, 154, 283, 311, 313, 317, 319, 323, 329, 336, 337, 340, 341, 342, 343, 345, 346, 347, 348, 349, 352, 353, 366, 367, 370, 371, 372, 373, 374, 375, 376, 377, 378, 379, 380, 381, 382, 383, 384, 385, 388, 389, 396, 397, 400, 401, 402, 403, 404, 406, 407, 408, 409, 412, 413,

TABLE 2-continued

List of strands for producing the nucleic acid structures of FIG. 3E. The individuals strands 0-4454 are designated as SEQ ID NOs. 6842-11296, respectively. See also Table 15 of U.S. provisional application number 61/675,309, filed Jul. 24, 2012, incorporated by reference herein.
Shape, total number of strands, [list of strands]

426, 432, 436, 438, 442, 444, 466, 2499, 2504, 2510, 2513, 2519, 2524, 2530, 2533, 2539, 2544, 2550, 2553, 2858, 2861, 2871, 2876, 2878, 2881, 2891, 2896, 2898, 2901, 2911, 2916, 3241, 3274, 3322, 3346, 3351, 3362, 3368, 3369, 3424, 3587, 3653, 3660, 3661, 3675, 3677, 3702, 3734, 3765, 640, 674, 675, 711, 722, 764, 765, 801, 812, 852, 982, 990, 1027, 1059, 1083, 1213, 1237, 1261, 1296, 1300, 1496, 1497, 1502, 1506, 1507, 1513, 1767, 1772, 1773, 1776, 1782, 1783, 1958, 1982, 1995, 1998, 2011, 2014, 2035, 2038, 2059, 2062, 2075, 2078, 2091, 2094, 2115, 2139, 3976, 3980, 3993, 4012, 4016, 4037, 4048, 4052, 4065]
25, 256, [1, 3, 6, 7, 8, 11, 12, 13, 16, 17, 18, 25, 27, 29, 30, 31, 32, 34, 35, 36, 37, 39, 40, 41, 42, 48, 49, 52, 53, 54, 57, 58, 59, 62, 63, 64, 67, 70, 72, 75, 76, 77, 80, 81, 82, 85, 86, 87, 93, 94, 98, 99, 103, 104, 108, 109, 112, 117, 121, 122, 126, 127, 131, 132, 227, 230, 233, 236, 239, 243, 244, 245, 249, 250, 251, 255, 256, 257, 261, 262, 263, 267, 268, 269, 273, 274, 275, 278, 279, 280, 281, 284, 285, 286, 287, 290, 291, 292, 293, 296, 297, 298, 299, 302, 303, 304, 305, 308, 309, 310, 311, 314, 315, 316, 317, 320, 321, 322, 323, 326, 327, 328, 329, 334, 335, 339, 340, 341, 345, 346, 347, 351, 352, 353, 357, 358, 359, 364, 365, 370, 371, 376, 377, 382, 383, 388, 389, 400, 406, 412, 418, 2221, 2241, 2261, 2281, 2293, 2391, 2411, 2431, 2451, 2574, 2594, 2614, 2634, 2650, 2759, 2764, 2779, 2784, 2799, 2804, 2819, 2824, 2836, 3107, 3163, 3179, 3195, 3211, 3230, 3390, 3395, 3406, 3422, 3438, 3454, 3491, 3507, 3523, 3539, 3558, 1212, 1220, 1228, 1236, 1244, 1305, 1307, 1317, 1320, 1323, 1326, 1328, 1338, 1355, 1357, 1361, 1365, 1369, 1373, 1396, 1406, 1416, 1426, 1436, 1442, 1452, 1462, 1472, 1534, 1544, 1554, 1564, 1572, 1626, 1636, 1646, 1656, 1866, 2030, 3826, 3859, 3861, 3862, 3894, 3896, 3898, 3931, 3934, 3968, 4006, 4040, 4187, 4188, 4189, 4191, 4192, 4193, 4195, 4196, 4197, 4199, 4200, 4201, 4203, 4204]
26, 319, [18, 23, 27, 28, 29, 33, 34, 38, 39, 42, 48, 50, 51, 55, 56, 60, 68, 69, 73, 74, 78, 79, 83, 84, 88, 91, 95, 96, 100, 101, 105, 106, 113, 114, 118, 119, 123, 124, 128, 129, 133, 136, 140, 141, 145, 146, 150, 151, 158, 163, 164, 168, 169, 173, 174, 179, 184, 185, 186, 190, 191, 195, 202, 206, 219, 227, 230, 231, 234, 239, 240, 241, 244, 245, 246, 247, 251, 252, 253, 258, 259, 264, 265, 268, 269, 270, 271, 274, 276, 277, 282, 283, 288, 289, 294, 295, 298, 300, 301, 306, 307, 312, 313, 318, 319, 324, 325, 330, 331, 336, 337, 342, 343, 348, 349, 354, 355, 360, 361, 366, 367, 372, 373, 378, 379, 384, 385, 390, 391, 396, 397, 402, 403, 408, 409, 414, 415, 420, 421, 425, 426, 427, 431, 432, 433, 438, 439, 444, 445, 449, 450, 455, 456, 460, 461, 462, 463, 468, 469, 474, 478, 479, 480, 483, 485, 486, 489, 492, 494, 2207, 2221, 2227, 2232, 2247, 2252, 2267, 2287, 2293, 2404, 2476, 2853, 2913, 3018, 3036, 3038, 3041, 3058, 3061, 3078, 3096, 3176, 3253, 3309, 3325, 3373, 3632, 3648, 3696, 3707, 3720, 3789, 1305, 1307, 1309, 1312, 1319, 1322, 1329, 1332, 1339, 1342, 1349, 1357, 1361, 1365, 1369, 1373, 1375, 1379, 1383, 1387, 1391, 1393, 1883, 1891, 1923, 1931, 1963, 1971, 1987, 1995, 2003, 2011, 2019, 2027, 2035, 2043, 2051, 2059, 2067, 2075, 2083, 2091, 2099, 2123, 2131, 2163, 2171, 2193, 2197, 3835, 3839, 3852, 3873, 3890, 3907, 3924, 3928, 4089, 4106, 4123, 4127, 4140, 4144, 4161, 4178, 4227, 4233, 4251, 4259, 4265, 4283, 4348, 4354, 4372, 4380, 4386, 4404, 3826, 3859, 3861, 3862, 3894, 3896, 3897, 3898, 3929, 3931, 3969, 4001, 4041, 4073, 4077, 4078, 4110, 4113, 4114, 4145, 4147, 4149, 4182, 4184, 4185, 4187, 4188, 4189, 4191, 4200, 4201, 4203, 4204, 4431, 4433, 4434, 4436, 4448, 4449, 4451, 4454]
27, 161, [8, 12, 30, 31, 32, 34, 35, 36, 37, 41, 48, 49, 51, 52, 53, 54, 55, 56, 57, 58, 59, 62, 63, 64, 67, 75, 76, 77, 79, 80, 81, 82, 86, 102, 103, 104, 149, 233, 236, 245, 251, 253, 255, 256, 257, 261, 263, 269, 275, 280, 281, 282, 283, 284, 285, 286, 287, 290, 291, 292, 293, 298, 299, 310, 312, 314, 315, 316, 317, 320, 322, 323, 328, 344, 346, 347, 376, 377, 406, 407, 2230, 2261, 2313, 2339, 2367, 2373, 2382, 2486, 2491, 2496, 2498, 2556, 2611, 2891, 3130, 3195, 3208, 3219, 3240, 3274, 3298, 3317, 3355, 3427, 3445, 3506, 3587, 3669, 509, 553, 574, 643, 664, 710, 749, 782, 791, 839, 952, 964, 971, 1003, 1057, 1081, 1092, 1101, 1124, 1152, 1268, 1316, 1318, 1365, 1367, 1416, 1446, 1452, 1552, 1566, 1596, 1690, 1870, 1910, 1916, 1956, 3851, 3855, 3980, 3984, 4020, 4212, 4295, 4305, 4327, 4337, 3862, 3968, 4192, 4193, 4195, 4196, 4199]
28, 244, [2, 3, 6, 7, 8, 11, 12, 13, 16, 17, 25, 26, 28, 29, 30, 31, 32, 33, 34, 35, 36, 37, 39, 40, 41, 44, 46, 51, 52, 53, 56, 57, 58, 62, 63, 66, 75, 79, 80, 81, 96, 97, 98, 101, 102, 103, 107, 120, 124, 125, 126, 141, 142, 143, 146, 147, 148, 152, 165, 169, 170, 171, 192, 230, 233, 236, 238, 246, 247, 250, 251, 252, 253, 255, 256, 257, 258, 259, 261, 262, 263, 267, 276, 278, 279, 280, 282, 284, 285, 286, 288, 290, 291, 292, 308, 314, 315, 320, 321, 344, 345, 350, 351, 374, 375, 380, 381, 404, 405, 410, 411, 434, 435, 440, 441, 464, 465, 470, 2210, 2227, 2241, 2247, 2261, 2267, 2280, 2281, 2298, 2313, 2359, 2376, 2397, 2406, 2424, 2446, 2447, 2464, 2503, 2512, 2542, 2549, 2683, 2692, 2722, 2729, 2863, 2872, 2902, 2909, 2951, 2956, 2957, 2971, 2977, 2994, 3046, 3068, 3109, 3138, 3151, 3156, 3211, 3224, 3230, 3259, 3275, 3301, 3332, 3349, 3365, 3406, 3409, 3487, 3492, 3566, 3569, 3647, 3652, 3726, 3764, 3810, 636, 665, 726, 755, 816, 845, 1009, 1013, 1048, 1080, 1305, 1317, 1355, 1361, 1365, 1369, 1371, 1374, 1385, 1824, 1827, 1846, 1866, 1871, 1911, 1962, 1970, 2002, 2007, 2010, 2015, 2042, 2047, 2050, 2055, 2082, 2087, 2090, 2095, 2122, 2127, 2130, 2135, 2167, 2175, 4251, 4265, 3859, 3861, 3894, 3898, 4188, 4189, 4191, 4192, 4193, 4195, 4196, 4197, 4199, 4200, 4441]
29, 294, [1, 6, 11, 16, 23, 24, 28, 29, 33, 34, 36, 38, 39, 43, 46, 50, 51, 53, 54, 55, 56, 57, 58, 59, 60, 61, 68, 69, 73, 74, 75, 77, 78, 79, 80, 81, 82, 83, 84, 88, 91, 95, 96, 98, 99, 100, 101, 102, 103, 104, 105, 106, 109, 113, 114, 118, 119, 120, 121, 122, 123, 124, 125, 126, 127, 128, 129, 140, 141, 145, 146, 147, 148, 150, 151, 163, 164, 168, 169, 190, 191, 240, 241, 246, 247, 248, 252, 253, 254, 257, 258, 259, 260, 263, 264, 265, 266, 270, 271, 276, 277, 278, 281, 282, 283, 285, 286, 287, 288, 289, 291, 292, 293, 294, 295, 296, 300, 301, 306, 307, 309, 310, 311, 312, 313, 314, 315, 316, 317, 318, 319, 320, 321, 322, 323, 324, 325, 326, 330, 336, 337, 338, 340, 341, 342, 343, 344, 345, 346, 347, 348, 349, 350, 351, 352, 353, 354, 355, 356, 360, 366, 367, 372, 373, 374, 376, 377, 378, 379, 380, 382, 383, 384, 386, 396, 398, 402, 403, 406, 408, 409, 414, 426, 432, 433, 434, 438, 440, 462, 464, 468, 486, 2207, 2227, 2241, 2247, 2261, 2267, 2287, 2333, 2353, 2461, 2485, 2548, 2665, 2728, 2737, 2749, 2776, 2804, 2813, 2901, 2949, 3061, 3149, 3232, 3309, 3387, 3392, 3469, 3493, 3531, 3563, 3605, 3613, 3645, 3675, 3739, 3757, 3801, 806, 812, 886, 912, 1125, 1197, 1213, 1269, 1305, 1307, 1309, 1312, 1319, 1322, 1329, 1357, 1361, 1365, 1369, 1373, 1383, 1399, 1409, 1419, 1429, 1437, 1445, 1475, 1489, 1527, 1579, 1617, 1725, 1735, 1779, 3874, 3889, 3903, 3925, 3940, 3963, 3975, 3997, 4035, 4056, 4194, 4198, 4211, 4216, 4220, 4236, 4323, 4355, 4359, 4365, 4391, 4397, 3897, 3929, 3969, 4001, 4185, 4189, 4193, 4197, 4201]
30, 389, [3, 8, 13, 18, 25, 29, 30, 31, 32, 35, 36, 39, 40, 41, 42, 46, 49, 52, 57, 59, 61, 62, 67, 70, 74, 75, 80, 84, 85, 93, 94, 97, 98, 102, 103, 104, 107, 108, 112, 115, 120, 121, 122, 125, 126, 130, 131, 132, 136, 139, 142, 147, 149, 151, 152, 157, 160, 164, 165, 170, 174, 175, 181, 183, 184, 187, 188, 192, 193, 194, 196, 197, 198, 202, 206, 211, 216, 221, 227, 230, 233, 236, 239, 243, 244, 245, 247, 249, 250, 255, 256, 257, 261, 262, 265, 267, 268, 269, 273, 274, 275, 276, 277, 278, 279, 285, 286, 287, 288, 290, 291, 294, 295, 296, 297, 298, 299, 303, 304, 305, 306, 308, 309, 315, 316, 317, 318, 320, 321, 324, 326, 327, 328, 329, 333, 334, 335, 341, 345, 346, 347, 353, 357, 358, 359, 363, 364, 365, 369, 370, 375, 376, 377, 381, 382, 387, 388, 389, 393, 394, 395, 397, 399, 405, 406, 407, 409, 411, 417, 418, 419, 423, 424, 425, 426, 427, 428, 429, 435, 436, 437, 438, 439, 440, 441, 444, 446, 447, 448, 449, 454, 455, 456, 458, 461, 466, 467, 468, 470, 473, 474, 476, 478, 479, 485, 488, 491, 494, 2215, 2221, 2235, 2241, 2255, 2261, 2275, 2281, 2291, 2293, 2299, 2316, 2356, 2359, 2400, 2417, 2440, 2457, 2478, 2538, 2601, 2641, 2676, 2716, 2760, 2767, 2777, 2800, 2807, 2817, 2946, 2961, 2986, 3001, 3026, 3036, 3046, 3056, 3066, 3076, 3086, 3096, 3167, 3194, 3199, 3215, 3275, 3406, 3438, 3454, 3567, 3599, 3610, 3615, 3691, 3715, 3789, 3794, 3810, 3818, 543, 551, 582, 585, 626, 633, 652, 659, 672, 765, 777, 788, 821, 832, 839, 867, 878, 896, 950, 958, 962, 1053, 1069, 1077, 1134, 1150, 1158, 1180, 1196, 1253, 1269, 1277, 1306, 1308, 1310, 1313, 1320, 1321, 1323, 1324, 1330, 1333, 1340, 1341, 1343, 1344, 1350, 1358, 1360, 1362, 1366, 1368, 1370, 1374, 1376, 1380, 1382, 1384, 1388, 1390, 1392, 1394, 1547, 1567, 1727, 1747, 1868, 1884, 1908, 1924, 1948, 1964, 1988, 2004, 2028, 2036, 2044, 2052, 2060, 2068, 2084, 2108, 2124, 2148, 2164, 2186, 2194, 3905, 3914, 3939, 3948, 3964, 4079, 4083, 4092, 4108, 4109, 4235, 4247, 4296, 4308, 4414, 4424, 3862, 3896, 3898, 3931, 3970, 4003, 4006, 4040, 4042, 4075, 4114, 4147, 4184, 4187, 4195, 4203, 4434, 4444]

TABLE 2-continued

List of strands for producing the nucleic acid structures of FIG. 3E. The individuals strands 0-4454 are designated as SEQ ID NOs. 6842-11296, respectively. See also Table 15 of U.S. provisional application number 61/675,309, filed Jul. 24, 2012, incorporated by reference herein.
Shape, total number of strands, [list of strands]

31, 349, [1, 3, 6, 7, 8, 11, 12, 13, 16, 17, 18, 23, 25, 26, 28, 29, 30, 31, 33, 34, 35, 36, 38, 39, 40, 41, 44, 46, 48, 50, 51, 52, 53, 54, 55, 56, 57, 58, 60, 61, 62, 63, 64, 70, 71, 74, 75, 76, 79, 80, 81, 84, 85, 86, 89, 93, 98, 103, 108, 115, 116, 121, 126, 130, 131, 134, 138, 143, 148, 153, 160, 161, 162, 166, 171, 175, 176, 177, 179, 183, 188, 193, 198, 206, 211, 243, 246, 247, 249, 250, 251, 252, 253, 255, 256, 258, 259, 261, 262, 263, 264, 265, 267, 268, 269, 272, 273, 276, 277, 278, 279, 280, 281, 282, 284, 285, 286, 288, 290, 291, 292, 293, 294, 295, 296, 297, 298, 299, 302, 303, 306, 308, 309, 310, 312, 314, 316, 318, 320, 322, 324, 326, 327, 328, 333, 339, 340, 346, 352, 357, 358, 363, 369, 370, 376, 382, 387, 388, 393, 399, 400, 401, 406, 412, 413, 417, 418, 419, 423, 429, 430, 431, 436, 442, 443, 447, 448, 449, 460, 466, 472, 478, 485, 488, 491, 494, 2207, 2227, 2247, 2267, 2313, 2353, 2373, 2387, 2404, 2466, 2473, 2478, 2483, 2496, 2498, 2516, 2518, 2538, 2556, 2781, 2821, 2833, 2876, 2893, 2944, 2964, 3004, 3026, 3071, 3086, 3091, 3101, 3107, 3146, 3157, 3227, 3240, 3317, 3347, 3363, 3390, 3400, 3406, 3454, 3477, 3560, 3637, 3715, 3720, 3789, 690, 709, 780, 799, 870, 889, 1053, 1061, 1069, 1077, 1305, 1307, 1315, 1317, 1320, 1330, 1333, 1340, 1343, 1350, 1355, 1357, 1361, 1365, 1369, 1373, 1376, 1380, 1382, 1386, 1392, 1403, 1413, 1423, 1433, 1436, 1439, 1459, 1513, 1559, 1583, 1593, 1603, 1613, 1619, 1629, 1639, 1649, 1659, 1673, 1693, 1783, 1799, 1809, 1819, 1829, 1839, 2006, 2014, 2028, 2036, 2046, 2054, 2060, 2068, 2076, 2086, 2094, 2100, 2108, 2116, 2126, 2134, 2140, 2148, 2156, 2166, 2174, 2180, 2186, 2190, 2202, 4297, 4303, 3826, 3859, 3861, 3894, 3898, 3931, 3966, 3970, 4003, 4042, 4075, 4114, 4147, 4187, 4188, 4189, 4191, 4192, 4193, 4195, 4196, 4197, 4199, 4200, 4201, 4203, 4204, 4434, 4449]
32, 487, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 68, 70, 72, 73, 77, 78, 82, 83, 85, 87, 93, 94, 95, 99, 100, 104, 105, 108, 109, 112, 113, 115, 117, 118, 122, 123, 127, 128, 130, 132, 138, 139, 140, 144, 145, 149, 150, 153, 154, 157, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 255, 256, 257, 258, 261, 262, 263, 264, 265, 267, 268, 269, 270, 271, 272, 273, 274, 275, 276, 277, 278, 279, 280, 281, 282, 283, 286, 287, 288, 289, 292, 293, 294, 295, 296, 297, 298, 299, 300, 301, 302, 303, 304, 305, 306, 307, 308, 309, 310, 311, 312, 313, 316, 317, 318, 319, 322, 323, 324, 325, 326, 327, 328, 329, 330, 331, 332, 333, 334, 335, 336, 337, 338, 339, 340, 341, 342, 343, 346, 347, 348, 349, 352, 353, 354, 355, 356, 357, 358, 359, 360, 361, 362, 363, 364, 365, 366, 367, 368, 369, 370, 371, 372, 373, 376, 377, 378, 379, 382, 383, 384, 385, 386, 387, 388, 389, 390, 391, 392, 393, 394, 395, 396, 397, 398, 399, 400, 401, 402, 403, 406, 407, 408, 409, 412, 413, 414, 415, 416, 417, 418, 419, 420, 421, 422, 423, 424, 425, 426, 427, 428, 429, 430, 431, 432, 435, 436, 437, 438, 441, 442, 443, 444, 445, 446, 447, 448, 449, 450, 452, 454, 455, 456, 458, 460, 461, 462, 466, 467, 468, 472, 473, 474, 476, 478, 479, 480, 483, 485, 486, 488, 489, 491, 492, 494, 2207, 2221, 2227, 2241, 2247, 2261, 2267, 2281, 2287, 2293, 2501, 2510, 2544, 2551, 2681, 2690, 2724, 2731, 3018, 3036, 3038, 3056, 3058, 3076, 3078, 3096, 3707, 3789, 1305, 1307, 1309, 1312, 1319, 1322, 1329, 1332, 1339, 1342, 1349, 1357, 1361, 1365, 1369, 1373, 1375, 1379, 1383, 1387, 1391, 1393, 1553, 1558, 1587, 1592, 1597, 1602, 1643, 1648, 1677, 1682, 1687, 1692, 3979, 3996, 4051, 4068, 4239, 4245, 4267, 4273, 4360, 4366, 4388, 4394, 3826, 3859, 3861, 3862, 3894, 3896, 3897, 3898, 3929, 3931, 3933, 3934, 3966, 3968, 3969, 3970, 4001, 4003, 4005, 4006, 4038, 4040, 4041, 4042, 4073, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
33, 489, [1, 3, 6, 7, 8, 11, 12, 13, 16, 17, 18, 23, 25, 27, 28, 29, 30, 31, 32, 33, 34, 35, 36, 37, 38, 39, 40, 41, 42, 49, 50, 54, 56, 58, 59, 60, 61, 62, 63, 64, 67, 68, 70, 72, 73, 74, 75, 76, 77, 78, 81, 82, 83, 87, 94, 95, 99, 101, 103, 104, 105, 106, 107, 108, 109, 112, 113, 115, 117, 118, 119, 120, 121, 123, 126, 127, 128, 132, 139, 140, 144, 148, 149, 150, 151, 152, 153, 154, 157, 158, 160, 162, 163, 164, 165, 166, 167, 168, 171, 172, 173, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 262, 263, 264, 265, 267, 268, 269, 270, 271, 272, 273, 274, 275, 276, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 323, 324, 325, 326, 327, 328, 329, 330, 331, 332, 333, 334, 335, 336, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 383, 384, 385, 386, 387, 388, 389, 390, 391, 392, 393, 394, 395, 396, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 443, 444, 445, 446, 447, 448, 449, 450, 452, 454, 455, 456, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 3018, 3036, 3038, 3056, 3058, 3076, 3078, 3096, 3196, 3254, 3673, 3707, 3735, 3789, 1305, 1307, 1309, 1312, 1315, 1316, 1319, 1322, 1323, 1325, 1326, 1329, 1332, 1333, 1335, 1336, 1339, 1342, 1343, 1349, 1357, 1359, 1361, 1362, 1365, 1369, 1373, 1375, 1379, 1383, 1387, 1388, 1389, 1391, 1393, 1913, 1969, 1976, 1993, 2000, 2049, 2056, 2073, 2080, 2136, 3899, 3902, 3906, 3910, 3951, 3960, 3971, 3974, 3978, 3982, 4023, 4032, 4043, 4046, 4050, 4054, 4095, 4104, 4218, 4231, 4396, 4411, 3826, 3859, 3861, 3862, 3894, 3896, 3929, 3931, 3933, 3934, 3968, 4001, 4003, 4005, 4006, 4040, 4073, 4075, 4077, 4078, 4112, 4113, 4114, 4145, 4147, 4149, 4182, 4184, 4185, 4187, 4188, 4191, 4193, 4195, 4196, 4197, 4199, 4200, 4201, 4203, 4204, 4431, 4433, 4434, 4436, 4438, 4439, 4441, 4443, 4444, 4449, 4451, 4454]
34, 475, [1, 3, 6, 7, 8, 11, 12, 13, 16, 17, 18, 23, 25, 27, 28, 29, 30, 31, 32, 33, 34, 35, 36, 37, 38, 39, 40, 41, 42, 49, 50, 54, 55, 58, 59, 60, 61, 62, 63, 64, 67, 68, 70, 72, 74, 76, 77, 78, 82, 83, 87, 94, 95, 99, 100, 103, 104, 105, 106, 107, 108, 109, 112, 113, 115, 117, 119, 121, 122, 123, 127, 128, 132, 139, 140, 144, 145, 148, 149, 150, 151, 152, 153, 154, 157, 158, 160, 162, 164, 166, 167, 168, 172, 173, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 262, 263, 264, 265, 267, 268, 269, 270, 271, 272, 273, 274, 275, 276, 281, 282, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 323, 324, 325, 326, 327, 328, 329, 330, 331, 332, 333, 334, 335, 336, 341, 342, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 383, 384, 385, 386, 387, 388, 389, 390, 391, 392, 393, 394, 395, 396, 401, 402, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 443, 444, 445, 446, 447, 448, 449, 450, 452, 454, 455, 456, 461, 462, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 3018, 3036, 3038, 3056, 3058, 3076, 3078, 3096, 3196, 3254, 3270, 3673, 3707, 3735, 3751, 3789, 1305, 1307, 1309, 1312, 1315, 1316, 1319, 1322, 1323, 1325, 1326, 1329, 1332, 1333, 1335, 1336, 1339, 1342, 1343, 1349, 1357, 1359, 1361, 1362, 1363, 1365, 1369, 1373, 1375, 1379, 1383, 1385, 1387, 1388, 1389, 1391, 1393, 1913, 1921, 1969, 1976, 1993, 2000, 2001, 2008, 2049, 2056, 2073, 2080, 2081, 2088, 2136, 3899, 3902, 3916, 3949, 3953, 3960, 3971, 3974, 3988, 4021, 4025, 4032, 4043, 4046, 4060, 4093, 4097, 4104, 4218, 4231, 4237, 4396, 4411, 4416, 3826, 3859, 3861, 3862, 3894, 3896, 3929, 3931, 3933, 3934, 3968, 4001, 4003, 4005, 4006, 4040, 4073, 4075, 4077, 4078, 4112, 4113, 4114, 4145, 4147, 4149, 4182, 4184, 4185, 4187, 4188, 4191, 4195, 4196, 4197, 4199, 4200, 4201, 4203, 4204, 4431, 4433, 4434, 4436, 4438, 4439, 4441, 4444, 4449, 4451, 4454]
35, 461, [1, 3, 6, 7, 8, 11, 12, 13, 16, 17, 18, 23, 25, 27, 28, 29, 30, 31, 32, 33, 34, 35, 36, 37, 38, 39, 40, 41, 42, 49, 50, 54, 55, 59, 61, 63, 64, 67, 68, 70, 72, 73, 76, 77, 78, 82, 83, 87, 94, 95, 99, 100, 104, 106, 108, 109, 112, 113, 115, 117, 118, 121, 122, 123, 127, 128, 132, 139, 140, 144, 145, 149, 151, 153, 154, 157, 158, 160, 162, 163, 166, 167, 168, 172, 173, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243,

TABLE 2-continued

List of strands for producing the nucleic acid structures of FIG. 3E. The
individuals strands 0-4454 are designated as SEQ ID NOs. 6842-11296, respectively. See also
Table 15 of U.S. provisional application number 61/675,309, filed Jul. 24, 2012, incorporated
by reference herein.
Shape, total number of strands, [list of strands]

244, 245, 246, 247, 249, 250, 251, 252, 256, 257, 258, 262, 263, 264, 265, 267, 268, 269, 270, 271, 272, 273, 274, 275, 276, 281, 282, 287, 288, 289, 290, 291, 292, 293, 294, 295, 296, 297, 298, 299, 300, 301, 302, 303, 304, 305, 306, 307, 308, 309, 310, 311, 312, 317, 318, 323, 324, 325, 326, 327, 328, 329, 330, 331, 332, 333, 334, 335, 336, 341, 342, 347, 348, 349, 350, 351, 352, 353, 354, 355, 356, 357, 358, 359, 360, 361, 362, 363, 364, 365, 366, 367, 368, 369, 370, 371, 372, 377, 378, 383, 384, 385, 386, 387, 388, 389, 390, 391, 392, 393, 394, 395, 396, 401, 402, 407, 408, 409, 410, 411, 412, 413, 414, 415, 416, 417, 418, 419, 420, 421, 422, 423, 424, 425, 426, 427, 428, 429, 430, 431, 432, 437, 438, 443, 444, 445, 446, 447, 448, 449, 450, 452, 454, 455, 456, 461, 462, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 3018, 3036, 3038, 3056, 3058, 3076, 3078, 3096, 3180, 3196, 3254, 3270, 3657, 3673, 3707, 3735, 3751, 3789, 1305, 1307, 1309, 1312, 1315, 1316, 1319, 1322, 1323, 1325, 1326, 1329, 1332, 1333, 1335, 1336, 1339, 1342, 1343, 1349, 1357, 1359, 1361, 1362, 1363, 1365, 1366, 1369, 1373, 1375, 1379, 1383, 1384, 1385, 1387, 1388, 1389, 1391, 1393, 1913, 1921, 1961, 1968, 1969, 1976, 1993, 2000, 2001, 2008, 2041, 2048, 2049, 2056, 2073, 2080, 2081, 2088, 2128, 2136, 3899, 3902, 3914, 3918, 3943, 3960, 3971, 3974, 3986, 3990, 4015, 4032, 4043, 4046, 4058, 4062, 4087, 4104, 4214, 4218, 4231, 4237, 4390, 4396, 4411, 4416, 3826, 3859, 3861, 3862, 3894, 3896, 3929, 3931, 3933, 3934, 3968, 4001, 4003, 4005, 4006, 4040, 4073, 4075, 4077, 4078, 4112, 4113, 4114, 4145, 4147, 4149, 4182, 4184, 4185, 4187, 4188, 4191, 4195, 4197, 4199, 4200, 4201, 4203, 4204, 4431, 4433, 4434, 4436, 4438, 4439, 4444, 4449, 4451, 4454]
36, 457, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 68, 72, 73, 77, 78, 82, 83, 87, 94, 95, 99, 100, 104, 105, 109, 112, 113, 117, 118, 122, 123, 127, 128, 132, 139, 140, 144, 145, 149, 150, 154, 157, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 249, 250, 251, 252, 255, 256, 257, 258, 261, 262, 263, 264, 265, 267, 268, 269, 270, 271, 272, 273, 274, 275, 276, 280, 281, 282, 286, 287, 288, 292, 293, 294, 295, 296, 297, 298, 299, 300, 301, 302, 303, 304, 305, 306, 311, 312, 317, 318, 323, 324, 325, 326, 327, 328, 329, 330, 331, 332, 333, 334, 335, 336, 341, 342, 347, 348, 353, 354, 355, 356, 357, 358, 359, 360, 361, 362, 363, 364, 365, 366, 371, 372, 377, 378, 383, 384, 385, 386, 387, 388, 389, 390, 391, 392, 393, 394, 395, 396, 401, 402, 407, 408, 413, 414, 415, 416, 417, 418, 419, 420, 421, 422, 423, 424, 425, 426, 429, 431, 432, 435, 437, 438, 441, 443, 444, 445, 446, 447, 448, 449, 450, 452, 454, 455, 456, 460, 461, 462, 466, 467, 468, 472, 473, 474, 476, 478, 479, 480, 483, 485, 486, 488, 489, 491, 492, 494, 2207, 2221, 2227, 2241, 2247, 2261, 2267, 2281, 2287, 2293, 3018, 3036, 3038, 3056, 3058, 3076, 3078, 3096, 3244, 3260, 3276, 3334, 3350, 3366, 3561, 3577, 3593, 3655, 3671, 3687, 3707, 3789, 1305, 1307, 1309, 1312, 1319, 1320, 1322, 1323, 1325, 1326, 1327, 1328, 1329, 1330, 1332, 1333, 1335, 1336, 1337, 1338, 1339, 1342, 1349, 1357, 1361, 1365, 1369, 1373, 1375, 1379, 1383, 1387, 1391, 1393, 1953, 1961, 1969, 1993, 2000, 2001, 2008, 2009, 2016, 2033, 2040, 2041, 2048, 2049, 2056, 2080, 2088, 2096, 3936, 3960, 3971, 3974, 3994, 3998, 4008, 4032, 4043, 4046, 4066, 4070, 4233, 4239, 4245, 4261, 4267, 4273, 4354, 4360, 4366, 4382, 4388, 4394, 3826, 3859, 3861, 3862, 3894, 3896, 3897, 3898, 3929, 3931, 3934, 3968, 4006, 4040, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
37, 447, [1, 3, 6, 7, 8, 11, 12, 13, 16, 17, 18, 23, 25, 27, 28, 29, 30, 31, 32, 33, 34, 35, 36, 37, 38, 39, 40, 41, 42, 49, 50, 54, 55, 59, 60, 63, 64, 67, 72, 73, 77, 78, 82, 83, 87, 94, 95, 99, 100, 104, 105, 108, 109, 112, 117, 118, 122, 123, 127, 128, 132, 139, 140, 144, 145, 149, 150, 153, 154, 157, 162, 163, 167, 168, 172, 173, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 256, 257, 258, 262, 263, 264, 265, 267, 268, 269, 270, 271, 272, 273, 274, 275, 276, 281, 282, 287, 288, 293, 294, 295, 296, 297, 298, 299, 300, 301, 302, 303, 304, 305, 306, 307, 308, 309, 310, 311, 312, 317, 318, 323, 324, 325, 326, 327, 328, 329, 330, 331, 332, 333, 334, 335, 336, 341, 342, 347, 348, 353, 354, 355, 356, 357, 358, 359, 360, 361, 362, 363, 364, 365, 366, 367, 368, 369, 370, 371, 372, 377, 378, 383, 384, 385, 386, 387, 388, 389, 390, 391, 392, 393, 394, 395, 396, 401, 402, 407, 408, 413, 414, 415, 416, 417, 418, 419, 420, 421, 422, 423, 424, 425, 426, 427, 428, 429, 430, 431, 432, 437, 438, 443, 444, 445, 446, 447, 448, 449, 450, 452, 454, 455, 456, 461, 462, 467, 468, 473, 474, 476, 478, 479, 480, 483, 485, 486, 488, 489, 491, 492, 494, 2207, 2221, 2227, 2241, 2247, 2261, 2267, 2281, 2287, 2293, 3018, 3036, 3038, 3056, 3058, 3076, 3078, 3096, 3180, 3196, 3254, 3270, 3286, 3657, 3673, 3707, 3735, 3751, 3767, 3789, 1305, 1307, 1309, 1312, 1315, 1316, 1319, 1322, 1323, 1325, 1326, 1329, 1332, 1333, 1335, 1336, 1339, 1342, 1343, 1349, 1357, 1359, 1361, 1362, 1363, 1365, 1366, 1367, 1369, 1373, 1375, 1379, 1381, 1383, 1384, 1385, 1387, 1388, 1389, 1391, 1393, 1913, 1921, 1929, 1961, 1968, 1969, 1976, 1993, 2000, 2001, 2008, 2009, 2016, 2041, 2048, 2049, 2056, 2073, 2080, 2081, 2088, 2089, 2096, 2128, 2136, 3899, 3902, 3924, 3941, 3945, 3960, 3971, 3974, 3996, 4013, 4017, 4032, 4043, 4046, 4068, 4085, 4089, 4104, 4214, 4218, 4231, 4237, 4243, 4390, 4396, 4411, 4416, 4421, 3826, 3859, 3861, 3862, 3894, 3896, 3929, 3931, 3933, 3934, 3968, 4001, 4003, 4005, 4006, 4040, 4073, 4075, 4077, 4078, 4112, 4113, 4114, 4145, 4147, 4149, 4182, 4184, 4185, 4187, 4188, 4191, 4195, 4199, 4200, 4201, 4203, 4204, 4431, 4433, 4434, 4436, 4439, 4444, 4449, 4451, 4454]
38, 490, [1, 3, 6, 7, 8, 11, 12, 13, 16, 17, 18, 23, 25, 27, 28, 29, 30, 31, 32, 33, 34, 35, 36, 37, 38, 39, 40, 41, 42, 49, 50, 54, 55, 59, 60, 64, 67, 68, 72, 73, 75, 77, 78, 79, 80, 81, 82, 83, 87, 94, 95, 98, 99, 100, 102, 103, 104, 105, 109, 112, 113, 117, 118, 120, 122, 123, 124, 125, 126, 127, 128, 132, 139, 140, 143, 144, 145, 147, 148, 149, 150, 154, 157, 158, 162, 163, 167, 168, 172, 173, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 250, 251, 252, 253, 256, 257, 258, 259, 262, 263, 264, 265, 267, 268, 269, 270, 271, 272, 273, 274, 275, 276, 277, 280, 281, 282, 283, 286, 287, 288, 289, 292, 293, 294, 295, 296, 297, 298, 299, 300, 301, 302, 303, 304, 305, 306, 307, 310, 311, 312, 315, 316, 317, 318, 321, 322, 323, 324, 325, 326, 327, 328, 329, 330, 331, 332, 333, 334, 335, 336, 337, 340, 341, 342, 343, 345, 346, 347, 348, 349, 351, 352, 353, 354, 355, 356, 357, 358, 359, 360, 361, 362, 363, 364, 365, 366, 367, 370, 371, 372, 374, 375, 376, 377, 378, 380, 381, 382, 383, 384, 385, 386, 387, 388, 389, 390, 391, 392, 393, 394, 395, 396, 397, 400, 401, 402, 403, 406, 407, 408, 409, 412, 413, 414, 415, 416, 417, 418, 419, 420, 421, 422, 423, 424, 425, 426, 427, 430, 431, 432, 433, 436, 437, 438, 439, 442, 443, 444, 445, 446, 447, 448, 449, 450, 452, 454, 455, 456, 460, 461, 462, 466, 467, 468, 472, 473, 474, 476, 478, 479, 480, 483, 485, 486, 488, 489, 491, 492, 494, 2207, 2221, 2227, 2241, 2247, 2261, 2267, 2281, 2287, 2293, 2392, 2399, 2449, 2458, 2504, 2511, 2541, 2550, 2572, 2579, 2629, 2638, 2684, 2691, 2721, 2730, 2752, 2759, 2809, 2818, 3018, 3036, 3038, 3056, 3058, 3076, 3078, 3096, 3707, 3789, 1305, 1307, 1309, 1312, 1319, 1320, 1322, 1323, 1329, 1330, 1332, 1333, 1339, 1340, 1342, 1343, 1349, 1357, 1359, 1361, 1362, 1363, 1365, 1366, 1367, 1369, 1370, 1373, 1375, 1379, 1380, 1381, 1383, 1384, 1385, 1387, 1388, 1389, 1391, 1393, 1497, 1502, 1507, 1512, 1723, 1728, 1733, 1738, 1743, 1748, 3936, 3960, 3980, 3995, 4008, 4032, 4052, 4067, 4080, 4104, 4210, 4214, 4218, 4231, 4237, 4240, 4243, 4246, 4268, 4274, 4359, 4365, 4384, 4387, 4390, 4393, 4396, 4411, 4416, 4421, 3826, 3859, 3861, 3862, 3894, 3896, 3897, 3898, 3929, 3931, 3934, 3968, 3969, 3970, 4001, 4003, 4006, 4040, 4041, 4042, 4073, 4075, 4078, 4112, 4113, 4114, 4145, 4147, 4149, 4182, 4184, 4185, 4187, 4188, 4191, 4195, 4199, 4201, 4203, 4204, 4431, 4433, 4434, 4439, 4444, 4449, 4451, 4454]
39, 487, [1, 3, 6, 7, 8, 11, 12, 13, 16, 17, 18, 23, 25, 27, 28, 29, 30, 31, 32, 33, 34, 35, 36, 37, 38, 39, 40, 41, 42, 49, 50, 54, 55, 59, 60, 64, 67, 68, 72, 73, 77, 78, 81, 82, 83, 87, 94, 95, 98, 99, 100, 102, 103, 104, 105, 109, 112, 113, 117, 118, 120, 122, 123, 124, 125, 126, 127, 128, 132, 139, 140, 144, 145, 147, 149, 150, 154, 157, 158, 162, 163, 167, 168, 172, 173, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 250, 251, 252, 253, 256, 257, 258, 259, 262, 263, 264, 265, 267, 268, 269, 270, 271, 272, 273, 274, 275, 276, 277, 280,

TABLE 2-continued

List of strands for producing the nucleic acid structures of FIG. 3E. The
individuals strands 0-4454 are designated as SEQ ID NOs. 6842-11296, respectively. See also
Table 15 of U.S. provisional application number 61/675,309, filed Jul. 24, 2012, incorporated
by reference herein.
Shape, total number of strands, [list of strands]

281, 282, 283, 286, 287, 288, 289, 292, 293, 294, 295, 296, 297, 298, 299, 300, 301, 302, 303, 304, 305, 306, 307, 310, 311, 312, 315, 316, 317, 318, 319, 322, 323, 324, 325, 326, 327, 328, 329, 330, 331, 332, 333, 334, 335, 336, 337, 340, 341, 342, 343, 345, 346, 347, 348, 351, 352, 353, 354, 355, 356, 357, 358, 359, 360, 361, 362, 363, 364, 365, 366, 367, 370, 371, 372, 374, 375, 376, 377, 378, 379, 382, 383, 384, 385, 386, 387, 388, 389, 390, 391, 392, 393, 394, 395, 396, 397, 400, 401, 402, 403, 406, 407, 408, 409, 412, 413, 414, 415, 416, 417, 418, 419, 420, 421, 422, 423, 424, 425, 426, 427, 430, 431, 432, 433, 436, 437, 438, 439, 442, 443, 444, 445, 446, 447, 448, 449, 450, 452, 454, 455, 456, 460, 461, 462, 466, 467, 468, 472, 473, 474, 476, 478, 479, 480, 483, 485, 486, 488, 489, 491, 492, 494, 2207, 2221, 2227, 2241, 2247, 2261, 2267, 2281, 2287, 2293, 2392, 2399, 2449, 2458, 2572, 2579, 2629, 2638, 2684, 2691, 2721, 2730, 2752, 2759, 2769, 2778, 2792, 2799, 2809, 2818, 3018, 3036, 3038, 3056, 3058, 3076, 3078, 3096, 3707, 3789, 655, 1153, 1192, 1305, 1307, 1309, 1312, 1319, 1320, 1322, 1323, 1329, 1330, 1332, 1333, 1339, 1340, 1342, 1343, 1349, 1357, 1359, 1361, 1362, 1363, 1365, 1366, 1367, 1369, 1370, 1373, 1375, 1379, 1380, 1381, 1383, 1384, 1385, 1387, 1388, 1389, 1391, 1393, 1497, 1502, 1507, 1512, 1543, 1548, 1563, 1568, 1723, 1728, 1733, 1738, 1743, 1748, 3936, 3944, 3960, 3980, 3995, 4008, 4032, 4080, 4104, 4210, 4214, 4218, 4231, 4237, 4240, 4243, 4268, 4276, 4304, 4359, 4384, 4387, 4390, 4396, 4411, 4416, 4421, 3826, 3859, 3861, 3862, 3894, 3896, 3897, 3898, 3929, 3931, 3934, 3968, 3969, 3970, 4001, 4003, 4006, 4040, 4041, 4042, 4073, 4075, 4078, 4112, 4113, 4114, 4145, 4147, 4149, 4182, 4184, 4185, 4187, 4188, 4191, 4195, 4199, 4201, 4203, 4204, 4431, 4433, 4434, 4439, 4444, 4449, 4451, 4454]

40, 478, [1, 3, 6, 7, 8, 11, 12, 13, 16, 17, 18, 23, 25, 27, 28, 29, 30, 31, 32, 33, 34, 35, 36, 37, 38, 39, 40, 41, 42, 49, 50, 54, 55, 59, 60, 64, 67, 68, 72, 73, 77, 78, 82, 83, 87, 94, 95, 99, 100, 102, 104, 105, 109, 112, 113, 117, 118, 122, 123, 126, 127, 128, 132, 139, 140, 144, 145, 149, 150, 154, 157, 158, 162, 163, 167, 168, 172, 173, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 250, 251, 252, 253, 256, 257, 258, 259, 262, 263, 264, 265, 267, 268, 269, 270, 271, 272, 273, 274, 275, 276, 277, 280, 281, 282, 283, 286, 287, 288, 289, 292, 293, 294, 295, 296, 297, 298, 299, 300, 301, 302, 303, 304, 305, 306, 307, 310, 311, 312, 313, 316, 317, 318, 319, 322, 323, 324, 325, 326, 327, 328, 329, 330, 331, 332, 333, 334, 335, 336, 337, 340, 341, 342, 345, 346, 347, 348, 349, 352, 353, 354, 355, 356, 357, 358, 359, 360, 361, 362, 363, 364, 365, 366, 367, 370, 371, 372, 373, 376, 377, 378, 379, 382, 383, 384, 385, 386, 387, 388, 389, 390, 391, 392, 393, 394, 395, 396, 397, 400, 401, 402, 403, 406, 407, 408, 409, 412, 413, 414, 415, 416, 417, 418, 419, 420, 421, 422, 423, 424, 425, 426, 427, 430, 431, 432, 433, 436, 437, 438, 439, 442, 443, 444, 445, 446, 447, 448, 449, 450, 452, 454, 455, 456, 460, 461, 462, 466, 467, 468, 472, 473, 474, 476, 478, 479, 480, 483, 485, 486, 488, 489, 491, 492, 494, 2207, 2221, 2227, 2241, 2247, 2261, 2267, 2281, 2287, 2293, 2392, 2399, 2449, 2458, 2572, 2579, 2589, 2598, 2612, 2619, 2629, 2638, 2752, 2759, 2809, 2818, 3018, 3036, 3038, 3056, 3058, 3076, 3078, 3096, 3707, 3789, 745, 1145, 1184, 1305, 1307, 1309, 1312, 1319, 1320, 1322, 1323, 1329, 1330, 1332, 1333, 1339, 1340, 1342, 1343, 1349, 1357, 1359, 1361, 1362, 1363, 1365, 1366, 1367, 1369, 1370, 1373, 1375, 1379, 1380, 1381, 1383, 1384, 1385, 1387, 1388, 1389, 1391, 1393, 1497, 1502, 1507, 1512, 1543, 1548, 1553, 1558, 1563, 1568, 1633, 1638, 1653, 1658, 1677, 1682, 1687, 1692, 1723, 1728, 1733, 1738, 1743, 1748, 3936, 3960, 4008, 4016, 4032, 4080, 4104, 4210, 4214, 4218, 4231, 4237, 4243, 4270, 4298, 4384, 4390, 4396, 4411, 4416, 4421, 3826, 3859, 3861, 3862, 3894, 3896, 3897, 3898, 3929, 3931, 3934, 3968, 3969, 3970, 4001, 4003, 4006, 4040, 4041, 4042, 4073, 4075, 4078, 4112, 4113, 4114, 4145, 4147, 4149, 4182, 4184, 4185, 4187, 4188, 4191, 4195, 4199, 4201, 4203, 4204, 4431, 4433, 4434, 4439, 4444, 4449, 4451, 4454]

41, 493, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 68, 70, 72, 73, 74, 75, 76, 77, 78, 79, 80, 81, 82, 83, 84, 85, 86, 87, 94, 95, 99, 100, 104, 105, 109, 112, 113, 115, 117, 118, 122, 123, 127, 128, 130, 132, 136, 138, 139, 140, 142, 144, 145, 149, 150, 151, 152, 153, 154, 157, 158, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 271, 272, 273, 274, 275, 276, 278, 279, 280, 281, 282, 284, 285, 286, 287, 288, 290, 291, 292, 293, 294, 295, 296, 297, 298, 299, 300, 301, 302, 303, 304, 305, 306, 307, 310, 311, 312, 313, 316, 317, 318, 319, 322, 323, 324, 325, 326, 327, 328, 329, 330, 331, 332, 333, 334, 335, 336, 337, 340, 341, 342, 343, 346, 347, 348, 349, 352, 353, 354, 355, 356, 357, 358, 359, 360, 361, 362, 363, 364, 365, 366, 369, 370, 371, 372, 373, 376, 377, 378, 379, 382, 383, 384, 385, 386, 387, 388, 389, 390, 391, 392, 393, 394, 395, 396, 397, 399, 400, 401, 402, 403, 406, 407, 408, 411, 412, 413, 414, 415, 416, 417, 418, 419, 420, 421, 422, 423, 424, 425, 426, 427, 428, 429, 430, 431, 432, 435, 436, 437, 438, 439, 441, 442, 443, 444, 445, 446, 447, 448, 449, 450, 452, 454, 455, 456, 458, 460, 461, 462, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2572, 2579, 2629, 2638, 2681, 2690, 2724, 2731, 2772, 2779, 2789, 2798, 3018, 3036, 3038, 3056, 3058, 3076, 3078, 3096, 3707, 3789, 1305, 1307, 1309, 1312, 1319, 1322, 1329, 1332, 1339, 1342, 1349, 1357, 1361, 1365, 1369, 1373, 1375, 1379, 1383, 1387, 1391, 1393, 1497, 1587, 1592, 1597, 1602, 1643, 1648, 4263, 4269, 4275, 4291, 4294, 4297, 4303, 4322, 4336, 4360, 4364, 4388, 3826, 3859, 3861, 3862, 3894, 3896, 3897, 3898, 3929, 3931, 3933, 3934, 3966, 3968, 3969, 3970, 4001, 4003, 4005, 4006, 4038, 4040, 4041, 4042, 4073, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]

42, 477, [1, 3, 6, 7, 8, 11, 12, 13, 16, 17, 18, 23, 25, 27, 28, 29, 30, 31, 32, 33, 34, 35, 36, 37, 38, 39, 40, 41, 42, 49, 50, 54, 55, 59, 60, 64, 67, 68, 72, 73, 77, 78, 82, 83, 87, 94, 95, 99, 100, 104, 105, 106, 108, 109, 112, 113, 115, 117, 118, 119, 121, 122, 123, 127, 128, 132, 139, 140, 144, 145, 146, 148, 149, 150, 151, 152, 153, 154, 157, 158, 160, 162, 163, 164, 165, 166, 167, 168, 169, 171, 172, 173, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 250, 251, 252, 253, 256, 257, 258, 259, 262, 263, 264, 265, 267, 268, 269, 270, 271, 272, 273, 274, 275, 276, 277, 281, 282, 283, 287, 288, 289, 293, 294, 295, 296, 297, 298, 299, 300, 301, 302, 303, 304, 305, 306, 309, 311, 312, 313, 317, 318, 319, 323, 324, 325, 326, 327, 328, 329, 330, 331, 332, 333, 334, 335, 336, 337, 341, 342, 343, 347, 348, 351, 353, 354, 355, 356, 357, 358, 359, 360, 361, 362, 363, 364, 365, 366, 367, 368, 369, 370, 371, 372, 375, 377, 378, 379, 383, 384, 385, 386, 387, 388, 389, 390, 391, 392, 393, 394, 395, 396, 397, 401, 402, 405, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 441, 443, 444, 445, 446, 447, 448, 449, 450, 452, 454, 455, 456, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2392, 2449, 2501, 2572, 2609, 2701, 2752, 2769, 2901, 3018, 3036, 3038, 3056, 3058, 3076, 3078, 3096, 3254, 3270, 3286, 3335, 3447, 3511, 3591, 3687, 3707, 3735, 3789, 1305, 1307, 1309, 1312, 1316, 1318, 1319, 1322, 1323, 1326, 1329, 1332, 1333, 1336, 1339, 1342, 1343, 1349, 1357, 1359, 1361, 1362, 1363, 1365, 1366, 1367, 1369, 1370, 1373, 1375, 1379, 1383, 1387, 1389, 1391, 1393, 1497, 1507, 1553, 1563, 1587, 1653, 1968, 1976, 2000, 2008, 2056, 2080, 3902, 3926, 3945, 3960, 3974, 3990, 4025, 4032, 4046, 4054, 4104, 4105, 4210, 4214, 4218, 4231, 4237, 4243, 4262, 4304, 4328, 4358, 4394, 4411, 3826, 3859, 3861, 3862, 3894, 3896, 3897, 3929, 3933, 3934, 3968, 3969, 4001, 4003, 4005, 4006, 4040, 4041, 4073, 4075, 4077, 4078, 4112, 4113, 4114, 4145, 4147, 4149, 4182, 4184, 4185, 4187, 4188, 4191, 4195, 4199, 4201, 4203, 4204, 4431, 4433, 4434, 4436, 4438, 4439, 4441, 4443, 4444, 4446, 4449, 4451, 4454]

43, 383, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 51, 52, 53, 56, 57, 58, 61, 62, 63, 67, 94, 112, 139, 157, 160, 162, 164, 165, 166, 169, 170, 171, 173, 174, 175, 176, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240,

TABLE 2-continued

List of strands for producing the nucleic acid structures of FIG. 3E. The
individuals strands 0-4454 are designated as SEQ ID NOs. 6842-11296, respectively. See also
Table 15 of U.S. provisional application number 61/675,309, filed Jul. 24, 2012, incorporated
by reference herein.
Shape, total number of strands, [list of strands]

241, 243, 244, 245, 246, 250, 251, 252, 256, 257, 258, 262, 263, 264, 265, 267, 268, 269, 270, 271, 272, 273, 274, 275, 276, 280, 282, 286, 288, 292, 294, 295, 296, 297, 298, 299, 300, 301, 302, 303, 304, 305, 324, 325, 326, 327, 328, 329, 330, 331, 332, 333, 334, 335, 354, 355, 356, 357, 358, 359, 360, 361, 362, 363, 364, 365, 384, 385, 386, 387, 388, 389, 390, 391, 392, 393, 394, 395, 414, 415, 416, 417, 418, 419, 420, 421, 422, 423, 424, 425, 431, 437, 443, 444, 445, 446, 447, 448, 449, 450, 452, 454, 455, 456, 460, 461, 462, 466, 467, 468, 472, 473, 474, 476, 478, 479, 480, 483, 485, 486, 488, 489, 491, 492, 494, 2207, 2221, 2227, 2241, 2247, 2261, 2267, 2281, 2287, 2293, 2406, 2424, 2426, 2444, 2446, 2464, 2839, 2859, 2873, 2879, 2893, 2913, 3018, 3036, 3038, 3056, 3058, 3076, 3078, 3096, 3707, 3789, 631, 662, 721, 752, 1013, 1021, 1029, 1174, 1182, 1190, 1305, 1307, 1309, 1312, 1319, 1320, 1321, 1322, 1323, 1324, 1325, 1326, 1327, 1328, 1329, 1330, 1331, 1332, 1333, 1334, 1335, 1336, 1337, 1338, 1339, 1342, 1349, 1357, 1361, 1365, 1369, 1373, 1375, 1379, 1383, 1387, 1391, 1393, 3936, 3939, 3960, 3964, 3971, 3974, 3994, 3998, 4008, 4011, 4032, 4036, 4043, 4046, 4066, 4070, 4233, 4239, 4245, 4261, 4265, 4267, 4271, 4273, 4277, 4354, 4360, 4366, 4382, 4386, 4388, 4392, 4394, 4398, 3826, 3859, 3861, 3862, 3894, 3896, 3897, 3898, 3929, 3931, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
44, 443, [1, 3, 6, 7, 8, 11, 12, 13, 16, 17, 18, 23, 25, 27, 29, 30, 31, 32, 34, 35, 36, 37, 38, 39, 40, 41, 42, 46, 48, 49, 52, 53, 54, 57, 58, 59, 61, 62, 63, 64, 67, 70, 72, 76, 82, 85, 86, 87, 93, 94, 99, 108, 109, 112, 115, 117, 130, 132, 138, 139, 142, 143, 144, 153, 154, 157, 160, 162, 165, 166, 167, 170, 171, 172, 173, 175, 176, 177, 181, 183, 184, 185, 186, 187, 188, 189, 191, 192, 193, 194, 196, 197, 198, 199, 202, 205, 206, 209, 210, 211, 214, 215, 216, 219, 220, 221, 227, 230, 233, 236, 239, 240, 241, 243, 244, 245, 246, 249, 250, 251, 252, 255, 256, 257, 258, 261, 262, 263, 264, 265, 267, 268, 269, 270, 271, 272, 273, 274, 275, 276, 278, 279, 280, 281, 284, 286, 287, 290, 291, 292, 293, 294, 295, 296, 297, 298, 299, 300, 301, 302, 303, 304, 305, 308, 309, 310, 311, 316, 320, 322, 323, 324, 325, 326, 327, 328, 329, 330, 331, 332, 333, 334, 335, 338, 339, 340, 341, 352, 353, 354, 355, 356, 357, 358, 359, 360, 361, 362, 363, 364, 365, 369, 370, 371, 382, 383, 384, 385, 386, 387, 388, 389, 390, 391, 392, 393, 394, 395, 399, 400, 401, 407, 411, 412, 413, 414, 415, 416, 417, 418, 419, 420, 421, 422, 423, 424, 425, 427, 428, 429, 430, 431, 435, 436, 437, 441, 442, 443, 444, 445, 446, 447, 448, 449, 450, 452, 454, 455, 456, 458, 460, 461, 464, 466, 467, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2318, 2338, 2516, 2531, 2571, 2630, 2751, 2798, 2801, 2810, 2815, 2839, 2862, 2903, 2967, 2987, 3018, 3036, 3038, 3056, 3058, 3076, 3078, 3096, 3163, 3267, 3363, 3486, 3522, 3567, 3586, 3679, 3707, 3789, 596, 631, 645, 656, 662, 690, 691, 702, 709, 721, 752, 981, 989, 1013, 1064, 1108, 1112, 1174, 1187, 1222, 1223, 1230, 1305, 1307, 1309, 1312, 1319, 1322, 1329, 1332, 1339, 1342, 1349, 1357, 1361, 1365, 1369, 1373, 1375, 1379, 1383, 1387, 1391, 1393, 1498, 1508, 1544, 1564, 1734, 2014, 4019, 4028, 3826, 3859, 3861, 3862, 3894, 3896, 3897, 3898, 3929, 3931, 3933, 3934, 3966, 3968, 3969, 3970, 4001, 4003, 4005, 4006, 4038, 4040, 4041, 4042, 4073, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
45, 350, [8, 12, 28, 29, 30, 31, 32, 33, 34, 35, 36, 37, 39, 41, 50, 51, 52, 53, 54, 55, 56, 57, 58, 60, 62, 68, 72, 73, 74, 78, 79, 83, 84, 87, 89, 94, 95, 96, 100, 101, 105, 112, 113, 117, 118, 119, 123, 124, 128, 129, 132, 140, 141, 145, 146, 150, 157, 162, 163, 164, 165, 166, 168, 169, 170, 171, 174, 176, 177, 185, 186, 187, 188, 190, 191, 192, 193, 194, 197, 198, 199, 214, 216, 233, 236, 251, 252, 253, 256, 257, 258, 259, 263, 269, 276, 277, 279, 280, 281, 282, 283, 286, 288, 289, 292, 294, 295, 297, 298, 299, 305, 306, 307, 308, 309, 310, 311, 312, 313, 318, 319, 324, 325, 326, 327, 328, 329, 330, 331, 333, 335, 336, 337, 338, 339, 340, 341, 342, 343, 348, 349, 354, 355, 356, 357, 358, 359, 360, 362, 364, 365, 366, 367, 368, 369, 370, 371, 372, 373, 378, 379, 384, 385, 386, 387, 388, 389, 390, 394, 396, 397, 398, 399, 400, 401, 402, 403, 408, 409, 414, 415, 416, 417, 418, 419, 426, 428, 430, 431, 432, 433, 437, 438, 439, 443, 444, 446, 448, 449, 456, 460, 462, 466, 467, 468, 472, 473, 474, 486, 488, 489, 491, 2247, 2261, 2299, 2313, 2359, 2373, 2444, 2464, 2764, 2826, 2873, 2893, 2964, 2986, 3038, 3056, 3058, 3076, 3130, 3208, 3306, 3341, 3357, 3400, 3664, 3680, 3691, 3781, 505, 543, 582, 585, 626, 896, 913, 934, 950, 962, 1006, 1047, 1165, 1253, 1277, 1302, 1322, 1329, 1332, 1337, 1361, 1365, 1367, 1383, 1387, 2003, 2011, 2043, 2051, 2083, 2091, 3836, 3851, 3855, 3866, 3895, 3901, 3904, 3930, 3932, 3945, 3962, 3979, 3983, 3996, 4000, 4017, 4034, 4051, 4055, 4068, 4072, 4079, 4082, 4109, 4111, 4117, 4120, 4146, 4162, 4177, 4190, 4202, 4209, 4212, 4221, 4224, 4228, 4239, 4245, 4260, 4271, 4277, 4347, 4360, 4366, 4375, 4379, 4392, 4398, 4412, 4427, 4435, 4437, 4452, 3933, 3934, 3966, 3969, 3970, 4001, 4003, 4005, 4006, 4038, 4040, 4041, 4042, 4075, 4192, 4193, 4195, 4196, 4199, 4438, 4439, 4441, 4443, 4444, 4446]
46, 459, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 51, 52, 53, 54, 56, 57, 58, 59, 61, 62, 63, 64, 67, 72, 77, 82, 87, 94, 99, 104, 109, 112, 117, 122, 125, 126, 127, 128, 129, 130, 131, 132, 136, 138, 139, 140, 141, 142, 143, 144, 147, 149, 154, 157, 160, 162, 163, 164, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 249, 250, 251, 252, 255, 256, 257, 258, 261, 262, 263, 264, 265, 267, 268, 269, 270, 271, 272, 273, 274, 275, 276, 280, 281, 282, 286, 287, 288, 292, 293, 294, 295, 296, 297, 298, 299, 300, 301, 302, 303, 304, 305, 310, 311, 316, 317, 322, 323, 324, 325, 326, 327, 328, 329, 330, 331, 332, 333, 334, 335, 340, 341, 346, 347, 352, 353, 354, 355, 356, 357, 358, 359, 360, 361, 362, 363, 364, 365, 370, 371, 375, 376, 377, 381, 382, 383, 384, 385, 386, 387, 388, 389, 390, 391, 392, 393, 394, 395, 396, 397, 399, 400, 401, 402, 403, 405, 406, 407, 412, 413, 414, 415, 416, 417, 418, 419, 420, 421, 422, 423, 424, 425, 429, 430, 431, 432, 433, 434, 435, 436, 437, 438, 439, 440, 441, 442, 443, 444, 445, 446, 447, 448, 449, 450, 452, 454, 455, 456, 458, 460, 461, 462, 464, 466, 467, 468, 472, 473, 474, 476, 478, 479, 480, 483, 485, 486, 488, 489, 491, 492, 494, 2207, 2221, 2227, 2241, 2247, 2261, 2267, 2281, 2287, 2293, 2406, 2426, 2446, 2579, 2638, 2699, 2799, 2818, 2839, 3018, 3036, 3038, 3056, 3058, 3076, 3078, 3096, 3498, 3707, 3789, 631, 662, 721, 1013, 1021, 1029, 1094, 1102, 1143, 1190, 1305, 1307, 1309, 1312, 1319, 1320, 1322, 1323, 1325, 1327, 1329, 1330, 1332, 1337, 1339, 1342, 1349, 1357, 1361, 1365, 1369, 1373, 1375, 1379, 1383, 1387, 1391, 1393, 1498, 1508, 1558, 1568, 1592, 1602, 1638, 3936, 3960, 3971, 3994, 4008, 4016, 4057, 4066, 4233, 4239, 4245, 4261, 4267, 4273, 4294, 4300, 4334, 4366, 4382, 3826, 3859, 3861, 3862, 3894, 3896, 3897, 3898, 3929, 3931, 3934, 3968, 3970, 4003, 4006, 4038, 4040, 4041, 4042, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
47, 392, [12, 30, 37, 49, 57, 64, 75, 82, 91, 93, 94, 96, 97, 99, 102, 109, 120, 123, 125, 127, 128, 129, 130, 131, 132, 136, 138, 139, 140, 141, 142, 144, 147, 154, 172, 173, 174, 175, 176, 177, 181, 183, 184, 185, 186, 187, 188, 189, 190, 191, 192, 193, 195, 196, 197, 198, 199, 205, 206, 209, 210, 211, 214, 215, 216, 219, 220, 221, 227, 233, 236, 246, 247, 249, 250, 251, 255, 258, 259, 261, 263, 264, 265, 267, 268, 269, 270, 271, 272, 273, 274, 275, 282, 283, 284, 285, 286, 287, 288, 289, 290, 291, 292, 293, 306, 307, 308, 309, 310, 311, 314, 315, 318, 319, 320, 321, 322, 323, 324, 325, 326, 327, 328, 329, 330, 331, 332, 333, 334, 335, 341, 342, 343, 344, 345, 346, 347, 348, 349, 350, 351, 352, 353, 366, 367, 368, 369, 370, 371, 374, 375, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 426, 427, 428, 429, 430, 431, 438, 439, 440, 441, 442, 443, 444, 445, 446, 447, 448, 449, 450, 452, 454, 455, 456, 458, 460, 461, 462, 464, 466, 467, 468, 470, 472, 473, 479, 480, 483, 485, 486, 488, 489, 491, 492, 494, 2207, 2221, 2250, 2257, 2267, 2281, 2343, 2352, 2430, 2437, 2523, 2532, 2587, 2610, 2617, 2703, 2712, 2790, 2797, 2981, 3007, 3013, 3018, 3036, 3038, 3056, 3058, 3076, 3078, 3096, 3122, 3208, 3707, 3789, 497, 505, 527, 542, 551, 559, 572, 595, 606, 614, 632, 641, 649, 662, 696, 722, 731, 739, 786, 812, 821, 825, 829, 1206, 1222, 1224, 1305, 1306, 1312, 1313, 1314, 1315, 1316, 1322, 1323, 1324, 1332, 1342, 1347, 1349, 1357, 1361, 1363, 1369, 1375, 1376, 1377, 1378, 1379, 1383, 1384, 1387, 1391, 1393, 3830, 3836, 3847, 3853, 3865, 3868, 3885, 3888, 3889, 3892, 3899, 3902, 3908, 3912, 3921, 3925, 3937, 3940, 3957, 3960, 3961, 3964, 3991,

TABLE 2-continued

List of strands for producing the nucleic acid structures of FIG. 3E. The
individuals strands 0-4454 are designated as SEQ ID NOs. 6842-11296, respectively. See also
Table 15 of U.S. provisional application number 61/675,309, filed Jul. 24, 2012, incorporated
by reference herein.
Shape, total number of strands, [list of strands]

3993, 3997, 4009, 4012, 4063, 4065, 4069, 4081, 4084, 4094, 4098, 4292, 4296, 4378, 4390, 4426, 4429, 3969, 3970, 4038, 4040, 4041, 4042, 4110, 4112, 4113, 4114, 4147, 4149, 4182, 4184, 4185, 4187, 4188, 4192, 4195, 4196, 4197, 4199, 4200, 4436, 4438, 4439, 4443, 4444, 4446, 4448, 4449, 4451, 4454]
48, 408, [3, 18, 23, 25, 27, 28, 29, 31, 32, 33, 34, 36, 37, 38, 39, 40, 41, 42, 48, 49, 54, 60, 63, 67, 72, 87, 94, 112, 117, 132, 139, 157, 158, 160, 162, 164, 173, 175, 176, 177, 183, 184, 185, 186, 188, 189, 190, 191, 193, 194, 195, 198, 199, 202, 205, 206, 211, 219, 220, 227, 230, 231, 233, 234, 236, 239, 240, 241, 243, 244, 245, 246, 247, 249, 250, 251, 252, 253, 256, 257, 258, 259, 262, 263, 264, 265, 267, 268, 269, 270, 271, 272, 273, 274, 275, 276, 277, 278, 279, 280, 281, 282, 286, 288, 292, 294, 295, 296, 297, 298, 299, 300, 301, 302, 303, 304, 305, 306, 307, 308, 309, 310, 311, 324, 325, 326, 327, 328, 329, 330, 331, 332, 333, 334, 335, 336, 337, 338, 339, 340, 341, 354, 355, 356, 357, 358, 359, 360, 361, 362, 363, 364, 365, 366, 367, 368, 369, 370, 371, 384, 385, 386, 387, 388, 389, 390, 391, 392, 393, 394, 395, 396, 397, 398, 399, 400, 401, 414, 415, 416, 417, 418, 419, 420, 421, 422, 423, 424, 425, 426, 427, 428, 429, 430, 431, 433, 437, 439, 443, 444, 445, 446, 447, 448, 449, 450, 452, 454, 455, 456, 458, 460, 461, 462, 463, 466, 467, 468, 469, 472, 473, 474, 476, 478, 479, 480, 483, 485, 486, 488, 489, 491, 492, 494, 2207, 2221, 2227, 2232, 2238, 2241, 2247, 2252, 2258, 2261, 2267, 2281, 2287, 2293, 2406, 2409, 2419, 2426, 2429, 2439, 2444, 2464, 2859, 2870, 2873, 2879, 2884, 2890, 2893, 2904, 3018, 3036, 3038, 3041, 3056, 3058, 3061, 3071, 3076, 3078, 3091, 3096, 3707, 3789, 686, 705, 776, 795, 1021, 1029, 1068, 1076, 1182, 1190, 1227, 1235, 1305, 1307, 1309, 1312, 1319, 1322, 1329, 1332, 1339, 1342, 1349, 1357, 1361, 1364, 1365, 1368, 1369, 1373, 1375, 1379, 1382, 1383, 1386, 1387, 1391, 1393, 1856, 1860, 1883, 1886, 1891, 1894, 1923, 1931, 2126, 2134, 2163, 2166, 2171, 2174, 2193, 2197, 3835, 3852, 3907, 3924, 3941, 3945, 3958, 3962, 3979, 3983, 3996, 4000, 4013, 4017, 4030, 4034, 4051, 4055, 4068, 4072, 4123, 4140, 3826, 3859, 3861, 3862, 3894, 3896, 3897, 3898, 3929, 3931, 3933, 3934, 3966, 3968, 3969, 3970, 4001, 4003, 4005, 4006, 4038, 4040, 4041, 4042, 4073, 4075, 4077, 4078, 4110, 4112, 4113, 4114, 4145, 4147, 4149, 4182, 4184, 4185, 4187, 4188, 4189, 4191, 4200, 4201, 4203, 4204, 4431, 4433, 4434, 4436, 4448, 4449, 4451, 4454]
49, 438, [1, 3, 6, 7, 8, 11, 12, 13, 16, 17, 18, 23, 25, 29, 30, 31, 34, 35, 36, 39, 40, 41, 42, 49, 67, 70, 72, 74, 76, 83, 85, 91, 93, 94, 99, 105, 106, 107, 108, 112, 117, 128, 130, 132, 136, 138, 139, 144, 148, 151, 152, 153, 154, 157, 158, 160, 162, 164, 166, 167, 173, 175, 177, 181, 183, 184, 185, 186, 187, 188, 189, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 250, 252, 256, 258, 262, 264, 265, 267, 268, 269, 270, 271, 272, 273, 274, 275, 294, 295, 296, 297, 298, 299, 300, 301, 302, 303, 304, 305, 311, 317, 323, 324, 325, 326, 327, 328, 329, 330, 331, 332, 333, 334, 335, 336, 337, 339, 340, 341, 348, 352, 354, 355, 356, 357, 358, 359, 360, 361, 362, 363, 364, 365, 366, 367, 368, 369, 370, 371, 378, 379, 380, 381, 382, 383, 384, 385, 386, 387, 388, 389, 390, 391, 392, 393, 394, 395, 396, 397, 398, 399, 400, 401, 413, 414, 415, 416, 417, 418, 419, 420, 421, 422, 423, 424, 425, 426, 427, 428, 429, 430, 431, 432, 433, 435, 437, 438, 439, 440, 441, 442, 443, 444, 445, 446, 447, 448, 449, 450, 452, 454, 455, 456, 458, 460, 461, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2316, 2318, 2336, 2338, 2356, 2358, 2479, 2499, 2513, 2553, 2644, 2807, 2967, 3018, 3036, 3038, 3056, 3058, 3076, 3078, 3096, 3339, 3354, 3672, 3707, 3789, 654, 742, 785, 832, 973, 981, 989, 1014, 1030, 1063, 1071, 1109, 1113, 1142, 1144, 1148, 1305, 1307, 1309, 1312, 1315, 1316, 1317, 1318, 1319, 1322, 1329, 1332, 1339, 1342, 1349, 1357, 1359, 1360, 1361, 1362, 1363, 1364, 1365, 1366, 1367, 1368, 1369, 1370, 1373, 1375, 1379, 1383, 1385, 1386, 1387, 1391, 1393, 3899, 3902, 3922, 3926, 3952, 3953, 3956, 3977, 3981, 3988, 3992, 4013, 4017, 4024, 4028, 4049, 4053, 4060, 4093, 4096, 4097, 4100, 4210, 4214, 4218, 4231, 4234, 4235, 4237, 4241, 4243, 4246, 4247, 4262, 4266, 4272, 4278, 4330, 4364, 4368, 4416, 4419, 3826, 3859, 3861, 3862, 3894, 3896, 3933, 3934, 3966, 3968, 3969, 3970, 4001, 4003, 4005, 4006, 4038, 4040, 4041, 4042, 4073, 4075, 4077, 4078, 4110, 4112, 4113, 4114, 4145, 4147, 4149, 4182, 4184, 4185, 4187, 4188, 4201, 4203, 4204, 4431, 4433, 4434, 4436, 4438, 4439, 4441, 4446, 4448, 4449, 4451, 4454]
50, 441, [1, 3, 6, 7, 8, 11, 12, 13, 16, 17, 18, 23, 25, 27, 28, 29, 30, 31, 32, 34, 35, 36, 37, 38, 39, 40, 41, 42, 46, 48, 49, 54, 60, 61, 62, 63, 67, 72, 83, 85, 87, 91, 93, 94, 99, 106, 108, 109, 112, 113, 115, 117, 119, 121, 122, 128, 130, 132, 138, 139, 151, 152, 153, 157, 181, 183, 184, 186, 187, 188, 191, 192, 193, 196, 197, 198, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 271, 272, 273, 274, 275, 276, 277, 278, 279, 280, 281, 288, 292, 294, 295, 296, 297, 298, 299, 300, 301, 302, 303, 304, 305, 306, 307, 308, 309, 310, 311, 312, 318, 319, 320, 321, 322, 323, 324, 325, 326, 327, 328, 329, 330, 331, 332, 333, 334, 335, 336, 337, 338, 339, 340, 341, 353, 354, 355, 356, 357, 358, 359, 360, 361, 362, 363, 364, 365, 366, 368, 370, 371, 377, 378, 380, 382, 383, 384, 385, 386, 387, 388, 389, 390, 391, 392, 393, 394, 395, 396, 400, 408, 412, 414, 415, 416, 417, 418, 419, 420, 421, 422, 423, 424, 425, 444, 445, 446, 447, 448, 449, 450, 452, 454, 455, 461, 467, 473, 474, 476, 478, 479, 480, 483, 485, 486, 488, 489, 491, 492, 494, 2207, 2221, 2227, 2241, 2247, 2261, 2267, 2281, 2287, 2293, 2338, 2464, 2627, 2679, 2766, 2784, 2806, 2824, 2947, 2961, 2967, 2981, 2987, 3001, 3018, 3036, 3038, 3056, 3058, 3076, 3078, 3096, 3349, 3499, 3707, 3789, 605, 642, 646, 652, 654, 658, 698, 742, 744, 777, 811, 842, 1029, 1061, 1143, 1173, 1189, 1214, 1222, 1224, 1228, 1230, 1305, 1307, 1309, 1312, 1319, 1322, 1329, 1332, 1339, 1340, 1341, 1342, 1343, 1344, 1349, 1357, 1361, 1363, 1364, 1365, 1369, 1373, 1375, 1379, 1380, 1381, 1382, 1383, 1384, 1385, 1386, 1387, 1388, 1389, 1390, 1391, 1393, 3905, 3909, 3916, 3920, 3941, 3945, 3952, 3956, 3977, 3981, 3990, 4024, 4025, 4028, 4053, 4060, 4064, 4080, 4083, 4104, 4108, 4237, 4241, 4245, 4269, 4304, 4308, 4332, 4353, 4365, 4381, 4384, 4385, 4390, 4393, 4396, 4397, 4411, 4414, 4416, 4419, 4421, 4424, 3826, 3859, 3861, 3862, 3894, 3896, 3897, 3898, 3929, 3931, 3933, 3934, 3966, 3968, 3969, 3970, 4001, 4003, 4005, 4006, 4038, 4040, 4041, 4042, 4073, 4075, 4113, 4114, 4145, 4147, 4149, 4182, 4184, 4185, 4187, 4188, 4189, 4191, 4192, 4196, 4197, 4199, 4200, 4201, 4203, 4204, 4431, 4433, 4434, 4451, 4454]
51, 306, [28, 30, 34, 35, 36, 48, 51, 52, 55, 56, 57, 58, 60, 62, 81, 89, 93, 108, 116, 134, 138, 153, 161, 171, 179, 181, 183, 185, 186, 187, 188, 190, 191, 192, 196, 197, 198, 205, 209, 210, 214, 215, 219, 220, 249, 252, 253, 255, 261, 276, 277, 279, 282, 283, 284, 285, 288, 297, 303, 306, 307, 308, 309, 312, 314, 324, 325, 327, 330, 331, 333, 336, 337, 338, 339, 342, 354, 355, 356, 357, 360, 361, 362, 363, 366, 367, 368, 369, 384, 385, 386, 387, 390, 391, 392, 393, 396, 397, 398, 399, 414, 415, 416, 417, 420, 421, 422, 423, 426, 427, 428, 429, 432, 433, 435, 444, 445, 446, 447, 450, 452, 453, 456, 458, 459, 462, 464, 465, 471, 474, 476, 477, 480, 483, 486, 489, 492, 2247, 2332, 2339, 2372, 2406, 2417, 2460, 2492, 2606, 2787, 2980, 2987, 3018, 3029, 3038, 3049, 3058, 3069, 3078, 3089, 3101, 3125, 3162, 3290, 3306, 3348, 3585, 3707, 508, 517, 571, 585, 642, 651, 655, 686, 688, 697, 705, 776, 778, 787, 795, 822, 831, 835, 950, 958, 975, 998, 1006, 1029, 1033, 1039, 1047, 1072, 1101, 1142, 1230, 1322, 1329, 1332, 1339, 1342, 1349, 1365, 1375, 1379, 1381, 1383, 1387, 1388, 1391, 1393, 1887, 1919, 1927, 1935, 1959, 1967, 1983, 1991, 1999, 2007, 2023, 2031, 2039, 2063, 2071, 2079, 2103, 2111, 2119, 2127, 2143, 2151, 2159, 2167, 2183, 2187, 2191, 2195, 2199, 2203, 3845, 3865, 3887, 3901, 3930, 3941, 3944, 3945, 3958, 3962, 3979, 3982, 3996, 4013, 4017, 4030, 4034, 4051, 4061, 4068, 4085, 4088, 4089, 4102, 4106, 4190, 4198, 4217, 4223, 4228, 4299, 4327, 4330, 4358, 4396, 4421, 3933, 3966, 3969, 3970, 4001, 4003, 4005, 4038, 4041, 4042, 4073, 4075, 4077, 4110, 4113, 4114, 4145, 4147, 4149, 4182, 4193, 4196, 4431, 4433, 4436, 4441, 4443, 4448, 4451]
52, 484, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 54, 55, 56, 57, 58, 59, 60, 61, 62, 63, 64, 67, 68, 70, 72, 73, 76, 77, 78, 80, 82, 83, 84, 85, 86, 87, 91, 93, 94, 95, 97, 99, 100, 104, 105, 108, 109, 112, 113, 117, 118, 122, 123, 127, 128, 130, 132, 139, 140, 144, 145, 149, 150, 154, 157, 158, 162, 163, 167, 168, 172, 173, 175, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 255, 256, 257, 258, 259, 261, 262, 263, 264, 265, 267,

TABLE 2-continued

List of strands for producing the nucleic acid structures of FIG. 3E. The individuals strands 0-4454 are designated as SEQ ID NOs. 6842-11296, respectively. See also Table 15 of U.S. provisional application number 61/675,309, filed Jul. 24, 2012, incorporated by reference herein.
Shape, total number of strands, [list of strands]

268, 269, 270, 271, 272, 273, 274, 275, 276, 277, 278, 279, 280, 281, 282, 284, 285, 286, 287, 288, 290, 291, 292, 293, 294, 295, 296, 297, 298, 299, 300, 301, 302, 303, 304, 305, 306, 308, 309, 310, 311, 312, 313, 316, 317, 318, 320, 321, 322, 323, 324, 325, 326, 327, 328, 329, 330, 331, 332, 333, 334, 335, 336, 338, 339, 340, 341, 342, 343, 346, 347, 348, 349, 352, 353, 354, 356, 357, 358, 359, 360, 361, 362, 363, 364, 365, 366, 367, 370, 371, 372, 373, 376, 377, 378, 379, 382, 383, 384, 385, 386, 387, 388, 389, 390, 391, 392, 393, 394, 395, 396, 397, 400, 401, 402, 403, 406, 407, 408, 409, 412, 413, 414, 415, 418, 419, 420, 421, 422, 423, 424, 425, 426, 427, 430, 431, 432, 435, 436, 437, 438, 439, 442, 443, 444, 445, 446, 447, 448, 449, 450, 452, 454, 455, 456, 460, 461, 462, 466, 467, 468, 472, 473, 474, 478, 479, 480, 483, 485, 486, 488, 489, 491, 492, 494, 2207, 2221, 2227, 2241, 2247, 2261, 2267, 2281, 2287, 2293, 2524, 2531, 2592, 2599, 2724, 2731, 2752, 2759, 2890, 2904, 2911, 3018, 3036, 3038, 3056, 3058, 3076, 3078, 3096, 3707, 3789, 807, 1305, 1307, 1309, 1312, 1319, 1322, 1329, 1330, 1332, 1338, 1339, 1340, 1342, 1349, 1357, 1361, 1365, 1369, 1373, 1375, 1379, 1380, 1381, 1383, 1385, 1387, 1388, 1391, 1393, 1597, 1602, 1633, 1638, 1643, 1648, 1677, 1682, 1687, 1692, 1697, 1702, 1723, 1728, 3943, 3996, 4008, 4080, 4267, 4297, 4303, 4321, 4333, 4351, 4354, 4369, 4372, 4384, 4388, 4396, 4416, 4421, 3826, 3859, 3861, 3862, 3894, 3896, 3897, 3898, 3929, 3931, 3933, 3934, 3966, 3968, 3969, 3970, 4001, 4003, 4006, 4038, 4040, 4041, 4042, 4073, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4439, 4441, 4444, 4448, 4449, 4451, 4454]
53, 429, [1, 3, 6, 7, 8, 11, 12, 13, 16, 17, 18, 23, 25, 29, 30, 31, 34, 35, 36, 39, 40, 41, 42, 49, 67, 79, 81, 94, 100, 102, 104, 112, 122, 124, 126, 127, 139, 145, 147, 148, 149, 157, 181, 183, 184, 186, 187, 188, 190, 191, 192, 193, 194, 196, 197, 198, 202, 205, 206, 209, 210, 211, 214, 215, 216, 219, 220, 221, 227, 230, 233, 236, 239, 240, 241, 243, 244, 245, 246, 250, 252, 256, 258, 262, 264, 265, 267, 268, 269, 270, 271, 272, 273, 274, 275, 294, 295, 296, 297, 298, 299, 300, 301, 302, 303, 304, 305, 317, 323, 324, 325, 326, 327, 328, 329, 330, 331, 332, 333, 334, 335, 342, 343, 345, 346, 347, 348, 349, 351, 352, 353, 354, 355, 356, 357, 358, 359, 360, 361, 362, 363, 364, 365, 372, 373, 374, 375, 376, 377, 378, 380, 382, 383, 384, 385, 386, 387, 388, 389, 390, 391, 392, 393, 394, 395, 402, 403, 404, 405, 406, 407, 408, 414, 415, 416, 417, 418, 419, 420, 421, 422, 423, 424, 425, 432, 433, 434, 435, 436, 437, 444, 445, 446, 447, 448, 449, 450, 452, 454, 455, 461, 462, 464, 466, 467, 473, 474, 476, 478, 479, 480, 483, 485, 486, 488, 489, 491, 492, 494, 2207, 2221, 2227, 2241, 2247, 2261, 2267, 2281, 2287, 2293, 2316, 2318, 2336, 2338, 2356, 2358, 2499, 2513, 2519, 2533, 2538, 2947, 2961, 2987, 3001, 3018, 3036, 3056, 3058, 3076, 3078, 3096, 3515, 3605, 3707, 3789, 631, 643, 662, 664, 685, 706, 721, 752, 796, 811, 822, 831, 835, 839, 842, 973, 981, 989, 1022, 1030, 1189, 1214, 1230, 1232, 1305, 1307, 1309, 1312, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1349, 1357, 1359, 1360, 1361, 1362, 1363, 1364, 1365, 1366, 1367, 1368, 1369, 1370, 1373, 1375, 1379, 1380, 1381, 1382, 1383, 1387, 1388, 1389, 1390, 1391, 1393, 3899, 3902, 3922, 3926, 3936, 3939, 3946, 3960, 3961, 3964, 3971, 3974, 3980, 3984, 3994, 3995, 3998, 3999, 4008, 4011, 4014, 4018, 4029, 4032, 4033, 4036, 4043, 4046, 4052, 4056, 4066, 4067, 4070, 4080, 4083, 4088, 4092, 4104, 4108, 4210, 4214, 4218, 4231, 4235, 4237, 4240, 4241, 4243, 4246, 4247, 4268, 4272, 4274, 4278, 4365, 4384, 4396, 4397, 4411, 4414, 4421, 4424, 4421, 3826, 3859, 3861, 3862, 3894, 3896, 4113, 4114, 4145, 4147, 4149, 4182, 4184, 4185, 4187, 4188, 4201, 4203, 4204, 4431, 4433, 4434, 4441, 4443, 4444, 4451, 4454]
54, 213, [6, 30, 34, 35, 55, 57, 73, 74, 75, 78, 79, 80, 84, 88, 91, 92, 95, 96, 97, 100, 101, 102, 105, 106, 107, 111, 113, 115, 118, 119, 120, 123, 124, 125, 128, 129, 130, 136, 140, 141, 145, 146, 147, 151, 152, 165, 169, 170, 190, 192, 214, 252, 253, 254, 258, 259, 282, 283, 284, 288, 289, 290, 312, 313, 314, 318, 319, 320, 330, 331, 336, 337, 338, 342, 343, 344, 348, 349, 350, 354, 355, 356, 360, 362, 366, 368, 372, 373, 374, 378, 379, 380, 384, 386, 390, 392, 396, 398, 402, 403, 404, 408, 409, 410, 414, 416, 432, 433, 434, 438, 439, 440, 462, 464, 468, 470, 486, 487, 489, 490, 2247, 2253, 2479, 2485, 2539, 2545, 2746, 2756, 2776, 2806, 2826, 2832, 3038, 3048, 3058, 3068, 3124, 3130, 3200, 3306, 3392, 505, 595, 616, 865, 886, 913, 934, 1006, 1014, 1038, 1047, 1165, 1173, 1197, 1322, 1329, 1332, 1335, 1337, 1361, 1365, 1367, 1383, 1387, 1855, 1859, 1885, 1893, 1925, 1933, 1949, 1957, 1965, 1973, 1981, 1989, 1997, 2005, 2013, 2021, 2029, 2037, 2045, 2053, 2061, 2085, 2093, 2125, 2133, 2165, 2173, 3851, 3870, 3885, 3908, 3923, 4086, 4101, 4124, 4139, 4262, 4280, 4375, 4381, 4399, 3933, 3969, 4001, 4005, 4038, 4193, 4438, 4443]
55, 331, [3, 7, 8, 12, 13, 17, 25, 30, 31, 32, 34, 35, 36, 40, 41, 42, 44, 49, 59, 67, 91, 93, 94, 97, 98, 101, 102, 103, 104, 107, 108, 112, 115, 117, 119, 120, 121, 122, 124, 125, 126, 130, 131, 132, 139, 157, 161, 162, 177, 187, 188, 192, 193, 197, 198, 199, 210, 211, 215, 216, 230, 233, 236, 239, 245, 250, 255, 256, 257, 262, 267, 269, 273, 275, 284, 285, 286, 287, 296, 297, 298, 299, 302, 303, 304, 305, 314, 315, 316, 317, 326, 327, 328, 329, 332, 333, 334, 335, 341, 344, 345, 346, 347, 353, 356, 357, 358, 359, 362, 363, 364, 365, 369, 370, 371, 374, 376, 377, 382, 386, 387, 388, 389, 392, 394, 395, 398, 399, 400, 401, 406, 416, 417, 418, 419, 428, 429, 430, 431, 446, 448, 449, 458, 460, 461, 467, 473, 488, 491, 2210, 2230, 2241, 2250, 2261, 2270, 2281, 2316, 2323, 2356, 2363, 2378, 2590, 2601, 2630, 2641, 2716, 2723, 2804, 2843, 2950, 2961, 2970, 2981, 2991, 3043, 3056, 3063, 3076, 3083, 3224, 3240, 3582, 3637, 3781, 3797, 499, 538, 587, 598, 607, 611, 618, 655, 659, 787, 791, 824, 843, 898, 906, 935, 967, 1016, 1032, 1095, 1111, 1153, 1185, 1192, 1196, 1224, 1248, 1263, 1271, 1302, 1313, 1315, 1316, 1317, 1318, 1320, 1321, 1323, 1324, 1325, 1327, 1335, 1337, 1340, 1359, 1360, 1362, 1363, 1367, 1368, 1370, 1371, 1381, 1382, 1384, 1385, 1386, 1388, 1389, 1850, 1854, 1858, 1862, 1866, 1882, 1898, 1906, 1922, 1938, 1946, 1962, 1978, 1986, 1994, 2002, 2010, 2018, 2026, 2034, 2042, 2058, 2066, 2074, 2098, 2114, 2138, 2154, 2162, 2170, 3860, 3902, 3910, 3926, 3936, 3939, 3944, 3948, 3960, 3964, 4051, 4054, 4055, 4068, 4072, 4089, 4106, 4117, 4120, 4179, 4186, 4208, 4210, 4218, 4235, 4247, 4264, 4276, 4296, 4308, 4377, 4390, 4391, 4396, 4408, 4419, 4424, 4427, 4452, 3861, 3862, 3970, 4003, 4005, 4006, 4038, 4040, 4042, 4075, 4110, 4112, 4188, 4195, 4196, 4203, 4436, 4449]
56, 311, [34, 35, 51, 52, 56, 57, 68, 70, 76, 81, 85, 86, 89, 91, 93, 96, 97, 98, 99, 101, 102, 103, 104, 106, 107, 108, 109, 116, 121, 122, 126, 127, 131, 134, 138, 143, 144, 147, 148, 149, 153, 154, 156, 163, 164, 165, 166, 169, 170, 171, 174, 176, 185, 186, 187, 188, 190, 191, 192, 193, 195, 197, 198, 210, 214, 215, 252, 255, 258, 259, 282, 288, 289, 290, 291, 303, 306, 309, 311, 317, 318, 320, 321, 323, 330, 331, 333, 336, 338, 340, 341, 345, 346, 347, 348, 350, 352, 353, 354, 355, 357, 360, 362, 370, 371, 372, 373, 374, 375, 376, 377, 382, 383, 384, 385, 386, 387, 390, 400, 401, 402, 403, 404, 405, 406, 407, 412, 413, 414, 415, 416, 417, 430, 432, 433, 434, 436, 442, 444, 446, 447, 456, 458, 459, 460, 462, 464, 465, 466, 468, 470, 471, 472, 474, 483, 486, 489, 2325, 2407, 2420, 2426, 2440, 2492, 2493, 2513, 2533, 2539, 2586, 2607, 2626, 2673, 2736, 2826, 2839, 2876, 2879, 2896, 2916, 2937, 3038, 3058, 3184, 3200, 3201, 3249, 3267, 3306, 3336, 3346, 3352, 3368, 3411, 3443, 3461, 3476, 3544, 3570, 3602, 3621, 3691, 3704, 3723, 3781, 505, 507, 515, 517, 588, 641, 652, 721, 732, 741, 745, 752, 787, 798, 813, 896, 902, 954, 958, 974, 1006, 1021, 1038, 1047, 1062, 1093, 1109, 1165, 1174, 1190, 1277, 1302, 1322, 1329, 1330, 1332, 1333, 1335, 1337, 1361, 1365, 1379, 1383, 1387, 1389, 1467, 1569, 1719, 1773, 1783, 1793, 1817, 1827, 1837, 1991, 2031, 2038, 2054, 2071, 3870, 3885, 3921, 3925, 3943, 3952, 4008, 4016, 4032, 4043, 4050, 4082, 4109, 4111, 4117, 4146, 4153, 4175, 4194, 4211, 4228, 4232, 4252, 4267, 4280, 4284, 4298, 4321, 4333, 4347, 4375, 4382, 4394, 4427, 4437, 4442, 4447, 3933, 3966, 3969, 3970, 4001, 4003, 4042, 4436, 4438, 4441, 4443, 4446]
57, 484, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 53, 54, 55, 56, 58, 59, 60, 61, 63, 64, 67, 68, 69, 72, 73, 74, 76, 77, 78, 79, 81, 82, 83, 84, 86, 87, 88, 91, 93, 94, 95, 96, 97, 98, 99, 100, 101, 102, 103, 104, 105, 106, 107, 108, 109, 112, 113, 115, 117, 118, 119, 120, 121, 124, 125, 126, 127, 128, 129, 130, 131, 132, 136, 138, 139, 144, 151, 153, 154, 157, 158, 160, 162, 173, 175, 177, 181, 183, 184, 185, 186, 187, 188, 189, 191, 192, 193, 195, 196, 197, 198, 199, 202, 205, 206, 209, 210, 211, 214, 215, 216, 219, 220, 221, 227, 230, 233, 236, 239, 240, 241, 244, 245, 246, 247, 250, 251, 252, 253, 256, 257, 258, 259, 262, 263, 264, 265, 268, 269, 270, 271, 274, 275, 276, 277, 280, 281, 282, 283, 286, 287, 288, 289, 292, 293, 294, 295, 298, 299, 300, 301, 304, 305, 306, 307, 310, 311, 312, 313, 316, 317, 318, 319, 322, 323, 324, 325, 328, 329, 330, 331, 333, 334, 335, 336, 337, 339, 340, 341,

TABLE 2-continued

List of strands for producing the nucleic acid structures of FIG. 3E. The individuals strands 0-4454 are designated as SEQ ID NOs. 6842-11296, respectively. See also Table 15 of U.S. provisional application number 61/675,309, filed Jul. 24, 2012, incorporated by reference herein.
Shape, total number of strands, [list of strands]

342, 346, 347, 348, 349, 351, 352, 353, 354, 355, 357, 358, 359, 360, 361, 362, 363, 364, 365, 366, 367, 368, 369, 370, 371, 372, 376, 378, 379, 380, 381, 382, 383, 384, 385, 386, 387, 388, 389, 390, 391, 392, 393, 394, 395, 396, 397, 398, 399, 400, 401, 408, 409, 410, 411, 412, 413, 414, 415, 416, 417, 418, 419, 420, 421, 422, 423, 424, 425, 426, 427, 428, 429, 430, 431, 438, 439, 440, 441, 442, 443, 444, 445, 446, 447, 448, 449, 450, 452, 454, 455, 456, 458, 460, 461, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2696, 2698, 2967, 2981, 3018, 3036, 3038, 3056, 3058, 3076, 3078, 3096, 3155, 3171, 3187, 3203, 3219, 3229, 3245, 3261, 3277, 3293, 3314, 3330, 3346, 3362, 3378, 3392, 3408, 3424, 3440, 3456, 3707, 3789, 821, 832, 1141, 1222, 1305, 1307, 1309, 1312, 1316, 1318, 1319, 1322, 1329, 1332, 1339, 1342, 1349, 1357, 1361, 1365, 1369, 1373, 1375, 1379, 1383, 1384, 1385, 1386, 1387, 1391, 1393, 1910, 1918, 1926, 1934, 1942, 1947, 1955, 1963, 1971, 1979, 4049, 4053, 4058, 4062, 4087, 4091, 4096, 4100, 4329, 4357, 4361, 4390, 4416, 4419, 3826, 3859, 3861, 3862, 3894, 3896, 3897, 3929, 3934, 3968, 3969, 3970, 4001, 4003, 4005, 4006, 4038, 4040, 4041, 4042, 4073, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4446, 4448, 4449, 4451, 4454]
58, 446, [1, 3, 6, 7, 8, 11, 12, 13, 16, 17, 18, 23, 25, 27, 28, 29, 30, 31, 32, 33, 34, 35, 36, 37, 38, 39, 40, 41, 42, 46, 48, 49, 50, 51, 52, 53, 56, 57, 58, 59, 60, 61, 62, 63, 67, 68, 74, 83, 84, 91, 94, 104, 106, 112, 113, 119, 128, 129, 136, 139, 149, 151, 157, 158, 160, 162, 164, 165, 166, 168, 169, 170, 171, 172, 173, 174, 175, 176, 181, 183, 184, 185, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 250, 251, 252, 255, 256, 257, 258, 259, 262, 263, 264, 265, 267, 268, 269, 270, 271, 272, 273, 274, 275, 276, 277, 280, 282, 284, 286, 287, 288, 289, 292, 294, 295, 296, 297, 298, 299, 300, 301, 302, 303, 304, 305, 306, 307, 316, 317, 318, 319, 324, 325, 326, 327, 328, 329, 330, 331, 332, 333, 334, 335, 336, 337, 346, 347, 348, 349, 354, 355, 356, 357, 358, 359, 360, 361, 362, 363, 364, 365, 366, 367, 376, 377, 378, 379, 384, 385, 386, 387, 388, 389, 390, 391, 392, 393, 394, 395, 396, 397, 406, 407, 408, 409, 414, 415, 416, 417, 418, 419, 420, 421, 422, 423, 424, 425, 426, 427, 431, 435, 436, 437, 438, 439, 443, 444, 445, 446, 447, 448, 449, 450, 452, 454, 455, 456, 460, 461, 462, 464, 466, 467, 468, 472, 473, 474, 476, 478, 479, 480, 483, 485, 486, 488, 489, 491, 492, 494, 2207, 2221, 2227, 2241, 2247, 2261, 2267, 2281, 2287, 2293, 2424, 2426, 2464, 2859, 2873, 2913, 3018, 3036, 3038, 3056, 3058, 3076, 3078, 3096, 3267, 3325, 3357, 3586, 3648, 3680, 3707, 3789, 641, 652, 659, 692, 701, 731, 742, 749, 782, 791, 1021, 1182, 1305, 1307, 1309, 1312, 1319, 1320, 1321, 1322, 1323, 1324, 1326, 1328, 1329, 1330, 1331, 1332, 1333, 1334, 1336, 1338, 1339, 1342, 1349, 1357, 1361, 1365, 1369, 1373, 1375, 1379, 1383, 1387, 1391, 1393, 1966, 1995, 2006, 2011, 2035, 2046, 2051, 2075, 2091, 3936, 3939, 3948, 3960, 3964, 3974, 3977, 3986, 3998, 4008, 4011, 4020, 4032, 4036, 4046, 4049, 4058, 4070, 4233, 4245, 4265, 4267, 4277, 4354, 4366, 4386, 4388, 4398, 3826, 3859, 3861, 3862, 3894, 3896, 3897, 3898, 3929, 3931, 3969, 4001, 4041, 4073, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]
59, 462, [1, 3, 7, 8, 11, 16, 17, 18, 23, 25, 27, 28, 31, 32, 33, 34, 36, 37, 38, 40, 41, 42, 46, 48, 49, 50, 51, 52, 54, 55, 58, 59, 60, 61, 62, 63, 64, 67, 68, 70, 72, 73, 82, 83, 85, 87, 91, 93, 94, 95, 99, 105, 106, 108, 109, 112, 113, 114, 117, 128, 132, 133, 138, 139, 140, 144, 150, 153, 154, 157, 158, 160, 162, 163, 166, 167, 168, 172, 173, 175, 176, 177, 181, 183, 184, 185, 186, 187, 188, 189, 190, 191, 193, 194, 195, 196, 197, 198, 199, 202, 205, 206, 211, 220, 221, 227, 230, 231, 233, 236, 239, 240, 241, 243, 244, 245, 246, 247, 249, 250, 251, 252, 253, 256, 257, 258, 261, 262, 263, 264, 265, 267, 268, 269, 270, 271, 272, 273, 274, 275, 276, 277, 278, 279, 280, 281, 282, 283, 286, 287, 288, 289, 292, 293, 294, 295, 296, 297, 298, 299, 300, 301, 302, 304, 305, 306, 307, 308, 310, 311, 312, 316, 318, 322, 323, 324, 325, 326, 328, 329, 330, 331, 334, 335, 336, 337, 340, 341, 348, 353, 354, 355, 358, 359, 360, 361, 364, 365, 366, 367, 370, 371, 378, 379, 383, 384, 385, 388, 389, 390, 391, 393, 394, 395, 396, 397, 399, 400, 401, 403, 407, 408, 409, 412, 413, 414, 415, 417, 418, 419, 420, 421, 422, 423, 424, 425, 426, 427, 428, 429, 430, 431, 432, 433, 436, 437, 438, 441, 442, 443, 444, 445, 446, 447, 448, 449, 450, 452, 454, 455, 456, 458, 460, 461, 462, 463, 466, 467, 468, 472, 473, 474, 476, 478, 479, 480, 483, 485, 486, 488, 489, 491, 492, 494, 2207, 2221, 2227, 2232, 2241, 2247, 2258, 2261, 2267, 2281, 2287, 2293, 2419, 2429, 2501, 2510, 2516, 2518, 2544, 2551, 2681, 2690, 2724, 2731, 2787, 2801, 2884, 2890, 3018, 3036, 3038, 3056, 3058, 3061, 3071, 3076, 3078, 3096, 3315, 3331, 3356, 3379, 3389, 3405, 3433, 3446, 3453, 3474, 3490, 3527, 3538, 3552, 3568, 3616, 3707, 3789, 731, 739, 742, 750, 1061, 1108, 1142, 1187, 1305, 1307, 1309, 1312, 1319, 1322, 1326, 1328, 1329, 1332, 1339, 1342, 1349, 1357, 1361, 1364, 1365, 1369, 1373, 1375, 1379, 1383, 1386, 1387, 1391, 1393, 1553, 1558, 1677, 1682, 1687, 1692, 1856, 1883, 1886, 1923, 1990, 1998, 2022, 2027, 2035, 2051, 2063, 2166, 2193, 3871, 3880, 4051, 4068, 4087, 4096, 4159, 4168, 4245, 4273, 4366, 4394, 3826, 3859, 3861, 3862, 3894, 3896, 3897, 3898, 3929, 3931, 3933, 3934, 3966, 3968, 3969, 4001, 4006, 4040, 4041, 4042, 4073, 4075, 4077, 4078, 4110, 4112, 4113, 4114, 4145, 4147, 4149, 4182, 4184, 4185, 4187, 4188, 4189, 4191, 4192, 4197, 4199, 4200, 4201, 4203, 4204, 4431, 4433, 4434, 4436, 4438, 4439, 4446, 4448, 4449, 4451, 4454]
60, 438, [1, 3, 7, 8, 11, 16, 17, 18, 23, 25, 31, 32, 33, 34, 36, 40, 41, 42, 49, 59, 67, 69, 79, 88, 91, 93, 94, 96, 97, 98, 100, 101, 103, 104, 106, 107, 108, 112, 113, 115, 117, 118, 121, 127, 128, 130, 131, 132, 136, 138, 139, 144, 151, 153, 154, 157, 158, 159, 162, 164, 173, 174, 177, 178, 181, 183, 184, 185, 187, 188, 189, 191, 195, 196, 197, 198, 199, 202, 205, 206, 211, 220, 221, 227, 230, 231, 233, 236, 239, 240, 241, 244, 245, 246, 250, 252, 253, 256, 257, 258, 262, 264, 265, 268, 269, 270, 271, 274, 275, 282, 283, 286, 287, 294, 295, 298, 299, 300, 301, 304, 305, 312, 313, 316, 317, 324, 325, 328, 329, 330, 331, 333, 334, 335, 341, 342, 343, 346, 347, 353, 354, 355, 357, 358, 359, 360, 361, 362, 364, 365, 366, 367, 370, 371, 372, 376, 378, 379, 382, 383, 384, 385, 386, 388, 389, 390, 391, 394, 395, 396, 397, 400, 401, 408, 409, 412, 413, 414, 415, 418, 419, 420, 421, 424, 425, 426, 427, 430, 431, 438, 439, 442, 443, 444, 445, 448, 449, 450, 454, 455, 456, 460, 461, 463, 467, 468, 472, 473, 474, 478, 479, 480, 483, 485, 486, 488, 489, 491, 492, 494, 2207, 2221, 2227, 2232, 2241, 2247, 2258, 2261, 2267, 2281, 2287, 2293, 2316, 2318, 2356, 2358, 2587, 2601, 2627, 2641, 2696, 2698, 2701, 2711, 2952, 2967, 2978, 2981, 3018, 3036, 3038, 3056, 3058, 3061, 3071, 3076, 3078, 3096, 3155, 3171, 3219, 3229, 3293, 3314, 3378, 3392, 3456, 3475, 3491, 3523, 3539, 3549, 3565, 3597, 3613, 3634, 3650, 3682, 3698, 3707, 3712, 3728, 3760, 3776, 3789, 591, 602, 607, 611, 622, 631, 642, 651, 659, 662, 781, 792, 821, 832, 973, 989, 1054, 1070, 1141, 1188, 1222, 1267, 1305, 1307, 1309, 1312, 1315, 1316, 1317, 1318, 1319, 1321, 1322, 1324, 1329, 1332, 1336, 1338, 1339, 1342, 1349, 1357, 1359, 1360, 1361, 1362, 1364, 1365, 1367, 1368, 1369, 1370, 1373, 1375, 1379, 1383, 1386, 1387, 1391, 1393, 1856, 1883, 1886, 1910, 1923, 1926, 1942, 1947, 1963, 1966, 1979, 2003, 2006, 2043, 2070, 2078, 2094, 2102, 2107, 2115, 2131, 2139, 2166, 2193, 3871, 3880, 3899, 3906, 3922, 3939, 3948, 3964, 4015, 4024, 4049, 4058, 4091, 4100, 4159, 4168, 4210, 4218, 4231, 4235, 4243, 4247, 4264, 4276, 4292, 4296, 4304, 4308, 3826, 3859, 3861, 3862, 3894, 3896, 3969, 3970, 4001, 4003, 4005, 4006, 4038, 4040, 4041, 4073, 4078, 4112, 4113, 4114, 4145, 4147, 4149, 4182, 4184, 4185, 4187, 4188, 4201, 4203, 4204, 4431, 4433, 4434, 4436, 4438, 4439, 4446, 4448, 4449, 4451, 4454]
61, 348, [1, 3, 6, 7, 8, 12, 28, 30, 32, 33, 34, 35, 36, 37, 38, 39, 40, 41, 42, 46, 48, 50, 51, 52, 53, 54, 56, 57, 58, 59, 60, 62, 64, 68, 70, 72, 82, 95, 97, 99, 111, 112, 113, 115, 117, 123, 125, 127, 144, 151, 153, 154, 157, 162, 164, 165, 166, 167, 168, 169, 170, 171, 172, 174, 175, 176, 177, 179, 181, 183, 186, 187, 188, 191, 192, 193, 227, 230, 233, 236, 251, 252, 256, 257, 258, 259, 261, 262, 263, 264, 268, 269, 270, 274, 276, 277, 278, 279, 280, 281, 282, 283, 284, 285, 286, 287, 288, 290, 292, 293, 299, 305, 306, 308, 310, 311, 318, 320, 322, 323, 336, 341, 342, 347, 354, 359, 360, 365, 366, 371, 378, 383, 396, 397, 399, 401, 402, 403, 405, 407, 413, 414, 419, 426, 428, 430, 431, 437, 438, 439, 440, 441, 442, 443, 449, 450, 456, 457, 458, 460, 462, 463, 464, 466, 468, 470, 472, 488, 491, 2207, 2221, 2227, 2241, 2247, 2261, 2386, 2404, 2426, 2483, 2645, 2807, 2826, 2838, 2859, 2899, 2926, 2944, 2946, 2964, 2966, 2984, 2986, 3004, 3061, 3071, 3081, 3091, 3097, 3130, 3162, 3275, 3290, 3324, 3332, 3356, 3364, 3406, 3414, 3422, 3430, 3454, 3462, 3481, 3489, 3513, 3521, 3567, 3575, 3583, 3591, 3615, 3623, 3707, 3720, 3731, 3747, 3756, 3763, 3801, 3809, 3817, 3822, 661, 696, 700, 704, 705, 709, 713, 751, 755, 759, 786, 788, 813,

TABLE 2-continued

List of strands for producing the nucleic acid structures of FIG. 3E. The
individuals strands 0-4454 are designated as SEQ ID NOs. 6842-11296, respectively. See also
Table 15 of U.S. provisional application number 61/675,309, filed Jul. 24, 2012, incorporated
by reference herein.
Shape, total number of strands, [list of strands]

887, 917, 975, 1005, 1039, 1047, 1112, 1166, 1249, 1305, 1312, 1315, 1320, 1329, 1330, 1331, 1337, 1342, 1345, 1357, 1361, 1365, 1367, 1382, 1383, 1386, 1387, 1390, 1391, 1812, 1819, 1822, 1829, 1832, 1839, 1993, 1997, 2001, 2005, 2017, 2021, 2028, 2032, 2036, 2040, 2052, 2056, 3851, 3855, 3865, 3868, 3930, 3932, 3943, 3947, 3950, 3954, 3959, 3963, 4044, 4047, 4059, 4062, 4063, 4082, 4141, 4212, 4227, 4254, 4267, 4271, 4279, 4283, 4307, 4348, 4364, 4368, 4388, 4392, 4400, 4404, 4425, 4428, 4435, 4437, 3826, 3894, 3896, 3898, 3934, 4075, 4110, 4114, 4185, 4187, 4188, 4189, 4191, 4192, 4193, 4195, 4196, 4199]

62, 281, [6, 7, 11, 12, 28, 29, 30, 31, 33, 34, 35, 36, 39, 41, 46, 48, 50, 51, 52, 53, 56, 57, 58, 62, 63, 83, 84, 87, 88, 91, 94, 99, 128, 129, 132, 133, 136, 139, 144, 164, 165, 166, 168, 169, 170, 171, 173, 174, 175, 176, 185, 186, 187, 188, 190, 191, 192, 193, 195, 197, 198, 210, 214, 215, 232, 235, 246, 252, 258, 259, 261, 275, 276, 277, 278, 280, 281, 282, 286, 288, 292, 294, 318, 319, 322, 323, 324, 325, 328, 329, 330, 331, 335, 336, 337, 340, 341, 378, 379, 383, 384, 385, 388, 389, 390, 394, 395, 396, 397, 400, 401, 438, 439, 441, 444, 447, 448, 456, 458, 459, 460, 462, 465, 466, 468, 471, 472, 474, 483, 486, 489, 2227, 2240, 2247, 2260, 2267, 2359, 2387, 2401, 2421, 2426, 2446, 2551, 2563, 2758, 2839, 2859, 2916, 2937, 3038, 3049, 3058, 3069, 3089, 3117, 3176, 3192, 3208, 3235, 3251, 3301, 3357, 3373, 3398, 3527, 3547, 3554, 3570, 3680, 3687, 3691, 3696, 3723, 3781, 3797, 3805, 3813, 498, 527, 582, 626, 652, 660, 742, 750, 813, 896, 902, 962, 1011, 1021, 1029, 1037, 1041, 1182, 1190, 1198, 1248, 1252, 1277, 1281, 1302, 1315, 1322, 1324, 1332, 1334, 1336, 1361, 1365, 1369, 1379, 1383, 1387, 1389, 1449, 1459, 1469, 1479, 1513, 1523, 1582, 1658, 1664, 1719, 1729, 1739, 1773, 1783, 1793, 1987, 1995, 2051, 2059, 2067, 2075, 3853, 3863, 3866, 3895, 3930, 3977, 4049, 4082, 4117, 4146, 4153, 4175, 4202, 4221, 4224, 4226, 4239, 4245, 4261, 4265, 4267, 4271, 4360, 4366, 4372, 4382, 4386, 4388, 4392, 3898, 3969, 4041, 4110, 4112, 4189, 4192, 4193, 4196, 4197, 4200, 4436, 4438, 4441, 4443, 4446]

63, 460, [1, 3, 6, 7, 8, 11, 12, 13, 16, 17, 18, 23, 25, 27, 29, 30, 31, 32, 34, 35, 36, 37, 39, 40, 41, 42, 48, 49, 52, 53, 54, 57, 58, 59, 62, 63, 64, 67, 70, 72, 75, 76, 77, 80, 81, 82, 85, 86, 87, 93, 94, 97, 98, 99, 102, 103, 104, 107, 108, 109, 112, 115, 117, 120, 121, 122, 124, 125, 126, 127, 130, 131, 132, 138, 139, 142, 143, 144, 147, 148, 149, 152, 153, 154, 157, 160, 162, 165, 166, 167, 170, 171, 172, 175, 176, 177, 181, 183, 184, 186, 187, 188, 189, 191, 192, 193, 194, 196, 197, 198, 199, 202, 205, 206, 209, 210, 211, 214, 215, 216, 219, 220, 221, 227, 230, 233, 236, 239, 240, 241, 243, 244, 245, 246, 249, 250, 251, 252, 255, 256, 257, 258, 261, 262, 263, 264, 265, 267, 268, 269, 270, 271, 272, 273, 274, 275, 279, 280, 281, 285, 286, 287, 291, 292, 293, 294, 295, 296, 297, 298, 299, 300, 301, 302, 303, 304, 305, 309, 310, 311, 315, 316, 317, 321, 322, 323, 324, 325, 326, 327, 328, 329, 330, 331, 332, 333, 334, 335, 339, 340, 341, 345, 346, 347, 351, 352, 353, 354, 355, 356, 357, 358, 359, 360, 361, 362, 363, 364, 365, 369, 370, 371, 372, 374, 375, 376, 377, 381, 382, 383, 384, 385, 386, 387, 388, 389, 390, 391, 392, 393, 394, 395, 399, 400, 401, 405, 406, 407, 411, 412, 413, 414, 415, 416, 417, 418, 419, 420, 421, 422, 423, 424, 425, 429, 430, 431, 435, 436, 437, 441, 442, 443, 444, 445, 446, 447, 448, 449, 450, 452, 454, 455, 460, 461, 466, 467, 472, 473, 474, 476, 478, 479, 480, 483, 485, 486, 488, 489, 491, 492, 494, 2207, 2221, 2227, 2241, 2247, 2261, 2267, 2281, 2287, 2293, 2318, 2338, 2358, 2607, 2947, 2967, 2987, 3018, 3036, 3038, 3056, 3058, 3076, 3078, 3096, 3246, 3262, 3278, 3419, 3423, 3582, 3707, 3727, 3743, 3759, 3789, 631, 662, 688, 697, 721, 732, 752, 811, 842, 973, 981, 989, 1062, 1141, 1214, 1222, 1230, 1305, 1307, 1309, 1312, 1315, 1317, 1319, 1322, 1325, 1327, 1329, 1332, 1335, 1337, 1339, 1342, 1349, 1357, 1361, 1365, 1369, 1373, 1375, 1379, 1383, 1387, 1391, 1393, 1956, 1964, 1972, 1996, 2012, 2036, 2052, 2076, 2092, 2116, 2124, 2132, 3899, 3922, 3971, 3994, 4043, 4066, 3826, 3859, 3861, 3862, 3894, 3896, 3898, 3931, 3933, 3934, 3966, 3968, 3970, 4003, 4005, 4006, 4038, 4040, 4042, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]

64, 480, [1, 3, 6, 7, 8, 11, 12, 13, 16, 17, 18, 23, 25, 27, 29, 30, 31, 32, 34, 35, 36, 37, 39, 40, 41, 42, 48, 49, 52, 53, 54, 57, 58, 59, 62, 63, 64, 67, 70, 72, 75, 76, 77, 79, 80, 81, 82, 85, 86, 87, 93, 94, 97, 98, 99, 102, 103, 104, 107, 108, 109, 112, 115, 117, 120, 121, 122, 125, 126, 127, 130, 131, 132, 138, 139, 141, 142, 143, 144, 146, 147, 148, 149, 152, 153, 154, 157, 160, 162, 165, 166, 167, 170, 171, 172, 175, 176, 177, 181, 183, 184, 186, 187, 188, 189, 191, 192, 193, 194, 196, 197, 198, 199, 202, 205, 206, 209, 210, 211, 214, 215, 216, 219, 220, 221, 227, 230, 233, 236, 239, 240, 241, 243, 244, 245, 246, 249, 250, 251, 252, 255, 256, 257, 258, 261, 262, 263, 264, 265, 267, 268, 269, 270, 271, 272, 273, 274, 275, 279, 280, 281, 285, 286, 287, 291, 292, 293, 294, 295, 296, 297, 298, 299, 300, 301, 302, 303, 304, 305, 309, 310, 311, 315, 316, 317, 319, 321, 322, 323, 324, 325, 326, 327, 328, 329, 330, 331, 332, 333, 334, 335, 339, 340, 341, 345, 346, 347, 348, 349, 350, 351, 352, 353, 354, 355, 356, 357, 358, 359, 360, 361, 362, 363, 364, 365, 369, 370, 371, 375, 376, 377, 378, 380, 381, 382, 383, 384, 385, 386, 387, 388, 389, 390, 391, 392, 393, 394, 395, 399, 400, 401, 405, 406, 407, 408, 410, 411, 412, 413, 414, 415, 416, 417, 418, 419, 420, 421, 422, 423, 424, 425, 429, 430, 431, 435, 436, 437, 441, 442, 443, 444, 445, 446, 447, 448, 449, 450, 452, 454, 455, 460, 461, 466, 467, 472, 473, 474, 476, 478, 479, 480, 483, 485, 486, 488, 489, 491, 492, 494, 2207, 2221, 2227, 2241, 2247, 2261, 2267, 2281, 2287, 2293, 2318, 2338, 2358, 2499, 2947, 2967, 2987, 3018, 3036, 3038, 3056, 3058, 3076, 3078, 3096, 3246, 3262, 3278, 3343, 3359, 3422, 3515, 3583, 3662, 3678, 3707, 3727, 3743, 3759, 3789, 631, 643, 662, 664, 685, 687, 698, 706, 721, 731, 733, 742, 752, 754, 796, 811, 842, 973, 981, 989, 1022, 1030, 1061, 1142, 1181, 1189, 1214, 1222, 1230, 1305, 1307, 1309, 1312, 1315, 1317, 1319, 1322, 1325, 1327, 1329, 1332, 1335, 1337, 1339, 1342, 1349, 1357, 1361, 1365, 1369, 1373, 1375, 1379, 1383, 1387, 1391, 1393, 1552, 1686, 1956, 1996, 2036, 2044, 2076, 2116, 3899, 3922, 3971, 3994, 4043, 4066, 3826, 3859, 3861, 3862, 3894, 3896, 3898, 3931, 3933, 3934, 3966, 3968, 3970, 4003, 4005, 4006, 4038, 4040, 4042, 4075, 4077, 4078, 4110, 4112, 4113, 4114, 4145, 4147, 4149, 4182, 4184, 4185, 4187, 4188, 4189, 4191, 4192, 4193, 4195, 4196, 4197, 4199, 4200, 4201, 4203, 4204, 4431, 4433, 4434, 4436, 4438, 4439, 4441, 4443, 4444, 4446, 4448, 4449, 4451, 4454]

65, 470, [1, 3, 6, 7, 8, 11, 12, 13, 16, 17, 18, 27, 31, 32, 36, 37, 41, 42, 48, 49, 53, 54, 57, 58, 59, 63, 64, 67, 72, 75, 76, 77, 79, 80, 81, 82, 86, 87, 93, 94, 98, 99, 100, 102, 103, 104, 108, 109, 112, 117, 120, 121, 122, 124, 125, 126, 127, 131, 132, 138, 139, 143, 144, 147, 148, 149, 153, 154, 157, 162, 166, 167, 171, 172, 176, 177, 181, 183, 184, 186, 187, 188, 189, 191, 192, 193, 194, 196, 197, 198, 199, 202, 205, 206, 209, 210, 211, 214, 215, 216, 219, 220, 221, 227, 230, 233, 236, 239, 240, 241, 243, 244, 245, 250, 251, 256, 257, 262, 263, 264, 265, 267, 268, 269, 270, 271, 272, 273, 274, 275, 280, 281, 285, 286, 287, 291, 292, 293, 294, 295, 296, 297, 298, 299, 300, 301, 302, 303, 304, 305, 310, 311, 312, 313, 314, 315, 316, 317, 318, 319, 320, 321, 322, 323, 324, 325, 326, 327, 328, 329, 330, 331, 332, 333, 334, 335, 340, 341, 342, 343, 344, 345, 346, 347, 348, 349, 350, 351, 352, 353, 354, 355, 356, 357, 358, 359, 360, 361, 362, 363, 364, 365, 370, 371, 372, 374, 375, 376, 377, 378, 380, 381, 382, 383, 384, 385, 386, 387, 388, 389, 390, 391, 392, 393, 394, 395, 400, 401, 402, 404, 406, 407, 408, 410, 412, 413, 414, 415, 416, 417, 418, 419, 420, 421, 422, 423, 424, 425, 430, 431, 436, 437, 442, 443, 444, 445, 446, 447, 448, 449, 450, 452, 454, 455, 460, 461, 466, 467, 472, 473, 474, 476, 478, 479, 480, 483, 485, 486, 488, 489, 491, 492, 494, 2207, 2221, 2241, 2261, 2281, 2287, 2293, 2427, 2786, 2947, 2967, 2987, 3018, 3036, 3038, 3056, 3058, 3076, 3078, 3096, 3119, 3127, 3135, 3186, 3202, 3274, 3515, 3587, 3603, 3650, 3666, 3682, 3707, 3789, 541, 572, 595, 631, 662, 685, 706, 721, 752, 796, 811, 842, 949, 953, 957, 976, 982, 984, 990, 992, 1031, 1181, 1189, 1214, 1222, 1230, 1232, 1305, 1307, 1309, 1310, 1312, 1313, 1315, 1317, 1319, 1320, 1322, 1323, 1325, 1327, 1329, 1330, 1332, 1333, 1335, 1337, 1339, 1340, 1342, 1343, 1349, 1357, 1359, 1360, 1361, 1362, 1363, 1364, 1365, 1366, 1367, 1368, 1369, 1370, 1373, 1375, 1379, 1381, 1383, 1385, 1387, 1389, 1391, 1393, 1406, 1416, 1426, 1878, 1918, 1958, 1998, 2038, 2078, 3864, 3888, 3899, 3908, 3922, 3923, 3936, 3942, 3957, 3960, 3971, 3980, 3994, 3995, 4008, 4014, 4029, 4032, 4043, 4052, 4066, 4067, 4080, 4104, 4238, 4387, 4411, 4416, 4421, 3826, 3859, 3862, 3896, 3898, 3931, 3934, 3968, 3970, 4003, 4006, 4040, 4042, 4075, 4078, 4112, 4113, 4114, 4145, 4147, 4149, 4182, 4184, 4185, 4187, 4188, 4201, 4203, 4204, 4431, 4433, 4434, 4436, 4439, 4441, 4444, 4446, 4449, 4451, 4454]

TABLE 2-continued

List of strands for producing the nucleic acid structures of FIG. 3E. The
individuals strands 0-4454 are designated as SEQ ID NOs. 6842-11296, respectively. See also
Table 15 of U.S. provisional application number 61/675,309, filed Jul. 24, 2012, incorporated
by reference herein.
Shape, total number of strands, [list of strands]

66, 501, [1, 3, 6, 7, 8, 11, 12, 13, 16, 17, 18, 27, 30, 31, 32, 33, 34, 35, 36, 37, 38, 39, 40, 41, 42, 46, 48, 49, 50, 51, 52, 53, 54, 55, 57, 58, 59, 63, 64, 67, 72, 75, 76, 77, 78, 79, 80, 81, 82, 83, 84, 85, 86, 87, 91, 93, 94, 95, 96, 97, 98, 99, 100, 102, 103, 104, 108, 109, 112, 117, 120, 121, 122, 123, 124, 125, 126, 127, 128, 129, 130, 131, 132, 136, 138, 139, 140, 141, 142, 143, 144, 145, 147, 148, 149, 153, 154, 157, 162, 165, 166, 167, 168, 169, 170, 171, 172, 173, 174, 175, 176, 177, 181, 183, 184, 185, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 250, 251, 252, 253, 255, 256, 257, 258, 259, 261, 262, 263, 264, 265, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 430, 431, 432, 433, 434, 435, 436, 437, 438, 439, 440, 441, 442, 443, 444, 445, 446, 447, 448, 449, 450, 452, 454, 455, 456, 458, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2281, 2287, 2293, 3018, 3036, 3038, 3056, 3058, 3076, 3078, 3096, 3650, 3707, 3789, 541, 616, 631, 706, 721, 796, 811, 976, 1214, 1305, 1307, 1309, 1310, 1312, 1317, 1319, 1320, 1322, 1327, 1329, 1330, 1332, 1337, 1339, 1340, 1342, 1349, 1357, 1361, 1365, 1369, 1370, 1373, 1375, 1379, 1383, 1387, 1391, 1393, 1426, 1878, 1958, 2038, 3864, 3870, 3922, 3923, 3936, 3942, 3994, 3995, 4008, 4014, 4066, 4067, 4080, 4086, 3826, 3859, 3862, 3894, 3896, 3897, 3898, 3931, 3934, 3966, 3968, 3969, 3970, 4003, 4006, 4038, 4040, 4041, 4042, 4075, 4078, 4110, 4112, 4113, 4114, 4145, 4147, 4149, 4182, 4184, 4185, 4187, 4188, 4189, 4191, 4192, 4193, 4195, 4196, 4197, 4199, 4201, 4203, 4204, 4431, 4433, 4434, 4436, 4438, 4439, 4441, 4443, 4444, 4446, 4448, 4449, 4451, 4454]

67, 470, [1, 3, 6, 7, 8, 11, 12, 13, 16, 17, 18, 27, 31, 32, 36, 37, 41, 42, 46, 48, 49, 51, 52, 53, 54, 57, 58, 59, 63, 64, 67, 72, 75, 76, 77, 79, 80, 81, 82, 84, 85, 86, 87, 93, 94, 98, 99, 103, 104, 108, 109, 112, 115, 117, 119, 120, 121, 122, 124, 125, 126, 127, 131, 132, 138, 139, 143, 144, 146, 147, 148, 149, 151, 152, 153, 154, 157, 162, 166, 167, 171, 172, 176, 177, 181, 183, 184, 186, 187, 188, 189, 191, 192, 193, 194, 196, 197, 198, 199, 202, 205, 206, 209, 210, 211, 214, 215, 216, 219, 220, 221, 227, 230, 233, 236, 239, 240, 241, 243, 244, 245, 250, 251, 256, 257, 262, 263, 264, 265, 267, 268, 269, 270, 271, 272, 273, 274, 275, 279, 280, 281, 285, 286, 287, 291, 292, 293, 294, 295, 296, 297, 298, 299, 300, 301, 302, 303, 304, 305, 310, 311, 312, 314, 316, 317, 318, 320, 322, 323, 324, 325, 326, 327, 328, 329, 330, 331, 332, 333, 334, 335, 340, 341, 346, 347, 352, 353, 354, 355, 356, 357, 358, 359, 360, 361, 362, 363, 364, 365, 369, 370, 371, 375, 376, 377, 381, 382, 383, 384, 385, 386, 387, 388, 389, 390, 391, 392, 393, 394, 395, 400, 401, 402, 404, 406, 407, 408, 410, 412, 413, 414, 415, 416, 417, 418, 419, 420, 421, 422, 423, 424, 425, 430, 431, 436, 437, 442, 443, 444, 445, 446, 447, 448, 449, 450, 452, 454, 455, 460, 461, 466, 467, 472, 473, 474, 476, 478, 479, 480, 483, 485, 486, 488, 489, 491, 492, 494, 2207, 2221, 2241, 2261, 2281, 2287, 2293, 2407, 2427, 2498, 2518, 2538, 2659, 2679, 2699, 2786, 2806, 2947, 2967, 2987, 3018, 3036, 3038, 3056, 3058, 3076, 3078, 3096, 3119, 3127, 3135, 3186, 3202, 3274, 3347, 3363, 3426, 3442, 3515, 3587, 3603, 3650, 3666, 3682, 3707, 3789, 541, 572, 631, 643, 752, 754, 811, 842, 949, 953, 957, 976, 982, 984, 990, 992, 1031, 1061, 1069, 1096, 1102, 1104, 1110, 1112, 1151, 1181, 1189, 1214, 1216, 1222, 1224, 1230, 1232, 1305, 1307, 1309, 1310, 1312, 1313, 1317, 1319, 1320, 1322, 1325, 1327, 1329, 1332, 1333, 1335, 1339, 1340, 1342, 1343, 1349, 1357, 1359, 1360, 1361, 1362, 1363, 1364, 1365, 1366, 1367, 1368, 1369, 1370, 1373, 1375, 1379, 1381, 1383, 1385, 1387, 1389, 1391, 1393, 1406, 1416, 1426, 1878, 1958, 1998, 2078, 3864, 3888, 3922, 3923, 3936, 3971, 3994, 4032, 4043, 4052, 4080, 4104, 4232, 4238, 4322, 4328, 4411, 4416, 4421, 3826, 3859, 3862, 3896, 3897, 3898, 3931, 3934, 3966, 3968, 3970, 4003, 4005, 4006, 4040, 4042, 4073, 4075, 4078, 4112, 4113, 4114, 4145, 4147, 4149, 4182, 4184, 4185, 4187, 4188, 4201, 4203, 4204, 4431, 4433, 4434, 4436, 4439, 4441, 4444, 4446, 4449, 4451, 4454]

68, 472, [1, 3, 6, 7, 8, 11, 12, 13, 16, 17, 18, 27, 31, 32, 36, 37, 41, 42, 48, 49, 53, 54, 56, 57, 58, 59, 61, 62, 63, 64, 67, 68, 70, 72, 74, 75, 76, 77, 79, 80, 81, 82, 86, 87, 93, 94, 98, 99, 103, 104, 108, 109, 112, 115, 117, 119, 120, 121, 122, 124, 125, 126, 127, 131, 132, 138, 139, 143, 144, 146, 147, 148, 149, 151, 152, 153, 154, 157, 162, 166, 167, 171, 172, 176, 177, 181, 183, 184, 186, 187, 188, 189, 191, 192, 193, 194, 196, 197, 198, 199, 202, 205, 206, 209, 210, 211, 214, 215, 216, 219, 220, 221, 227, 230, 233, 236, 239, 240, 241, 243, 244, 245, 250, 251, 256, 257, 262, 263, 264, 265, 267, 268, 269, 270, 271, 272, 273, 274, 275, 280, 281, 285, 286, 287, 291, 292, 293, 294, 295, 296, 297, 298, 299, 300, 301, 302, 303, 304, 305, 308, 310, 311, 312, 314, 316, 317, 318, 320, 322, 323, 324, 325, 326, 327, 328, 329, 330, 331, 332, 333, 334, 335, 340, 341, 346, 347, 352, 353, 354, 355, 356, 357, 358, 359, 360, 361, 362, 363, 364, 365, 369, 370, 371, 375, 376, 377, 381, 382, 383, 384, 385, 386, 387, 388, 389, 390, 391, 392, 393, 394, 395, 400, 401, 402, 404, 406, 407, 408, 410, 412, 413, 414, 415, 416, 417, 418, 419, 420, 421, 422, 423, 424, 425, 430, 431, 436, 437, 442, 443, 444, 445, 446, 447, 448, 449, 450, 452, 454, 455, 460, 461, 466, 467, 472, 473, 474, 476, 478, 479, 480, 483, 485, 486, 488, 489, 491, 492, 494, 2207, 2221, 2241, 2261, 2281, 2287, 2293, 2427, 2447, 2498, 2518, 2659, 2679, 2699, 2786, 2806, 2947, 2967, 2987, 3018, 3036, 3038, 3056, 3058, 3076, 3078, 3096, 3119, 3127, 3135, 3170, 3186, 3202, 3331, 3347, 3363, 3426, 3442, 3515, 3587, 3603, 3650, 3666, 3682, 3707, 3789, 541, 572, 595, 662, 664, 752, 754, 811, 842, 949, 953, 957, 974, 976, 982, 984, 990, 992, 1053, 1061, 1069, 1102, 1104, 1110, 1112, 1151, 1181, 1189, 1214, 1216, 1222, 1224, 1230, 1232, 1305, 1307, 1309, 1310, 1312, 1313, 1315, 1319, 1322, 1323, 1325, 1327, 1329, 1332, 1333, 1335, 1339, 1340, 1342, 1343, 1349, 1357, 1359, 1360, 1361, 1362, 1363, 1364, 1365, 1366, 1367, 1368, 1369, 1370, 1373, 1375, 1379, 1381, 1383, 1385, 1387, 1389, 1391, 1393, 1406, 1416, 1426, 1918, 1998, 2078, 3864, 3888, 3899, 3908, 3960, 3971, 3994, 4032, 4043, 4052, 4080, 4104, 4238, 4244, 4322, 4328, 4411, 4416, 4421, 3826, 3859, 3862, 3896, 3898, 3929, 3931, 3933, 3934, 3968, 3970, 4003, 4005, 4006, 4040, 4042, 4073, 4075, 4078, 4112, 4113, 4114, 4145, 4147, 4149, 4182, 4184, 4185, 4187, 4188, 4201, 4203, 4204, 4431, 4433, 4434, 4436, 4439, 4441, 4444, 4446, 4449, 4451, 4454]

69, 482, [1, 3, 6, 7, 8, 11, 12, 13, 16, 17, 18, 23, 25, 27, 28, 29, 30, 31, 32, 34, 35, 36, 37, 41, 42, 48, 49, 53, 54, 55, 56, 57, 58, 59, 60, 61, 62, 63, 64, 67, 68, 70, 72, 74, 75, 76, 77, 79, 80, 81, 82, 86, 87, 93, 94, 98, 99, 103, 104, 108, 109, 112, 117, 120, 121, 122, 124, 125, 126, 127, 131, 132, 138, 139, 143, 144, 145, 147, 148, 149, 153, 154, 157, 162, 165, 166, 167, 169, 170, 171, 172, 176, 177, 181, 183, 184, 186, 187, 188, 189, 190, 191, 192, 193, 194, 195, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 271, 272, 273, 274, 275, 280, 281, 282, 284, 285, 286, 287, 288, 290, 291, 292, 293, 294, 295, 296, 297, 298, 299, 300, 301, 302, 303, 304, 305, 306, 308, 310, 311, 312, 314, 316, 317, 318, 320, 322, 323, 324, 325, 326, 327, 328, 329, 330, 331, 332, 333, 334, 335, 340, 341, 346, 347, 352, 353, 354, 355, 356, 357, 358, 359, 360, 361, 362, 363, 364, 365, 370, 371, 375, 376, 377, 381, 382, 383, 384, 385, 386, 387, 388, 389, 390, 391, 392, 393, 394, 395, 400, 401, 402, 403, 404, 405, 406, 407, 408, 409, 410, 411, 412, 413, 414, 415, 416, 417, 418, 419, 420, 421, 422, 423, 424, 425, 430, 431, 432, 433, 434, 435, 436, 437, 438, 439, 440, 441, 442, 443, 444, 445, 446, 447, 448, 449, 450, 452, 454, 455, 460, 461, 462, 464, 466, 467, 468, 470, 472, 473, 474, 476, 478, 479, 480, 483, 485, 486, 488, 489, 491, 492, 494, 2207, 2221, 2227, 2241, 2247, 2261, 2267, 2281, 2287, 2293, 2498, 2518, 2679, 2699, 2947, 3018, 3036, 3038, 3056, 3058, 3076, 3078, 3096, 3119, 3331, 3347, 3363, 3426, 3442, 3650, 3707, 3789, 572, 595, 662, 664, 721, 733, 752, 754, 775, 796, 811, 842, 949, 1053, 1061, 1069, 1102, 1110, 1214, 1305, 1307, 1309, 1312, 1313, 1315, 1319, 1322, 1323, 1325, 1327, 1329, 1330, 1332, 1333, 1335, 1337, 1339, 1340, 1342, 1343, 1349, 1357, 1359, 1360, 1361, 1365, 1369, 1373, 1375, 1379, 1383, 1387, 1389, 1391, 1393, 1918, 1998, 2038, 2078, 3885, 3888, 3899, 3908, 3960, 3971, 3994, 4008, 4032, 4043, 4052, 4066, 4067, 4080, 4086, 4101, 4104, 4297, 4303, 4328, 4334, 4411, 3826, 3859, 3861, 3862, 3896, 3898, 3929, 3931, 3933, 3934, 3968, 3970, 4003, 4006, 4040, 4042, 4075, 4078, 4112, 4113, 4114, 4145, 4147, 4149, 4182, 4184,

TABLE 2-continued

List of strands for producing the nucleic acid structures of FIG. 3E. The individuals strands 0-4454 are designated as SEQ ID NOs. 6842-11296, respectively. See also Table 15 of U.S. provisional application number 61/675,309, filed Jul. 24, 2012, incorporated by reference herein.
Shape, total number of strands, [list of strands]

4185, 4187, 4188, 4192, 4193, 4195, 4196, 4197, 4199, 4200, 4201, 4203, 4204, 4431, 4433, 4434, 4436, 4438, 4439, 4441, 4443, 4444, 4446, 4449, 4451, 4454]
70, 471, [1, 3, 6, 7, 8, 11, 12, 13, 16, 17, 18, 27, 31, 32, 36, 37, 41, 42, 48, 49, 53, 54, 57, 58, 59, 63, 64, 67, 70, 72, 74, 75, 76, 77, 79, 80, 81, 82, 86, 87, 93, 94, 98, 99, 103, 104, 108, 109, 112, 117, 120, 121, 122, 124, 125, 126, 127, 128, 129, 130, 131, 132, 136, 138, 139, 141, 142, 143, 144, 147, 148, 149, 153, 154, 157, 162, 166, 167, 171, 172, 176, 177, 181, 183, 184, 186, 187, 188, 189, 191, 192, 193, 194, 196, 197, 198, 199, 202, 205, 206, 209, 210, 211, 214, 215, 216, 219, 220, 221, 227, 230, 233, 236, 239, 240, 241, 243, 244, 245, 250, 251, 256, 257, 262, 263, 264, 265, 267, 268, 269, 270, 271, 272, 273, 274, 275, 280, 281, 285, 286, 287, 291, 292, 293, 294, 295, 296, 297, 298, 299, 300, 301, 302, 303, 304, 305, 310, 311, 312, 314, 316, 317, 318, 320, 322, 323, 324, 325, 326, 327, 328, 329, 330, 331, 332, 333, 334, 335, 340, 341, 346, 347, 352, 353, 354, 355, 356, 357, 358, 359, 360, 361, 362, 363, 364, 365, 370, 371, 375, 376, 377, 381, 382, 383, 384, 385, 386, 387, 388, 389, 390, 391, 392, 393, 394, 395, 396, 398, 400, 401, 402, 404, 406, 407, 408, 410, 412, 413, 414, 415, 416, 417, 418, 419, 420, 421, 422, 423, 424, 425, 430, 431, 436, 437, 442, 443, 444, 445, 446, 447, 448, 449, 450, 452, 454, 455, 460, 461, 466, 467, 472, 473, 474, 476, 478, 479, 480, 483, 485, 486, 488, 489, 491, 492, 494, 2207, 2221, 2241, 2261, 2281, 2287, 2293, 2427, 2479, 2498, 2518, 2679, 2699, 2766, 2786, 2947, 2967, 2987, 3018, 3036, 3038, 3056, 3058, 3076, 3078, 3096, 3119, 3127, 3135, 3186, 3202, 3274, 3331, 3347, 3363, 3410, 3426, 3442, 3571, 3587, 3603, 3650, 3666, 3682, 3707, 3789, 541, 572, 595, 662, 664, 721, 733, 796, 811, 842, 949, 953, 957, 976, 982, 984, 990, 992, 1031, 1053, 1055, 1061, 1069, 1094, 1102, 1104, 1110, 1112, 1173, 1181, 1189, 1214, 1222, 1224, 1230, 1232, 1305, 1307, 1309, 1310, 1312, 1313, 1315, 1317, 1319, 1322, 1323, 1325, 1327, 1329, 1330, 1332, 1337, 1339, 1340, 1342, 1343, 1349, 1357, 1359, 1360, 1361, 1362, 1363, 1364, 1365, 1366, 1367, 1368, 1369, 1370, 1373, 1375, 1379, 1381, 1383, 1385, 1387, 1389, 1391, 1393, 1406, 1416, 1426, 1878, 1918, 2038, 3864, 3888, 3899, 3908, 3922, 3923, 3960, 3971, 3994, 4008, 4066, 4067, 4080, 4104, 4238, 4328, 4334, 4411, 4416, 4421, 3826, 3859, 3862, 3896, 3898, 3931, 3933, 3934, 3968, 3970, 4003, 4006, 4038, 4040, 4041, 4042, 4075, 4078, 4112, 4113, 4114, 4145, 4147, 4149, 4182, 4184, 4185, 4187, 4188, 4201, 4203, 4204, 4431, 4433, 4434, 4436, 4439, 4441, 4444, 4446, 4449, 4451, 4454]
71, 469, [[1, 3, 6, 7, 8, 11, 12, 13, 16, 17, 18, 27, 31, 32, 36, 37, 41, 42, 48, 49, 53, 54, 57, 58, 59, 63, 64, 67, 72, 75, 76, 77, 79, 80, 81, 82, 86, 87, 93, 94, 98, 99, 103, 104, 108, 109, 112, 117, 120, 121, 122, 124, 125, 126, 127, 128, 129, 130, 131, 132, 136, 138, 139, 141, 142, 143, 144, 147, 148, 149, 153, 154, 157, 162, 166, 167, 171, 172, 176, 177, 181, 183, 184, 186, 187, 188, 189, 191, 192, 193, 194, 196, 197, 198, 199, 202, 205, 206, 209, 210, 211, 214, 215, 216, 219, 220, 221, 227, 230, 233, 236, 239, 240, 241, 243, 244, 245, 250, 251, 256, 257, 262, 263, 264, 265, 267, 268, 269, 270, 271, 272, 273, 274, 275, 280, 281, 285, 286, 287, 291, 292, 293, 294, 295, 296, 297, 298, 299, 300, 301, 302, 303, 304, 305, 310, 311, 312, 314, 316, 317, 318, 320, 322, 323, 324, 325, 326, 327, 328, 329, 330, 331, 332, 333, 334, 335, 340, 341, 346, 347, 352, 353, 354, 355, 356, 357, 358, 359, 360, 361, 362, 363, 364, 365, 370, 371, 375, 376, 377, 381, 382, 383, 384, 385, 386, 387, 388, 389, 390, 391, 392, 393, 394, 395, 396, 398, 400, 401, 402, 404, 406, 407, 408, 410, 412, 413, 414, 415, 416, 417, 418, 419, 420, 421, 422, 423, 424, 425, 430, 431, 436, 437, 442, 443, 444, 445, 446, 447, 448, 449, 450, 452, 454, 455, 460, 461, 466, 467, 472, 473, 474, 476, 478, 479, 480, 483, 485, 486, 488, 489, 491, 492, 494, 2207, 2221, 2241, 2261, 2281, 2287, 2293, 2427, 2498, 2518, 2679, 2699, 2766, 2786, 2947, 2967, 2987, 3018, 3036, 3038, 3056, 3058, 3076, 3078, 3096, 3119, 3127, 3135, 3186, 3202, 3274, 3347, 3410, 3426, 3442, 3571, 3587, 3603, 3650, 3666, 3682, 3707, 3789, 541, 572, 595, 631, 643, 662, 664, 721, 733, 796, 811, 842, 949, 953, 957, 976, 982, 984, 990, 992, 1031, 1061, 1069, 1094, 1102, 1104, 1110, 1112, 1173, 1181, 1189, 1214, 1222, 1224, 1230, 1232, 1305, 1307, 1309, 1310, 1312, 1313, 1315, 1317, 1319, 1320, 1322, 1323, 1325, 1327, 1329, 1330, 1332, 1337, 1339, 1340, 1342, 1343, 1349, 1357, 1359, 1360, 1361, 1362, 1363, 1364, 1365, 1366, 1367, 1368, 1369, 1370, 1373, 1375, 1379, 1381, 1383, 1385, 1387, 1389, 1391, 1393, 1406, 1416, 1426, 1878, 1918, 1958, 2038, 3864, 3888, 3899, 3908, 3922, 3923, 3936, 3960, 3971, 3994, 4008, 4066, 4067, 4080, 4104, 4238, 4328, 4334, 4411, 4416, 4421, 3826, 3859, 3862, 3896, 3898, 3931, 3934, 3968, 3970, 4003, 4006, 4038, 4040, 4041, 4042, 4075, 4078, 4112, 4113, 4114, 4145, 4147, 4149, 4182, 4184, 4185, 4187, 4188, 4201, 4203, 4204, 4431, 4433, 4434, 4436, 4439, 4441, 4444, 4446, 4449, 4451, 4454]
72, 488, [1, 3, 6, 7, 8, 11, 12, 13, 16, 17, 18, 23, 25, 27, 28, 29, 30, 31, 32, 34, 35, 36, 37, 41, 42, 48, 49, 53, 54, 55, 56, 57, 58, 59, 60, 61, 62, 63, 64, 67, 68, 70, 72, 73, 74, 75, 76, 77, 79, 80, 81, 82, 86, 87, 93, 94, 98, 99, 100, 101, 102, 103, 104, 105, 106, 107, 108, 109, 112, 113, 115, 117, 118, 119, 120, 121, 122, 124, 125, 126, 127, 131, 132, 138, 139, 143, 144, 146, 147, 148, 149, 151, 152, 153, 154, 157, 162, 166, 167, 171, 172, 176, 177, 181, 183, 184, 186, 187, 188, 189, 191, 192, 193, 194, 196, 197, 198, 199, 202, 205, 206, 209, 210, 211, 214, 215, 216, 219, 220, 221, 227, 230, 233, 236, 239, 240, 241, 243, 244, 245, 246, 247, 249, 250, 251, 252, 253, 255, 256, 257, 258, 259, 261, 262, 263, 264, 265, 267, 268, 269, 270, 271, 272, 273, 274, 275, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 340, 341, 342, 343, 344, 345, 346, 347, 348, 349, 350, 351, 352, 353, 354, 355, 356, 357, 358, 359, 360, 361, 362, 363, 364, 365, 366, 368, 369, 370, 371, 372, 374, 375, 376, 377, 378, 380, 381, 382, 383, 384, 385, 386, 387, 388, 389, 390, 391, 392, 393, 394, 395, 400, 401, 402, 404, 406, 407, 408, 410, 412, 413, 414, 415, 416, 417, 418, 419, 420, 421, 422, 423, 424, 425, 430, 431, 436, 437, 442, 443, 444, 445, 446, 447, 448, 449, 450, 452, 454, 455, 460, 461, 466, 467, 472, 473, 474, 476, 478, 479, 480, 483, 485, 486, 488, 489, 491, 492, 494, 2207, 2221, 2227, 2241, 2247, 2261, 2267, 2281, 2287, 2293, 2786, 2806, 2947, 2967, 2987, 3018, 3036, 3038, 3056, 3058, 3076, 3078, 3096, 3119, 3515, 3587, 3603, 3650, 3666, 3682, 3707, 3789, 572, 595, 662, 685, 752, 811, 842, 949, 1181, 1189, 1214, 1222, 1230, 1232, 1305, 1307, 1309, 1312, 1313, 1315, 1319, 1322, 1323, 1325, 1329, 1332, 1333, 1335, 1339, 1340, 1342, 1343, 1349, 1357, 1359, 1360, 1361, 1365, 1369, 1373, 1375, 1379, 1381, 1383, 1385, 1387, 1389, 1391, 1393, 1918, 1998, 2078, 3885, 3888, 3899, 3908, 3957, 3960, 3971, 3980, 4029, 4032, 4043, 4052, 4080, 4104, 4381, 4387, 4411, 4416, 4421, 3826, 3859, 3861, 3862, 3896, 3898, 3929, 3931, 3933, 3934, 3968, 3970, 4001, 4003, 4005, 4006, 4040, 4042, 4073, 4075, 4078, 4112, 4113, 4114, 4145, 4147, 4149, 4182, 4184, 4185, 4187, 4188, 4192, 4193, 4195, 4196, 4197, 4199, 4200, 4201, 4203, 4204, 4431, 4433, 4434, 4436, 4439, 4441, 4444, 4446, 4449, 4451, 4454]
73, 464, [1, 3, 6, 7, 8, 11, 12, 13, 16, 17, 18, 27, 31, 32, 36, 37, 41, 42, 48, 49, 53, 54, 57, 58, 59, 63, 64, 67, 72, 75, 76, 77, 79, 80, 81, 82, 86, 87, 93, 94, 98, 99, 103, 104, 108, 109, 112, 117, 120, 121, 122, 124, 125, 126, 127, 131, 132, 138, 139, 143, 144, 147, 148, 149, 153, 154, 157, 162, 166, 167, 171, 172, 176, 177, 181, 183, 184, 186, 187, 188, 189, 191, 192, 193, 194, 196, 197, 198, 199, 202, 205, 206, 209, 210, 211, 214, 215, 216, 219, 220, 221, 227, 230, 233, 236, 239, 240, 241, 243, 244, 245, 250, 251, 256, 257, 262, 263, 264, 265, 267, 268, 269, 270, 271, 272, 273, 274, 275, 280, 281, 285, 286, 287, 291, 292, 293, 294, 295, 296, 297, 298, 299, 300, 301, 302, 303, 304, 305, 310, 311, 312, 314, 316, 317, 318, 320, 322, 323, 324, 325, 326, 327, 328, 329, 330, 331, 332, 333, 334, 335, 340, 341, 346, 347, 352, 353, 354, 355, 356, 357, 358, 359, 360, 361, 362, 363, 364, 365, 370, 371, 375, 376, 377, 381, 382, 383, 384, 385, 386, 387, 388, 389, 390, 391, 392, 393, 394, 395, 400, 401, 402, 404, 406, 407, 408, 410, 412, 413, 414, 415, 416, 417, 418, 419, 420, 421, 422, 423, 424, 425, 430, 431, 436, 437, 442, 443, 444, 445, 446, 447, 448, 449, 450, 452, 454, 455, 460, 461, 466, 467, 472, 473, 474, 476, 478, 479, 480, 483, 485, 486, 488, 489, 491, 492, 494, 2207, 2221, 2241, 2261, 2281, 2287, 2293, 2427, 2498, 2518, 2679, 2699, 2786, 2947, 2967, 2987, 3018, 3036, 3038, 3056, 3058, 3076, 3078, 3096, 3119, 3127, 3135, 3186, 3202, 3274, 3347, 3363, 3426, 3442, 3515, 3587, 3603, 3650, 3666, 3682, 3707, 3789, 541, 572, 595, 631, 643, 662, 664, 721, 733, 752, 754, 796, 811, 842, 949, 953, 957, 976, 982, 984, 990, 992, 1031, 1061, 1069, 1102, 1104, 1110, 1112, 1151, 1181, 1189, 1214, 1222, 1224, 1230, 1232, 1305, 1307, 1309, 1310, 1312, 1313, 1315, 1317, 1319, 1320, 1322, 1323, 1325, 1327, 1329, 1330, 1332, 1333, 1335, 1337, 1339, 1340, 1342, 1343, 1349, 1357, 1359, 1360, 1361, 1362, 1363, 1364, 1365, 1366, 1367, 1368, 1369, 1370, 1373, 1375, 1379, 1381, 1383, 1385, 1387, 1389, 1391, 1393, 1406, 1416, 1426, 1878, 1918, 1958, 1998, 2038,

TABLE 2-continued

List of strands for producing the nucleic acid structures of FIG. 3E. The
individuals strands 0-4454 are designated as SEQ ID NOs. 6842-11296, respectively. See also
Table 15 of U.S. provisional application number 61/675,309, filed Jul. 24, 2012, incorporated
by reference herein.
Shape, total number of strands, [list of strands]

2078, 3864, 3888, 3899, 3908, 3922, 3923, 3936, 3960, 3971, 3994, 4008, 4032, 4043, 4052, 4066, 4067, 4080, 4104, 4238, 4328, 4411,
4416, 4421, 3826, 3859, 3862, 3896, 3898, 3931, 3934, 3968, 3970, 4003, 4006, 4040, 4042, 4075, 4078, 4112, 4113, 4114, 4145, 4147,
4149, 4182, 4184, 4185, 4187, 4188, 4201, 4203, 4204, 4431, 4433, 4434, 4436, 4439, 4441, 4444, 4446, 4449, 4451, 4454]
74, 466, [1, 3, 6, 7, 8, 11, 12, 13, 16, 17, 18, 27, 31, 32, 36, 37, 41, 42, 48, 49, 53, 54, 57, 58, 59, 63, 64, 67, 70, 72, 74, 75, 76, 77, 79, 80, 81,
82, 86, 87, 93, 94, 98, 99, 103, 104, 108, 109, 112, 117, 120, 121, 122, 124, 125, 126, 127, 131, 132, 138, 139, 143, 144, 147, 148, 149, 153,
154, 157, 162, 166, 167, 171, 172, 176, 177, 181, 183, 184, 186, 187, 188, 189, 191, 192, 193, 194, 196, 197, 198, 199, 202, 205, 206, 209,
210, 211, 214, 215, 216, 219, 220, 221, 227, 230, 233, 236, 239, 240, 241, 243, 244, 245, 250, 251, 256, 257, 262, 263, 264, 265, 267, 268,
269, 270, 271, 272, 273, 274, 275, 280, 281, 285, 286, 287, 291, 292, 293, 294, 295, 296, 297, 298, 299, 300, 301, 302, 303, 304, 305, 310,
311, 312, 314, 316, 317, 318, 320, 322, 323, 324, 325, 326, 327, 328, 329, 330, 331, 332, 333, 334, 335, 340, 341, 346, 347, 352, 353, 354,
355, 356, 357, 358, 359, 360, 361, 362, 363, 364, 365, 370, 371, 375, 376, 377, 381, 382, 383, 384, 385, 386, 387, 388, 389, 390, 391, 392,
393, 394, 395, 400, 401, 402, 404, 406, 407, 408, 410, 412, 413, 414, 415, 416, 417, 418, 419, 420, 421, 422, 423, 424, 425, 430, 431, 436,
437, 442, 443, 444, 445, 446, 447, 448, 449, 450, 452, 454, 455, 460, 461, 466, 467, 472, 473, 474, 476, 478, 479, 480, 483, 485, 486, 488,
489, 491, 492, 494, 2207, 2221, 2241, 2261, 2281, 2287, 2293, 2427, 2479, 2498, 2518, 2679, 2699, 2786, 2947, 2967, 2987, 3018, 3036,
3038, 3056, 3058, 3076, 3078, 3096, 3119, 3127, 3135, 3186, 3202, 3274, 3331, 3347, 3363, 3426, 3442, 3515, 3587, 3603, 3650, 3666,
3682, 3707, 3789, 541, 572, 595, 662, 664, 721, 733, 752, 754, 796, 811, 842, 949, 953, 957, 976, 982, 984, 990, 992, 1031, 1053, 1055,
1061, 1069, 1102, 1104, 1110, 1112, 1151, 1181, 1189, 1214, 1222, 1224, 1230, 1232, 1305, 1307, 1309, 1310, 1312, 1313, 1315, 1317,
1319, 1322, 1323, 1325, 1327, 1329, 1330, 1332, 1333, 1335, 1337, 1339, 1340, 1342, 1343, 1349, 1357, 1359, 1360, 1361, 1362, 1363,
1364, 1365, 1366, 1367, 1368, 1369, 1370, 1373, 1375, 1379, 1381, 1383, 1385, 1387, 1389, 1391, 1393, 1406, 1416, 1426, 1878, 1918,
1998, 2038, 2078, 3864, 3888, 3899, 3908, 3922, 3923, 3960, 3971, 3994, 4008, 4032, 4043, 4052, 4066, 4067, 4080, 4104, 4238, 4328,
4411, 4416, 4421, 3826, 3859, 3862, 3896, 3898, 3931, 3933, 3934, 3968, 3970, 4003, 4006, 4040, 4042, 4075, 4078, 4112, 4113, 4114,
4145, 4147, 4149, 4182, 4184, 4185, 4187, 4188, 4201, 4203, 4204, 4431, 4433, 4434, 4436, 4439, 4441, 4444, 4446, 4449, 4451, 4454]
75, 441, [1, 3, 7, 8, 11, 12, 13, 17, 18, 25, 27, 28, 29, 30, 31, 32, 34, 35, 36, 37, 39, 40, 41, 42, 46, 48, 49, 52, 53, 54, 57, 58, 59, 61, 62, 63,
64, 67, 70, 72, 74, 75, 76, 77, 80, 81, 82, 84, 85, 86, 87, 91, 93, 94, 97, 98, 99, 102, 103, 104, 106, 107, 108, 109, 112, 115, 117, 119, 120,
121, 122, 125, 126, 127, 129, 130, 131, 132, 136, 138, 139, 141, 142, 143, 144, 146, 147, 148, 149, 150, 151, 152, 153, 154, 157, 160, 162,
164, 165, 166, 167, 169, 170, 171, 172, 175, 176, 177, 183, 184, 187, 188, 189, 192, 193, 194, 197, 198, 199, 202, 206, 211, 216, 221, 227,
230, 233, 236, 239, 243, 244, 245, 246, 247, 249, 250, 251, 252, 255, 256, 257, 259, 261, 262, 263, 264, 265, 267, 268, 269, 273, 274, 275,
276, 277, 278, 279, 280, 281, 285, 286, 287, 288, 289, 290, 291, 292, 293, 294, 295, 296, 297, 298, 299, 303, 304, 305, 306, 307, 308, 309,
310, 311, 315, 316, 317, 318, 319, 320, 321, 322, 323, 324, 325, 326, 327, 328, 329, 333, 334, 335, 336, 337, 338, 339, 340, 341, 345, 346,
347, 348, 349, 350, 351, 352, 353, 354, 355, 356, 357, 358, 359, 363, 364, 365, 366, 367, 368, 369, 370, 371, 375, 376, 377, 378, 379, 380,
381, 382, 383, 384, 385, 386, 387, 388, 389, 393, 394, 395, 396, 397, 398, 399, 400, 401, 405, 406, 407, 408, 409, 410, 411, 412, 413, 414,
416, 417, 418, 419, 423, 424, 425, 426, 428, 429, 430, 431, 432, 434, 435, 436, 437, 441, 442, 443, 444, 446, 447, 448, 449, 454, 455, 460,
461, 466, 467, 472, 473, 478, 479, 485, 488, 491, 494, 2215, 2221, 2241, 2247, 2261, 2267, 2241, 2291, 2293, 2766, 2787, 2858, 2898,
3026, 3036, 3046, 3056, 3066, 3076, 3086, 3096, 3114, 3199, 3262, 3579, 3583, 3678, 3715, 3726, 3742, 3758, 3789, 495, 508, 527, 585,
626, 641, 652, 675, 716, 731, 742, 765, 806, 812, 843, 852, 962, 981, 1142, 1197, 1213, 1221, 1237, 1306, 1308, 1310, 1313, 1320, 1323,
1330, 1333, 1340, 1343, 1350, 1357, 1359, 1362, 1365, 1369, 1374, 1376, 1380, 1384, 1388, 1392, 1394, 1462, 1868, 1908, 1948, 1964,
1988, 2004, 2028, 2044, 2068, 2108, 2148, 2180, 2186, 2190, 2194, 2198, 2202, 2863, 3893, 3905, 3914, 3935, 3965, 3977, 3986, 4007,
4037, 3862, 3896, 3898, 3931, 3934, 3968, 3970, 4003, 4006, 4040, 4042, 4075, 4078, 4112, 4114, 4147, 4184, 4187, 4188, 4191, 4193,
4195, 4196, 4197, 4199, 4200, 4203, 4434, 4439, 4444, 4449]
76, 430, [3, 6, 7, 8, 11, 12, 13, 17, 18, 25, 27, 28, 29, 30, 31, 32, 34, 35, 36, 37, 39, 40, 41, 42, 46, 48, 49, 52, 53, 54, 56, 57, 58, 59, 62, 63,
64, 67, 70, 72, 74, 75, 76, 77, 80, 81, 82, 85, 86, 87, 91, 93, 94, 95, 96, 97, 98, 99, 101, 102, 103, 104, 107, 108, 109, 112, 115, 117, 118,
119, 120, 121, 122, 124, 125, 126, 127, 129, 130, 131, 132, 138, 139, 142, 143, 144, 146, 147, 148, 149, 152, 153, 154, 157, 160, 162, 164,
165, 166, 167, 170, 171, 172, 175, 176, 177, 183, 184, 187, 188, 189, 191, 192, 193, 194, 197, 198, 199, 202, 206, 209, 210, 211, 216, 221,
227, 230, 233, 236, 239, 243, 244, 245, 246, 247, 249, 250, 251, 252, 253, 255, 256, 257, 258, 261, 262, 263, 265, 267, 268, 269, 273, 274,
275, 276, 277, 278, 279, 280, 281, 285, 286, 287, 288, 289, 290, 291, 292, 293, 297, 298, 299, 303, 304, 305, 306, 307, 308, 309, 310, 311,
312, 313, 314, 315, 316, 317, 321, 322, 323, 324, 326, 327, 328, 329, 333, 334, 335, 336, 338, 339, 340, 341, 343, 345, 346, 347, 348, 349,
350, 351, 352, 353, 357, 358, 359, 363, 364, 365, 366, 367, 368, 369, 370, 371, 372, 373, 374, 375, 376, 377, 378, 380, 381, 382, 383, 387,
388, 389, 393, 394, 395, 399, 400, 401, 405, 406, 407, 408, 409, 410, 411, 412, 413, 417, 418, 419, 423, 424, 425, 426, 427, 428, 429, 430,
431, 432, 433, 434, 435, 436, 437, 441, 442, 443, 447, 448, 449, 454, 455, 460, 461, 466, 467, 468, 470, 472, 473, 478, 479, 483, 485, 486,
488, 491, 494, 2215, 2221, 2227, 2241, 2247, 2261, 2267, 2281, 2291, 2293, 2338, 2359, 2607, 2698, 3026, 3036, 3038, 3056, 3066, 3076,
3086, 3096, 3215, 3262, 3371, 3403, 3423, 3534, 3566, 3582, 3715, 3789, 498, 527, 542, 582, 585, 596, 605, 632, 672, 722, 785, 812, 875,
902, 924, 989, 1070, 1149, 1306, 1308, 1310, 1313, 1320, 1323, 1330, 1333, 1340, 1343, 1350, 1358, 1361, 1365, 1369, 1374, 1376, 1379,
1383, 1388, 1392, 1394, 1868, 1908, 1940, 1948, 1972, 1988, 2020, 2028, 2068, 2108, 2132, 2140, 2148, 2156, 2164, 2180, 2186,
2198, 2202, 3921, 3949, 3958, 3993, 4065, 4093, 4137, 3862, 3896, 3898, 3931, 3934, 3968, 3970, 4003, 4006, 4040, 4042, 4075, 4078,
4112, 4114, 4147, 4184, 4187, 4189, 4191, 4192, 4193, 4195, 4196, 4197, 4199, 4200, 4203, 4434, 4436, 4438, 4439, 4441, 4444, 4449]
77, 426, [3, 6, 7, 8, 11, 12, 13, 17, 18, 25, 27, 28, 29, 30, 31, 32, 34, 35, 36, 37, 39, 40, 41, 42, 46, 48, 49, 52, 53, 54, 57, 58, 59, 61, 62, 63,
64, 67, 70, 72, 74, 75, 76, 77, 80, 81, 82, 85, 86, 87, 93, 94, 97, 98, 99, 102, 103, 104, 106, 107, 108, 109, 112, 115, 117, 119, 120, 121, 122,
125, 126, 127, 129, 130, 131, 132, 136, 138, 139, 140, 141, 142, 143, 144, 146, 147, 148, 150, 151, 152, 153, 154, 157, 160, 162, 164,
165, 166, 167, 169, 170, 171, 172, 174, 175, 176, 177, 183, 184, 187, 188, 189, 192, 193, 194, 197, 198, 199, 202, 206, 211, 216, 221, 227,
230, 233, 236, 239, 243, 244, 245, 246, 247, 249, 250, 251, 252, 255, 256, 257, 258, 259, 261, 262, 263, 267, 268, 269, 273, 274, 275, 276,
278, 279, 280, 281, 285, 286, 287, 288, 289, 290, 291, 292, 293, 294, 295, 296, 297, 298, 299, 303, 304, 305, 306, 307, 308, 309, 310, 311,
315, 316, 317, 321, 322, 323, 327, 328, 329, 333, 334, 335, 340, 341, 345, 346, 347, 348, 349, 350, 351, 352, 353, 354, 355, 356, 357,
358, 359, 363, 364, 365, 366, 367, 368, 369, 370, 371, 375, 376, 377, 381, 382, 383, 387, 388, 389, 393, 394, 395, 396, 398, 399, 400, 401,
403, 405, 406, 407, 408, 409, 410, 411, 412, 413, 414, 416, 417, 418, 419, 423, 424, 425, 426, 428, 429, 430, 431, 432, 434, 435, 436, 437,
438, 440, 441, 442, 443, 447, 448, 449, 454, 455, 460, 461, 466, 467, 472, 473, 478, 479, 485, 488, 491, 494, 2215, 2221, 2227, 2241, 2247,
2261, 2267, 2281, 2291, 2293, 2338, 2359, 2406, 2719, 2787, 2858, 2878, 3026, 3036, 3046, 3056, 3066, 3076, 3086, 3096, 3211, 3215,
3262, 3358, 3374, 3514, 3519, 3531, 3535, 3563, 3583, 3694, 3715, 3726, 3742, 3758, 3789, 498, 527, 582, 597, 626, 641, 716, 731, 762,
806, 812, 962, 981, 1013, 1094, 1142, 1197, 1213, 1221, 1229, 1306, 1308, 1310, 1313, 1320, 1323, 1330, 1333, 1340, 1343, 1350, 1358,
1361, 1365, 1369, 1374, 1376, 1380, 1384, 1388, 1392, 1394, 1868, 1908, 1948, 1964, 1988, 1996, 2004, 2028, 2044, 2068, 2108, 2148,
2180, 2186, 2190, 2194, 2198, 2202, 3863, 3914, 3935, 3986, 4007, 3862, 3896, 3898, 3931, 3934, 3968, 3970, 4003, 4006, 4040, 4042,
4075, 4078, 4112, 4114, 4147, 4184, 4187, 4189, 4191, 4192, 4193, 4195, 4196, 4197, 4199, 4200, 4203, 4434, 4439, 4444, 4449]
78, 452, [1, 3, 6, 7, 8, 11, 12, 13, 17, 18, 25, 27, 28, 29, 30, 31, 32, 34, 35, 36, 37, 38, 39, 40, 41, 42, 46, 48, 49, 52, 53, 54, 57, 58, 59, 61, 62,
63, 64, 67, 70, 72, 75, 76, 77, 80, 81, 82, 85, 86, 87, 91, 93, 94, 97, 98, 99, 102, 103, 104, 106, 107, 108, 109, 112, 115, 117, 119, 120, 121,
122, 123, 124, 125, 126, 127, 128, 129, 130, 131, 132, 136, 138, 139, 141, 142, 143, 144, 146, 147, 148, 149, 152, 153, 154, 157, 160, 162,
165, 166, 167, 170, 171, 172, 175, 176, 177, 181, 183, 184, 187, 188, 189, 192, 193, 194, 197, 198, 199, 202, 206, 211, 216, 220, 221, 227,

TABLE 2-continued

List of strands for producing the nucleic acid structures of FIG. 3E. The individuals strands 0-4454 are designated as SEQ ID NOs. 6842-11296, respectively. See also Table 15 of U.S. provisional application number 61/675,309, filed Jul. 24, 2012, incorporated by reference herein.
Shape, total number of strands, [list of strands]

230, 233, 236, 239, 243, 244, 245, 246, 247, 249, 250, 251, 252, 255, 256, 257, 258, 259, 261, 262, 263, 264, 265, 267, 268, 269, 270, 271, 272, 273, 274, 275, 276, 277, 278, 279, 280, 281, 285, 286, 287, 288, 290, 291, 292, 293, 294, 295, 296, 297, 298, 299, 303, 304, 305, 306, 307, 308, 309, 310, 311, 315, 316, 317, 321, 322, 323, 324, 325, 326, 327, 328, 329, 330, 331, 332, 333, 334, 335, 336, 337, 338, 339, 340, 341, 345, 346, 347, 349, 351, 352, 353, 354, 355, 356, 357, 358, 359, 363, 364, 365, 366, 367, 368, 369, 370, 371, 373, 375, 376, 377, 378, 379, 380, 381, 382, 383, 384, 385, 386, 387, 388, 389, 390, 391, 392, 393, 394, 395, 396, 397, 398, 399, 400, 401, 402, 404, 405, 406, 407, 408, 410, 411, 412, 413, 417, 418, 419, 423, 424, 425, 429, 430, 431, 435, 436, 437, 441, 442, 443, 444, 445, 446, 447, 448, 449, 450, 452, 454, 455, 456, 458, 460, 461, 466, 467, 472, 473, 478, 479, 485, 488, 491, 492, 494, 2207, 2221, 2227, 2241, 2247, 2261, 2267, 2281, 2291, 2293, 2338, 2406, 2627, 2658, 2679, 2766, 2786, 2806, 3026, 3036, 3046, 3056, 3066, 3076, 3078, 3096, 3262, 3358, 3439, 3503, 3614, 3646, 3662, 3678, 3707, 3789, 527, 597, 626, 644, 698, 716, 723, 797, 866, 933, 962, 981, 1029, 1070, 1102, 1181, 1189, 1305, 1308, 1310, 1312, 1320, 1322, 1330, 1332, 1340, 1342, 1350, 1357, 1361, 1365, 1369, 1374, 1376, 1380, 1384, 1388, 1391, 1393, 1868, 1948, 1964, 2004, 2028, 2108, 2164, 2172, 2180, 2186, 2190, 2194, 2198, 3863, 3914, 3935, 3958, 3977, 4102, 3826, 3862, 3894, 3896, 3897, 3898, 3931, 3934, 3966, 3968, 3969, 3970, 4003, 4006, 4038, 4040, 4041, 4042, 4075, 4078, 4110, 4112, 4113, 4114, 4147, 4182, 4184, 4185, 4187, 4188, 4189, 4191, 4192, 4193, 4195, 4196, 4197, 4199, 4200, 4203, 4434, 4439, 4444, 4448, 4449, 4451, 4454]
79, 442, [3, 6, 7, 8, 11, 12, 13, 17, 18, 25, 27, 28, 29, 30, 31, 32, 34, 35, 36, 37, 39, 40, 41, 42, 48, 49, 52, 53, 54, 57, 58, 59, 61, 62, 63, 64, 67, 70, 72, 74, 75, 76, 77, 79, 80, 81, 82, 84, 85, 86, 87, 91, 93, 94, 95, 96, 97, 98, 99, 101, 102, 103, 104, 105, 106, 107, 108, 109, 112, 115, 117, 119, 120, 121, 122, 125, 126, 127, 129, 130, 131, 132, 136, 138, 139, 140, 141, 142, 143, 144, 146, 147, 148, 149, 150, 151, 152, 153, 154, 157, 160, 162, 164, 165, 166, 167, 169, 170, 171, 172, 174, 175, 176, 177, 183, 184, 187, 188, 189, 192, 193, 194, 197, 198, 199, 202, 206, 211, 216, 221, 227, 230, 233, 236, 239, 243, 244, 245, 246, 247, 249, 250, 251, 252, 255, 256, 257, 258, 261, 262, 263, 267, 268, 269, 273, 274, 275, 279, 280, 281, 285, 286, 287, 288, 289, 290, 291, 292, 293, 294, 295, 296, 297, 298, 299, 303, 304, 305, 306, 307, 308, 309, 310, 311, 313, 315, 316, 317, 319, 321, 322, 323, 325, 327, 328, 329, 333, 334, 335, 336, 337, 338, 339, 340, 341, 342, 344, 345, 346, 347, 348, 349, 350, 351, 352, 353, 354, 355, 356, 357, 358, 359, 363, 364, 365, 366, 367, 368, 369, 370, 371, 375, 376, 377, 378, 379, 380, 381, 382, 383, 384, 386, 387, 388, 389, 393, 394, 395, 396, 398, 399, 400, 401, 403, 405, 406, 407, 408, 409, 410, 411, 412, 413, 414, 416, 417, 418, 419, 423, 424, 425, 426, 428, 429, 430, 431, 432, 434, 435, 436, 437, 438, 440, 441, 442, 443, 447, 448, 449, 454, 455, 460, 461, 466, 467, 472, 473, 478, 479, 485, 488, 491, 494, 2215, 2221, 2227, 2241, 2247, 2261, 2267, 2281, 2291, 2293, 2338, 2499, 2519, 2539, 2606, 2787, 2858, 2878, 3026, 3036, 3046, 3056, 3066, 3076, 3086, 3096, 3215, 3246, 3262, 3343, 3359, 3375, 3502, 3531, 3563, 3583, 3694, 3715, 3726, 3742, 3758, 3789, 498, 527, 582, 626, 672, 675, 716, 731, 742, 806, 812, 962, 981, 989, 997, 1014, 1022, 1101, 1142, 1197, 1213, 1221, 1229, 1306, 1308, 1310, 1313, 1320, 1323, 1330, 1333, 1340, 1343, 1350, 1358, 1361, 1365, 1369, 1374, 1376, 1380, 1384, 1388, 1392, 1394, 1472, 1868, 1908, 1948, 1988, 2028, 2068, 2108, 2148, 2180, 2186, 2190, 2194, 2198, 2202, 3863, 3914, 3935, 4007, 4037, 3862, 3896, 3898, 3931, 3934, 3968, 3970, 4003, 4006, 4040, 4042, 4075, 4078, 4112, 4114, 4147, 4184, 4187, 4189, 4191, 4192, 4193, 4195, 4196, 4197, 4199, 4200, 4203, 4434, 4439, 4444, 4449]
80, 426, [3, 8, 11, 13, 17, 18, 25, 27, 29, 30, 31, 32, 35, 36, 37, 40, 41, 42, 48, 49, 52, 53, 54, 56, 57, 58, 59, 62, 63, 64, 67, 70, 72, 74, 75, 76, 77, 80, 81, 82, 85, 86, 87, 93, 94, 96, 97, 98, 99, 101, 102, 103, 104, 105, 106, 107, 108, 109, 112, 115, 117, 118, 119, 120, 121, 122, 124, 125, 126, 127, 129, 130, 131, 132, 138, 139, 142, 143, 144, 146, 147, 148, 149, 152, 153, 154, 157, 160, 162, 164, 165, 166, 167, 170, 171, 172, 174, 175, 176, 177, 183, 184, 186, 187, 188, 189, 191, 192, 193, 194, 197, 198, 199, 202, 206, 210, 211, 214, 215, 216, 221, 227, 230, 233, 236, 239, 243, 244, 245, 246, 247, 249, 250, 251, 252, 253, 255, 256, 257, 261, 262, 263, 267, 268, 269, 273, 274, 275, 279, 280, 281, 285, 286, 287, 288, 289, 290, 291, 292, 293, 297, 298, 299, 303, 304, 305, 306, 307, 308, 309, 310, 311, 312, 313, 314, 315, 316, 317, 321, 322, 323, 327, 328, 329, 333, 334, 335, 339, 340, 341, 343, 345, 346, 347, 348, 349, 350, 351, 352, 353, 355, 357, 358, 359, 360, 362, 363, 364, 365, 366, 367, 368, 369, 370, 371, 372, 373, 374, 375, 376, 377, 378, 380, 381, 382, 383, 387, 388, 389, 393, 394, 395, 399, 400, 401, 405, 406, 407, 408, 409, 410, 411, 412, 413, 417, 418, 419, 423, 424, 425, 426, 427, 428, 429, 430, 431, 432, 433, 434, 435, 436, 437, 441, 442, 443, 447, 448, 449, 454, 455, 456, 458, 460, 461, 466, 467, 468, 472, 473, 478, 479, 485, 486, 488, 489, 491, 494, 2215, 2221, 2235, 2241, 2255, 2261, 2267, 2281, 2291, 2293, 2587, 2607, 2647, 2658, 2698, 2967, 2986, 3026, 3036, 3038, 3056, 3058, 3076, 3086, 3096, 3403, 3407, 3423, 3455, 3566, 3582, 3614, 3674, 3679, 3715, 3743, 3789, 3794, 515, 527, 542, 605, 632, 678, 785, 812, 841, 887, 913, 934, 1046, 1070, 1125, 1149, 1174, 1253, 1306, 1308, 1310, 1313, 1320, 1323, 1327, 1329, 1333, 1340, 1343, 1350, 1358, 1362, 1365, 1369, 1374, 1376, 1380, 1383, 1387, 1392, 1394, 1868, 1892, 1900, 1908, 1916, 1924, 1940, 1948, 1972, 1980, 1988, 2060, 2068, 2108, 2140, 2148, 2180, 2186, 2202, 3877, 3921, 3949, 4065, 4093, 4116, 3862, 3896, 3898, 3931, 3934, 3968, 3970, 4003, 4005, 4006, 4040, 4042, 4075, 4078, 4112, 4114, 4147, 4184, 4187, 4191, 4195, 4196, 4197, 4199, 4200, 4203, 4434, 4438, 4439, 4441, 4443, 4444, 4446, 4449]
81, 463, [3, 6, 7, 8, 11, 12, 13, 17, 18, 25, 27, 28, 29, 30, 31, 32, 34, 35, 36, 37, 39, 40, 41, 42, 46, 48, 49, 52, 53, 54, 57, 58, 59, 61, 62, 63, 64, 67, 70, 72, 75, 76, 77, 80, 81, 82, 84, 85, 86, 87, 91, 93, 94, 95, 96, 97, 98, 99, 101, 102, 103, 104, 107, 108, 109, 112, 115, 117, 118, 119, 120, 121, 122, 124, 125, 126, 127, 129, 130, 131, 132, 136, 138, 139, 142, 143, 144, 147, 148, 149, 151, 152, 153, 154, 157, 160, 162, 164, 165, 166, 167, 170, 171, 172, 174, 175, 176, 177, 181, 183, 184, 185, 186, 187, 188, 189, 191, 192, 193, 194, 195, 196, 197, 198, 199, 202, 206, 209, 210, 211, 214, 215, 216, 219, 220, 221, 227, 230, 233, 236, 239, 243, 244, 245, 246, 247, 249, 250, 251, 252, 255, 256, 257, 258, 259, 261, 262, 263, 265, 267, 268, 269, 273, 274, 275, 276, 277, 278, 279, 280, 281, 285, 286, 287, 288, 290, 291, 292, 293, 294, 296, 297, 298, 299, 303, 304, 305, 309, 310, 311, 315, 316, 317, 318, 319, 320, 321, 322, 323, 324, 325, 326, 327, 328, 329, 333, 334, 335, 336, 337, 338, 339, 340, 341, 343, 345, 346, 347, 349, 351, 352, 353, 357, 358, 359, 363, 364, 365, 366, 367, 368, 369, 370, 371, 372, 374, 375, 376, 377, 378, 379, 380, 381, 382, 383, 384, 385, 386, 387, 388, 389, 393, 394, 395, 396, 397, 398, 399, 400, 401, 405, 406, 407, 408, 409, 410, 411, 412, 413, 414, 415, 416, 417, 418, 419, 423, 424, 425, 426, 427, 428, 429, 430, 431, 435, 436, 437, 438, 439, 440, 441, 442, 443, 444, 446, 447, 448, 449, 454, 455, 456, 458, 460, 461, 466, 467, 468, 470, 472, 473, 474, 476, 478, 479, 483, 485, 486, 488, 489, 491, 494, 2215, 2221, 2227, 2241, 2247, 2261, 2267, 2281, 2291, 2293, 2338, 2359, 2446, 2607, 2627, 2698, 2967, 3026, 3036, 3038, 3056, 3058, 3076, 3096, 3215, 3262, 3326, 3423, 3439, 3582, 3691, 3715, 3723, 3743, 3789, 3818, 498, 527, 582, 585, 608, 626, 652, 675, 707, 765, 806, 821, 832, 896, 902, 962, 981, 1029, 1037, 1054, 1062, 1118, 1141, 1222, 1277, 1306, 1308, 1310, 1313, 1320, 1323, 1330, 1333, 1340, 1343, 1350, 1358, 1361, 1365, 1369, 1374, 1376, 1379, 1383, 1387, 1389, 1392, 1394, 1868, 1908, 1948, 1964, 1988, 2020, 2028, 2068, 2108, 2124, 2148, 2186, 3863, 3905, 3965, 4007, 4037, 4049, 4058, 4079, 4109, 3862, 3896, 3898, 3931, 3934, 3968, 3970, 4003, 4006, 4040, 4042, 4075, 4078, 4112, 4114, 4147, 4184, 4187, 4189, 4191, 4192, 4193, 4195, 4196, 4197, 4199, 4200, 4203, 4434, 4436, 4438, 4439, 4441, 4443, 4444, 4446, 4449]
82, 438, [1, 3, 7, 8, 13, 16, 17, 18, 25, 27, 29, 30, 31, 32, 35, 36, 37, 39, 40, 41, 42, 46, 48, 49, 52, 53, 54, 57, 58, 59, 61, 62, 63, 64, 67, 70, 72, 74, 75, 76, 77, 78, 79, 80, 81, 82, 84, 85, 86, 87, 91, 93, 94, 95, 96, 97, 98, 99, 100, 101, 102, 103, 104, 105, 106, 107, 108, 109, 112, 115, 117, 118, 119, 120, 121, 122, 124, 125, 126, 127, 129, 130, 131, 132, 138, 139, 142, 143, 144, 147, 148, 149, 151, 152, 153, 154, 157, 160, 162, 164, 165, 166, 167, 170, 171, 172, 175, 176, 177, 183, 184, 187, 188, 189, 192, 193, 194, 196, 197, 198, 199, 202, 205, 206, 209, 210, 211, 216, 221, 227, 230, 233, 236, 239, 243, 244, 245, 246, 247, 249, 250, 251, 255, 256, 257, 258, 259, 261, 262, 263, 264, 265, 267, 268, 269, 273, 274, 275, 276, 277, 278, 279, 280, 281, 285, 286, 287, 288, 289, 290, 291, 292, 293, 294, 295, 296, 297, 298, 299, 303, 304, 305, 306, 307, 308, 309, 310, 311, 313, 315, 316, 317, 318, 319, 320, 321, 322, 323, 324, 326, 327, 328, 329, 333, 334, 335, 336, 338, 339, 340, 341, 342, 343, 344, 345, 346, 347, 348, 349, 350, 351, 352, 353, 354, 355, 356, 357, 358, 359, 363, 364, 365, 366, 367, 368, 369, 370, 371, 372, 374, 375, 376, 377, 378, 380, 381, 382, 383, 387, 388, 389, 393, 394, 395, 399, 400, 401, 405, 406, 407, 408, 409, 410, 411, 412,

TABLE 2-continued

List of strands for producing the nucleic acid structures of FIG. 3E. The
individuals strands 0-4454 are designated as SEQ ID NOs. 6842-11296, respectively. See also
Table 15 of U.S. provisional application number 61/675,309, filed Jul. 24, 2012, incorporated
by reference herein.
Shape, total number of strands, [list of strands]

413, 414, 415, 416, 417, 418, 419, 423, 424, 425, 426, 427, 428, 429, 430, 431, 435, 436, 437, 441, 442, 443, 447, 448, 449, 454, 455, 460, 461, 466, 467, 468, 470, 472, 473, 474, 476, 478, 479, 483, 485, 488, 491, 494, 2215, 2221, 2227, 2241, 2255, 2261, 2267, 2281, 2293, 2499, 2698, 3018, 3036, 3056, 3066, 3076, 3086, 3096, 3138, 3343, 3371, 3403, 3534, 3566, 3582, 3715, 3755, 3789, 495, 507, 518, 551, 562, 585, 626, 716, 806, 821, 896, 903, 1022, 1141, 1149, 1306, 1310, 1313, 1320, 1323, 1330, 1333, 1340, 1343, 1350, 1357, 1361, 1366, 1369, 1371, 1374, 1376, 1379, 1381, 1384, 1388, 1392, 1394, 1868, 1884, 1908, 1924, 1948, 1988, 2028, 2068, 2108, 2124, 2132, 2140, 2148, 2156, 2164, 2186, 2194, 2198, 2202, 3863, 3893, 3905, 3914, 3935, 3965, 4007, 4058, 4079, 4130, 3859, 3862, 3896, 3898, 3931, 3934, 3968, 3970, 4003, 4006, 4040, 4042, 4075, 4078, 4112, 4114, 4147, 4184, 4187, 4188, 4189, 4191, 4192, 4195, 4197, 4199, 4200, 4203, 4433, 4434, 4436, 4439, 4444, 4449]
83, 399, [3, 6, 7, 8, 11, 12, 13, 17, 18, 25, 27, 30, 31, 32, 33, 34, 35, 36, 37, 39, 40, 41, 42, 48, 49, 51, 52, 53, 54, 55, 56, 57, 58, 59, 62, 63, 64, 67, 70, 72, 75, 76, 77, 79, 80, 81, 82, 85, 86, 87, 93, 94, 97, 98, 99, 101, 102, 103, 104, 107, 108, 109, 112, 115, 117, 120, 121, 122, 125, 126, 127, 130, 131, 132, 138, 139, 142, 143, 144, 146, 147, 148, 149, 152, 153, 154, 157, 160, 162, 165, 166, 167, 169, 170, 171, 172, 175, 176, 177, 183, 184, 187, 188, 189, 191, 192, 193, 194, 197, 198, 199, 202, 206, 211, 216, 221, 227, 230, 233, 236, 239, 243, 244, 245, 249, 250, 251, 252, 253, 255, 256, 257, 258, 259, 261, 262, 263, 267, 268, 269, 273, 274, 275, 276, 278, 279, 280, 281, 282, 283, 284, 285, 286, 287, 288, 289, 290, 291, 292, 293, 297, 298, 299, 303, 304, 305, 309, 310, 311, 312, 313, 314, 315, 316, 317, 321, 322, 323, 327, 328, 329, 333, 334, 335, 339, 340, 341, 342, 344, 345, 346, 347, 348, 350, 351, 352, 353, 357, 358, 359, 363, 364, 365, 369, 370, 371, 375, 376, 377, 381, 382, 383, 387, 388, 389, 393, 394, 395, 399, 400, 401, 403, 405, 406, 407, 411, 412, 413, 417, 418, 419, 423, 424, 425, 429, 430, 431, 432, 433, 434, 435, 436, 437, 441, 442, 443, 447, 448, 449, 454, 455, 460, 461, 462, 464, 466, 467, 468, 470, 472, 473, 478, 479, 485, 488, 491, 494, 2215, 2221, 2227, 2241, 2247, 2261, 2281, 2291, 2293, 2406, 2606, 2787, 2966, 3026, 3036, 3046, 3056, 3066, 3076, 3086, 3096, 3130, 3358, 3502, 3583, 3594, 3599, 3715, 3789, 3802, 498, 571, 588, 616, 651, 688, 706, 778, 831, 868, 886, 1013, 1101, 1109, 1142, 1261, 1269, 1306, 1308, 1310, 1313, 1320, 1323, 1330, 1333, 1340, 1343, 1350, 1358, 1361, 1365, 1367, 1370, 1374, 1376, 1380, 1384, 1388, 1392, 1394, 1868, 1876, 1900, 1908, 1940, 1948, 1956, 1980, 1988, 1996, 2020, 2028, 2036, 2052, 2060, 2068, 2076, 2100, 2108, 2116, 2132, 2140, 2148, 2156, 2180, 2186, 2190, 2198, 2202, 3870, 3942, 4086, 3862, 3896, 3898, 3931, 3934, 3968, 3970, 4003, 4006, 4040, 4042, 4075, 4078, 4112, 4114, 4147, 4184, 4187, 4189, 4191, 4192, 4193, 4195, 4196, 4199, 4203, 4434, 4434, 4439, 4444, 4449]
84, 403, [3, 6, 8, 11, 12, 13, 16, 17, 18, 25, 27, 29, 30, 31, 32, 34, 35, 36, 37, 40, 41, 42, 48, 49, 51, 52, 53, 54, 57, 58, 59, 61, 62, 63, 64, 67, 70, 72, 75, 76, 77, 79, 80, 81, 82, 85, 86, 87, 93, 94, 96, 97, 98, 99, 102, 103, 104, 107, 108, 109, 112, 115, 117, 120, 121, 122, 124, 125, 126, 127, 130, 131, 132, 138, 139, 142, 143, 144, 147, 148, 149, 152, 153, 154, 157, 160, 162, 165, 166, 167, 169, 170, 171, 172, 175, 176, 177, 183, 184, 186, 187, 188, 189, 192, 193, 194, 197, 198, 199, 202, 206, 211, 214, 215, 216, 221, 227, 230, 233, 236, 239, 243, 244, 245, 246, 249, 250, 251, 252, 253, 255, 256, 257, 258, 259, 261, 262, 263, 267, 268, 269, 273, 274, 275, 279, 280, 281, 282, 283, 284, 285, 286, 287, 291, 292, 293, 294, 296, 297, 298, 299, 303, 304, 305, 309, 310, 311, 312, 313, 314, 315, 316, 317, 318, 319, 320, 321, 322, 323, 327, 328, 329, 333, 334, 335, 339, 340, 341, 342, 343, 344, 345, 346, 347, 351, 352, 353, 357, 358, 359, 363, 364, 365, 369, 370, 371, 372, 374, 375, 376, 377, 378, 380, 381, 382, 383, 387, 388, 389, 393, 394, 395, 399, 400, 401, 405, 406, 407, 411, 412, 413, 417, 418, 419, 423, 424, 425, 429, 430, 431, 435, 436, 437, 439, 441, 442, 443, 447, 448, 449, 454, 455, 460, 461, 462, 464, 466, 467, 472, 473, 478, 479, 485, 486, 488, 489, 491, 494, 2215, 2221, 2235, 2241, 2247, 2261, 2267, 2281, 2293, 2318, 2698, 2879, 3026, 3036, 3046, 3056, 3058, 3076, 3086, 3096, 3138, 3163, 3278, 3326, 3582, 3658, 3663, 3679, 3715, 3789, 505, 595, 626, 642, 685, 732, 754, 844, 865, 912, 934, 1037, 1141, 1149, 1182, 1306, 1310, 1313, 1320, 1323, 1330, 1333, 1340, 1343, 1350, 1358, 1361, 1365, 1369, 1371, 1374, 1376, 1380, 1383, 1387, 1392, 1394, 1868, 1900, 1908, 1916, 1948, 1980, 1988, 1996, 2012, 2020, 2028, 2036, 2060, 2068, 2076, 2092, 2100, 2108, 2116, 2140, 2148, 2156, 2172, 2180, 2186, 2190, 2202, 3863, 3885, 3913, 3957, 3985, 4129, 3859, 3862, 3896, 3898, 3931, 3934, 3968, 3970, 4003, 4006, 4040, 4042, 4075, 4078, 4112, 4114, 4147, 4184, 4187, 4191, 4192, 4193, 4195, 4196, 4197, 4199, 4200, 4203, 4434, 4439, 4441, 4443, 4444, 4446, 4449]
85, 451, [1, 3, 7, 8, 11, 13, 17, 18, 25, 27, 29, 30, 31, 32, 35, 36, 37, 40, 41, 42, 46, 48, 49, 52, 53, 54, 56, 57, 58, 59, 62, 63, 64, 67, 70, 72, 73, 74, 75, 76, 77, 79, 80, 81, 82, 83, 84, 85, 86, 87, 91, 93, 94, 95, 96, 97, 98, 99, 100, 101, 102, 103, 104, 107, 108, 109, 112, 115, 117, 118, 119, 120, 121, 122, 124, 125, 126, 127, 130, 131, 132, 138, 139, 141, 142, 143, 144, 145, 146, 147, 148, 149, 152, 153, 154, 157, 160, 162, 164, 165, 166, 167, 170, 171, 172, 174, 175, 176, 177, 181, 183, 184, 187, 188, 189, 191, 192, 193, 194, 197, 198, 199, 202, 206, 209, 210, 211, 216, 221, 227, 230, 233, 236, 239, 243, 244, 245, 246, 247, 249, 250, 251, 252, 253, 255, 256, 257, 261, 262, 263, 264, 265, 267, 268, 269, 270, 272, 273, 274, 275, 276, 277, 278, 279, 280, 281, 285, 286, 287, 288, 289, 290, 291, 292, 293, 297, 298, 299, 303, 304, 305, 306, 307, 308, 309, 310, 311, 312, 313, 314, 315, 316, 317, 319, 321, 322, 323, 324, 326, 327, 328, 329, 333, 334, 335, 336, 338, 339, 340, 341, 342, 343, 344, 345, 346, 347, 348, 349, 350, 351, 352, 353, 357, 358, 359, 363, 364, 365, 366, 367, 368, 369, 370, 371, 372, 373, 374, 375, 376, 377, 378, 379, 380, 381, 382, 383, 387, 388, 389, 393, 394, 395, 397, 399, 400, 401, 402, 404, 405, 406, 407, 408, 409, 410, 411, 412, 413, 417, 418, 419, 423, 424, 425, 426, 427, 428, 429, 430, 431, 432, 433, 434, 435, 436, 437, 438, 440, 441, 442, 443, 445, 447, 448, 449, 454, 455, 456, 458, 460, 461, 466, 467, 468, 470, 472, 473, 478, 479, 483, 485, 486, 488, 491, 494, 2207, 2221, 2241, 2255, 2261, 2267, 2281, 2291, 2293, 2519, 2767, 2899, 3026, 3036, 3038, 3056, 3066, 3076, 3086, 3096, 3114, 3227, 3359, 3371, 3390, 3534, 3567, 3695, 3711, 3715, 3789, 3818, 515, 527, 542, 596, 605, 632, 722, 768, 812, 832, 852, 866, 875, 902, 924, 1022, 1093, 1181, 1229, 1245, 1253, 1305, 1308, 1310, 1312, 1320, 1330, 1333, 1340, 1343, 1345, 1350, 1357, 1359, 1362, 1365, 1369, 1374, 1376, 1379, 1383, 1388, 1392, 1394, 1756, 1868, 1892, 1924, 1940, 1948, 2020, 2028, 2068, 2100, 2108, 2164, 2180, 2186, 2198, 3877, 3886, 3921, 3993, 4029, 4065, 4093, 4137, 3826, 3862, 3894, 3896, 3897, 3898, 3931, 3934, 3966, 3968, 3970, 4003, 4006, 4040, 4042, 4075, 4078, 4112, 4114, 4147, 4184, 4185, 4187, 4188, 4191, 4195, 4196, 4197, 4199, 4200, 4203, 4434, 4436, 4438, 4439, 4441, 4444, 4449]
86, 422, [3, 6, 7, 8, 11, 12, 13, 17, 18, 25, 27, 28, 29, 30, 31, 32, 33, 34, 35, 36, 37, 39, 40, 41, 42, 46, 48, 49, 50, 51, 52, 53, 54, 55, 56, 57, 58, 59, 62, 63, 64, 67, 70, 72, 74, 75, 76, 77, 80, 81, 82, 84, 85, 86, 87, 93, 94, 97, 98, 99, 101, 102, 103, 104, 107, 108, 109, 112, 115, 117, 119, 120, 121, 122, 125, 126, 127, 130, 131, 132, 138, 139, 142, 143, 144, 146, 147, 148, 149, 152, 153, 154, 157, 160, 162, 164, 165, 166, 167, 170, 171, 172, 175, 176, 177, 183, 184, 187, 188, 189, 191, 192, 193, 194, 197, 198, 199, 202, 206, 209, 210, 211, 216, 221, 227, 230, 233, 236, 239, 243, 244, 245, 249, 250, 251, 252, 253, 255, 256, 257, 258, 259, 261, 262, 263, 265, 267, 268, 269, 273, 274, 275, 276, 277, 278, 279, 280, 281, 282, 284, 285, 286, 287, 288, 289, 290, 291, 292, 293, 297, 298, 299, 303, 304, 305, 306, 307, 308, 309, 310, 311, 312, 313, 314, 315, 316, 317, 318, 320, 321, 322, 323, 324, 326, 327, 328, 329, 333, 334, 335, 339, 340, 341, 345, 346, 347, 348, 349, 350, 351, 352, 353, 357, 358, 359, 363, 364, 365, 366, 367, 368, 369, 370, 371, 372, 373, 374, 375, 376, 377, 381, 382, 383, 387, 388, 389, 393, 394, 395, 399, 400, 401, 405, 406, 407, 408, 409, 410, 411, 412, 413, 417, 418, 419, 423, 424, 425, 426, 427, 428, 429, 430, 431, 432, 433, 434, 435, 436, 437, 441, 442, 443, 447, 448, 449, 454, 455, 460, 461, 466, 467, 468, 470, 472, 473, 478, 479, 483, 485, 486, 488, 491, 494, 2215, 2221, 2227, 2241, 2247, 2261, 2281, 2291, 2293, 2359, 2538, 3026, 3036, 3038, 3056, 3066, 3076, 3086, 3096, 3130, 3162, 3167, 3215, 3406, 3715, 3789, 498, 582, 585, 632, 652, 672, 695, 722, 785, 812, 875, 902, 924, 1021, 1069, 1077, 1306, 1308, 1310, 1313, 1320, 1323, 1330, 1333, 1340, 1343, 1350, 1358, 1361, 1365, 1367, 1370, 1374, 1376, 1379, 1383, 1388, 1392, 1394, 1868, 1908, 1940, 1948, 1988, 2004, 2020, 2028, 2052, 2060, 2068, 2076, 2084, 2100, 2108, 2132, 2140, 2148, 2156, 2164, 2180, 2186, 2198, 2202, 3921, 3949, 3993, 4021, 4065, 4093, 4137, 3862, 3896, 3898, 3931, 3934, 3968, 3970, 4003, 4006, 4040, 4042, 4075, 4078, 4112, 4114, 4147, 4184, 4187, 4189, 4191, 4192, 4193, 4195, 4196, 4199, 4203, 4434, 4436, 4438, 4439, 4441, 4444, 4449]
87, 438, [3, 8, 13, 18, 25, 27, 30, 31, 32, 35, 36, 37, 40, 41, 42, 48, 49, 52, 53, 54, 57, 58, 59, 62, 63, 64, 67, 70, 72, 75, 76, 77, 79, 80, 81, 82, 85, 86, 87, 93, 94, 96, 97, 98, 99, 102, 103, 104, 106, 107, 108, 109, 112, 113, 115, 117, 118, 119, 120, 121, 122, 123, 124, 125, 126, 127,

TABLE 2-continued

List of strands for producing the nucleic acid structures of FIG. 3E. The individuals strands 0-4454 are designated as SEQ ID NOs. 6842-11296, respectively. See also Table 15 of U.S. provisional application number 61/675,309, filed Jul. 24, 2012, incorporated by reference herein.
Shape, total number of strands, [list of strands]

128, 129, 130, 131, 132, 136, 138, 139, 141, 142, 143, 144, 145, 146, 147, 148, 149, 152, 153, 154, 157, 160, 162, 165, 166, 167, 169, 170, 171, 172, 175, 176, 177, 183, 184, 187, 188, 189, 192, 193, 194, 197, 198, 199, 202, 206, 211, 216, 221, 227, 230, 233, 236, 239, 240, 241, 243, 244, 245, 249, 250, 251, 255, 256, 257, 261, 262, 263, 264, 265, 267, 268, 269, 270, 271, 272, 273, 274, 275, 279, 280, 281, 285, 286, 287, 291, 292, 293, 294, 295, 296, 297, 298, 299, 300, 301, 302, 303, 304, 305, 309, 310, 311, 315, 316, 317, 321, 322, 323, 324, 325, 326, 327, 328, 329, 330, 331, 332, 333, 334, 335, 339, 340, 341, 342, 343, 344, 345, 346, 347, 351, 352, 353, 354, 355, 356, 357, 358, 359, 360, 361, 362, 363, 364, 365, 366, 368, 369, 370, 371, 372, 373, 374, 375, 376, 377, 378, 379, 380, 381, 382, 383, 384, 385, 386, 387, 388, 389, 390, 392, 393, 394, 395, 396, 398, 399, 400, 401, 402, 404, 405, 406, 407, 408, 410, 411, 412, 413, 414, 416, 417, 418, 419, 420, 422, 423, 424, 425, 429, 430, 431, 432, 434, 435, 436, 437, 441, 442, 443, 444, 446, 447, 448, 449, 454, 455, 460, 461, 466, 467, 472, 473, 478, 479, 485, 488, 491, 494, 2207, 2221, 2235, 2241, 2255, 2261, 2275, 2281, 2287, 2293, 2766, 3026, 3036, 3046, 3056, 3066, 3076, 3086, 3096, 3338, 3343, 3579, 3611, 3678, 3715, 3742, 3774, 3789, 497, 528, 541, 572, 631, 651, 662, 685, 705, 796, 822, 842, 852, 1022, 1054, 1070, 1094, 1110, 1133, 1165, 1173, 1189, 1205, 1221, 1237, 1305, 1307, 1309, 1312, 1315, 1317, 1319, 1322, 1325, 1329, 1332, 1337, 1339, 1343, 1350, 1357, 1362, 1366, 1370, 1373, 1376, 1380, 1384, 1388, 1392, 1394, 1876, 1884, 1892, 1916, 1924, 1932, 1956, 1972, 1996, 2012, 2116, 2148, 2156, 2172, 2186, 2190, 2194, 2198, 2202, 3899, 3922, 3971, 3985, 4066, 3826, 3859, 3861, 3862, 3894, 3896, 3898, 3931, 3933, 3934, 3966, 3968, 3970, 4001, 4003, 4005, 4006, 4038, 4040, 4041, 4042, 4075, 4077, 4078, 4112, 4114, 4147, 4184, 4185, 4187, 4188, 4191, 4195, 4199, 4201, 4203, 4204, 4434, 4439, 4444, 4449]
88, 436, [1, 3, 7, 8, 13, 16, 17, 18, 25, 27, 29, 30, 31, 32, 35, 36, 37, 39, 40, 41, 42, 46, 48, 49, 52, 53, 54, 57, 58, 59, 61, 62, 63, 64, 67, 70, 72, 74, 75, 76, 77, 80, 81, 82, 84, 85, 86, 87, 91, 93, 94, 97, 98, 99, 102, 103, 104, 106, 107, 108, 109, 112, 115, 117, 119, 120, 121, 122, 123, 124, 125, 126, 127, 129, 130, 131, 132, 136, 138, 139, 140, 141, 142, 143, 144, 146, 147, 148, 149, 150, 151, 152, 153, 154, 157, 160, 162, 164, 165, 166, 167, 170, 171, 172, 174, 175, 176, 177, 183, 184, 187, 188, 189, 192, 193, 194, 197, 198, 199, 202, 206, 211, 216, 221, 227, 230, 233, 236, 239, 243, 244, 245, 246, 247, 249, 250, 251, 255, 256, 257, 258, 259, 261, 262, 263, 264, 265, 267, 268, 269, 273, 274, 275, 276, 277, 278, 279, 280, 281, 285, 286, 287, 288, 289, 290, 291, 292, 293, 294, 295, 296, 297, 298, 299, 303, 304, 305, 306, 307, 308, 309, 310, 311, 315, 316, 317, 318, 319, 320, 321, 322, 323, 324, 325, 326, 327, 328, 329, 333, 334, 335, 336, 337, 338, 339, 340, 341, 345, 346, 347, 348, 349, 350, 351, 352, 353, 354, 355, 356, 357, 358, 359, 363, 364, 365, 366, 367, 368, 369, 370, 371, 373, 375, 376, 377, 378, 379, 380, 381, 382, 383, 384, 386, 387, 388, 389, 393, 394, 395, 396, 398, 399, 400, 401, 402, 403, 404, 405, 406, 407, 408, 410, 411, 412, 413, 414, 415, 416, 417, 418, 419, 423, 424, 425, 426, 428, 429, 430, 431, 435, 436, 437, 438, 440, 441, 442, 443, 447, 448, 449, 454, 455, 460, 461, 466, 467, 472, 473, 478, 479, 485, 488, 491, 494, 2215, 2221, 2227, 2241, 2255, 2261, 2267, 2281, 2293, 2679, 2786, 2838, 2878, 3026, 3036, 3046, 3056, 3066, 3076, 3086, 3096, 3138, 3503, 3531, 3563, 3595, 3662, 3694, 3715, 3726, 3742, 3758, 3774, 3789, 495, 507, 518, 551, 562, 585, 626, 641, 652, 675, 716, 806, 813, 833, 1102, 1213, 1229, 1306, 1310, 1313, 1320, 1323, 1330, 1333, 1340, 1343, 1350, 1357, 1361, 1366, 1369, 1371, 1374, 1376, 1380, 1384, 1388, 1392, 1394, 1868, 1884, 1908, 1924, 1948, 1964, 1988, 2004, 2028, 2068, 2108, 2148, 2186, 2190, 2194, 2198, 2202, 3863, 3893, 3905, 3914, 3935, 3965, 3977, 3986, 4007, 4037, 3859, 3862, 3896, 3898, 3931, 3934, 3968, 3970, 4003, 4006, 4040, 4042, 4075, 4078, 4112, 4114, 4147, 4184, 4187, 4188, 4189, 4191, 4192, 4195, 4197, 4199, 4200, 4203, 4434, 4439, 4444, 4449]
89, 447, [3, 6, 7, 8, 11, 12, 13, 17, 18, 25, 27, 28, 29, 30, 31, 32, 33, 34, 35, 36, 37, 39, 40, 41, 42, 46, 48, 49, 50, 51, 52, 53, 54, 56, 57, 58, 59, 60, 61, 62, 63, 64, 67, 70, 72, 74, 75, 76, 77, 80, 81, 82, 84, 85, 86, 87, 91, 93, 94, 97, 98, 99, 102, 103, 104, 106, 107, 108, 109, 112, 115, 117, 119, 120, 121, 122, 123, 124, 125, 126, 127, 129, 130, 131, 132, 136, 138, 139, 140, 141, 142, 143, 144, 145, 146, 147, 148, 149, 150, 151, 152, 153, 154, 157, 160, 162, 164, 165, 166, 167, 169, 170, 171, 172, 174, 175, 176, 177, 183, 184, 187, 188, 189, 192, 193, 194, 197, 198, 199, 202, 206, 211, 216, 221, 227, 230, 233, 236, 239, 243, 244, 245, 246, 247, 249, 250, 251, 252, 253, 255, 256, 257, 258, 259, 261, 262, 263, 265, 267, 268, 269, 273, 274, 275, 276, 277, 278, 279, 280, 281, 282, 284, 285, 286, 287, 288, 289, 290, 291, 292, 293, 294, 295, 296, 297, 298, 299, 303, 304, 305, 306, 307, 308, 309, 310, 311, 315, 316, 317, 318, 319, 320, 321, 322, 323, 324, 325, 326, 327, 328, 329, 333, 334, 335, 336, 337, 338, 339, 340, 341, 345, 346, 347, 348, 349, 350, 351, 352, 353, 354, 355, 356, 357, 358, 359, 363, 364, 365, 366, 367, 368, 369, 370, 371, 373, 375, 376, 377, 378, 379, 380, 381, 382, 383, 384, 386, 387, 388, 389, 393, 394, 395, 396, 398, 399, 400, 401, 402, 403, 404, 405, 406, 407, 408, 409, 410, 411, 412, 413, 414, 416, 417, 418, 419, 423, 424, 425, 426, 428, 429, 430, 431, 432, 434, 435, 436, 437, 438, 440, 441, 442, 443, 447, 448, 449, 454, 455, 460, 461, 466, 467, 472, 473, 478, 479, 485, 488, 491, 494, 2215, 2221, 2227, 2241, 2247, 2261, 2267, 2281, 2291, 2293, 2359, 2426, 2679, 2858, 2878, 3026, 3036, 3046, 3056, 3066, 3076, 3086, 3096, 3215, 3342, 3503, 3531, 3563, 3694, 3715, 3726, 3742, 3758, 3789, 498, 527, 582, 585, 626, 641, 652, 675, 716, 806, 812, 962, 1021, 1102, 1197, 1213, 1221, 1229, 1306, 1308, 1310, 1313, 1320, 1323, 1330, 1333, 1340, 1343, 1350, 1358, 1361, 1365, 1369, 1374, 1376, 1380, 1384, 1388, 1392, 1394, 1868, 1908, 1948, 1988, 2004, 2028, 2068, 2108, 2148, 2180, 2186, 2190, 2194, 2198, 2202, 3863, 3935, 3965, 3977, 3986, 4007, 4037, 3862, 3896, 3898, 3931, 3934, 3968, 3970, 4003, 4006, 4040, 4042, 4075, 4078, 4112, 4114, 4147, 4184, 4187, 4189, 4191, 4192, 4193, 4195, 4196, 4197, 4199, 4200, 4203, 4434, 4439, 4444, 4449]
90, 441, [3, 8, 13, 16, 17, 18, 25, 27, 29, 30, 31, 32, 35, 36, 37, 40, 41, 42, 48, 49, 52, 53, 54, 57, 58, 59, 61, 62, 63, 64, 67, 70, 72, 74, 75, 76, 77, 80, 81, 82, 85, 86, 87, 93, 94, 96, 97, 98, 99, 101, 102, 103, 104, 105, 106, 107, 108, 109, 112, 115, 117, 118, 119, 120, 121, 122, 124, 125, 126, 127, 129, 130, 131, 132, 136, 138, 139, 142, 143, 144, 147, 148, 149, 151, 152, 153, 154, 157, 160, 162, 164, 165, 166, 167, 170, 171, 172, 174, 175, 176, 177, 181, 183, 184, 185, 186, 187, 188, 189, 191, 192, 193, 194, 195, 196, 197, 198, 199, 202, 205, 206, 209, 210, 211, 214, 215, 216, 219, 220, 221, 227, 230, 233, 236, 239, 243, 244, 245, 246, 247, 249, 250, 251, 255, 256, 257, 261, 262, 263, 267, 268, 269, 273, 274, 275, 279, 280, 281, 285, 286, 287, 288, 289, 290, 291, 292, 293, 294, 295, 296, 297, 298, 299, 303, 304, 305, 306, 307, 308, 309, 310, 311, 315, 316, 317, 321, 322, 323, 327, 328, 329, 333, 334, 335, 337, 339, 340, 341, 343, 345, 346, 347, 348, 349, 350, 351, 352, 353, 354, 355, 356, 357, 358, 359, 363, 364, 365, 366, 367, 368, 369, 370, 371, 372, 374, 375, 376, 377, 378, 379, 380, 381, 382, 383, 385, 387, 388, 389, 393, 394, 395, 396, 397, 398, 399, 400, 401, 405, 406, 407, 408, 409, 410, 411, 412, 413, 414, 415, 416, 417, 418, 419, 423, 424, 425, 426, 427, 428, 429, 430, 431, 435, 436, 437, 438, 439, 440, 441, 442, 443, 444, 446, 447, 448, 449, 454, 455, 456, 458, 460, 461, 466, 467, 468, 470, 472, 473, 474, 476, 478, 479, 483, 485, 486, 488, 489, 491, 494, 2215, 2221, 2235, 2241, 2255, 2261, 2267, 2281, 2293, 2587, 2607, 2698, 2719, 2967, 3018, 3036, 3038, 3056, 3058, 3076, 3096, 3138, 3407, 3423, 3535, 3582, 3691, 3715, 3723, 3743, 3789, 3818, 518, 551, 626, 641, 678, 716, 762, 765, 806, 821, 832, 896, 903, 1062, 1070, 1141, 1222, 1306, 1310, 1313, 1320, 1323, 1330, 1333, 1340, 1343, 1350, 1358, 1362, 1366, 1369, 1371, 1374, 1376, 1379, 1383, 1387, 1389, 1392, 1394, 1868, 1884, 1892, 1900, 1908, 1916, 1924, 1948, 1964, 1972, 1980, 1988, 2028, 2068, 2108, 2124, 2148, 2186, 3863, 3914, 3935, 4007, 4049, 4058, 4079, 4109, 3859, 3862, 3896, 3898, 3931, 3934, 3968, 3970, 4003, 4006, 4040, 4042, 4075, 4078, 4112, 4114, 4147, 4184, 4187, 4191, 4195, 4197, 4199, 4200, 4203, 4433, 4434, 4436, 4438, 4439, 4441, 4443, 4444, 4446, 4449]
91, 447, [1, 3, 6, 7, 8, 12, 13, 18, 25, 27, 30, 31, 32, 35, 36, 37, 38, 39, 40, 41, 42, 46, 48, 49, 50, 51, 52, 53, 54, 57, 58, 59, 62, 63, 64, 67, 70, 72, 75, 76, 77, 80, 81, 82, 84, 85, 86, 87, 93, 94, 96, 97, 98, 99, 100, 101, 102, 103, 104, 106, 107, 108, 109, 112, 113, 115, 117, 119, 120, 121, 122, 123, 124, 125, 126, 127, 129, 130, 131, 132, 138, 139, 141, 142, 143, 144, 147, 148, 149, 151, 152, 153, 154, 157, 160, 162, 165, 166, 167, 170, 171, 172, 174, 175, 176, 177, 183, 184, 186, 187, 188, 189, 190, 191, 192, 193, 194, 196, 197, 198, 199, 202, 205, 206, 209, 210, 211, 214, 215, 216, 221, 227, 230, 233, 236, 239, 243, 244, 245, 249, 250, 251, 255, 256, 257, 258, 259, 261, 262, 263, 264, 265, 267, 268, 269, 270, 272, 273, 274, 275, 276, 277, 278, 279, 280, 281, 282, 283, 284, 285, 286, 287, 291, 292, 293, 297, 298, 299, 303, 304, 305, 309, 310, 311, 315, 316, 317, 318, 319, 320, 321, 322, 323, 327, 328, 329, 333, 334, 335, 336, 337, 338, 339, 340, 341, 342, 343, 344, 345, 346, 347, 349, 351, 352, 353, 357, 358, 359, 363, 364, 365, 366, 367, 368, 369, 370, 371, 372, 374, 375, 376, 377, 378, 379, 380, 381, 382,

TABLE 2-continued

List of strands for producing the nucleic acid structures of FIG. 3E. The individuals strands 0-4454 are designated as SEQ ID NOs. 6842-11296, respectively. See also Table 15 of U.S. provisional application number 61/675,309, filed Jul. 24, 2012, incorporated by reference herein.
Shape, total number of strands, [list of strands]

383, 387, 388, 389, 393, 394, 395, 396, 397, 398, 399, 400, 401, 402, 403, 404, 405, 406, 407, 411, 412, 413, 414, 415, 416, 417, 418, 419, 420, 421, 422, 423, 424, 425, 426, 427, 428, 429, 430, 431, 435, 436, 437, 438, 439, 440, 441, 442, 443, 447, 448, 449, 454, 455, 456, 458, 460, 461, 462, 464, 466, 467, 472, 473, 474, 476, 478, 479, 483, 485, 486, 488, 489, 491, 494, 2207, 2221, 2227, 2241, 2261, 2275, 2281, 2291, 2293, 2386, 2627, 2678, 2987, 3006, 3018, 3036, 3038, 3056, 3058, 3076, 3086, 3096, 3122, 3374, 3439, 3450, 3455, 3466, 3471, 3598, 3715, 3759, 3786, 3789, 606, 661, 751, 786, 795, 841, 903, 934, 1005, 1054, 1062, 1141, 1222, 1253, 1305, 1308, 1310, 1312, 1315, 1320, 1323, 1333, 1339, 1343, 1347, 1350, 1357, 1361, 1363, 1366, 1370, 1374, 1376, 1379, 1383, 1387, 1392, 1394, 1868, 1876, 1884, 1932, 1940, 1948, 1956, 1964, 1988, 2060, 2068, 2124, 2140, 2148, 2202, 3878, 3950, 3972, 4044, 4085, 4094, 4116, 3826, 3862, 3894, 3896, 3898, 3931, 3934, 3968, 3970, 4003, 4005, 4006, 4040, 4042, 4073, 4075, 4077, 4078, 4112, 4114, 4147, 4184, 4185, 4187, 4188, 4189, 4191, 4192, 4195, 4199, 4203, 4433, 4434, 4436, 4438, 4439, 4441, 4443, 4444, 4446, 4449]
92, 413, [3, 8, 13, 16, 17, 18, 25, 27, 29, 30, 31, 32, 35, 36, 37, 40, 41, 42, 48, 49, 52, 53, 54, 57, 58, 59, 61, 62, 63, 64, 67, 70, 72, 74, 75, 76, 77, 80, 81, 82, 85, 86, 87, 91, 93, 94, 97, 98, 99, 102, 103, 104, 106, 107, 108, 109, 112, 115, 117, 119, 120, 121, 122, 124, 125, 126, 127, 129, 130, 131, 132, 136, 138, 139, 140, 141, 142, 143, 144, 145, 146, 147, 148, 149, 150, 151, 152, 153, 154, 157, 160, 162, 165, 166, 167, 169, 170, 171, 172, 174, 175, 176, 177, 183, 184, 187, 188, 189, 192, 193, 194, 197, 198, 199, 202, 206, 211, 216, 221, 227, 230, 233, 236, 239, 243, 244, 245, 246, 247, 249, 250, 251, 255, 256, 257, 261, 262, 263, 267, 268, 269, 273, 274, 275, 279, 280, 281, 285, 286, 287, 288, 289, 290, 291, 292, 293, 294, 295, 296, 297, 298, 299, 303, 304, 305, 306, 307, 308, 309, 310, 311, 315, 316, 317, 321, 322, 323, 327, 328, 329, 333, 334, 335, 339, 340, 341, 345, 346, 347, 348, 349, 350, 351, 352, 353, 354, 355, 356, 357, 358, 359, 363, 364, 365, 366, 367, 368, 369, 370, 371, 373, 375, 376, 377, 379, 381, 382, 383, 384, 386, 387, 388, 389, 393, 394, 395, 396, 398, 399, 400, 401, 402, 403, 404, 405, 406, 407, 408, 410, 411, 412, 413, 414, 415, 416, 417, 418, 419, 423, 424, 425, 426, 428, 429, 430, 431, 432, 434, 435, 436, 437, 438, 440, 441, 442, 443, 447, 448, 449, 454, 455, 460, 461, 466, 467, 472, 473, 478, 479, 485, 488, 491, 494, 2215, 2221, 2235, 2241, 2255, 2261, 2267, 2281, 2293, 2679, 2699, 2838, 2878, 3026, 3036, 3046, 3056, 3066, 3076, 3086, 3096, 3138, 3402, 3407, 3503, 3519, 3531, 3563, 3694, 3715, 3726, 3742, 3774, 3789, 518, 551, 626, 641, 675, 716, 806, 813, 822, 824, 1078, 1102, 1189, 1213, 1221, 1229, 1306, 1310, 1313, 1320, 1323, 1330, 1333, 1340, 1343, 1350, 1358, 1362, 1366, 1369, 1371, 1374, 1376, 1380, 1384, 1388, 1392, 1394, 1868, 1884, 1892, 1900, 1908, 1916, 1924, 1948, 1964, 1972, 1980, 1988, 2004, 2028, 2068, 2108, 2148, 2172, 2186, 2190, 2194, 2198, 2202, 3863, 3914, 3935, 3986, 4007, 4037, 3859, 3862, 3896, 3898, 3931, 3934, 3968, 3970, 4003, 4006, 4040, 4042, 4075, 4078, 4112, 4114, 4147, 4184, 4187, 4191, 4195, 4197, 4199, 4200, 4203, 4434, 4439, 4444, 4449]
93, 448, [3, 6, 7, 8, 11, 12, 13, 17, 18, 25, 27, 28, 29, 30, 31, 32, 34, 35, 36, 37, 39, 40, 41, 42, 46, 48, 49, 52, 53, 54, 57, 58, 59, 61, 62, 63, 64, 67, 70, 72, 75, 76, 77, 80, 81, 82, 84, 85, 86, 87, 93, 94, 96, 97, 98, 99, 102, 103, 104, 107, 108, 109, 112, 115, 117, 118, 119, 120, 121, 122, 124, 125, 126, 127, 130, 131, 132, 136, 138, 139, 142, 143, 144, 147, 148, 149, 151, 152, 153, 154, 157, 160, 162, 164, 165, 166, 167, 170, 171, 172, 174, 175, 176, 177, 181, 183, 184, 185, 186, 187, 188, 189, 191, 192, 193, 194, 195, 196, 197, 198, 199, 202, 206, 209, 210, 211, 214, 215, 216, 219, 220, 221, 227, 230, 233, 236, 239, 243, 244, 245, 246, 247, 249, 250, 251, 252, 255, 256, 257, 258, 259, 261, 262, 263, 265, 267, 268, 269, 273, 274, 275, 276, 277, 278, 279, 280, 281, 285, 286, 287, 288, 290, 291, 292, 293, 294, 295, 296, 297, 298, 299, 303, 304, 305, 306, 308, 309, 310, 311, 315, 316, 317, 318, 319, 320, 321, 322, 323, 324, 326, 327, 328, 329, 333, 334, 335, 336, 338, 339, 340, 341, 345, 346, 347, 351, 352, 353, 357, 358, 359, 363, 364, 365, 369, 370, 371, 372, 374, 375, 376, 377, 381, 382, 383, 387, 388, 389, 393, 394, 395, 399, 400, 401, 405, 406, 407, 408, 409, 410, 411, 412, 413, 417, 418, 419, 423, 424, 425, 426, 427, 428, 429, 430, 431, 435, 436, 437, 441, 442, 443, 444, 446, 447, 448, 449, 454, 455, 456, 458, 460, 461, 466, 467, 468, 470, 472, 473, 474, 476, 478, 479, 483, 485, 486, 488, 489, 491, 494, 2215, 2221, 2227, 2241, 2247, 2261, 2267, 2281, 2293, 2338, 2359, 2478, 2586, 2607, 2967, 3026, 3036, 3038, 3056, 3058, 3076, 3096, 3215, 3262, 3419, 3423, 3454, 3482, 3487, 3518, 3562, 3567, 3582, 3610, 3615, 3674, 3679, 3691, 3715, 3723, 3743, 3789, 3818, 498, 527, 582, 585, 626, 633, 644, 652, 678, 697, 765, 821, 896, 902, 962, 981, 1029, 1053, 1062, 1077, 1093, 1110, 1141, 1158, 1222, 1277, 1306, 1308, 1310, 1313, 1320, 1323, 1330, 1333, 1340, 1343, 1350, 1358, 1361, 1365, 1369, 1374, 1376, 1379, 1383, 1387, 1389, 1392, 1394, 1868, 1908, 1948, 1964, 1988, 2012, 2028, 2060, 2068, 2108, 2124, 2148, 2186, 3863, 3905, 3914, 3965, 4058, 4079, 4109, 3862, 3896, 3898, 3931, 3934, 3968, 3970, 4003, 4006, 4040, 4042, 4075, 4078, 4112, 4114, 4147, 4184, 4187, 4189, 4191, 4192, 4193, 4195, 4196, 4197, 4199, 4200, 4203, 4434, 4436, 4438, 4439, 4441, 4443, 4444, 4446, 4449]
94, 426, [3, 6, 7, 8, 12, 13, 18, 25, 27, 30, 31, 32, 33, 34, 35, 36, 37, 39, 40, 41, 42, 46, 48, 49, 52, 53, 54, 56, 57, 58, 59, 62, 63, 64, 67, 70, 72, 75, 76, 77, 79, 80, 81, 82, 85, 86, 87, 93, 94, 97, 98, 99, 101, 102, 103, 104, 107, 108, 109, 112, 115, 117, 118, 119, 120, 121, 122, 124, 125, 126, 127, 129, 130, 131, 132, 138, 139, 141, 142, 143, 144, 145, 146, 147, 148, 149, 151, 152, 153, 154, 157, 160, 162, 165, 166, 167, 169, 170, 171, 172, 175, 176, 177, 183, 184, 187, 188, 189, 191, 192, 193, 194, 197, 198, 199, 202, 206, 210, 211, 214, 215, 216, 221, 227, 230, 233, 236, 239, 243, 244, 245, 249, 250, 251, 252, 253, 255, 256, 257, 258, 261, 262, 263, 267, 268, 269, 273, 274, 275, 276, 278, 279, 280, 281, 282, 283, 284, 285, 286, 287, 288, 289, 290, 291, 292, 293, 297, 298, 299, 303, 304, 305, 309, 310, 311, 312, 313, 314, 315, 316, 317, 321, 322, 323, 327, 328, 329, 333, 334, 335, 339, 340, 341, 342, 343, 344, 345, 346, 347, 348, 349, 350, 351, 352, 353, 357, 358, 359, 363, 364, 365, 367, 369, 370, 371, 372, 373, 374, 375, 376, 377, 379, 381, 382, 383, 387, 388, 389, 393, 394, 395, 396, 398, 399, 400, 401, 402, 403, 404, 405, 406, 407, 408, 409, 410, 411, 412, 413, 414, 416, 417, 418, 419, 423, 424, 425, 429, 430, 431, 432, 433, 434, 435, 436, 437, 441, 442, 443, 447, 448, 449, 454, 455, 460, 461, 462, 464, 466, 467, 468, 470, 472, 473, 478, 479, 485, 486, 488, 491, 494, 2215, 2221, 2227, 2241, 2247, 2261, 2275, 2281, 2291, 2293, 2359, 2659, 2699, 2766, 2806, 3026, 3036, 3038, 3056, 3076, 3086, 3096, 3211, 3215, 3374, 3487, 3519, 3646, 3678, 3715, 3739, 3789, 498, 517, 582, 596, 616, 651, 706, 723, 751, 768, 806, 831, 886, 913, 958, 989, 1013, 1094, 1118, 1173, 1197, 1306, 1308, 1310, 1313, 1320, 1323, 1330, 1333, 1340, 1343, 1350, 1358, 1361, 1365, 1370, 1374, 1376, 1380, 1383, 1385, 1388, 1392, 1394, 1868, 1876, 1908, 1940, 1948, 1956, 1972, 1988, 1996, 2020, 2028, 2060, 2068, 2108, 2140, 2148, 2156, 2180, 2186, 2190, 2198, 2202, 2870, 3906, 3942, 3978, 4076, 4086, 4122, 3862, 3896, 3898, 3931, 3934, 3968, 3970, 4003, 4006, 4040, 4042, 4075, 4078, 4112, 4114, 4147, 4184, 4187, 4189, 4191, 4192, 4193, 4195, 4196, 4199, 4203, 4434, 4438, 4439, 4441, 4444, 4449]
95, 441, [1, 3, 7, 8, 11, 12, 13, 17, 18, 25, 27, 28, 29, 30, 31, 32, 34, 35, 36, 37, 39, 40, 41, 42, 46, 48, 49, 50, 51, 52, 53, 54, 56, 57, 58, 59, 60, 61, 62, 63, 64, 67, 70, 72, 74, 75, 76, 77, 80, 81, 82, 84, 85, 86, 87, 91, 93, 94, 97, 98, 99, 102, 103, 104, 106, 107, 108, 109, 112, 115, 117, 119, 120, 121, 122, 125, 126, 127, 129, 130, 131, 132, 136, 138, 139, 141, 142, 143, 144, 147, 148, 151, 152, 153, 154, 157, 160, 162, 164, 165, 166, 167, 170, 171, 172, 174, 175, 176, 177, 183, 184, 187, 188, 189, 192, 193, 194, 197, 198, 199, 202, 206, 211, 216, 221, 227, 230, 233, 236, 239, 243, 244, 245, 246, 247, 249, 250, 251, 252, 253, 255, 256, 257, 259, 261, 262, 263, 264, 265, 267, 268, 269, 273, 274, 275, 276, 277, 278, 279, 280, 281, 282, 284, 285, 286, 287, 288, 289, 290, 291, 292, 293, 294, 295, 296, 297, 298, 299, 303, 304, 305, 306, 307, 308, 309, 310, 311, 315, 316, 317, 318, 319, 320, 321, 322, 323, 324, 325, 326, 327, 328, 329, 333, 334, 335, 337, 338, 339, 340, 341, 345, 346, 347, 348, 349, 350, 351, 352, 353, 354, 355, 356, 357, 358, 359, 363, 364, 365, 366, 367, 368, 369, 370, 371, 375, 376, 377, 378, 379, 380, 381, 382, 383, 384, 385, 386, 387, 388, 389, 393, 394, 395, 396, 397, 398, 399, 400, 401, 405, 406, 407, 408, 410, 411, 412, 413, 414, 415, 416, 417, 418, 419, 423, 424, 425, 426, 428, 429, 430, 431, 435, 436, 437, 438, 440, 441, 442, 443, 444, 446, 447, 448, 449, 454, 455, 460, 461, 466, 467, 473, 478, 479, 485, 488, 491, 494, 2215, 2221, 2241, 2247, 2261, 2267, 2281, 2291, 2293, 2339, 2426, 2838, 2898, 3026, 3036, 3046, 3056, 3066, 3076, 3086, 3096, 3114, 3199, 3342, 3595, 3715, 3726, 3758, 3774, 3789, 495, 508, 527, 585, 626, 641, 652, 675, 716, 731, 742, 765, 806, 813, 832, 852, 962, 1021, 1213, 1229, 1237, 1306, 1308, 1310, 1313, 1320, 1323, 1330, 1333, 1340, 1343, 1350, 1357, 1359, 1362, 1365, 1369, 1374, 1376, 1380, 1384, 1388, 1392, 1394, 1868, 1908, 1948, 1988, 2004, 2028, 2044, 2068, 2084, 2108, 2124, 2148, 2164, 2186, 2190, 2194, 2198, 2202, 3863, 3893, 3935, 3965, 3977, 3986, 4007, 4037, 4049, 4058, 3862, 3896, 3898, 3931, 3934, 3968, 3970, 4003, 4006, 4040, 4042, 4075, 4078, 4112, 4114, 4147, 4184, 4187, 4188, 4191, 4193, 4195, 4196,

TABLE 2-continued

List of strands for producing the nucleic acid structures of FIG. 3E. The
individuals strands 0-4454 are designated as SEQ ID NOs. 6842-11296, respectively. See also
Table 15 of U.S. provisional application number 61/675,309, filed Jul. 24, 2012, incorporated
by reference herein.
Shape, total number of strands, [list of strands]

4197, 4199, 4200, 4203, 4434, 4439, 4444, 4449]
96, 426, [3, 8, 12, 13, 18, 25, 27, 30, 31, 32, 34, 35, 36, 37, 40, 41, 42, 48, 49, 51, 52, 53, 54, 55, 56, 57, 58, 59, 62, 63, 64, 67, 70, 72, 73, 74, 75, 76, 77, 79, 80, 81, 82, 84, 85, 86, 87, 91, 93, 94, 97, 98, 99, 102, 103, 104, 106, 107, 108, 109, 112, 115, 117, 119, 120, 121, 122, 125, 126, 127, 129, 130, 131, 132, 136, 138, 139, 142, 143, 144, 147, 148, 149, 151, 152, 153, 154, 157, 160, 162, 164, 165, 166, 167, 170, 171, 172, 174, 175, 176, 177, 183, 184, 187, 188, 189, 192, 193, 194, 197, 198, 199, 202, 206, 211, 216, 221, 227, 230, 233, 236, 239, 243, 244, 245, 249, 250, 251, 252, 253, 255, 256, 257, 259, 261, 262, 263, 267, 268, 269, 273, 274, 275, 277, 279, 280, 281, 282, 283, 284, 285, 286, 287, 288, 289, 290, 291, 292, 293, 297, 298, 299, 303, 304, 305, 306, 307, 308, 309, 310, 311, 312, 314, 315, 316, 317, 318, 319, 320, 321, 322, 323, 325, 327, 328, 329, 333, 334, 335, 336, 337, 338, 339, 340, 341, 345, 346, 347, 348, 349, 350, 351, 352, 353, 354, 355, 356, 357, 358, 359, 363, 364, 365, 366, 367, 368, 369, 370, 371, 375, 376, 377, 378, 379, 380, 381, 382, 383, 384, 385, 386, 387, 388, 389, 393, 394, 395, 396, 397, 398, 399, 400, 401, 405, 406, 407, 408, 410, 411, 412, 413, 414, 415, 416, 417, 418, 419, 423, 424, 425, 426, 428, 429, 430, 431, 435, 436, 437, 438, 440, 441, 442, 443, 444, 446, 447, 448, 449, 454, 455, 460, 461, 466, 467, 472, 473, 478, 479, 485, 488, 491, 494, 2215, 2221, 2235, 2241, 2247, 2261, 2275, 2281, 2291, 2293, 2339, 2407, 2518, 2539, 2838, 2898, 3026, 3036, 3046, 3056, 3066, 3076, 3086, 3096, 3199, 3247, 3375, 3422, 3595, 3715, 3726, 3758, 3774, 3789, 508, 517, 574, 588, 672, 675, 716, 731, 742, 765, 806, 813, 832, 852, 958, 974, 1038, 1061, 1213, 1229, 1237, 1306, 1308, 1310, 1313, 1320, 1323, 1330, 1333, 1340, 1343, 1350, 1358, 1362, 1365, 1370, 1374, 1376, 1380, 1384, 1388, 1392, 1394, 1868, 1876, 1900, 1908, 1940, 1948, 1988, 2028, 2044, 2068, 2084, 2108, 2124, 2148, 2164, 2186, 2190, 2194, 2198, 2202, 3870, 3921, 3935, 3977, 3986, 4007, 4037, 4049, 4058, 3862, 3896, 3898, 3931, 3934, 3968, 3970, 4003, 4006, 4040, 4042, 4075, 4078, 4112, 4114, 4147, 4184, 4187, 4191, 4193, 4195, 4196, 4199, 4203, 4434, 4439, 4444, 4449]
97, 435, [3, 7, 8, 13, 17, 18, 25, 27, 29, 30, 31, 32, 33, 34, 35, 36, 37, 39, 40, 41, 42, 46, 48, 49, 50, 51, 52, 53, 54, 55, 56, 57, 58, 59, 61, 62, 63, 64, 67, 70, 72, 75, 76, 77, 79, 80, 81, 82, 85, 86, 87, 93, 94, 97, 98, 99, 102, 103, 104, 107, 108, 109, 112, 115, 117, 119, 120, 121, 122, 124, 125, 126, 127, 130, 131, 132, 138, 139, 142, 143, 144, 147, 148, 149, 152, 153, 154, 157, 160, 162, 165, 166, 167, 170, 171, 172, 175, 176, 177, 183, 184, 187, 188, 189, 192, 193, 194, 197, 198, 199, 202, 206, 211, 216, 221, 227, 230, 233, 236, 239, 243, 244, 245, 246, 247, 249, 250, 251, 253, 255, 256, 257, 258, 259, 261, 262, 263, 265, 267, 268, 269, 271, 273, 274, 275, 276, 278, 279, 280, 281, 282, 283, 284, 285, 286, 287, 288, 289, 290, 291, 292, 293, 294, 295, 296, 297, 298, 299, 300, 301, 302, 303, 304, 305, 309, 310, 311, 312, 313, 314, 315, 316, 317, 318, 320, 321, 322, 323, 324, 325, 326, 327, 328, 329, 330, 331, 332, 333, 334, 335, 339, 340, 341, 342, 344, 345, 346, 347, 351, 352, 353, 354, 355, 356, 357, 358, 359, 360, 361, 362, 363, 364, 365, 369, 370, 371, 372, 374, 375, 376, 377, 381, 382, 383, 384, 385, 386, 387, 388, 389, 390, 392, 393, 394, 395, 399, 400, 401, 405, 406, 407, 411, 412, 413, 414, 416, 417, 418, 419, 420, 422, 423, 424, 425, 429, 430, 431, 435, 436, 437, 441, 442, 443, 444, 446, 447, 448, 449, 454, 455, 460, 461, 466, 467, 472, 473, 478, 479, 485, 488, 491, 494, 2215, 2221, 2227, 2241, 2255, 2261, 2267, 2281, 2291, 2293, 2319, 2359, 2387, 2446, 2498, 3026, 3036, 3046, 3056, 3066, 3076, 3086, 3096, 3183, 3215, 3231, 3326, 3419, 3438, 3547, 3582, 3611, 3710, 3715, 3774, 3789, 498, 507, 518, 527, 582, 631, 643, 662, 697, 721, 732, 752, 842, 954, 962, 966, 1013, 1069, 1141, 1205, 1237, 1306, 1308, 1310, 1313, 1315, 1319, 1322, 1325, 1327, 1329, 1332, 1335, 1337, 1339, 1350, 1358, 1361, 1366, 1369, 1374, 1376, 1380, 1384, 1388, 1392, 1394, 1868, 1996, 2036, 2052, 2076, 2092, 2116, 2124, 2132, 2156, 2164, 2172, 2186, 2190, 2194, 2198, 2202, 2863, 3957, 3971, 3978, 3994, 4003, 4066, 3862, 3896, 3898, 3929, 3931, 3933, 3934, 3966, 3968, 3970, 4003, 4005, 4006, 4038, 4040, 4042, 4075, 4077, 4078, 4110, 4112, 4114, 4147, 4184, 4187, 4189, 4191, 4192, 4195, 4197, 4199, 4200, 4203, 4434, 4439, 4444, 4449]
98, 418, [1, 3, 7, 8, 13, 16, 18, 25, 27, 29, 30, 31, 32, 35, 36, 37, 39, 40, 41, 42, 48, 49, 51, 52, 53, 54, 56, 57, 58, 59, 62, 63, 64, 67, 70, 72, 75, 76, 77, 79, 80, 81, 82, 85, 86, 87, 93, 94, 96, 97, 98, 99, 100, 101, 102, 103, 104, 107, 108, 109, 112, 115, 117, 118, 119, 120, 121, 122, 124, 125, 126, 127, 129, 130, 131, 132, 136, 138, 139, 142, 143, 144, 147, 148, 149, 151, 152, 153, 154, 157, 160, 162, 165, 166, 167, 170, 171, 172, 175, 176, 177, 183, 184, 187, 188, 189, 192, 193, 194, 197, 198, 199, 202, 206, 211, 216, 221, 227, 230, 233, 236, 239, 243, 244, 245, 246, 247, 249, 250, 251, 255, 256, 257, 261, 262, 263, 264, 267, 268, 269, 273, 274, 275, 276, 278, 279, 280, 281, 283, 285, 286, 287, 288, 289, 290, 291, 292, 293, 297, 298, 299, 303, 304, 305, 309, 310, 311, 312, 313, 314, 315, 316, 317, 318, 319, 320, 321, 322, 323, 327, 328, 329, 333, 334, 335, 339, 340, 341, 342, 343, 344, 345, 346, 347, 348, 349, 350, 351, 352, 353, 357, 358, 359, 363, 364, 365, 369, 370, 371, 372, 374, 375, 376, 377, 378, 379, 380, 381, 382, 383, 387, 388, 389, 393, 394, 395, 396, 397, 398, 399, 400, 401, 405, 406, 407, 408, 410, 411, 412, 413, 417, 418, 419, 423, 424, 425, 426, 428, 429, 430, 431, 435, 436, 437, 441, 442, 443, 444, 446, 447, 448, 449, 454, 455, 460, 461, 466, 467, 472, 473, 478, 479, 485, 488, 491, 494, 2215, 2221, 2241, 2255, 2261, 2275, 2281, 2293, 2298, 2427, 2446, 2698, 2766, 2838, 2898, 3026, 3036, 3046, 3056, 3066, 3076, 3086, 3096, 3114, 3138, 3194, 3199, 3263, 3294, 3326, 3482, 3487, 3582, 3610, 3615, 3678, 3715, 3726, 3774, 3789, 495, 525, 543, 551, 617, 685, 706, 751, 765, 777, 813, 824, 843, 852, 958, 982, 997, 1013, 1094, 1141, 1158, 1189, 1213, 1237, 1306, 1310, 1313, 1320, 1323, 1330, 1333, 1340, 1343, 1350, 1357, 1359, 1362, 1366, 1369, 1371, 1374, 1376, 1380, 1384, 1388, 1392, 1394, 1868, 1884, 1908, 1948, 1980, 1988, 1996, 2020, 2028, 2060, 2068, 2108, 2124, 2148, 2164, 2172, 2186, 2190, 2194, 2198, 2202, 3893, 3900, 3942, 3957, 4058, 3859, 3862, 3896, 3898, 3931, 3934, 3968, 3970, 4003, 4006, 4040, 4042, 4075, 4078, 4112, 4114, 4147, 4184, 4187, 4188, 4191, 4195, 4199, 4200, 4203, 4434, 4439, 4444, 4449]
99, 451, [3, 6, 7, 8, 11, 12, 13, 17, 18, 25, 27, 29, 30, 31, 32, 34, 35, 36, 37, 39, 40, 41, 42, 46, 48, 49, 52, 53, 54, 57, 58, 59, 62, 63, 64, 67, 70, 72, 75, 76, 77, 80, 81, 82, 84, 85, 86, 87, 91, 93, 94, 95, 96, 97, 98, 99, 101, 102, 103, 104, 107, 108, 109, 112, 115, 117, 118, 119, 120, 121, 122, 124, 125, 126, 127, 129, 130, 131, 132, 136, 138, 139, 142, 143, 144, 147, 148, 149, 151, 152, 153, 154, 157, 160, 162, 164, 165, 166, 167, 170, 171, 172, 174, 175, 176, 177, 181, 183, 184, 187, 188, 189, 192, 193, 194, 196, 197, 198, 199, 202, 205, 206, 209, 210, 211, 216, 219, 220, 221, 227, 230, 233, 236, 239, 243, 244, 245, 246, 249, 250, 251, 252, 255, 256, 257, 258, 259, 261, 262, 263, 265, 267, 268, 269, 273, 274, 275, 276, 277, 278, 279, 280, 281, 285, 286, 287, 291, 292, 293, 297, 298, 299, 303, 304, 305, 309, 310, 311, 315, 316, 317, 318, 319, 320, 321, 322, 323, 324, 325, 326, 327, 328, 329, 333, 334, 335, 336, 337, 338, 339, 340, 341, 343, 345, 346, 347, 349, 351, 352, 353, 357, 358, 359, 363, 364, 365, 366, 367, 368, 369, 370, 371, 372, 374, 375, 376, 377, 378, 379, 380, 381, 382, 383, 384, 385, 386, 387, 388, 389, 393, 394, 395, 396, 397, 398, 399, 400, 401, 405, 406, 407, 408, 409, 410, 411, 412, 413, 414, 415, 416, 417, 418, 419, 423, 424, 425, 426, 427, 428, 429, 430, 431, 435, 436, 437, 438, 439, 440, 441, 442, 443, 444, 445, 446, 447, 448, 449, 454, 455, 456, 458, 460, 461, 466, 467, 468, 470, 472, 473, 474, 476, 478, 479, 483, 485, 488, 491, 492, 494, 2215, 2221, 2227, 2241, 2247, 2261, 2267, 2281, 2291, 2293, 2318, 2338, 2359, 2607, 2627, 2698, 3018, 3036, 3056, 3066, 3076, 3078, 3096, 3215, 3262, 3278, 3423, 3439, 3582, 3715, 3755, 3789, 498, 527, 542, 582, 585, 652, 675, 707, 765, 806, 821, 832, 855, 896, 903, 922, 942, 973, 981, 1054, 1062, 1118, 1141, 1306, 1308, 1310, 1313, 1320, 1323, 1330, 1333, 1340, 1343, 1350, 1358, 1361, 1365, 1369, 1374, 1376, 1379, 1381, 1384, 1387, 1391, 1394, 1868, 1908, 1940, 1948, 1956, 1964, 1988, 2020, 2028, 2068, 2108, 2124, 2148, 2164, 2186, 2194, 3905, 3965, 4007, 4037, 4049, 4058, 4079, 4109, 4121, 4130, 3862, 3896, 3898, 3931, 3934, 3968, 3970, 4003, 4006, 4040, 4042, 4075, 4078, 4112, 4114, 4147, 4184, 4187, 4189, 4191, 4192, 4193, 4195, 4196, 4197, 4199, 4200, 4203, 4433, 4434, 4436, 4439, 4444, 4446, 4448, 4449, 4451]
100, 426, [1, 3, 6, 7, 8, 11, 12, 13, 16, 17, 18, 25, 27, 28, 29, 30, 31, 32, 34, 35, 36, 37, 39, 40, 41, 42, 48, 49, 52, 53, 54, 56, 57, 58, 59, 62, 63, 64, 67, 70, 72, 75, 76, 77, 79, 80, 81, 82, 85, 86, 87, 93, 94, 96, 97, 98, 99, 102, 103, 104, 107, 108, 109, 112, 115, 117, 120, 121, 122, 125, 126, 127, 129, 130, 131, 132, 136, 138, 139, 140, 141, 142, 143, 144, 145, 146, 147, 148, 149, 151, 152, 153, 154, 157, 160, 162, 164, 165, 166, 167, 169, 170, 171, 172, 174, 175, 176, 177, 183, 184, 187, 188, 189, 192, 193, 194, 197, 198, 199, 202, 206, 211, 216, 221, 227, 230, 233, 236, 239, 243, 244, 245, 246, 247, 249, 250, 251, 252, 253, 255, 256, 257, 258, 261, 262, 263, 264, 267, 268, 269, 273, 274, 275, 279, 280, 281, 285, 286, 287, 288, 289, 290, 291, 292, 293, 297, 298, 299, 303, 304, 305, 309, 310, 311, 312, 313, 314, 315, 316, 317, 321, 322, 323, 327, 328, 329, 333, 334, 335, 339, 340, 341, 342, 343, 344, 345, 346, 347, 351, 352, 353, 357, 358, 359, 363, 364, 365, 369, 370,

| | |
|---|---|
| | TABLE 2-continued |

List of strands for producing the nucleic acid structures of FIG. 3E. The individuals strands 0-4454 are designated as SEQ ID NOs. 6842-11296, respectively. See also Table 15 of U.S. provisional application number 61/675,309, filed Jul. 24, 2012, incorporated by reference herein.
Shape, total number of strands, [list of strands]

371, 375, 376, 377, 378, 379, 380, 381, 382, 383, 387, 388, 389, 393, 394, 395, 396, 397, 398, 399, 400, 401, 402, 403, 404, 405, 406, 407, 409, 411, 412, 413, 417, 418, 419, 423, 424, 425, 426, 428, 429, 430, 431, 432, 434, 435, 436, 437, 438, 440, 441, 442, 443, 444, 446, 447, 448, 449, 454, 455, 460, 461, 466, 467, 472, 473, 478, 479, 485, 488, 491, 494, 2215, 2221, 2227, 2241, 2247, 2261, 2267, 2281, 2293, 2298, 2338, 2358, 2446, 2498, 2606, 2807, 2838, 2858, 2878, 2898, 3026, 3036, 3046, 3056, 3066, 3076, 3086, 3096, 3138, 3246, 3262, 3294, 3326, 3438, 3502, 3599, 3610, 3615, 3715, 3726, 3742, 3758, 3774, 3789, 495, 543, 582, 605, 617, 643, 651, 685, 697, 751, 765, 813, 852, 989, 997, 1022, 1070, 1094, 1134, 1142, 1158, 1213, 1221, 1229, 1237, 1306, 1310, 1313, 1320, 1323, 1330, 1333, 1340, 1343, 1350, 1357, 1361, 1365, 1369, 1371, 1374, 1376, 1380, 1384, 1388, 1392, 1394, 1868, 1908, 1948, 1972, 1980, 1988, 1996, 2020, 2028, 2036, 2060, 2068, 2108, 2148, 2186, 2190, 2194, 2198, 2202, 4022, 3859, 3862, 3896, 3898, 3931, 3934, 3968, 3970, 4003, 4006, 4040, 4042, 4075, 4078, 4112, 4114, 4147, 4184, 4187, 4188, 4189, 4191, 4192, 4193, 4195, 4196, 4197, 4199, 4200, 4203, 4434, 4439, 4444, 4449]

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described to herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10604543B2). An electronic copy of the "Sequence Listing" will also be available from the USPTO upon request and payment of the fee set forth in 37 CFR 1.19(b)(3).

What is claimed is:

1. A three-dimensional nucleic acid structure comprising a plurality of 10 or more single-stranded oligonucleotides, wherein each of the single-stranded oligonucleotides has a length of 28 nucleotides to 36 nucleotides and forms two adjacent antiparallel double helices connected to each other by a single phosphate bond, wherein one of the double helices comprises two adjacent nucleotide domains and the other of the double helices comprises two adjacent nucleotide domains, and each nucleotide domain of a single-stranded oligonucleotide of the plurality is complementary to and binds to a nucleotide domain of another single-stranded oligonucleotide of the plurality to form a 90° dihedral angle.

2. The nucleic acid structure of claim 1, wherein the nucleotide domains of the double helices are of equal nucleotide length.

3. The nucleic acid structure of claim 1, wherein each domain is 8 nucleotides in length.

4. The nucleic acid structure of claim 1, wherein the structure further comprises single-stranded 2-domain oligonucleotides.

5. The nucleic acid structure of claim 1, wherein the oligonucleotides are DNA oligonucleotides.

6. The nucleic acid structure of claim 1, wherein the DNA oligonucleotides are L-DNA oligonucleotides.

7. The nucleic acid structure of claim 1, wherein the single-stranded oligonucleotides of the plurality are cross-linked to each other.

8. The nucleic acid structure of claim 1, wherein the nucleic acid structure comprises 100, 500, or 1000 of the single-stranded oligonucleotides.

9. The nucleic acid structure of claim 1, wherein the structure is a cuboid structure, a cylindrical structure, a sheet, a honeycomb structure, or a hexagonal lattice structure.

10. The nucleic acid structure of claim 1, wherein the structure is a Z-crystal, a ZX-crystal, a Y-crystal, an X-crystal, an XY-crystal, or a ZXY crystal.

11. A method of producing a three-dimensional nucleic acid nanostructure, comprising:
annealing in a vessel a plurality of 10 or more single-stranded oligonucleotides, wherein each of the single-stranded oligonucleotides has a length of 28 nucleotides to 36 nucleotides and forms two adjacent antiparallel double helices connected to each other by a single phosphate bond, wherein one of the double helices comprises two nucleotide domains and the other of the double helices comprises two nucleotide domains, and each nucleotide domain of a single-stranded oligonucleotide of the plurality is complementary to and binds to a nucleotide domain of another single-stranded oligonucleotide of the plurality to form a 90° dihedral angle, thereby producing a three-dimensional nucleic acid nanostructure.

12. The method of claim 11, wherein the single-stranded oligonucleotides are present at equal molar concentrations.

13. The method of claim 11, wherein annealing occurs through a temperature transition over a period of time.

14. The method of claim 13, wherein the temperature transition is a change in temperature from an elevated temperature to room temperature.

15. The method of claim 14, wherein the temperature transition is a change in temperature from 90° C. to room temperature.

16. The method of claim 11, wherein the annealing occurs over a period of 12-24 hours.

17. The method of claim 11, wherein each domain is 8 nucleotides in length.

18. The method of claim 11, wherein the single-stranded oligonucleotides are DNA oligonucleotides.

19. The method of claim 18, wherein the single-stranded DNA oligonucleotides are L-DNA oligonucleotides.

* * * * *